(12) United States Patent
Foster et al.

(10) Patent No.: US 10,934,346 B2
(45) Date of Patent: Mar. 2, 2021

(54) MODIFIED T CELL COMPRISING A POLYNUCLEOTIDE ENCODING AN INDUCIBLE STIMULATING MOLECULE COMPRISING MYD88, CD40 AND FKBP12

(71) Applicant: BELLICUM PHARMACEUTICALS, INC., Houston, TX (US)

(72) Inventors: Aaron Edward Foster, Houston, TX (US); David Spencer, Houston, TX (US); Matthew Robert Collinson-Pautz, Houston, TX (US); Kevin Slawin, Houston, TX (US)

(73) Assignee: Bellicum Pharmaceuticals, Inc., Houston, TX (US)

( * ) Notice: Subject to any disclaimer, the term of this patent is extended or adjusted under 35 U.S.C. 154(b) by 349 days.

(21) Appl. No.: 14/622,018

(22) Filed: Feb. 13, 2015

(65) Prior Publication Data
US 2016/0046700 A1    Feb. 18, 2016

Related U.S. Application Data

(60) Provisional application No. 61/940,347, filed on Feb. 14, 2014, provisional application No. 61/952,839, filed on Mar. 13, 2014, provisional application No. 62/047,875, filed on Sep. 9, 2014.

(51) Int. Cl.
| C07K 14/705 | (2006.01) |
| C07K 16/18 | (2006.01) |
| A61K 35/14 | (2015.01) |
| C07K 14/00 | (2006.01) |
| C07K 14/47 | (2006.01) |
| A61K 38/00 | (2006.01) |

(52) U.S. Cl.
CPC .............. *C07K 16/18* (2013.01); *A61K 35/14* (2013.01); *C07K 14/00* (2013.01); *C07K 14/4705* (2013.01); *C07K 14/70578* (2013.01); *A61K 38/00* (2013.01); *C07K 2317/622* (2013.01); *C07K 2319/30* (2013.01); *C07K 2319/33* (2013.01); *Y02A 50/30* (2018.01)

(58) Field of Classification Search
None
See application file for complete search history.

(56) References Cited

U.S. PATENT DOCUMENTS

| 4,514,506 A | 4/1985 | Braatz et al. |
| 5,384,253 A | 1/1995 | Krzyek et al. |
| 5,538,880 A | 7/1996 | Lundquist et al. |
| 5,550,214 A | 8/1996 | Eberlein et al. |
| 5,550,318 A | 8/1996 | Eberlein et al. |
| 5,589,343 A | 12/1996 | Marchand et al. |
| 5,610,042 A | 3/1997 | Chang et al. |
| 5,645,992 A | 7/1997 | Lott et al. |
| 5,648,226 A | 7/1997 | Van Den Eynde et al. |
| 5,709,995 A | 1/1998 | Chisari et al. |
| 5,719,054 A | 2/1998 | Bouursnell et al. |
| 5,741,899 A | 4/1998 | Capon et al. |
| 5,750,395 A | 5/1998 | Fikes et al. |
| 5,780,036 A | 7/1998 | Chisari |
| 5,830,462 A | 11/1998 | Crabtree et al. |
| 5,834,266 A | 11/1998 | Crabtree et al. |
| 5,840,839 A | 11/1998 | Wang et al. |
| 5,869,337 A | 2/1999 | Crabtree et al. |
| 5,869,608 A | 2/1999 | Cadlwell et al. |
| 5,871,753 A | 2/1999 | Crabtree et al. |
| 5,925,565 A | 7/1999 | Berlioz et al. |
| 5,935,819 A | 8/1999 | Eichner et al. |
| 5,955,596 A | 9/1999 | Zagursky et al. |
| 5,965,242 A | 10/1999 | Patton et al. |
| 5,994,313 A | 11/1999 | Crabtree et al. |
| 6,011,018 A | 1/2000 | Crabtree et al. |
| 6,043,082 A | 3/2000 | Crabtree et al. |
| 6,046,047 A | 4/2000 | Crabtree et al. |
| 6,046,158 A | 4/2000 | Ariizumi et al. |
| 6,054,436 A | 4/2000 | Crabtree et al. |
| 6,497,876 B1 | 12/2002 | Maraskovsky et al. |
| 6,558,951 B1 | 5/2003 | Tomai et al. |
| 6,670,186 B1 | 12/2003 | Nair et al. |
| 6,943,245 B2 | 9/2005 | Killary et al. |
| 7,404,950 B2 | 7/2008 | Spencer et al. |
| 8,404,817 B2 | 3/2013 | Sherman et al. |
| 8,486,693 B2 | 7/2013 | Park |

(Continued)

FOREIGN PATENT DOCUMENTS

| EP | 0273085 | 7/1988 |
| EP | 0 510 691 | 10/1992 |

(Continued)

OTHER PUBLICATIONS

Office Action dated Feb. 7, 2017 in U.S. Appl. No. 14/210,034, filed Mar. 13, 2014 and published as US 2014-0286987 on Sep. 25, 2014.
Chang et al., "Transgene-enforced co-stimulation of CD4+ T cells leads to enhanced and sustained anti-tumor effector functioning" Cytotherapy (2007) 9:771-784.
Warner et al., "MyD88: a critical adaptor protein in innate immunity signal transduction" J. Immunol. (2013) 190:3-4.
Nelson et al., "Toll-like receptor agonist therapy can profoundly augment the antitumor activity of adoptively transferred CD8(+) T cells without host preconditioning" J. Immunother. Cancer (2016) 4:6.

(Continued)

*Primary Examiner* — Phillip Gambel
(74) *Attorney, Agent, or Firm* — Jones Day

(57) ABSTRACT

The technology relates generally to the field of immunology and relates in part to methods for activating cells, including for example T cells and T cells that express chimeric antigen receptors, using an inducible chimeric polypeptide including CD40, MyD88, or CD40 and MyD88 polypeptides. The technology further relates in part to therapeutic methods for inducing an immune response and treating tumors in a patient.

15 Claims, 64 Drawing Sheets
Specification includes a Sequence Listing.

(56) References Cited

U.S. PATENT DOCUMENTS

| | | | |
|---|---|---|---|
| 8,691,210 | B2 | 4/2014 | Spencer et al. |
| 8,822,647 | B2 | 9/2014 | Jensen |
| 8,999,949 | B2 | 4/2015 | Spencer et al. |
| 9,428,569 | B2* | 8/2016 | Spencer ............... C12N 5/0639 |
| 9,572,835 | B2 | 2/2017 | Spencer |
| 9,944,690 | B2 | 4/2018 | Spencer et al. |
| 9,976,122 | B2 | 5/2018 | Spencer et al. |
| 2003/0082163 | A1 | 5/2003 | Shu |
| 2003/0091593 | A1 | 5/2003 | Bachmann et al. |
| 2003/0092132 | A1 | 5/2003 | Williams |
| 2003/0108527 | A1 | 6/2003 | Seya et al. |
| 2003/0147881 | A1 | 8/2003 | Cheung |
| 2003/0153518 | A1 | 8/2003 | Foxwell et al. |
| 2003/0206917 | A1 | 11/2003 | Tykocinski et al. |
| 2003/0232055 | A1 | 12/2003 | Medzhitov |
| 2004/0019195 | A1 | 1/2004 | Scholm et al. |
| 2004/0116333 | A1 | 6/2004 | Lin et al. |
| 2004/0209836 | A1 | 10/2004 | Spencer |
| 2005/0113564 | A1 | 5/2005 | Campana |
| 2005/0215472 | A1 | 9/2005 | Schulke et al. |
| 2006/0247191 | A1 | 11/2006 | Finney et al. |
| 2007/0081963 | A1 | 4/2007 | Oh et al. |
| 2008/0269160 | A1 | 10/2008 | Spencer et al. |
| 2008/0274140 | A1 | 11/2008 | Weiner et al. |
| 2009/0175880 | A1 | 7/2009 | Keler et al. |
| 2009/0311183 | A1 | 12/2009 | Devy et al. |
| 2010/0105136 | A1 | 4/2010 | Carter |
| 2010/0196336 | A1 | 8/2010 | Park et al. |
| 2010/0203067 | A1 | 8/2010 | Spencer et al. |
| 2011/0033383 | A1 | 2/2011 | Spencer et al. |
| 2011/0201780 | A1 | 8/2011 | Reed et al. |
| 2011/0286980 | A1 | 11/2011 | Brenner et al. |
| 2011/0287038 | A1* | 11/2011 | Slawin ................. A61K 31/711 424/184.1 |
| 2013/0071414 | A1* | 3/2013 | Dotti ................... C12N 5/0636 424/184.1 |
| 2013/0131315 | A1* | 5/2013 | Su ......................... C12P 21/00 530/350 |
| 2013/0183333 | A1 | 7/2013 | Spencer et al. |
| 2013/0280220 | A1 | 10/2013 | Ahmed |
| 2013/0287748 | A1* | 10/2013 | June ....................... A61K 35/17 424/93.21 |
| 2013/0287752 | A1 | 10/2013 | Davila |
| 2013/0295110 | A1* | 11/2013 | Binder ............... A61K 39/0011 424/142.1 |
| 2013/0315884 | A1 | 11/2013 | Galetto |
| 2013/0323834 | A1 | 12/2013 | Brenner |
| 2014/0023647 | A1 | 1/2014 | Slawin et al. |
| 2014/0087468 | A1 | 3/2014 | Spencer et al. |
| 2014/0120622 | A1* | 5/2014 | Gregory ................. A61K 35/26 435/462 |
| 2014/0134142 | A1 | 5/2014 | Cellectis |
| 2014/0255360 | A1 | 9/2014 | Spencer et al. |
| 2014/0255363 | A1 | 9/2014 | Metelitsa |
| 2014/0286987 | A1 | 9/2014 | Spencer et al. |
| 2014/0287490 | A1 | 9/2014 | Spencer et al. |
| 2014/0308259 | A1 | 10/2014 | Scholler |
| 2014/0322275 | A1* | 10/2014 | Brogdon ................ A61K 38/00 424/277.1 |
| 2015/0093401 | A1 | 4/2015 | Pule et al. |
| 2015/0111294 | A1 | 4/2015 | Spencer et al. |
| 2015/0139943 | A1 | 5/2015 | Campana et al. |
| 2015/0306140 | A1 | 10/2015 | Spencer et al. |
| 2015/0328292 | A1 | 11/2015 | Spencer et al. |
| 2016/0046700 | A1 | 2/2016 | Foster et al. |
| 2016/0058857 | A1 | 3/2016 | Spencer et al. |
| 2017/0002321 | A1 | 1/2017 | Spencer et al. |
| 2017/0166652 | A1 | 6/2017 | Schreiber et al. |
| 2017/0182140 | A1 | 6/2017 | Spencer et al. |
| 2018/0265566 | A1 | 9/2018 | Spencer et al. |

FOREIGN PATENT DOCUMENTS

| | | |
|---|---|---|
| WO | WO 2016/123143 | 8/1916 |
| WO | WO 2018/208849 | 11/1918 |
| WO | WO 2019/113509 | 6/1919 |
| WO | WO 94/09699 | 5/1994 |
| WO | WO 94/018317 | 8/1994 |
| WO | WO 96/012796 | 5/1996 |
| WO | WO 01/083551 | 11/2001 |
| WO | WO 02/036769 | 5/2002 |
| WO | WO 04/073641 | 9/2004 |
| WO | WO 2005/044996 | 5/2005 |
| WO | WO 08/049113 | 4/2008 |
| WO | WO 09/061996 | 5/2009 |
| WO | WO 10/033949 | 5/2010 |
| WO | WO 11/130566 | 10/2011 |
| WO | WO 11/146862 | 11/2011 |
| WO | WO 2012/079000 | 6/2012 |
| WO | WO 2012/127464 | 9/2012 |
| WO | WO 2013/126720 | 8/2013 |
| WO | WO 13/154765 | 10/2013 |
| WO | WO 14/127261 | 8/2014 |
| WO | WO 14/151960 | 9/2014 |
| WO | WO 14/164348 | 10/2014 |
| WO | WO 14/197638 | 12/2014 |
| WO | WO 15/123527 | 8/2015 |
| WO | WO 2015/134877 | 9/2015 |
| WO | WO 16/036746 | 3/2016 |

OTHER PUBLICATIONS

Paulos et al., "Microbial translocation augments the function of adoptively transferred self/tumor-specific CD8+ T cells via TLR4 signaling" J. Clin. Invest. (2007) 117:2197-2204.
International Preliminary Report on Patentability dated Mar. 16, 2017 in International Application No. PCT/US2015/047957, filed on Sep. 1, 2015 and published as WO 2016/036749 on Mar. 10, 2016.
Adema, G. J., et al., Nature, Jun. 12, 1997, 387: p. 713-7.
Anderson, D. M., et al., Nature, Nov. 13, 1997, 390: p. 175-9.
Anurathapan, U. et al. Kinetics of tumor destruction by chimeric antigen receptor-modified T cells. Molecular therapy : the journal of the American Society of Gene Therapy 22, 623-633 (2014).
Arcane, et al., (1988) Nucl. Acids Res., 16(8), 3195-3207.
Ardeshna KM, et al., Blood. 2000;96:1039-1046.
Banchereau J, et al., Ann N Y Acad Sci. 2003; 987:180-187.
Banchereau, J., & Steinman, R. M., Nature 392, 245-252 (1998).
Banchereau, J., et al., Annu Rev Immunol, 2000,. 18: p. 767-811.
Bander NH, et al., J Clin Oncol. 23: 4591-601, 2005.
Becker ML, Near R, Mudgett-Hunter M, et al: Expression of a hybrid immunoglobulin-T cell receptor protein in transgenic mice. Cell 58:911-21, 1989.
Bennett, S. R., et al., . Nature, Jun. 4, 1998, 393: p. 478-80.
Bernard et al., AIDS, 12(16):2125-2139, 1998.
Bianco FJ, et al., Cancer Symposium: Abstract 278, 2005.
Blau, C. A. et al., Proc Natl Acad.Sci. USA 1997, 94:3076-3081.
Bojak, A., et al., 2002. Vaccine 20:1975-79.
Bollard, C.J., et al., (2002) Blood 99:3179-3187.
Bollard, C.M., et al., (2004) J. Exptl. Med. 200:1623-1633.
Brentjens RJ, Davila ML, Riviere I, et al: CD19-targeted T cells rapidly induce molecular remissions in adults with chemotherapy-refractory acute lymphoblastic leukemia. Sci Transl Med 5:177ra38, 2013.
Carpenito, et al: Control of large, established tumor xenografts with genetically retargeted human T cells containing CD28 and CD137 domains. Proc Natl Acad Sci U S A 106:3360-5, 2009.
Carter RE, et al., Proc Natl Acad Sci U S A. 93: 749-53, 1996.
Caux, C. Adv Exp Med Biol. 1997, 417:21-5.
Cazeaux, N., et al., 2002. Vaccine 20:3322-31.
Chang SS, et al., Clin Cancer Res. 5: 2674-81, 1999.
Chang SS, et al., Urology. 57: 801-5, 2001.
Chatteijee, et al., (1995) Ann. N.Y. Acad. Sci., 770,79-90.
Chen and Okayama, Mol. Cell Biol., 7(8):2745-2752, 1987.
Chen et al PNAS 94: 1914-1918, 1997.
Cheung, Y.K., et al., 2004. Vaccine 23:629-38.

(56) References Cited

OTHER PUBLICATIONS

Christiansen JJ, et al., Mol Cancer Ther. 4: 704-14, 2005.
Ciceri, F. et al. Antitumor effects of HSV-TK-engineered donor lymphocytes after allogeneic stem-cell transplantation. Blood 109, 4698-4707 (2007).
Clackson T (2006) Chem Biol Drug Des 67:440-2.
Clarke, S. R., J Leukoc Biol, May 2000, 67: p. 607-14.
Coffin, (1990) In: Virology, ed., New York: Raven Press, pp. 1437-1500.
Cohen et al Nucleic Acid Res. 18:2807-2808, 1990.
Coupar et al., Gene, 68:1-10, 1988.
Craddock JA, Lu A, Bear A, et al: Enhanced tumor trafficking of GD2 chimeric antigen receptor T cells by expression of the chemokine receptor CCR2b. J Immunother 33:780-8, 2010.
Crawford ED, et al., N Engl J Med. 321: 419-24, 1989.
De la Taille A, et al., Cancer Detect Prev. 24: 579-88, 2000.
Deml, L.A., et al., 2001. J. Virol. 75:1099-11001.
Di Stasi, A. et al. Inducible apoptosis as a safety switch for adoptive cell therapy. The New England journal of medicine 365, 1673-1683 (2011).
Donnelly, J.J., et al., 1997. Annu. Rev. Immunol. 15:617-48.
Donnelly, ML 2001, J. Gen. Virol. 82:1013-25.
Dotti, G., Gottschalk, S., Savoldo, B. & Brenner, M.K. Design and development of therapies using chimeric antigen receptor-expressing T cells. Immunological reviews 257, 107-126 (2014).
Farrar et al., "Activation of the Raf-1 kinase cascade by courmycin-induced dimerization," Nature 383, Sep. 12, 1996, 178-181.
Fearon et al. "The instructive role of innate immunity in the acquired immune response," (1996) Science 272: 50-53.
Fechheimer et al., (1987) Proc. Nat'l Acad. Sci. USA, 84,8463-8467.
Fedorov, V.D., Themeli, M. & Sadelain, M. PD-1- and CTLA-4-based inhibitory chimeric antigen receptors (iCARs) divert off-target immunotherapy responses. Science translational medicine 5, 215ra172 (2013).
Fernandez, N. C., et al.,. Nat Med, Apr. 5, 1999: p. 405-11.
Ferrari et al., (1996) J. Virol., 70,3227-3234.
Ferraro, B. et al., Human Vaccines 7:120-127 (2011).
Finney HM, Akbar AN, Lawson AD: Activation of resting human primary T cells with chimeric receptors: costimulation from CD28, inducible costimulator, CD134, and CD137 in series with signals from the TCR zeta chain. J Immunol 172:104-13, 2004.
Finney HM, Lawson AD, Bebbington CR, et al: Chimeric receptors providing both primary and costimulatory signaling in T cells from a single gene product. J Immunol 161:2791-7, 1998.
Fisher et al., "Transduction with Recombinant Adeno-Associated Virus for Gene Therapy Is Limited by Leading-Strand Synthesis" (1996) J. Virol., 70,520-532.
Fisher, D.T. et al. IL-6 trans-signaling licenses mouse and human tumor microvascular gateways for trafficking of cytotoxic T cells. The Journal of clinical investigation 121, 3846-3859 (2011).
Flotte et al., Proc. Nat'l Acad. Sci. USA, 90,10613-10617, (1993).
Foster, A.E. et al. Autologous designer antigen-presenting cells by gene modification of T lymphocyte blasts with IL-7 and IL-12. Journal of immunotherapy 30, 506-516 (2007).
Freeman LM, et al., Q J Nucl Med. 46: 131-7, 2002.
Gaubert, G.; Wengel, J. "Synthesis of 1-(2'-O-methyl-β-d-ribofuranosyl)-5-nitroindole and its phosphoramidite derivative," Tetrahedron Letters 2004, 45, 5629-5632.
Gauthier-Campbell et al., Molecular Biology of the Cell 15: 2205-2217 (2004).
Gay, N.J., Symmons, M.F., Gangloff, M. & Bryant, C.E. Assembly and localization of Toll-like receptor signalling complexes. Nature reviews. Immunology 14, 546-558 (2014).
Gefter et al., Somatic Cell Genet., 3:231-236, 1977.
Gestwicki, J.E., et al., Combinatorial Chem. & High Throughput Screening 10:667-675 (2007).
Gibson, D.G. et al. Enzymatic assembly of DNA molecules up to several hundred kilobases. Nature methods 6, 343-345 (2009).
Gilboa, E, Nat Rev Cancer 4, 401-11 (2004).
Gilboa, E. & Vieweg, J., Immunol Rev 199, 251-63 (2004).
Gittes RF, N Engl J Med. 324: 236-45, 1991.
Galbiati et al., "N-terminal fatty acylation of the alpha-subunit of the G-protein Gi1 : only the myristoylated protein is a substrate for palmitoylation." Biochem. J. 303: 697-700 (1994).
Goodman et al. (1994), Blood, 84,1492-1500.
Goodwin JS, Curr Opin Immunol. 1989;2:264-268.
Goodwin JS, et al., J Exp Med. 1977;146:1719-1734.
Gopal, T.V., Mol Cell Biol. May 1985;5(5):1188-90.
Gossen and Bujard, Proc. Natl. Acad. Sci. USA, 89:5547-5551, 1992.
Gossen et al., Science, 268:1766-1769, 1995.
Goverman J, Gomez SM, Segesman KD, et al: Chimeric immuno-globulin-T cell receptor proteins form functional receptors: implications for T cell receptor complex formation and activation. Cell 60:929-39, 1990.
Graham and van der Eb, (1973) Virology, 52,456-467.
Gross G, Waks T, Eshhar Z: Expression of immunoglobulin-T-cell receptor chimeric molecules as functional receptors with antibody-type specificity. Proc Natl Acad Sci U S A 86:10024-8, 1989.
Gross, G., and Eshar, Z., FASEB Journal 6:3370-3378 (1992).
Grupp, S.A. et al. Chimeric antigen receptor-modified T cells for acute lymphoid leukemia. The New England journal of medicine 368, 1509-1518 (2013).
Guedan S, Chen X, Madar A, et al: ICOS-based chimeric antigen receptors program bipolar TH17/TH1 cells. Blood, 2014, 1070-1080.
Hanks BA, et al., Nat Med. 2005;11:130-137.
Hauer et al., PNAS 102(8): 2874-2879 (2005)).
Hay, R.T., et al., J Mol Biol. Jun. 5, 1984;175(4):493-510.
Haynes, N.M., et al. J. Immunol. 166:182-7 (2001).
Hearing and Shenk, (1983) J. Mol. Biol. 167,809-822.
Hearing et al., J. (1987) Virol., 67, 2555-2558.
Ho, S. N. et al., Nature 1996, 382:822-826.
Hollstein et al Nucleic Acids Res. 22:3551-3555, 1994.
Holsinger, L. J. et al., Proc.Natl.Acad.Sci. USA 1995, 95:9810-9814.
Hombach A, Wieczarkowiecz A, Marquardt T, et al: Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167:6123-31, 2001.
Imai C, Mihara K, Andreansky M, et al: Chimeric receptors with 4-1BB signaling capacity provoke potent cytotoxicity against acute lymphoblastic leukemia. Leukemia 18:676-84, 2004.
Inman, B.A., Frigola, X., Dong, H. & Kwon, E.D. Costimulation, coinhibition and cancer. Current cancer drug targets 7, 15-30 (2007).
Introna, M. et al. Genetic modification of human T cells with CD20: a strategy to purify and lyse transduced cells with anti-CD20 antibodies. Human gene therapy 11, 611-620 (2000).
Ismaili J, et al., J Immunol. 2002;168:926-932.
Israeli et al Cancer Res. 53:227-230, 1993.
Israeli RS, et al., Cancer Res. 54: 1807-11, 1994.
Israeli RS, et al., Cancer Res. 54: 6306-10, 1994.
Iuliucci JD, et al., J Clin Pharmacol. 41: 870-9, 2001.
Jackson et al EMBOJ, 11:527-535, 1992.
Janeway et al. (1989) Cold Spring Harb. Symp. Quant. Biol., 54: 1-13.
Jemal A, et al., Cancer statistics, 2008. CA Cancer J Clin. 58: 71-96, 2008.
Jena, B., Moyes, J.S., Huls, H. & Cooper, L.J. Driving CAR-based T-cell therapy to success. Current hematologic malignancy reports 9, 50-56 (2014).
Jensen MC, Popplewell L, Cooper LJ, et al: Antitransgene rejection responses contribute to attenuated persistence of adoptively transferred CD20/CD19-specific chimeric antigen receptor redirected T cells in humans. Biol Blood Marrow Transplant 16:1245-56, 2010.
Kadowaki N, et al., J Exp Med. 2001;194:863-869.
Kageyama et al., (1987) J. Biol. Chem., 262,2345-2351.
Kalinski P, Blood. 2001;97:3466-3469.

(56) References Cited

OTHER PUBLICATIONS

Kalinski P, Hilkens CM, Wierenga EA, et al: T-cell priming by type-1 and type-2 polarized dendritic cells: the concept of a third signal. Immunol Today 20:561-7, 1999.
Kalos, M. et al. T cells with chimeric antigen receptors have potent antitumor effects and can establish memory in patients with advanced leukemia. Science translational medicine 3, 95ra73 (2011).
Kamburov, A., Wierling, C., Lehrach, H. & Herwig, R. ConsensusPathDB—a database for integrating human functional interaction networks. Nucleic acids research 37, D623-628 (2009).
Kaplitt et al., (1994) Nat'l Genet., 8,148-153.
Kaplitt, M.G., et al., Ann Thorac Surg. Dec. 1996;62(6):1669-76.
Katari, U.L. et al. Engineered T cells for pancreatic cancer treatment. HPB : the official journal of the International Hepato Pancreato Biliary Association 13, 643-650 (2011).
Kawakami et al Proc. Nat'l Acad. Sci. USA 91:6458-6462, 1992.
Kawakarni et al, J. Exp. Med. 180:347-352, 1994.
Kelly WK and Slovin SF, Curr Oncol Rep. 2: 394-401, 2000.
Kemnade JO, Seethammagari M, Narayanan P, et al: Off-the-shelf Adenoviral-mediated Immunotherapy via Bicistronic Expression of Tumor Antigen and iMyD88/CD40 Adjuvant. Mol Ther, Jul. 2012;20(7):1462-71.
Kershaw MH, Westwood JA, Parker LL, et al: A phase I study on adoptive immunotherapy using gene-modified T cells for ovarian cancer. Clin Cancer Res 12:6106-15, 2006.
Kessler et al., (1996) Proc. Nat'l Acad. Sci. USA, 93, 14082-14087.
Klein et al., (1987) Nature, 327,70-73.
Kloss, C.C., Condomines, M., Cartellieri, M., Bachmann, M. & Sadelain, M. Combinatorial antigen recognition with balanced signaling promotes selective tumor eradication by engineered T cells. Nature biotechnology 31, 71-75 (2013).
Kochenderfer, J.N. et al. Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor. Journal of clinical oncology : official journal of the American Society of Clinical Oncology (2014), 540-549.
Koeberl et al., (1997) Proc. Nat'l Acad. Sci. USA, 94,1426-1431.
Kohler & Milstein, Eur. J. Immunol., 6:511-519, 1976.
Kohler & Milstein, Nature, 256:495-497, 1975.
Kopytek, S.J., et al., Chemistry & Biology 7:313-321 (2000).
Kraaij R, et al., Prostate. 62: 253-9, 2005.
Kuby, 2000, Immunology, 4.sup.th edition, W.H. Freeman.
Kumar, S., et al., 2006. DNA Cell Biol. 25:383-92.
Kutzler, M.A., and Weiner, D.B., 2008. Nature Rev. Gen. 9:776-88.
Kutzler, M.A., et al., 2005. J. Immunol. 175:112-125.
Kuwana Y, Asakura Y, Utsunomiya N, et al: Expression of chimeric receptor composed of immunoglobulin-derived V regions and T-cell receptor-derived C regions. Biochem Biophys Res Commun 149:960-8, 1987.
Kwon et al PNAS 84:7473-7477, 1987.
Laddy, D.J., et al., 2008. PLoS.One 3 e2517.
Lanitis, E. et al. Chimeric antigen receptor T Cells with dissociated signaling domains exhibit focused antitumor activity with reduced potential for toxicity in vivo. Cancer immunology research 1, 43-53 (2013).
Lanzavecchia, A. and F. Sallusto, Science, 2000. 290: p. 92-96.
Lapointe R, et al., Eur J Immunol. 2000;30:3291-3298.
Lee DW, Gardner R, Porter DL, et al: Current concepts in the diagnosis and management of cytokine release syndrome. Blood 124:188-95, 2014.
Levrero et al., Gene, 101:195-202, 1991.
Leyton, J.V. et al. Engineered humanized diabodies for microPET imaging of prostate stem cell antigen-expressing tumors. Protein engineering, design & selection: PEDS 22, 209-216 (2009).
Leyton, J.V. et al. Humanized radioiodinated minibody for imaging of prostate stem cell antigen-expressing tumors. Clinical cancer research: an official journal of the American Association for Cancer Research 14, 7488-7496 (2008).
Li, V., et al., 2000. Virology 272:417-28.
Linette, G.P. et al. Cardiovascular toxicity and titin cross-reactivity of affinity-enhanced T cells in myeloma and melanoma. Blood 122, 863-871 (2013).
Liu H, et al., Cancer Res. 57: 3629-34, 1997.
Liu H, et al., Cancer Res. 58: 4055-60, 1998.
Luft T, et al., Blood. 2002;100:1362-1372.
Luo, Z. et al., Nature 1996,383:181-185.
MacCorkle, R. A. et al., Proc Natl Acad Sci USA 1998, 95:3655-3660.
Macejak and Sarnow, Nature, 353:90-94, 1991.
Maher J, Brentjens RJ, Gunset G, et al: Human T-lymphocyte cytotoxicity and proliferation directed by a single chimeric TCRzeta/CD28 receptor. Nat Biotechnol 20:70-5, 2002.
Malin, A.S., et al., 2000. Microbes Infect. 2:1677-85.
Mann et al., (1983) Cell, 33,153-159.
Martin S, Pahari S, Sudan R, et al: CD40 signaling in $CD8^+CD40^+$ T cells turns on contra-T regulatory cell functions. J Immunol 184:5510-8, 2010.
Maude, S.L. et al. Chimeric antigen receptor T cells for sustained remissions in leukemia. The New England journal of medicine 371, 1507-1517 (2014).
McCown et al., (1996) Brain Res., 713,99-107.
McWhirter, S. M., et al., Proc Natl Acad Sci U S A, Jul. 20, 1999, 96: p. 8408-13.
Medzhitov et al., "A human homologue of the *Drosophila* Toll protein signals activation of immunity," Letters to Nature, Nature vol. 388:394-397, Jul. 24, 1997.
Meylan, E., et al., Nature (2006) 442:39-44.
Milone MC, Fish JD, Carpenito C, et al: Chimeric receptors containing CD137 signal transduction domains mediate enhanced survival of T cells and increased antileukemic efficacy in vivo. Mol Ther 17:1453-64, 2009.
Mizukami et al., (1996) Virology, 217,124-130.
Montgomery, D.L., et al., 1993. DNA Cell Biol. 12:777-83.
Morgan, R.A., et al., "Case Report of a Serious Adverse Event Following the Administration of T Cells Transduced With a Chimeric Antigen Receptor Recognizing ERBB2" (2010) Molecular Therapy 18:843-851.
Nabel et al., Science, 244(4910):1342-1344, 1989.
Narayanan P, Lapteva N, Seethammagari M, et al: A composite MyD88/CD40 switch synergistically activates mouse and human dendritic cells for enhanced antitumor efficacy. J Clin Invest 121:1524-34, 2011.
Narum, D.L., et al., 2001. 69:7250-55.
Ni, C., et al., PNAS, 2000, 97(19): 10395-10399.
Nicolau et al., (1987) Methods Enzymol., 149,157-176.
Nociari et al., J. Immunol. Methods, 213(2): 157-167, 1998.
Ohshima, Y., et al., J Immunol, Oct. 15, 1997, 159: p. 3838-48.
Oliviero et al., (1987) EMBO J., 6, 1905-1912.
O'Neill DW, et al., Blood. 2004;104:2235-2246.
Page, B., et al., Anticancer Res. Jul.-Aug. 1998;18(4A):2313-6.
Park JR, Digiusto DL, Slovak M, et al: Adoptive transfer of chimeric antigen receptor re-directed cytolytic T lymphocyte clones in patients with neuroblastoma. Mol Ther 15:825-33, 2007.
Paskind et al., (1975) Virology, 67,242-248.
Pelletier and Sonenberg, Nature, 334:320-325, 1988.
Perales et al., Proc. Natl. Acad. Sci. USA, 91:4086-4090, 1994.
Philip, B. et al. A highly compact epitope-based marker/suicide gene for easier and safer T-cell therapy. Blood 124, 1277-1287 (2014).
Ping et al., (1996) Microcirculation, 3,225-228.
Pinto JT, et al., Clin Cancer Res. 2: 1445-51, 1996.
Poli and Cortese, (1989) Proc. Nat'l Acad. Sci. USA, 86,8202-8206.
Porter, D.L., Levine, B.L., Kalos, M, Bagg, A. & June, C.H. Chimeric antigen receptor-modified T cells in chronic lymphoid leukemia. The New England journal of medicine 365, 725-733 (2011).
Potter et al., (1984) Proc. Nat'l Acad. Sci. USA, 81, 7161-7165.
Prowse and Baumann, (1988) Mol Cell Biol, 8,42-51.
Pule, et al: A chimeric T cell antigen receptor that augments cytokine release and supports clonal expansion of primary human T cells. Mol Ther 12:933-41, 2005.

(56) References Cited

OTHER PUBLICATIONS

Pule, et al: Virus-specific T cells engineered to coexpress tumor-specific receptors: persistence and antitumor activity in individuals with neuroblastoma. Nat Med 14:1264-70, 2008.
Pullen, S.S., et al., J Biol Chem, May 14, 1999,274: p. 14246-54.
Ramos CA, Dotti G: Chimeric antigen receptor (CAR)-engineered lymphocytes for cancer therapy. Expert Opin Biol Ther 11:855-73, 2011.
Renan, M. J. (1990) Radiother Oncol., 19, 197-218.
Rescigno M, et al., J Exp Med. 1998;188:2175-2180.
Rickert, R.C., Jellusova, J. & Miletic, A.V. Signaling by the tumor necrosis factor receptor superfamily in B-cell biology and disease. Immunological reviews 244, 115-133 (2011).
Ridge, J. P., D. R. F, and P. Nature, Jun. 4, 1998, 393: p. 474-8.
Rippe et al., Mol. Cell Biol., 10:689-695, 1990.
Rivera, V. M. et al., Nat.Med. 1996, 2:1028-1032.
Riviere, et al., "Effects of retroviral vector design on expression of human adenosine deaminase in murine bone marrow transplant recipients engrafted with genetically modified cells" PNAS, USA 92, 6733-6737 (1995).
Ron, et al., (1991) Mol. Cell. Biol., 2887-2895.
Rosenberg SA, Immunity. 1999;10:281-287.
Roux et al., (1989) Proc. Nat'l Acad. Sci. USA, 86, 9079-9083.
Sallusto, F., et al., Eur J Immunol, Sep. 28, 1998: p. 2760-9.
Samulski et al., J. Virol., 61:3096-3101 (1987).
Sardesai, N.Y., and Weiner, D.B., Current Opinion in Immunotherapy 23:421-9 (2011).
Savoldo B, Ramos CA, Liu E, et al: CD28 costimulation improves expansion and persistence of chimeric antigen receptor-modified T cells in lymphoma patients. J Clin Invest 121:1822-6, 2011.
Scandella E, et al., Blood. 2002;100:1354-1361.
Schellhammer PF, et al., J Urol. 157: 1731-5, 1997.
Schenten D, Nish SA, Yu S, et al: Signaling through the adaptor molecule MyD88 in CD4$^+$ T cells is required to overcome suppression by regulatory T cells. Immunity 40:78-90, 2014.
Scher HI, et al., J Natl Cancer Inst. 88: 1623-34, 1996.
Scher, H.I. and Kelly, W.K., Journal of Clinical Oncology 11, 1566-72 (1993).
Schneider, R. M., et al., 1997. J. Virol. 71:4892-4903.
Schoenberger, S. P., et al., Nature, Jun. 4, 1998, 393: p. 480-3.
Schweitzer et al., J. Org. Chem., 59:7238-7242 (1994).
Silver DA, et al., Clin Cancer Res. 3: 81-5, 1997.
Simpson et al., Gastroenterology, 115(4):849-855, 1998.
Small EJ and Srinivas S, Cancer. 76: 1428-34, 1995.
Small EJ and Vogelzang NJ, J Clin Oncol. 15: 382-8, 1997.
Smith, J.M., et al., 2004. AIDS Res. Hum. Retroviruses 20:1335-47.
Snyder DS, Nature. 1982;299:163-165.
Song, D.G. et al. CD27 costimulation augments the survival and antitumor activity of redirected human T cells in vivo. Blood 119, 696-706 (2012).
Spencer D. M. et al., Curr Biol 1996, 6:839-847.
Spencer D. M. et al., Proc.Natl.Acad.Sci. USA 1995, 92:9805-9809.
Spencer DM, et al., Science. 1993;262:1019-1024.
Steinman RM, Annu Rev Immunol. 2003;21:685-711.
Straathof, K.C. et al. An inducible caspase 9 safety switch for T-cell therapy. Blood 105, 4247-4254 (2005).
Strober, W., et al., Nature Reviews (2006) 6:9-20.
Su SL, et al., Cancer Res. 55: 1441-3, 1995.
Subramanian et al. "Gene set enrichment analysis: a knowledge-based approach for interpreting genome-wide expression profiles", PNAS, USA, 102, 15545-15550 (2005).
Tai et al., Cancer Research 64, 2846-2852 (2004).
Ten Klooster JP et al, Biology of the Cell (2007) 99, 1-12.
Tepler, I, et al. (1989) J. Biol. Chem. 264:5912.
Termeer, C. C., et al., J Immunol, Aug. 15, 2000, 165: p. 1863-70.
Tibbetts et. al. (1977) Cell, 12,243-249.
Till, et al: "CD20-specific adoptive immunotherapy for lymphoma using a chimeric antigen receptor with both CD28 and 4-1BB domains: pilot clinical trial results". Blood 119:3940-50, 2012.

Tone, M., et al., Proc Natl Acad Sci U S A, 2001. 98(4): p. 1751-1756.
Troyer JK, et al., Int J Cancer. 62: 552-8, 1995.
Tur-Kaspa et al., (1986) Mol. Cell Biol., 6,716-718.
Van der Pouw Kraan TC, et al., J Exp Med. 1995;181:775-779.
Vera, J. et al. "T lymphocytes redirected against the kappa light chain of human immunoglobulin efficiently kill mature B lymphocyte-derived malignant cells", Blood 108, 3890-3897 (2006).
Vieweg J, et al., Springer Semin Immunopathol. 2005;26:329-341.
Vincent, S., et al., Nature Biotechnology 21:936-40, 1098 (2003).
Wagner et al., Proc. Natl. Acad. Sci. USA, 87(9):3410-3414, 1990.
Wang J, Jensen M, Lin Y, et al: Optimizing adoptive polyclonal T cell immunotherapy of lymphomas, using a chimeric T cell receptor possessing CD28 and CD137 costimulatory domains. Hum Gene Ther 18:712-25, 2007.
Wang, S., et al., 2006. Vaccine 24:4531-40.
Werts C., et al., Cell Death and Differentiation (2006) 13:798-815.
Wilson et al., (1990) Mol. Cell. Biol., 6181-6191.
Wilson et al., Science, 244:1344-1346, 1989.
Wright GL, Jr., et al., Urology. 48: 326-34, 1996.
Wu and Wu, (1987) J. Biol. Chem., 262, 4429-4432.
Wu and Wu, Adv. Drug Delivery Rev., 12:159-167, 1993.
Wu, X., et al., 2004. Biochem. Biophys. Res. Commun. 313:89-96.
Xiao et al., (1996) J. Virol., 70,8098-8108.
Xu, Z.L., et al. 2001. Gene 272:149-56.
Yadava, A., and Ockenhouse, C.F., 2003. Infect. Immun. 71:4962-69.
Yan, J. et al., 2007. Mol. Ther. 15:411-21.
Yang et al., (1990) Proc. Nat'l Acad. Sci. USA, 87, 9568-9572.
Yang, J.S., et al., 2002. Emerg. Infect. Dis. 8:1379-84.
Yvon E, Del Vecchio M, Savoldo B, et al: Immunotherapy of metastatic melanoma using genetically engineered GD2-specific T cells. Clin Cancer Res 15:5852-60, 2009.
Zechner et al., Mol. Cell. Biol., 2394-2401, 1988.
Zhang, W., et al., 2006. Biochem. Biophys. Res. Commun. 349:69-78.
Zhang, Y., et al., "Transduction of human T cells with a novel T-cell receptor confers anti-HCV reactivity", PLoS Pathog. Jul. 29, 2010;6(7).
Zhao Y, Wang QJ, Yang S, et al: A herceptin-based chimeric antigen receptor with modified signaling domains leads to enhanced survival of transduced T lymphocytes and antitumor activity. J Immunol 183:5563-74, 2009.
Zhong XS, et al., Mol Ther. Feb. 2010; 18(2):413-20.
Zhou, W., et al., 2002. Vet. Microbiol. 88:127-51.
Zitvogel L, et al., J Exp Med 1996. 183:87-97.
Zlakine et al., J. Cell Science 110: 673-679 (1997).
Zur Megede, J., et al., 2000. J. Virol. 74:2628-2635.
International Search Report and Written Opinion dated Dec. 3, 2014 in International Application No. PCT/US2014/26734 filed Mar. 13, 2014 and published as: WO 2014/151960 on: Sep. 24, 2014.
International Preliminary Report on Patentability dated Aug. 25, 2016 in International Application No. PCT/US2015/015829, filed on Feb. 13, 2015 and published as WO 2015/123527 dated Aug. 20, 2015.
Extended European Search Report dated Sep. 21, 2016 in European Patent Application No. 14770399.5, filed on Mar. 13, 2014 and published as EP 2 968 502 on Jan. 20, 2016.
Search Report and Written Opinion dated Oct. 4, 2016 in Singapore Patent Application No. 11201506974X, filed on Mar. 13, 2014.
Curran et al., "Chimeric antigen receptors for T cell immunotherapy: current understanding and future directions" J. Gene Med. (2012) 14:405-415.
ARIAD Pharmaceuticals, Inc., "ARGENT Regulated Homodimerization Kit" Version 2.0, product brochure, Sep. 9, 2002.
"Sipuleucel-T:APC 8015, APC-8015, prostate cancer vaccine—Dendreon." Drugs R D. 2006;7(3):197-201.
Adam et al., "Cross-linking of the p55 Tumor Necrosis Factor Receptor Cytoplasmic Domain by a Dimeric Ligand Induces nuclear Factor-kB and Mediates Cell Death," The Journal of Biological Chemistry vol. 270, No. 29, Jul. 21, 1995, pp. 17482-17487.
Adema et al., "Migration of dendritic cell based cancer vaccines: in vivo veritas?" Curr Opin Immunol. Apr. 2005;17(2):170-174.

(56) References Cited

OTHER PUBLICATIONS

Albert et al., "Dendritic cell maturation is required for the cross-tolerization of CD8+ T cells." Nat Immunol. Nov. 2001;2(11):1010-1017.
Aliprantis et al., "The apoptotic signaling pathway activated by Toll-like receptor-2," EMBO J. 19(13):3325-3336, (2000).
Amara et al, "A versatile synthetic dimerizer for the regulation of protein-protein interactions." PNAS 1997;94:10618-10623.
Amara et al., "Cell surface tagging and a suicide mechanism in a single chimeric human protein" Hum. Gene Ther. (1999) 10(16):2651-5.
Banchereau et al., "Dendritic cells as therapeutic vaccines against cancer." Nat Rev Immunol. Apr. 2005;5(4):296-306.
Belshaw et al. (Sep. 1996). "Controlling programmed cell death with a cyclophilin-cyclosporin-based chemical inducer of dimerization." Chemistry & Biology. 3(9): pp. 731-738.
Bennett et al., "Apoptosis of rat vascular smooth muscle cells is regulated by p53-dependent and -independent pathways." Circ Res. Aug. 1995;77(2):266-273.
Beutler B., "Inferences, questions and possibilities in Toll-like receptor signalling." Nature. Jul. 8, 2004;430(6996):257-263.
Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.
Bloom, J.D. and F.H. Arnold, In the light of directed evolution: pathways of adaptive protein evolution. Proc Natl Acad Sci U S A, 2009. 106 Suppl 1: p. 9995-10000.
Boldin et al., "Involvement of MACH, a Novel MORT1/FADD-Interacting Protease, in Fas/APO-1- and TNF Receptor—Induced Cell Death," Cell vol. 85, 803-815, Jun. 14, 1996.
Boatright, K.M. and G.S. Salvesen, Mechanisms of Caspase activation. Curr Opin Cell Biol, 2003. 15(6): p. 725-31.
Boatright, K.M., et al., A unified model for apical Caspase activation. Mol Cell, 2003. 11(2): p. 529-41.
Bonnert et al., GeneBank: AAC50954.1; GI: 1814020; Feb. 2, 1997.
Bonnert et al., GenBank Accession No. U84408, 1997.
Bowie et al, "Deciphering the message in protein sequences: tolerance to amino acid substitutions." Science Mar. 1990; 247:1306-1310.
Boss, W.F., et al., Basal signaling regulates plant growth and development. Plant Physiol, 2010. 154(2): p. 439-43.
Brady, S.C., L.A. Allan, and P.R. Clarke, Regulation of Caspase-9 through phosphorylation by protein kinase C zeta in response to hyperosmotic stress. Mol Cell Biol, 2005. 25(23): p. 10543-55.
Burns et al., Inhibition of Interleukin 1 Receptor/Toll-like Receptor Signaling through the Alternatively Spliced, Short Form of MyD88 Is Due to Its Failure to Recruit IRAK-4, J. Exp. Med 197(2):263-268, Jan. 20, 2003.
Cardone, M.H., et al., Regulation of cell death protease Caspase-9 by phosphorylation. Science, 1998. 282(5392): p. 1318-21.
Caux et al., "Activation of human dendritic cells through CD40 cross-linking" J. Exp. Med. (1994) 180:1263-72.
Caux et al., "In vitro regulation of development and function of dendritic cells." Hematol Cell Ther. Oct. 1996;38(5):463.
Chan et al., "A Domain in TNF Receptors that mediates ligand-independent receptor assembly and signaling," Science 288, 2351-2354, (2001).
Chan, Francis Ka-Ming, "Three is Better Than One: Pre-Ligand Receptor Assembly in the Regulation of TNF Receptor Signaling," Cytokine, Feb. 2007; 37(2) 101-107.
Chang, W.C., et al., Modifying ligand-induced and constitutive signaling of the human 5-HT4 receptor. PLoS One, 2007. 2(12): p. e1317.
Chao, Y., et al., Engineering a dimeric Caspase-9: a re-evaluation of the induced proximity model for Caspase activation. PLoS Biol, 2005. 3(6): p. e183.
Chiodoni et ai, "Dendritic Cells Infiltrating Tumors Cotransduced with Granulocyte/Macrophage Colony-Stimulating factor (GM-CSF) and CD40 Ligand Genes Take Up and Present Endo-genous Tumor-Associated Antigens, and Prime Naive Mice for a Cytotoxic T Lymphocyte Response," J. Exp. Med. vol. 190, No. 1, Jul. 5, 1999. pp. 125-133.
Choe et al., "Crystal structure of human toll-like receptor 3 (TLR3) ectodomain." Science. Jul. 22, 2005;309(5734):581-585.
Cisco et al., "Induction of human dendritic cell maturation using transfection with RNA encoding a dominant positive toll-like receptor 4." J Immunol. Jun. 1, 2004;172(11):7162-7168.
Clackson et al., "Redesigning an FKBP-ligand interface to generate chemical dimerizers with novel specificity." Proc Natl Acad Sci USA. Sep. 1, 1998;95(18):10437-10442.
Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.
Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).
Coffin "Molecular Mechanisms of Nucleic Acid Integration," Journal of Mecical Virology, 31:43-19 (1990).
Contin et al., "Membrane-anchored CD40 is processed by the tumor necrosis factor-alpha-converting enzyme. Implications for CD40 signaling." J Biol Chem. Aug. 29, 2003;278(35):32801-32809.
Cranmer et al., "Clinical applications of dendritic cell vaccination in the treatment of cancer." Cancer Immunol Immunother. Apr. 2004;54(4):275-306.
Cremer et al., "Long-lived immature dendritic cells mediated by TRANCE-RANK interaction." Blood. Nov. 15, 2002;100(10):3646-3655.
Cristofanilli et al., "Circulating tumor cells, disease progression, and survival in metastatic breast cancer." N Engl J Med. Aug. 19, 2004;351(8):781-91.
Cyster JG., "Chemokines and cell migration in secondary lymphoid organs." Science. Dec. 10, 1999;286(5447):2098-2102.
Dallal RM, Lotze MT., "The dendritic cell and human cancer vaccines." Curr Opin Immunol. Oct. 2000;12(5):583-588.
Davis et al., "Crystal structure of prostate-specific membrane antigen, a tumor marker and peptidase." Proc Natl Acad Sci USA. Apr. 26, 2005;102(17):5981-5986.
De Becker et al., "The adjuvant monophosphoryl lipid A increases the function of antigen-presenting cells." Int Immunol. Jun. 2000;12(6):807-815.
De Gruijl et al, "Prolonged Maturation and Enhanced Transduction of Dendritic Cells Migrated from Human Skin Explants After In Situ Delivery of CD40-Targeted Adenoviral Vectors," The Journal of Immunology vol. 169,2002 PQS 5322-5331.
De Vries et al., "Effective migration of antigen-pulsed dendritic cells to lymph nodes in melanoma patients is determined by their maturation state." Cancer Res. Jan. 1, 2003;63(1):12-17.
Deonarain, "Ligand-targeted receptor-mediated vectors for gene delivery," 1998, Expert Opin. Ther. Pat., vol. 8, pp. 53-69.
Diehl et al., "CD40 activation in vivo overcomes peptide-induced peripheral cytotoxic T-lymphocyte tolerance and augments anti-tumor vaccine efficacy." Nat Med. Jul. 1999;5(7):774-779.
Donnelly et al., "DNA vaccines." Annu Rev Immunol. 1997;15:617-48.
Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.
Elgueta et al., "Molecular mechanism and function of CD40/CD40L engagement in the immune system," Immunological Reviews, 229, (2009) 152-172.
Evel-Kabler et al., "SOCS1 restricts dendritic cells' ability to break self tolerance and induce antitumor immunity by regulating IL-12 production and signaling." J Clin Invest. Jan. 2006;116(1):90-100.
Fan et al., "Improved artificial death switches based on caspases and FADD." Hum Gene Ther. Sep. 20, 1999;10(14):2273-2285.
Flotte TR, Carter BJ. "Adeno-associated virus vectors for gene therapy." Gene Ther. Aug. 1995;2(6):357-362.

(56) References Cited

OTHER PUBLICATIONS

Flotte, "Prospects for Virus-Based Gene Therapy for Cystic Fibrosis," Journal of Bioenergetics and Bioinformatics, vol. 25, No. 1, 1993.
Fujio Y, Walsh K., "Akt mediates cytoprotection of endothelial cells by vascular endothelial growth factor in an anchorage-dependent manner." J Biol Chem. Jun. 4, 1999;274(23):16349-16354.
GenBank Accession No. M29540, Human carcinoembryonic antigen mRNA (CEA), complete cds, Nov. 1, 1994.
Glode, "The case for adjuvant therapy for prostate cancer" Journal of Urology (2006) 176:S30-S33.
Granucci et al., "Eerly events in dendritic cell maturation induced by LPS." Microbes Infect. Nov. 1999;1(13):1079-1084.
Granucci et al., "Inducible IL-2 production by dendritic cells revealed by global gene expression analysis." Nat Immunol. Sep. 2001;2(9):882-888.
Granucci et al., "Modulation of cytokine expression in mouse dendritic cell clones." Eur J Immunol. Oct. 1994;24(10):2522-2526.
Grewal IS, Flavell RA., "CD40 and CD154 in cell-mediated immunity." Annu Rev Immunol. 1998;16:111-135.
Giudicelli et al., "IMGT/LIGM-DB, the IMGT comprehensive database of immunoglobulin and T cell receptor nucleotide sequences" Nucleic Acids Research (2006) 34:D781-4.
Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.
Harbury et al., "Crystal structure of an isoleucine-zipper trimer," Nature, vol. 371, Sep. 1, 1994, 80-83.
He et al., "A simplified system for generating recombinant adenoviruses." Proc Natl Acad Sci USA. Mar. 3, 1998;95(5):2509-2514.
Hermans et al., "CD8+ T cell-dependent elimination of dendritic cells in vivo limits the induction of antitumor immunity." J Immunol. Mar. 15, 2000;164(6):3095-3101.
Hodge et al., "Vector-based delivery of tumor-associated antigens and T-cell co-stimulatory molecules in the induction of immune responses and anti-tumor immunity," Cancer Detect Prevent 2002; 26;275-291.
Holler et al., "Development of improved soluble inhibitors of FasL and CD40L based on oligomerized receptors," Journal of Immunologial Methods 237(2000) 159-173.
Hong, T., et al., A simple theoretical framework for understanding heterogeneous differentiation of CD4+ T cells. BMC Syst Biol, 2012. 6: p. 66.
Horng et al., "*Drosophila* MyD88 is an adapter in the Toll signaling pathway," PNAS 98(22):12654-12658, Oct. 23, 2001.
Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.
Hostager et al., "Different: CD40-mediated Signaling Events Require Distinct CD40 Structural features," J. Immunol. 157:1047-1053, Aug. 1, 1996.
Hou WS, Van Parijs L., "A Bcl-2-dependent molecular timer regulates the lifespan and immunogenicity of dendritic cells." Nat Immunol. Jun. 2004;5(6):583-589.
Hsiao, E.C., et al., Constitutive Gs activation using a single-construct tetracycline-inducible expression system in embryonic stem cells and mice. Stem Cell Res Ther, 2011. 2(2): p. 11.
Inaba et al., "Generation of large numbers of dendritic cells from mouse bone marrow cultures supplemented with granulocyte/macrophage colony-stimulating factor" J. Exp. Med. (1992) 176:1693-702.
Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.
Jonuleit et al., "Pro-inflammatory cytokines and prostaglandins induce maturation of potent immunostimulatory dendritic cells under fetal calf serum-free conditions," Eur. J. Immunol 27:3135-3142, Dec. 1997.
Josien et al., "TRANCE, a tumor necrosis factor family member, enhances the longevity and adjuvant properties of dendritic cells in vivo." J Exp Med Feb. 7, 2000;191(3):495-502.
Kagan JC, Medzhitov R., "Phosphoinositide-mediated adaptor recruitment controls Toll-like receptor signaling." Cell. Jun. 2, 2006;125(5):943-955.
Kalams et al., "The critical need for CD4 help in maintaining effective cytotoxic T lymphocyte responses." J Exp Med. Dec. 21, 1998;188(12):2199-2204.
Kalinski et al., "Dendritic cells, obtained from peripheral blood precursors in the presence of PGE2, promote Th2 responses." Adv Exp Med Biol. 1997;417:363-367.
Kandel ES, Hay N., "The regulation and activities of the multifunctional serine/threonine kinase Akt/PKB." Exp Cell Res. Nov. 25, 1999;253(1):210-229.
Kanto et al., "Ceramide mediates tumor-induced dendritic cell apoptosis." J Immunol. Oct. 1, 2001;167(7):3773-3784.
Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7)1099-105.
Kantoff et al., "Sipuleucel-T immunotherapy for castration-resistant prostate cancer." N Engl J Med. Jul. 29, 2010;363(5):411-22.
Kehry, Marilyn R., "CD40-Mediated Signaling in B Cells, Balancing Cell Survival, Growth and Death," The American Association of Immunologists, 1996, 2345-2348.
Kelleher et al., "Lipopolysaccharide Modulation of Dendritic Cells is Insufficient to Mature Dendritic Cells to Generate CTLs from Native Polyclonal CD8+ T Cells In Vitro, Whereas CD40 Ligation is Essential," The Journal of Immunology, The American Society of Immunologists, vol. 167, No. 11, Jan. 1, 2001, pp. 6247-6255.
Kempf et al, "Improved stimulation of human dendritic cells by receptor engagement with surface-modified microparticles," J Drug Target vol. 11 No. 1, Jan. 2003 pp. 11-18.
Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.
Kim et al., "High cleavage efficiency of a 2A peptide derived from porcine teschovirus-1 in human cell lines, zebrafish and mice" PLoS One (2011) 6(4):e18556.
Kobayashi et al., "IRAK-M is a negative regulator of Toll-like receptor signaling." Cell. Jul. 26, 2002;110(2):191-202.
Korst et al., "Effect of adenovirus gene transfer vectors on the immunologic functions of mouse dendritic cells." Mol Ther. Mar. 2002;5(3):307-315.
Kouskoff, V., et al., B cell receptor expression level determines the fate of developing B lymphocytes: receptor editing versus selection. Proc Natl Acad Sci U S A, 2000. 97(13): p. 7435-9.
Krug et al., "Toll-like receptor expression reveals CpG DNA as a unique microbial stimulus for plasmacytoid dendritic cells which synergizes with CD40 ligand to induce high amounts of IL-12." Eur J. Immunol. 31:3026-3037.
Kudo et al., "T lymphocytes expressing a CD16 signaling receptor exert antibody-dependent cancer cell killing" Cancer Research (2014) 74:93-103.
Labeur et al., "Generation of tumor immunity by bone marrow-derived dendritic cells correlates with dendritic cell maturation stage." J Immunol. Jan. 1, 1999;162(1):168-175.
Langenkamp et al., "Kinetics of dendritic cell activation: impact on priming of TH1, TH1 and nonpolarized T cells." Nat Immunol. Oct. 2000;1(4):311-316.
Lanzavecchia A, Sallusto F., "Regulation of T cell immunity by dendritic cells." Cell. Aug. 10, 2001;106(3):263-266.
Lapteva et al., "Development of Novel CD4-Independent iCD40-Dendritic Cell Vaccine for HIV-1 Immunotherapy," vol. 17, No. Suppl 1, May 2009, 12th Annual Meeting of the American Society of Gene Therapy: San Diego, CA, May 27-30, 2009.

(56) References Cited

OTHER PUBLICATIONS

Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.

Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.

Lee et al., "Cytoplasmic domain-mediated dimerizations of toll-like receptor 4 observed by beta-lactamase enzyme fragment complementation." J Biol Chem. Mar. 12, 2004;279(11)10564-10574.

Leo et al., "Partition coefficients and their uses." Chem Rev. Dec. 1971;71(6):525-616.

Li et al., "A novel conditional Akt 'survival+A185 switch' reversibly protects cells from apoptosis." Gene Ther. Feb. 2002;9(4):233-244.

Liu et al., "Differential regulation of interleukin (IL)-12 p35 and p40 gene expression and interferon (IFN)-gamma-primed IL-12 production by IFN regulatory factor 1." J Exp Med. Oct. 2003;198(8):1265-1276.

Livak et al., "Analysis of relative gene expression data using real-time quantitative PCR and the 2(-Delta Delta C(T)) Method." Methods. Dec. 2001;25(4):402-408.

Lodge et al., Dendridic Cell-based Immunotherapy of Prostate Cancer: Immune Monitoring of a Phase II Clincal Trial, Cancer Res. 60:829-833, 2000.

Loiarro et al., "Peptide-mediated interference of TIR domain dimerization in MyD88 inhibits interleukin-1-dependent activation of NF-{kappa}B." J Biol. Chem. Apr. 22, 2005;280(16)1 5809-15814.

Luke et al., "The family of five: TIR-domain-containing adaptors in Toll-like receptors signaling" Nature Reviews Immunology (2007) 7:353-364.

Luliucci et al., "Intravenous safety and pharmacokinetics of a novel dimerizer drug, AP1903, in healthy volunteers" J. Clin. Pharmacol. (2001) 41:870-879.

Luning Prak, E.T., M. Monestier, and R.A. Eisenberg, B cell receptor editing in tolerance and autoimmunity. Ann N Y Acad Sci, 2011. 1217: p. 96-121.

Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.

Malissen B, Ewbank JJ., "'TaiLoRing' the response of dendritic cells to pathogens." Nat Immunol. Aug. 2005;6(8):750-769.

Marsland et al., "CCL19 and CCL21 induce a potent proinflammatory differentiation program in licensed dendritic cells." Immunity. Apr. 2005;22(4):493-505.

Martin, M.C., et al., Protein kinase A regulates Caspase-9 activation by Apaf-1 downstream of cytochrome c. J Biol Chem, 2005. 280(15): p. 15449-55.

Martln-Fontecha et al., "Regulation of dendritic cell migration to the draining lymph node: impact on T lymphocyte traffic and priming." J Exp Med. Aug. 18, 2003;198(4):615-621.

Mazouz et al., "CD40 triggering increases the efficiency of dendritic cells for antitumoral immunization." Cancer Immun. Mar. 27, 2002;2:2.

McIlroy et al., "Histamine and prostaglandin E up-regulate the production of Th2-attracting chemokines (CCL17 and CCL22) and down-regulate IFN-gamma-induced CXCL10 production by immature human dendritic cells." Immunology. Apr. 2006;117(4):507-516.

Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.

Medzhitov et al., Molecular Cell, 2:253-258, 1998.

Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.

Melief et al., "Effective therapeutic anticancer vaccines based on preCision guiding of cytolytic T lymphocytes" Immunol Rev. vol. 188, Oct. 2002, pp. 177-182.

Meyer et al., "Cutting edge: cyclooxygenase-2 activation suppresses Th1 polarization in response to helicobacter pylori." J Immunol. Oct. 15, 2003;171(8):3913-3917.

Miga et al., "Dendritic cell longevity and T cell persistence is controlled by CD154-CD40 interactions." Eur J Immunol. Mar. 2001;31(3):959-965.

Mochizuki et al., "Akt protein kinase inhibits non-apoptotic programmed cell death induced by ceramide." J Biol Chem. Jan. 25, 2002;277(4):2790-2797.

Morgan et al., "Cancer regression in patients after transfer of genetically engineered lymphocytes." Science. Oct. 6, 2006;314(5796):126-129.

Morse et al., "Migration of human dendritic cells after injection in patients with metastic malignancies." Cancer Res. Jan. 1, 1999;5((1):56-58.

Mukherjee et al., "Lipid-dependent recruitment of neuronal Src to lipid rafts in the brain." J Biol Chem. Oct. 17, 2003;278(42):40806-40814.

Nakagami et al., "Safety and efficacy of docetaxel, estramustine phosphate and hydrocortisone in hormone-refractory prostate cancer patients." Int J Urol. Jul. 2010;17(7):629-34.

Napolitani et al., "Selected Toll-like receptor agonist combinations synergistically trigger a T helper type 1-polarizing program in dendrinic cells," Nat Immunol. Aug. 2005; vol. 6. No. 8, pp. 769-776.

Narayanan et al. A composite MyD88/CD40 switch synergistically activates mouse and human dendritic cells for enhanced antitumor efficacy. J Clin Invest. 2011, vol. 121(4), p. 1524-1534, and Supplementary Materials pp. 1-16.

Narayanan et al., Abstract: 4761 "The iCD40.MyD88 combovector: A new platform for enhanced DC tumor immunotherapy", Proceedings of the American Association for Cancer Research Annual Meeting, vol. 51, Apr. 15, 2010.

Nestle et al., "Dendritic cells: On the move from bench to bedside." Nat Med. Jul. 2001;7(7):761-765.

Nishiya et al., "Ligand-regulated chimeric receptor approach reveals distinctive subcellular localization and signaling properties of the Toll-like receptors," J. Biol, Chem. 279(18):19008-19017, 2004.

Nopora A, Brocker T., "Bcl-2 controls dendritic cell longevity in vivo." J Immunol. Sep. 15, 2002;169(6):3006-3014.

Oehm et al., "Purification and Molecular Cloning of the APO-1 Cell Surface Antigen, a Member of the Tumor Necrosis Factorperve Growth Factor Receptor Superfamily, Sequence Identity With the Fas Antigen," The Journal of Biological Chemistry, vol. 267, No. 15, May 25, 1992 10709-10715.

O'Sullivan B, Thomas R., "CD40 and dendritic cell function." Crit Rev Immunol. 2003 ;23(1-2):83-107.

Ozinsky et al., "The repertoire for pattern recognition of pathogens by the innate immune system is defined by cooperation between toll-like receptors." Proc Natl Acad Sci USA. Dec. 5, 2000;97(25):13766-13771.

Palecek et al., "Integrin-ligand binding properties govern cell migration speed through cell-substratum adhesiveness." Nature. Feb. 6, 1997;385(6616):537-540.

Papworth, C., Bauer, J. C., Braman, J. and Wright, D. A. , Site-directed mutagenesis in one day with >80% efficiency. Strategies, 1996. 9(3): p. 3-4.

Park et al, "An essential role for Akt1 in dendritic cell function and tumor immunotherapy," Nature Biology, vol. 24, No. 12, Dec. 2006, pp. 1581-1590.

Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.

Pasare C, Medzhitov R., "Toll pathway-dependent blockade of CD4+CD25+ T cell-mediated suppression by dendritic cells." Science. Feb. 14, 2003;299(5609)1033-1036.

(56) References Cited

OTHER PUBLICATIONS

Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.

Pruschy et al., "Mechanistic Sutdies of a Signaling Pathway Activated by the Organic Dimerizer FK1012," Chemistry and Biology 1994 vol. 1, No. 3, 163-172.

Puccetti et al., "Effects of IL-12 and IL-23 on antigen-presenting cells at the interface between innate and adaptive immunity." Crit Rev Immunol. 2002;22(5-6):373-390.

Raina, D., et al., c-Abl tyrosine kinase regulates Caspase-9 autocleavage in the apoptotic response to DNA damage. J Biol Chem, 2005. 280(12): p. 11147-51.

Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.

Randall, K.L., et al., Dock8 mutations cripple B cell immunological synapses, germinal centers and long-lived antibody production. Nat Immunol, 2009. 10(12): p. 1283-91.

Re F, Strominger JL., "Toll-Ike receptor 2(TLR2) and TLR4 differentially activate human dendritic cells." J Biol Chem. Oct. 5, 2001;276(40):37692-37699.

Reis e Sousa C., "Dendritic cells as sensors of infection." Immunity. May 2001;14(5):495-498.

Renatus, M., et al., Dimer formation drives the activation of the cell death protease Caspase-9. Proc Natl Acad Sci U S A, 2001. 98(25): p. 14250-5.

Resh et al., "Fatty acylation of proteins: new insights into membrane targeting of myristoylated and palmitoylated proteins" Biochim. Biophys. Acta. (1999) 1451:1-16.

Richard et al, "Expansion of Genetically modified Primary Human HemopOietic cells Using Chemical Inducers of Dimerization," Blood vol. 95, 2000 pp. 430-436.

Ridgway D., "The first 1000 dendritic cell vaccinees." Cancer Invest. 2003;21(6):873-886.

Riol-Blanco et al., "The chemokine receptor CCR7 activates in dendritic cells two signaling modules that independently regulate chemotaxis and migratory speed." J Immunol. Apr. 1, 2005;174(7):4070-4080.

Rivera, V.M., "Controlling Gene Expression USing SynthetiC Ligands," Methods: A companion to Methods in Enzymology vol. 14,1998 pp. 421-429.

Roose, J.P., et al., T cell receptor-independent basal signaling via Erk and Abl kinases suppresses RAG gene expression. PLoS Biol, 2003. 1(2): p. E53.

Ronni et al., "Common interaction surfaces of the toll-like receptor 4 cytoplasmic domain stimulate multiple nuclear targets," Molecular and Cellular Biology, Apr. 2003, vol. 23, No. 7, pp. 2543-2555.

Rudd, M.L., A. Tua-Smith, and D.B. Straus, Lck SH3 domain function is required for T-cell receptor signals regulating thymocyte development. Mol Cell Biol, 2006. 26(21): p. 7892-900.

Rudinger, "Characteristics in the amino acids as components of a peptide hormone sequence" Chapter 1 in Peptide Hormones, Biological Council, The Co-ordinating Committee for Symposia on Drug Action, Edited by J.A. Parsons, University Park Press, Baltimore, London, Tokyo, Jun. 1976; pp. 1-7.

Salkowski et al., "Lipopolysaccharide and monophosphoryl lipid A differentially regulate interleukin-12, gamma interferon, and interleukin-10 mRNA production in murine macrophages." Infect Immun. Aug. 1997;65(8):3239-3247.

Sanchez-Sanchez et al., "The multiple personalities of the chemokine receptor CCR7 in dendritic cells." J Immunol. May 1, 2006;176(9):5153-5159.

Sato et al., "Combination of monocyte-derived dendrinic cells and activated T cells which express CD40 ligand an new approach to cancer Imminotherapy," Cancer Imminol Immunther, vol. 53, No. 1, Jan. 2004, pp. 53-61.

Scandella et al., "CCL19/CCL21-triggered signal transduction and migration of dendritic cells requires prostaglandin E2." Blood. Mar. 1, 2004;103(5)1595-1601.

Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7)1148-59.

Schram, B.R., et al., B cell receptor basal signaling regulates antigen-induced Ig light chain rearrangements. J Immunol, 2008. 180(7): p. 4728-41.

Schuler et al., "The use of dendritic cells in cancer immunotherapy." Curr Opin Immunol. Apr. 2003; 15(2):138-147.

Schuler et al., "Dendritic cells as adjuvants for immune-mediated resistance to tumors" J. Exp. Med. (1997) 186:1183-7.

Schultz et al., "CD40 triggering of heterodimeric IL-12 p70 production by dendritic cells in vivo requires a microbial priming signal," Immunity, vol. 13, No. 4, Oct. 2000. pp. 453-462.

Schuster, et al., "ALD518, a humanized anti-IL-6 antibody, treats anemia in patients with advanced non-small cell lung cancer (NSCLC): Results of a phase II, randomized, double-blind, placebo-controlled trial," 2010, J. Clin. Oncol. 28-7s (suppl.; abstr. 7631).

Shaffer et al., "Circulating tumor cell analysis in patients with progressive castration-resistant prostate cancer." Clin Cancer Res. Apr. 1, 2007;13(7):2023-9.

Seifert, R. and K. Wenzel-Seifert, Constitutive activity of G-protein-coupled receptors: cause of disease and common property of wild-type receptors. Naunyn Schmiedebergs Arch Pharmacol, 2002. 366(5): p. 381-416.

Shen et al., "Silencing of SOCS1 enhances antigen presentation by dendritic cells and antigen-specific anti-tumor immunity." Nat Biotechnol. Dec. 2004;22(12):1546-1553.

Shiozaki, E.N., J. Chai, and Y. Shi, Oligomerization and activation of Caspase-9, induced by Apaf-1 Card. Proc Natl Acad Sci U S A, 2002. 99(7): p. 4197-202.

Shiozaki, E.N., et al., Mechanism of XIAP-mediated inhibition of Caspase-9. Mol Cell, 2003. 11(2): p. 519-27.

Shi, Y., Mechanisms of Caspase activation and inhibition during apoptosis. Mol Cell, 2002. 9(3): p. 459-70.

Smith et al., "Cognate CD4(+) T cell licensing of dendritic cells in CD8(+) T cell immunity." Nat Immunol. Nov. 2004;5(11):1142-1148.

Sonpavde, et al., "Vaccine therapy for prostate cancer", Urologic Oncology, Elsevier, NY, vol. 25, No. 6, Nov. 1, 2007, 451-459.

Sorensen et al., "Endostatin reduces cascularization, blood flow, and growth in a rat gliosarcoma." Neuro Oncol. Jan. 2002;4(1):1-8.

Sorkin, A. and M. von Zastrow, Endocytosis and signaling: intertwining molecular networks. Nat Rev Mol Cell Biol, 2009. 10(9): p. 609-22.

Spiegel, A.M., Defects in G protein-coupled signal transduction in human disease. Annu Rev Physiol, 1996. 58: p. 143-70.

Sporri R, Reis e Sousa C., "Inflammatory mediators are insufficient for full dendritic cell activation and promote expansion of CD4+ T cell populations lacking helper function." Nat Immunol. Feb. 2005;6(2):163-170.

Steinman RM, Pope M., "Exploiting dendritic cells to improve vaccine efficacy." J Clin Invest. Jun. 2002;109(12):1519-1526.

Strasser et al., "Integrin Activation by Regulated Dimerization and Oligomerization of Platelet Endothelial Cell Adhesion Molecule (PECAM)-1 from Within the Cell," Immunity Review 30, Feb. 20, 2009, 180-192.

Stennicke, H.R., et al., Caspase-9 can be activated without proteolytic processing. J Biol Chem, 1999. 274(13): p. 8359-62.

Straathof, K.C., et al., An inducible Caspase-9 safety switch for T-cell therapy. Blood, 2005. 105(11): p. 4247-54.

Su et al., "Telomerase mRNA-transfected dendritic cells stimulate antigen-specific CD8+ and CD4+ T cell responses in patients with metastatic prostate cancer." J Immunol. Mar. 15, 2005;174(6):3798-3807.

Suarez-Alvarez et al, Epigenetic Mechanisms Regulate MHC and Antigen Processing Molecules in Human Embryonic and Induced Pluripotent Stem Cells. PLoS One (Apr.) 5(4):e10192, 2010, pp. 1-12.

(56) References Cited

OTHER PUBLICATIONS

Suda et al., "Molecular Cloning and Expression of the Fas Ligand, a Novel Member of the Tumor Necrosis Factor Family," Cell vol. 75, 1169-1176 Dec. 17, 1993.
Szymczak et al., "Correction of multi-gene deficiency in vivo using a single 'self-cleaving' 2A peptide-based retroviral vector" Nature Biotechnology (2004) 22:589-94.
Tao, Y.X., Constitutive activation of G protein-coupled receptors and diseases: insights into mechanisms of activation and therapeutics. Pharmacol Ther, 2008. 120(2): p. 129-48.
Temin et al., (1986) In: Gene Transfer, Kucherlapati (ed.), New York: Plenum Press, pp. 149-188.
Thompson et al., "The low-toxicity versions of LPS, MPL adjuvant and RC529, are efficient adjuvants for CD4+ T Cells." J Leukoc Biol. Dec. 2005;78(6):1273-1280.
Timmerman et al., "Dendritic cell vaccines for cancer immunotherapy", Annu. Rev. Med. (1999) 50:507-29.
Tong et al, "Prospects for CD40-directed Experimental Therapy of Human Cancer," Cancer Gene Therapy vol. 10, 2003, pp. 1-13.
Tze, L.E., et al., Basal immunoglobulin signaling actively maintains developmental stage in immature B cells. PLoS Biol, 2005. 3(3): p. e82.
Vassiliou et al., "Prostaglandin E2 promotes the survival of bone marrow-derived dendritic cells." J Immunol. Dec. 1, 2004;173(11):6955-6964.
Vidalain et al., "CD40 signaling in human dendritic cells is initiated within membrane rafts." EMBO J. 2000; 19:3304-3313.
Vieweg, "Immunotherapy for Advanced Prostate Cancer," vol. 9 Suppl. 1 (2007) Reviews in Urology S29-S38.
Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.
Wagner et al., "IL-12p70-Dependent Th1 Induction by Human B Cells Requires Combined Activation with CD40 Ligand and CpG DNA", Journal of Immunology, vol. 172, 2004, 954-963.
Waldner, C., et al., Double conditional human embryonic kidney cell line based on FLP and PhiC31 mediated transgene integration. BMC Res Notes, 2011. 4: p. 420.
Werneburg et al., "Molecular Characterization of CD40 Signaling Intermediates," The Journal of Biological Chemistry, vol. 276, Nov. 16, 2001, 43334-43342.
Wesemann et al., "Suppressor of cytokine signaling 1 inhibits cytokine induction of CD40 expression in macrophages." J Immunol. Sep. 1, 2002;169(5):2354-2360.
Wolchok et al., "Guidelines for the Evaluation of Immune Therapy Activity in Solid Tumors: Immune-Related Response Criteria," Clin Cancer Res 2009;15(23) Dec. 1, 2009, pp. 7412-7420.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fas Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xie et al., "Adenovirus-mediated tissue-targeted expression of a caspase-9-based artificial death switch for the treatment of prostate cancer." Cancer Res. Sep. 15, 2001;61(18):6795-6804.
Yanagawa Y, Onoe K., "CCL19 induces rapid dendritic extension of murine dendritic cells." Blood. Sep. 15, 2002;100(6):1948-1956.
Zhang et al., "Anti-melanoma activity of T cells redirected with a TCR-like chimeric antigen receptor" Scientific Reports (2014) 4:3571.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2):171-176.
Zhang et al., "Retargeting NK-92 for anti-melanoma activity by a TCR-like single-domain antibody" Immunol. Cell. Biol. (2013) 91(10):615-24.
Zhao et al., "Integrin Activation by Regulated Dimerization and Oligomerization of Platelet Endothelial Cell Adhesion Molecule (PECAM)-1 from Within the Cell," Jan. 8, 2001, The Journal of Cell Biology, vol. 152, 65-73.
Zur Medege et al., "Expression and immunogenicity of sequence-modified human immunodeficiency virus type 1 subtype B pol and gagpol DNA vaccines." J Virol. Jun. 2003;77(11):6197-6207.
International Search Report and Written Opinion dated Jun. 29, 2015 in International Application No. PCT/US2015/015829, filed on Feb. 13, 2015 and published as WO 2015/123527 on Aug. 20, 2015.
International Preliminary Report on Patentability dated Sep. 24, 2015 in International Application No. PCT/US2014/026734, filed on Mar. 13, 2014 and published as WO 2014/151960 on Sep. 25, 2014.
International Search Report and Written Opinion dated Dec. 28, 2015 in International Application No. PCT/US2015/047957, filed on Sep. 1, 2015 and published as WO 2016/036749 on Mar. 10, 2016.
Office Action dated Feb. 8, 2016 in U.S. Appl. No. 14/210,034, filed Mar. 13, 2014 and published as US 2014-0286987 on Sep. 25, 2014.
Geng et al., "Amplifying TLR-MyD88 signals within tumor-specific T cells enhances antitumor activity to suboptimal levels of weakly immunogenic tumor antigens" Cancer Research (2010) 70(19):7442-7454.
Ladanyi, "Prognostic and predictive significance of immune cells infiltrating cutaneous melanoma" Pigment Cell Melanoma Res. (2015) 28:490-500.
Office Action dated Jul. 7, 2016 in U.S. Appl. No. 14/210,034, filed Mar. 13, 2014 and published as US 2014-0286987 on Sep. 25, 2014.
Extended European Search Report dated Jul. 4, 2017 in European Patent Application No. 15748478.3, filed on Feb. 13, 2015 and published as EP 3 104 866 on Dec. 21, 2016.
Collinson-Pautz et al., "MyD88/CD40 Genetic Adjuvant Function in Cutaneous Atypical Antigen-Presenting Cells Contributes to DNA Vaccine Immunogenicity" PLOS One (2016) 11(10):e0164547.
Foster et al., "Regulated Expansion and Survival of Chimeric Antigen Receptor-Modified T Cells Using Small Molecule-Dependent Inducible MyD88/CD40" Molecular Therapy (2017) 25(9):1-13.
Office Action dated May 8, 2017 in U.S. Appl. No. 14/191,167, filed Feb. 26, 2014 and Published as 2014-0287490 on Sep. 25, 2014.
Hacker et al., "Specificity in Toll-like receptor signalling through distinct effector functions of TRAF3 and TRAF6" Nature (2006) 439:204-207.
Office Action dated Dec. 5, 2017 in U.S. Appl. No. 14/210,034, filed Mar. 13, 2014 and published as US 2014-0286987 on Sep. 25, 2014.
Written Opinion dated Feb. 7, 2018 in Singapore Patent Application No. 11201506974X, filed on Mar. 13, 2014.
Extended European Search Report dated Apr. 5, 2018 in European Patent Application No. 15838927.0, filed on Sep. 1, 2015 and published as EP 3 189 148 on Jul. 12, 2017.
Office Action dated Aug. 11, 2017 in U.S. Appl. No. 14/210,034, filed Mar. 13, 2014 and published as US 2014-0286987 on Sep. 25, 2014.
Chicaybam et al., "Chimeric Antigen Receptors in Cancer Immuno-Gene Therapy: Current Status and Future Directions" International Reviews of Immunology (2011) 30(5-6):294-311.
Koehler et al., "Engineered T Cells for the Adoptive Therapy of B-Cell Chronic Lymphocytic Leukaemia" Advances in Hematology (2012) 2012:595060. doi: 10.1155/2012/595060 1-13.
Abraham and Weiss, "Jurkat T cells and development of the T-cell receptor signalling paradigm," *Nat. Rev. Immunol.*, 4(4):301-308 (2004).

(56) References Cited

OTHER PUBLICATIONS

Foster et al., "MyD88/CD40 enhanced CD19-specific CAR-T cells maintain therapeutic efficacy following resolution of cytokine-related toxicity using inducible caspase-9," *Blood*, 130(S1):4615 (2017).
GenBank Accession No. AAA58476.1, FK506-binding protein 12 [*Homo sapiens*], Feb. 12, 2001 [retrieved Mar. 12, 2019]. Retrieved from the internet <URL: https://www.ncbi.nlm.nih.gov/protein/182649?sat=4&satkey=34111166>.
Klooster and Kordijk, "Targeting and localized sigalling by small GTPases," *Biol. Cell*, 99:1-12 (2007).
Kuby, J., *Immunology*, New York, W. H. Freeman and Company, 1997, p. 47-83.
Leriche et al., "Cleavable linkers in chemical biology," *Bioorg. & Med. Chem.*, 20:571-582 (2012).
Nakagawa et al., "Development of next-generation adoptive immunotherapy using cytotoxic T-lymphocyte (CTL) expressing chimeric antigen-receptor (CAR)," *Drug Delivery System*, 28(1):35-44 (2013), in Japanese with an English abstract.
Vincent et al., "Targeting of proteins to membranes through hedgehog auto-processing," *Nat. Biotechnol.*, 21(8):936-940 (2003).
Office Action dated Dec. 17, 2018, in U.S. Appl. No. 15/399,512, filed Jan. 5, 2017.
Office Action dated Jan. 17, 2019, in U.S. Appl. No. 14/842,710, filed Sep. 1, 2015.
Office Action dated Jul. 10, 2018, in U.S. Appl. No. 14/842,710, filed Sep. 1, 2015.
Office Action dated May 25, 2018, in U.S. Appl. No. 15/399,512, filed Jan. 5, 2017.
Mackay et al., 2017, "Single-cell multiplex proteomics reveals synergistic impact of antigen and rimiducid-dependent stimulatory signals on promoting polyfunctional GoCAR-T cells targeting prostate stem cell antigen," Blood, 130, Supplement 1:2281.
Chen et al., "Molecular mechanisms of T cell co-stimulation and co-inhibition," Nat. Rev. Immunol. 2013, 13(4): 227-242.
Sharpe, "Mechanisms of Costimulation," Immunol. Rev. 2009, 229(1): 5-11.
Preliminary Amendment as filed on Apr. 12, 2018 in U.S. Appl. No. 15/857,265; 4 pages.
Barrett et al., "Chimeric Antigen Receptor Therapy for Cancer," *Annu. Rev. Med.*, 65:333-347 (2014).
Chen et al., "Erratum: Molecular mechanisms of T cell co-stimulation and co-inhibition," *Nat. Rev. Immunol.*, 13:542 (2013).
Foster et al., "Regulated Expansion and Survival of Chimeric Antigen Receptor-Modified T Cells Using Small Molecule-Dependent Inducible MyD88/CD40," *Mol Ther.* 25(9):2176-2188 (2017).
Munroe et al., "A Costimulatory Function for T Cell CD401," *J. Immunol.*, 178:671-682 (2007).
Pear et al., "Production of high-titer helper-free retroviruses by transient transfection," *Proc. Natl. Acad. Sci. USA*, 90:8392-8396 (1993).

\* cited by examiner

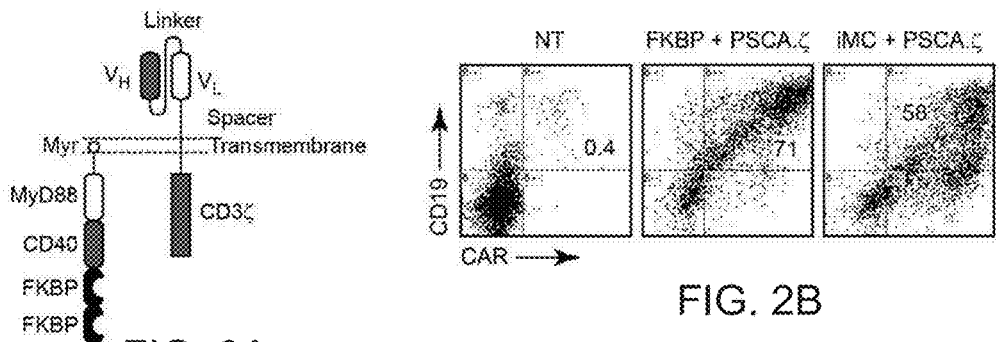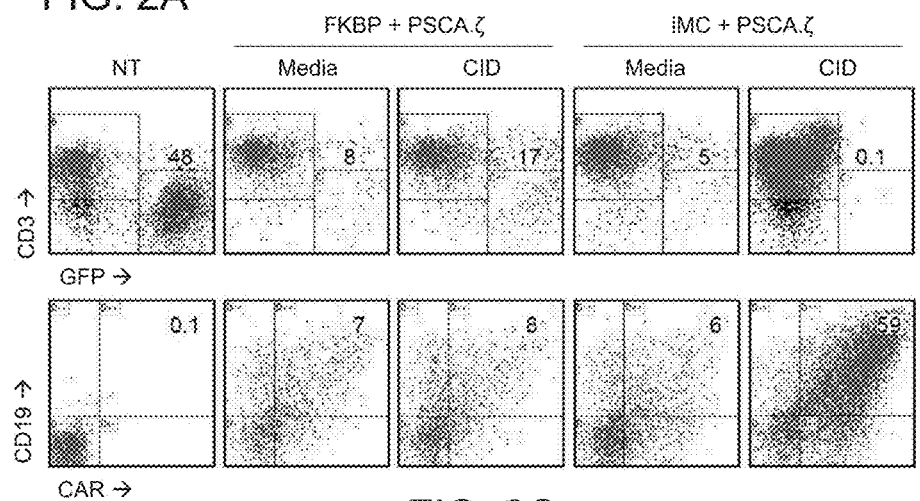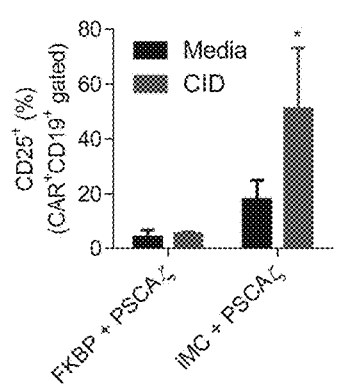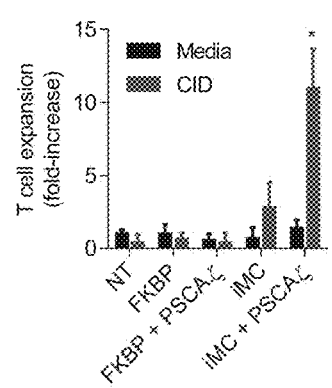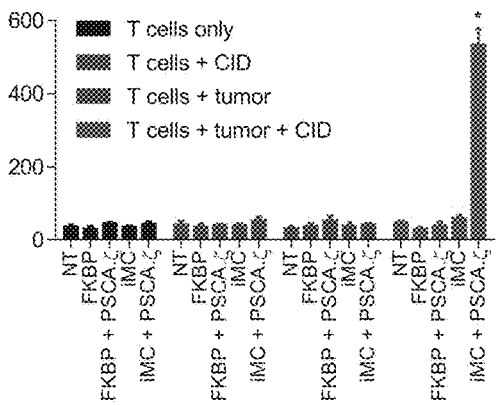
FIG. 2A, FIG. 2B, FIG. 2C, FIG. 2D, FIG. 2E, FIG. 2F SFG-iMCfl-2A-PSCA(A11)scFv-CD34e-CD8stm-zeta
9588 bp

| IC21 | B16-F10 |
|---|---|
| Non-Infected | Non-infected |
| Ad5-iMC-P2A-FL 18000 vp/cell | Ad5-iMC-P2A-FL 20000 vp/cell |
| Ad5f35-iMC-RP-FL 20000 vp/cell | |

MODIFIED T CELL COMPRISING A POLYNUCLEOTIDE ENCODING AN INDUCIBLE STIMULATING MOLECULE COMPRISING MYD88, CD40 AND FKBP12

FIELD

The technology relates generally to the field of immunology and relates in part to methods for activating cells, including for example, T cells and T cells that express chimeric antigen receptors, using an inducible chimeric polypeptide including CD40, MyD88, or CD40 and MyD88 polypeptides. The technology further relates in part to therapeutic methods for inducing an immune response and treating tumors in a patient.

RELATED APPLICATIONS

Priority is claimed to U.S. Provisional Patent Application Ser. No. 61/940,347, filed Feb. 14, 2014, entitled Methods for Activating T Cells Using an Inducible Chimeric Polypeptide; to U.S. Provisional Patent Application Ser. No. 61/952,839, filed Mar. 13, 2014, entitled Methods for Activating T Cells Using an Inducible Chimeric Polypeptide; and to U.S. Provisional Patent Application Ser. No. 62/047,875, filed Sep. 9, 2014, and entitled "Methods for Activating T Cells Using an Inducible Chimeric Polypeptide, which are all referred to and incorporated by reference herein in their entireties.

SEQUENCE LISTING

The instant application contains a Sequence Listing which has been submitted electronically in ASCII format and is hereby incorporated by reference in its entirety. Said ASCII copy, created on Mar. 31, 2015, is named BEL-2013-UT_SL.txt and is 149,742 bytes in size.

BACKGROUND

T cell activation is an important step in the protective immunity against pathogenic microorganisms (e.g., viruses, bacteria, and parasites), foreign proteins, and harmful chemicals in the environment, and also as immunity against cancer and other hyperproliferative diseases. T cells express receptors on their surfaces (i.e., T cell receptors) that recognize antigens presented on the surface of cells. During a normal immune response, binding of these antigens to the T cell receptor initiates intracellular changes leading to T cell activation.

SUMMARY

The antitumor efficacy of T cells engineered with chimeric antigen receptors (CARs) is dependent on their survival and in vivo expansion following adoptive transfer. While the inclusion of costimulatory domains, such as CD28 and 4-1BB, have enhanced T cell expansion of CD19-targeted CARs for the treatment of leukemia[1-4], inseparably linking these signaling domains to antigen recognition via the CAR has led to severe toxicities from unchecked T cell activations[5,6]. Provided herein is a method for controlling CAR T cell therapy that in one embodiment relies on a T cell costimulatory switch, the costimulatory molecule inducible MyD88/CD40 (iMC), activatable in vivo by the small molecule, chemical inducer of dimerization (CID), rimiducid (AP1903), to provide costimulation to CAR-modified T cells, inducing T cell proliferation, survival and antitumor efficacy. iMC-based, inducible costimulation may be used to regulate T cell expansion in vivo and serves as a new therapeutic option to control the safety and efficacy of CAR-T cell therapies.

Chimeric antigen receptors (CARs) are artificial receptors designed to convey antigen specificity to T cells. They generally include an antigen-specific component, a transmembrane component, and an intracellular component selected to activate the T cell and provide specific immunity. Chimeric antigen receptor-expressing T cells may be used in various therapies, including cancer therapies. While effective against tumors, in some cases these therapies have led to side effects due, in part to non-specific attacks on healthy tissue. A method for controllable T cell therapy is needed that provides a strong immunotherapeutic response and avoids toxic side effects.

Provided in part are inducible chimeric signaling molecules (CSMs), that may be used, for example, to induce or increase an immune response. The CSMs may be used alone, or in combination with chimeric antigen receptors (CARs), which allows the immune response to be specifically directed against particular tumor cells. The controlled T cell activation methods avoid many of the toxic side effects of earlier CAR-based treatments.

Also provided herein are activated T cells that express an inducible MyD88, inducible CD40, or inducible chimeric MyD88/CD40 polypeptide. The activated cells may be used to increase the immune response against a disease, or to treat cancer by, for example, reducing the size of a tumor. Therapeutic courses of treatment using the activated T cells and activated CAR T cells may be monitored by determining the size and vascularity of tumors by various imaging modalities (e.g. CT, bone scan MRI, PET scans, TROFEX scans), by various standard blood biomarkers (e.g. PSA, Circulating Tumor Cells), or by serum levels of various inflammatory, hypoxic cytokines, or other factors in the treated patient.

The inducible chimeric signaling molecules discussed herein allow for a sustained, modulated control of a chimeric antigen receptor (CAR) that is co-expressed in the cell. The inducible chimeric signaling molecules comprise the inducible MyD88/CD40 polypeptides discussed herein. The activation of the antigen-specific T cell, designed to target a cellular antigen implicated in a disease or condition, is dependent on the administration of a ligand inducer. The ligand inducer activates the CAR-expressing cell by multimerizing the inducible chimeric signaling molecules, which, in turn, activates NF-κB signaling and other intracellular signaling, pathways, which activates the cell, for example, a T cell, a tumor-infiltrating lymphocyte, a natural killer cell, or a natural killer T cell. (see, for example, FIG. 57) In the absence of the ligand inducer, the T cell is quiescent, or has a basal level of activity. Dosing of the ligand determines the rate and magnitude of the CAR-expressing T cell proliferation and activation.

Full activation and tumor cell killing remains dependent on antigen recognition and additional activation of NFAT via CD3 zeta signaling. Once a complete response (CR) is achieved, the dosing of the ligand is ceased. If the disease or condition reoccurs, the ligand dosing is reinitiated, leading to re-expansion and reactivation of quiescent, tumor-target, T cells.

In one example of cell therapy, T cells transduced with a nucleic acid encoding a chimeric antigen receptor have been administered to patients to treat cancer (Zhong, X.-S., (2010) Molecular Therapy 18:413-420). For example, T cells expressing a chimeric antigen receptor based on the humanized monoclonal antibody Trastuzumab (Herceptin) has been used to treat cancer patients. Adverse events are possible, however, and in at least one reported case, the therapy had fatal consequences to the patient (Morgan, R. A., et al., (2010) Molecular Therapy 18:843-851). Transducing the cells with a controllable inducible safety switch, as presented herein, would provide a safety switch that could stop the adverse event from progressing, by stopping the administration of the ligand inducer. Although a low level basal activity might remain, removing the presence of the inducer should drastically reduce, if not cease, the symptoms of the adverse event.

Chimeric antigen receptors (CARs) are artificial receptors designed to convey antigen specificity to T cells without the requirement for MHC antigen presentation. They include an antigen-specific component, a transmembrane component, and an intracellular component selected to activate the T cell and provide specific immunity. Chimeric antigen receptor-expressing T cells may be used in various therapies, including cancer therapies. Costimulating polypeptides may be used to enhance the activation of CAR-expressing T cells against target antigens, and therefore increase the potency of adoptive immunotherapy.

For example, T cells expressing a chimeric antigen receptor based on the humanized monoclonal antibody Trastuzumab (HERCEPTIN) has been used to treat cancer patients. Adverse events are possible, however, and in at least one reported case, the therapy had fatal consequences to the patient (Morgan, R. A., et al., (2010) Molecular Therapy 18:843-851). Transducing the cells with an inducible chimeric stimulating molecule, as presented herein, would allow for additional activation of the CAR T cell in the presence of ligand inducer; cessation of ligand therapy would allow the CAR T cells to be less active.

The antitumor efficacy from immunotherapy with T cells engineered to express chimeric antigen receptors (CARs) has steadily improved as CAR molecules have incorporated additional signaling domains to increase their potency. T cells transduced with first generation CARs, containing only the CD3ζ intracellular signaling molecule, have demonstrated poor persistence and expansion in vivo following adoptive transfer (Till B G, Jensen M C, Wang J, et al: CD20-specific adoptive immunotherapy for lymphoma using a chimeric antigen receptor with both CD28 and 4-1BB domains: pilot clinical trial results. Blood 119:3940-50, 2012; Pule M A, Savoldo B, Myers G D, et al: Virus-specific T cells engineered to coexpress tumor-specific receptors: persistence and antitumor activity in individuals with neuroblastoma. Nat Med 14:1264-70, 2008; Kershaw M H, Westwood J A, Parker L L, et al: A phase I study on adoptive immunotherapy using gene-modified T cells for ovarian cancer. Clin Cancer Res 12:6106-15, 2006), as tumor cells often lack the requisite costimulating molecules necessary for complete T cell activation. Second generation CAR T cells were designed to improve proliferation and survival of the cells. Second generation CAR T cells that incorporate the intracellular costimulating domains from either CD28 or 4-1BB (Carpenito C, Milone M C, Hassan R, et al: Control of large, established tumor xenografts with genetically retargeted human T cells containing CD28 and CD137 domains. Proc Natl Acad Sci USA 106:3360-5, 2009; Song D G, Ye Q, Poussin M, et al: CD27 costimulation augments the survival and antitumor activity of redirected human T cells in vivo. Blood 119:696-706, 2012), show improved survival and in vivo expansion following adoptive transfer, and more recent clinical trials using anti-CD19 CAR-modified T cells containing these costimulating molecules have shown remarkable efficacy for the treatment of CD19+ leukemia. (Kalos M, Levine B L, Porter D L, et al: T cells with chimeric antigen receptors have potent antitumor effects and can establish memory in patients with advanced leukemia. Sci Transl Med 3:95ra73, 2011; Porter D L, Levine B L, Kalos M, et al: Chimeric antigen receptor-modified T cells in chronic lymphoid leukemia. N Engl J Med 365:725-33, 2011; Brentjens R J, Davila M L, Riviere I, et al: CD19-targeted T cells rapidly induce molecular remissions in adults with chemotherapy-refractory acute lymphoblastic leukemia. Sci Transl Med 5:177ra38, 2013).

While others have explored additional signaling molecules from tumor necrosis factor (TNF)-family proteins, such as OX40 and 4-1BB, called "third generation" CART cells, (Finney H M, Akbar A N, Lawson A D: Activation of resting human primary T cells with chimeric receptors: costimulation from CD28, inducible costimulator, CD134, and CD137 in series with signals from the TCR zeta chain. J Immunol 172:104-13, 2004; Guedan S, Chen X, Madar A, et al: ICOS-based chimeric antigen receptors program bipolar TH17/TH1 cells. Blood, 2014), other molecules which induce T cell signaling distinct from the CD3ζ nuclear factor of activated T cells (NFAT) pathway may provide necessary costimulation for T cell survival and proliferation, and possibly endow CAR T cells with additional, valuable functions, not supplied by more conventional costimulating molecules. Some second and third-generation CAR T cells have been implicated in patient deaths, due to cytokine storm and tumor lysis syndrome caused by highly activated T cells.

By "chimeric antigen receptor" or "CAR" is meant, for example, a chimeric polypeptide which comprises a polypeptide sequence that recognizes a target antigen (an antigen-recognition domain) linked to a transmembrane polypeptide and intracellular domain polypeptide selected to activate the T cell and provide specific immunity. The antigen-recognition domain may be a single-chain variable fragment (ScFv), or may, for example, be derived from other molecules such as, for example, a T cell receptor or Pattern Recognition Receptor. The intracellular domain comprises at least one polypeptide which causes activation of the T cell, such as, for example, but not limited to, CD3 zeta, and, for example, co-stimulatory molecules, for example, but not limited to, CD28, OX40 and 4-1BB. The term "chimeric antigen receptor" may also refer to chimeric receptors that are not derived from antibodies, but are chimeric T cell receptors. These chimeric T cell receptors may comprise a polypeptide sequence that recognizes a target antigen, where the recognition sequence may be, for example, but not limited to, the recognition sequence derived from a T cell receptor or an scFv. The intracellular domain polypeptides are those that act to activate the T cell. Chimeric T cell receptors are discussed in, for example, Gross, G., and Eshhar, Z., FASEB Journal 6:3370-3378 (1992), and Zhang, Y., et al., PLOS Pathogens 6:1-13 (2010).

In one type of chimeric antigen receptor (CAR), the variable heavy (VH) and light (VL) chains for a tumor-specific monoclonal antibody are fused in-frame with the CD3 zeta chain (ζ) from the T cell receptor complex. The VH and VL are generally connected together using a flexible glycine-serine linker, and then attached to the transmembrane domain by a spacer (CH2CH3) to extend the scFv away from the cell surface so that it can interact with tumor antigens. Following transduction, T cells now express the CAR on their surface, and upon contact and ligation with a tumor antigen, signal through the CD3 zeta chain inducing cytotoxicity and cellular activation.

Investigators have noted that activation of T cells through CD3 zeta is sufficient to induce a tumor-specific killing, but is insufficient to induce T cell proliferation and survival. Early clinical trials using T cells modified with first generation CARs expressing only the zeta chain showed that gene-modified T cells exhibited poor survival and proliferation in vivo.

As co-stimulation through the B7 axis is necessary for complete T cell activation, investigators added the co-stimulating polypeptide CD28 signaling domain to the CAR construct. This region generally contains the transmembrane region (in place of the CD3 zeta version) and the YMNM motif for binding PI3K and Lck. In vivo comparisons between T cells expressing CARs with only zeta or CARs with both zeta and CD28 demonstrated that CD28 enhanced expansion in vivo, in part due to increased IL-2 production following activation. The inclusion of CD28 is called a 2nd generation CAR. The most commonly used costimulating molecules include CD28 and 4-1BB, which, following tumor recognition, can initiate a signaling cascade resulting in NF-κB activation, which promotes both T cell proliferation and cell survival.

The use of co-stimulating polypeptides 4-1BB or OX40 in CAR design has further improved T cell survival and efficacy. 4-1BB in particular appears to greatly enhance T cell proliferation and survival. This 3rd generation design (with 3 signaling domains) has been used in PSMA CARs (Zhong X S, et al., Mol Ther. 2010 February; 18(2):413-20) and in CD19 CARs, most notably for the treatment of CLL (Milone, M. C., et al., (2009) Mol. Ther. 17:1453-1464; Kalos, M., et al., Sci. Transl. Med. (2011) 3:95ra73; Porter, D., et al., (2011) N. Engl. J. Med. 365: 725-533). These cells showed impressive function in 3 patients, expanding more than a 1000-fold in vivo, and resulted in sustained remission in all three patients.

It is understood that by "derived" is meant that the nucleotide sequence or amino acid sequence may be derived from the sequence of the molecule. The intracellular domain comprises at least one polypeptide which causes activation of the T cell, such as, for example, but not limited to, CD3 zeta, and, for example, co-stimulatory molecules, for example, but not limited to, CD28, OX40 and 4-1BB.

Thus the present technology provides, in some embodiments a nucleic acid comprising a) a first polynucleotide encoding an inducible chimeric stimulating molecule, wherein the inducible chimeric stimulating molecule comprises (i) a MyD88 polypeptide region or a truncated MyD88 polypeptide region lacking the TIR domain; (ii) a CD40 cytoplasmic polypeptide region lacking the CD40 extracellular domain, and (iii) a multimerization region; and b) a second polynucleotide encoding a chimeric antigen receptor. In some embodiments, the inducible chimeric stimulating molecule further comprises (iv) a membrane targeting region. In certain embodiments, the membrane targeting region is a myristoylation region. In some embodiments, the multimerization region is a ligand binding region. In some embodiments, the ligand binding region is an FKBP region. In some embodiments, the nucleic acid further comprises a third polynucleotide encoding a linker polypeptide between the first and second polynucleotides, wherein the linker polypeptide separates the translation products of the first and second polynucleotides during or after translation. In some embodiments, the chimeric antigen receptor comprises (i) a transmembrane region; (ii) a T cell activation molecule; and (iii) an antigen recognition moiety. In some embodiments, the T cell activation molecule is a CD3 polypeptide. In some embodiments, the antigen recognition moiety binds to an antigen on a cell involved in a hyperproliferative disease. In certain embodiments, the antigen recognition moiety binds to an antigen selected from the group consisting of PSMA, PSCA, MUC1, CD19, ROR1, Mesothelin, GD2, CD123, MUC16, and Her2/Neu.

Also provided are modified cells transfected or transformed with a nucleic acid of the present application. In some embodiments, the modified cell is a T cell, tumor infiltrating lymphocyte, NK-T cell, TCR-expressing cell, or NK cell. Also provided are methods for stimulating a T cell-mediated immune response in a subject, comprising administering modified cells of the present application, and an effective amount of a multimeric ligand that binds to the multimerization region to stimulate a T cell-mediated immune response in the subject. In some embodiments, the chimeric antigen receptor binds to a target cell. In some embodiments, the number or concentration of target cells in the subject is reduced following administration of the modified cell.

Also provided are methods for treating a subject having a disease or condition associated with an elevated expression of a target antigen, comprising administering a multimeric ligand that binds to a multimeric ligand binding region, wherein a) the multimeric ligand binds to an inducible chimeric stimulating molecule comprising the multimeric ligand region, a MyD88 polypeptide region or a truncated MyD88 polypeptide region lacking the TIR domain, and a CD40 cytoplasmic polypeptide region lacking the CD40 extracellular domain; b) T cells circulating in the subject express (i) the inducible chimeric stimulating molecule; and (ii) a chimeric antigen receptor that binds to the target antigen; c) the target antigen is present on target cells circulating in the subject; and d) the number or concentration of target cells in the subject is reduced following administration of the multimeric ligand. In some embodiments, the inducible chimeric stimulating molecule further comprises a membrane targeting region.

Also provided in some embodiments are modified T cells transfected or transduced with a nucleic acid comprising a polynucleotide encoding an inducible chimeric stimulating molecule, wherein the inducible chimeric stimulating molecule comprises (i) a MyD88 polypeptide region or a truncated MyD88 polypeptide region lacking the TIR domain; (ii) a CD40 cytoplasmic polypeptide region lacking the CD40 extracellular domain, and (iii) a multimerization region. In some embodiments, wherein the inducible chimeric stimulating molecule further comprises (iv) a membrane targeting region. In some embodiments, the membrane targeting region is selected from the group consisting of a myristoylation region, palmitoylation region, prenylation region, and transmembrane sequences of receptors. In some embodiments, the modified T cells further comprise a polynucleotide encoding a chimeric antigen receptor.

Also provided in some embodiments are methods for stimulating a T cell-mediated immune response in a subject, comprising administering a) a modified T cell of the present application to the subject; and b) an effective amount of a multimeric ligand that binds to the multimerization region to stimulate a T cell-mediated immune response in the subject. In some embodiments, the chimeric antigen receptor binds to a target cell. In some embodiments, the number or concentration of target cells in the subject is reduced following administration of the ligand.

Also provided are nucleic acids comprising a polynucleotide encoding an inducible chimeric stimulating molecule, wherein the inducible chimeric stimulating molecule comprises (i) a MyD88 polypeptide region or a truncated MyD88 polypeptide region lacking the TIR domain; (ii) a CD40 cytoplasmic polypeptide region lacking the CD40 extracellular domain, and (iii) a multimerization region. In some embodiments, a modified cell is provided that is transfected or transformed with a nucleic acid of the present application. In other embodiments, the modified cells are T cells, tumor infiltrating lymphocytes, NK-T cells, TCR-expressing cells or NK cells.

In some embodiments, the modified cells further comprise a polynucleotide encoding a chimeric antigen receptor. In some embodiments, a method is provided for stimulating a T cell-mediated immune response in a subject, comprising administering a modified cell of the present application to the subject; and an effective amount of a multimeric ligand that binds to the multimerization region to stimulate a T cell-mediated immune response in the subject.

The present technology also provides a method for activating a T cell, comprising: transfecting or transducing a T cell with a nucleic acid comprising a polynucleotide that encodes a chimeric protein, wherein the chimeric protein comprises a membrane targeting region, a multimerization region, and a MyD88 polypeptide; whereby the T cell is activated. The present technology also provides a method for activating a T cell, comprising: transfecting or transducing a T cell with a nucleic acid comprising a polynucleotide that encodes a chimeric protein, wherein the chimeric protein comprises a membrane targeting region, a multimerization region, a MyD88 polypeptide, and a CD40 polypeptide cytoplasmic region, wherein the CD40 polypeptide does not have a functional extracellular domain; whereby the T cell is activated. Featured in the present technology is a method for activating a T cell, comprising: transfecting or transducing a T cell with a nucleic acid comprising a polynucleotide that encodes a chimeric protein, wherein the chimeric protein comprises a membrane targeting region, a multimerization region, and a CD40 polypeptide cytoplasmic region, wherein the CD40 polypeptide does not have a functional extracellular domain; whereby the T cell is activated.

In some embodiments, a methods are provided for inducing an immune response against a tumor antigen in a subject, reducing in a subject the size of a tumor having a surface tumor antigen, or treating prostate cancer in a subject, comprising activating a T cell according to the methods of the present technology and administering the activated T cell to a subject.

In some embodiments compositions are provided comprising a T cell, comprising a nucleic acid comprising a polynucleotide that encodes a chimeric protein, wherein the chimeric protein comprises a membrane targeting region, a multimerization region, and a MyD88 polypeptide. Also featured in some embodiments is a T cell, comprising a nucleic acid comprising a polynucleotide that encodes a chimeric protein, wherein the chimeric protein comprises a membrane targeting region, a multimerization region, a MyD88 polypeptide, and a CD40 polypeptide cytoplasmic region wherein the CD40 polypeptide does not have a functional extracellular domain. Also provided in some embodiments is a composition comprising a T cell, comprising a nucleic acid comprising a polynucleotide that encodes a chimeric protein, wherein the chimeric protein comprises a membrane targeting region, a multimerization region, and a CD40 polypeptide cytoplasmic region wherein the CD40 polypeptide does not have a functional extracellular domain.

In some embodiments, methods are provided for inducing an immune response or reducing tumor size using the cell compositions of the present technology.

In embodiments, a method is provided for activating a T cell in a subject, comprising: administering to the subject a nucleic acid comprising a polynucleotide that encodes a chimeric protein, wherein the chimeric protein comprises a membrane targeting region, a multimerization region, and a MyD88 polypeptide; whereby the T cell is activated. Featured in some embodiments is a method for activating a T cell in a subject, comprising administering to the subject a nucleic acid comprising a polynucleotide that encodes a chimeric protein, wherein the chimeric protein comprises a membrane targeting region, a multimerization region, a MyD88 polypeptide, and a CD40 polypeptide cytoplasmic region, wherein the CD40 polypeptide does not have a functional extracellular domain; whereby the T cell is activated. Also provided is a method for activating a T cell in a subject, comprising administering to the subject a nucleic acid comprising a polynucleotide that encodes a chimeric protein, wherein the chimeric protein comprises a membrane targeting region, a multimerization region, and a CD40 polypeptide cytoplasmic region, wherein the CD40 polypeptide does not have a functional extracellular domain; whereby the T cell is activated.

In yet other embodiments, provided are methods and compositions as discussed herein in regard to T cells, using cells that are not dendritic cells or B cells, such as, for example, non-lymphocytic hematopoietic cells or non-hematopoietic cells, such as, for example, macrophages, melanoma cells, fibroblasts, and keratinocytes.

In some embodiments, the membrane targeting region is selected from the group consisting of a myristoylation region, palmitoylation region, prenylation region, and transmembrane sequences of receptors. In some embodiments, the membrane targeting region is a myristoylation region. In some embodiments, the multimeric ligand binding region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof. In some embodiments, the multimeric ligand binding region is an FKBP12 region. In some embodiments, the multimeric ligand is an FK506 dimer or a dimeric FK506 analog ligand. In some embodiments, the ligand is AP1903. In some embodiments, the cell is administered to the subject by intravenous, intradermal, subcutaneous, intratumor, intraprotatic, or intraperitoneal administration. In some embodiments, the prostate cancer is selected from the group consisting of metastatic, metastatic castration resistant, metastatic castration sensitive, regionally advanced, and localized prostate cancer. In some embodiments, at least two doses of the cell and the ligand are administered to the subject. In some embodiments, the cell is a dendritic cell. In some embodiments, the CD40 cytoplasmic polypeptide region is encoded by a polynucleotide sequence in SEQ ID NO: 8. In some embodiments, the cell is transfected with a vector, for example, a virus vector, for example, an adenovirus vector. In some embodiments, the cell is transfected with an Ad5f35 vector. In some embodiments, the FKBP12 region is an FKBP12v36 region.

In some embodiments, progression of prostate cancer is prevented or delayed at least 6 months. In some embodiments, progression of prostate cancer is prevented or delayed at least 12 months. In some embodiments, the prostate cancer has a Gleason score of 7, 8, 9, 10, or greater.

In some embodiments, the subject has a partial or complete response by 3 months after administration of the multimeric ligand. In some embodiments, the subject has a partial or complete response by 6 months after administration of the multimeric ligand. In some embodiments, the subject has a partial or complete response by 9 months after administration of the multimeric ligand. In some embodiments, the level of serum PSA in the subject is reduced 20%, 30%, 40%. 50%, 60%, 70%, 80% 90% or 95% by 6 weeks after administration of the multimeric ligand. In some embodiments, the level of serum PSA in the subject is reduced by 3 months 20%, 30%, 40%. 50%, 60%, 70%, 80% 90% or 95% after administration of the multimeric ligand. In some embodiments, the level of serum PSA in the subject is reduced 20%, 30%, 40%. 50%, 60%, 70%, 80% 90% or 95% by 6 months after administration of the multimeric ligand. In some embodiments, the level of serum PSA in the subject is reduced 20%, 30%, 40%. 50%, 60%, 70%, 80% 90% or 95% by 9 months after administration of the multimeric ligand. In some embodiments, the size of the prostate cancer tumor is reduced 30%, 40%. 50%, 60%, 70%, 80% 90% or 95% by 3 months after administration of the multimeric ligand. In some embodiments, the size of the prostate cancer tumor is reduced 30%, 40%. 50%, 60%, 70%, 80% 90% or 95% by 6 months after administration of the multimeric ligand. In some embodiments, the size of the prostate cancer tumor is reduced 30%, 40%. 50%, 60%, 70%, 80% 90% or 95% by 9 months after administration of the multimeric ligand. In some embodiments, the vascularization of the prostate cancer tumor is reduced 30%, 40%. 50%, 60%, 70%, 80% 90% or 95% by 3 months after administration of the multimeric ligand. In some embodiments, the vascularization of the prostate cancer tumor is reduced 30%, 40%. 50%, 60%, 70%, 80% 90% or 95% by 6 months after administration of the multimeric ligand. In some embodiments, the vascularization of the prostate cancer tumor is reduced 30%, 40%. 50%, 60%, 70%, 80% 90% or 95% by 9 months after administration of the multimeric ligand. In some embodiments, a $T_H1$ or $T_H2$ antigen-specific immune response is detected in the subject after administration of the multimeric ligand.

In some embodiments, the methods further comprise administering a chemotherapeutic agent. In some embodiments, whereby the composition, ligand, and the chemotherapeutic agent are administered in an amount effective to treat the prostate cancer in the subject. In some embodiments, the composition or the nucleotide sequences, the ligand, and the chemotherapeutic agent are administered in an amount effective to treat the prostate cancer in the subject. In some embodiments, the chemotherapeutic agent is selected from the group consisting of carboplatin, estramustine phosphate (EMCYT), and thalidomide. In some embodiments, the chemotherapeutic agent is a taxane. The taxane may be, for example, selected from the group consisting of docetaxel (TAXOTERE), paclitaxel, and cabazitaxel. In some embodiments, the taxane is docetaxel. In some embodiments, the chemotherapeutic agent is administered at the same time or within one week after the administration of the cell, nucleic acid or the ligand. In other embodiments, the chemotherapeutic agent is administered after the administration of the ligand. In other embodiments, the chemotherapeutic agent is administered from 1 to 4 weeks or from 1 week to 1 month, 1 week to 2 months, or 1 week to 3 months after the administration of the ligand. In other embodiments, the methods further comprise administering the chemotherapeutic agent from 1 to 4 weeks, or from 1 week to 1 month, 1 week to 2 months, or 1 week to 3 months before the administration of the cell or nucleic acid. In some embodiments, the chemotherapeutic agent is administered at least 2 weeks before administering the cell or nucleic acid. In some embodiments, the chemotherapeutic agent is administered at least 1 month before administering the cell or nucleic acid. In some embodiments, the chemotherapeutic agent is administered after administering the multimeric ligand. In some embodiments, the chemotherapeutic agent is administered at least 2 weeks after administering the multimeric ligand. In some embodiments, wherein the chemotherapeutic agent is administered at least 1 month after administering the multimeric ligand.

In some embodiments, the methods further comprise administering two or more chemotherapeutic agents. In some embodiments, the chemotherapeutic agents are selected from the group consisting of carboplatin, Estramustine phosphate, and thalidomide. In some embodiments, at least one chemotherapeutic agent is a taxane. The taxane may be, for example, selected from the group consisting of docetaxel, paclitaxel, and cabazitaxel. In some embodiments, the taxane is docetaxel. In some embodiments, the chemotherapeutic agents are administered at the same time or within one week after the administration of the cell, nucleic acid or the ligand. In other embodiments, the chemotherapeutic agents are administered after the administration of the ligand. In other embodiments, the chemotherapeutic agents are administered from 1 to 4 weeks or from 1 week to 1 month, 1 week to 2 months, or 1 week to 3 months after the administration of the ligand. In other embodiments, the methods further comprise administering the chemotherapeutic agents from 1 to 4 weeks or from 1 week to 1 month, 1 week to 2 months, or 1 week to 3 months before the administration of the cell or nucleic acid.

In some embodiments, the subject is a mammal. In some embodiments, the subject is a human.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A) Schematic diagram of dimerization of the MyD88 and CD40 cytoplasmic signaling domains in T cells following rimiducid exposure. FIG. 1B) T cells transduced by iMC show AP1903 dose-dependent activation compared to NT and control vector (FKBP)-transduced T cells. FIG. 1C) Analysis of IL-6 production following 10 nM treatment with rimiducid in T cells transduced with vectors containing only FKBPs, or inducible MyD88, inducible CD40 or iMC. FIG. 1D) Multiplex array measuring time-dependent phosphorylation JNK, RelA and p38 (MAPK) signaling molecules following transduced T cell exposure to 10 nM rimiducid. FIG. 1E) Western plot analyses of phosphorylated signaling proteins in T cells transduced with FKPBs or iMC following rimiducid treatment for 0, 15 and 60 minutes. Positive control indicates T cell treatment with PHA and ionomycin. FIG. 1F) T cells transduced with vectors containing only FKBPs, or inducible MyD88, inducible CD40 or iMC were activated with and without 10 nM rimiducid and/or 50 ng/ml soluble anti-CD3 and supernatants measured for IL-2 by ELISA and assessed for CD25 expression by flow cytometry (FIG. 1G and FIG. 1H). * indicates p-value <0.05.

FIGS. 2A-2F provide the results of assays showing that T cells cotransduced with iMC and PSCA.ζ CAR show improved tumor killing and expansion in a rimiducid-dependent manner. FIG. 2A) A schematic representation of T cells genetically modified with a CAR and iMC. FIG. 2B) T cells were transduced with PSCA.ζ CAR and either FKBP or iMC retrovirus and measured for coexpression by flow cytometry using CD19-PE and anti-CAR-APC. FIG. 2C) Non-transduced and PSCA.ζ CAR T cells modified with either FKBP or iMC were cocultured with Capan-1-GFP tumor cells at a 1:1 T cell to tumor cell ratio with and without 10 nM rimiducid. Tumor cell and T cell frequency were assessed after 7 days by flow cytometry. Tumor cell frequency was assessed by flow cytometry by measuring CD3$^-$GFP$^+$ tumor cells by SSC/GFP gating. Enrichment of T cells coexpressing iMC and CAR were assessed in coculture assays by flow cytometry by measuring CD19-PE and anti-CAR-APC frequency, respectively. FIG. 2D) T cells were subsequently assessed for CD25 expression and measured for T cell proliferation (FIG. 2E) using flow cytometry and cell enumeration. FIG. 2F) T cells cotransduced with iMC or Ctrl vector, and PSCA.ζ CAR were cocultured with and without Capan-1 tumor cells, and with and without 10 nM rimiducid and the supernatants measured for IL-2 levels after 48 hours. * indicates p-value <0.05. ** indicates p-value <0.01.

FIG. 3A) Shorn mice were engrafted with Capan-1 tumor cells and treated with PSCA.ζ CAR T cells cotransduced with control vector or iMC, or non-transduced T cells, and injected i.v. on days 7 and 14. Exogenous IL-2 was given i.p. until day 21 and then withdrawn. All mice received 5 mg/kg rimiducid i.p. twice per week (biw). Tumor size was measured by calipers (FIG. 3B) and survival assessed over a 100-day period (FIG. 3C). FIG. 3D) to measure in vivo CAR T cell persistence and expansion, NSG mice were used. Mice were injected s.c. with Capan-1 tumor cells and then treated with non-transduced (NT) or FKBP and PSCA.ζ-modified T cells or iMC and PSCA.ζ-modified T cells. Mice treated with iMC-enabled T cells received 2.5 mg/kg rimiducid once (qw), twice weekly (biw) or saline only via i.p. injection. FIG. 3E) Subcutaneous tumor size was measured by calipers over a 30 day period.

FIG. 3F) In vivo bioluminescence imaging was performed on mice treated with iMC-transduced T cells receiving saline only, or with systemic rimiducid administration. Region-of-interest (ROI) measurements were performed on the whole animal (FIG. 3G.) or on individual tumors within the groups (FIG. 3H). * indicates p-value <0.05.

FIG. 4A) Four constructs were generated using the SFG retroviral backbone encoding a myristoylation domain (Myr) and two tandem FKBP12v36 dimer binding domains in-frame with truncated CD19 (ΔCD19). These vectors either lack signaling molecules, or contain the intracellular signaling domains from MyD88 and/or CD40. FIG. 4B) Two PSCA-targeted CARs were generated using the anti-PSCA single chain variable fragment (scFv) bm2B3[4, 5] in-frame with the IgG1 CH2CH3 spacer and the CD3ζ cytoplasmic signaling domain. In addition, a second generation CAR was constructed that includes the intracellular CD28 signaling domain.

FIG. 5A and FIG. 5B) Flow cytometric analysis of non-transduced T cells or T cells transduced with FKBP control vector (SFG-FKBP-2A-ΔCD19) or with iMC (SFG-iMC-2A-ΔCD19) (n=7). FIG. 5C) Induction of IFN-γ following 10 nM rimiducid (CID) exposure after 24 hours from non-transduced T cells or T cells transduced with the FKBP or iMC vector. FIG. 5D) Phenotyping of FKBP or iMC transduced T cells after 14 days in culture following gating on CD3$^+$CD19$^+$ transduced T cells. * indicates p-value <0.05.

FIG. 6A) A schematic diagram of the design of control and iMC retroviral vectors. FIG. 6B) Transduction efficiency of T cells transduced with FKBP, iMyD88, iCD40 and iMC.

FIG. 7A) Hierarchical clustering was performed with genes upregulated in iMC following CID activation, compared to iMC-modified T cells alone. FIG. 7B) Data set comparisons between control T cells (FKBP) with and without CID and iMC-modified T cells with and without CID. FIG. 7C) Gene set extracted from FKBP$^+$CID treated T cells versus iMC$^+$ CID treated T cells (433 upregulate genes) were analyzed via ConsensusPathDB for induced network modules demonstrating a signaling network association centered on NK-κB and TRAF pathways.

FIG. 8A and FIG. 8B) FKBP and iMC transduced T cells were cultured in media supplemented with or without 100 U/ml IL-2 and stimulated on a weekly basis with 10 nM rimiducid (CID) and measured for growth by cell counting. FIG. 8C) iMC-modified T cells cultured in media without IL-2, with and without CID stimulation, were measured for viability by flow cytometry (SSC, FSC) after 42 days in culture. * indicates p-value <0.05.

FIG. 10A) A schematic representation of PSCA.ζ CAR T cells transduced with either FKBP control or iMC retrovirus. FIG. 10B) Phenotype of T cells cotransduced with both PSCA.ζ CAR and either FKBP and iMC retrovirus compared to non-transduced (NT) T cells. FIG. 10C) T cells transduced with PSCA.ζ and either FKBP or iMC were assayed for cytotoxicity at different effector: target ratios against PSCA$^+$ tumor cell lines, Capan-1 and HPAC, using DELPHIA cytotoxicity assay. FIG. 10D) For IL-2 production in the context of tumor and rimiducid stimulation, T cells were transduced with FKBP or iMC alone, PSCA.ζ alone or in combinations, then phenotyped using flow cytometry to detect coexpression of CAR or signaling vector.

FIG. 12A) A schematic representation of T cells engineered with FKBP and iMC molecules, and first (PSCA.ζ) and second (PSCA.28.ζ) CAR constructs. FIG. 12B) Non-transduced T cells and T cells transduced with FKBP$^+$PSCA.ζ, FKBP$^+$PSCA.28.ζ) or iMC$^+$PSCA.ζ were cocultured with Capan-1-GFP tumor cells at a 1:1 effector:target ratio for 7 days and analyzed for residual tumor cells (CD3$^-$GFP$^+$) by flow cytometry. FIG. 12C) IL-2 ELISA was performed on coculture supernatants that were treated with and without rimiducid (CID). FIG. 12D) T cell numbers were assessed by multiplying the total cell count by the frequency of CD3$^+$ GFP$^-$ cells as measured by flow cytometry obtained in the coculture assay.

FIG. 13A) A comparison of CD28 costimulation and iMC, rimiducid (CID)-dependent costimulation was compared in Shorn mice bearing s.c. Capan-1 tumors. 7 days post-tumor injection, mice received one i.v. dose of 1×10$^7$ non-transduced T cells, or T cells modified with FKBP$^+$PSCA.ζ, FKBP$^+$PSCA.28.ζ or iMC$^+$PSCA.ζ. Mice receiving transduced T cells were subsequently treated with 5 mg/kg rimiducid (CID) i.p. twice weekly. FIG. 13B) Tumor size was measured by calipers for each of the groups and survival assessed (FIG. 13C).

FIG. 17A and FIG. 17B are bar graphs showing rimiducid-dependent IL-6 production by myristoylated (172, 607, 180, 609) inducible MyD88/CD40 compared to non-myristoylated (606, 608) inducible MyD88/CD40 expressing T cells.

FIG. 18A and FIG. 18B are bar graphs showing rimiducid-dependent IL-2 and IL-6 production by myistoylated (180) inducible MyD88/CD40 compared to non-myristoylated (608) inducible MyD88/CD40 expressing T cells cocultured with CD19$^+$ Raji cells.

FIG. 20 discloses SEQ ID NOS 195 and 196, respectively, in order of appearance.

FIG. 21 discloses SEQ ID NOS 195 and 196, respectively, in order of appearance.

FIG. 24A and FIG. 24B are line graphs from an assay of transduced macrophages.

FIG. 25A and FIG. 25B are line graphs from an assay of transduced macrophages.

FIG. 26A, FIG. 26B, FIG. 26C. and FIG. 26D. are bar graphs of results using macrophages.

FIG. 27A and FIG. 27B are line graphs from an assay of transduced melanoma cells.

FIG. 28A and FIG. 28B are line graphs from an assay of transduced melanoma cells.

FIG. 29A and FIG. 29B are bar graphs of results using melanoma cells.

FIG. 30A and FIG. 30B are line graphs from an assay of transduced fibroblasts.

FIG. 31A and FIG. 31B are bar graphs of results using fibroblasts.

FIG. 60A provides a graphic illustration of the general polypeptide elements of the inducible chimeric stimulating molecules. FIG. 60B provides flow cytometry results of CD19 marker detection in T cells that express the chimeric stimulating molecules. FIG. 60C is a graph of IFN γ production in T cells that express the chimeric stimulating molecules. FIG. 60D is a graph of IL-6 production in T cells that express the chimeric stimulating molecules.

FIG. 63 discloses SEQ ID NOS 195 and 196, respectively, in order of appearance.

DETAILED DESCRIPTION

Figure 1A:
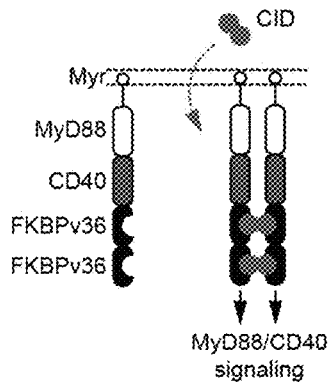
FIGS. 1A-1H provide the results of assays showing that iMC functions provide inducible costimulation T cells.

T cells expressing chimeric antigen receptors (CARs) have shown long-term efficacy for the treatment of some types of cancer, however, toxicity associated with excessive T cell activation, such as cytokine release syndrome (CRS) remain a concern. Steroids or incorporation of a suicide gene (e.g., inducible caspase-9, HSV-TK, CD20, truncated EGFR)[7-12] within the vector can be used to improve the safety profile, but these current approaches may reduce the level of or terminate the therapy and hence may impair efficacy. More recently, an IL-6 receptor blockade has been used to manage CRS[6]; however, this strategy may be less effective when direct T cell cytotoxicity is responsible for tissue damage[13]. Additionally, CAR-T cell efficacy has been more limited in solid tumors due to poor CAR-T cell survival, activation and proliferation, presumably due to the more profound inhibitory effects of the tumor microenvironment[14,15] Thus, strategies that allow controlled expansion and survival of tumor-targeted T cells would maximize therapeutic potency while minimizing toxicities.

T cells bearing first generation CARs, including a tumor antigen-specific, single-chain variable fragment (scFv) domain and the T cell receptor (TCR)-associated CD3 intracellular signaling molecule, fail to persist or expand in vivo[16-18], as tumor cells often lack the requisite costimulatory molecules necessary for complete T cell activation[19]. Second generation CAR-T cells that incorporate potent intracellular costimulatory domains, like CD28 or 4-1BB[20,21], show improved survival and in vivo expansion following adoptive transfer[1-4]. Several studies have engineered CAR-T cells with healthy tissue-activated inhibitory domains[22] or have employed a tumor-sensing approach by separating costimulatory domains and CD3ζ on CARs with different antigen targets to limit "on-target, off-tumor" toxicities[23,24]. While these approaches may improve tumor specificity, they rely on often unpredictable cell autonomous factors. In contrast, physician-enabled approaches to control T cell amplification and elimination in vivo would facilitate patient-tailored therapy coordinated with clinical course, potentially avoiding acute or long-term therapy-associated toxicities.

In general, T cell therapy has involved the difficulty of poor in vivo expansion of the infused cells. One way this issue has been addressed is by administering high doses of IL-2 to the patient. This therapy helps T cell growth and anti-tumor function, but is also very toxic to the patient. This has generally been used in melanoma as high dose IL-2 is considered a standard-of-care therapy for that disease. Most other T cell therapy applications have not used IL-2 with T cell therapy due to toxic effects. Another issue arising in T cell therapy is the poor engraftment and persistence of infused T cells (also a function of in vivo proliferation), which has been addressed by lymphodepleting conditioning prior to T cell infusion. Investigators generally use chemotherapy (cyclophosphamide in particular) to achieve this, although some use antibodies including.CAMPATH Conditioning appears to greatly facilitate T cell therapy through creating lymphoid "space" and depleting regulatory immune cells that compete for growth and survival factors. However, it is very toxic to the patient, completely ablates normal immune cells (e.g. pathogen-specific) and cannot be readily used for some types of cancer or older patients. In addition, use of a lymphodepleting regimen might push a T cell therapy toward a "procedure" rather than a standalone therapeutic.

T cell therapy has largely been considered a boutique therapy since each patient needs to have a unique cell product manufactured for them. Conventional T cell therapies (generated by repetitive antigen stimulation or isolation of tumor infiltrating lymphocytes (TILs) are not reproducible in their specificity or function and lead to extremely variable results, and in some cases the inability to produce a product for treatment. Gene transfer of natural or chimeric T cell receptors has started to solve this problem (where highly tumor specific T cells can be generated in less than 2 weeks), but it is apparent that gene-modified T cells can function differently than naturally occurring T cells. In addition, highly specific CAR T cells or T cells expressing optimized TCR alpha and beta chains can cause off-target toxicity, necessitating the inclusion of a suicide gene.

Figure 38:
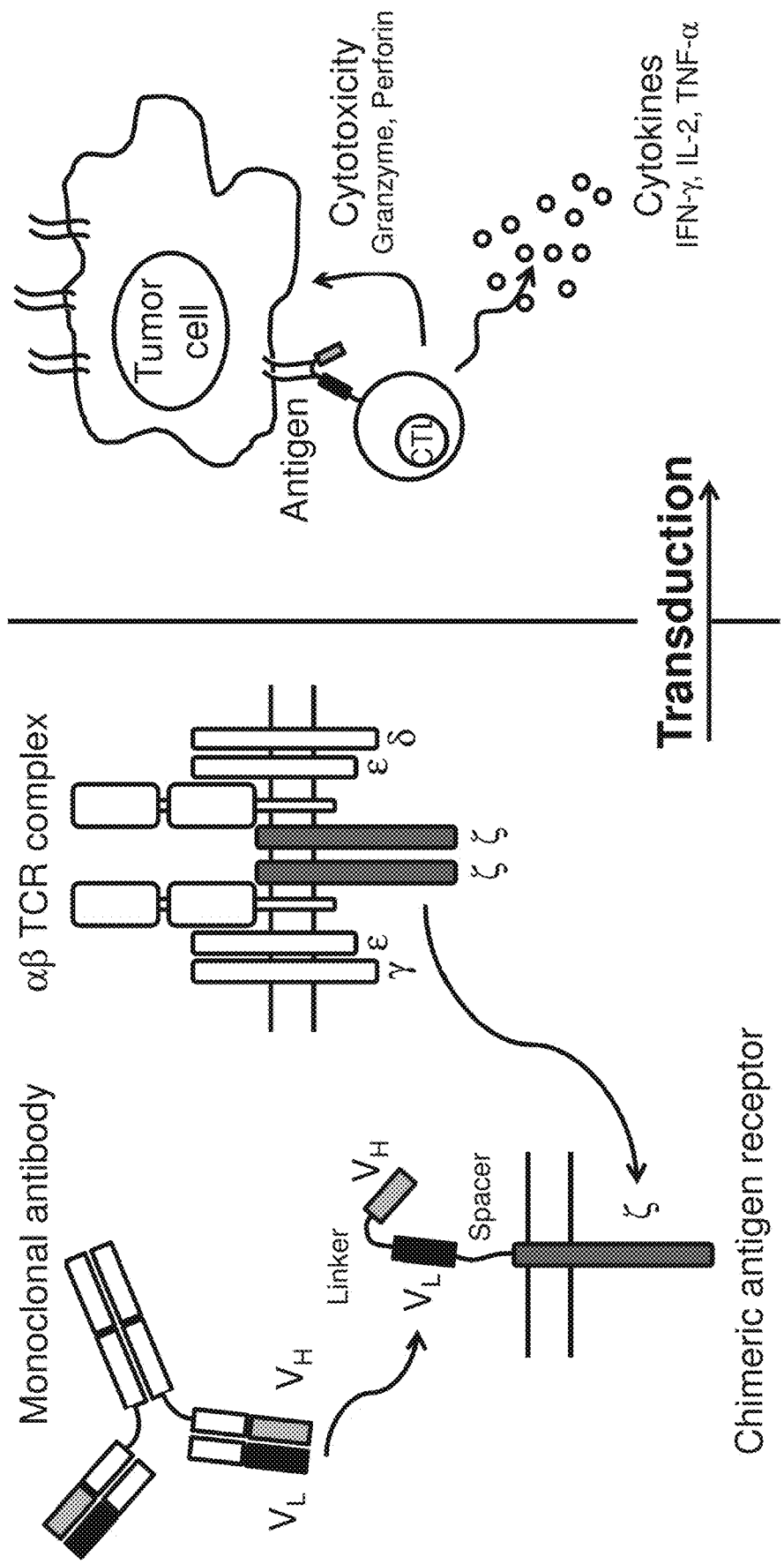
FIG. 38 provides an illustration of gene transfer of chimeric antigen receptors (CARs).

FIG. 38 illustrates the most basic components of a chimeric antigen receptor (CAR). The variable heavy ($V_H$) and light ($V_L$) chains for a tumor-specific monoclonal antibody are fused in-frame with the CD3 zeta chain (ζ) from the T cell receptor complex. The $V_H$ and $V_L$ are generally connected together using a flexible glycine-serine linker, and then attached to the transmembrane domain by a spacer ($CH_2CH_3$) to extend the scFv away from the cell surface so that it can interact with tumor antigens.

Following transduction, T cells now express the CAR on their surface, and upon contact and ligation with a tumor antigen, signal through the CD3 zeta chain inducing cytotoxicity and cellular activation.

Figure 39:
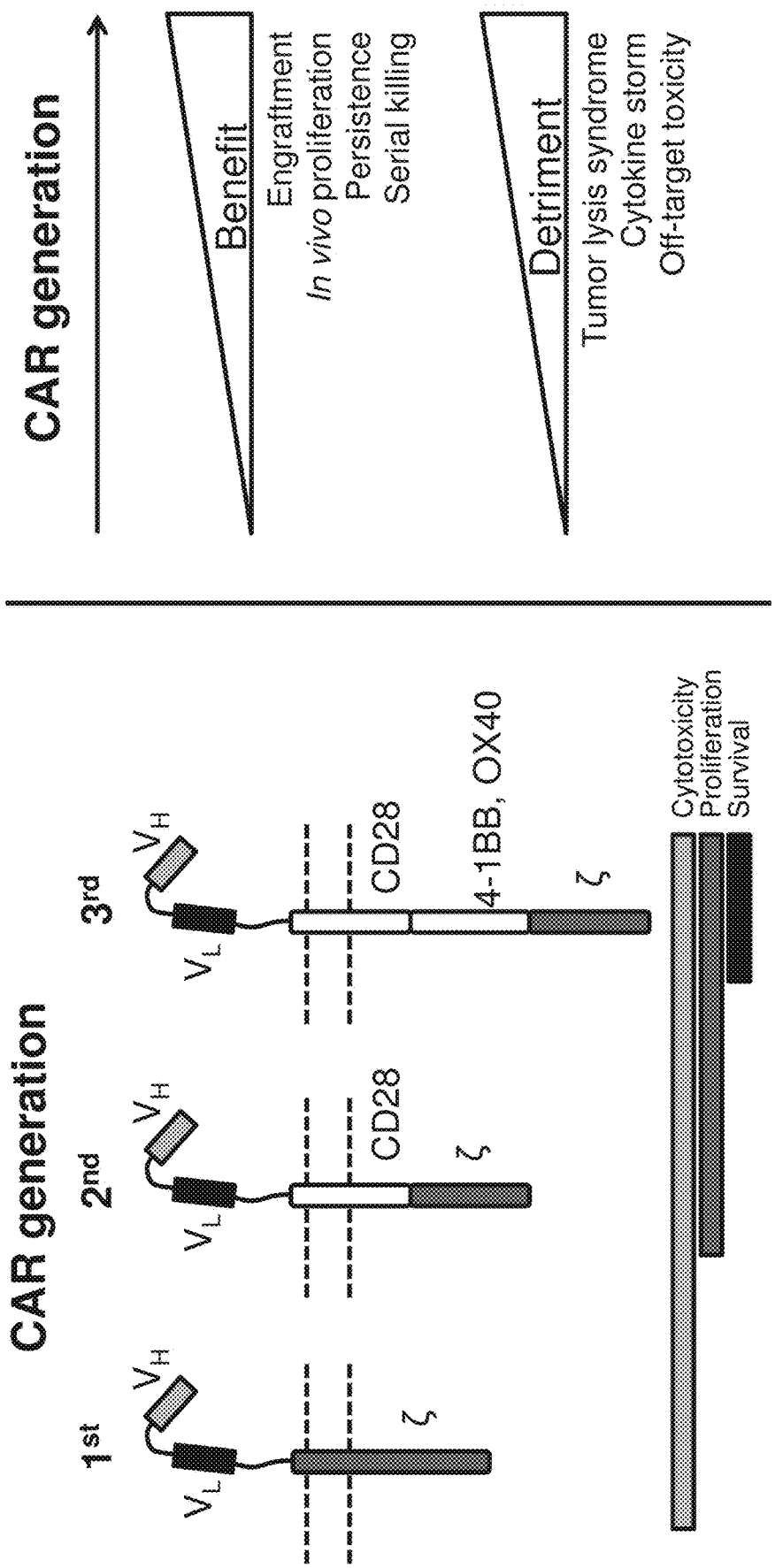
FIG. 39 provides an illustration of CAR improvements and associated toxicity.

FIG. 39 illustrates the development of various chimeric antigen receptors. Investigators have noted that activation of T cells through CD3 zeta is sufficient to induce a tumor-specific killing, but is insufficient to induce T cell proliferation and survival. Early clinical trials using T cells modified with CARs expressing only the zeta chain showed that gene-modified T cells exhibited poor survival and proliferation in vivo. These constructs are termed 1st generation CARs.

As co-stimulation through the B7 axis is necessary for complete T cell activation, investigators added the co-stimulatory polypeptide CD28 signaling domain to the CAR construct. This region generally contains the transmembrane region (in place of the CD3 zeta version) and the YMNM motif for binding PI3K and Lck. In vivo comparisons between T cells expressing CARs with only zeta or CARs with both zeta and CD28 demonstrated that CD28 enhanced expansion in vivo, in part due to increased IL-2 production following activation. The inclusion of CD28 is called a 2nd generation CAR.

The use of co-stimulatory polypeptides 4-1BB or OX40 in CAR design has further improved T cell survival and efficacy. 4-1BB in particular appears to greatly enhance T cell proliferation and survival. This 3rd generation design (with 3 signaling domains) has been used in PSMA CARs (Zhong X S, et al., Mol Ther. 2010 February; 18(2):413-20), and in CD19 CARs, most notably for the treatment of CLL (Milone, M. C., et al., (2009) Mol. Ther. 17:1453-1464; Kalos, M., et al., Sci. Transl. Med. (2011) 3:95ra73; Porter, D., et al., (2011) N. Engl. J. Med. 365: 725-533). These cells showed impressive function in 3 patients, expanding more than a 1000-fold in vivo, and resulted in sustained remission in all three patients.

However, as CARs have improved in their anti-tumor effects, they have also become more dangerous. There have been two high-profile deaths using 2nd and 3rd generation CARs, which is high considering only a handful of patients have been treated. These deaths resulted from sepsis due to cytokine storm and tumor lysis syndrome caused by highly activated T cells (Morgan, R. A., et al. (2010) Mol. Ther. 14:843-851).

T cell receptor signaling can be induced using a chemical inducer of dimerization (CID) in combination with a chimeric receptor that includes a multimerization region that binds to the CID, T cells were engineered to express the CD3 zeta chain, which was linked with 1, 2, or 3 FKBP fragments. The cells expressed the chimeric receptor, and demonstrated CID-dependent T cell activation (Spencer, D. M., et al., Science, 1993. 262: p. 1019-1024). The present application provides, in part, inducible chimeric signaling molecules (CSMs) that are controlled by CID.

Contacting T cells that express the inducible CSMs with a CID results in cell activation, and induction of an immune response.

Dendritic cells (DCs) may be activated by chemical induction of dimerization (CID) using a small molecule (i.e., rimiducid/AP1903)-response chimeric signaling molecule, comprising the "universal" Toll-like receptor (TLR) adapter, MyD88, and the TNF family member, CD40[25].

Figure 40:
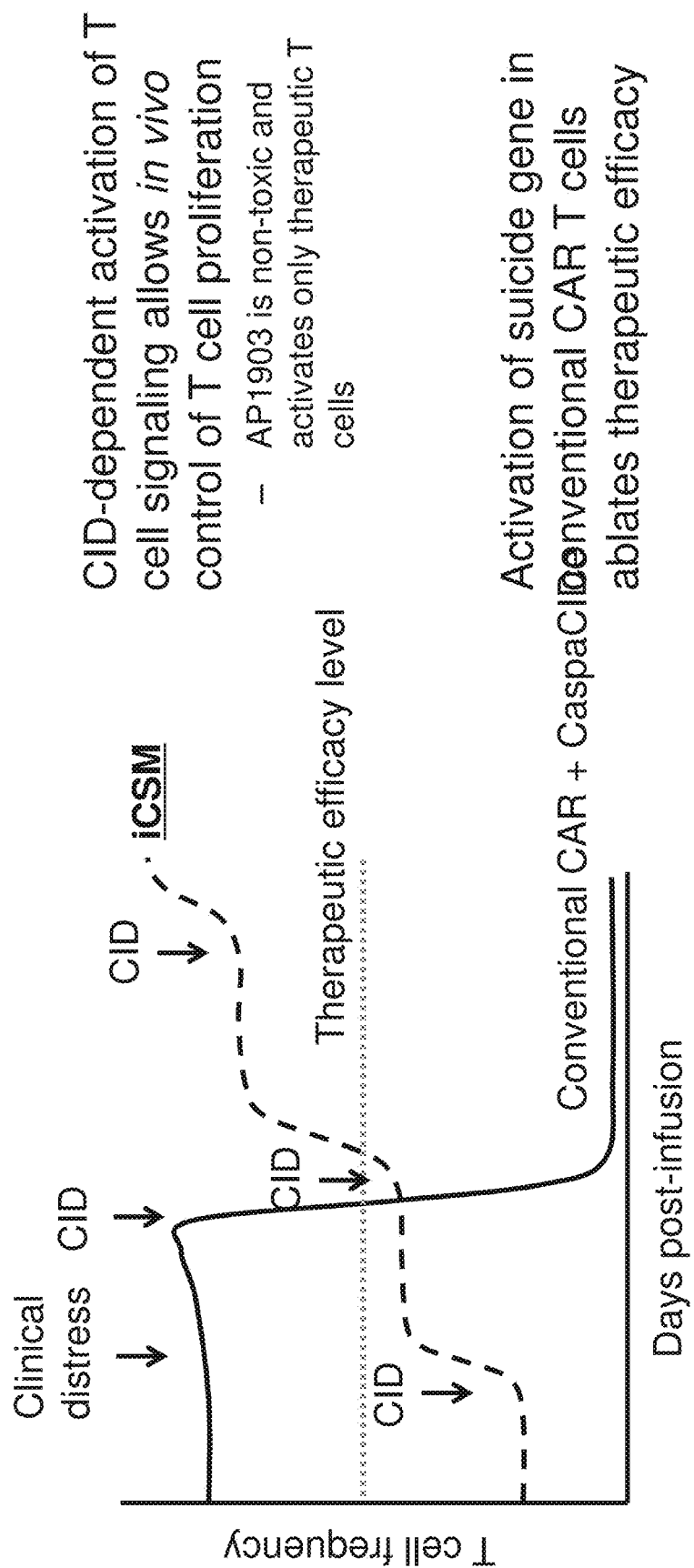
FIG. 40 provides a graphical depiction of a theoretical analysis of a CID-controlled chimeric signaling molecule compared to CAR-expressing cells that also express a suicide (apoptosis) gene.

FIG. 40 compares the therapies of the present application with methods of CAR treatment using a suicide gene. The present application provides, in part, a gene-engineering approach to amplify T cell proliferation and function in vivo so that the anti-tumor effect is gradually increased. A chemical inducer of dimerization is used in a controllable system for activating T cells in vivo to increase their function and frequency.

Figure 63:
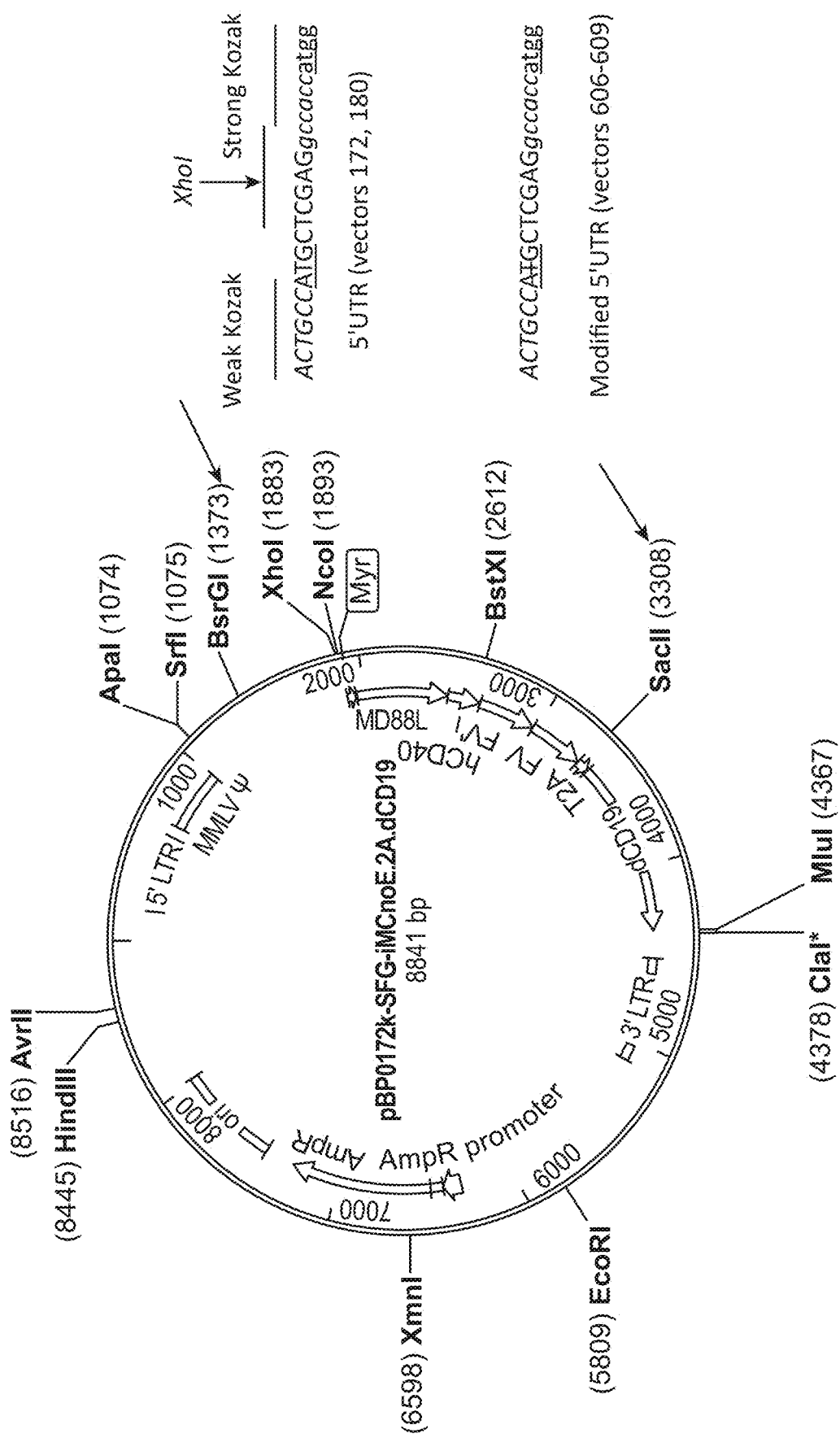
FIG. 63 is a plasmid map of pBP0172, encoding an inducible MyD88/CD40 polypeptide comprising a myristoylation region, along with a first generation anti-CD19-CAR. To remove the extraneous upstream start site and accompanying short peptide in the next generation of vectors, for example, as discussed in Example 8 herein, the 5' "ATG" was changed to "AG" (indicated by underlined "ATG" sequences and crossed-out "T". This identical 5' untranslated region was shared between plasmids 606, 607, 608, and 609.

As shown in FIGS. 63 and 64, in some embodiments the CSM uses a multimerization region, such as Fv domains, in tandem with one or more co-stimulatory polypeptides, such as, for example, CD28 and 4-1BB, with and without the CD3 zeta chain to enable CID-dependent proliferation and co-stimulation. The CSM may be used alone to provide co-stimulation, and increase a T cell immune response. Using this method, a population of T cells, for example a population with non-specific targets, may be transfected or transduced with DNA coding for CSM, then administered to a subject to enhance a general immune response.

Figure 41:
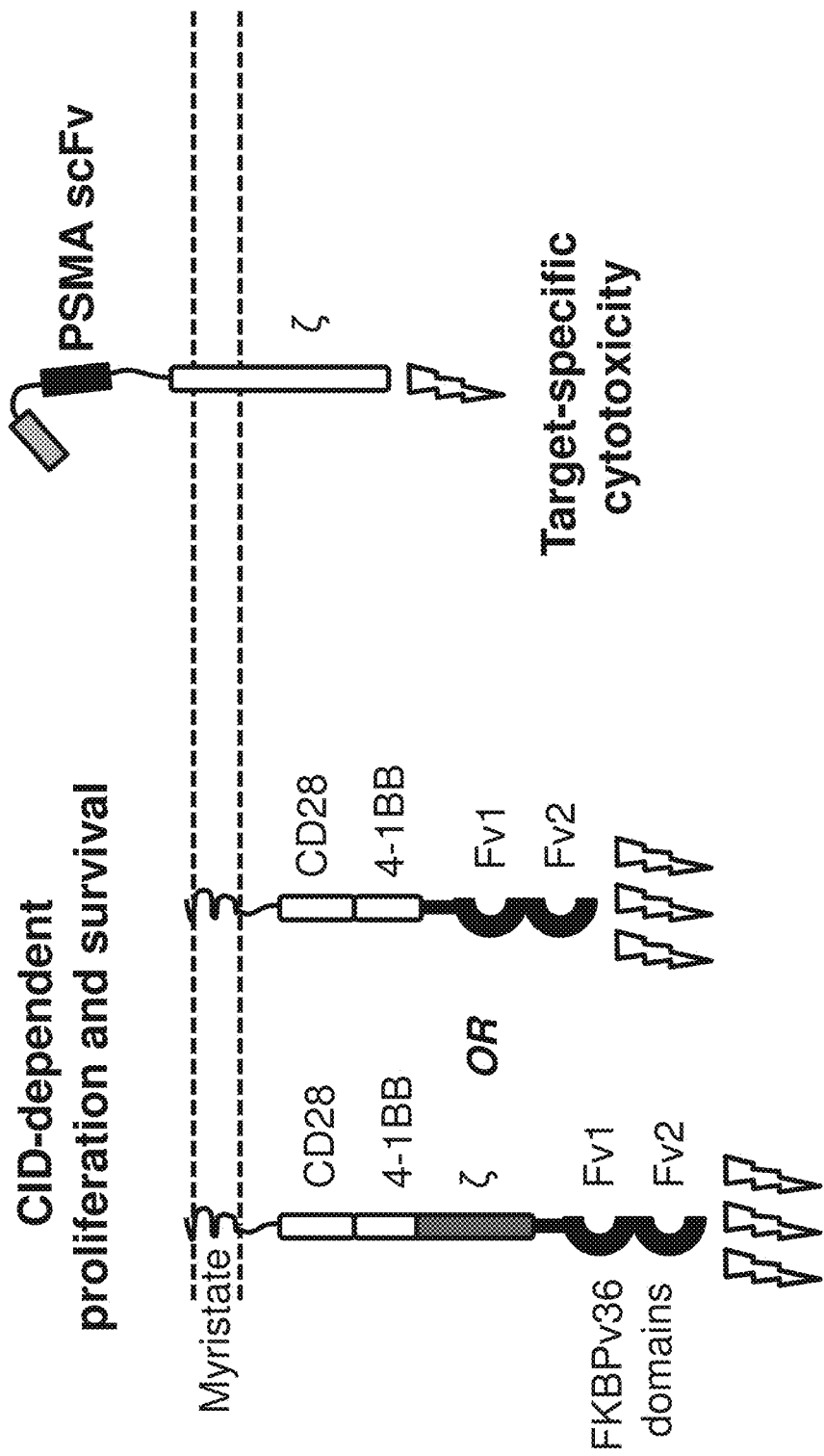
FIG. 41 provides an illustration of some examples of CID-controlled CSMs.
Figure 42:
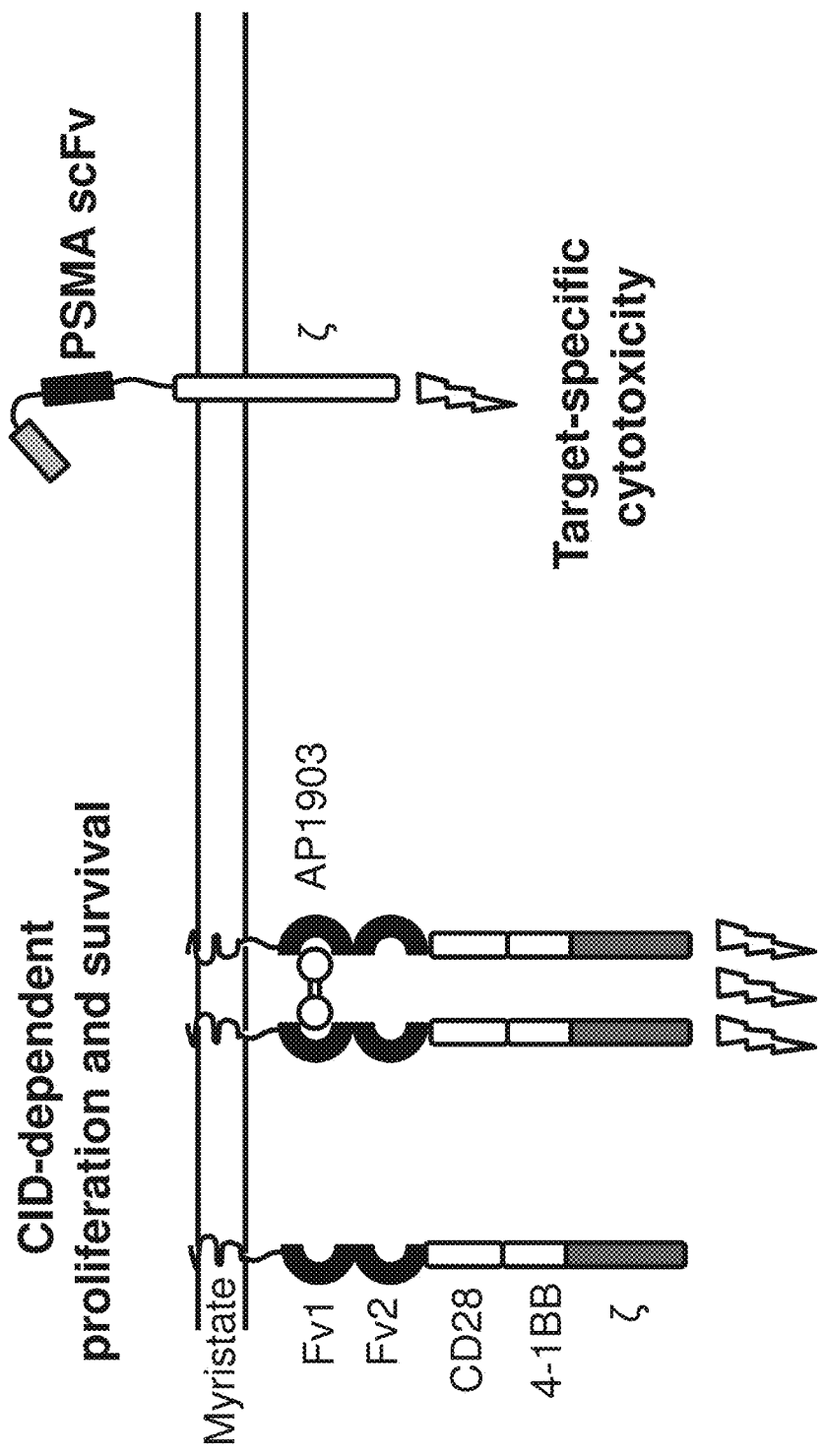
FIG. 42 provides an illustration of CID-induction of a CSM, and inducible CSM activation of a T cell comprising a CAR.
Figure 43:
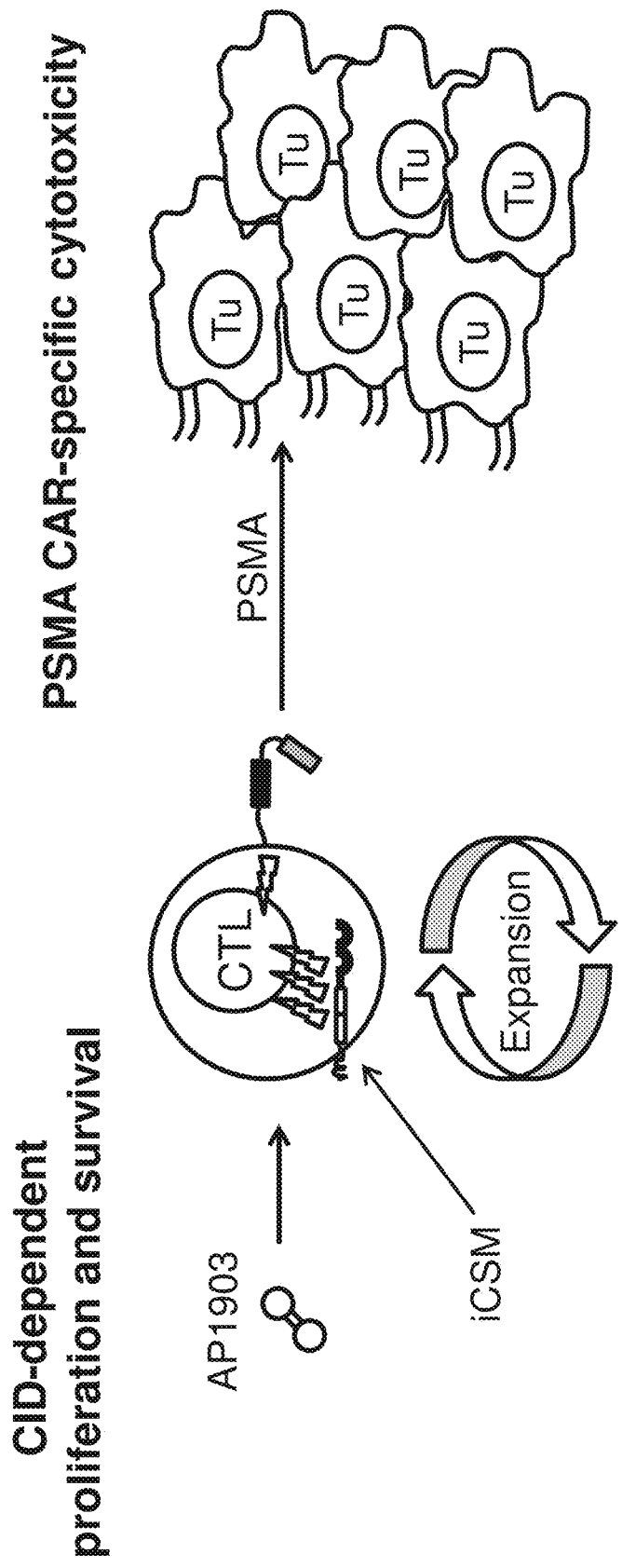
FIG. 43 provides an illustration of CID-controlled T cell killing of tumor cells.
Figure 44:
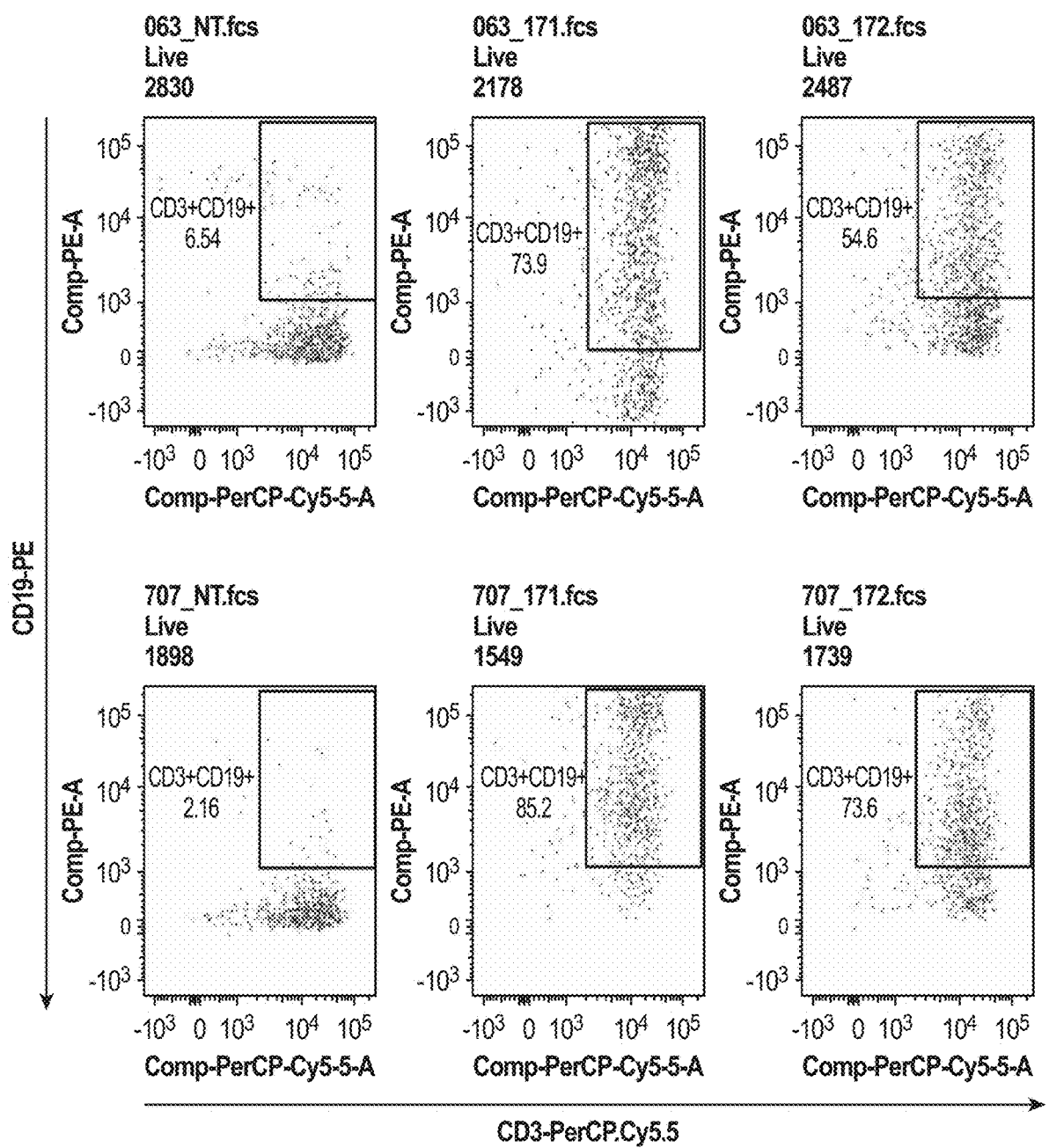
FIG. 44 provides the results of FACs sorting analysis of modified T cells.
Figure 45:
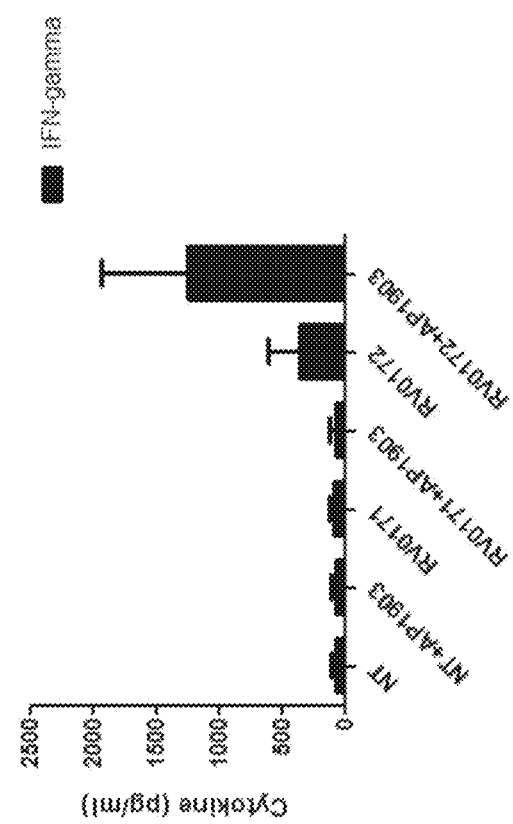
FIG. 45 provides bar graphs of GM-CSF and Interferon gamma levels in the modified and control T cells.
Figure 45:
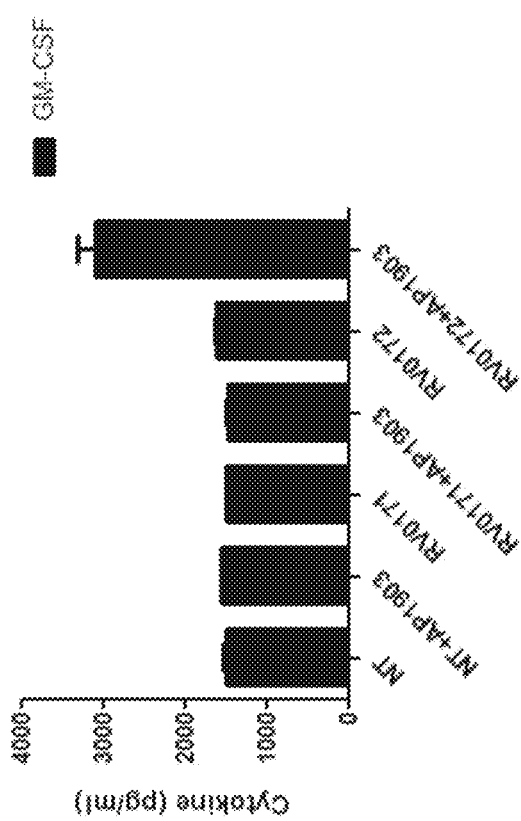
Figure 46:
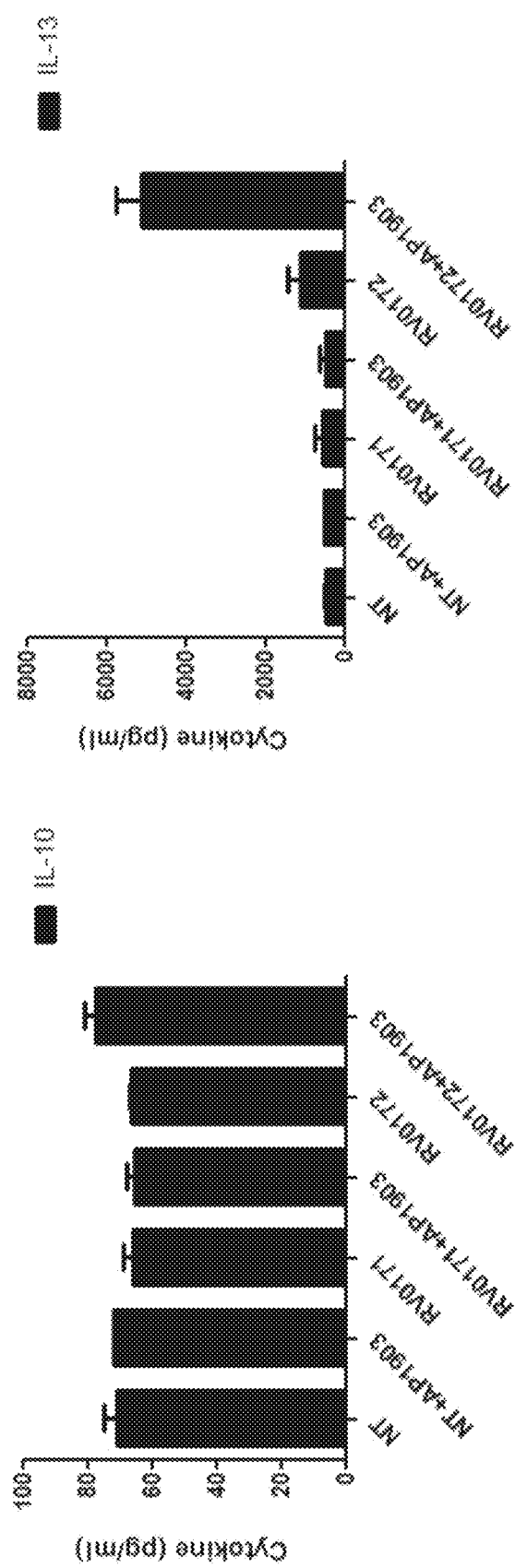
FIG. 46 provides bar graphs of IL-10 and IL-13 levels in the modified and control T cells.
Figure 47:
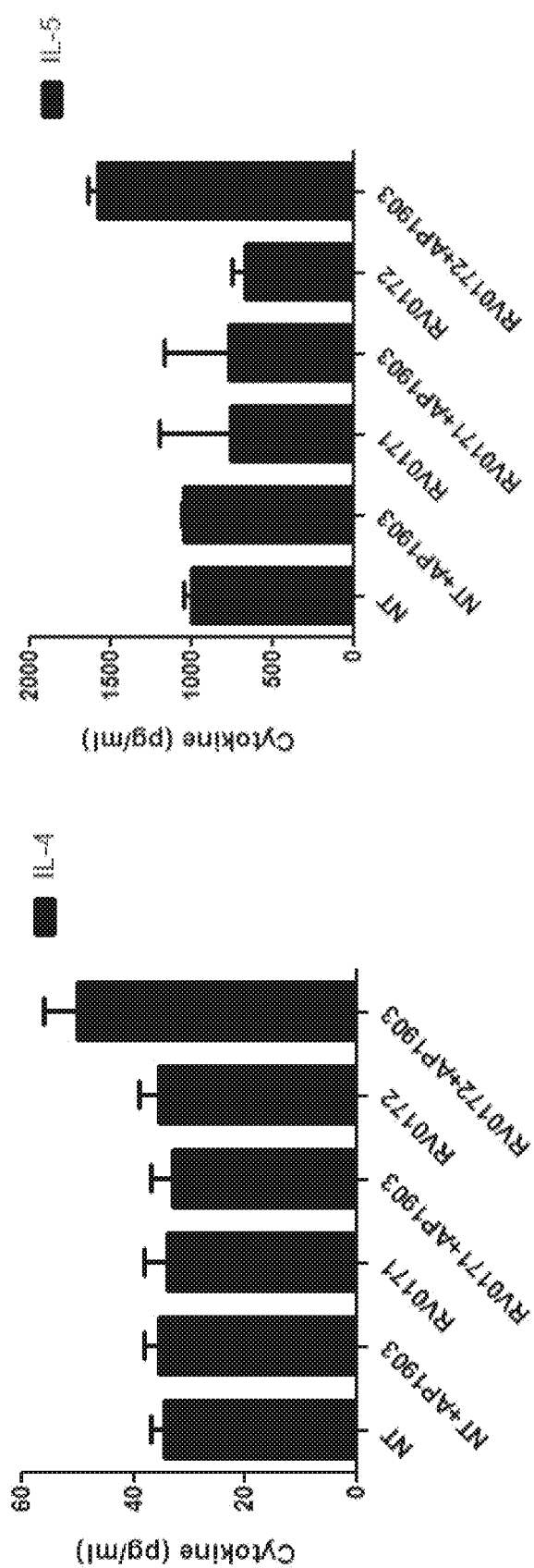
FIG. 47 provides bar graphs of IL-4 and IL-5 levels in the modified and control T cells.
Figure 48:
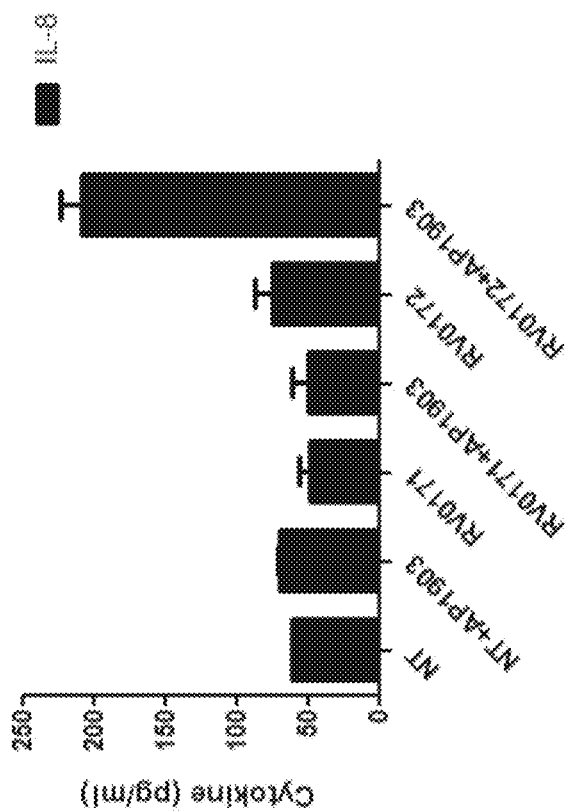
FIG. 48 provides bar graphs of IL-6 and IL-8 levels in the modified and control T cells.
Figure 48:
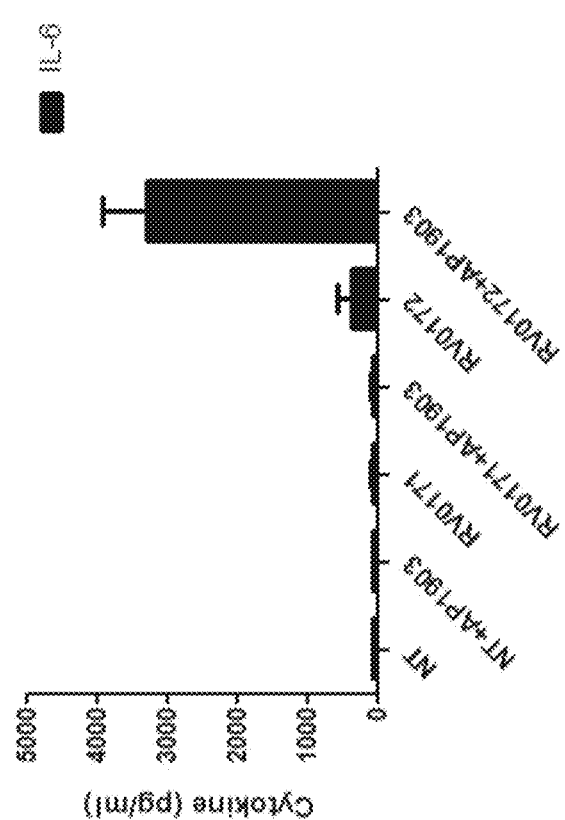
Figure 49:
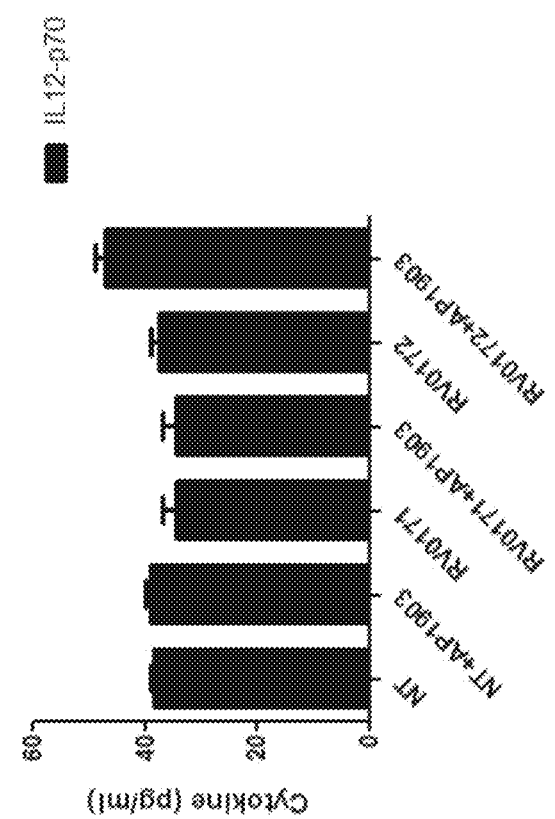
FIG. 49 provides bar graphs of IL-1β and IL-12-p70 levels in the modified and control T cells.
Figure 49:
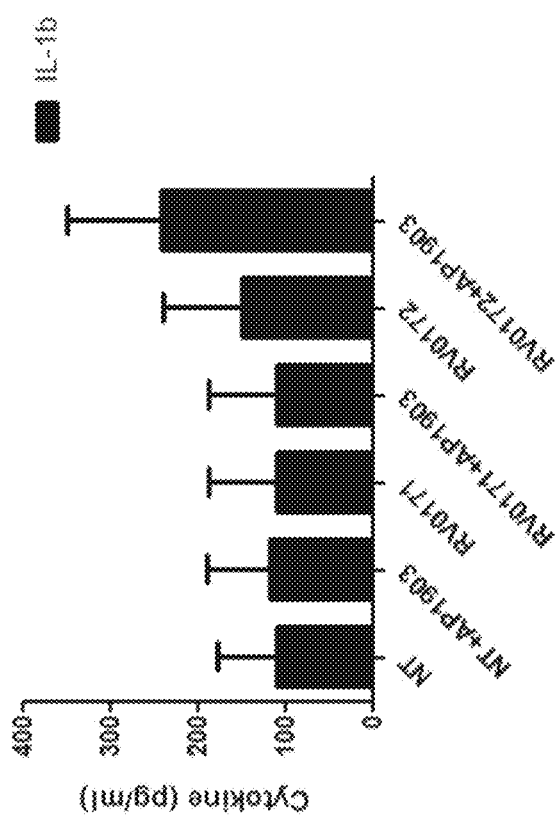
Figure 50:
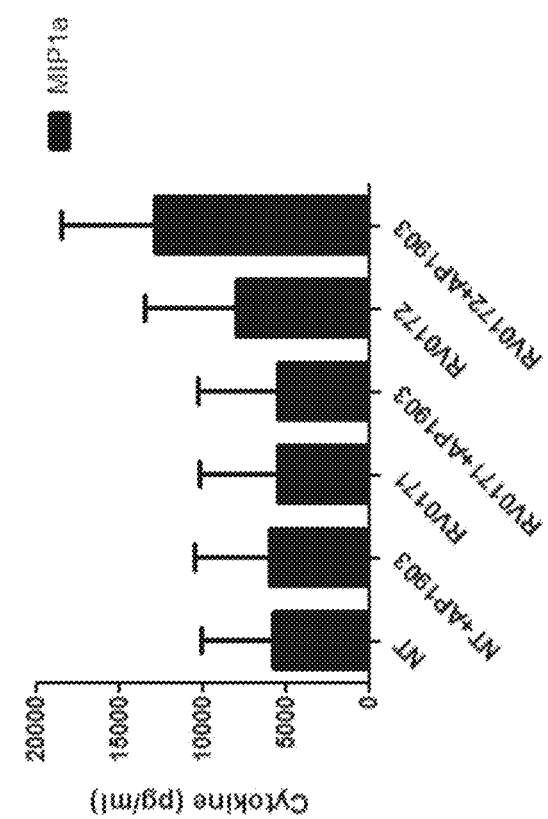
FIG. 50 provides bar graphs of IP-10 and MIP1α levels in the modified and control T cells.
Figure 50:
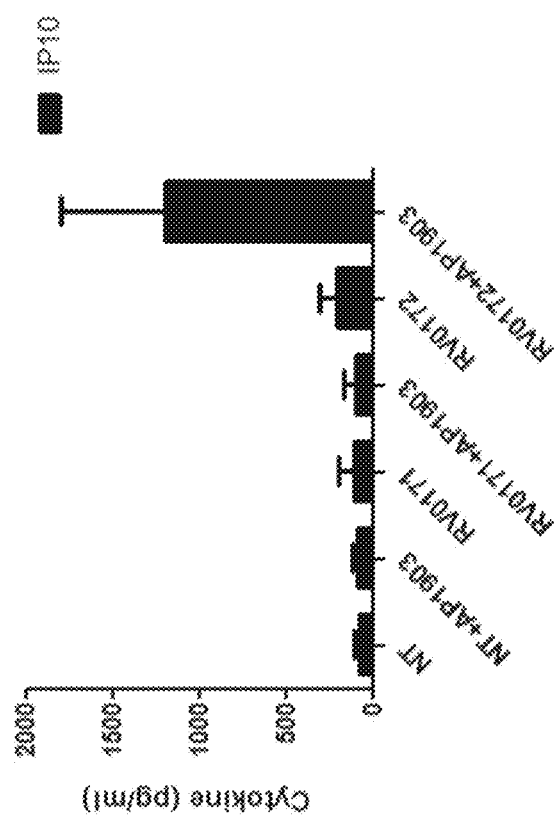
Figure 51:
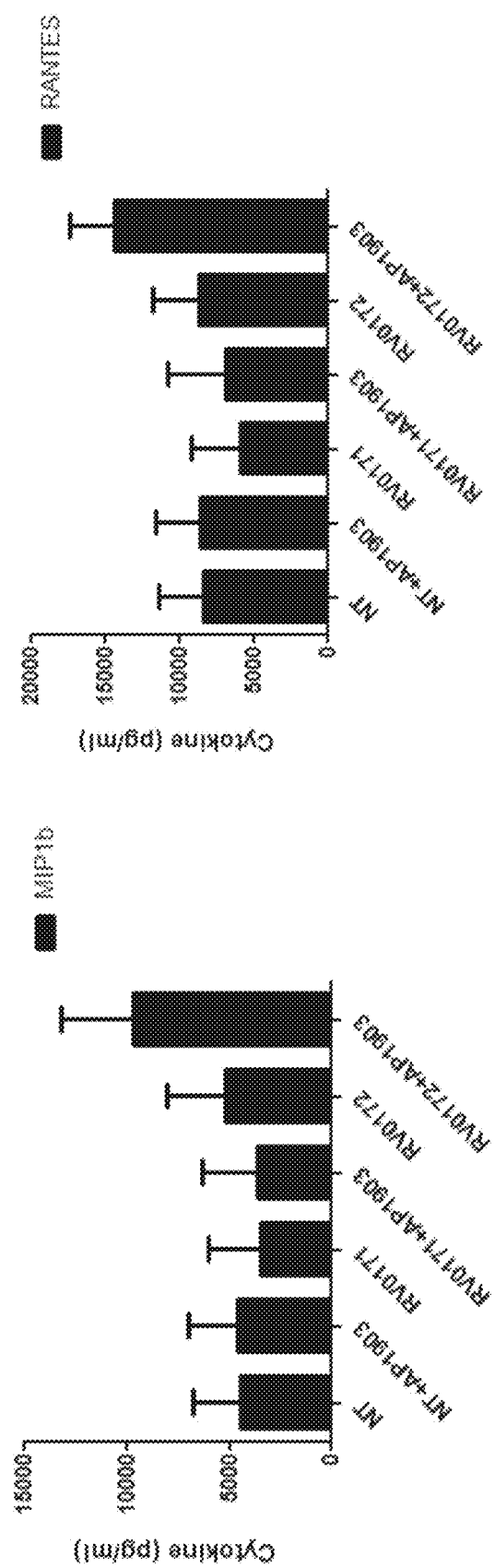
FIG. 51 provides bar graphs of MIP1β and RANTES levels in the modified and control T cells.
Figure 52:
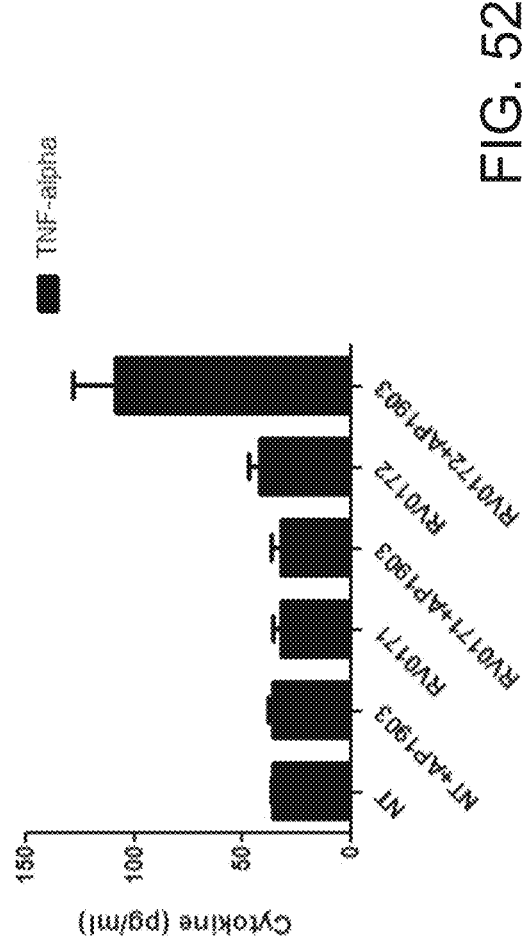
FIG. 52 provides a bar graph of TNF-α levels in the modified and control T cells.
Figure 53:
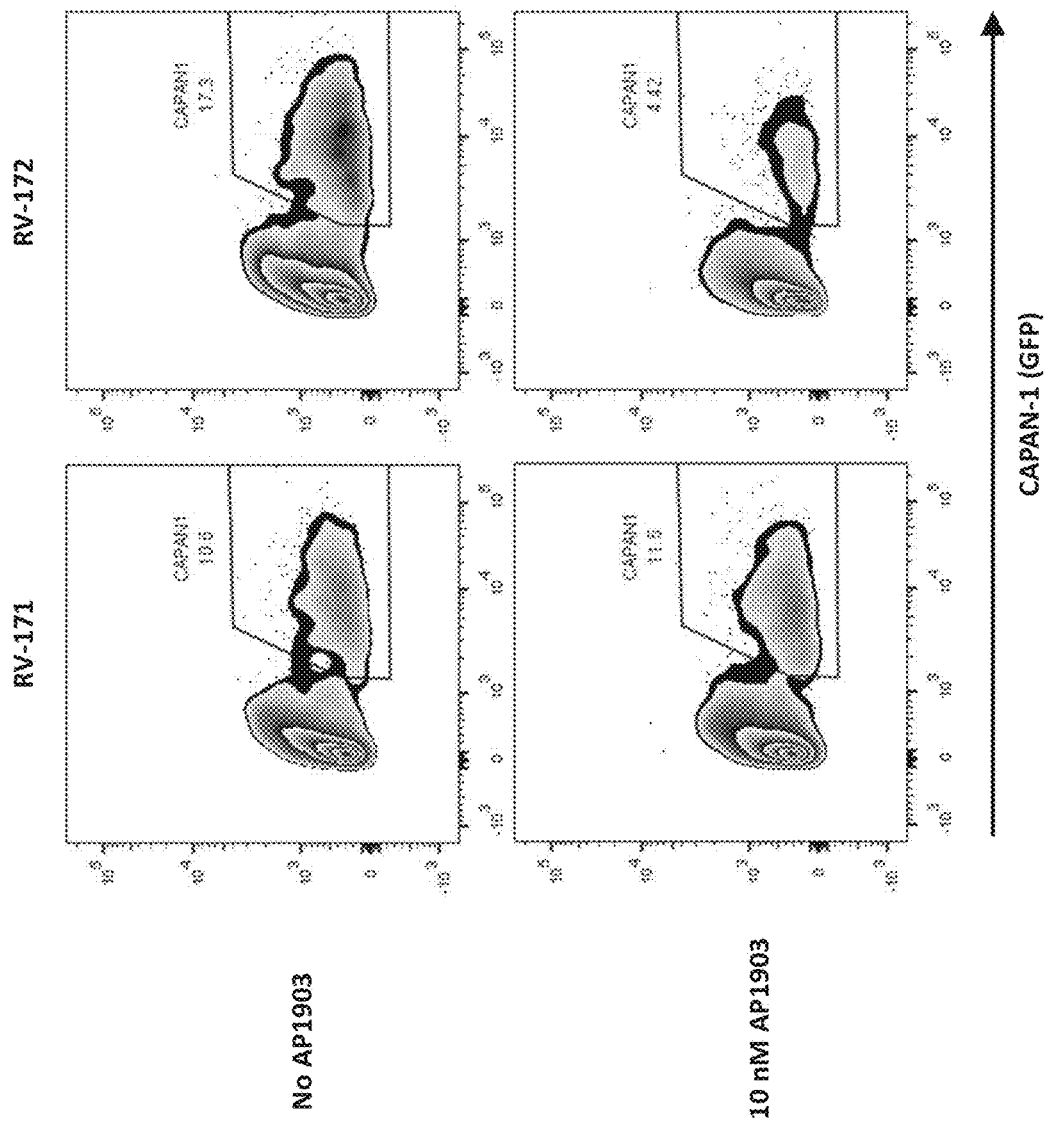
FIG. 53 Activation of iMC-transduced T cells with AP1903 induces T cell killing of tumor cells. T cells transduced with a control vector (lacking MyD88/CD40 signaling domains) or with iMC activation in macrophages were cultured with CAPAN-1-GFP tumor cells at a ratio of 5:1 T cells to tumor cells. Co-cultures were cultured with or without 10 nM AP1903. After 72 hours, co-cultures were analyzed for GFP+ tumor cells (X-axis) by flow cytometry.
Figure 54:
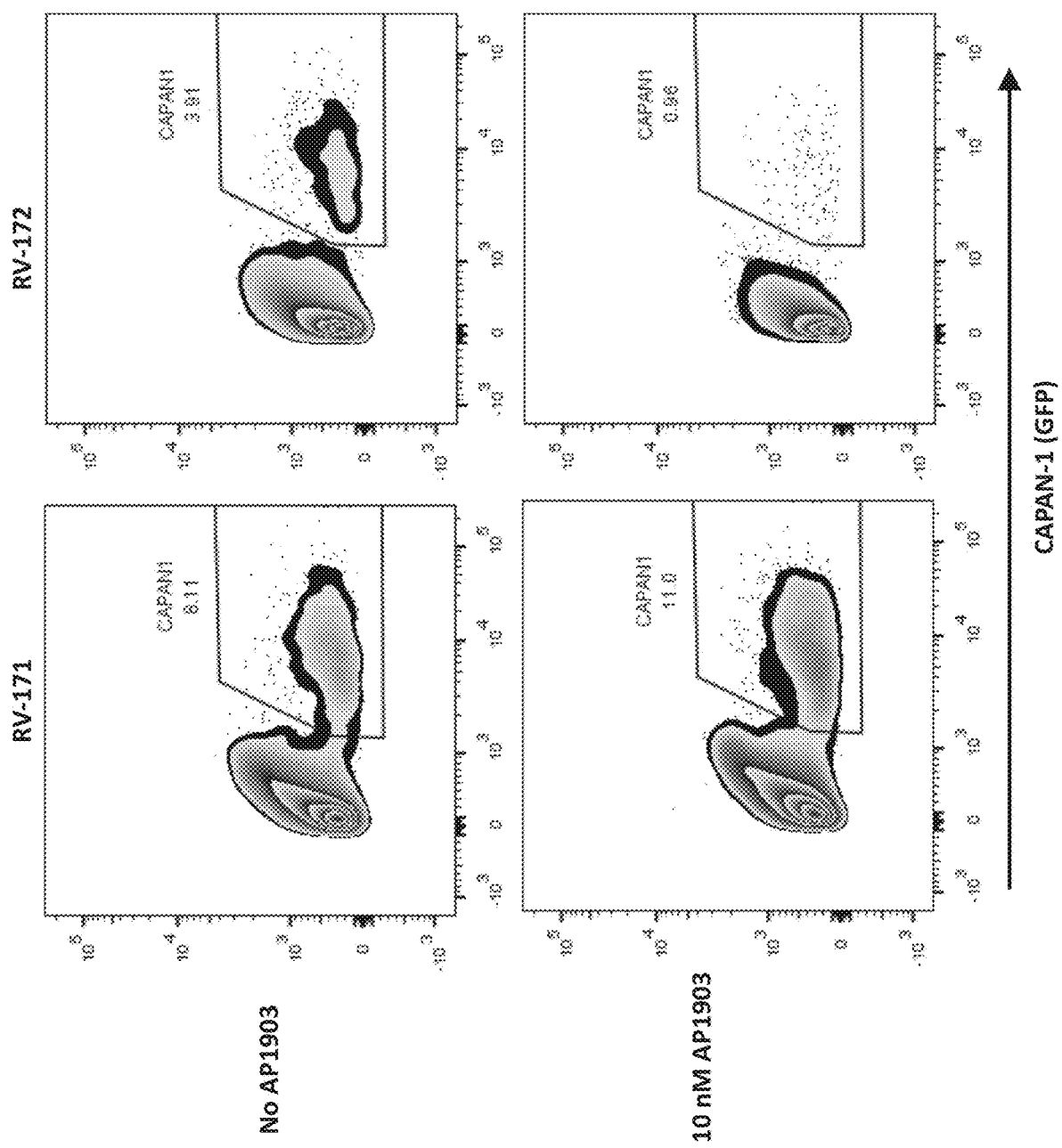
FIG. 54 depicts the results of a similar experiment to that discussed for FIG. 53, for a different donor.
Figure 55:
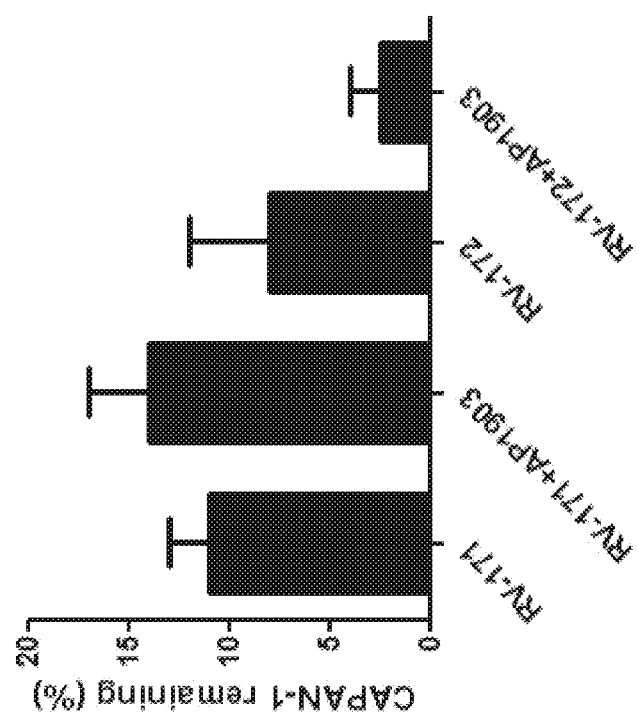
FIG. 55: Activation of iMC-transduced T cells with AP1903 induces T cell killing of tumor cells. T cells transduced with a control vector (lacking MyD88/CD40 signaling domains) or with iMC were cultured with CAPAN-1-GFP tumor cells at a ratio of 5:1 T cells to tumor cells. Co-cultures were cultured with or without 10 nM AP1903. After 72 hours, co-cultures were analyzed for GFP+ tumor cells by flow cytometry (n=2).
Figure 56:
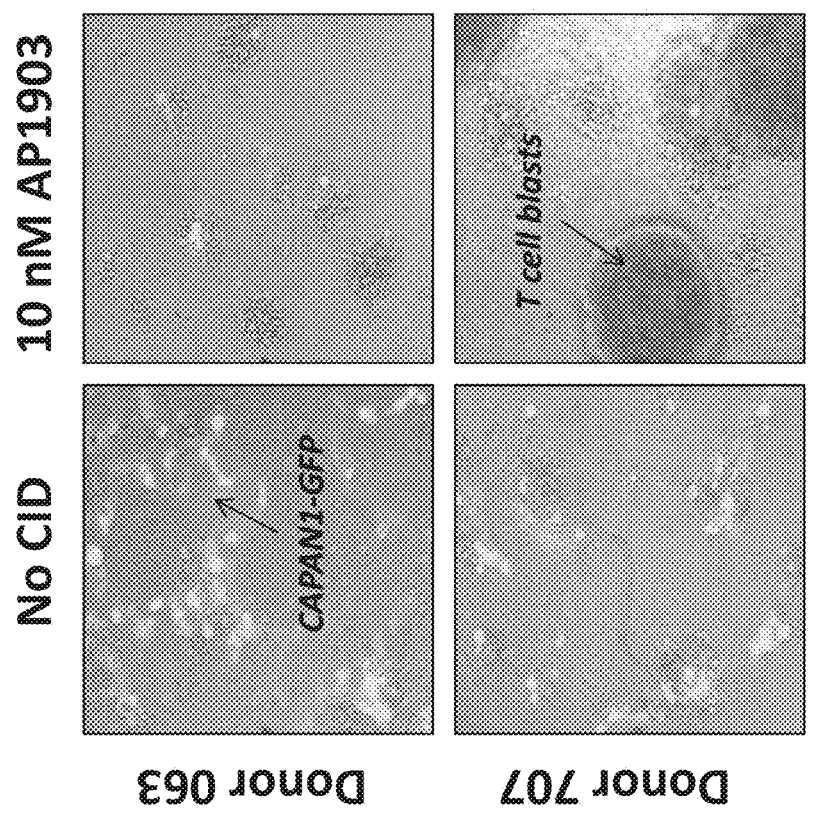
FIG. 56: Activation of iMC-transduced T cells with AP1903 induces T cell killing of tumor cells. T cells transduced with a control vector (lacking MyD88/CD40 signaling domains) or with iMC were cultured with CAPAN-1-GFP tumor cells at a ratio of 5:1 T cells to tumor cells. Co-cultures were cultured with or without 10 nM AP1903. After 72 hours, co-cultures were analyzed by fluorescent microscopy, showing the activation of T cell blasts (right two panels) and the elimination of GFP+ tumor cells when activated with 10 nM AP1903.
Figure 57:
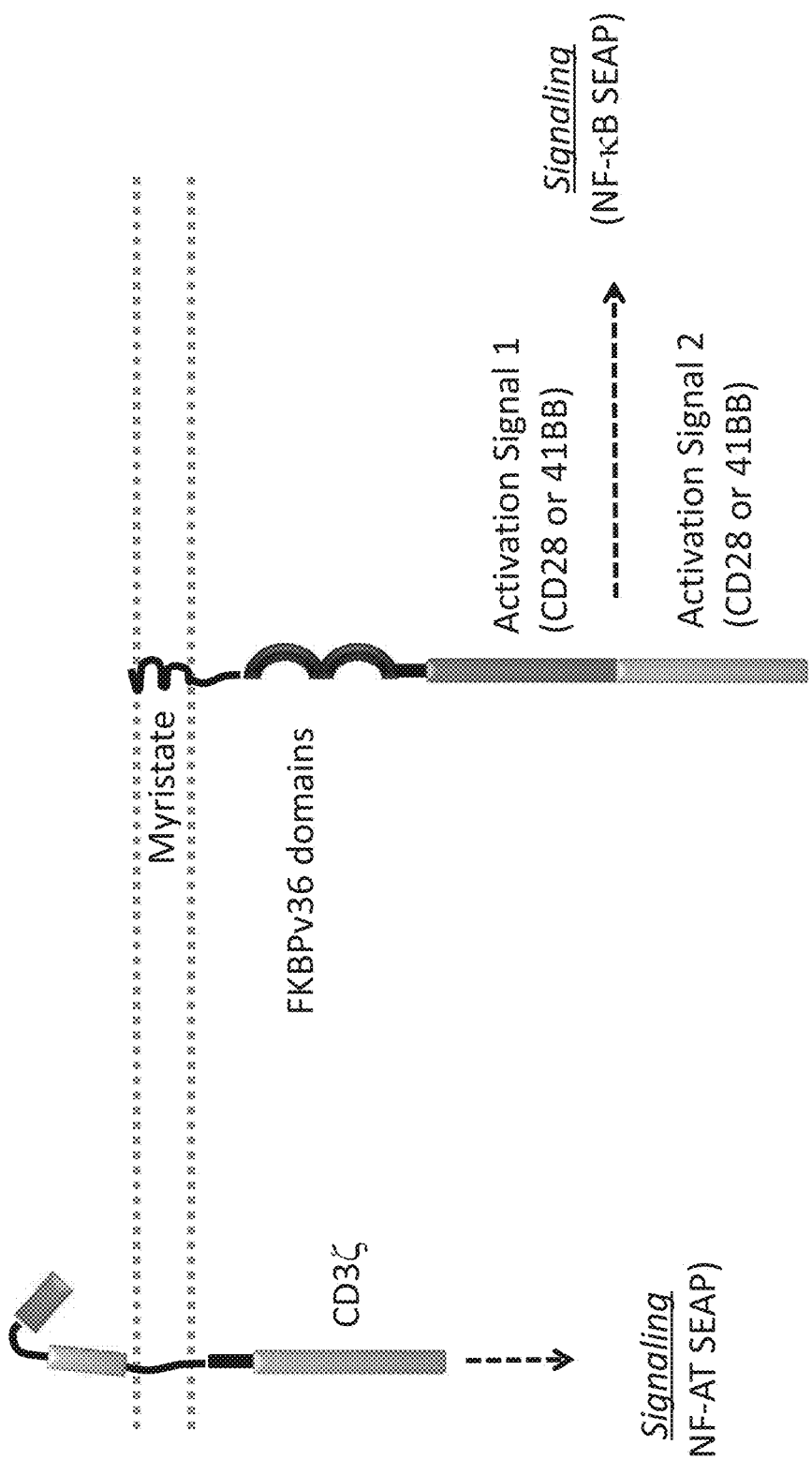
FIG. 57 is a schematic of a cell transduced or transfected with a chimeric antigen receptor (left) and an example of a chimeric signaling molecule as provided herein.
Figure 58:
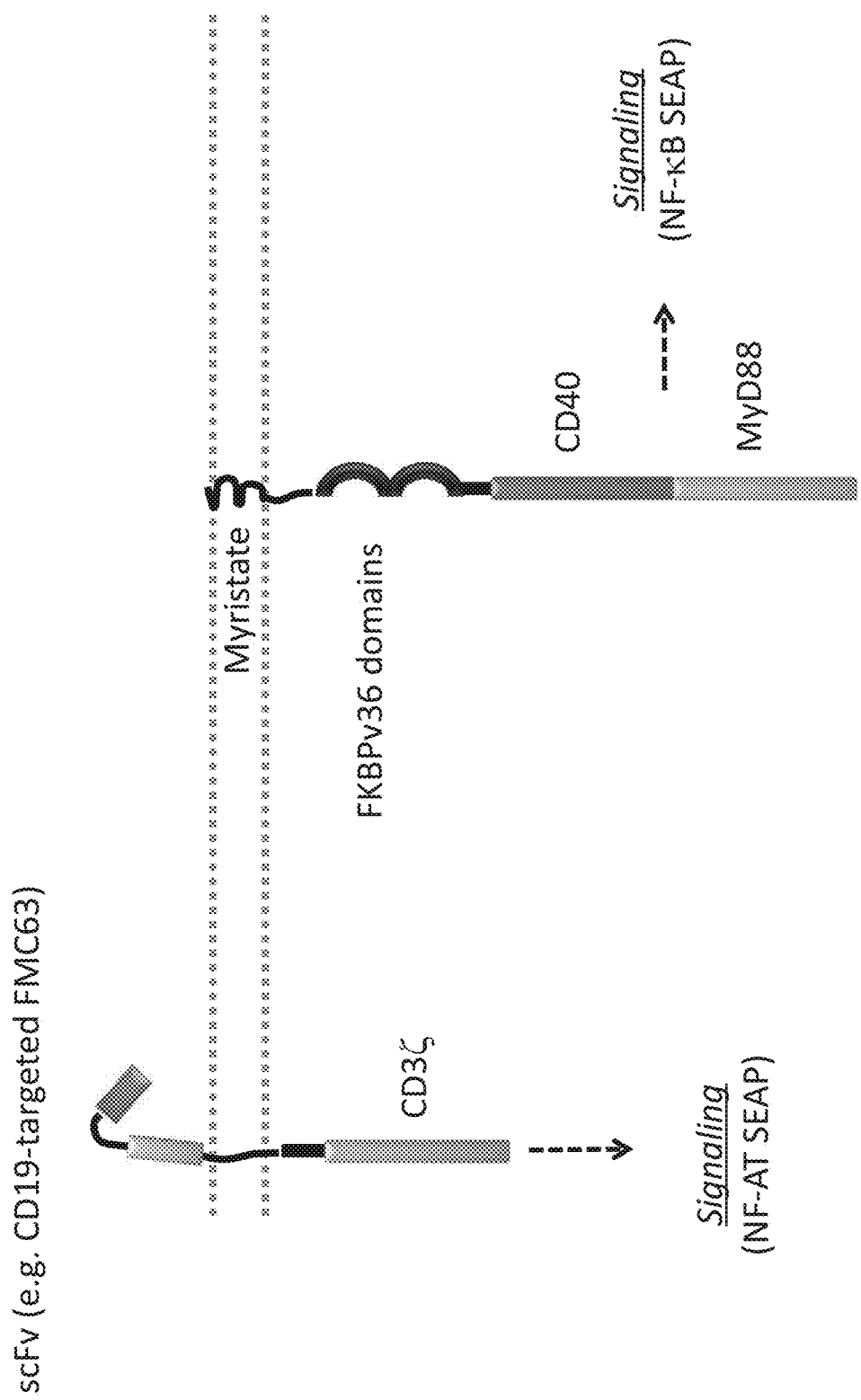
FIG. 58 is a schematic of a cell transduced or transfected with a chimeric antigen receptor (left) and an example of a chimeric signaling molecule as provided herein.

This CSM may also be expressed in a cell along with a CAR, which may, for example, comprise the scFv polypeptide, and the CD3 zeta chain. In this method, an inducible CSM molecule is used in combination with a CAR, thereby segregating CAR signaling into two separate functions. This second function, provided by the CAR, provides antigen-specific cytotoxicity to the engineered T cells. In FIG. 41, the example shows a CAR with specificity against PSMA; these engineered T cells may, for example, be administered to a subject to generate a specific immune response, for example one directed against a prostate cancer tumor (FIG. 43).

Figure 59:
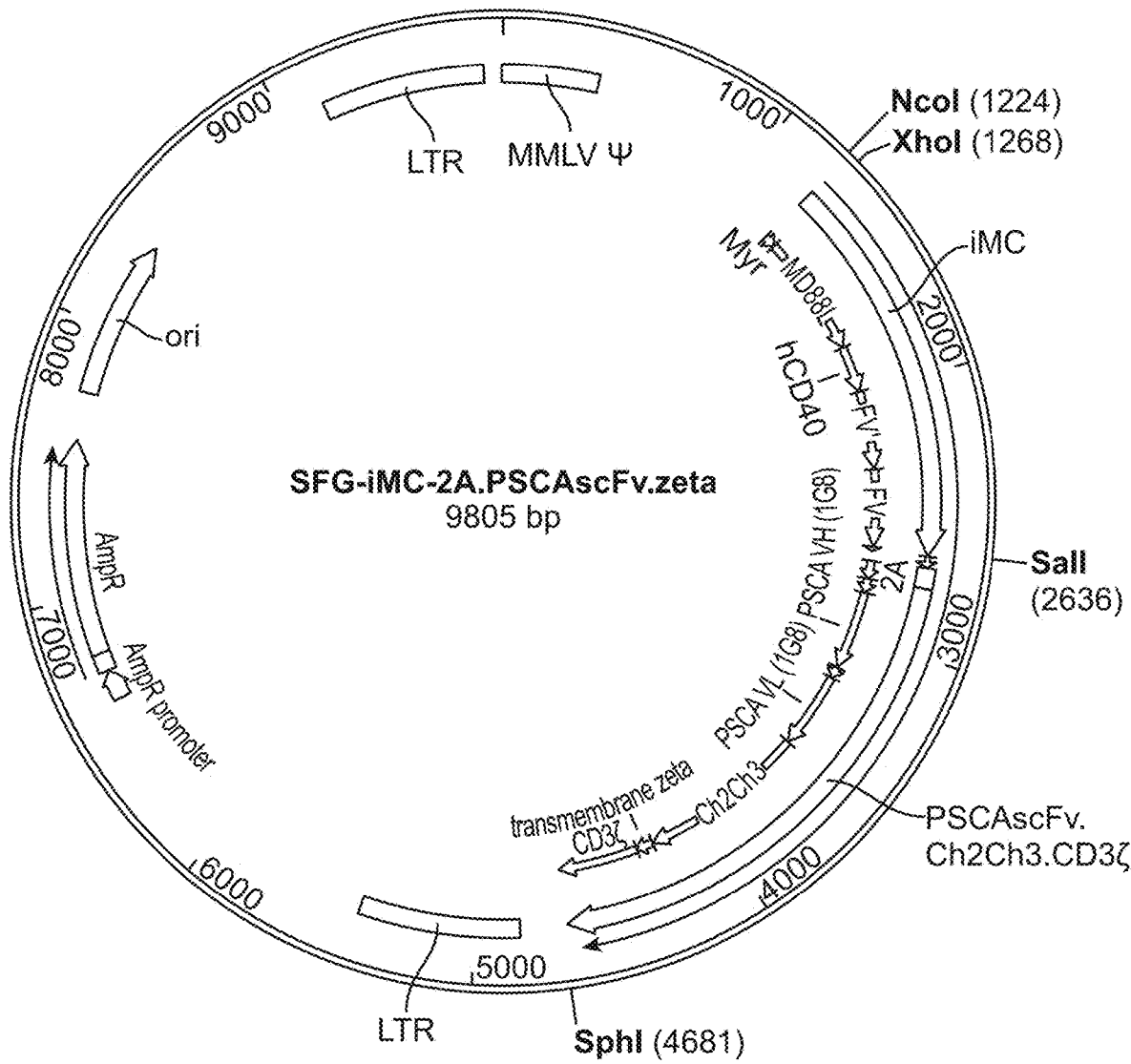
FIG. 59 is a plasmid map of an inducible chimeric stimulating molecule co-expressed with a chimeric antigen receptor, with a 2A polypeptide between the two chimeric polypeptides.
Figure 60C:
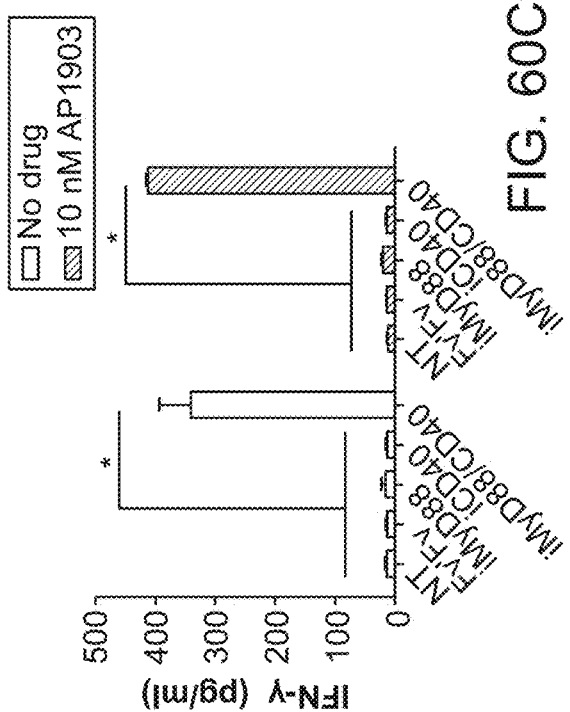
FIGS. 60A-60D provide examples of inducible chimeric stimulating molecules.
Figure 60D:
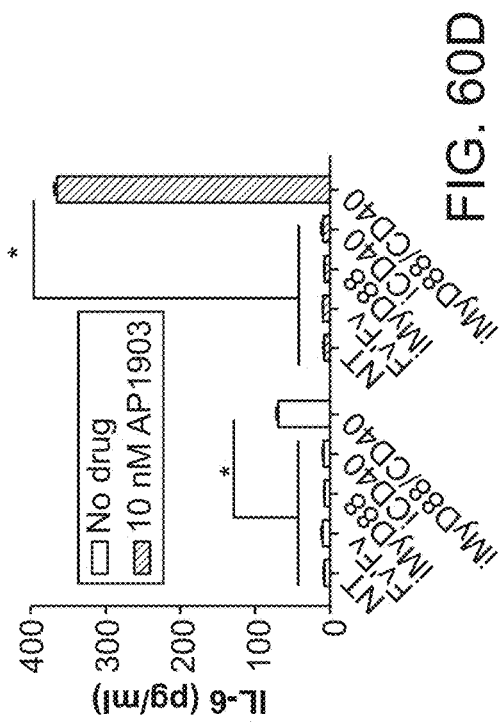
Figure 60A:
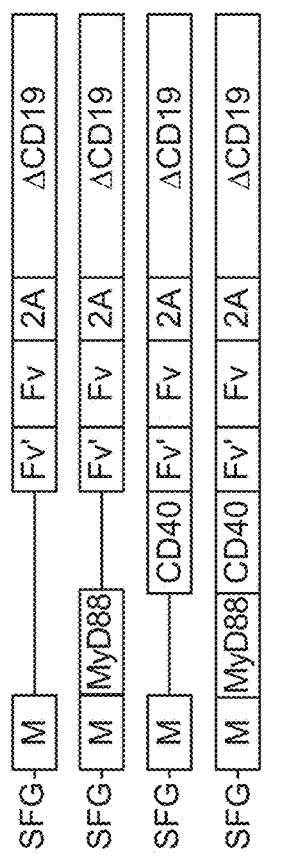
Figure 60B:
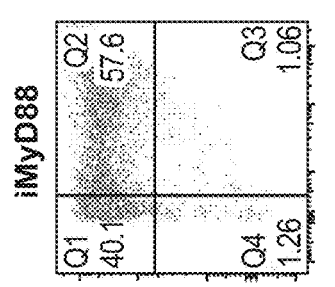
Figure 60B:
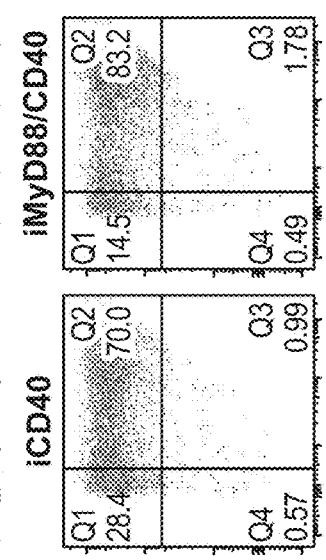
Figure 60B:
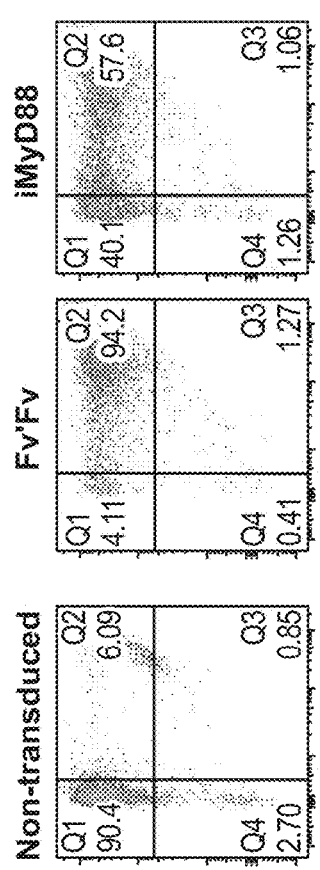
Figure 61:
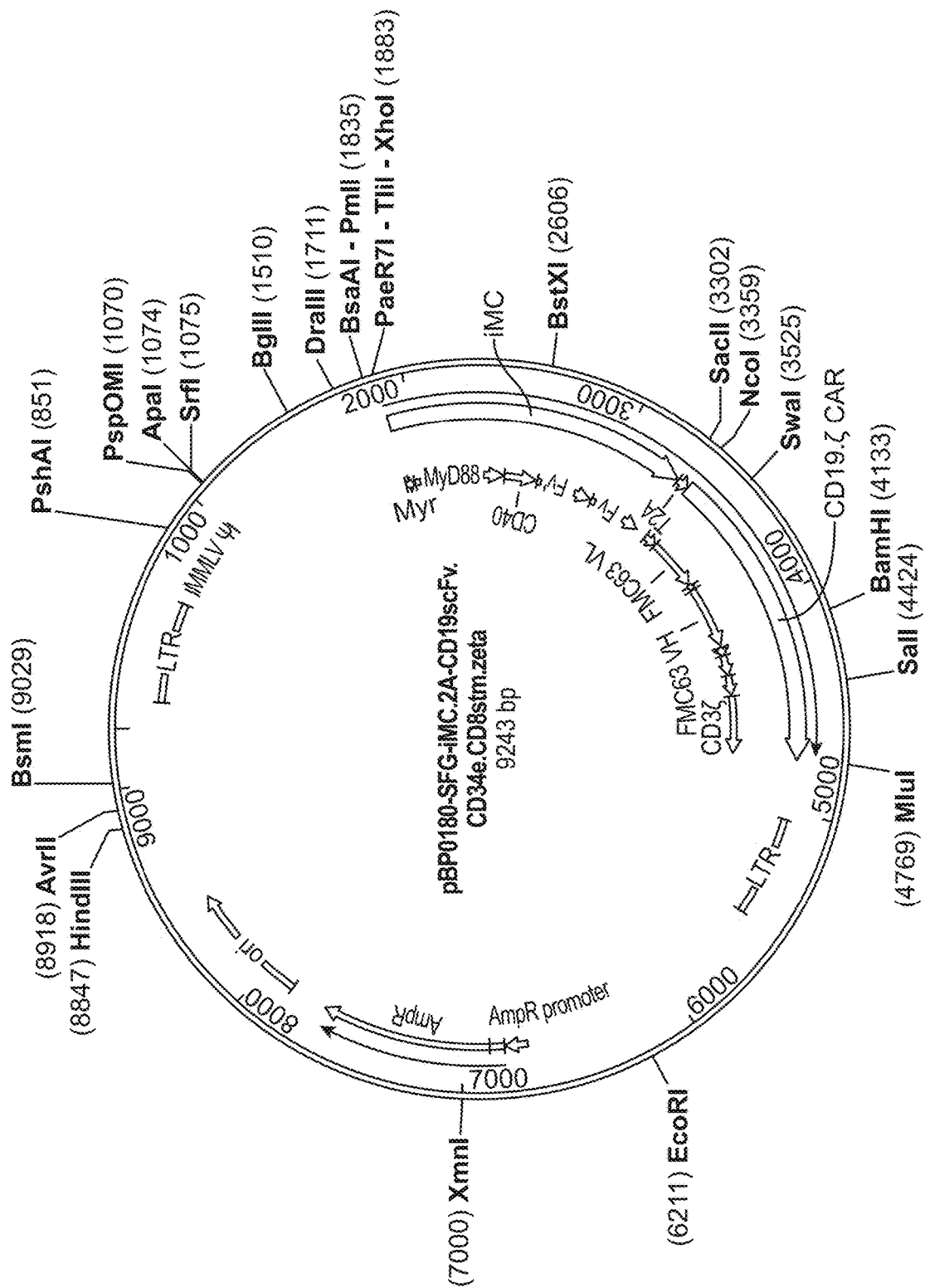
FIG. 61 is a plasmid map of a plasmid that encodes a polynucleotide coding for an inducible MyD88/CD40 chimeric stimulating molecule and a polynucleotide coding for a chimeric antigen receptor, where both polynucleotides are operably linked to the same promoter.
Figure 62:
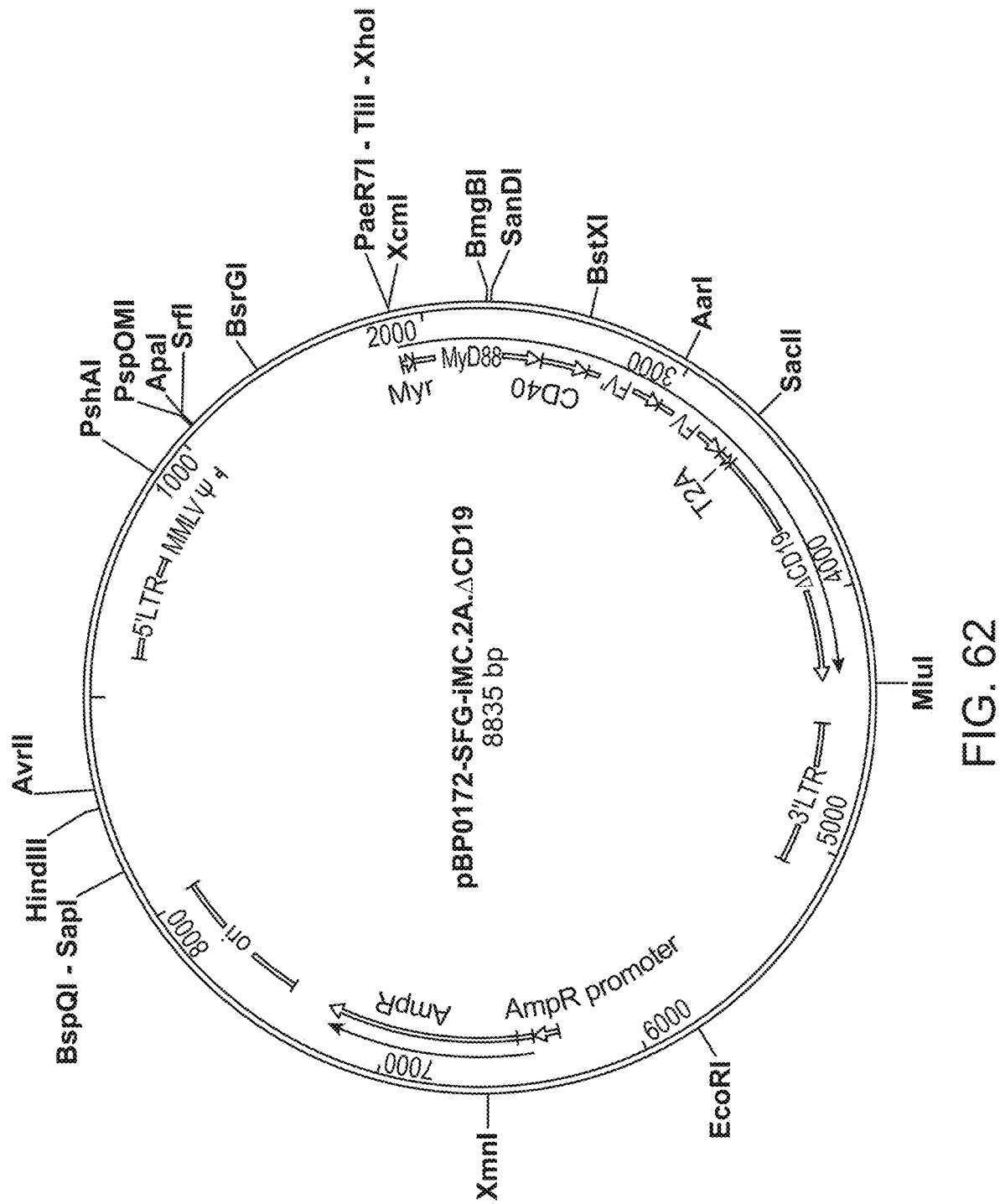
FIG. 62 is a plasmid map of a chimeric inducible costimulating molecule. The plasmid also encodes CD19 as a polypeptide marker.

As shown in FIG. 59, in some embodiments, the inducible co-stimulatory polypeptide, such as, for example, a CD40 cytoplasmic region polypeptide or a truncated MyD88 polypeptide is used to control activation of the chimeric antigen receptor itself. A polynucleotide that encodes this modified inducible chimeric antigen receptor may be used to transduce cells, such as, for example T cells. The cells may further express a chimeric signaling molecule as discussed herein, and in certain embodiments, the chimeric signaling molecule comprises a CD3 zeta polypeptide. In some embodiments, the inducible chimeric antigen receptor comprises both a CD40 cytoplasmic region polypeptide and a MyD88 polypeptide.

Chimeric inducible MyD88/CD40 protein can function as a potent costimulatory signal that enhances T cell survival, and augments T cell proliferation in the context of TCR or CAR signaling. In addition, this costimulatory pathway(s) can be activated in vivo using a highly specific, synthetic, small molecule dimerizing ligand, rimiducid. The separation of the cytolytic signal 1 (CD3) domain from costimulatory signal 2 (iMC) provides a unique mechanism by which T cells may be expanded in response to an administered ligand and tumor antigen, or potentially decreased in number by withdrawing stimulatory drug and allowing insufficient T cell activation to induce anergy and cell elimination. Moreover, the possible increased potency of iMC-driven CAR-T cells associated with regulated tumor-specific T cell expansion may accommodate previously CAR-T-resistant tumor targets, such as solid tumors.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to HLA or MHC loci that are antigenically distinct between the host and donor cells.

Thus, cells or tissue transferred from the same species can be antigenically distinct. Syngeneic mice can differ at one or more loci (congenics) and allogeneic mice can have the same background.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis*, influenza virus, parainfluenza viruses, respiratory syncytial virus, *Borrelia burgdorferi, Plasmodium*, herpes simplex viruses, human immunodeficiency virus, papillomavirus, *Vibrio cholera, E. coli*, measles virus, rotavirus, *shigella, Salmonella typhi, Neisseria gonorrhea. Therefore, any macromolecules, including virtually all proteins or peptides, can serve as antigens. Furthermore, antigens can be derived from recombinant or genomic DNA. Any DNA that contains nucleotide sequences or partial nucleotide sequences of a pathogenic genome or a gene or a fragment of a gene for a protein that elicits an immune response results in synthesis of an antigen. Furthermore, the present methods are not limited to the use of the entire nucleic acid sequence of a gene or genome. It is readily inherent that the present invention includes, but is not limited to, the use of partial nucleic acid sequences of more than one gene or genome and that these nucleic acid sequences are arranged in various combinations to elicit the desired immune response.*

An "antigen recognition moiety" may be any polypeptide or fragment thereof, such as, for example, an antibody fragment variable domain, either naturally-derived, or synthetic, which binds to an antigen. Examples of antigen recognition moieties include, but are not limited to, polypeptides derived from antibodies, such as, for example, single chain variable fragments (scFv), Fab, Fab', F(ab')2, and Fv fragments; polypeptides derived from T Cell receptors, such as, for example, TCR variable domains; and any ligand or receptor fragment that binds to the extracellular cognate protein.

The term "antigen-presenting cell" is any of a variety of cells capable of displaying, acquiring, or presenting at least one antigen or antigenic fragment on (or at) its cell surface. In general, the term "cell" can be any cell that accomplishes the goal of aiding the enhancement of an immune response (i.e., from the T-cell or -B-cell arms of the immune system) against an antigen or antigenic composition. As discussed in Kuby, 2000, Immunology, 4.sup.th edition, W.H. Freeman and company, for example, (incorporated herein by reference), and used herein in certain embodiments, a cell that displays or presents an antigen normally or with a class II major histocompatibility molecule or complex to an immune cell is an "cell." In certain aspects, a cell (e.g., an APC cell) may be fused with another cell, such as a recombinant cell or a tumor cell that expresses the desired antigen. Methods for preparing a fusion of two or more cells are discussed in, for example, Goding, J. W., Monoclonal Antibodies: Principles and Practice, pp. 65-66, 71-74 (Academic Press, 1986); Campbell, in: Monoclonal Antibody Technology, Laboratory Techniques in Biochemistry and Molecular Biology, Vol. 13, Burden & Von Knippenberg, Amsterdam, Elseview, pp. 75-83, 1984; Kohler & Milstein, Nature, 256:495-497, 1975; Kohler & Milstein, Eur. J. Immunol., 6:511-519, 1976, Gefter et al., Somatic Cell Genet., 3:231-236, 1977, each incorporated herein by reference. In some cases, the immune cell to which a cell displays or presents an antigen to is a $CD4^+TH$ cell. Additional molecules expressed on the APC or other immune cells may aid or improve the enhancement of an immune response. Secreted or soluble molecules, such as for example, cytokines and adjuvants, may also aid or enhance the immune response against an antigen. Various examples are discussed herein.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "iCD40 molecule" is defined as an inducible CD40. This iCD40 can bypass mechanisms that extinguish endogenous CD40 signaling. The term "iCD40" embraces "iCD40 nucleic acids," "iCD40 polypeptides" and/or iCD40 expression vectors.

As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There are times when the full or partial genomic sequence is used, such as where the non-coding regions are required for optimal expression or where non-coding regions such as introns are to be targeted in an antisense strategy.

The term "dendritic cell" (DC) is an cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. The DC has a characteristic morphology with thin sheets (lamellipodia) extending in multiple directions away from the dendritic cell body. Typically, dendritic cells express high levels of MHC and costimulatory (e.g., B7-1 and B7-2) molecules. Dendritic cells can induce antigen specific differentiation of T cells in vitro, and are able to initiate primary T cell responses in vitro and in vivo.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. The term "therapeutic construct" may also be used to refer to the expression construct or transgene. The expression construct or transgene may be used, for example, as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra.

As used herein, the term "ex vivo" refers to "outside" the body. The terms "ex vivo" and "in vitro" can be used interchangeably herein.

As used herein, the term "functionally equivalent," as it relates to CD40, for example, refers to a CD40 nucleic acid fragment, variant, or analog, refers to a nucleic acid that codes for a CD40 polypeptide, or a CD40 polypeptide, that stimulates an immune response to destroy tumors or hyperproliferative disease. "Functionally equivalent" or "a functional fragment" of a CD40 polypeptide refers, for example, to a CD40 polypeptide that is lacking the extracellular domain, but is capable of amplifying the T cell-mediated tumor killing response by upregulating dendritic cell expression of antigen presentation molecules. When the term "functionally equivalent" is applied to other nucleic acids or polypeptides, such as, for example, PSA peptide, PSMA peptide, MyD88, or truncated MyD88, it refers to fragments, variants, and the like that have the same or similar activity as the reference polypeptides of the methods herein. For example, a functional fragment of a tumor antigen polypeptide, such as, for example, PSMA, may be antigenic, allowing for antibodies to be produced that recognize the particular tumor antigen. A functional fragment of a ligand binding region, for example, Fvls, would include a sufficient portion of the ligand binding region polypeptide to bind the appropriate ligand. "Functionally equivalent" refers, for example, to a co-stimulatory polypeptide that is lacking the extracellular domain, but is capable of amplifying the T cell-mediated tumor killing response when expressed in T cells.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

As used herein, the term "gene" is defined as a functional protein, polypeptide, or peptide-encoding unit. As will be understood, this functional term includes genomic sequences, cDNA sequences, and smaller engineered gene segments that express, or are adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term "immunocompromised" as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body's defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions. In some embodiments, the subject is a mammal. In some embodiments, the subject is a human.

As used herein, the term "polynucleotide" is defined as a chain of nucleotides. Furthermore, nucleic acids are polymers of nucleotides. Thus, nucleic acids and polynucleotides as used herein are interchangeable. Nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PORT", and the like, and by synthetic means. Furthermore, polynucleotides include mutations of the polynucleotides, include but are not limited to, mutation of the nucleotides, or nucleosides by methods well known in the art. A nucleic acid may comprise one or more polynucleotides.

As used herein, the term "polypeptide" is defined as a chain of amino acid residues, usually having a defined sequence. As used herein the term polypeptide may be interchangeable with the term "proteins".

As used herein, the term "promoter" is defined as a DNA sequence recognized by the synthetic machinery of the cell, or introduced synthetic machinery, required to initiate the specific transcription of a gene.

As used herein, the terms "regulate an immune response," "modulate an immune response," or "control an immune response," refer to the ability to modify the immune response. For example, the composition is capable of enhancing and/or activating the immune response. Still further, the composition is also capable of inhibiting the immune response. The form of regulation is determined by the ligand that is used with the composition. For example, a dimeric analog of the chemical results in dimerization of the co-stimulatory polypeptide leading to activation of the T cell, however, a monomeric analog of the chemical does not result in dimerization of the co-stimulatory polypeptide, which would not activate the T cells.

The term "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term "syngeneic" refers to cells, tissues or animals that have genotypes that are identical or closely related enough to allow tissue transplant, or are immunologically compatible. For example, identical twins or animals of the same inbred strain. Syngeneic and isogeneic can be used interchangeably.

The term "patient" or "subject" are interchangeable, and, as used herein includes, but is not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

By "T cell activation molecule" is meant a polypeptide that, when incorporated into a T cell expressing a chimeric antigen receptor, enhances activation of the T cell. Examples include, but are not limited to, ITAM-containing, Signal 1 conferring molecules such as, for example, CD3 ζ polypeptide, and Fc receptor gamma, such as, for example. Fc epsilon receptor gamma (FcεR1γ) subunit (Haynes, N. M., et al. J. Immunol. 166:182-7 (2001).

As used herein, the term "vaccine" refers to a formulation that contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

As used herein, the term "under transcriptional control" or "operatively linked" is defined as the promoter is in the correct location and orientation in relation to the nucleic acid to control RNA polymerase initiation and expression of the gene.

As used herein, the terms "treatment", "treat", "treated", or "treating" refer to prophylaxis and/or therapy. When used with respect to a solid tumor, such as a cancerous solid tumor, for example, the term refers to prevention by prophylactic treatment, which increases the subject's resistance to solid tumors or cancer. In some examples, the subject may be treated to prevent cancer, where the cancer is familial, or is genetically associated. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e. g., reduce or eliminate the infection or prevent it from becoming worse.

As used herein, the term "vaccine" refers to a formulation which contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

Blood disease: The terms "blood disease", "blood disease" and/or "diseases of the blood" as used herein, refers to conditions that affect the production of blood and its components, including but not limited to, blood cells, hemoglobin, blood proteins, the mechanism of coagulation, production of blood, production of blood proteins, the like and combinations thereof. Non-limiting examples of blood diseases include anemias, leukemias, lymphomas, hematological neoplasms, albuminemias, haemophilias and the like.

Bone marrow disease: The term "bone marrow disease" as used herein, refers to conditions leading to a decrease in the production of blood cells and blood platelets. In some bone marrow diseases, normal bone marrow architecture can be displaced by infections (e.g., tuberculosis) or malignancies, which in turn can lead to the decrease in production of blood cells and blood platelets. Non-limiting examples of bone marrow diseases include leukemias, bacterial infections (e.g., tuberculosis), radiation sickness or poisoning, apnocytopenia, anemia, multiple myeloma and the like.

T cells and Activated T cells (include that this means $CD3^+$ cells): T cells (also referred to as T lymphocytes) belong to a group of white blood cells referred to as lymphocytes. Lymphocytes generally are involved in cell-mediated immunity. The "T" in "T cells" refers to cells derived from or whose maturation is influenced by the thymus. T cells can be distinguished from other lymphocytes types such as B cells and Natural Killer (NK) cells by the presence of cell surface proteins known as T cell receptors. The term "activated T cells" as used herein, refers to T cells that have been stimulated to produce an immune response (e.g., clonal expansion of activated T cells) by recognition of an antigenic determinant presented in the context of a Class II major histocompatibility (MHC) marker. T-cells are activated by the presence of an antigenic determinant, cytokines and/or lymphokines and cluster of differentiation cell surface proteins (e.g., CD3, CD4, CD8, the like and combinations thereof). Cells that express a cluster of differential protein often are said to be "positive" for expression of that protein on the surface of T-cells (e.g., cells positive for CD3 or CD 4 expression are referred to as CD3⁺ or CD4⁺). CD3 and CD4 proteins are cell surface receptors or co-receptors that may be directly and/or indirectly involved in signal transduction in T cells.

Peripheral blood: The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow.

Umbilical cord blood: Umbilical cord blood is distinct from peripheral blood and blood sequestered within the lymphatic system, spleen, liver or bone marrow. The terms "umbilical cord blood", "umbilical blood" or "cord blood", which can be used interchangeably, refers to blood that remains in the placenta and in the attached umbilical cord after child birth. Cord blood often contains stem cells including hematopoietic cells.

By "obtained or prepared" as, for example, in the case of cells, is meant that the cells or cell culture are isolated, purified, or partially purified from the source, where the source may be, for example, umbilical cord blood, bone marrow, or peripheral blood. The terms may also apply to the case where the original source, or a cell culture, has been cultured and the cells have replicated, and where the progeny cells are now derived from the original source.

By "kill" or "killing" as in a percent of cells killed, is meant the death of a cell through apoptosis, as measured using any method known for measuring apoptosis. The term may also refer to cell ablation.

Donor T cell: The term "donor T cell" as used here refers to T cells that often are administered to a recipient to confer anti-viral and/or anti-tumor immunity following allogeneic stem cell transplantation. Donor T cells often are utilized to inhibit marrow graft rejection and increase the success of alloengraftment, however the same donor T cells can cause an alloaggressive response against host antigens, which in turn can result in graft versus host disease (GVHD). Certain activated donor T cells can cause a higher or lower GvHD response than other activated T cells. Donor T cells may also be reactive against recipient tumor cells, causing a beneficial graft vs. tumor effect.

Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, preferably at least 80%, more preferably at least 90%, and most preferably at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the preferred settings are those that results in the highest sequence similarity.

Mesenchymal stromal cell: The terms "mesenchymal stromal cell" or "bone marrow derived mesenchymal stromal cell" as used herein, refer to multipotent stem cells that can differentiate ex vivo, in vitro and in vivo into adipocytes, osteoblasts and chondroblasts, and may be further defined as a fraction of mononuclear bone marrow cells that adhere to plastic culture dishes in standard culture conditions, are negative for hematopoietic lineage markers and are positive for CD73, CD90 and CD105.

Embryonic stem cell: The term "embryonic stem cell" as used herein, refers to pluripotent stem cells derived from the inner cell mass of the blastocyst, an early-stage embryo of between 50 to 150 cells. Embryonic stem cells are characterized by their ability to renew themselves indefinitely and by their ability to differentiate into derivatives of all three primary germ layers, ectoderm, endoderm and mesoderm. Pluripotent is distinguished from multipotent in that pluripotent cells can generate all cell types, while multipotent cells (e.g., adult stem cells) can only produce a limited number of cell types.

Inducible pluripotent stem cell: The terms "inducible pluripotent stem cell" or "induced pluripotent stem cell" as used herein refers to adult, or differentiated cells, that are "reprogrammed" or induced by genetic (e.g., expression of genes that in turn activates pluripotency), biological (e.g., treatment viruses or retroviruses) and/or chemical (e.g., small molecules, peptides and the like) manipulation to generate cells that are capable of differentiating into many if not all cell types, like embryonic stem cells. Inducible pluripotent stem cells are distinguished from embryonic stem cells in that they achieve an intermediate or terminally differentiated state (e.g., skin cells, bone cells, fibroblasts, and the like) and then are induced to dedifferentiate, thereby regaining some or all of the ability to generate multipotent or pluripotent cells.

CD34⁺ cell: The term "CD34⁺ cell" as used herein refers to a cell expressing the CD34 protein on its cell surface. "CD34" as used herein refers to a cell surface glycoprotein (e.g., sialomucin protein) that often acts as a cell-cell adhesion factor and is involved in T cell entrance into lymph nodes, and is a member of the "cluster of differentiation" gene family. CD34 also may mediate the attachment of stem cells to bone marrow, extracellular matrix or directly to stromal cells. CD34⁺ cells often are found in the umbilical cord and bone marrow as hematopoietic cells, a subset of mesenchymal stem cells, endothelial progenitor cells, endothelial cells of blood vessels but not lymphatics (except pleural lymphatics), mast cells, a sub-population of dendritic cells (which are factor XIIIa negative) in the interstitium and around the adnexa of dermis of skin, as well as cells in certain soft tissue tumors (e.g., alveolar soft part sarcoma, pre-B acute lymphoblastic leukemia (Pre-B-ALL), acute myelogenous leukemia (AML), AML-M7, dermatofibrosarcoma protuberans, gastrointestinal stromal tumors, giant cell fibroblastoma, granulocytic sarcoma, Kaposi's sarcoma, liposarcoma, malignant fibrous histiocytoma, malignant peripheral nerve sheath tumors, mengingeal hemangiopericytomas, meningiomas, neurofibromas, schwannomas, and papillary thyroid carcinoma).

Tumor infiltrating lymphocytes (TILs) refer to T cells having various receptors which infiltrate tumors and kill tumor cells in a targeted manor. Regulating the activity of the TILs using the methods of the present application would allow for more direct control of the elimination of tumor cells.

Gene expression vector: The terms "gene expression vector", "nucleic acid expression vector", or "expression vector" as used herein, which can be used interchangeably throughout the document, generally refers to a nucleic acid molecule (e.g., a plasmid, phage, autonomously replicating sequence (ARS), artificial chromosome, yeast artificial chromosome (e.g., YAC) that can be replicated in a host cell and be utilized to introduce a gene or genes into a host cell. The genes introduced on the expression vector can be endogenous genes (e.g., a gene normally found in the host cell or organism) or heterologous genes (e.g., genes not normally found in the genome or on extra-chromosomal nucleic acids of the host cell or organism). The genes introduced into a cell by an expression vector can be native genes or genes that have been modified or engineered. The gene expression vector also can be engineered to contain 5' and 3' untranslated regulatory sequences that sometimes can function as enhancer sequences, promoter regions and/or terminator sequences that can facilitate or enhance efficient transcription of the gene or genes carried on the expression vector. A gene expression vector sometimes also is engineered for replication and/or expression functionality (e.g., transcription and translation) in a particular cell type, cell location, or tissue type. Expression vectors sometimes include a selectable marker for maintenance of the vector in the host or recipient cell.

Developmentally regulated promoter: The term "developmentally regulated promoter" as used herein refers to a promoter that acts as the initial binding site for RNA polymerase to transcribe a gene which is expressed under certain conditions that are controlled, initiated by or influenced by a developmental program or pathway. Developmentally regulated promoters often have additional control regions at or near the promoter region for binding activators or repressors of transcription that can influence transcription of a gene that is part of a development program or pathway. Developmentally regulated promoters sometimes are involved in transcribing genes whose gene products influence the developmental differentiation of cells.

Developmentally differentiated cells: The term "developmentally differentiated cells", as used herein refers to cells that have undergone a process, often involving expression of specific developmentally regulated genes, by which the cell evolves from a less specialized form to a more specialized form in order to perform a specific function. Non-limiting examples of developmentally differentiated cells are liver cells, lung cells, skin cells, nerve cells, blood cells, and the like. Changes in developmental differentiation generally involve changes in gene expression (e.g., changes in patterns of gene expression), genetic re-organization (e.g., remodeling or chromatin to hide or expose genes that will be silenced or expressed, respectively), and occasionally involve changes in DNA sequences (e.g., immune diversity differentiation). Cellular differentiation during development can be understood as the result of a gene regulatory network. A regulatory gene and its cis-regulatory modules are nodes in a gene regulatory network that receive input (e.g., protein expressed upstream in a development pathway or program) and create output elsewhere in the network (e.g., the expressed gene product acts on other genes downstream in the developmental pathway or program).

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

In some embodiments, the nucleic acid is contained within a viral vector. In certain embodiments, the viral vector is an adenoviral vector, or a retroviral or lentiviral vector. It is understood that in some embodiments, the cell is contacted with the viral vector ex vivo, and in some embodiments, the cell is contacted with the viral vector in vivo.

In some embodiments, the cell is a dendritic cell, for example, a mammalian dendritic cell. Often, the cell is a human dendritic cell.

In certain embodiments, the cell is also contacted with an antigen. Often, the cell is contacted with the antigen ex vivo. Sometimes, the cell is contacted with the antigen in vivo. In some embodiments, the cell is in a subject and an immune response is generated against the antigen. Sometimes, the immune response is a cytotoxic T-lymphocyte (CTL) immune response. Sometimes, the immune response is generated against a tumor antigen. In certain embodiments, the cell is activated without the addition of an adjuvant.

In some embodiments, the cell is transduced with the nucleic acid ex vivo and administered to the subject by intradermal administration. In some embodiments, the cell is transduced with the nucleic acid ex vivo and administered to the subject by subcutaneous administration. Sometimes, the cell is transduced with the nucleic acid ex vivo. Sometimes, the cell is transduced with the nucleic acid in vivo.

By MyD88 is meant the myeloid differentiation primary response gene 88, for example, but not limited to the human version, cited as ncbi Gene ID 4615. By "truncated," is meant that the protein is not full length and may lack, for example, a domain. For example, a truncated MyD88 is not full length and may, for example, be missing the Toll/Interleukin-1 receptor domain (TIR domain). One example of a truncated MyD88 is indicated as MyD88L herein, and is also presented as SEQ ID NOs: 4 and 5. SEQ ID NOs 71 and 72 include the linkers added during subcloning. By a nucleic acid sequence coding for "truncated MyD88" is meant the nucleic acid sequence coding for the truncated MyD88 peptide, the term may also refer to the nucleic acid sequence including the portion coding for any amino acids added as an artifact of cloning, including any amino acids coded for by the linkers. The inducible MyD88/CD40 polypeptide may also include full length MyD88 polypeptide, for example, having the nucleotide or amino acid sequence provided in SEQ ID NOs: 48 or 49. The nucleic acid sequence coding for MyD88 or other polypeptides of the present application may be, for example, codon-optimized, comprising preferred codons in modified cells, or wobbled codons as provided herein.

In the methods herein, the inducible CD40 portion of the peptide may be located either upstream or downstream from the inducible MyD88 or truncated MyD88 polypeptide portion. Also, the inducible CD40 portion and the inducible MyD88 or truncated MyD88 adapter protein portions may be transfected or transduced into the cells either on the same vector, in cis, or on separate vectors, in trans.

The cell in some embodiments is contacted with an antigen, sometimes ex vivo. In certain embodiments the cell is in a subject and an immune response is generated against the antigen, such as a cytotoxic T-lymphocyte (CTL) immune response. In certain embodiments, an immune response is generated against a tumor antigen (e.g., PSMA). In some embodiments, the nucleic acid is prepared ex vivo and administered to the subject by intradermal administration or by subcutaneous administration, for example. Sometimes the cell is transduced or transfected with the nucleic acid ex vivo or in vivo.

In some embodiments, the nucleic acid comprises a promoter sequence operably linked to the polynucleotide sequence. Alternatively, the nucleic acid comprises an ex vivo-transcribed RNA, containing the protein-coding region of the chimeric protein.

By "reducing tumor size" or "inhibiting tumor growth" of a solid tumor is meant a response to treatment, or stabilization of disease, according to standard guidelines, such as, for example, the Response Evaluation Criteria in Solid Tumors (RECIST) criteria. For example, this may include a reduction in the diameter of a solid tumor of about 5%, 10%, 20%, 30%, 40%, 50%, 60%, 70%, 80%, 90%, or 100%, or the reduction in the number of tumors, circulating tumor cells, or tumor markers, of about 5%, 10%, 20%, 30%, 40%, 50%, 60%, 70%, 80%, 90%, or 100%. The size of tumors may be analyzed by any method, including, for example, CT scan, MRI, for example, CT-MRI, chest X-ray (for tumors of the lung), or molecular imaging, for example, PET scan, such as, for example, a PET scan after administering an iodine 123-labelled PSA, for example, PSMA ligand, such as, for example, where the inhibitor is TROFEX™/MIP-1072/1095, or molecular imaging, for example, SPECT, or a PET scan using PSA, for example, PSMA antibody, such as, for example, capromad pendetide (PROSTASCINT), a 111-iridium labeled PSMA antibody.

By "reducing, slowing, or inhibiting tumor vascularization is meant a reduction in tumor vascularization of about 5%, 10%, 20%, 30%, 40%, 50%, 60%, 70%, 80%, 90%, or 100%, or a reduction in the appearance of new vasculature of about 5%, 10%, 20%, 30%, 40%, 50%, 60%, 70%, 80%, 90%, or 100%, when compared to the amount of tumor vascularization before treatment. The reduction may refer to one tumor, or may be a sum or an average of the vascularization in more than one tumor. Methods of measuring tumor vascularization include, for example, CAT scan, MRI, for example, CT-MRI, or molecular imaging, for example, SPECT, or a PET scan, such as, for example, a PET scan after administering an iodine 123-labelled PSA, for example, PSMA ligand, such as, for example, where the inhibitor is TROFEX™/MIP-1072/1095, or a PET scan using PSA, for example, PSMA antibody, such as, for example, capromad pendetide (PROSTASCINT), a 111-iridium labeled PSMA antibody.

A tumor is classified as a prostate cancer tumor when, for example, the tumor is present in the prostate gland, or has derived from or metastasized from a tumor in the prostate gland, or produces PSA. A tumor has metastasized from a tumor in the prostate gland, when, for example, it is determined that the tumor has chromosomal breakpoints that are the same as, or similar to, a tumor in the prostate gland of the subject.

Incorporated by reference in their entirety is U.S. Pat. No. 7,404,950, issued Jun. 29, 2008, to Spencer, D. et al. and U.S. Pat. No. 8,691,210 by Spencer, D., et al., issued Apr. 8, 2014. Also incorporated by reference in their entirety are U.S. patent application Ser. No. 12/445,939 by Spencer, D., et al., filed Oct. 26, 2010; 12/563,991 by Spencer, D., et al., filed Sep. 21, 2009; 13/087,329 by Slawin, K., et al., filed Apr. 14, 2011; 13/763,591 by Spencer, D., et al., filed Feb. 8, 2013; International Patent Application PCT/US2009/057738, filed Sep. 21, 2009, published Mar. 28, 2010 as WO2010/033949; International Patent Application PCT/US2011/032572, filed Apr. 14, 2011, published as WO2011/130566, Oct. 20, 2011.

Prostate Cancer

In the United States, prostate cancer is the most common solid tumor malignancy in men. It was expected to account for an estimated 186,320 new cases of prostate cancer in 2008 and 28,660 deaths. Jemal A, et al., Cancer statistics, 2008. CA Cancer J Clin. 58: 71-96, 2008. Approximately 70% of patients who experience PSA-progression after primary therapy will have metastases at some time during the course of their disease. Gittes R F, N Engl J Med. 324: 236-45, 1991. Androgen deprivation therapy (ADT) is the standard therapy for metastatic prostate cancer and achieves temporary tumor control or regression in 80-85% of patients. Crawford E D, et al., N Engl J Med. 321: 419-24, 1989; Schellhammer P F, et al., J Urol. 157: 1731-5, 1997; Scher H I and Kelly W K, J Clin Oncol. 11: 1566-72, 1993; Small E J and Srinivas S, Cancer. 76: 1428-34, 1995. Duration of response to hormone therapy, as well as survival after the initiation of hormone therapy, has been shown to be dependent on a number of factors, including the Gleason Sum of the original tumor, the ability to achieve an undetectable nadir PSA after initiation of ADT, and the PSA doubling time prior to initiation of ADT. Despite hormonal therapy, virtually all patients with metastatic prostate cancer ultimately develop progressive disease. Kelly W K and Slovin S F, Curr Oncol Rep. 2: 394-401, 2000; Scher H I, et al., J Natl Cancer Inst. 88: 1623-34, 1996; Small E J and Vogelzang N J, J Clin Oncol. 15: 382-8, 1997. The Gleason Sum of the original tumor, or the Gleason score, is used to grade levels of prostate cancer in men, based on the microscopic evaluation of the tumor. A higher Gleason score denotes a cancer that has a worse prognosis as it is more aggressive, and is more likely to spread. An example of the grading system is discussed in Gleason D F., The Veteran's Administration Cooperative Urologic Research Group: histologic grading and clinical staging of prostatic carcinoma. In Tannenbaum M (ed.) Urologic Pathology: The Prostate. Lea and Febiger, Philadelphia, 1977; 171-198.

Most patients with prostate cancer who have been started on ADT are treated for a rising PSA after failure of primary therapy (e.g. radical prostatectomy, brachytherapy, external beam radiation therapy, cryo-ablation, etc.). In the absence of clinical metastases, these patients experience a relatively long disease-free interval in the range of 7-11 years; however, the majority of these patients eventually develop hormone-resistant disease as evidenced by the return of a rising PSA level in the face of castrate levels of serum testosterone. These patients, too, have a poor prognosis, with the majority developing clinical metastases within 9 months and a median survival of 24 months. Bianco F J, et al., Cancer Symposium: Abstract 278, 2005. The term "prostate cancer" includes different forms or stages, including, for example, metastatic, metastatic castration resistant, metastatic castration sensitive, regionally advanced, and localized prostate cancer.

Antigen Presenting Cells

Antigen presenting cells (APCs) are cells that can prime T-cells against a foreign antigen by displaying the foreign antigen with major histocompatibility complex (MHC) molecules on their surface. There are two types of APCs, professional and non-professional. The professional APCs express both MHC class I molecules and MHC class II molecules, the non-professional APCs do not constitutively express MHC class II molecules. In particular embodiments, professional APCs are used in the methods herein. Professional APCs include, for example, B-cells, macrophages, and dendritic cells.

An cell is "activated," when one or more activities associated with activated cells may be observed and/or measured. For example, an cell is activated when following contact with an expression vector presented herein, an activity associated with activation may be measured in the expression vector-contacted cell as compared to an cell that has either not been contacted with the expression vector, or has been contacted with a negative control vector. In one example, the increased activity may be at a level of two, three, four, five, six, seven, eight, nine, or ten fold, or more, than that of the non-contacted cell, or the cell contacted with the negative control. For example, one of the following activities may be enhanced in an cell that has been contacted with the expression vector: co-stimulatory molecule expression on the cell, nuclear translocation of NF-kappaB in cells, DC maturation marker expression, such as, for example, toll-like receptor expression or CCR7 expression, specific cytotoxic T lymphocyte responses, such as, for example, specific lytic activity directed against tumor cells, or cytokine (for example, IL-2) or chemokine expression.

An amount of a composition that activates cells or that "enhances" an immune response refers to an amount in which an immune response is observed that is greater or intensified or deviated in any way with the addition of the composition when compared to the same immune response measured without the addition of the composition. For example, the lytic activity of cytotoxic T cells can be measured, for example, using a 51Cr release assay, with and without the composition. The amount of the substance at which the CTL lytic activity is enhanced as compared to the CTL lytic activity without the composition is said to be an amount sufficient to enhance the immune response of the animal to the antigen. For example, the immune response may be enhanced by a factor of at least about 2, or, for example, by a factor of about 3 or more. The amount of cytokines secreted may also be altered.

The enhanced immune response may be an active or a passive immune response. Alternatively, the response may be part of an adaptive immunotherapy approach in which cells are obtained with from a subject (e.g., a patient), then transduced or transfected with a composition comprising the expression vector or construct presented herein. The cells may be obtained from, for example, the blood of the subject or bone marrow of the subject. The cells may then be administered to the same or different animal, or same or different subject (e.g., same or different donors). In certain embodiments the subject (for example, a patient) has or is suspected of having a cancer, such as for example, prostate cancer, or has or is suspected of having an infectious disease. In other embodiments the method of enhancing the immune response is practiced in conjunction with a known cancer therapy or any known therapy to treat the infectious disease.

Dendritic Cells

The innate immune system uses a set of germline-encoded receptors for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism (Janeway et al. (1989) Cold Spring Harb. Symp. Quant. Biol., 54: 1-13; Medzhitov et al., Nature, 388:394-397, 1997).

The receptors of the innate immune system that recognize PAMPs are called Pattern Recognition Receptors (PRRs) (Janeway et al., 1989; Medzhitov et al., 1997). These receptors vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: 1) humoral receptors circulating in the plasma; 2) endocytic receptors expressed on immune-cell surfaces, and 3) signaling receptors that can be expressed either on the cell surface or intracellularly (Medzhitov et al., 1997; Fearon et al. (1996) Science 272: 50-3).

Cellular PRRs are expressed on effector cells of the innate immune system, including cells that function as professional cells (APC) in adaptive immunity. Such effector cells include, but are not limited to, macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, as discussed below. This latter function allows efficient mobilization of effector forces to combat the invaders.

The primary function of dendritic cells (DCs) is to acquire antigen in the peripheral tissues, travel to secondary lymphoid tissue, and present antigen to effector T cells of the immune system (Banchereau, J., et al., Annu Rev Immunol, 2000, 18: p. 767-811; Banchereau, J., & Steinman, R. M., Nature 392, 245-252 (1998)). As DCs carry out their crucial role in the immune response, they undergo maturational changes allowing them to perform the appropriate function for each environment (Termeer, C. C., et al., J Immunol, 2000, Aug. 15. 165: p. 1863-70). During DC maturation, antigen uptake potential is lost, the surface density of major histocompatibility complex (MHC) class I and class II molecules increases by 10-100 fold, and CD40, costimulatory and adhesion molecule expression also greatly increases (Lanzavecchia, A. and F. Sallusto, Science, 2000. 290: p. 92-96). In addition, other genetic alterations permit the DCs to home to the T cell-rich paracortex of draining lymph nodes and to express T-cell chemokines that attract naïve and memory T cells and prime antigen-specific naïve TH0 cells (Adema, G. J., et al., Nature, 1997, Jun. 12. 387: p. 713-7). During this stage, mature DCs present antigen via their MHC II molecules to CD4$^+$ T helper cells, inducing the upregulation of T cell CD40 ligand (CD40L) that, in turn, engages the DC CD40 receptor. This DC:T cell interaction induces rapid expression of additional DC molecules that are crucial for the initiation of a potent CD8$^+$ cytotoxic T lymphocyte (CTL) response, including further upregulation of MHC I and II molecules, adhesion molecules, costimulatory molecules (e.g., B7.1, B7.2), cytokines (e.g., IL-12) and anti-apoptotic proteins (e.g., Bcl-2) (Anderson, D. M., et al., Nature, 1997, Nov. 13. 390: p. 175-9; Ohshima, Y., et al., J Immunol, 1997, Oct. 15. 159: p. 3838-48; Sallusto, F., et al., Eur J Immunol, 1998, Sep. 28: p. 2760-9; Caux, C. Adv Exp Med Biol. 1997, 417:21-5;). CD8$^+$ T cells exit lymph nodes, reenter circulation and home to the original site of inflammation to destroy pathogens or malignant cells.

One key parameter influencing the function of DCs is the CD40 receptor, serving as the "on switch" for DCs (Bennett, S. R., et al., Nature, 1998, Jun. 4. 393: p. 478-80; Clarke, S. R., J Leukoc Biol, 2000, May. 67: p. 607-14; Fernandez, N. C., et al., Nat Med, 1999, Apr. 5: p. 405-11; Ridge, J. P., D. R. F, and P. Nature, 1998, Jun. 4. 393: p. 474-8; Schoenberger, S. P., et al., Nature, 1998, Jun. 4. 393: p. 480-3). CD40 is a 48-kDa transmembrane member of the TNF receptor superfamily (McWhirter, S. M., et al., Proc Natl Acad Sci USA, 1999, Jul. 20. 96: p. 8408-13). CD40-CD40L interaction induces CD40 trimerization, necessary for initiating signaling cascades involving TNF receptor associated factors (TRAFs) (Ni, C., et al., PNAS, 2000, 97(19): 10395-10399; Pullen, S. S., et al., J Biol Chem, 1999, May 14.274: p. 14246-54). CD40 uses these signaling molecules to activate several transcription factors in DCs, including NF-kappa B, AP-1, STAT3, and p38MAPK (McWhirter, S. M., et al., 1999).

Due to their unique method of processing and presenting antigens and the potential for high-level expression of costimulatory and cytokine molecules, dendritic cells (DC) are effective cells (APCs) for priming and activating naïve T cells (Banchereau J, et al., Ann N Y Acad Sci. 2003; 987:180-187). This property has led to their widespread use as a cellular platform for vaccination in a number of clinical trials with encouraging results (O'Neill D W, et al., Blood. 2004; 104:2235-2246; Rosenberg S A, Immunity. 1999; 10:281-287). However, the clinical efficacy of DC vaccines in cancer patients has been unsatisfactory, probably due to a number of key deficiencies, including suboptimal activation, limited migration to draining lymph nodes, and an insufficient life span for optimal T cell activation in the lymph node environment.

A parameter in the optimization of DC-based cancer vaccines is the interaction of DCs with immune effector cells, such as CD4$^+$, CD8$^+$ T cells and T regulatory (Treg) cells. In these interactions, the maturation state of the DCs is a key factor in determining the resulting effector functions (Steinman R M, Annu Rev Immunol. 2003; 21:685-711). To maximize CD4$^+$ and CD8$^+$ T cell priming while minimizing Treg expansion, DCs need to be fully mature, expressing high levels of co-stimulatory molecules, (like CD40, CD80, and CD86), and pro-inflammatory cytokines, like IL-12p70 and IL-6. Equally important, the DCs must be able to migrate efficiently from the site of vaccination to draining lymph nodes to initiate T cell interactions (Vieweg J, et al., Springer Semin Immunopathol. 2005; 26:329-341).

For the ex vivo maturation of monocyte-derived immature DCs, the majority of DC-based trials have used a standard maturation cytokine cocktail (MC), comprised of TNF-alpha, IL-1beta, IL-6, and PGE2. The principal function of prostaglandin E2 (PGE2) in the standard maturation cocktail is to sensitize the CC chemokine receptor 7 (CCR7) to its ligands, CC chemokine ligand 19 (CCL19) and CCL21 and thereby enhance the migratory capacity of DCs to the draining lymph nodes (Scandella E, et al., Blood. 2002; 100:1354-1361; Luft T, et al., Blood. 2002; 100:1362-1372). However, PGE2 has also been reported to have numerous properties that are potentially deleterious to the stimulation of an immune response, including suppression of T-cell proliferation, (Goodwin J S, et al., J Exp Med. 1977; 146:1719-1734; Goodwin J S, Curr Opin Immunol. 1989; 2:264-268) inhibition of pro-inflammatory cytokine production (e.g., IL-12p70 and TNF-alpha (Kalinski P, Blood. 2001; 97:3466-3469; van der Pouw Kraan T C, et al., J Exp Med. 1995; 181:775-779)), and down-regulation of major histocompatibility complex (MHC) II surface expression (Snyder D S, Nature. 1982; 299:163-165). Therefore, maturation protocols that can avoid PGE2 while promoting migration are likely to improve the therapeutic efficacy of DC-based vaccines.

A DC activation system based on targeted temporal control of the CD40 signaling pathway has been developed to extend the pro-stimulatory state of DCs within lymphoid tissues. DC functionality was improved by increasing both the amplitude and the duration of CD40 signaling (Hanks B A, et al., Nat Med. 2005; 11:130-137). To accomplish this, the CD40 receptor was re-engineered so that the cytoplasmic domain of CD40 was fused to synthetic ligand-binding domains along with a membrane-targeting sequence. Administration of a lipid-permeable, dimerizing drug, AP20187 (AP), called a chemical inducer of dimerization (CID) (Spencer D M, et al., Science. 1993; 262:1019-1024), led to the in vivo induction of CD40-dependent signaling cascades in murine DCs. This induction strategy significantly enhanced the immunogenicity against both defined antigens and tumors in vivo beyond that achieved with other activation modalities (Hanks B A, et al., Nat Med. 2005; 11:130-137).

Pattern recognition receptor (PRR) signaling, an example of which is Toll-like receptor (TLR) signaling also plays a critical role in the induction of DC maturation and activation; human DCs express, multiple distinct TLRs (Kadowaki N, et al., J Exp Med. 2001; 194:863-869). The eleven mammalian TLRs respond to various pathogen-derived macromolecules, contributing to the activation of innate immune responses along with initiation of adaptive immunity. Lipopolysaccharide (LPS) and a clinically relevant derivative, monophosphoryl lipid A (MPL), bind to cell surface TLR-4 complexes (Kadowaki N, et al., J Exp Med. 2001; 194:863-869), leading to various signaling pathways that culminate in the induction of transcription factors, such as NF-kappaB and IRF3, along with mitogen-activated protein kinases (MAPK) p38 and c-Jun kinase (JNK) (Ardeshna K M, et al., Blood. 2000; 96:1039-1046; Ismaili J, et al., J Immunol. 2002; 168:926-932). During this process DCs mature, and partially upregulate pro-inflammatory cytokines, like IL-6, IL-12, and Type I interferons (Rescigno M, et al., J Exp Med. 1998; 188:2175-2180). LPS-induced maturation has been shown to enhance the ability of DCs to stimulate antigen-specific T cell responses in vitro and in vivo (Lapointe R, et al., Eur J Immunol. 2000; 30:3291-3298). Methods for activating an cell, comprising transducing the cell with a nucleic acid coding for a CD40 peptide have been discussed in U.S. Pat. No. 7,404,950, and methods for activating an cell, comprising transfecting the cell with a nucleic acid coding for a chimeric protein including an inducible CD40 peptide and a Pattern Recognition Receptor, or other downstream proteins in the pathway have been discussed in International Patent Application No. PCT/US2007/081963, filed Oct. 19, 2007, published as WO 2008/049113, which are hereby incorporated by reference herein.

An inducible CD40 (iCD40) system has been applied to human dendritic cells (DCs) and it has been demonstrated that combining iCD40 signaling with Pattern recognition receptor (PRR) adapter ligation causes persistent and robust activation of human DCs. (Spencer, et al., U.S. Ser. No. 12/563,991, filed Sep. 21, 2009, related international application published on Mar. 25, 2010 as WO 2010/033949, hereby incorporated by reference herein).

Engineering Expression Constructs

Expression constructs encode a co-stimulatory polypeptide and a ligand-binding domain, all operatively linked. In general, the term "operably linked" is meant to indicate that the promoter sequence is functionally linked to a second sequence, wherein the promoter sequence initiates and mediates transcription of the DNA corresponding to the second sequence. More particularly, more than one ligand-binding domain is used in the expression construct. Yet further, the expression construct contains a membrane-targeting sequence. Appropriate expression constructs may include a co-stimulatory polypeptide element on either side of the above FKBP ligand-binding elements. The expression construct may be inserted into a vector, for example a viral vector or plasmid. The steps of the methods provided may be performed using any suitable method; these methods include, without limitation, methods of transducing, transforming, or otherwise providing nucleic acid to the cell, presented herein. In some embodiments, the truncated MyD88 peptide is encoded by the nucleotide sequence of SEQ ID NO: 4 (with or without DNA linkers or has the amino acid sequence of SEQ ID NO: 5). In some embodiments, the CD40 cytoplasmic polypeptide region is encoded by a polynucleotide sequence in SEQ ID NO: 8.

In some embodiments, the polynucleotide may encode the inducible chimeric stimulating polypeptide and heterologous polypeptide, which may be, for example a marker polypeptide and may be, for example, a chimeric antigen receptor. The heterologous polypeptide, for example, the chimeric antigen receptor, may be linked to the inducible chimeric stimulating molecule via a polypeptide sequence, such as, for example, a 2A-like linker polypeptide.

In certain examples, a nucleic acid comprising a polynucleotide coding for an inducible chimeric stimulating molecule is included in the same vector, such as, for example, a viral or plasmid vector, as a polynucleotide coding for a second polypeptide. This second polypeptide may be, for example, a chimeric antigen receptor polypeptide, as discussed herein, or a marker polypeptide. In these examples, the construct may be designed with one promoter operably linked to a nucleic acid comprising a polynucleotide coding for the two polypeptides, linked by a 2A polypeptide. In this example, the first and second polypeptides are separated during translation, resulting in a chimeric stimulating molecule polypeptide, and the second polypeptide. In other examples, the two polypeptides may be expressed separately from the same vector, where each nucleic acid comprising a polynucleotide coding for one of the polypeptides is operably linked to a separate promoter. In yet other examples, one promoter may be operably linked to the two nucleic acids, directing the production of two separate RNA transcripts, and thus two polypeptides. Therefore, the expression constructs discussed herein may comprise at least one, or at least two promoters.

The expression constructs may further comprise a marker polypeptide. In certain embodiments, the marker polypeptide is linked to the inducible chimeric signaling molecule. For example, the marker polypeptide may be linked to the inducible chimeric signaling molecule via a polypeptide sequence, such as, for example, a cleavable 2A-like sequence. The marker polypeptide may be, for example, CD19, ΔCD19, or may be, for example, a heterologous protein, selected to not affect the activity of the inducible chimeric signaling molecule.

2A-like sequences, or "cleavable" 2A sequences, are derived from, for example, many different viruses, including, for example, from Thosea asigna. These sequences are sometimes also known as "peptide skipping sequences." When this type of sequence is placed within a cistron, between two peptides that are intended to be separated, the ribosome appears to skip a peptide bond, in the case of Thosea asigna sequence; the bond between the Gly and Pro amino acids is omitted. This leaves two polypeptides, in this case the Caspase-9 polypeptide and the marker polypeptide. When this sequence is used, the peptide that is encoded 5' of the 2A sequence may end up with additional amino acids at the carboxy terminus, including the Gly residue and any upstream in the 2A sequence. The peptide that is encoded 3' of the 2A sequence may end up with additional amino acids at the amino terminus, including the Pro residue and any downstream in the 2A sequence. "2A" or "2A-like" sequences are part of a large family of peptides that can cause peptide bond-skipping. (Donnelly, M L 2001, J. Gen. Virol. 82:1013-25). Various 2A sequences have been characterized (e.g., F2A, P2A, T2A), and are examples of 2A-like sequences that may be used in the polypeptides of the present application.

Co-Stimulatory Polypeptides

Co-stimulatory polypeptide molecules are capable of amplifying the cell-mediated immune response through activation of signaling pathways involved in cell survival and proliferation. Co-stimulatory proteins that are contemplated include, for example, but are not limited, to the members of tumor necrosis factor receptor (TNFR) family (i.e., CD40, RANK/TRANCE-R, OX40, 4-1BB) and CD28 family members (CD28, ICOS). Co-stimulatory proteins may include, for example, CD28, 4-1BB, OX40, and the CD3 zeta chain, or, for example, the cytoplasmic regions thereof. More than one co-stimulatory polypeptide, or co-stimulatory polypeptide cytoplasmic region may be used in the inducible chimeric signaling molecules discussed herein. For example, the inducible CSM may comprise a CD28 cytoplasmic polypeptide and a 4-1BB cytoplasmic polypeptide. Or, for example, the inducible CSM may comprise a CD28 cytoplasmic polypeptide and an OX40 cytoplasmic polypeptide. Or, for example, the inducible CSM may further comprise a CD3 zeta domain polypeptide.

Co-stimulatory polypeptides include any molecule or polypeptide that activates the NF-kappaB pathway, Akt pathway, and/or p38 pathway. The cellular activation system is based upon utilizing a recombinant signaling molecule fused to one or more ligand-binding domains (i.e., a small molecule binding domain) in which the co-stimulatory polypeptide is activated and/or regulated with a ligand resulting in oligomerization (i.e., a lipid-permeable, organic, dimerizing drug). Other systems that may be used for crosslinking, or for oligomerization, of co-stimulatory polypeptides include antibodies, natural ligands, and/or artificial cross-reacting or synthetic ligands. Yet further, another dimerization system contemplated include the coumermycin/DNA gyrase B system.

Co-stimulatory polypeptides that can be used include those that activate NF-kappaB and other variable signaling cascades for example the p38 pathway and/or Akt pathway. Such co-stimulatory polypeptides include, but are not limited to CD28 family members (e.g. CD28, ICOS), TNF receptors (i.e., CD40, RANK/TRANCE-R, OX40, 4-1BB).

Pattern Recognition Receptors include, but are not limited to endocytic pattern-recognition receptors (i.e., mannose receptors, scavenger receptors (i.e., Mac-1, LRP, peptidoglycan, techoic acids, toxins, CD11c/CR4)); external signal pattern-recognition receptors (Toll-like receptors (TLR1, TLR2, TLR3, TLR4, TLR5, TLR6, TLR7, TLR8, TLR9, TLR10), peptidoglycan recognition protein, (PGRPs bind bacterial peptidoglycan, and CD14); internal signal pattern-recognition receptors (i.e., NOD-receptors 1 & 2), RIG1, and PRRs. Pattern Recognition Receptors suitable for the present methods and composition, also include, for example, those discussed in, for example, Werts C., et al., Cell Death and Differentiation (2006) 13:798-815; Meylan, E., et al., Nature (2006) 442:39-44; and Strober, W., et al., Nature Reviews (2006) 6:9-20. Co-stimulatory proteins also contemplated include, for example, the CD40 and MyD88 polypeptides, and the chimeric CD40 and MyD88 polypeptides discussed herein. In some embodiments, the chimeric signaling molecule comprises a CD40 cytoplasmic region polypeptide and a truncated MyD88 polypeptide. Polypeptides comprising CD40 cytoplasmic region polypeptides and truncated MyD88 polypeptides are discussed in U.S. patent application Ser. No. 12/563,991, filed Sep. 21, 2009, entitled METHODS AND COMPOSITIONS FOR GENERATING AN IMMUNE RESPONSE BY INDUCING CD40 AND PATTERN RECOGNITION RECEPTOR ADAPTERS, which is hereby incorporated by reference herein in its entirety.

In specific embodiments, the co-stimulatory polypeptide molecule is CD40. The CD40 molecule comprises a nucleic acid molecule which: (1) hybridizes under stringent conditions to a nucleic acid having the sequence of a known CD40 gene and (2) codes for a CD40 polypeptide. The CD40 polypeptide may, in certain examples, lack the extracellular domain. Exemplary polynucleotide sequences that encode CD40 polypeptides include, but are not limited to SEQ.ID.NO: 1 and CD40 isoforms from other species. It is contemplated that other normal or mutant variants of CD40 can be used in the present methods and compositions. Thus, a CD40 region can have an amino acid sequence that differs from the native sequence by one or more amino acid substitutions, deletions and/or insertions. For example, one or more TNF receptor associated factor (TRAF) binding regions may be eliminated or effectively eliminated (e.g., a CD40 amino acid sequence is deleted or altered such that a TRAF protein does not bind or binds with lower affinity than it binds to the native CD40 sequence). In particular embodiments, a TRAF 3 binding region is deleted or altered such that it is eliminated or effectively eliminated (e.g., amino acids 250-254 may be altered or deleted; Hauer et al., PNAS 102(8): 2874-2879 (2005)).

In certain embodiments, the present methods involve the manipulation of genetic material to produce expression constructs that encode an inducible form of CD40 (iCD40). Such methods involve the generation of expression constructs containing, for example, a heterologous nucleic acid sequence encoding CD40 cytoplasmic domain and a means for its expression. The vector can be replicated in an appropriate helper cell, viral particles may be produced therefrom, and cells infected with the recombinant virus particles.

Thus, the CD40 molecule presented herein may, for example, lack the extracellular domain. In specific embodiments, the extracellular domain is truncated or removed. It is also contemplated that the extracellular domain can be mutated using standard mutagenesis, insertions, deletions, or substitutions to produce a CD40 molecule that does not have a functional extracellular domain. A CD40 nucleic acid may have the nucleic acid sequence of SEQ.ID.NO: 1. The CD40 nucleic acids also include homologs and alleles of a nucleic acid having the sequence of SEQ.ID.NO: 1, as well as, functionally equivalent fragments, variants, and analogs of the foregoing nucleic acids. Methods of constructing an inducible CD40 vector are discussed in, for example, U.S. Pat. No. 7,404,950, issued Jul. 29, 2008.

In the context of gene therapy, the gene will be a heterologous polynucleotide sequence derived from a source other than the viral genome, which provides the backbone of the vector. The gene is derived from a prokaryotic or eukaryotic source such as a bacterium, a virus, yeast, a parasite, a plant, or even an animal. The heterologous DNA also is derived from more than one source, i.e., a multigene construct or a fusion protein. The heterologous DNA also may include a regulatory sequence, which is derived from one source and the gene from a different source.

Co-stimulatory polypeptides may comprise, but are not limited to, the amino acid sequences provided herein, and may include functional conservative mutations, including deletions or truncations, and may comprise amino acid sequences that are 70%, 75%, 80%, 85%, 90%, 95% or 100% identical to the amino acid sequences provided herein.

Co-stimulatory polypeptide expression in cells, such as T cells, is discussed, for example, in U.S. patent application Ser. No. 14/210,034, titled METHODS FOR CONTROLLING T CELL PROLIFERATION, filed Mar. 13, 2014, and International Patent Application No: PCT/US2014/026734, published on Sep. 25, 2014 as WO 2014/151960 which are hereby incorporated by reference herein in their entirety.

Ligand-Binding Regions

The ligand-binding ("dimerization") domain of the expression construct can be any convenient domain that will allow for induction using a natural or unnatural ligand, for example, an unnatural synthetic ligand. The multimerizing region or ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain can be interchangeable with the term "receptor". Of particular interest are ligand-binding proteins for which ligands (for example, small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises an $F_vF_{vls}$ sequence. Sometimes, the $F_vF_{vls}$ sequence further comprises an additional Fv' sequence. Examples include, for example, those discussed in Kopytek, S. J., et al., Chemistry & Biology 7:313-321 (2000) and in Gestwicki, J. E., et al., Combinatorial Chem. & High Throughput Screening 10:667-675 (2007); Clackson T (2006) Chem Biol Drug Des 67:440-2; Clackson, T., in Chemical Biology: From Small Molecules to Systems Biology and Drug Design (Schreiber, s., et al., eds., Wiley, 2007)).

For the most part, the ligand-binding domains or receptor domains will be at least about 50 amino acids, and fewer than about 350 amino acids, usually fewer than 200 amino acids, either as the natural domain or truncated active portion thereof. The binding domain may, for example, be small (<25 kDa, to allow efficient transfection in viral vectors), monomeric, nonimmunogenic, have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or may have a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen).

Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the receptor, the ligand for the ligand-binding domains/receptor domains of the chimeric surface membrane proteins will usually be multimeric in the sense that it will have at least two binding sites, with each of the binding sites capable of binding to the ligand receptor domain. By "multimeric ligand binding region" is meant a ligand binding region that binds to a multimeric ligand. The term "multimeric ligands" include dimeric ligands. A dimeric ligand will have two binding sites capable of binding to the ligand receptor domain. Desirably, the subject ligands will be a dimer or higher order oligomer, usually not greater than about tetrameric, of small synthetic organic molecules, the individual molecules typically being at least about 150 Da and less than about 5 kDa, usually less than about 3 kDa. A variety of pairs of synthetic ligands and receptors can be employed. For example, in embodiments involving natural receptors, dimeric FK506 can be used with an FKBP12 receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits, single chain antibodies comprised of heavy and light chain variable regions in tandem, separated by a flexible linker domain, or modified receptors, and mutated sequences thereof, and the like, any of a large variety of compounds can be used. A significant characteristic of these ligand units is that each binding site is able to bind the receptor with high affinity and they are able to be dimerized chemically. Also, methods are available to balance the hydrophobicity/hydrophilicity of the ligands so that they are able to dissolve in serum at functional levels, yet diffuse across plasma membranes for most applications.

In certain embodiments, the present methods utilize the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor.

The CID system uses synthetic bivalent ligands to rapidly crosslink signaling molecules that are fused to ligand-binding domains. This system has been used to trigger the oligomerization and activation of cell surface (Spencer, D. M., et al., Science, 1993. 262: p. 1019-1024; Spencer D. M. et al., Curr Biol 1996, 6:839-847; Blau, C. A. et al., Proc Natl Acad. Sci. USA 1997, 94:3076-3081), or cytosolic proteins (Luo, Z. et al., Nature 1996, 383:181-185; MacCorkle, R. A. et al., Proc Natl Acad Sci USA 1998, 95:3655-3660), the recruitment of transcription factors to DNA elements to modulate transcription (Ho, S. N. et al., Nature 1996, 382:822-826; Rivera, V. M. et al., Nat. Med. 1996, 2:1028-1032) or the recruitment of signaling molecules to the plasma membrane to stimulate signaling (Spencer D. M. et al., Proc. Natl. Acad. Sci. USA 1995, 92:9805-9809; Holsinger, L. J. et al., Proc. Natl. Acad. Sci. USA 1995, 95:9810-9814).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12 permits specific activation of the recombinant receptor in vivo without the induction of non-specific side effects through endogenous FKBP12. FKBP12 variants having amino acid substitutions and deletions, such as FKBP12,36, that bind to a dimerizer drug, may also be used. In addition, the synthetic ligands are resistant to protease degradation, making them more efficient at activating receptors in vivo than most delivered protein agents.

The ligands used are capable of binding to two or more of the ligand-binding domains. The chimeric proteins may be able to bind to more than one ligand when they contain more than one ligand-binding domain. The ligand is typically a non-protein or a chemical. Exemplary ligands include, but are not limited to dimeric FK506 (e.g., FK1012).

Other ligand binding regions may be, for example, dimeric regions, or modified ligand binding regions with a wobble substitution, such as, for example, FKBP12(V36): The human 12 kDa FK506-binding protein with an F36 to V substitution, the complete mature coding sequence (amino acids 1-107), provides a binding site for synthetic dimerizer drug AP1903 (Jemal, A. et al., CA Cancer J. Clinic. 58, 71-96 (2008); Scher, H. I. and Kelly, W. K., Journal of Clinical Oncology 11, 1566-72 (1993)). Two tandem copies of the protein may also be used in the construct so that higher-order oligomers are induced upon cross-linking by AP1903.

F36V'-FKBP: F36V'-FKBP is a codon-wobbled version of F36V-FKBP. It encodes the identical polypeptide sequence as F36V-FKPB but has only 62% homology at the nucleotide level. F36V'-FKBP was designed to reduce recombination in retroviral vectors (Schellhammer, P. F. et al., J. Urol. 157, 1731-5 (1997)). F36V'-FKBP was constructed by a PCR assembly procedure. The transgene contains one copy of F36V'-FKBP linked directly to one copy of F36V-FKBP.

In some embodiments, the ligand is a small molecule. The appropriate ligand for the selected ligand-binding region may be selected. Often, the ligand is dimeric, sometimes, the ligand is a dimeric FK506 or a dimeric FK506 analog. In certain embodiments, the ligand is AP1903 (CAS Index Name: 2-Piperidinecarboxylic acid, 1-[(2S)-1-oxo-2-(3, 4, 5-trimethoxyphenyl)butyl]-, 1,2-ethanediylbis [imino(2-oxo-2,1-ethanediyl)oxy-3,1-phenylene[(1R)-3-(3,4-Dimethoxyphenyl)propylidene]] ester, [2S-[1(R*),2R*[S*[S*[1(R*),2R*]]]]-(9Cl)

CAS Registry Number: 195514-63-7; Molecular Formula: C78H98NO20 Molecular Weight: 1411.65). In certain embodiments, the ligand is AP20187. In certain embodiments, the ligand is an AP20187 analog, such as, for example, AP1510. In some embodiments, certain analogs will be appropriate for the FKBP12, and certain analogs appropriate for the wobbled version of FKBP12. In certain embodiments, one ligand binding region is included in the chimeric protein. In other embodiments, two or more ligand binding regions are included. Where, for example, the ligand binding region is FKBP12, where two of these regions are included, one may, for example, be the wobbled version.

In such methods, the multimeric molecule can be an antibody that binds to an epitope in the CD40 extracellular domain (e.g., humanized anti-CD40 antibody; Tai et al., Cancer Research 64, 2846-2852 (2004)), can be a CD40 ligand (e.g., U.S. Pat. No. 6,497,876 (Maraskovsky et al.)) or may be another co-stimulatory molecule (e.g., B7/CD28). It is understood that conservative variations in sequence, that do not affect the function, as assayed herein, are within the scope of the present claims.

Since the mechanism of CD40 activation is fundamentally based on trimerization, this receptor is particularly amenable to the CID system. CID regulation provides the system with 1) temporal control, 2) reversibility by addition of a non-active monomer upon signs of an autoimmune reaction, and 3) limited potential for non-specific side effects. In addition, inducible in vivo DC CD40 activation would circumvent the requirement of a second "danger" signal normally required for complete induction of CD40 signaling and would potentially promote DC survival in situ allowing for enhanced T cell priming. Thus, engineering DC vaccines to express iCD40 amplifies the T cell-mediated killing response by upregulating DC expression of antigen presentation molecules, adhesion molecules, TH1 promoting cytokines, and pro-survival factors.

Other dimerization systems contemplated include the coumermycin/DNA gyrase B system. Coumermycin-induced dimerization activates a modified Raf protein and stimulates the MAP kinase cascade. See Farrar et al., 1996.

Membrane-Targeting

A membrane-targeting sequence provides for transport of the chimeric protein to the cell surface membrane, where the same or other sequences can encode binding of the chimeric protein to the cell surface membrane. Molecules in association with cell membranes contain certain regions that facilitate the membrane association, and such regions can be incorporated into a chimeric protein molecule to generate membrane-targeted molecules. For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety (often followed by several positively charged residues (e.g. human c-Src: M-G-S-N-K-S-K-P-K-D-A-S-Q-R-R-R (SEQ ID NO: 190)) to improve association with anionic lipid head groups) and others are capable of being modified with multiple acyl moieties. For example the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 191), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can modified with C15 or 010 isoprenyl moieties, from the C-terminus of G-protein gamma subunits and other proteins (e.g., World Wide Web address ebi.ac.uk/interpro/DisplaylproEntry?ac=IPR001230) also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997), and can be incorporated in chimeric molecules to induce membrane localization. In certain embodiments, a native sequence from a protein containing an acylation motif is incorporated into a chimeric protein. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric protein. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric protein.

In some embodiments, an acyl moiety has a log p value of +1 to +6, and sometimes has a log p value of +3 to +4.5. Log p values are a measure of hydrophobicity and often are derived from octanol/water partitioning studies, in which molecules with higher hydrophobicity partition into octanol with higher frequency and are characterized as having a higher log p value. Log p values are published for a number of lipophilic molecules and log p values can be calculated using known partitioning processes (e.g., Chemical Reviews, Vol. 71, Issue 6, page 599, where entry 4493 shows lauric acid having a log p value of 4.2). Any acyl moiety can be linked to a peptide composition discussed above and tested for antimicrobial activity using known methods and those discussed hereafter. The acyl moiety sometimes is a C1-C20 alkyl, C2-C20 alkenyl, C2-C20 alkynyl, C3-C6 cycloalkyl, C1-C4 haloalkyl, C4-C12 cyclalkylalkyl, aryl, substituted aryl, or aryl (C1-C4) alkyl, for example. Any acyl-containing moiety sometimes is a fatty acid, and examples of fatty acid moieties are propyl (C3), butyl (C4), pentyl (C5), hexyl (C6), heptyl (C7), octyl (C8), nonyl (C9), decyl (C10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturations (i.e., double bonds). An acyl moiety sometimes is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphingosine, ceramide, ganglioside, cerebroside), or modified versions thereof. In certain embodiments, one, two, three, four or five or more acyl moieties are linked to a membrane association region.

A chimeric protein herein also may include a single-pass or multiple pass transmembrane sequence (e.g., at the N-terminus or C-terminus of the chimeric protein). Single pass transmembrane regions are found in certain CD molecules, tyrosine kinase receptors, serine/threonine kinase receptors, TGFbeta, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span to anchor the protein in the membrane. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule.

Any membrane-targeting sequence can be employed that is functional in the host and may, or may not, be associated with one of the other domains of the chimeric protein. In some embodiments, such sequences include, but are not limited to myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster J P et al, Biology of the Cell (2007) 99, 1-12, Vincent, S., et al., Nature Biotechnology 21:936-40, 1098 (2003).

Additional protein domains exist that can increase protein retention at various membranes. For example, an ~120 amino acid pleckstrin homology (PH) domain is found in over 200 human proteins that are typically involved in intracellular signaling. PH domains can bind various phosphatidylinositol (PI) lipids within membranes (e.g. PI (3,4,5)-P3, PI (3,4)-P2, PI (4,5)-P2) and thus play a key role in recruiting proteins to different membrane or cellular compartments. Often the phosphorylation state of PI lipids is regulated, such as by PI-3 kinase or PTEN, and thus, interaction of membranes with PH domains are not as stable as by acyl lipids.

AP1903 API is manufactured by Alphora Research Inc. and AP1903 Drug Product for Injection is made by AAI Pharma Services Corp. It is formulated as a 5 mg/mL solution of AP1903 in a 25% solution of the non-ionic solubilizer Solutol HS 15 (250 mg/mL, BASF). At room temperature, this formulation is a clear solution. Upon refrigeration, this formulation undergoes a reversible phase transition on extended storage, resulting in a milky solution. This phase transition is reversed upon re-warming to room temperature. The fill is 8 mL in a 10 mL glass vial (~40 mg AP1903 for Injection total per vial).

For use, the AP1903 will be warmed to room temperature and diluted prior to administration. For subjects over 50 kg, the AP1903 is administered via i.v. infusion at a dose of 40 mg diluted in 100 mL physiological saline over 2 hours at a rate of 50 mL per hour using a DEHP-free saline bag and solution set. Subjects less than 50 kg receive 0.4 mg/kg AP1903.

All study medication is maintained at a temperature between 2 degrees C. and 8 degrees C., protected from excessive light and heat, and stored in a locked area with restricted access.

Upon determining a need to administer AP1903 and activate the therapeutic T cells, for example the chimeric antigen-receptor and inducible chimeric costimulatory polypeptide-expressing T cells, patients may be, for example, administered a single fixed dose of AP1903 for Injection (0.4 mg/kg) via IV infusion over 2 hours, using a non-DEHP, non-ethylene oxide sterilized infusion set. The dose of AP1903 is calculated individually for all patients, and is not be recalculated unless body weight fluctuates by ≥10%. The calculated dose is diluted in 100 mL in 0.9% normal saline before infusion.

In a previous Phase I study of AP1903, 24 healthy volunteers were treated with single doses of AP1903 for Injection at dose levels of 0.01, 0.05, 0.1, 0.5 and 1.0 mg/kg infused IV over 2 hours. AP1903 plasma levels were directly proportional to dose, with mean Cmax values ranging from approximately 10-1275 ng/mL over the 0.01-1.0 mg/kg dose range. Following the initial infusion period, blood concentrations demonstrated a rapid distribution phase, with plasma levels reduced to approximately 18, 7, and 1% of maximal concentration at 0.5, 2 and 10 hours post-dose, respectively. AP1903 for Injection was shown to be safe and well tolerated at all dose levels and demonstrated a favorable pharmacokinetic profile. Iuliucci J D, et al., J Clin Pharmacol. 41: 870-9, 2001.

The fixed dose of AP1903 for injection used, for example, may be 0.4 mg/kg intravenously infused over 2 hours. The amount of AP1903 needed in vitro for effective signaling of cells is about 10-100 nM (MW: 1412 Da). This equates to 14-140 µg/L or ~0.014-0.14 mg/kg (1.4-140 µg/kg). The dosage may vary according to the application, and may, in certain examples, be more in the range of 0.1-10 nM, or in the range of 50-150 nM, 10-200 nM, 75-125 nM, 100-500 nM, 100-600 nM, 100-700 nM, 100-800 nM, or 100-900 nM. Doses up to 1 mg/kg were well-tolerated in the Phase I study of AP1903 described above.

Selectable Markers

In certain embodiments, the expression constructs contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as Herpes Simplex Virus thymidine kinase (tk) are employed. Immunologic surface markers containing the extracellular, non-signaling domains or various proteins (e.g. CD34, CD19, LNGFR) also can be employed, permitting a straightforward method for magnetic or fluorescence antibody-mediated sorting. The selectable marker employed is not believed to be important, so long as it is capable of being expressed simultaneously with the nucleic acid encoding a gene product. Further examples of selectable markers include, for example, reporters such as GFP, EGFP, beta-gal or chloramphenicol acetyltransferase (CAT). In certain embodiments, the marker protein, such as, for example, CD19 is used for selection of the cells for transfusion, such as, for example, in immunomagnetic selection.

As discussed herein, a CD19 marker is distinguished from an anti-CD19 antibody, or, for example, an scFv, TCR, or other antigen recognition moiety that binds to CD19.

In some embodiments, a polypeptide may be included in the expression vector to aid in sorting cells. For example, the CD34 minimal epitope may be incorporated into the vector. In some embodiments, the expression vectors used to express the chimeric antigen receptors or chimeric stimulating molecules provided herein further comprise a polynucleotide that encodes the 16 amino acid CD34 minimal epitope. In some embodiments, such as certain embodiments provided in the examples herein, the CD34 minimal epitope is incorporated at the amino terminal position of the CD8 stalk.

Transmembrane Regions

A chimeric antigen receptor herein may include a single-pass or multiple pass transmembrane sequence (e.g., at the N-terminus or C-terminus of the chimeric protein). Single pass transmembrane regions are found in certain CD molecules, tyrosine kinase receptors, serine/threonine kinase receptors, TGFβ, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span to anchor the protein in the membrane. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule.

In some embodiments, the transmembrane domain is fused to the extracellular domain of the CAR. In one embodiment, the transmembrane domain that naturally is associated with one of the domains in the CAR is used. In other embodiments, a transmembrane domain that is not naturally associated with one of the domains in the CAR is used. In some instances, the transmembrane domain can be selected or modified by amino acid substitution (e.g., typically charged to a hydrophobic residue) to avoid binding of such domains to the transmembrane domains of the same or different surface membrane proteins to minimize interactions with other members of the receptor complex.

Transmembrane domains may, for example, be derived from the alpha, beta, or zeta chain of the T cell receptor, CD3-ε, CD3 ζ, CD4, CD5, CD8, CD8α, CD9, CD16, CD22, CD28, CD33, CD38, CD64, CD80, CD86, CD134, CD137, or CD154. Or, in some examples, the transmembrane domain may be synthesized de novo, comprising mostly hydrophobic residues, such as, for example, leucine and valine. In certain embodiments a short polypeptide linker may form the linkage between the transmembrane domain and the intracellular domain of the chimeric antigen receptor. The chimeric antigen receptors may further comprise a stalk, that is, an extracellular region of amino acids between the extracellular domain and the transmembrane domain. For example, the stalk may be a sequence of amino acids naturally associated with the selected transmembrane domain. In some embodiments, the chimeric antigen receptor comprises a CD8 transmembrane domain, in certain embodiments, the chimeric antigen receptor comprises a CD8 transmembrane domain, and additional amino acids on the extracellular portion of the transmembrane domain, in certain embodiments, the chimeric antigen receptor comprises a CD8 transmembrane domain and a CD8 stalk. The chimeric antigen receptor may further comprise a region of amino acids between the transmembrane domain and the cytoplasmic domain, which are naturally associated with the polypeptide from which the transmembrane domain is derived.

Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted the polynucleotide sequence-coding region may, for example, be placed adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, ß-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest, is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that may be useful is the Tet-Off™ or Tet-On™ system (CLONTECH, Palo Alto, Calif.) originally developed by Gossen and Bujard (Gossen and Bujard, Proc. Natl. Acad. Sci. USA, 89:5547-5551, 1992; Gossen et al., Science, 268:1766-1769, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tetracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system may be used so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter is often used to provide strong transcriptional activation. The CMV promoter is reviewed in Donnelly, J. J., et al., 1997. Annu. Rev. Immunol. 15:617-48. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Similarly tissue specific promoters are used to effect transcription in specific tissues or cells so as to reduce potential toxicity or undesirable effects to non-targeted tissues. These promoters may result in reduced expression compared to a stronger promoter such as the CMV promoter, but may also result in more limited expression, and immunogenicity. (Bojak, A., et al., 2002. Vaccine. 20:1975-79; Cazeaux, N., et al., 2002. Vaccine 20:3322-31). For example, tissue specific promoters such as the PSA associated promoter or prostate-specific glandular kallikrein, or the muscle creatine kinase gene may be used where appropriate.

Examples of tissue specific or differentiation specific promoters include, but are not limited to, the following: B29 (B cells); CD14 (monocytic cells); CD43 (leukocytes and platelets); CD45 (hematopoietic cells); CD68 (macrophages); desmin (muscle); elastase-1 (pancreatic acinar cells); endoglin (endothelial cells); fibronectin (differentiating cells, healing tissues); and Flt-1 (endothelial cells); GFAP (astrocytes).

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., (1987) J. Biol. Chem., 262, 2345-2351), c-fos, TNF-alpha, C-reactive protein (Arcone, et al., (1988) Nucl. Acids Res., 16(8), 3195-3207), haptoglobin (Oliviero et al., (1987) EMBO J., 6, 1905-1912), serum amyloid A2, C/EBP alpha, IL-1, IL-6 (Poli and Cortese, (1989) Proc. Nat'l Acad. Sci. USA, 86, 8202-8206), Complement C3 (Wilson et al., (1990) Mol. Cell. Biol., 6181-6191), IL-8, alpha-1 acid glycoprotein (Prowse and Baumann, (1988) Mol Cell Biol, 8, 42-51), alpha-1 antitrypsin, lipoprotein lipase (Zechner et al., Mol. Cell. Biol., 2394-2401, 1988), angiotensinogen (Ron, et al., (1991) Mol. Cell. Biol., 2887-2895), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 anti-chymotrypsin. Other promoters include, for example, SV40, MMTV, Human Immunodeficiency Virus (MV), Moloney virus, ALV, Epstein Barr virus, Rous Sarcoma virus, human actin, myosin, hemoglobin, and creatine.

It is envisioned that any of the above promoters alone or in combination with another can be useful depending on the action desired. Promoters, and other regulatory elements, are selected such that they are functional in the desired cells or tissue. In addition, this list of promoters should not be construed to be exhaustive or limiting; other promoters that are used in conjunction with the promoters and methods disclosed herein.

2. Enhancers

Enhancers are genetic elements that increase transcription from a promoter located at a distant position on the same molecule of DNA. Early examples include the enhancers associated with immunoglobulin and T cell receptors that both flank the coding sequence and occur within several introns. Many viral promoters, such as CMV, SV40, and retroviral LTRs are closely associated with enhancer activity and are often treated like single elements. Enhancers are organized much like promoters. That is, they are composed of many individual elements, each of which binds to one or more transcriptional proteins. The basic distinction between enhancers and promoters is operational. An enhancer region as a whole stimulates transcription at a distance and often independent of orientation; this need not be true of a promoter region or its component elements. On the other hand, a promoter has one or more elements that direct initiation of RNA synthesis at a particular site and in a particular orientation, whereas enhancers lack these specificities. Promoters and enhancers are often overlapping and contiguous, often seeming to have a very similar modular organization. A subset of enhancers includes locus-control regions (LCRs) that can not only increase transcriptional activity, but (along with insulator elements) can also help to insulate the transcriptional element from adjacent sequences when integrated into the genome. Any promoter/enhancer combination (as per the Eukaryotic Promoter Data Base EPDB) can be used to drive expression of the gene, although many will restrict expression to a particular tissue type or subset of tissues. (reviewed in, for example, Kutzler, M. A., and Weiner, D. B., 2008. Nature Reviews Genetics 9:776-88). Examples include, but are not limited to, enhancers from the human actin, myosin, hemoglobin, muscle creatine kinase, sequences, and from viruses CMV, RSV, and EBV. Appropriate enhancers may be selected for particular applications. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the present methods, and any such sequence is employed such as human or bovine growth hormone and SV40 polyadenylation signals and LTR polyadenylation signals. One non-limiting example is the SV40 polyadenylation signal present in the pCEP3 plasmid (Invitrogen, Carlsbad, Calif.). Also contemplated as an element of the expression cassette is a terminator. These elements can serve to enhance message levels and to minimize read through from the cassette into other sequences. Termination or poly(A) signal sequences may be, for example, positioned about 11-30 nucleotides downstream from a conserved sequence (AAUAAA) at the 3' end of the mRNA. (Montgomery, D. L., et al., 1993. DNA Cell Biol. 12:777-83; Kutzler, M. A., and Weiner, D. B., 2008. Nature Rev. Gen. 9:776-88).

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. The initiation codon is placed in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, Nature, 334:320-325, 1988). IRES elements from two members of the picornavirus family (polio and encephalomyocarditis) have been discussed (Pelletier and Sonenberg, 1988), as well as an IRES from a mammalian message (Macejak and Sarnow, Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Sequence Optimization

Protein production may also be increased by optimizing the codons in the transgene. Species specific codon changes may be used to increase protein production. Also, codons may be optimized to produce an optimized RNA, which may result in more efficient translation. By optimizing the codons to be incorporated in the RNA, elements such as those that result in a secondary structure that causes instability, secondary mRNA structures that can, for example, inhibit ribosomal binding, or cryptic sequences that can inhibit nuclear export of mRNA can be removed. (Kutzler, M. A., and Weiner, D. B., 2008. Nature Rev. Gen. 9:776-88; Yan, J. et al., 2007. Mol. Ther. 15:411-21; Cheung, Y. K., et al., 2004. Vaccine 23:629-38; Narum, D. L., et al., 2001. 69:7250-55; Yadava, A., and Ockenhouse, C. F., 2003. Infect. Immun. 71:4962-69; Smith, J. M., et al., 2004. AIDS Res. Hum. Retroviruses 20:1335-47; Zhou, W., et al., 2002. Vet. Microbiol. 88:127-51; Wu, X., et al., 2004. Biochem. Biophys. Res. Commun. 313:89-96; Zhang, W., et al., 2006. Biochem. Biophys. Res. Commun. 349:69-78; Deml, L. A., et al., 2001. J. Virol. 75:1099-11001; Schneider, R. M., et al., 1997. J. Virol. 71:4892-4903; Wang, S. D., et al., 2006. Vaccine 24:4531-40; zur Megede, J., et al., 2000. J. Virol. 74:2628-2635). For example, the FBP12 or other multimerizing region polypeptide, the co-stimulatory polypeptide cytoplasmic signaling region, and the CD19 sequences may be optimized by changes in the codons.

Leader Sequences

Leader sequences may be added to enhance the stability of mRNA and result in more efficient translation. The leader sequence is usually involved in targeting the mRNA to the endoplasmic reticulum. Examples include the signal sequence for the HIV-1 envelope glycoprotein (Env), which delays its own cleavage, and the IgE gene leader sequence (Kutzler, M. A., and Weiner, D. B., 2008. Nature Rev. Gen. 9:776-88; Li, V., et al., 2000. Virology 272:417-28; Xu, Z. L., et al. 2001. Gene 272:149-56; Malin, A. S., et al., 2000. Microbes Infect. 2:1677-85; Kutzler, M. A., et al., 2005. J. Immunol. 175:112-125; Yang, J. S., et al., 2002. Emerg. Infect. Dis. 8:1379-84; Kumar, S., et al., 2006. DNA Cell Biol. 25:383-92; Wang, S., et al., 2006. Vaccine 24:4531-40). The IgE leader may be used to enhance insertion into the endoplasmic reticulum (Tepler, I, et al. (1989) J. Biol. Chem. 264:5912).

Expression of the transgenes may be optimized and/or controlled by the selection of appropriate methods for optimizing expression. These methods include, for example, optimizing promoters, delivery methods, and gene sequences, (for example, as presented in Laddy, D. J., et al., 2008. PLoS.ONE 3 e2517; Kutzler, M. A., and Weiner, D. B., 2008. Nature Rev. Gen. 9:776-88).

Nucleic Acids

A "nucleic acid" as used herein generally refers to a molecule (one, two or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." Nucleic acids may be, be at least, be at most, or be about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length.

Nucleic acids herein provided may have regions of identity or complementarity to another nucleic acid. It is contemplated that the region of complementarity or identity can be at least 5 contiguous residues, though it is specifically contemplated that the region is, is at least, is at most, or is about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides.

As used herein, "hybridization", "hybridizes" or "capable of hybridizing" is understood to mean forming a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are known, and are often used for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42 degrees C. to about 70 degrees C. It is understood that the temperature and ionic strength of a desired stringency are determined in part by the length of the particular nucleic acid(s), the length and nucleobase content of the target sequence(s), the charge composition of the nucleic acid(s), and the presence or concentration of formamide, tetramethylammonium chloride or other solvent(s) in a hybridization mixture.

It is understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization may be employed to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20 degrees C. to about 50 degrees C. The low or high stringency conditions may be further modified to suit a particular application.

"Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, preferably at least 80%, more preferably at least 90%, and most preferably at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the preferred settings are those that results in the highest sequence similarity.

Nucleic Acid Modification

Any of the modifications discussed below may be applied to a nucleic acid. Examples of modifications include alterations to the RNA or DNA backbone, sugar or base, and various combinations thereof. Any suitable number of backbone linkages, sugars and/or bases in a nucleic acid can be modified (e.g., independently about 5%, 10%, 15%, 20%, 25%, 30%, 35%, 40%, 45%, 50%, 55%, 60%, 65%, 70%, 75%, 80%, 85%, 90%, 95%, up to 100%). An unmodified nucleoside is any one of the bases adenine, cytosine, guanine, thymine, or uracil joined to the 1' carbon of beta-D-ribo-furanose.

A modified base is a nucleotide base other than adenine, guanine, cytosine and uracil at a 1' position. Non-limiting examples of modified bases include inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e. g., 5-methylcytidine), 5-alkyluridines (e. g., ribothymidine), 5-halouridine (e. g., 5-bromouridine) or 6-azapyrimidines or 6-alkylpyrimidines (e. g. 6-methyluridine), propyne, and the like. Other non-limiting examples of modified bases include nitropyrrolyl (e.g., 3-nitropyrrolyl), nitroindolyl (e.g., 4-, 5-, 6-nitroindolyl), hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, difluorotolyl, 4-fluoro-6-methylbenzimidazole, 4-methylbenzimidazole, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl and the like.

In some embodiments, for example, a nucleic acid may comprise modified nucleic acid molecules, with phosphate backbone modifications. Non-limiting examples of backbone modifications include phosphorothioate, phosphorodithioate, methylphosphonate, phosphotriester, morpholino, amidate carbamate, carboxymethyl, acetamidate, polyimide, sulfonate, sulfonamide, sulfamate, formacetal, thioformacetal, and/or alkylsilyl modifications. In certain instances, a ribose sugar moiety that naturally occurs in a nucleoside is replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. The hexose may be a D-hexose, glucose, or mannose. In certain instances, the polycyclic heteroalkyl group may be a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane.

Nitropyrrolyl and nitroindolyl nucleobases are members of a class of compounds known as universal bases. Universal bases are those compounds that can replace any of the four naturally occurring bases without substantially affecting the melting behavior or activity of the oligonucleotide duplex. In contrast to the stabilizing, hydrogen-bonding interactions associated with naturally occurring nucleobases, oligonucleotide duplexes containing 3-nitropyrrolyl nucleobases may be stabilized solely by stacking interactions. The absence of significant hydrogen-bonding interactions with nitropyrrolyl nucleobases obviates the specificity for a specific complementary base. In addition, 4-, 5- and 6-nitroindolyl display very little specificity for the four natural bases. Procedures for the preparation of 1-(2'-O-methyl-beta.-D-ribofuranosyl)-5-nitroindole are discussed in Gaubert, G.; Wengel, J. Tetrahedron Letters 2004, 45, 5629. Other universal bases include hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, and structural derivatives thereof.

Difluorotolyl is a non-natural nucleobase that functions as a universal base. Difluorotolyl is an isostere of the natural nucleobase thymine. But unlike thymine, difluorotolyl shows no appreciable selectivity for any of the natural bases. Other aromatic compounds that function as universal bases are 4-fluoro-6-methylbenzimidazole and 4-methylbenzimidazole. In addition, the relatively hydrophobic isocarbostyrilyl derivatives 3-methyl isocarbostyrilyl, 5-methyl isocarbostyrilyl, and 3-methyl-7-propynyl isocarbostyrilyl are universal bases which cause only slight destabilization of oligonucleotide duplexes compared to the oligonucleotide sequence containing only natural bases. Other non-natural nucleobases include 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl, and structural derivates thereof. For a more detailed discussion, including synthetic procedures, of difluorotolyl, 4-fluoro-6-methylbenzimidazole, 4-methylbenzimidazole, and other non-natural bases mentioned above, see: Schweitzer et al., J. Org. Chem., 59:7238-7242 (1994);

In addition, chemical substituents, for example cross-linking agents, may be used to add further stability or irreversibility to the reaction. Non-limiting examples of cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio] propioimidate.

A nucleotide analog may also include a "locked" nucleic acid. Certain compositions can be used to essentially "anchor" or "lock" an endogenous nucleic acid into a particular structure. Anchoring sequences serve to prevent disassociation of a nucleic acid complex, and thus not only can prevent copying but may also enable labeling, modification, and/or cloning of the endogenous sequence. The locked structure may regulate gene expression (i.e. inhibit or enhance transcription or replication), or can be used as a stable structure that can be used to label or otherwise modify the endogenous nucleic acid sequence, or can be used to isolate the endogenous sequence, i.e. for cloning.

Nucleic acid molecules need not be limited to those molecules containing only RNA or DNA, but further encompass chemically-modified nucleotides and non-nucleotides. The percent of non-nucleotides or modified nucleotides may be from 1% to 100% (e.g., about 5, 10, 15, 20, 25, 30, 35, 40, 45, 50, 55, 60, 65, 70, 75, 80, 85, 90 or 95%).

Nucleic Acid Preparation

In some embodiments, a nucleic acid is provided for use as a control or standard in an assay, or therapeutic, for example. A nucleic acid may be made by any technique known in the art, such as for example, chemical synthesis, enzymatic production or biological production. Nucleic acids may be recovered or isolated from a biological sample. The nucleic acid may be recombinant or it may be natural or endogenous to the cell (produced from the cell's genome). It is contemplated that a biological sample may be treated in a way so as to enhance the recovery of small nucleic acid molecules. Generally, methods may involve lysing cells with a solution having guanidinium and a detergent.

Nucleic acid synthesis may also be performed according to standard methods. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques or via deoxynucleoside H-phosphonate intermediates. Various different mechanisms of oligonucleotide synthesis have been disclosed elsewhere.

Nucleic acids may be isolated using known techniques. In particular embodiments, methods for isolating small nucleic acid molecules, and/or isolating RNA molecules can be employed. Chromatography is a process used to separate or isolate nucleic acids from protein or from other nucleic acids. Such methods can involve electrophoresis with a gel matrix, filter columns, alcohol precipitation, and/or other chromatography. If a nucleic acid from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

Methods may involve the use of organic solvents and/or alcohol to isolate nucleic acids. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column is effective for such isolation procedures.

A nucleic acid isolation processes may sometimes include: a) lysing cells in the sample with a lysing solution comprising guanidinium, where a lysate with a concentration of at least about 1 M guanidinium is produced; b) extracting nucleic acid molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the nucleic acid molecules from the solid support with an ionic solution; and, f) capturing the nucleic acid molecules. The sample may be dried down and resuspended in a liquid and volume appropriate for subsequent manipulation.

Methods of Gene Transfer

In order to mediate the effect of the transgene expression in a cell, it will be necessary to transfer the expression constructs into a cell. Such transfer may employ viral or non-viral methods of gene transfer. This section provides a discussion of methods and compositions of gene transfer.

A transformed cell comprising an expression vector is generated by introducing into the cell the expression vector. Suitable methods for polynucleotide delivery for transformation of an organelle, a cell, a tissue or an organism for use with the current methods include virtually any method by which a polynucleotide (e.g., DNA) can be introduced into an organelle, a cell, a tissue or an organism.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials. In specific embodiments, the host cell is a T cell, a tumor-infiltrating lymphocyte, a natural killer cell, or a natural killer T cell.

An appropriate host may be determined. Generally this is based on the vector backbone and the desired result. A plasmid or cosmid, for example, can be introduced into a prokaryote host cell for replication of many vectors. Bacterial cells used as host cells for vector replication and/or expression include DH5alpha, JM109, and KCB, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

Nucleic acid vaccines may include, for example, non-viral DNA vectors, "naked" DNA and RNA, and viral vectors. Methods of transforming cells with these vaccines, and for optimizing the expression of genes included in these vaccines are known and are also discussed herein.

Examples of Methods of Nucleic Acid or Viral Vector Transfer

Any appropriate method may be used to transfect or transduce the cells, for example, the T cells, or to administer the nucleotide sequences or compositions of the present methods. Certain examples are presented herein, and further include methods such as delivery using cationic polymers, lipid like molecules, and certain commercial products such as, for example, IN-VIVO-JET PEI.

1. Ex Vivo Transformation

Various methods are available for transfecting vascular cells and tissues removed from an organism in an ex vivo setting. For example, canine endothelial cells have been genetically altered by retroviral gene transfer in vitro and transplanted into a canine (Wilson et al., Science, 244:1344-1346, 1989). In another example, Yucatan minipig endothelial cells were transfected by retrovirus in vitro and transplanted into an artery using a double-balloon catheter (Nabel et al., Science, 244(4910):1342-1344, 1989). Thus, it is contemplated that cells or tissues may be removed and transfected ex vivo using the polynucleotides presented herein. In particular aspects, the transplanted cells or tissues may be placed into an organism. For example, dendritic cells from an animal, transfect the cells with the expression vector and then administer the transfected or transduced cells back to the animal.

2. Injection

In certain embodiments, a cell or a nucleic acid or viral vector may be delivered to an organelle, a cell, a tissue or an organism via one or more injections (i.e., a needle injection), such as, for example, subcutaneous, intradermal, intramuscular, intravenous, intraprotatic, intratumor, intraperitoneal, etc. Methods of injection include, for example, injection of a composition comprising a saline solution. Further embodiments include the introduction of a polynucleotide by direct microinjection. The amount of the expression vector used may vary upon the nature of the antigen as well as the organelle, cell, tissue or organism used.

Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair is clipped in order to observe proper needle placement). Intranodal injection allows for direct delivery of antigen to lymphoid tissues. Intralymphatic injection allows direct administration of DCs.

3. Electroporation

In certain embodiments, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human kappa-immunoglobulin genes (Potter et al., (1984) Proc. Nat'l Acad. Sci. USA, 81, 7161-7165), and rat hepatocytes have been transfected with the chloramphenicol acetyltransferase gene (Tur-Kaspa et al., (1986) Mol. Cell Biol., 6, 716-718) in this manner.

In vivo electroporation for vaccines, or eVac, is clinically implemented through a simple injection technique. A DNA vector encoding tumor antigen is injected intradermally in a patient. Then electrodes apply electrical pulses to the intradermal space causing the cells localized there, especially resident dermal dendritic cells, to take up the DNA vector and express the encoded tumor antigen. These tumor antigen-expressing dendritic cells activated by local inflammation can then migrate to lymph-nodes, presenting tumor antigens and priming tumor antigen-specific T cells. A nucleic acid is electroporetically administered when it is administered using electroporation, following, for example, but not limited to, injection of the nucleic acid or any other means of administration where the nucleic acid may be delivered to the cells by electroporation Methods of electroporation are discussed in, for example, Sardesai, N. Y., and Weiner, D. B., Current Opinion in Immunotherapy 23:421-9 (2011) and Ferraro, B. et al., Human Vaccines 7:120-127 (2011), which are hereby incorporated by reference herein in their entirety.

4. Calcium Phosphate

In other embodiments, a polynucleotide is introduced to the cells using calcium phosphate precipitation. Human KB cells have been transfected with adenovirus 5 DNA (Graham and van der Eb, (1973) Virology, 52, 456-467) using this technique. Also in this manner, mouse L(A9), mouse C127, CHO, CV-1, BHK, NI H3T3 and HeLa cells were transfected with a neomycin marker gene (Chen and Okayama, Mol. Cell Biol., 7(8):2745-2752, 1987), and rat hepatocytes were transfected with a variety of marker genes (Rippe et al., Mol. Cell Biol., 10:689-695, 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, T. V., Mol Cell Biol. 1985 May; 5(5):1188-90).

6. Sonication Loading

Additional embodiments include the introduction of a polynucleotide by direct sonic loading. LTK-fibroblasts have been transfected with the thymidine kinase gene by sonication loading (Fechheimer et al., (1987) Proc. Nat'l Acad. Sci. USA, 84, 8463-8467).

7. Liposome-Mediated Transfection

In a further embodiment, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, (1991) In: Liver Diseases, Targeted Diagnosis and Therapy Using Specific Receptors and Ligands. pp. 87-104). Also contemplated is a polynucleotide complexed with Lipofectamine (Gibco BRL) or Superfect (Qiagen).

8. Receptor Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity.

Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, (1987) J. Biol. Chem., 262, 4429-4432; Wagner et al., Proc. Natl. Acad. Sci. USA, 87(9):3410-3414, 1990; Perales et al., Proc. Natl. Acad. Sci. USA, 91:4086-4090, 1994; Myers, EPO 0273085), which establishes the operability of the technique. Specific delivery in the context of another mammalian cell type has been discussed (Wu and Wu, Adv. Drug Delivery Rev., 12:159-167, 1993; incorporated herein by reference). In certain aspects, a ligand is chosen to correspond to a receptor specifically expressed on the target cell population.

In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which may, for example, comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., (1987) Methods Enzymol., 149, 157-176). It is contemplated that the tissue-specific transforming constructs may be specifically delivered into a target cell in a similar manner.

9. Microprojectile Bombardment

Microprojectile bombardment techniques can be used to introduce a polynucleotide into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., (1987) Nature, 327, 70-73). There are a wide variety of microprojectile bombardment techniques known in the art, many of which are applicable to the present methods. In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., (1990) Proc. Nat'l Acad. Sci. USA, 87, 9568-9572). The microprojectiles used have consisted of biologically inert substances such as tungsten or gold particles or beads. Exemplary particles include those comprised of tungsten, platinum, and, in certain examples, gold, including, for example, nanoparticles. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

Examples of Methods of Viral Vector-Mediated Transfer

Any viral vector suitable for administering nucleotide sequences, or compositions comprising nucleotide sequences, to a cell or to a subject, such that the cell or cells in the subject may express the genes encoded by the nucleotide sequences may be employed in the present methods. In certain embodiments, a transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, M. J. (1990) Radiother Oncol., 19, 197-218). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them useful for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present methods, it is possible to achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay, R. T., et al., J Mol Biol. 1984 Jun. 5; 175(4):493-510). Therefore, inclusion of these elements in an adenoviral vector may permits replication.

In addition, the packaging signal for viral encapsulation is localized between 194-385 bp (0.5-1.1 map units) at the left end of the viral genome (Hearing et al., J. (1987) Virol., 67, 2555-2558). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., Gene, 101:195-202, 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element derives from the packaging function of adenovirus.

It has been shown that a packaging signal for adenovirus exists in the left end of the conventional adenovirus map (Tibbetts et. al. (1977) Cell, 12, 243-249). Later studies showed that a mutant with a deletion in the E1A (194-358 bp) region of the genome grew poorly even in a cell line that complemented the early (E1A) function (Hearing and Shenk, (1983) J. Mol. Biol. 167, 809-822). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved toward the interior of the Ad5 DNA molecule (Hearing et al., J. (1987) Virol., 67, 2555-2558).

By using mutated versions of the packaging signal, it is possible to create helper viruses that are packaged with varying efficiencies. Typically, the mutations are point mutations or deletions.

When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity may be achieved.

To improve the tropism of ADV constructs for particular tissues or species, the receptor-binding fiber sequences can often be substituted between adenoviral isolates. For example the Coxsackie-adenovirus receptor (CAR) ligand found in adenovirus 5 can be substituted for the CD46-binding fiber sequence from adenovirus 35, making a virus with greatly improved binding affinity for human hematopoietic cells. The resulting "pseudotyped" virus, Ad5f35, has been the basis for several clinically developed viral isolates. Moreover, various biochemical methods exist to modify the fiber to allow re-targeting of the virus to target cells, such as, for example, T cells. Methods include use of bifunctional antibodies (with one end binding the CAR ligand and one end binding the target sequence), and metabolic biotinylation of the fiber to permit association with customized avidin-based chimeric ligands. Alternatively, one could attach ligands (e.g. anti-CD205 by heterobifunctional linkers (e.g. PEG-containing), to the adenovirus particle.

2. Retrovirus

The retroviruses are a group of single-stranded RNA viruses characterized by an ability to convert their RNA to double-stranded DNA in infected cells by a process of reverse-transcription (Coffin, (1990) In: Virology, ed., New York: Raven Press, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990). Thus, for example, the present technology includes, for example, cells whereby the polynucleotide used to transduce the cell is integrated into the genome of the cell.

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., (1983) Cell, 33, 153-159). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas, J. F., and Rubenstein, J. L. R., (1988) In: Vectors: a Survey of Molecular Cloning Vectors and Their Uses, Rodriquez and Denhardt, Eds.). Nicolas and Rubenstein; Temin et al., (1986) In: Gene Transfer, Kucherlapati (ed.), New York: Plenum Press, pp. 149-188; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., (1975) Virology, 67, 242-248). An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, may this be desired.

A different approach to targeting of recombinant retroviruses was designed which used biotinylated antibodies against a retroviral envelope protein and against a specific cell receptor. The antibodies were coupled via the biotin components by using streptavidin (Roux et al., (1989) Proc. Nat'l Acad. Sci. USA, 86, 9079-9083). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., J. Virol., 61:3096-3101 (1987)), or by other methods, including but not limited to chemical or enzymatic synthesis of the terminal repeats based upon the published sequence of AAV. It can be determined, for example, by deletion analysis, the minimum sequence or part of the AAV ITRs which is required to allow function, i.e., stable and site-specific integration. It can also be determined which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, (1995) Ann. N.Y. Acad. Sci., 770; 79-90; Chatteijee, et al., (1995) Ann. N.Y. Acad. Sci., 770, 79-90; Ferrari et al., (1996) J. Virol., 70, 3227-3234; Fisher et al., (1996) J. Virol., 70, 520-532; Flotte et al., Proc. Nat'l Acad. Sci. USA, 90, 10613-10617, (1993); Goodman et al. (1994), Blood, 84, 1492-1500; Kaplitt et al., (1994) Nat'l Genet., 8, 148-153; Kaplitt, M. G., et al., Ann Thorac Surg. 1996 December; 62(6):1669-76; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130).

AAV-mediated efficient gene transfer and expression in the lung has led to clinical trials for the treatment of cystic fibrosis (Carter and Flotte, 1995; Flotte et al., Proc. Nat'l Acad. Sci. USA, 90, 10613-10617, (1993)). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., (1996) J. Virol., 70, 520-532; Flotte et al., 1993; Kaplitt et al., 1994; 1996; Koeberl et al., 1997; McCown et al., (1996) Brain Res., 713, 99-107; Ping et al., (1996) Microcirculation, 3, 225-228; Xiao et al., (1996) J. Virol., 70, 8098-8108).

4. Other Viral Vectors

Other viral vectors are employed as expression constructs in the present methods and compositions. Vectors derived from viruses such as vaccinia virus (Ridgeway, (1988) In: Vectors: A survey of molecular cloning vectors and their uses, pp. 467-492; Baichwal and Sugden, (1986) In, Gene Transfer, pp. 117-148; Coupar et al., Gene, 68:1-10, 1988) canary poxvirus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

Methods for Treating a Disease

The present methods also encompass methods of treatment or prevention of a disease where administration of cells by, for example, infusion, may be beneficial.

Cells, such as, for example, T cells, tumor infiltrating lymphocytes, natural killer cells, TCR-expressing cells, natural killer T cells, or progenitor cells, such as, for example, hematopoietic stem cells, mesenchymal stromal cells, stem cells, pluripotent stem cells, and embryonic stem cells may be used for cell therapy. The cells may be from a donor, or may be cells obtained from the patient. The cells may, for example, be used in regeneration, for example, to replace the function of diseased cells. The cells may also be modified to express a heterologous gene so that biological agents may be delivered to specific microenvironments such as, for example, diseased bone marrow or metastatic deposits. Mesenchymal stromal cells have also, for example, been used to provide immunosuppressive activity, and may be used in the treatment of graft versus host disease and autoimmune disorders. The cells provided in the present application contain a safety switch that may be valuable in a situation where following cell therapy, the activity of the therapeutic cells needs to be increased, or decreased. For example, where progenitor T cells that express a chimeric antigen receptor are provided to the patient, in some situations there may be an adverse event, such as inappropriate differentiation of the cell into a more mature cell type, or an undesired invitation into another tissue off-target toxicity. Ceasing the administration of the ligand would return the therapeutic T cells to a non-activated state, remaining at a low, non-toxic, level of expression. Or, for example, where it is necessary to remove the therapeutic cells. The therapeutic cell may work to decrease the tumor cell, or tumor size, and may no longer be needed. In this situation, administration of the ligand may cease, and the therapeutic cells would no longer be activated. If the tumor cells return, or the tumor size increases following the initial therapy, the ligand may be administered again, in order to activate the chimeric antigen receptor-expressing T cells, and re-treat the patient.

By "therapeutic cell" is meant a cell used for cell therapy, that is, a cell administered to a subject to treat or prevent a condition or disease.

The term "unit dose" as it pertains to the inoculum refers to physically discrete units suitable as unitary dosages for mammals, each unit containing a predetermined quantity of pharmaceutical composition calculated to produce the desired immune-stimulating effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition, such as the multimeric ligand presented herein, would be the amount that achieves this selected result of activating the inducible chimeric signaling molecule-expressing T cells, such that over 60%, 70%, 80%, 85%, 90%, 95%, or 97%, or that under 80%, 70%, 60%, 50%, 40%, 30%, 20%, or 10% of the therapeutic cells are activated. The term is also synonymous with "sufficient amount." The effective amount may also be the amount that achieves the desired therapeutic response, such as, the reduction of tumor size, the decrease in the level of tumor cells, or the decrease in the level of CD19-expressing leukemic cells, compared to the time before the ligand inducer is administered.

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

Optimized and Personalized Therapeutic Treatment

The dosage and administration schedule of the ligand inducer may be optimized by determining the level of the disease or condition to be treated. For example, the size of any remaining solid tumor, or the level of targeted cells such as, for example, tumor cells or CD19-expressing B cells, that remain in the patient, may be determined.

For example, determining that a patient has clinically relevant levels of tumor cells, or a solid tumor, after initial therapy, provides an indication to a clinician that it may be necessary to activate the chimeric-antigen receptor-expressing T cells by activating the cells by administering the multimeric ligand. In another example, determining that a patient has a reduced level of tumor cells or reduced tumor size after treatment with the multimeric ligand may indicate to the clinician that no additional dose of the multimeric ligand is needed. Similarly, after treatment with the multimeric ligand, determining that the patient continues to exhibit disease or condition symptoms, or suffers a relapse of symptoms may indicate to the clinician that it may be necessary to administer at least one additional dose of multimeric ligand. The term "dosage" is meant to include both the amount of the dose and the frequency of administration, such as, for example, the timing of the next dose. The term "dosage level" refers to the amount of the multimeric ligand administered in relation to the body weight of the subject. Thus increasing the dosage level would mean increasing the amount of the ligand administered relative to the subject's weight. In addition, increasing the concentration of the dose administered, such as, for example, when the multimeric ligand is administered using a continuous infusion pump would mean that the concentration administered (and thus the amount administered) per minute, or second, is increased.

Thus, for example, in certain embodiments, the methods comprise determining the presence or absence of a tumor size increase and/or increase in the number of tumor cells in a subject relative to the tumor size and/or the number of tumor cells following administration of the multimeric ligand, and administering an additional dose of the multimeric ligand to the subject in the event the presence of a tumor size increase and/or increase in the number of tumor cells is determined. The methods also comprise, for example, determining the presence or absence of an increase in CD19-expressing B cells in the subject relative to the level of CD19-expressing B cells following administration of the multimeric ligand, and administering an additional dose of the multimeric ligand to the subject in the event the presence of an increase in CD19-expressing B cells in the subject is determined. In these embodiments, for example, the patient is initially treated with the therapeutic cells and ligand according to the methods provided herein. Following the initial treatment, the size of the tumor, the number of tumor cells, or the number of CD19-expressing B cells, for example, may decrease relative to the time prior to the initial treatment. At a certain time after this initial treatment, the patient is again tested, or the patient may be continually monitored for disease symptoms. If it is determined that the size of the tumor, the number of tumor cells, or the number of CD19-expressing B cells, for example, is increased relative to the time just after the initial treatment, then the ligand may be administered for an additional dose. This monitoring and treatment schedule may continue, because the therapeutic cells that express inducible chimeric signaling molecules remain in the patient, although in a relatively inactive state in the absence of additional ligand.

An indication of adjusting or maintaining a subsequent drug dose, such as, for example, a subsequent dose of the multimeric ligand, and/or the subsequent drug dosage, can be provided in any convenient manner. An indication may be provided in tabular form (e.g., in a physical or electronic medium) in some embodiments. For example, the size of the tumor cell, or the number or level of tumor cells in a sample may be provided in a table, and a clinician may compare the symptoms with a list or table of stages of the disease. The clinician then can identify from the table an indication for subsequent drug dose. In certain embodiments, an indication can be presented (e.g., displayed) by a computer, after the symptoms are provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of an activated cell, a nucleic acid, or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

Enhancement of an Immune Response

In certain embodiments, a DC activation strategy is contemplated, that incorporates the manipulation of signaling co-stimulatory polypeptides that activate biological pathways, for example, immunological pathways, such as, for example, NF-kappaB pathways, Akt pathways, and/or p38 pathways. This DC activation system can be used in conjunction with or without standard vaccines to enhance the immune response since it replaces the requirement for $CD4^+$ T cell help during APC activation (Bennett, S. R., et al., Nature, 1998, Jun. 4. 393: p. 478-80; Ridge, J. P., D. R. F, and P. Nature, 1998, Jun. 4. 393: p. 474-8; Schoenberger, S. P., et al., Nature, 1998, Jun. 4. 393: p. 480-3). Thus, the DC activation system presented herein enhances immune responses by circumventing the need for the generation of MHC class II-specific peptides.

In specific embodiments, the DC activation is via CD40 activation. Thus, DC activation via endogenous CD40/CD40L interactions may be subject to downregulation due to negative feedback, leading rapidly to the "IL-12 burn-out effect". Within 7 to 10 hours after CD40 activation, an alternatively spliced isoform of CD40 (type II) is produced as a secretable factor (Tone, M., et al., Proc Natl Acad Sci USA, 2001. 98(4): p. 1751-1756). Type II CD40 may act as a dominant negative receptor, downregulating signaling through CD40L and potentially limiting the potency of the immune response generated. Therefore, the present methods co-opt the natural regulation of CD40 by creating an inducible form of CD40 (iCD40), lacking the extracellular domain and activated instead by synthetic dimerizing ligands (Spencer, D. M., et al., Science, 1993. 262: p. 1019-1024) through a technology termed chemically induced dimerization (CID).

Included are methods of enhancing the immune response in a subject comprising the step of administering the expression vector, expression construct or transduced cells to the subject. The expression vector encodes a co-stimulatory polypeptide, such as iCD40.

In certain embodiments the cells are in an animal, such as human, non-human primate, cow, horse, pig, sheep, goat, dog, cat, or rodent. The subject may be, for example, an animal, such as a mammal, for example, a human, non-human primate, cow, horse, pig, sheep, goat, dog, cat, or rodent. The subject may be, for example, human, for example, a patient suffering from an infectious disease, and/or a subject that is immunocompromised, or is suffering from a hyperproliferative disease.

In further embodiments, the expression construct and/or expression vector can be utilized as a composition or substance that activates cells. Such a composition that "activates cells" or "enhances the activity cells" refers to the ability to stimulate one or more activities associated with cells. For example, a composition, such as the expression construct or vector of the present methods, can stimulate upregulation of co-stimulatory molecules on cells, induce nuclear translocation of NF-kappaB in cells, activate toll-like receptors in cells, or other activities involving cytokines or chemokines.

The expression construct, expression vector and/or transduced cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improving the efficacy of vaccines in subjects with reduced or weakened immune responses, such as newborns, the aged, and immunocompromised individuals, and enhancing the immunity at a target tissue, such as mucosal immunity, or promote cell-mediated or humoral immunity by eliciting a particular cytokine profile.

In certain embodiments, the cell is also contacted with an antigen. Often, the cell is contacted with the antigen ex vivo. Sometimes, the cell is contacted with the antigen in vivo. In some embodiments, the cell is in a subject and an immune response is generated against the antigen. Sometimes, the immune response is a cytotoxic T-lymphocyte (CTL) immune response. Sometimes, the immune response is generated against a tumor antigen. In certain embodiments, the cell is activated without the addition of an adjuvant.

In some embodiments, the cell is transduced with the nucleic acid ex vivo and administered to the subject by intradermal administration. In some embodiments, the cell is transduced with the nucleic acid ex vivo and administered to the subject by subcutaneous administration. Sometimes, the cell is transduced with the nucleic acid ex vivo. Sometimes, the cell is transduced with the nucleic acid in vivo.

In certain embodiments, the cell can be transduced ex vivo or in vivo with a nucleic acid that encodes the chimeric protein. The cell may be sensitized to the antigen at the same time the cell is contacted with the multimeric ligand, or the cell can be pre-sensitized to the antigen before the cell is contacted with the multimerization ligand. In some embodiments, the cell is contacted with the antigen ex vivo. In certain embodiments the cell is transduced with the nucleic acid ex vivo and administered to the subject by intradermal administration, and sometimes the cell is transduced with the nucleic acid ex vivo and administered to the subject by subcutaneous administration. The antigen may be a tumor antigen, and the CTL immune response can be induced by migration of the cell to a draining lymph node. A tumor antigen is any antigen such as, for example, a peptide or polypeptide, that triggers an immune response in a host. The tumor antigen may be a tumor-associated antigen that is associated with a neoplastic tumor cell.

In some embodiments, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired CD4 T helper cells. It is contemplated that the present methods can be utilized to enhance the amount and/or activity of CD4 T helper cells in an immunocompromised subject.

Challenge with Target Antigens

In specific embodiments, prior to administering the transduced cell, the cells are challenged with antigens (also referred herein as "target antigens"). After challenge, the transduced, loaded cells are administered to the subject parenterally, intradermally, intranodally, or intralymphatically. Additional parenteral routes include, but are not limited to subcutaneous, intramuscular, intraperitoneal, intravenous, intraarterial, intramyocardial, transendocardial, transepicardial, intrathecal, intraprotatic, intratumor, and infusion techniques.

The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition may, for example, be a T lymphocyte response.

The target antigen may be derived or isolated from, for example, a pathogenic microorganism such as viruses including HIV, (Korber et al, eds HIV Molecular Immunology Database, Los Alamos National Laboratory, Los Alamos, N. Mex. 1977) influenza, Herpes simplex, human papilloma virus (U.S. Pat. No. 5,719,054), Hepatitis B (U.S. Pat. No. 5,780,036), Hepatitis C (U.S. Pat. No. 5,709,995), EBV, Cytomegalovirus (CMV) and the like. Target antigen may be derived or isolated from pathogenic bacteria such as, for example, from *Chlamydia* (U.S. Pat. No. 5,869,608), *Mycobacteria, Legionella, Meningiococcus*, Group A *Streptococcus, Salmonella, Listeria, Hemophilus influenzae* (U.S. Pat. No. 5,955,596) and the like.

Target antigen may be derived or isolated from, for example, pathogenic yeast including *Aspergillus*, invasive *Candida* (U.S. Pat. No. 5,645,992), *Nocardia, Histoplasmosis, Cryptosporidia* and the like.

Target antigen may be derived or isolated from, for example, a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589,343) and *Toxoplasma gondii*. Target antigen includes an antigen associated with a preneoplastic or hyperplastic state. Target antigen may also be associated with, or causative of cancer. Such target antigen may be, for example, tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D and the like (GenBank Accession No. M29540), MART-1 (Kawakarni et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated ras oncogene, normal and point mutated p53 oncogenes (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987) TRP-1 (gp75) (Cohen et al Nucleic Acid Res. 18:2807-2808, 1990; U.S. Pat. No. 5,840,839), NY-ESO-1 (Chen et al PNAS 94: 1914-1918, 1997), TRP-2 (Jackson et al EMBOJ, 11:527-535, 1992), TAG72, KSA, CA-125, PSA, HER-2/neu/c-erb/B2, (U.S. Pat. No. 5,550,214), BRC-I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each. An antigen may be expressed more frequently in cancer cells than in non-cancer cells. The antigen may result from contacting the modified dendritic cell with a prostate specific membrane antigen, for example, a prostate specific membrane antigen (PSMA) or fragment thereof.

Prostate antigen (PA001) is a recombinant protein consisting of the extracellular portion of PSMA antigen. PSMA is a ~100 kDa (84 kDa before glycosylation, 180 kDa as dimer) type II membrane protein with neuropeptidase and folate hydrolase activities, but the true function of PSMA is currently unclear. Carter R E, et al., Proc Natl Acad Sci USA. 93: 749-53, 1996; Israeli R S, et al., Cancer Res. 53: 227-30, 1993; Pinto J T, et al., Clin Cancer Res. 2: 1445-51, 1996.

Expression is largely, but not exclusively, prostate-specific and is maintained in advanced and hormone refractory disease. Israeli R S, et al., Cancer Res. 54: 1807-11, 1994. Weak non-prostatic detection in normal tissues has also been seen in the salivary gland, brain, small intestines, duodenal mucosa, proximal renal tubules and neuroendocrine cells in colonic crypts. Silver D A, et al., Clin Cancer Res. 3: 81-5, 1997; Troyer J K, et al., Int J Cancer. 62: 552-8, 1995. Moreover, PSMA is up-regulated following androgen deprivation therapy (ADT). Wright G L, Jr., et al., Urology. 48: 326-34, 1996. While most PSMA is expressed as a cytoplasmic protein, the alternatively-spliced transmembrane form is the predominate form on the apical surface of neoplastic prostate cells. Su S L, et al., Cancer Res. 55: 1441-3, 1995; Israeli R S, et al., Cancer Res. 54: 6306-10, 1994.

Moreover, PSMA is internalized following cross-linking and has been used to internalize bound antibody or ligand complexed with radionucleotides or viruses and other complex macromolecules. Liu H, et al., Cancer Res. 58: 4055-60, 1998; Freeman L M, et al., Q J Nucl Med. 46: 131-7, 2002; Kraaij R, et al., Prostate. 62: 253-9, 2005. Bander and colleagues demonstrated that pretreatment of tumors with microtubule inhibitors increases aberrant basal surface targeting and antibody-mediated internalization of PSMA. Christiansen J J, et al., Mol Cancer Ther. 4: 704-14, 2005. Tumor targeting may be facilitated by the observation of ectopic expression of PSMA in tumor vascular endothelium of not only prostate, but also renal and other tumors. Liu H, et al., Cancer Res. 57: 3629-34, 1997; Chang S S, et al., Urology. 57: 801-5, 2001; Chang S S, et al., Clin Cancer Res. 5: 2674-81, 1999.

PSMA is not found in the vascular endothelial cells of corresponding benign tissue. de la Taille A, et al., Cancer Detect Prev. 24: 579-88, 2000. Although one early histological study of metastatic prostate disease suggested that only ~50% (8 of 18) of bone metastases (with 7 of 8 lymph node metastases) expressed PSMA, the more sensitive reagent, 177Lu-radiolabeled MoAb J591, targeted to the ectodomain of PSMA, could target all known sites of bone and soft tissue metastasis in 30 of 30 patients, suggesting near universal expression in advanced prostate disease. Bander N H, et al., J Clin Oncol. 23: 4591-601, 2005.

A prostate specific antigen, or PSA, is meant to include any antigen that can induce an immune response, such as, for example, a cytotoxic T lymphocyte response, against a PSA, for example, a PSMA, and may be specifically recognized by any anti-PSA antibody. PSAs used in the present method are capable of being used to load the cell, as assayed using conventional methods. Thus, "prostate specific antigen" or "PSA" may, for example, refer to a protein having the wild type amino acid sequence of a PSA, or a polypeptide that includes a portion of the a PSA protein, A prostate specific membrane antigen, or PSMA, is meant to include any antigen that can induce an immune response, such as, for example, a cytotoxic T lymphocyte response, against PSMA, and may be specifically recognized by an anti-PSMA antibody. PSMAs used in the present method are capable of being used to load the cell, as assayed using conventional methods. Thus, "prostate specific membrane antigen" or "PSMA" may, for example, refer to a protein having the wild type amino acid sequence of PSMA, or a polypeptide that includes a portion of the PSMA protein. Also included are variants of any of the foregoing, including, for example, those having substitutions and deletions. Proteins, polypeptides, and peptides having differential post-translational processing, such as differences in glycosylation, from the wild type PSMA, may also be used in the present methods. Further, various sugar molecules that are capable of inducing an immune response against PSMA, are also contemplated.

A PSA, for example, a PSMA, polypeptide may be used to load the modified cell. In certain embodiments, the modified cell is contacted with a PSMA polypeptide fragment. In some embodiments, the PSA, for example, PSMA polypeptide fragment does not include the signal peptide sequence. In other embodiments, the modified cell is contacted with a PSA, for example, PSMA polypeptide fragment comprising substitutions or deletions of amino acids in the polypeptide, and the fragment is sufficient to load cells.

A prostate specific protein antigen, or s PSPA, also referred to in this specification as a prostate specific antigen, or a PSA, is meant to include any antigen that can induce an immune response, such as, for example, a cytotoxic T lymphocyte response, against a prostate specific protein antigen. This includes, for example, a prostate specific protein antigen or Prostate Specific Antigen. PSPAs used in the present method are capable of being used to load the cell, as assayed using conventional methods. Prostate Specific Antigen, or PSA, may, for example, refer to a protein having the wild type amino acid sequence of a PSA, or a polypeptide that includes a portion of the PSA protein, A prostate specific membrane antigen, or PSMA, is meant to include any antigen that can induce an immune response, such as, for example, a cytotoxic T lymphocyte response, against PSMA, and may be specifically recognized by an anti-PSMA antibody. PSMAs used in the present method are capable of being used to load the cell, as assayed using conventional methods. Thus, "prostate specific membrane antigen" or "PSMA" may, for example, refer to a protein having the wild type amino acid sequence of PSMA, or a polypeptide that includes a portion of the PSMA protein. Also included are variants of any of the foregoing, including, for example, those having substitutions and deletions. Proteins, polypeptides, and peptides having differential post-translational processing, such as differences in glycosylation, from the wild type PSMA, may also be used in the present methods. Further, various sugar molecules that are capable of inducing an immune response against PSMA, are also contemplated.

A PSPA, for example, a PSMA, polypeptide may be used to load the modified cell. In certain embodiments, the modified cell is contacted with a PSMA polypeptide fragment. In some embodiments, the PSA, for example, PSMA polypeptide fragment does not include the signal peptide sequence. In other embodiments, the modified cell is contacted with a PSPA, for example, PSMA polypeptide fragment comprising substitutions or deletions of amino acids in the polypeptide, and the fragment is sufficient to load cells.

A tumor antigen is any antigen such as, for example, a peptide or polypeptide, that triggers an immune response in a host against a tumor. The tumor antigen may be a tumor-associated antigen, that is associated with a neoplastic tumor cell.

A prostate cancer antigen, or PCA, is any antigen such as, for example, a peptide or polypeptide, that triggers an immune response in a host against a prostate cancer tumor. A prostate cancer antigen may, or may not, be specific to prostate cancer tumors. A prostate cancer antigen may also trigger immune responses against other types of tumors or neoplastic cells. A prostate cancer antigen includes, for example, prostate specific protein antigens, prostate specific antigens, and prostate specific membrane antigens.

The cell may be contacted with tumor antigen, such as PSA, for example, PSMA polypeptide, by various methods, including, for example, pulsing immature DCs with unfractionated tumor lysates, MHC-eluted peptides, tumor-derived heat shock proteins (HSPs), tumor associated antigens (TAAs (peptides or proteins)), or transfecting DCs with bulk tumor mRNA, or mRNA coding for TAAs (reviewed in Gilboa, E. & Vieweg, J., Immunol Rev 199, 251-63 (2004); Gilboa, E, Nat Rev Cancer 4, 401-11 (2004)).

For organisms that contain a DNA genome, a gene encoding a target antigen or immunological epitope thereof of interest is isolated from the genomic DNA. For organisms with RNA genomes, the desired gene may be isolated from cDNA copies of the genome. If restriction maps of the genome are available, the DNA fragment that contains the gene of interest is cleaved by restriction endonuclease digestion by routine methods. In instances where the desired gene has been previously cloned, the genes may be readily obtained from the available clones. Alternatively, if the DNA sequence of the gene is known, the gene can be synthesized by any of the conventional techniques for synthesis of deoxyribonucleic acids.

Genes encoding an antigen of interest can be amplified, for example, by cloning the gene into a bacterial host. For this purpose, various prokaryotic cloning vectors can be used. Examples are plasmids pBR322, pUC and pEMBL.

The genes encoding at least one target antigen or immunological epitope thereof can be prepared for insertion into the plasmid vectors designed for recombination with a virus by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with a virus, then purified prior to insertion into the vectors at restriction endonuclease cleavage sites (cloning sites).

Antigen loading of cells, such as, for example, dendritic cells, with antigens may be achieved, for example, by contacting cells, such as, for example, dendritic cells or progenitor cells with an antigen, for example, by incubating the cells with the antigen. Loading may also be achieved, for example, by incubating DNA (naked or within a plasmid vector) or RNA that code for the antigen; or with antigen-expressing recombinant bacterium or viruses (e.g., vaccinia, fowl pox, adenovirus or lentivirus vectors). Prior to loading, the antigen may be covalently conjugated to an immunological partner that provides T cell help (e.g., a carrier molecule). Alternatively, a dendritic cell may be pulsed with a non-conjugated immunological partner, separately or in the presence of the polypeptide. Antigens from cells or MHC molecules may be obtained by acid-elution or other methods (see Zitvogel L, et al., J Exp Med 1996. 183:87-97). The cells may be transduced or transfected with the chimeric protein-encoding nucleotide sequence according to the present methods either before, after, or at the same time as the cells are loaded with antigen. In particular embodiments, antigen loading is subsequent to transduction or transfection.

In further embodiments, the transduced cell is transfected with tumor cell mRNA. The transduced transfected cell is administered to an animal to effect cytotoxic T lymphocytes and natural killer cell anti-tumor antigen immune response and regulated using dimeric FK506 and dimeric FK506 analogs. The tumor cell mRNA may be, for example, mRNA from a prostate tumor cell.

In some embodiments, the transduced cell may be loaded by pulsing with tumor cell lysates. The pulsed transduced cells are administered to an animal to effect cytotoxic T lymphocytes and natural killer cell anti-tumor antigen immune response and regulated using dimeric FK506 and dimeric FK506 analogs. The tumor cell lysate may be, for example, a prostate tumor cell lysate.

Immune Cells and Cytotoxic T Lymphocyte Response

T-lymphocytes may be activated by contact with the cell that comprises the expression vector discussed herein, where the cell has been challenged, transfected, pulsed, or electrofused with an antigen.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines that are crucial for the activation of B cells, T cytotoxic cells, macrophages and other cells of the immune system. In contrast, a naïve CD8 T cell that recognizes an antigen-MHC complex proliferates and differentiates into an effector cell called a cytotoxic CD8 T lymphocyte (CTL). CTLs eliminate cells of the body displaying antigen, such as virus-infected cells and tumor cells, by producing substances that result in cell lysis.

CTL activity can be assessed by methods discussed herein, for example. For example, CTLs may be assessed in freshly isolated peripheral blood mononuclear cells (PBMC), in a phytohaemaglutinin-stimulated IL-2 expanded cell line established from PBMC (Bernard et al., AIDS, 12(16):2125-2139, 1998) or by T cells isolated from a previously immunized subject and restimulated for 6 days with DC infected with an adenovirus vector containing antigen using standard 4 hour 51Cr release microtoxicity assays. One type of assay uses cloned T-cells. Cloned T-cells have been tested for their ability to mediate both perforin and Fas ligand-dependent killing in redirected cytotoxicity assays (Simpson et al., Gastroenterology, 115(4):849-855, 1998). The cloned cytotoxic T lymphocytes displayed both Fas- and perforin-dependent killing. Recently, an in vitro dehydrogenase release assay has been developed that takes advantage of a new fluorescent amplification system (Page, B., et al., Anticancer Res. 1998 July-August; 18(4A):2313-6). This approach is sensitive, rapid, and reproducible and may be used advantageously for mixed lymphocyte reaction (MLR). It may easily be further automated for large-scale cytotoxicity testing using cell membrane integrity, and is thus considered. In another fluorometric assay developed for detecting cell-mediated cytotoxicity, the fluorophore used is the non-toxic molecule AlamarBlue (Nociari et al., J. Immunol. Methods, 213(2): 157-167, 1998). The AlamarBlue is fluorescently quenched (i.e., low quantum yield) until mitochondrial reduction occurs, which then results in a dramatic increase in the AlamarBlue fluorescence intensity (i.e., increase in the quantum yield). This assay is reported to be extremely sensitive, specific and requires a significantly lower number of effector cells than the standard 51Cr release assay.

Other immune cells that can be induced by the present methods include natural killer cells (NK). NKs are lymphoid cells that lack antigen-specific receptors and are part of the innate immune system. Typically, infected cells are usually destroyed by T cells alerted by foreign particles bound to the cell surface MHC. However, virus-infected cells signal infection by expressing viral proteins that are recognized by antibodies. These cells can be killed by NKs. In tumor cells, if the tumor cells lose expression of MHC I molecules, then it may be susceptible to NKs.

Formulations and Routes for Administration to Patients

Where clinical applications are contemplated, it will be necessary to prepare pharmaceutical compositions—expression constructs, expression vectors, fused proteins, transduced cells, activated T cells, transduced and loaded T cells—in a form appropriate for the intended application. Generally, this will entail preparing compositions that are essentially free of pyrogens, as well as other impurities that could be harmful to humans or animals.

The multimeric ligand, such as, for example, AP1903, may be delivered, for example at doses of about 0.01 to 1 mg/kg subject weight, of about 0.05 to 0.5 mg/kg subject weight, 0.1 to 2 mg/kg subject weight, of about 0.05 to 1.0 mg/kg subject weight, of about 0.1 to 5 mg/kg subject weight, of about 0.2 to 4 mg/kg subject weight, of about 0.3 to 3 mg/kg subject weight, of about 0.3 to 2 mg/kg subject weight, or about 0.3 to 1 mg/kg subject weight, for example, about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight. In some embodiments, the ligand is provided at 0.4 mg/kg per dose, for example at a concentration of 5 mg/mL. Vials or other containers may be provided containing the ligand at, for example, a volume per vial of about 0.25 ml to about 10 ml, for example, about 0.25, 0.5, 1, 1.5, 2, 2.5, 3, 3.5, 4, 4.5, 5, 5.5, 6, 6.5, 7, 7.5, 8, 8.5, 9, 9.5, or 10 ml, for example, about 2 ml.

AP1903 for Injection

AP1903 API is manufactured by Alphora Research Inc. and AP1903 Drug Product for Injection is made by Formatech Inc. It is formulated as a 5 mg/mL solution of AP1903 in a 25% solution of the non-ionic solubilizer Solutol HS 15 (250 mg/mL, BASF). At room temperature, this formulation is a clear, slightly yellow solution. Upon refrigeration, this formulation undergoes a reversible phase transition, resulting in a milky solution. This phase transition is reversed upon re-warming to room temperature. The fill is 2.33 mL in a 3 mL glass vial (~10 mg AP1903 for Injection total per vial).

AP1903 is removed from the refrigerator the night before the patient is dosed and stored at a temperature of approximately 21° C. overnight, so that the solution is clear prior to dilution. The solution is prepared within 30 minutes of the start of the infusion in glass or polyethylene bottles or non-DEHP bags and stored at approximately 21° C. prior to dosing.

All study medication is maintained at a temperature between 2 degrees C. and 8 degrees C., protected from excessive light and heat, and stored in a locked area with restricted access.

Administration

In one example, patients are administered a single fixed dose of AP1903 for Injection (0.4 mg/kg) via IV infusion over 2 hours, using a non-DEHP, non-ethylene oxide sterilized infusion set. The dose of AP1903 is calculated individually for all patients, and is not be recalculated unless body weight fluctuates by ≥10. The calculated dose is diluted in 100 mL in 0.9% normal saline before infusion.

Patients are observed for 15 minutes following the end of the infusion for untoward adverse effects.

One may generally desire to employ appropriate salts and buffers to render delivery vectors stable and allow for uptake by target cells. Buffers also may be employed when recombinant cells are introduced into a patient. Aqueous compositions comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is known. Except insofar as any conventional media or agent is incompatible with the vectors or cells, its use in therapeutic compositions is contemplated. Supplementary active ingredients also can be incorporated into the compositions.

The active compositions may include classic pharmaceutical preparations. Administration of these compositions will be via any common route so long as the target tissue is available via that route. This includes, for example, oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, discussed herein.

The pharmaceutical forms suitable for injectable use include sterile aqueous solutions or dispersions and sterile powders for the extemporaneous preparation of sterile injectable solutions or dispersions. In all cases the form is sterile and is fluid to the extent that easy syringeability exists. It is stable under the conditions of manufacture and storage and is preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In certain examples, isotonic agents, for example, sugars or sodium chloride may be included. Prolonged absorption of the injectable compositions can be brought about by the use in the compositions of agents delaying absorption, for example, aluminum monostearate and gelatin.

For oral administration, the compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including, for example: gels, pastes, powders and slurries. The active ingredient may be added in a therapeutically effective amount to a paste dentifrice that may include, for example, water, binders, abrasives, flavoring agents, foaming agents, and humectants.

The compositions may be formulated in a neutral or salt form. Pharmaceutically-acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media can be employed. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, and general safety and purity standards as required by FDA Office of Biologics standards.

The administration schedule may be determined as appropriate for the patient and may, for example, comprise a dosing schedule where the nucleic acid is administered at week 0, followed by induction by administration of the chemical inducer of dimerization, followed by administration of additional inducer when needed to obtain an effective therapeutic result or, for example, at 2, 4, 6, 8, 10, 12, 14, 16, 18, 20 intervals thereafter for a total of, for example, 2, 4, 6, 8, 10, 12, 14, 16, 18, 20, 22, 24, 26, 28, or 30, 40, 50, 60, 70, 80, 90, or 100 weeks.

The administration schedule may be determined as appropriate for the patient and may, for example, comprise a dosing schedule where the nucleic acid-transduced T cell or other cell is administered at week 0, followed by induction by administration of the chemical inducer of dimerization, followed by administration of additional inducer when needed to obtain an effective therapeutic result or, for example, at 2, 4, 6, 8, 10, 12, 14, 16, 18, 20 intervals thereafter for a total of, for example, 2, 4, 6, 8, 10, 12, 14, 16, 18, 20, 22, 24, 26, 28, or 30, 40, 50, 60, 70, 80, 90, or 100 weeks.

Although for administration of transduced T cells, one dose is likely to be sufficient, followed by multiple doses of ligand, T cells may be provided more than once, or other cells, such as the non-dendritic cells and non-B cells discussed herein may also be administered multiple times. In addition, nucleic acids targeted to the non-T cell aspects of the present technology may also be administered more than one time for optimum therapeutic efficacy. Therefore, for example, The administration schedule may be determined as appropriate for the patient and may, for example, comprise a dosing schedule where the nucleic acid or nucleic acid-transduced cell is administered at week 0, followed by induction by administration of the chemical inducer of dimerization, followed by administration of additional nucleic acid or nucleic acid-transduced cell and inducer at 2 week intervals thereafter for a total of, for example, 2, 4, 6, 8, 10, 12, 14, 16, 18, 20, 22, 24, 26, 28, or 30 weeks.

Other dosing schedules include, for example, a schedule where one dose of the cells and one dose of the inducer are administered. In another example, the schedule may comprise administering the cells and the inducer are administered at week 0, followed by the administration of additional cells and inducer at 4 week intervals, for a total of, for example, 4, 8, 12, 16, 20, 24, 28, or 32 weeks.

Administration of a dose of cells may occur in one session, or in more than one session, but the term dose may refer to the total amount of cells administered before administration of the ligand.

If needed, the method may further include additional leukaphereses to obtain more cells to be used in treatment.

Methods for Treating a Disease

The present methods also encompass methods of treatment or prevention of a disease caused by pathogenic microorganisms and/or a hyperproliferative disease.

Diseases that may be treated or prevented include diseases caused by viruses, bacteria, yeast, parasites, protozoa, cancer cells and the like. The pharmaceutical composition (transduced T cells, expression vector, expression construct, etc.) may be used as a generalized immune enhancer (T cell activating composition or system) and as such has utility in treating diseases. Exemplary diseases that can be treated and/or prevented include, but are not limited, to infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using the pharmaceutical composition (transduced T cells, expression vector, expression construct, etc.) include but are not limited to preneoplastic or hyperplastic states such as colon polyps, Crohn's disease, ulcerative colitis, breast lesions and the like.

Cancers, including solid tumors, which may be treated using the pharmaceutical composition include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases, including solid tumors, that may be treated using the T cell and other therapeutic cell activation system presented herein include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In the method of treatment, the administration of the pharmaceutical composition (expression construct, expression vector, fused protein, transduced cells, activated T cells, transduced and loaded T cells) may be for either "prophylactic" or "therapeutic" purpose. When provided prophylactically, the pharmaceutical composition is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the compositions presented herein may be provided either prior to the anticipated exposure to a disease-causing agent or disease state or after the initiation of the infection or disease. Thus provided herein are methods for prophylactic treatment of solid tumors such as those found in cancer, or for example, but not limited to, prostate cancer, using the nucleic acids and ligands discussed herein. For example, methods are provided of prophylactically preventing or reducing the size of a tumor in a subject comprising administering a nucleic acid comprising a promoter operably linked to a polynucleotide that encodes a chimeric protein, and a nucleic acid comprising a polynucleotide comprising a promoter operably linked to a polynucleotide encoding a tumor antigen to a subject in need thereof, wherein the chimeric protein comprises a membrane targeting region, a multimeric ligand binding region, a CD40 cytoplasmic polypeptide lacking the CD40 extracellular domain, a MyD88 polypeptide, and administering a multimeric ligand that binds to the multimeric ligand binding region, whereby the nucleic acids and ligand are administered in an amount effect to prevent or reduce the size of a tumor in a subject. Also provided are methods of prophylactically preventing or reducing the size of a tumor in a subject comprising administering a nucleic acid comprising a polynucleotide that encodes a chimeric protein, and to a polynucleotide encoding a tumor antigen to a subject in need thereof, wherein the chimeric protein comprises a membrane targeting region, a multimeric ligand binding region, a CD40 cytoplasmic polypeptide lacking the CD40 extracellular domain, a MyD88 polypeptide, and administering a multimeric ligand that binds to the multimeric ligand binding region, whereby the nucleic acid and ligand are administered in an amount effect to prevent or reduce the size of a tumor in a subject. The term multimerization region may be used in place of the term ligand binding region for purposes of this application.

Solid tumors from any tissue or organ may be treated using the present methods, including, for example, any tumor expressing PSA, for example, PSMA, in the vasculature, for example, solid tumors present in, for example, lungs, bone, liver, prostate, or brain, and also, for example, in breast, ovary, bowel, testes, colon, pancreas, kidney, bladder, neuroendocrine system, soft tissue, boney mass, and lymphatic system. Other solid tumors that may be treated include, for example, glioblastoma, and malignant myeloma.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation. Thus, for example, in one embodiment, the transduced T cells or other cells are administered to a subject in an amount effective to, for example, induce an immune response, or, for example, to reduce the size of a tumor or reduce the amount of tumor vasculature.

In some embodiments, multiple doses of multimeric ligand are administered to the subject, with an escalation of dosage levels among the multiple doses. In some embodiments, the escalation of dosage levels increases the level of CAR-T cell activity, and therefore increases the therapeutic effect, such as, for example, the reduction in the amount or concentration of target cells, such as, for example, tumor cells. In some embodiments, the dose is escalated from 0.01 to 1 mg/kg. In some embodiments, the doses are administered in increments of about 15 to 30 minutes. In some embodiments, the multimeric ligand is administered using a continuous infusion pump, and the concentration of multimeric ligand is increased during the infusion. In some embodiments, the multimeric ligand is administered in separate doses 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days apart, or 1, 2, 3, 4, 5, 6, 7, 8, 9, 10, or 11 months apart, or 1, 2, 3, 4, 5, 6, 7, 8, 9, or 10 years apart.

In some embodiments, personalized treatment is provided wherein the stage or level of the disease or condition is determined before administration of the multimeric ligand, before the administration of an additional dose of the multimeric ligand, or in determining method and dosage involved in the administration of the multimeric ligand. These methods may be used in any of the methods of the present application. Where these methods of assessing the patient before administering the ligand are discussed in the context of, for example, the treatment of a subject with a solid tumor, it is understood that these methods may be similarly applied to the treatment of other conditions and diseases. Thus, for example, in some embodiments of the present application, the method comprises administering the modified cells of the present application to a subject, and further comprises determining the appropriate dose of multimeric ligand to achieve the effective level of reduction of tumor size. In some examples, a smaller dose may be sufficient to activate the CAR-T cell, by inducing a sufficient level of costimulatory molecule activity to achieve the required therapeutic result. In some examples, a higher dose may be necessary to achieve a higher level of costimulation of CAR-T cell activity. The amount of ligand may be determined, for example, based on the subject's clinical condition, weight, and/or gender or other relevant physical characteristic. By controlling the amount of multimeric ligand administered to the subject, the likelihood of adverse events such as, for example, a cytokine storm may be reduced. The anti-tumor activity of modified cells that express the inducible MyD88/CD40 costimulatory molecule along with a CAR may be modulated using appropriate dosages of the multimeric ligand. Thus provided in certain embodiments are methods where the modified cell is administered to a subject, and a dosage of multimeric ligand is administered; following this first administration, the method may comprise identifying a presence or absence of a condition in the patient that requires an increase or decrease in the level of CAR-T cell activity, which may be achieved by an additional dose of multimeric ligand in either greater or lower concentrations than the first dose. Thus the method comprises administering a multimeric ligand that binds to the multimerization region of the inducible MyD88/CD40 costimulatory molecule, maintaining a subsequent dosage of the multimeric ligand, or adjusting a subsequent dosage of the multimeric ligand to the patient based on the presence or absence of the condition identified in the patient.

The term "dosage" is meant to include both the amount of the dose and the frequency of administration, such as, for example, the timing of the next dose. The term "dosage level" refers to the amount of the multimeric ligand administered in relation to the body weight of the subject. Thus increasing the dosage level would mean increasing the amount of the ligand administered relative to the subject's weight. In addition, increasing the concentration of the dose administered, such as, for example, when the multimeric ligand is administered using a continuous infusion pump would mean that the concentration administered (and thus the amount administered) per minute, or second, is increased.

An indication of adjusting or maintaining a subsequent drug dose, such as, for example, a subsequence dose of the multimeric ligand, and/or the subsequent drug dosage, can be provided in any convenient manner. An indication may be provided in tabular form (e.g., in a physical or electronic medium) in some embodiments. For example, the disease or condition symptoms may be provided in a table, and a clinician may compare the symptoms with a list or table of stages of the disease. The clinician then can identify from the table an indication for subsequent drug dose.

In certain embodiments, an indication can be presented (e.g., displayed) by a computer, after the symptoms or the stage is provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of an activated cell, a nucleic acid, or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

A. Genetic Based Therapies

In certain embodiments, a cell is provided with an expression construct capable of providing a co-stimulatory polypeptide, such as those discussed herein, and, for example, in a T cell. The lengthy discussion of expression vectors and the genetic elements employed therein is incorporated into this section by reference. In certain examples, the expression vectors may be viral vectors, such as adenovirus, adeno-associated virus, herpes virus, vaccinia virus and retrovirus. In another example, the vector may be a lysosomal-encapsulated expression vector.

Gene delivery may be performed in both in vivo and ex vivo situations. For viral vectors, one generally will prepare a viral vector stock. Examples of viral vector-mediated gene delivery ex vivo and in vivo are presented in the present application. For in vivo delivery, depending on the kind of virus and the titer attainable, one will deliver, for example, about 1, 2, 3, 4, 5, 6, 7, 8, or $9\times10^4$, 1, 2, 3, 4, 5, 6, 7, 8, or $9\times10^5$, 1, 2, 3, 4, 5, 6, 7, 8, or $9\times10^6$, 1, 2, 3, 4, 5, 6, 7, 8, or $9\times10^7$, 1, 2, 3, 4, 5, 6, 7, 8, or $9\times10^8$, 1, 2, 3, 4, 5, 6, 7, 8, or $9\times10^9$, 1, 2, 3, 4, 5, 6, 7, 8, or $9\times10^{10}$, 1, 2, 3, 4, 5, 6, 7, 8, or $9\times10^{11}$ or 1, 2, 3, 4, 5, 6, 7, 8, or $9\times10^{12}$ infectious particles to the patient. Similar figures may be extrapolated for liposomal or other non-viral formulations by comparing relative uptake efficiencies. Formulation as a pharmaceutically acceptable composition is discussed below. The multimeric ligand, such as, for example, AP1903, may be delivered, for example at doses of about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight.

B. Cell Based Therapy

Another therapy that is contemplated is the administration of transduced T cells. The T cells may be transduced in vitro. Formulation as a pharmaceutically acceptable composition is discussed herein.

In cell based therapies, the transduced cells may be, for example, transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

C. Combination Therapies

In order to increase the effectiveness of the expression vectors presented herein, it may be desirable to combine these compositions and methods with an agent effective in the treatment of the disease.

In certain embodiments, anti-cancer agents may be used in combination with the present methods. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In further embodiments antibiotics can be used in combination with the pharmaceutical composition to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixindefensins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition at the same time or within a period of time wherein separate administration of the pharmaceutical composition and an agent to a cell, tissue or organism produces a desired therapeutic benefit. This may be achieved by contacting the cell, tissue or organism with a single composition or pharmacological formulation that includes both the pharmaceutical composition and one or more agents, or by contacting the cell with two or more distinct compositions or formulations, wherein one composition includes the pharmaceutical composition and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

In some embodiments, the chemotherapeutic agent may be TAXOTERE (docetaxel), or another taxane, such as, for example, cabazitaxel. The chemotherapeutic may be administered either before, during, or after treatment with the cells and inducer. For example, the chemotherapeutic may be administered about 1 year, 11, 10, 9, 8, 7, 6, 5, or 4 months, or 18, 17, 16, 15, 14, 13, 12, 11, 10, 9, 8, 7, 6, 5, 4, 3, 2, weeks or 1 week prior to administering the first dose of activated nucleic acid. Or, for example, the chemotherapeutic may be administered about 1 week or 2, 3, 4, 5, 6, 7, 8, 9, 10, 11, 12, 13, 14, 15, 16, 17, or 18 weeks or 4, 5, 6, 7, 8, 9, 10, or 11 months or 1 year after administering the first dose of cells or inducer.

Administration of a chemotherapeutic agent may comprise the administration of more than one chemotherapeutic agent. For example, cisplatin may be administered in addition to TAXOTERE or other taxane, such as, for example, cabazitaxel.

Generating an Immune Response Targeted to a Specific Tumor or Disease

Chimeric antigen receptors (CARs) are artificial receptors designed to convey antigen specificity to T cells. They include an antigen-specific component, a transmembrane component, and an intracellular component selected to activate the T cell and provide specific immunity. Chimeric antigen receptor-expressing T cells may be used in various therapies, including cancer therapies.

The T cells and other cells transduced with the inducible CD40, inducible MyD88, or the inducible MyD88/CD40 may also be transduced with a nucleic acid coding for a chimeric antigen receptor, or CAR. The chimeric antigen receptor may be selected to target tumor antigens present on the surface of the tumor to be treated, or other antigens associated with disease. Activated T cells expressing the chimeric antigen receptor would then target tumors, or other diseases. Transduced T cells may also include memory T cells, which would maintain the immune defense against the particular tumor or disease.

Optimized and Personalized Therapeutic Treatment

Treatment for solid tumor cancers, including, for example, prostate cancer, may be optimized by determining the concentration of IL-6, IL6-sR, or VCAM-1 during the course of treatment. IL-6 refers to interleukin 6. IL-6-sR refers to the IL-6 soluble receptor, the levels of which often correlate closely with levels of IL-6. VCAM-1 refers to vascular cell adhesion molecule. Different patients having different stages or types of cancer, may react differently to various therapies. The response to treatment may be monitored by following the IL-6, IL-6sR, or VCAM-1 concentrations or levels in various body fluids or tissues. The determination of the concentration, level, or amount of a polypeptide, such as, IL-6, IL-6sR, or VCAM-1, may include detection of the full length polypeptide, or a fragment or variant thereof. The fragment or variant may be sufficient to be detected by, for example, immunological methods, mass spectrometry, nucleic acid hybridization, and the like. Optimizing treatment for individual patients may help to avoid side effects as a result of overdosing, may help to determine when the treatment is ineffective and to change the course of treatment, or may help to determine when doses may be increased. Technology discussed herein optimizes therapeutic methods for treating solid tumor cancers by allowing a clinician to track a biomarker, such as, for example, IL-6, IL-6sR, or VCAM-1, and determine whether a subsequent dose of a drug or vaccine for administration to a subject may be maintained, reduced or increased, and to determine the timing for the subsequent dose.

Treatment for solid tumor cancers, including, for example, prostate cancer, may also be optimized by determining the concentration of urokinase-type plasminogen activator receptor (uPAR), hepatocyte growth factor (HGF), epidermal growth factor (EGF), or vascular endothelial growth factor (VEGF) during the course of treatment. Different patients having different stages or types of cancer, may react differently to various therapies. The levels of uPAR, HGF, EGF, and VEGF over the course of treatment for subject 1003 were measured. Subject 1003 shows systemic perturbation of hypoxic factors in serum, which may indicate a positive response to treatment. Without limiting the interpretation of this observation, this may indicate the secretion of hypoxic factors by tumors in response to treatment. Thus, the response to treatment may be monitored, for example, by following the uPAR, HGF, EGF, or VEGF concentrations or levels in various body fluids or tissues. The determination of the concentration, level, or amount of a polypeptide, such as, uPAR, HGF, EGF, or VEGF may include detection of the full length polypeptide, or a fragment or variant thereof. The fragment or variant may be sufficient to be detected by, for example, immunological methods, mass spectrometry, nucleic acid hybridization, and the like. Optimizing treatment for individual patients may help to avoid side effects as a result of overdosing, may help to determine when the treatment is ineffective and to change the course of treatment, or may help to determine when doses may be increased. Technology discussed herein optimizes therapeutic methods for treating solid tumor cancers by allowing a clinician to track a biomarker, such as, for example, uPAR, HGF, EGF, or VEGF, and determine whether a subsequent dose of a drug or vaccine for administration to a subject may be maintained, reduced or increased, and to determine the timing for the subsequent dose.

For example, it has been determined that amount or concentration of certain biomarkers changes during the course of treatment of solid tumors. Predetermined target levels of such biomarkers, or biomarker thresholds may be identified in normal subject, are provided, which allow a clinician to determine whether a subsequent dose of a drug administered to a subject in need thereof, such as a subject with a solid tumor, such as, for example, a prostate tumor, may be increased, decreased or maintained. A clinician can make such a determination based on whether the presence, absence or amount of a biomarker is below, above or about the same as a biomarker threshold, respectively, in certain embodiments.

For example, determining that an over-represented biomarker level is significantly reduced and/or that an under-represented biomarker level is significantly increased after drug treatment or vaccination provides an indication to a clinician that an administered drug is exerting a therapeutic effect. By "level" is meant the concentration of the biomarker in a fluid or tissue, or the absolute amount in a tissue. Based on such a biomarker determination, a clinician could make a decision to maintain a subsequent dose of the drug or raise or lower the subsequent dose, including modifying the timing of administration. The term "drug" includes traditional pharmaceuticals, such as small molecules, as well as biologics, such as nucleic acids, antibodies, proteins, polypeptides, modified cells and the like. In another example, determining that an over-represented biomarker level is not significantly reduced and/or that an under-represented biomarker level is not significantly increased provides an indication to a clinician that an administered drug is not significantly exerting a therapeutic effect. Based on such a biomarker determination, a clinician could make a decision to increase a subsequent dose of the drug. Given that drugs can be toxic to a subject and exert side effects, methods provided herein optimize therapeutic approaches as they provide the clinician with the ability to "dial in" an efficacious dosage of a drug and minimize side effects. In specific examples, methods provided herein allow a clinician to "dial up" the dose of a drug to an therapeutically efficacious level, where the dialed up dosage is below a toxic threshold level. Accordingly, treatment methods discussed herein enhance efficacy and reduce the likelihood of toxic side effects.

Cytokines are a large and diverse family of polypeptide regulators produced widely throughout the body by cells of diverse origin. Cytokines are small secreted proteins, including peptides and glycoproteins, which mediate and regulate immunity, inflammation, and hematopoiesis. They are produced de novo in response to an immune stimulus. Cytokines generally (although not always) act over short distances and short time spans and at low concentration. They generally act by binding to specific membrane receptors, which then signal the cell via second messengers, often tyrosine kinases, to alter cell behavior (e.g., gene expression). Responses to cytokines include, for example, increasing or decreasing expression of membrane proteins (including cytokine receptors), proliferation, and secretion of effector molecules.

The term "cytokine" is a general description of a large family of proteins and glycoproteins. Other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on cells that secrete them (autocrine action), on nearby cells (paracrine action), or in some instances on distant cells (endocrine action).

Examples of cytokines include, without limitation, interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 and the like), interferons (e.g., IFN-beta, IFN-gamma and the like), tumor necrosis factors (e.g., TNF-alpha, TNF-beta and the like), lymphokines, monokines and chemokines; growth factors (e.g., transforming growth factors (e.g., TGF-alpha, TGF-beta and the like)); colony-stimulating factors (e.g. GM-CSF, granulocyte colony-stimulating factor (G-CSF) etc.); and the like.

A cytokine often acts via a cell-surface receptor counterpart. Subsequent cascades of intracellular signaling then alter cell functions. This signaling may include upregulation and/or downregulation of several genes and their transcription factors, resulting in the production of other cytokines, an increase in the number of surface receptors for other molecules, or the suppression of their own effect by feedback inhibition.

VCAM-1 (vascular cell adhesion molecule-1, also called CD106), contains six or seven immunoglobulin domains and is expressed on both large and small vessels only after the endothelial cells are stimulated by cytokines. Thus, VCAM-1 expression is a marker for cytokine expression.

Cytokines may be detected as full-length (e.g., whole) proteins, polypeptides, metabolites, messenger RNA (mRNA), complementary DNA (cDNA), and various intermediate products and fragments of the foregoing (e.g., cleavage products (e.g., peptides, mRNA fragments)). For example, IL-6 protein may be detected as the complete, full-length molecule or as any fragment large enough to provide varying levels of positive identification. Such a fragment may comprise amino acids numbering less than 10, from 10 to 20, from 20 to 50, from 50 to 100, from 100 to 150, from 150 to 200 and above. Likewise, VCAM-1 protein can be detected as the complete, full-length amino acid molecule or as any fragment large enough to provide varying levels of positive identification. Such a fragment may comprise amino acids numbering less than 10, from 10 to 20, from 20 to 50, from 50 to 100, from 100 to 150 and above.

In certain embodiments, cytokine mRNA may be detected by targeting a complete sequence or any sufficient fragment for specific detection. A mRNA fragment may include fewer than 10 nucleotides or any larger number. A fragment may comprise the 3' end of the mRNA strand with any portion of the strand, the 5' end with any portion of the strand, and any center portion of the strand.

Detection may be performed using any suitable method, including, without limitation, mass spectrometry (e.g., matrix-assisted laser desorption ionization mass spectrometry (MALDI-MS), electrospray mass spectrometry (ES-MS)), electrophoresis (e.g., capillary electrophoresis), high performance liquid chromatography (HPLC), nucleic acid affinity (e.g., hybridization), amplification and detection (e.g., real-time or reverse-transcriptase polymerase chain reaction (RT-PCR)), and antibody assays (e.g., antibody array, enzyme-linked immunosorbant assay (ELISA)). Examples of IL-6 and other cytokine assays include, for example, those provided by Millipore, Inc., (MILLIPLEX-Human Cytokine/Chemokine Panel). Examples of IL6-sR assays include, for example, those provided by Invitrogen, Inc. (Soluble IL-6R: (Invitrogen Luminex® Bead-based assay)). Examples of VCAM-1 assays include, for example, those provided by R & D Systems ((CD106) ELISA development Kit, DUOSET from R&D Systems (#DY809)).

Sources of Biomarkers

The presence, absence or amount of a biomarker can be determined within a subject (e.g., in situ) or outside a subject (e.g., ex vivo). In some embodiments, presence, absence or amount of a biomarker can be determined in cells (e.g., differentiated cells, stem cells), and in certain embodiments, presence, absence or amount of a biomarker can be determined in a substantially cell-free medium (e.g., in vitro). The term "identifying the presence, absence or amount of a biomarker in a subject" as used herein refers to any method known in the art for assessing the biomarker and inferring the presence, absence or amount in the subject (e.g., in situ, ex vivo or in vitro methods).

A fluid or tissue sample often is obtained from a subject for determining presence or amount of biomarker ex vivo. Non-limiting parts of the body from which a tissue sample may be obtained include leg, arm, abdomen, upper back, lower back, chest, hand, finger, fingernail, foot, toe, toenail, neck, rectum, nose, throat, mouth, scalp, face, spine, throat, heart, lung, breast, kidney, liver, intestine, colon, pancreas, bladder, cervix, testes, muscle, skin, hair, tumor or area surrounding a tumor, and the like, in some embodiments. A tissue sample can be obtained by any suitable method known in the art, including, without limitation, biopsy (e.g., shave, punch, incisional, excisional, curettage, fine needle aspirate, scoop, scallop, core needle, vacuum assisted, open surgical biopsies) and the like, in certain embodiments. Examples of a fluid that can be obtained from a subject includes, without limitation, blood, cerebrospinal fluid, spinal fluid, lavage fluid (e.g., bronchoalveolar, gastric, peritoneal, ductal, ear, arthroscopic), urine, interstitial fluid, feces, sputum, saliva, nasal mucous, prostate fluid, lavage, semen, lymphatic fluid, bile, tears, sweat, breast milk, breast fluid, fluid from region of inflammation, fluid from region of muscle wasting and the like, in some embodiments.

A sample from a subject may be processed prior to determining presence, absence or amount of a biomarker. For example, a blood sample from a subject may be processed to yield a certain fraction, including without limitation, plasma, serum, buffy coat, red blood cell layer and the like, and biomarker presence, absence or amount can be determined in the fraction. In certain embodiments, a tissue sample (e.g., tumor biopsy sample) can be processed by slicing the tissue sample and observing the sample under a microscope before and/or after the sliced sample is contacted with an agent that visualizes a biomarker (e.g., antibody). In some embodiments, a tissue sample can be exposed to one or more of the following non-limiting conditions: washing, exposure to high salt or low salt solution (e.g., hypertonic, hypotonic, isotonic solution), exposure to shearing conditions (e.g., sonication, press (e.g., French press)), mincing, centrifugation, separation of cells, separation of tissue and the like. In certain embodiments, a biomarker can be separated from tissue and the presence, absence or amount determined in vitro. A sample also may be stored for a period of time prior to determining the presence, absence or amount of a biomarker (e.g., a sample may be frozen, cryopreserved, maintained in a preservation medium (e.g., formaldehyde)).

A sample can be obtained from a subject at any suitable time of collection after a drug is delivered to the subject. For example, a sample may be collected within about one hour after a drug is delivered to a subject (e.g., within about 5, 10, 15, 20, 25, 30, 35, 40, 45, 55 or 60 minutes of delivering a drug), within about one day after a drug is delivered to a subject (e.g., within about 2, 3, 4, 5, 6, 7, 8, 9, 10, 11, 12, 13, 14, 15, 16, 17, 18, 19, 20, 21, 22, 23 or 24 hours of delivering a drug) or within about two weeks after a drug is delivered to a subject (e.g., within about 2, 3, 4, 5, 6, 7, 8, 9, 10, 11, 12, 13 or 14 days of delivering the drug). A collection may be made on a specified schedule including hourly, daily, semi-weekly, weekly, bi-weekly, monthly, bi-monthly, quarterly, and yearly, and the like, for example. If a drug is administered continuously over a time period (e.g., infusion), the delay may be determined from the first moment of drug is introduced to the subject, from the time the drug administration ceases, or a point in-between (e.g., administration time frame midpoint or other point).

Biomarker Detection

The presence, absence or amount of one or more biomarkers may be determined by any suitable method known in the art, and non-limiting determination methods are discussed herein. Determining the presence, absence or amount of a biomarker sometimes comprises use of a biological assay. In a biological assay, one or more signals detected in the assay can be converted to the presence, absence or amount of a biomarker. Converting a signal detected in the assay can comprise, for example, use of a standard curve, one or more standards (e.g., internal, external), a chart, a computer program that converts a signal to a presence, absence or amount of biomarker, and the like, and combinations of the foregoing.

Biomarker detected in an assay can be full-length biomarker, a biomarker fragment, an altered or modified biomarker (e.g., biomarker derivative, biomarker metabolite), or sum of two or more of the foregoing, for example. Modified biomarkers often have substantial sequence identity to a biomarker discussed herein. For example, percent identity between a modified biomarker and a biomarker discussed herein may be in the range of 15-20%, 20-30%, 31-40%, 41-50%, 51-60%, 61-70%, 71-80%, 81-90% and 91-100%, (e.g. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 percent identity). A modified biomarker often has a sequence (e.g., amino acid sequence or nucleotide sequence) that is 90% or more identical to a sequence of a biomarker discussed herein. Percent sequence identity can be determined using alignment methods known in the art.

Detection of biomarkers may be performed using any suitable method known in the art, including, without limitation, mass spectrometry, antibody assay (e.g., ELISA), nucleic acid affinity, microarray hybridization, Northern blot, reverse PCR and RT-PCR. For example, RNA purity and concentration may be determined spectrophotometrically (260/280>1.9) on a Nanodrop 1000.

RNA quality may be assessed using methods known in the art (e.g., Agilent 2100 Bioanalyzer; RNA 6000 Nano LabChip® and the like).

Indication for Adjusting or Maintaining Subsequent Drug Dose

An indication for adjusting or maintaining a subsequent drug dose can be based on the presence or absence of a biomarker. For example, when (i) low sensitivity determinations of biomarker levels are available, (ii) biomarker levels shift sharply in response to a drug, (iii) low levels or high levels of biomarker are present, and/or (iv) a drug is not appreciably toxic at levels of administration, presence or absence of a biomarker can be sufficient for generating an indication of adjusting or maintaining a subsequent drug dose.

An indication for adjusting or maintaining a subsequent drug dose often is based on the amount or level of a biomarker. An amount of a biomarker can be a mean, median, nominal, range, interval, maximum, minimum, or relative amount, in some embodiments. An amount of a biomarker can be expressed with or without a measurement error window in certain embodiments. An amount of a biomarker in some embodiments can be expressed as a biomarker concentration, biomarker weight per unit weight, biomarker weight per unit volume, biomarker moles, biomarker moles per unit volume, biomarker moles per unit weight, biomarker weight per unit cells, biomarker volume per unit cells, biomarker moles per unit cells and the like. Weight can be expressed as femtograms, picograms, nano-grams, micrograms, milligrams and grams, for example. Volume can be expressed as femtoliters, picoliters, nanoliters, microliters, milliliters and liters, for example. Moles can be expressed in picomoles, nanomoles, micromoles, millimoles and moles, for example. In some embodiments, unit weight can be weight of subject or weight of sample from subject, unit volume can be volume of sample from the subject (e.g., blood sample volume) and unit cells can be per one cell or per a certain number of cells (e.g., micrograms of biomarker per 1000 cells). In some embodiments, an amount of biomarker determined from one tissue or fluid can be correlated to an amount of biomarker in another fluid or tissue, as known in the art.

An indication for adjusting or maintaining a subsequent drug dose often is generated by comparing a determined level of biomarker in a subject to a predetermined level of biomarker. A predetermined level of biomarker sometimes is linked to a therapeutic or efficacious amount of drug in a subject, sometimes is linked to a toxic level of a drug, sometimes is linked to presence of a condition, sometimes is linked to a treatment midpoint and sometimes is linked to a treatment endpoint, in certain embodiments. A predetermined level of a biomarker sometimes includes time as an element, and in some embodiments, a threshold is a time-dependent signature.

For example, an IL-6 or IL6-sR level of about 8-fold more than a normal level, or greater (e.g. about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75-fold more than a normal level) may indicate that the dosage of the drug or the frequency of administration may be increased in a subsequent administration.

The term "dosage" is meant to include both the amount of the dose and the frequency of administration, such as, for example, the timing of the next dose. An IL-6 or IL-6sR level less than about 8-fold more than a normal level (e.g. about 7, 6, 5, 4, 3, 2, or 1-fold more than a normal level, or less than or equal to a normal level) may indicate that the dosage may be maintained or decreased in a subsequent administration. A VCAM-1 level of about 8 fold more than a normal level, or greater (e.g. e.g. about 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75-fold more than a normal level) may indicate that the dosage of the drug may be increased in a subsequent administration. A VCAM-1 level less than about 8-fold more than a normal level (e.g. about 7, 6, 5, 4, 3, 2, or 1-fold more than a normal level, or less than or equal to a normal level) may indicate that the dosage may be maintained or decreased in a subsequent administration. A normal level of IL-6, IL-6sR, or VCAM-1 may be assessed in a subject not diagnosed with a solid tumor or the type of solid tumor under treatment in a patient.

Other indications for adjusting or maintaining a drug dose include, for example, a perturbation in the concentration of an individual secreted factor, such as, for example, GM-CSF, MIP-1alpha, MIP-1beta, MCP-1, IFN-gamma, RANTES, EGF or HGF, or a perturbation in the mean concentration of a panel of secreted factors, such as two or more of the markers selected from the group consisting of GM-CSF, MIP-1alpha, MIP-1beta, MCP-1, IFN-gamma, RANTES, EGF and HGF. This perturbation may, for example, consist of an increase, or decrease, in the concentration of an individual secreted factor by at least 5%, 10%, 20%, 30%, 40%, 50%, 60%, 70%, 80%, 90%, or 100% or an increase or decrease in the mean relative change in serum concentration of a panel of secreted factors by at least 5%, 10%, 20%, 30%, 40%, 50%, 60%, 70%, 80%, 90%, or 100%. This increase may, or may not, be followed by a return to baseline serum concentrations before the next administration. The increase or decrease in the mean relative change in serum concentration may involve, for example, weighting the relative value of each of the factors in the panel. Also, the increase or decrease may involve, for example, weighting the relative value of each of the time points of collected data. The weighted value for each time point, or each factor may vary, depending on the state or the extent of the cancer, metastasis, or tumor burden. An indication for adjusting or maintaining the drug dose may include a perturbation in the concentration of an individual secreted factor or the mean concentration of a panel of secreted factors, after 1, 2, 3, 4, 5, 6, 7, 8, 9, or 10 or more administrations. For example, where it is observed that over the course of treatment, for example, 6 administrations of a drug or the vaccines or compositions discussed herein, that the concentration of an individual secreted factor or the mean concentration of a panel of secreted factors is perturbed after at least one administration, then this may be an indication to maintain, decrease, or increase the frequency of administration or the subsequent dosage, or it may be an indication to continue treatment by, for example, preparing additional drug, adenovirus vaccine, or adenovirus transfected or transduced cells.

Some treatment methods comprise (i) administering a drug to a subject in one or more administrations (e.g., 1, 2, 3, 4, 5, 6, 7, 8, 9 or 10 doses), (ii) determining the presence, absence or amount of a biomarker in or from the subject after (i), (iii) providing an indication of increasing, decreasing or maintaining a subsequent dose of the drug for administration to the subject, and (iv) optionally administering the subsequent dose to the subject, where the subsequent dose is increased, decreased or maintained relative to the earlier dose(s) in (i). In some embodiments, presence, absence or amount of a biomarker is determined after each dose of drug has been administered to the subject, and sometimes presence, absence or amount of a biomarker is not determined after each dose of the drug has been administered (e.g., a biomarker is assessed after one or more of the first, second, third, fourth, fifth, sixth, seventh, eighth, ninth or tenth dose, but not assessed every time after each dose is administered).

An indication for adjusting a subsequent drug dose can be considered a need to increase or a need to decrease a subsequent drug dose. An indication for adjusting or maintaining a subsequent drug dose can be considered by a clinician, and the clinician may act on the indication in certain embodiments. In some embodiments, a clinician may opt not to act on an indication. Thus, a clinician can opt to adjust or not adjust a subsequent drug dose based on the indication provided.

An indication of adjusting or maintaining a subsequent drug dose, and/or the subsequent drug dosage, can be provided in any convenient manner. An indication may be provided in tabular form (e.g., in a physical or electronic medium) in some embodiments. For example, a biomarker threshold may be provided in a table, and a clinician may compare the presence, absence or amount of the biomarker determined for a subject to the threshold. The clinician then can identify from the table an indication for subsequent drug dose. In certain embodiments, an indication can be presented (e.g., displayed) by a computer after the presence, absence or amount of a biomarker is provided to computer (e.g., entered into memory on the computer). For example, presence, absence or amount of a biomarker determined for a subject can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount. A subsequent dose can be determined based on certain factors other than biomarker presence, absence or amount, such as weight of the subject, one or more metabolite levels for the subject (e.g., metabolite levels pertaining to liver function) and the like, for example.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

A subject can be prescreened to determine whether or not the presence, absence or amount of a particular biomarker may be determined. Non-limiting examples of prescreens include identifying the presence or absence of a genetic marker (e.g., polymorphism, particular nucleotide sequence); identifying the presence, absence or amount of a particular metabolite. A prescreen result can be used by a clinician in combination with the presence, absence or amount of a biomarker to determine whether a subsequent drug dose may be adjusted or maintained.

Antibodies and Small Molecules

In some embodiments, an antibody or small molecule is provided for use as a control or standard in an assay, or a therapeutic, for example. In some embodiments, an antibody or other small molecule configured to bind to a cytokine or cytokine receptor, including without limitation IL-6, IL-6sR, and alter the action of the cytokine, or it may be configured to bind to VCAM-1. In certain embodiments an antibody or other small molecule may bind to an mRNA structure encoding for a cytokine or receptor.

The term small molecule as used herein means an organic molecule of approximately 800 or fewer Daltons. In certain embodiments small molecules may diffuse across cell membranes to reach intercellular sites of action. In some embodiments a small molecule binds with high affinity to a biopolymer such as protein, nucleic acid, or polysaccharide and may sometimes alter the activity or function of the biopolymer. In various embodiments small molecules may be natural (such as secondary metabolites) or artificial (such as antiviral drugs); they may have a beneficial effect against a disease (such as drugs) or may be detrimental (such as teratogens and carcinogens). By way of non-limiting example, small molecules may include ribo- or deoxyribonucleotides, amino acids, monosaccharides and small oligomers such as dinucleotides, peptides such as the antioxidant glutathione, and disaccharides such as sucrose.

The term antibody as used herein is to be understood as meaning a gamma globulin protein found in blood or other bodily fluids of vertebrates, and used by the immune system to identify and neutralize foreign objects, such as bacteria and viruses. Antibodies typically include basic structural units of two large heavy chains and two small light chains.

Specific binding to an antibody requires an antibody that is selected for its affinity for a particular protein. For example, polyclonal antibodies raised to a particular protein, polymorphic variants, alleles, orthologs, and conservatively modified variants, or splice variants, or portions thereof, can be selected to obtain only those polyclonal antibodies that are specifically immunoreactive with GM-CSF, TNF-alpha or NF-kappa-B modulating protein and not with other proteins. This selection may be achieved by subtracting out antibodies that cross-react with other molecules.

Methods as presented herein include without limitation the delivery of an effective amount of an activated cell, a nucleic acid, or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

EXAMPLES

The examples set forth below illustrate certain embodiments and do not limit the technology. Examples herein that discuss the methods for transforming or transfecting cells in vitro, or ex vivo, provide examples of, but do not limit, the use of nucleic acids that express chimeric polypeptides.

Examples of the delivery of the transduced or transfected cells, and ligand inducer, to laboratory animals or human subjects provide examples of, but do not limit, the direct administration of nucleic acids expressing chimeric polypeptides, tumor antigens, and ligand inducer to subjects in need thereof.

In addition, the following sections, in particular, examples 21 et seq., provide examples of methods of expressing an inducible chimeric signaling molecule in therapeutic cells, for example, T cells, and methods of using the transformed cells. Methods of expressing inducible polypeptides, use of the transduced or transfected cells, and assays are discussed, for example, in Spencer, D. M., et al., Science 262: 1019-1024 (1993); U.S. Pat. No. 7,404,950, entitled "Induced Activation in Dendritic Cells," issued Jul. 29, 2008; U.S. patent application Ser. No. 13/087,329, entitled "Methods for Treating Solid Tumors," filed Apr. 14, 2011; and U.S. patent application Ser. No. 13/112,739, entitled "Methods for Inducing Selective Apoptosis, filed May 20, 2011, which are hereby incorporated by reference herein in their entirety.

Example 1: Materials and Methods

Discussed hereafter are materials and methods utilized in studies discussed in subsequent Examples.

Mice. NOD.Cg-Prkdc$^{scid}$Hr$^{hr}$/NCrHsd mice were purchased from Harlan Laboratories (Indianapolis, Ind.) and NOD.Cg-Prkdc$^{scid}$ Il2rg$^{tm1Wjl}$/SzJ (NSG) mice were obtained from Jackson Laboratories (Bar Harbor, Me.) and maintained in a pathogen-free mouse facility at the University of Texas Health Sciences (UTHSC) vivarium according to institutional guidelines. This study was approved by the Institutional Animal Care and Use Committees of UTHSC.

Cell lines, media and reagents. 293T (HEK 293T/17), Capan-1, HPAC, Raji cell lines were obtained from the American Type Culture Collection. 293T, Capan-1 and HPAC cell lines were maintained in DMEM (Invitrogen, Grand Island, N.Y.) supplemented with 10% fetal calf serum (FCS) and 2 mM GLUTAMAX (Invitrogen) at 37° C. and 5% $CO_2$. Raji tumor cells were cultured in RPMI with 10% FSC and 2 mM.GLUTAMAX T cells generated from peripheral blood mononuclear cells (PBMC) obtained from the Gulf Coast Blood Bank (Houston, Tex.) were cultured in 45% RPMI 1640, 45% Click's media (Invitrogen) supplemented with 10% fetal bovine serum (FBS), 2 mM GLUTAMAX (T cell media; TCM) and 100 U/ml IL-2 (Miltenyi Biotec, Bergisch Gladbach, Germany), unless otherwise noted. Clinical grade rimiducid was diluted in ethanol to a 100 mM working solution for in vitro assays, or 0.9% saline for animal studies.

Retroviral and plasmid constructs. Inducible MyD88/CD40 (iMC) comprising of the myristoylation-targeting sequence (M)[1], the TLR adaptor molecule, MyD88, the CD40 cytoplasmic region, and 2 tandem ligand-binding FKBP12v36 domains (Fv'Fv) were cloned in-frame with 2A-ΔCD19 in the SFG retroviral backbone[2] using Gibson assembly (New England Biolabs, Ipswich, Mass.)[3] to generate SFG-M.MyD88/CD40.Fv'Fv-2A-ΔCD19. Similarly, a control vector was generated that contained only the myristoylation sequence and tandem FKBP12v36 domains (termed FKBP, or SFG-FKBP-2A-ΔCD19). Additional retroviral vectors were constructed using a synthetic DNA approach (Integrated DNA Technologies, San Diego, Calif.) to generate MyD88 or CD40-only constructs, termed SFG-M.MyD88-2A-ΔCD19 or SFG-M.CD40-2A-ΔCD19, respectively. A first generation PSCA CAR was synthesized containing the murine bm2B3 single chain variable fragment (scFv)[4,5], the IgG1 CH2CH3 spacer region, the CD28 transmembrane domain and CD3ζ cytoplasmic domain (PSCA.ζ), as previously described[6]. A second generation CAR was constructed by PCR amplification, containing the CD28 transmembrane and cytoplasmic domain (PSCA.28.ζ). For coculture assays with PSCA-CAR modified cells, Capan-1 and HPAC tumor cells were modified by transfection with a GFP expression plasmid (pcDNA3.1-GFP.2A.puromycin) and stably selected with 1 μg/ml puromycin (Sigma). For in vivo tumor bioluminescence studies, T cells were cotransduced with SFG-EGFPluciferase.

Retroviral supernatant. Retroviral supernatants were produced by transient cotransfection of 293T cells with the SFG vector plasmid, Peg-Pam-e plasmid, containing the sequence for MoMLV gag-pol and the RD114 envelope-encoding plasmid using GENEJUICE (EMD Biosciences, Gibbstown, N.J.) transfection reagent, as previously described[7]. Supernatant containing the retrovirus was collected 48 and 72 hours after transfection.

Generation of activated T cells. Using peripheral blood mononuclear cells (PBMCs) obtained from the Gulf Coast Blood Bank (Houston, Tex.), anti-CD3/anti-CD28-activated T cells were generated essentially as discussed[7]. Briefly, $5 \times 10^5$ PBMCs resuspended in TCM and stimulated on non-tissue culture-treated 24-well plates coated with 0.5 μg/ml each of anti-CD3 and anti-CD28 antibodies (Miltenyi Biotec) in the presence of 100 U/ml IL-2. On day 3, activated T cells were harvested and transduced with retrovirus vectors or expanded in media supplemented with IL-2, as described below.

Transduction of T cells. Non-tissue culture-treated 24-well plates were coated with 7 μg/ml RETRONECTIN (Takara Bio, Otsu, Shiga, Japan) overnight at 4° C. The wells were washed with phosphate-buffered saline, then coated with retroviral supernatant. Subsequently, activated T cells were plated at $3 \times 10^5$ cells per well in viral supernatant supplemented with 100 U/ml IL-2. After three days in culture, cells were harvested and expanded in tissue culture-treated plates containing TCM plus 100 U/ml IL-2. For two or three-gene transductions, the protocol was identical to above except the wells were coated with equal amounts of each retroviral supernatant, and activated T cells were then plated into each well containing equal amounts of viral supernatant, supplemented with 100 U/ml IL-2.

Immunophenotyping. Gene-modified T cells were analyzed for iMC transgene expression 10-14 days post-transduction by using CD3-PerCP.Cy5 and CD19-PE (BioLegend). To detect CAR-transduced cells, T cells were also stained with an Fc-specific APC-conjugated monoclonal antibody (Jackson ImmunoResearch Laboratories, West Grove, Pa.), which recognizes the IgG1 CH2CH3 component of the receptor. T cells were also analyzed for CD4, CD8 and CD25 (BioLegend) following activation with 10 nM rimiducid and Capan-1 tumor cells. All flow cytometry was performed using an LSRII flow cytometer (Becton Dickenson, East Rutherford, N.J.), and the data analyzed using FLOWJO (Tree star, Ashland, Oreg.) or KALUZA software (Beckman Coulter, Pasadena, Calif.).

Cytokine and chemokine production. Production of IFN-γ, IL-2 and IL-6 by T cells modified with iMC or control vectors were analyzed by ELISA per the manufacturer's protocol (eBioscience, San Diego, Calif.). In addition, a panel of cytokines and chemokines were analyzed using a multiplex array system (BIOPLEX MAGPIX; Bio-Rad, Hercules, Calif.). In this assay, non-transduced T cells and iMC- or control vector (FKBP)-modified T cells were activated with and without 10 nM rimiducid, and supernatants collected at 24 and 48 hours. In some experiments, T cells were also stimulated with 50 ng/ml soluble anti-CD3. Additional experiments were performed with T cells modified with iMC (or control vector) and cotransduced with PSCA.ζ CAR, with and without rimiducid and Capan-1 target cells to measure the effect of cytokine and chemokine production with both PSCA. CAR and iMC signaling. Supernatants were collected and analyzed after 48 hours.

Immunoblotting. Primary human T cells transduced with either SFG-FKBP-2A-ΔCD19 or SFG-iMC-2A-ΔCD19 ($4 \times 10^6$ per point) were cultured for the indicated time points in a 37° C. water bath with either 10 nM rimiducid, 250 nM each PMA and ionomycin, or media alone. Media as removed by aspiration after centrifugation at 6000 rpm for 2 min at 4° C. Cytoplasmic extracts were prepared by lysis in 100 μl radioimmuno-precipitation assay buffer (50 mM Tris, 150 mM NaCl, 1% NP40, 2 mM EDTA, 0.1% SDS, 0.25% sodium deoxycholate) containing 1×MS-SAFE (Roche). Lysates were incubated on ice for 10 min and cytoplasmic fractions were cleared by centrifugation at 11,000 rpm for 20 min at 4° C. Cytoplasmic extracts equivalent to $1.5 \times 10^6$ cells were denatured in 1× Laemmli buffer by boiling for 5 min at 98° C. Proteins were separated by SDS-PAGE and electrotransferred to polyvinylidene difluoride membrane (Immobilon; Millipore). Membranes were sequentially probed with Abs specific for p-RelA (S536), p-Akt(5473), p-p38(T180/Y182), p-JNK(T183/Y185), p-ERK1/2(T202/Y204) (Cell Signaling Technology) or total β-tubulin (Santa Cruz). Bound Abs were detected by HRP-conjugated goat-anti-rabbit IgG Ab (Pierce), followed by ECL (Pierce) and detection on a Gel Logic imaging system (Carestream).

Milliplex MAP assay. Primary human T cells harvested from three healthy donors were transduced with either SFG-FKBP-2A-ΔCD19 or SFG-iMC-2A-ΔCD19. Cells ($2×10^6$ per point) were either maintained in T cell media (non-stimulated) or treated with either 10 nM rimiducid or 250 nM each of PMA and ionomycin in a 37° C. water bath for the indicated times. Cells were collected by centrifugation at 5000 rpm for 5 min at 4° C. Pellets were lysed with 200 μl Cell Signaling Lysis Buffer (MILLIPLEX MAP kit; Millipore) supplemented with Protease Inhibitor Cocktail (Cell Signaling Technology) and incubated on ice for 10 min. Lysates were agitated by tabletop rocker for 15 min and pelleted at 10,000 rpm for 10 min all at 4° C. The liquid phase was transferred to a new Eppendorf tubes, and individual aliquots were processed following the manufacturer's suggested protocol and analyzed on a BIOPLEX MAGPIX Multiplex Reader (Bio-Rad).

Phosphorylated epitopes were detected in Assay Buffer 2 (MILLIPLEX MAP kit) with antibodies specific for p-RelA (S536), p-Akt(S473), p-p38(T180/Y182), p-JNK(T183/Y185), p-ERK1/2(T202/Y204) (custom MILLIPLEX Magnetic Bead MAPMATE kit; Millipore) or GAPDH as a control for total protein content. Fold increase in phosphorylation was calculated by net MFI of rimiducid treatment at a given time point divided by the net MFI of the corresponding non-stimulated time point.

Gene expression analysis. Non-transduced or T cells modified with either FKBP or iMC retroviral vectors were generated from PBMCs from three healthy donors. T cells were stimulated with and without 10 nM rimiducid for 24 hours, then harvested and mRNA extracted (RNeasy; Qiagen, Valencia, Calif.) for hybridization on Human Genome U133 Plus 2.0 arrays (Affymetrix, Santa Clara, Calif.) using the Baylor College of Medicine Genomics and RNA Profiling Core (Baylor College of Medicine, Houston, Tex.). Signal data were extracted from the image files using ARRAYSTAR Ver 12.0.0 software (DNASTAR, Madison, Wis.). Genes that showed a >95% Benjamini-Hochberg confidence interval and >2-fold increase between data sets. Gene ontology was performed using Molecular Signatures Database (MSigDB) (Broad Institute, Cambridge, Mass.)[8] using C2 CP:KEGG gene sets, C3 Transcription factor targets and C7 immunological targets gene sets. Induced network module analysis was performed using the ConsensusPathDB-human (Max Plank Institute for Molecular Genetics, Berlin, Germany)[9].

Cytotoxicity assay. The specific cytotoxicity of CAR T cells against Capan-1 tumor cells was measured in 4-hour DELFIA cytotoxicity assay (Perkin Elmer, Waltham, Mass.) per the manufacturer's recommendations (Clontech Laboratories, Mountain View, Calif.) using effector to target (E:T) ratios ranging from 10:1 to 0.5:1 and using Capan-1 and HPAC as target cells.

Coculture experiment. To test the cytotoxicity, activation, proliferation and cytokine production following rimiducid-dependent and PSCA.ζ CAR activation, coculture assays were performed with Capan-1-GFP tumor cells at various effector:target ratios in TCM with or without 10 nM rimiducid, and in the absence of exogenous IL-2. After 7 days, all residual cells were collected by trypsinization, counted and stained with CD3, CD19 and Fc-specific antibodies and analyzed by flow cytometry.

In vivo studies. To evaluate the efficacy of iMC-modified CAR-T cells in vivo against solid tumors, immune deficient Shorn mice were engrafted with $1×10^6$ Capan-1 tumor cells re-suspended in MATRIGEL (BD Biosciences) and injected subcutaneously in the right flank. Mice were either given one (day 7) or two (day 7 and 14) i.v. injections of $1×10^7$ T cells. In some experiments, exogenous IL-2 was given intra-peritoneally twice weekly (biw) (4,000 U/animal). For Shorn experiments, rimiducid was administered at 5 mg/kg in 0.9% saline biw. Tumors were measured by calipers and tumor size calculated. NSG mice were used to evaluate the contribution of iMC and CAR to T cell in vivo expansion and efficacy. Here, NSG mice were engrafted s.c. with $1×10^6$ Capan-1 tumor cells. After 7 days, mice were treated with a single i.v. dose of $5×10^6$ of iMC and PSCA.ζ CAR-modified T cells cotransduced EGFPluciferase. Mice were subsequently treated with rimiducid i.p. weekly or twice weekly and then imaged using an IVIS imaging camera (Perkin Elmer) following i.p. injection of 150 mg/kg D-luciferin (Perkin Elmer). Photon emission was analyzed by constant region-of-interest (ROI) drawn over the tumor region and the signal measured as total counts as previously validated[10]. As above, efficacy was assessed by measuring tumors using calipers.

Statistics. Data are represented as mean±SEM. Data were analyzed using unpaired Student's t-test to calculate 2-tailed or 1-tailed P values to determine statistical significance in differences when comparing 2 treatment groups in all assays. One-way ANOVA followed by Bonferroni's multiple comparison test was used to compare multiple treatment groups. Two-way ANOVA followed by Bonferroni's test was used to assess statistical significance of differences in tumor growth between multiple treatment groups at different time points. Survival was recorded by Kaplan-Meier graphs, with significance determined by the log-rank test. Data were analyzed using GRAPHPAD PRISM version 5.0 software (GraphPad).

METHOD REFERENCES

1. Narayanan, P. et al. A composite MyD88/CD40 switch synergistically activates mouse and human dendritic cells for enhanced antitumor efficacy. *The Journal of clinical investigation* 121, 1524-1534 (2011).
2. Riviere, I., Brose, K. & Mulligan, R. C. Effects of retroviral vector design on expression of human adenosine deaminase in murine bone marrow transplant recipients engrafted with genetically modified cells. *Proceedings of the National Academy of Sciences of the United States of America* 92, 6733-6737 (1995).
3. Gibson, D. G. et al. Enzymatic assembly of DNA molecules up to several hundred kilobases. *Nature methods* 6, 343-345 (2009).
4. Leyton, J. V. et al. Humanized radioiodinated minibody for imaging of prostate stem cell antigen-expressing tumors. *Clinical cancer research: an official journal of the American Association for Cancer Research* 14, 7488-7496 (2008).
5. Leyton, J. V. et al. Engineered humanized diabodies for microPET imaging of prostate stem cell antigen-expressing tumors. *Protein engineering, design & selection: PEDS* 22, 209-216 (2009).
6. Katari, U. L. et al. Engineered T cells for pancreatic cancer treatment. *HPB: the official journal of the International Hepato Pancreato Biliary Association* 13, 643-650 (2011).
7. Foster, A. E. et al. Autologous designer antigen-presenting cells by gene modification of T lymphocyte blasts with IL-7 and IL-12. *Journal of immunotherapy* 30, 506-516 (2007).
8. Subramanian, A. et al. Gene set enrichment analysis: a knowledge-based approach for interpreting genome-wide expression profiles. *Proceedings of the National Academy of Sciences of the United States of America* 102, 15545-15550 (2005).
9. Kamburov, A., Wierling, C., Lehrach, H. & Herwig, R. ConsensusPathDB—a database for integrating human functional interaction networks. *Nucleic acids research* 37, D623-628 (2009).
10. Vera, J. et al. T lymphocytes redirected against the kappa light chain of human immunoglobulin efficiently kill mature B lymphocyte-derived malignant cells. *Blood* 108, 3890-3897 (2006).

Example 2: Activation of T Cells with Inducible MyD88/CD40

Figure 1B:
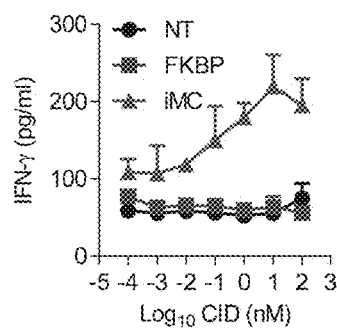
Figure 1C:
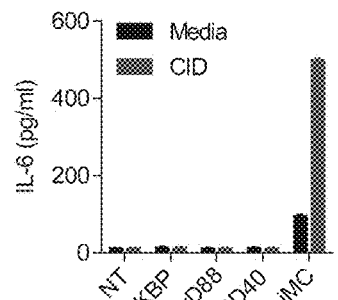
Figure 4A:
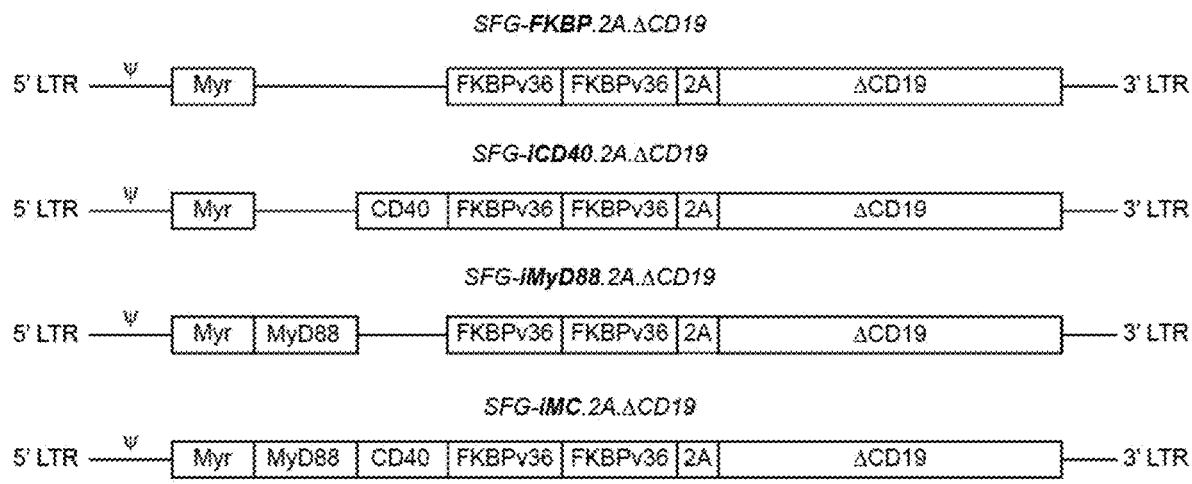
FIGS. 4A and 4B are schematics of the design of retroviral constructs.
Figure 5A:
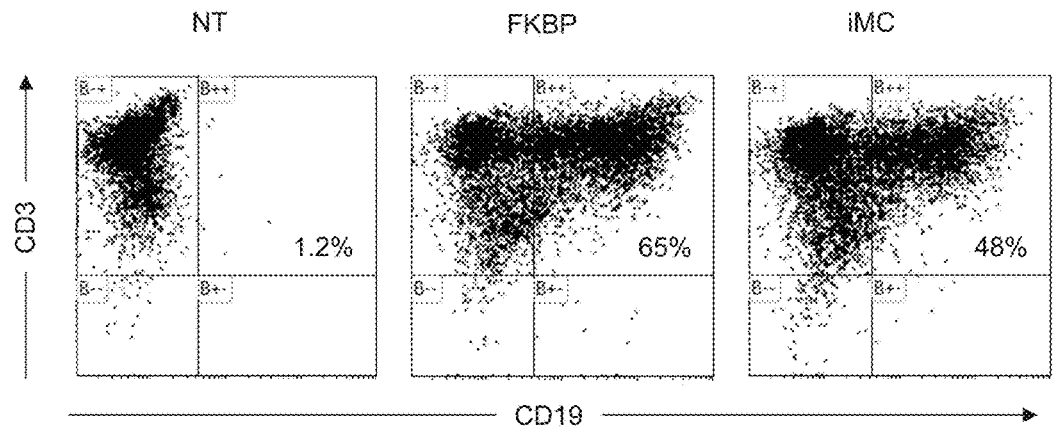
FIGS. 5A-5D provide assay results of the transduction efficiency, function and phenotype of iMC-modified T cells.
Figure 5B:
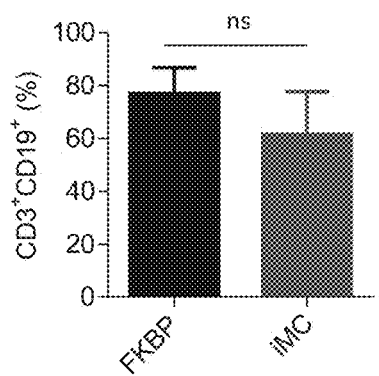
Figure 5C:
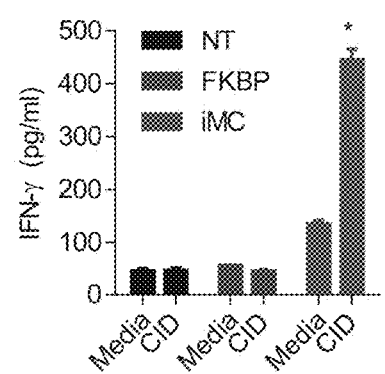
Figure 5D:
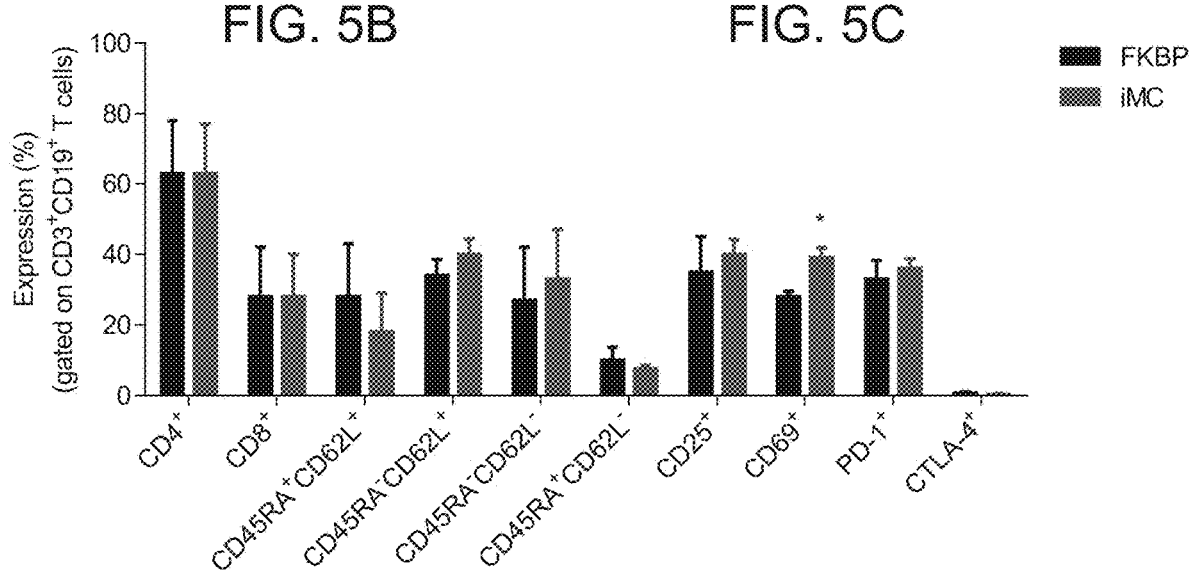
Figure 6A:
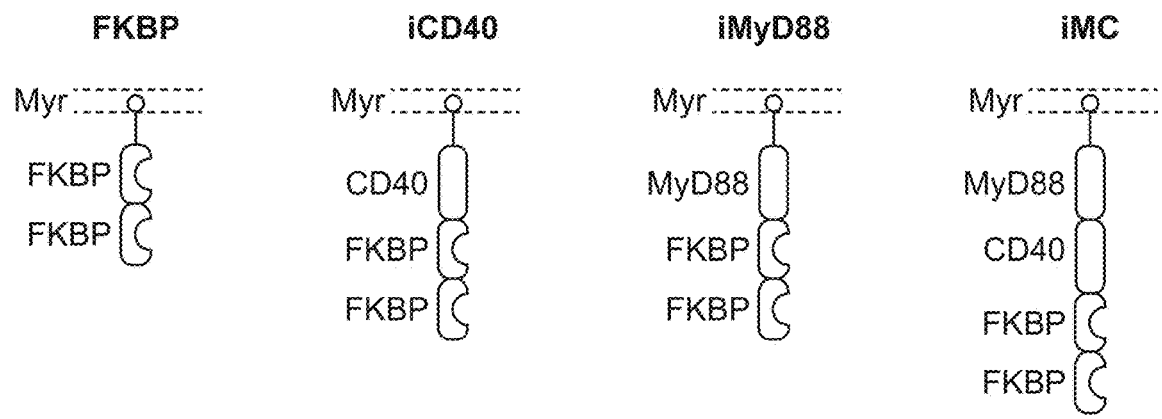
FIGS. 6A and 6B provide assay results of the transduction efficiency of iMC and control constructs.
Figure 6B:
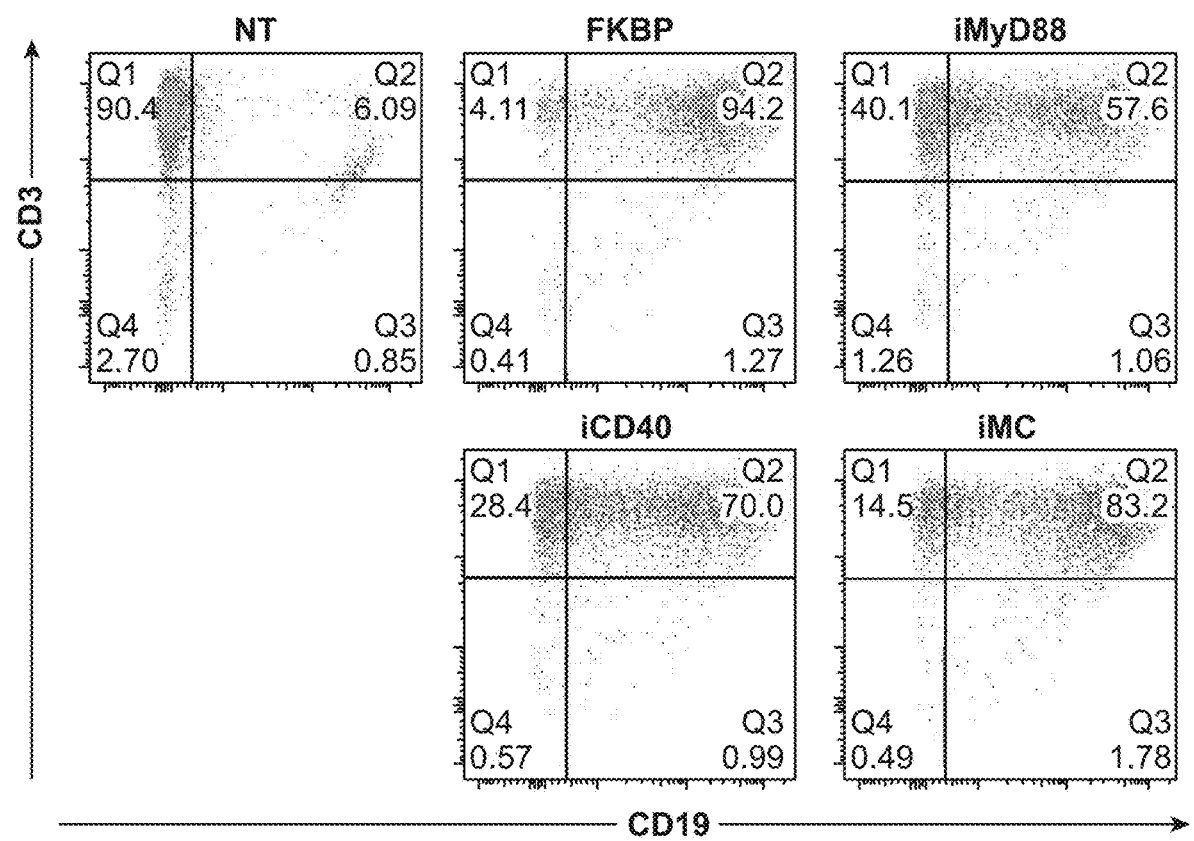

T cells were transduced with a bicistronic vector encoding iMC and surface marker, ΔCD19, the extracellular portion of CD19, or a control vector, which lacks the MyD88/CD40 signaling components, but retains the tandem FKBP12v36 ligand-binding domains (FIGS. 1a and 4a). After confirming comparable transduction efficiency by flow cytometry (77±10% and 62±16% CD3$^+$CD19$^+$, respectively) (FIG. 5a,b), transduced and non-transduced T cells were contacted with 10 nM rimiducid; dimerization elicited IFN-γ production only in iMC-modified T cells (FIG. 5c). Importantly, expression of iMC did not alter the phenotype or differentiation status of transduced T cells (FIG. 5D). As observed in dendritic cells[25], titration of rimiducid demonstrated the high sensitivity of the iMC switch, activating T cells in the sub-nanomolar range ($EC_{50}$=~0.12 nM) (FIG. 1b). Additional vectors expressing only MyD88 or CD40 (FIGS. 4a, 6a, and 6b) showed that both molecules act synergistically to activate T cells following rimiducid exposure (FIG. 1c).

Figure 1D:
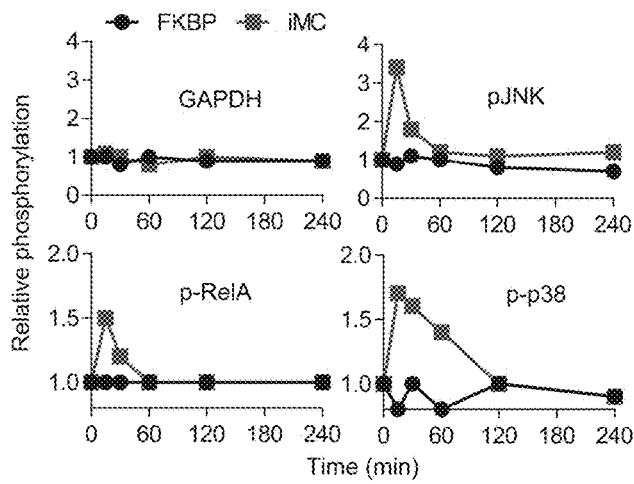
Figure 1E:
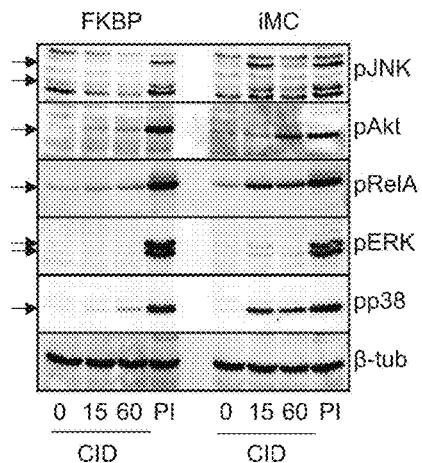
Figure 7A:
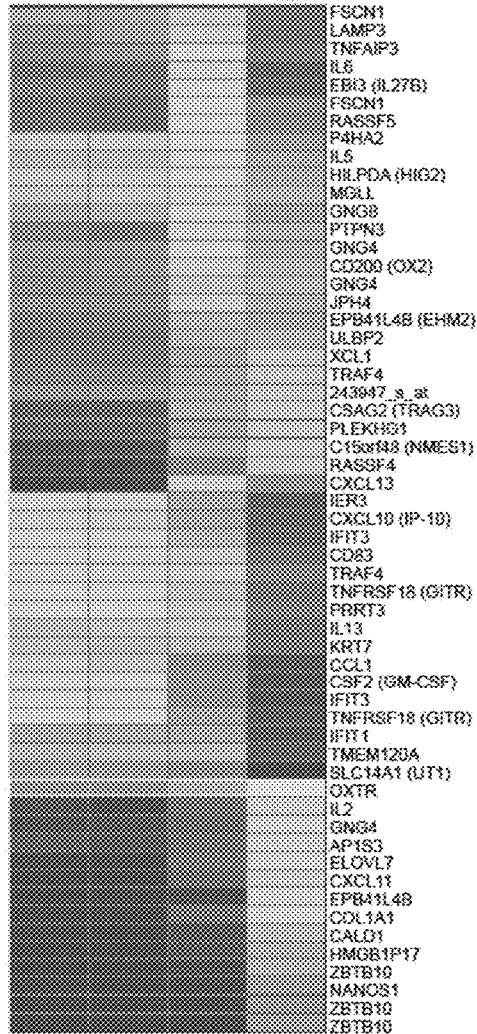
FIGS. 7A-7C provide results of gene expression analysis of iMC-modified T cells. T cells generated from healthy donors (n=3) were transduced with FKBP or iMC retrovirus and then treated with and without 10 nM rimiducid (CID). After 48 hours, mRNA was extracted and hybridized to human gene expression chips. Data was extracted using ARRAYSTAR (DNASTAR Inc., Madison, Wis.).
Figure 7B:
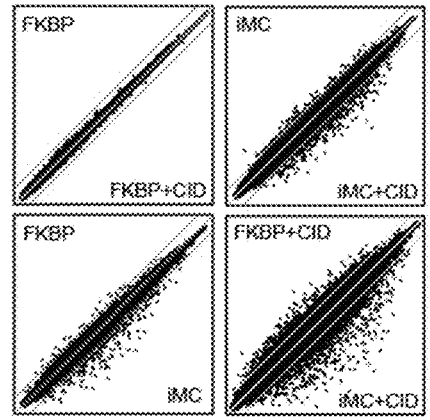
Figure 7C:
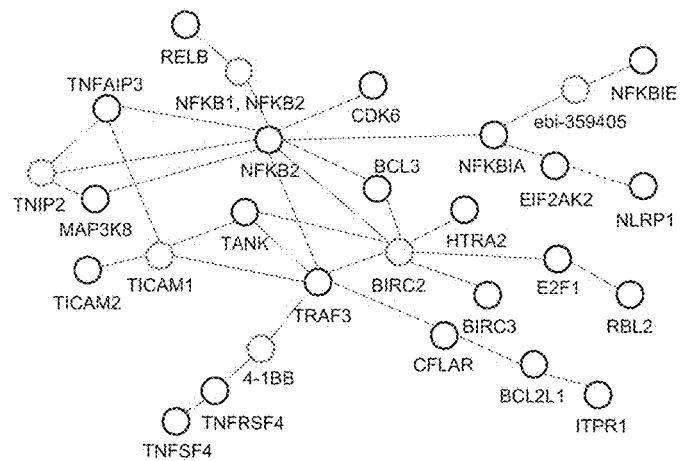
Figure 8A:
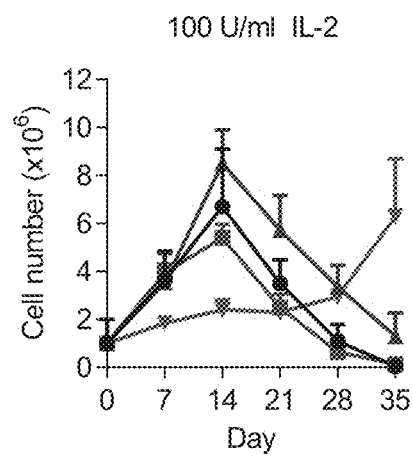
FIGS. 8A-8C provide assay results of iMC signaling in primary T cells induces cell survival in the absence of IL-2.
Figure 8B:
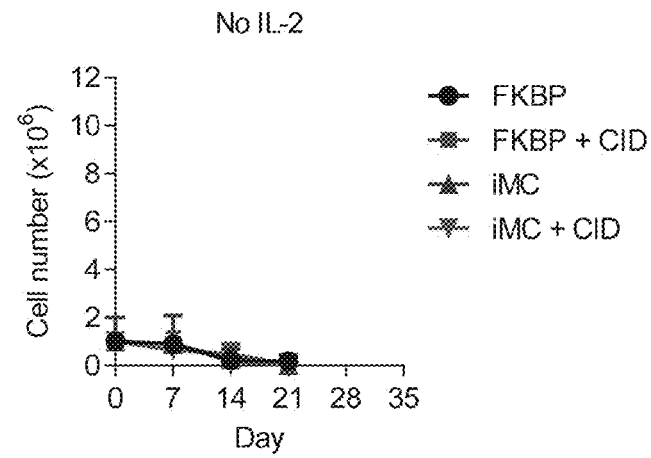
Figure 8C:
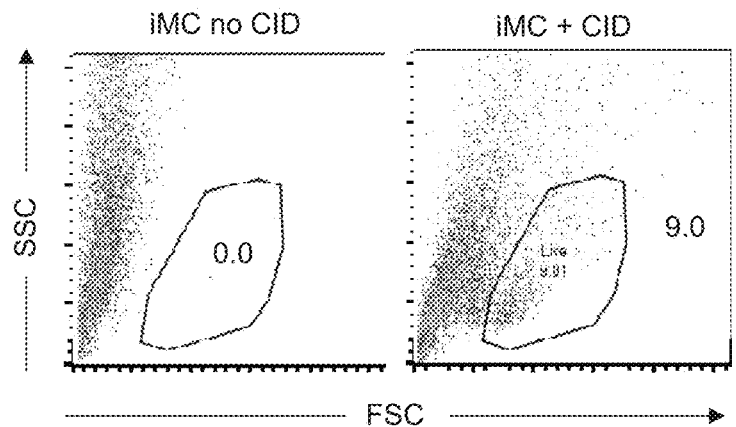

The phosphorylation of key downstream signaling molecules, including JNK, Akt, RelA, ERK and p38 MAPK was measured in the induced iMC T cells. Time course analyses indicated that rimiducid induces signaling in T cells as early as 15 minutes after exposure (FIG. 1d), and that each of these signaling pathways show increased phosphorylation in T cells, with MAPK and JNK showing the greatest rimiducid-dependent activation (FIG. 1e). A comparative microarray study indicated that iMC-modified T cells principally upregulated cytokine-related genes associated with IFN-γ cytokine production (e.g., IFIT1, IFIT3, CXCL10 and CXCL11), genes downstream of MyD88-dependent Toll-like receptor signaling (e.g., IL-5, IL-6, IL-13), and CD40-associated genes that regulate apoptosis (e.g., BCL2L1) upon rimiducid activation (FIGS. 7a and 7b). Gene ontology pathway analysis showed an increase in apoptosis-associated, and MAPK pathways corresponding to increased phosphorylation events identified by protein analyses (FIGS. 1d and 1e). In addition, gene set enrichment analysis (MSigDB and ConsensusPathDB) showed a significant association with NF-κB activation ($p=4.4 \times 10^{-15}$), as well as significant overlap with gene expression profiling in DCs activated by TLR4, 7 and 8 agonists ($p=6.1 \times 10^{-40}$) (Tables 1-3). These data suggests that iMC activate a number of pathways that induce a network of pro-survival genes (FIG. 7c). Indeed, rimiducid activation of iMC-expressing T cells allowed increased T cell survival and cell expansion in the presence of exogenous IL-2, but no proliferation was observed when IL-2 was withdrawn (FIGS. 8a-8c).

Example 3: Additional Characterization of Activated Modified T Cells

Figure 1F:
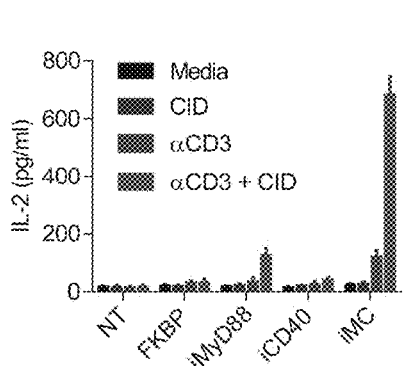
Figure 1G:
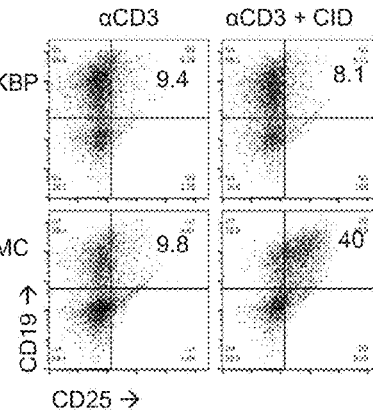
Figure 1H:
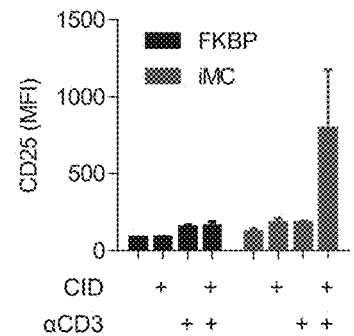
Figure 9A:
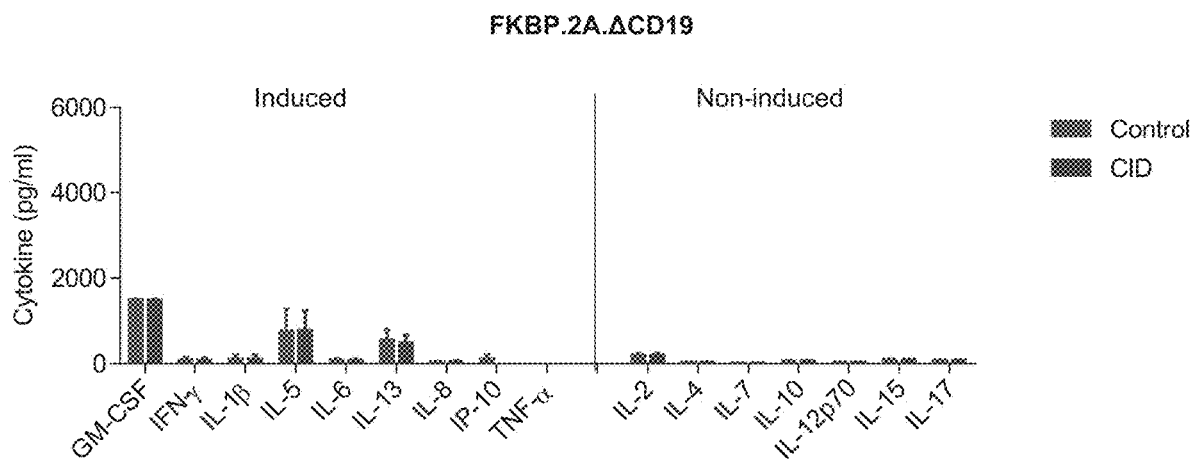
FIGS. 9A and 9B provide assay results of the induction of cytokines by rimiducid in iMC-transduced T cells. T cells transduced with either FKBP control vector (FIG. 9A) or iMC retrovirus (FIG. 9B) were treated with 10 nM rimiducid (CID) for 48 hours. Supernatants were then collected and analyzed using a multiplex cytokine/chemokine array.
Figure 9B:
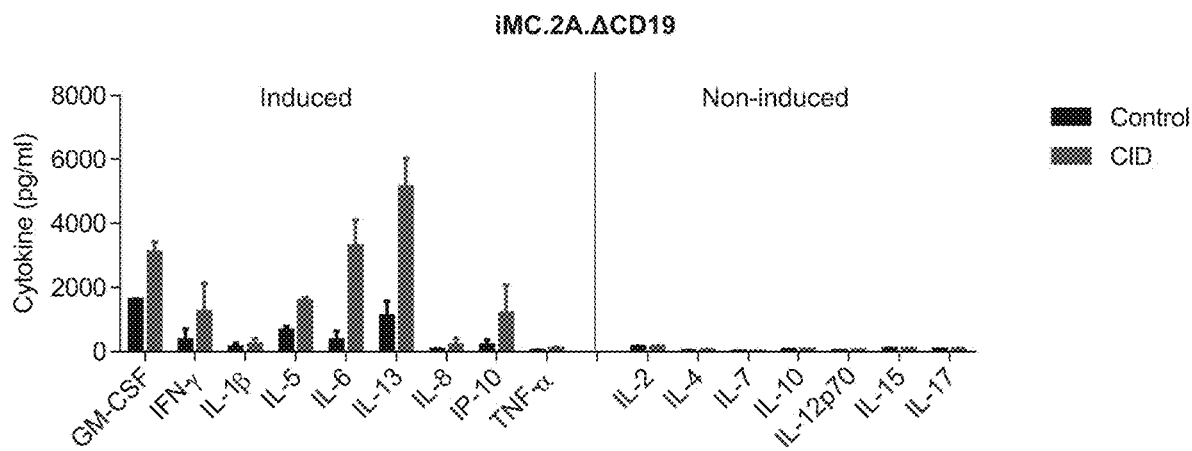

To further characterize T cell activation, multiplex array analysis was performed to measure a variety of cytokines and chemokines (FIGS. 9a and 9b). While GM-CSF, TNF-α, IL-5, IL-6, IL-8 and IL-13 secretion were induced by rimiducid, production of IL-2 and other cytokines was not upregulated, consistent with the hypothesis that complete T cell activation requires both NFAT and NF-κB signaling[19]. To test this, costimulated T cells were treated with rimiducid with and without CD3 cross-linking, followed by measuring IL-2 production and CD25 (high affinity IL-2 receptor) expression. Only iMC (and to a much lesser degree iM)-modified T cells activated with both signals (e.g., TCR and iMC) produced measurable IL-2 (FIG. 1f) and increased CD25 expression (FIGS. 1g and 1h). These data indicate that iMC may function in T cells as a costimulatory signal in which concurrent signaling of the native TCR and iMC is required to produce IL-2 and sustain T cell proliferation.

Example 4: Stimulation of CAR-Expressing T Cells by Inducible MyD88/CD40

Figure 4B:
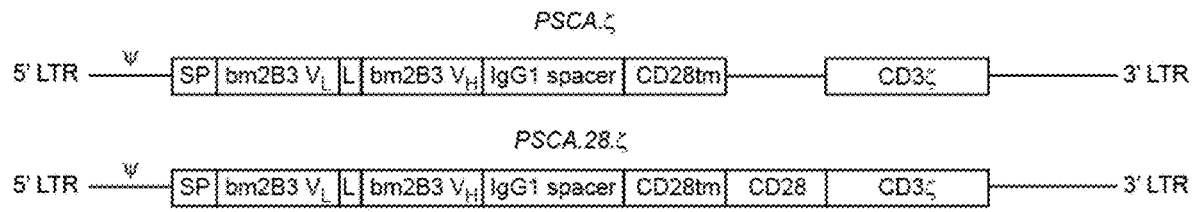
Figure 10A:
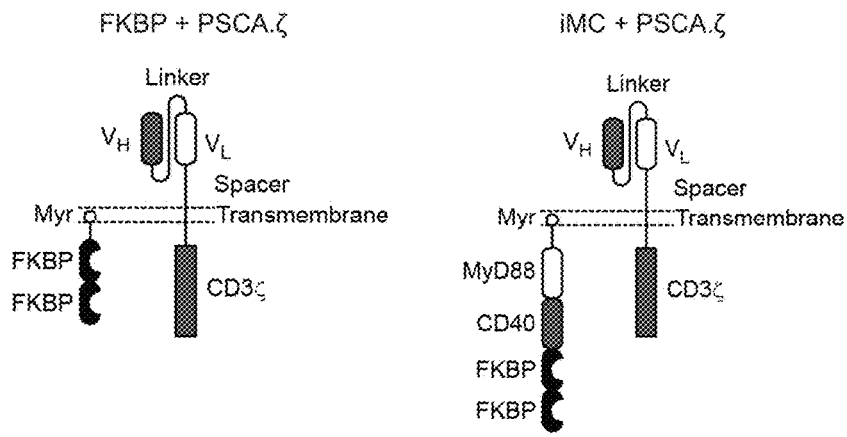
FIGS. 10A-10D provide assay results of the phenotype and function of T cells modified with iMC and PSCA.ζ CAR.
Figures 10B, 10C:
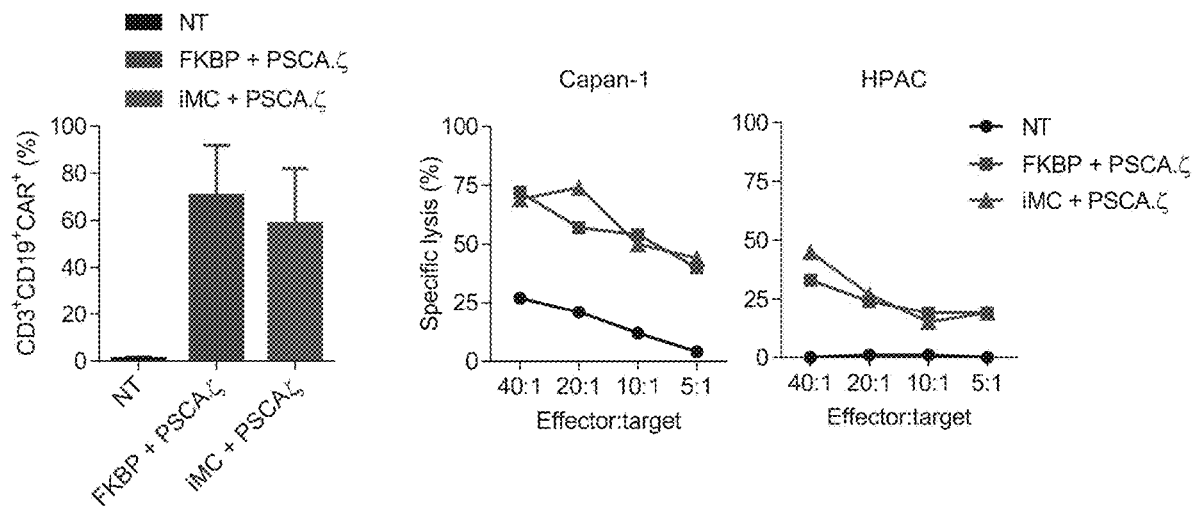
Figure 10D:
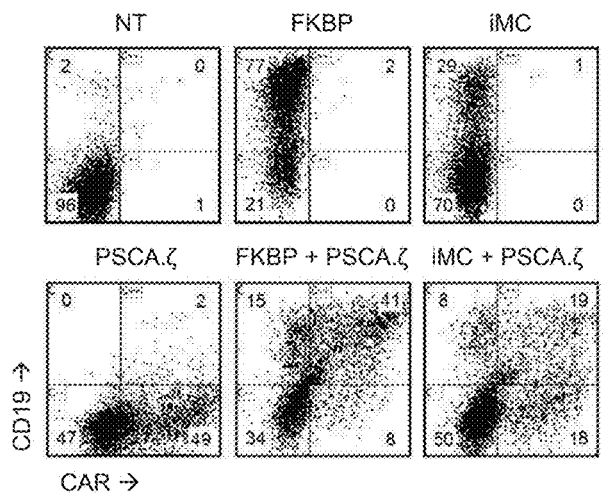
Figure 11:
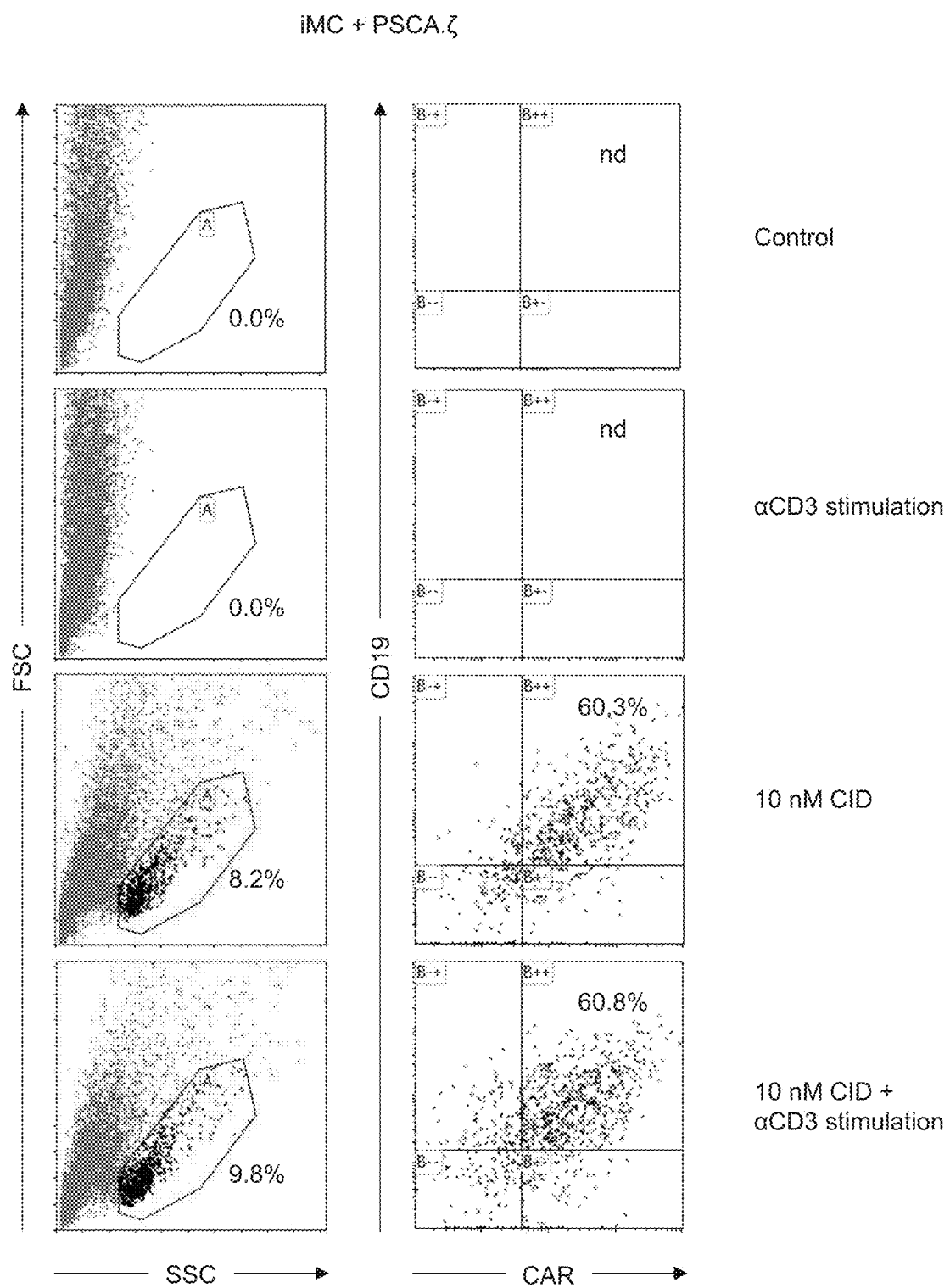
FIG. 11 provides assay results showing that iMC activation enhances CAR survival in the absence of IL-2. T cells transduced with iMC and PSCA.ζ CAR were cultured in media without IL-2 for 42 days. T cells received no treatment (media change only), αCD3 stimulation (50 ng/ml OKT3), 10 nM rimiducid (CID) or both CD3 and CID stimulation on a weekly basis. Cultures were phenotyped by flow cytometry for T cell survival (FSC/SSC) and iMC$^+$ CAR$^+$ expression by flow cytometry.

The primary signaling component of the TCR complex includes two non-covalently linked CD3ζ chains, each containing three immunoreceptor tyrosine-based activation motifs (ITAMs), which bind t activation protein 70 kDa (ZAP70), a tyrosine kinase that initiates the signaling cascade resulting in NFAT activation. First generation CARs are typically constructed with a protein-specific scFv region coupled to the CD3ζ cytoplasmic region, so that recognition of a target antigen by the scFv mimics native TCR signaling and induces T cell activation and cytolysis of the target cell. To examine whether inducible MyD88/CD40 would provide costimulatory activity to a chimeric antigen receptor comprising a CD3ζ polypeptide molecule, a first generation CAR recognizing tumor-associated surface protein, prostate stem cell antigen (PSCA)[28] was constructed and used to cotransduce T cells with either iMC or the FKBP only control vector. (FIGS. 4b and 5a). Flow cytometric analysis with CD3, CD19 and anti-CAR antibody showed that approximately 70±21% and 58±23% of the T cells were transduced with both CAR and control or CAR and iMC vectors, respectively (FIGS. 2b, 10a, and 10b), and that CAR-modified T cells retained cytotoxic function against PSCA$^+$ tumor cell lines (i.e., Capan-1 and HPAC) (FIG. 10c). To test whether coactivation of CAR (with tumor antigen) and iMC (with rimiducid) would result in T cell expansion and increased tumor control, coculture assays were performed against a GFP-modified, PSCA$^+$ tumor cell line (Capan-1). In the absence of rimiducid, T cells engineered with PSCA.ζ and control vector, or with PSCA.ζ CAR and iMC showed significant tumor killing relative to non-transduced T cells; however, activation of iMC by rimiducid addition further enhanced Capan-1-GFP elimination (FIG. 2c). Flow cytometry analysis showed a dramatic increase in the frequency of rimiducid-activated CAR$^+$iMC$^+$ T cells (FIG. 2c). Further, T cells modified with both CAR and iMC not only produced IL-2, they upregulated CD25 expression and proliferated in the presence of both tumor antigen and rimiducid (FIGS. 2d and 2e). To further define the requirements for IL-2 production, T cells were transduced with iMC or control vector (FKBP), with or without PSCA.ζ (FIG. 10d) and a comprehensive analysis was performed, altering tumor antigen stimulation and rimiducid activation (FIG. 2f). Only iMC and CAR-transduced T cells, stimulated with both tumor antigen and rimiducid produced IL-2. Importantly, rimiducid-induced activation of iMC similarly improved survival of CAR T cells in the absence of exogenous IL-2 or TCR activation (FIG. 11), suggesting that coactivation via CAR and iMC may amplify T cell responses, while iMC activation alone may improve survival and persistence.

Figure 3A:
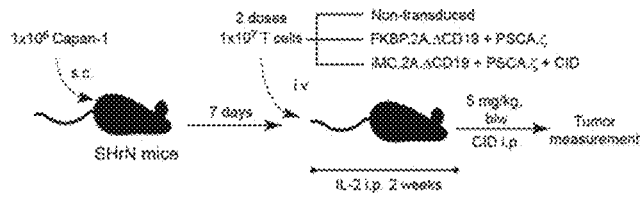
FIGS. 3A-3H provide the results of assays showing that CAR T cells cotransduced with iMC show enhanced antitumor efficacy in vivo in a rimiducid-dependent manner.
Figure 3B:
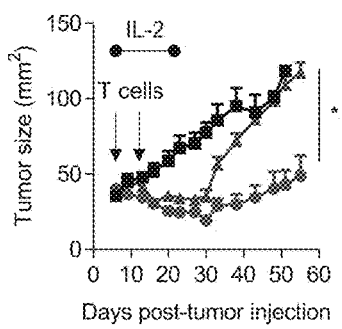
Figure 3C:
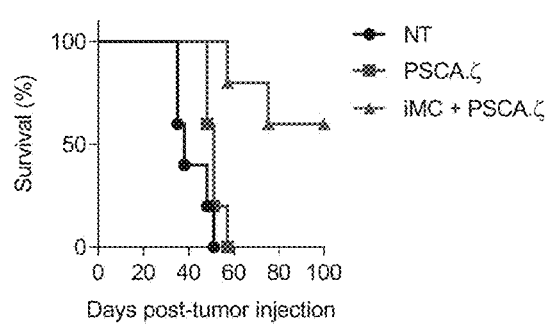
Figure 12A:
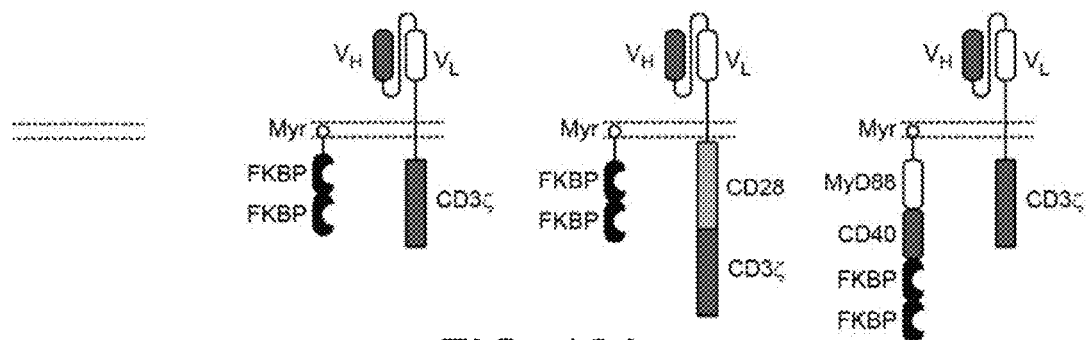
FIGS. 12A-12D provide assay results comparing CD28 and iMC costimulation in PSCA.ζ CAR T cells.
Figure 12B:
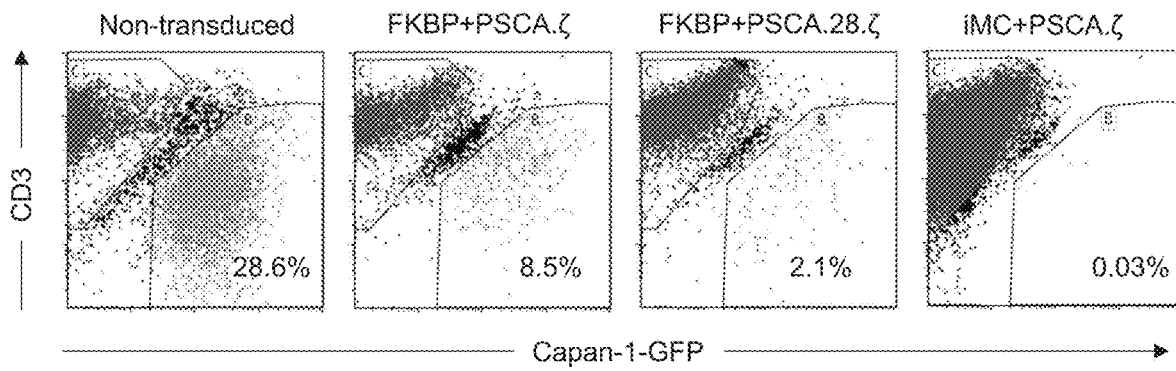
Figure 12C:
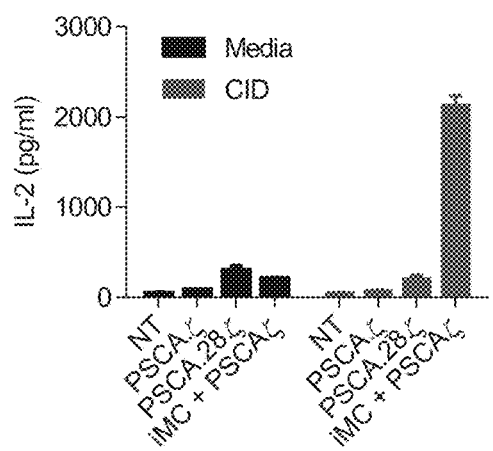
Figure 12D:
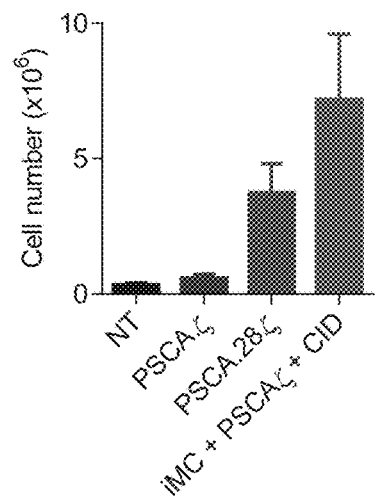
Figure 13A:
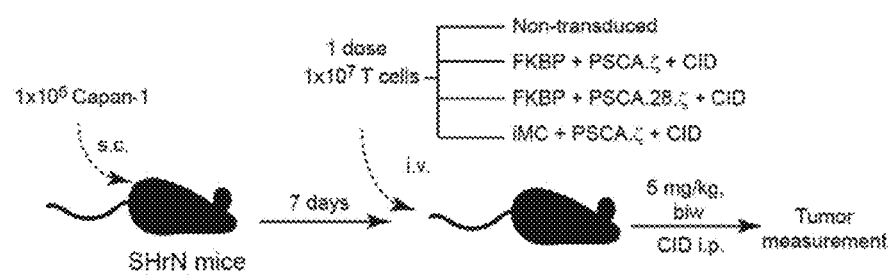
FIGS. 13A-13C Costimulation of iMC in PSCA.ζ CAR T cells enhances anti-tumor efficacy compared to CD28 costimulation.
Figure 13B:
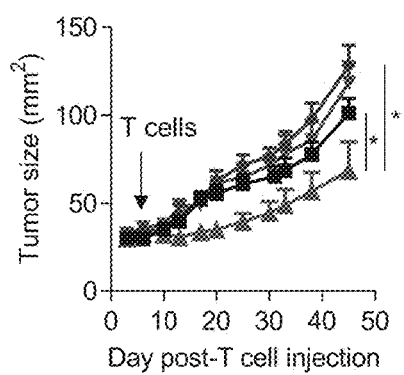
Figure 13C:
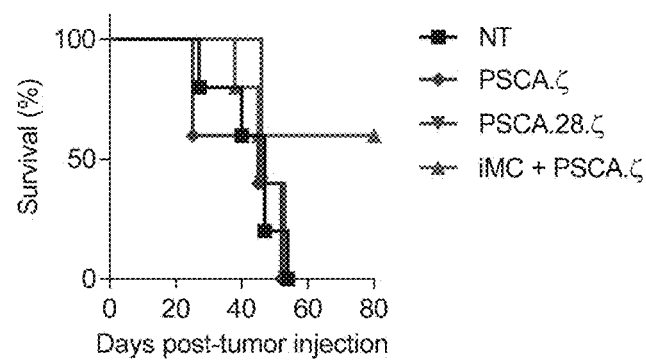

Example 5: Activation of CAR-Expressing T Cells by Inducible MyD88/CD40 Enhances Anti-Tumor Activity To evaluate whether CAR and iMC coactivation by tumor cells and rimiducid translates into improved antitumor efficacy, tumor xenograft studies in immune deficient mice were performed. Shorn ("SHrN" hairless NOD.SCID) mice engrafted with subcutaneous Capan-1 tumor cells were treated intravenously with two doses of non-transduced T cells, or T cells cotransduced with PSCA.ζ CAR with iMC or control vector (FIG. 3a). Rimiducid (5 mg/kg) was administered from days 1 to 100 by twice weekly intraperitoneal (i.p.) injections and exogenous IL-2 was administered until day 21. In accordance with in vitro studies, mice treated with iMC and PSCA.ζ CAR-transduced T cells showed significantly improved tumor control and survival compared to non-transduced T cells or T cells transduced with PSCA.ζ CAR and control vector (FIGS. 3b and 3c). Since iMC crosslinking appears to provide T cell costimulation, iMC was tested to determine whether it could replace CD28 function (e.g., increased proliferation and survival) in a second generation PSCA-CAR (PSCA.28.ζ) (FIG. 4b). Here, non-transduced T cells or T cells modified with FKBP and either PSCA.ζ or PSCA.28.ζ, or with iMC and PSCA.ζ (FIG. 12a) were examined for tumor killing and IL-2 secretion in coculture assays. While inclusion of the CD28 signaling domain improved tumor killing, T cell proliferation and IL-2 production, these features were even more highly augmented by iMC activation (FIGS. 12b-12d), suggesting that iMC could act as a rimiducid-dependent costimulatory switch in place of accessory signaling domains incorporated within the CAR molecule. To evaluate this in vivo, Capan-1 tumor-bearing immune-deficient mice were treated with a single dose of PSCA.ζ, PSCA.28.ζ or PSCA.ζ and iMC-modified T cells, then administered rimiducid at 5 mg/kg biweekly without IL-2 supplementation (FIG. 13a). Compared to T cells expressing PSCA.ζ and control vector, or PSCA.28.ζ-expressing T cells, PSCA.ζ and iMC-modified T cells led to a significant reduction in tumor burden and improved overall survival (FIGS. 13b and 13c). These data indicate that increased IL-2 production, and possibly other factors, improve T cell persistence and antitumor function above that achieved by CAR molecules containing the CD28 endodomain.

Figure 3D:
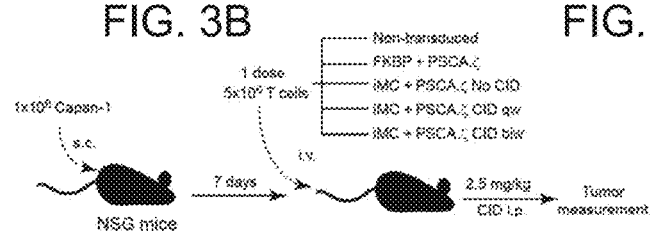
Figure 3E:
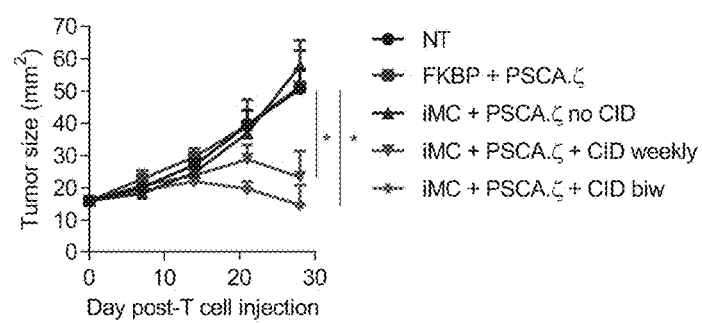
Figure 3F:
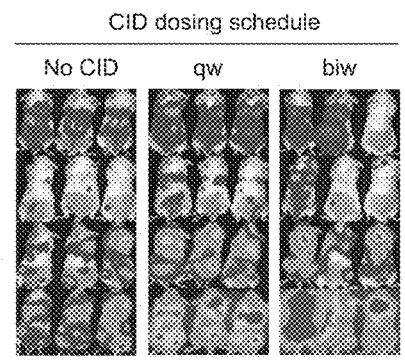
Figure 3G:
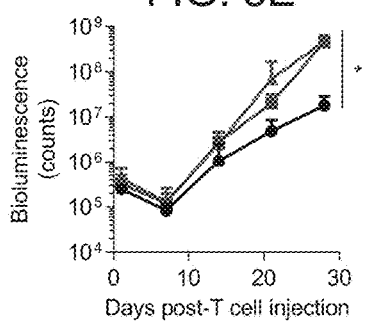
Figure 3H:
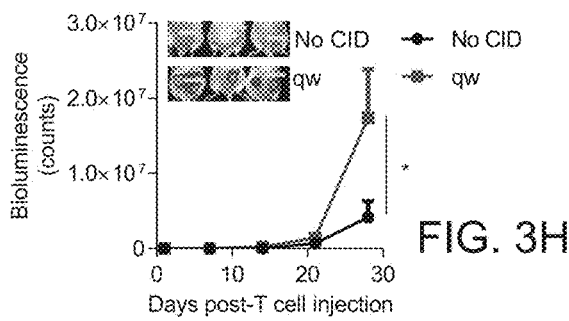
Figure 14:
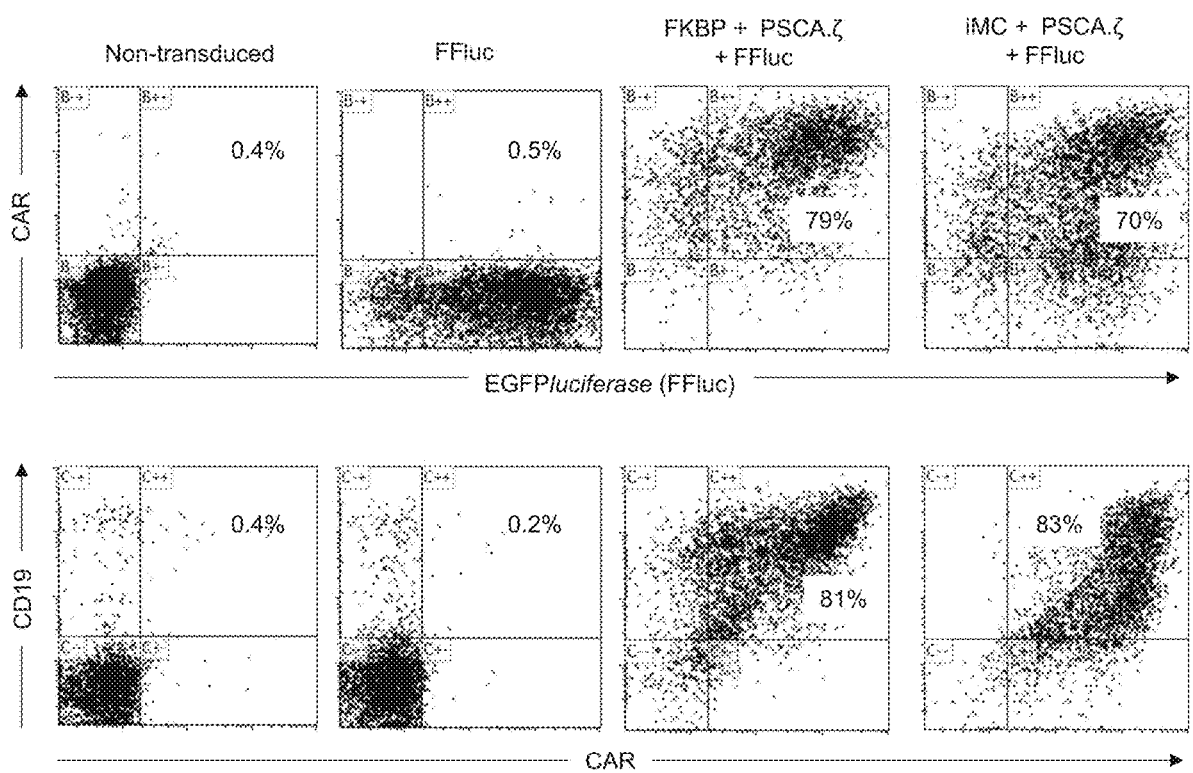
FIG. 14 provides scatter plots assessing of transduction efficiency of T cells cotransduced with multiple retroviral vectors. Non-transduced T cells were compared to T cells transduced with EGFPluciferase (EGFPluc) only, and FKBP$^+$PSCA.ζ, FKBP$^+$PSCA.28.ζ additionally transduced with EGFPluc. FKBP and iMC, and CAR expression were analyzed by flow cytometry.

Example 6: CAR-Modified T Cell Expansion in Inducible MyD88/CD40 Stimulated Cells As rimiducid-mediated iMC activation provided a growth advantage to CAR-modified T cells, T cell expansion in vivo was examined using bioluminescence (BLI) in NOD/SCID IL-2Rγ-deficient (NSG) mice. Non-transduced and PSCA.ζ CAR cotransduced with either iMC or FKBP were subsequently transduced a retrovirus encoding the EGFP-firefly luciferase fusion protein (EGFPluc) (FIG. 14) and infused into Capan-1 tumor-bearing NSG mice, treated with 2.5 mg/kg rimiducid once (qw) or twice weekly (biw) and imaged for bioluminescence (FIG. 3d). Activation of iMC by systemic administration of rimiducid enabled enhanced tumor control compared to T cells lacking iMC activation (FIG. 3e). In vivo imaging showed a dramatic increase in T cell BLI in rimiducid-treated mice both systemically (FIGS. 3f and 3g) and at the subcutaneous tumor site (FIG. 3h). These data show that external control of T cell costimulation using rimiducid can modulate T cell expansion and efficacy in vivo.

Example 7: Citations for Examples 2-6 and Herein

1. Kalos, M. et al. T cells with chimeric antigen receptors have potent antitumor effects and can establish memory in patients with advanced leukemia. *Science translational medicine* 3, 95ra73 (2011).

2. Porter, D. L., Levine, B. L., Kalos, M., Bagg, A. & June, C. H. Chimeric antigen receptor-modified T cells in chronic lymphoid leukemia. *The New England journal of medicine* 365, 725-733 (2011).

3. Brentjens, R. J. et al. CD19-targeted T cells rapidly induce molecular remissions in adults with chemotherapy-refractory acute lymphoblastic leukemia. *Science translational medicine* 5, 177ra138 (2013).

4. Kochenderfer, J. N. et al. Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor. *Journal of clinical oncology: official journal of the American Society of Clinical Oncology* (2014).

5. Grupp, S. A. et al. Chimeric antigen receptor-modified T cells for acute lymphoid leukemia. *The New England journal of medicine* 368, 1509-1518 (2013).

6. Maude, S. L. et al. Chimeric antigen receptor T cells for sustained remissions in leukemia. *The New England journal of medicine* 371, 1507-1517 (2014).

7. Straathof, K. C. et al. An inducible caspase 9 safety switch for T-cell therapy. *Blood* 105, 4247-4254 (2005).

8. Di Stasi, A. et al. Inducible apoptosis as a safety switch for adoptive cell therapy. *The New England journal of medicine* 365, 1673-1683 (2011).

9. Introna, M. et al. Genetic modification of human T cells with CD20: a strategy to purify and lyse transduced cells with anti-CD20 antibodies. *Human gene therapy* 11, 611-620 (2000).

10. Ciceri, F. et al. Antitumor effects of HSV-TK-engineered donor lymphocytes after allogeneic stem-cell transplantation. *Blood* 109, 4698-4707 (2007).

11. Fisher, D. T. et al. IL-6 trans-signaling licenses mouse and human tumor microvascular gateways for trafficking of cytotoxic T cells. *The Journal of clinical investigation* 121, 3846-3859 (2011).

12. Philip, B. et al. A highly compact epitope-based marker/suicide gene for easier and safer T-cell therapy. *Blood* 124, 1277-1287 (2014).

13. Linette, G. P. et al. Cardiovascular toxicity and titin cross-reactivity of affinity-enhanced T cells in myeloma and melanoma. *Blood* 122, 863-871 (2013).

14. Jena, B., Moyes, J. S., Huls, H. & Cooper, L. J. Driving CAR-based T-cell therapy to success. *Current hematologic malignancy reports* 9, 50-56 (2014).

15. Dotti, G., Gottschalk, S., Savoldo, B. & Brenner, M. K. Design and development of therapies using chimeric antigen receptor-expressing T cells. *Immunological reviews* 257, 107-126 (2014).

16. Kershaw, M. H. et al. A phase I study on adoptive immunotherapy using gene-modified T cells for ovarian cancer. *Clinical cancer research: an official journal of the American Association for Cancer Research* 12, 6106-6115 (2006).
17. Pule, M. A. et al. Virus-specific T cells engineered to coexpress tumor-specific receptors: persistence and antitumor activity in individuals with neuroblastoma. *Nature medicine* 14, 1264-1270 (2008).
18. Till, B. G. et al. CD20-specific adoptive immunotherapy for lymphoma using a chimeric antigen receptor with both CD28 and 4-1BB domains: pilot clinical trial results. *Blood* 119, 3940-3950 (2012).
19. Inman, B. A., Frigola, X., Dong, H. & Kwon, E. D. Costimulation, coinhibition and cancer. *Current cancer drug targets* 7, 15-30 (2007).
20. Carpenito, C. et al. Control of large, established tumor xenografts with genetically retargeted human T cells containing CD28 and CD137 domains. *Proceedings of the National Academy of Sciences of the United States of America* 106, 3360-3365 (2009).
21. Song, D. G. et al. CD27 costimulation augments the survival and antitumor activity of redirected human T cells in vivo. *Blood* 119, 696-706 (2012).
22. Fedorov, V. D., Themeli, M. & Sadelain, M. PD-1- and CTLA-4-based inhibitory chimeric antigen receptors (iCARs) divert off-target immunotherapy responses. *Science translational medicine* 5, 215ra172 (2013).
23. Kloss, C. C., Condomines, M., Cartellieri, M., Bachmann, M. & Sadelain, M. Combinatorial antigen recognition with balanced signaling promotes selective tumor eradication by engineered T cells. *Nature biotechnology* 31, 71-75 (2013).
24. Lanitis, E. et al. Chimeric antigen receptor T Cells with dissociated signaling domains exhibit focused antitumor activity with reduced potential for toxicity in vivo. *Cancer immunology research* 1, 43-53 (2013).
25. Narayanan, P. et al. A composite MyD88/CD40 switch synergistically activates mouse and human dendritic cells for enhanced antitumor efficacy. *The Journal of clinical investigation* 121, 1524-1534 (2011).
26. Rickert, R. C., Jellusova, J. & Miletic, A. V. Signaling by the tumor necrosis factor receptor superfamily in B-cell biology and disease. *Immunological reviews* 244, 115-133 (2011).
27. Gay, N. J., Symmons, M. F., Gangloff, M. & Bryant, C. E. Assembly and localization of Toll-like receptor signalling complexes. *Nature reviews. Immunology* 14, 546-558 (2014).
28. Anurathapan, U. et al. Kinetics of tumor destruction by chimeric antigen receptor-modified T cells. *Molecular therapy: the journal of the American Society of Gene Therapy* 22, 623-633 (2014).

TABLE 1

Gene ontology pathway analysis

| Name | P-value |
| --- | --- |
| Apoptosis GenMAPP | 5.41E−08 |
| Apoptosis | 7.14E−08 |
| Eicosanoid synthesis | 0.0004 |
| Cholesterol biosynthesis | 0.002 |
| Inflammatory response pathway | 0.002 |
| Small ligand GPCRs | 0.002 |
| Apoptosis KEGG | 0.003 |
| Nuclear receptors | 0.004 |
| Hypertrophy model | 0.004 |
| S1P signaling | 0.006 |
| Smooth muscle contraction | 0.01 |
| MAPK cascade | 0.03 |

TABLE 2

KEGG pathway gene enrichment signature

| Gene Set Name | # Genes in Gene Set (K) | # Genes in Overlap (k) | k/K | p-value | FDR q-value |
| --- | --- | --- | --- | --- | --- |
| KEGG_SMALL_CELL_LUNG_CANCER | 84 | 10 | 0.119 | 1.52E-10 | 2.82E-08 |
| KEGG_PATHWAYS_IN_CANCER | 328 | 16 | 0.0488 | 4.04E-10 | 3.76E-08 |
| KEGG_CYTOKINE_CYTOKINE_RECEPTOR_INTERACTION | 267 | 13 | 0.0487 | 1.85E-08 | 1.15E-06 |
| KEGG_MAPK_SIGNALING_PATHWAY | 267 | 11 | 0.0412 | 1.21E-06 | 5.64E-05 |
| KEGG_TOLL_LIKE_RECEPTOR_SIGNALING_PATHWAY | 102 | 7 | 0.0686 | 4.01E-06 | 1.49E-04 |
| KEGG_JAK_STAT_SIGNALING_PATHWAY | 155 | 8 | 0.0516 | 6.87E-06 | 2.13E-04 |
| KEGG_APOPTOSIS | 88 | 6 | 0.0682 | 2.07E-05 | 5.49E-04 |
| KEGG_FOCAL_ADHESION | 201 | 8 | 0.0398 | 4.47E-05 | 9.48E-04 |
| KEGG_NOD_LIKE_RECEPTOR_SIGNALING_PATHWAY | 62 | 5 | 0.0806 | 4.59E-05 | 9.48E-04 |
| KEGG_T_CELL_RECEPTOR_SIGNALING_PATHWAY | 108 | 6 | 0.0556 | 6.57E-05 | 1.22E-03 |

TABLE 3

Transcription factor target gene enrichment signature

| Gene Set Name | # Genes in Gene Set (K) | # Genes in Overlap (k) | k/K | p-value | FDR q-value |
| --- | --- | --- | --- | --- | --- |
| GGGCGGR_V$SP1_Q6 | 2940 | 64 | 0.0218 | 1.56E-18 | 9.57E-16 |
| V$NFKB_Q6 | 254 | 19 | 0.0748 | 4.43E-15 | 1.36E-12 |
| CAGGTG_V$E12_Q6 | 2485 | 52 | 0.0209 | 2.17E-14 | 4.45E-12 |
| V$NFKAPPAB_01 | 251 | 17 | 0.0677 | 6.32E-13 | 9.72E-11 |
| GGGAGGRR_V$MAZ_Q6 | 2274 | 45 | 0.0198 | 1.02E-11 | 1.06E-09 |
| V$CREL_01 | 256 | 16 | 0.0625 | 1.03E-11 | 1.06E-09 |
| V$NFKAPPAB65_01 | 237 | 15 | 0.0633 | 3.86E-11 | 3.39E-09 |
| RYTTCCTG_V$ETS2_B | 1085 | 29 | 0.0267 | 8.17E-11 | 6.28E-09 |
| RTAAACA_V$FREAC2_01 | 919 | 25 | 0.0272 | 1.23E-09 | 7.76E-08 |
| TGGAAA_V$NFAT_Q4_01 | 1896 | 37 | 0.0195 | 1.26E-09 | 7.76E-08 |

TABLE 4

Immunological gene enrichment signature

| Gene Set Name | # Genes in Gene Set (K) | # Genes in Overlap (k) | k/K | p-value | FDR q-value |
|---|---|---|---|---|---|
| GSE2706_UNSTIM_VS_2H_LPS_DC_DN | 200 | 35 | 0.175 | 6.09E-40 | 1.16E-36 |
| GSE9988_LOW_LPS_VS_CTRL_TREATED_MONOCYTE_UP | 200 | 34 | 0.17 | 2.29E-38 | 2.19E-35 |
| GSE2706_UNSTIM_VS_2H_LPS_AND_R848_DC_DN | 200 | 33 | 0.165 | 8.31E-37 | 5.29E-34 |
| GSE2706_UNSTIM_VS_8H_R848_DC_DN | 200 | 30 | 0.15 | 3.10E-32 | 9.87E-30 |
| GSE9988_ANTI_TREM1_VS_ANTI_TREM1_AND_LPS_MONOCYTE_DN | 200 | 30 | 0.15 | 3.10E-32 | 9.87E-30 |
| GSE9988_ANTI_TREM1_VS_LOW_LPS_MONOCYTE_DN | 200 | 30 | 0.15 | 3.10E-32 | 9.87E-30 |
| GSE2706_UNSTIM_VS_2H_R848_DC_DN | 200 | 29 | 0.145 | 9.53E-31 | 2.28E-28 |
| GSE9988_LOW_LPS_VS_VEHICLE_TREATED_MONOCYTE_UP | 200 | 29 | 0.145 | 9.53E-31 | 2.28E-28 |
| GSE22886_CTRL_VS_LPS_24H_DC_DN | 200 | 28 | 0.14 | 2.81E-29 | 4.47E-27 |
| GSE9988_ANTI_TREM1_VS_LPS_MONOCYTE_DN | 200 | 28 | 0.14 | 2.81E-29 | 4.47E-27 |

Example 8: Inducible MyD88/CD40 Chimeric Stimulating Molecule Having a Lower Basal Activity Moderate dimerizer-independent ("basal") NF-κB induction and IL-6 secretion is sometimes observed using the inducible MyD88/CD40 chimeric stimulating molecules. Although this activity is low, a modified MyD88/CD40 chimeric stimulating molecule that does not include an amino-terminal myristoylation region has been designed. This modified MyD88/CD40 chimeric stimulating molecule has been tested to determine if it has a lower level of spontaneous dimerization, or lower basal activity, than the chimeric stimulating molecule that comprises an amino-terminal myristoylation region.

Figure 15:
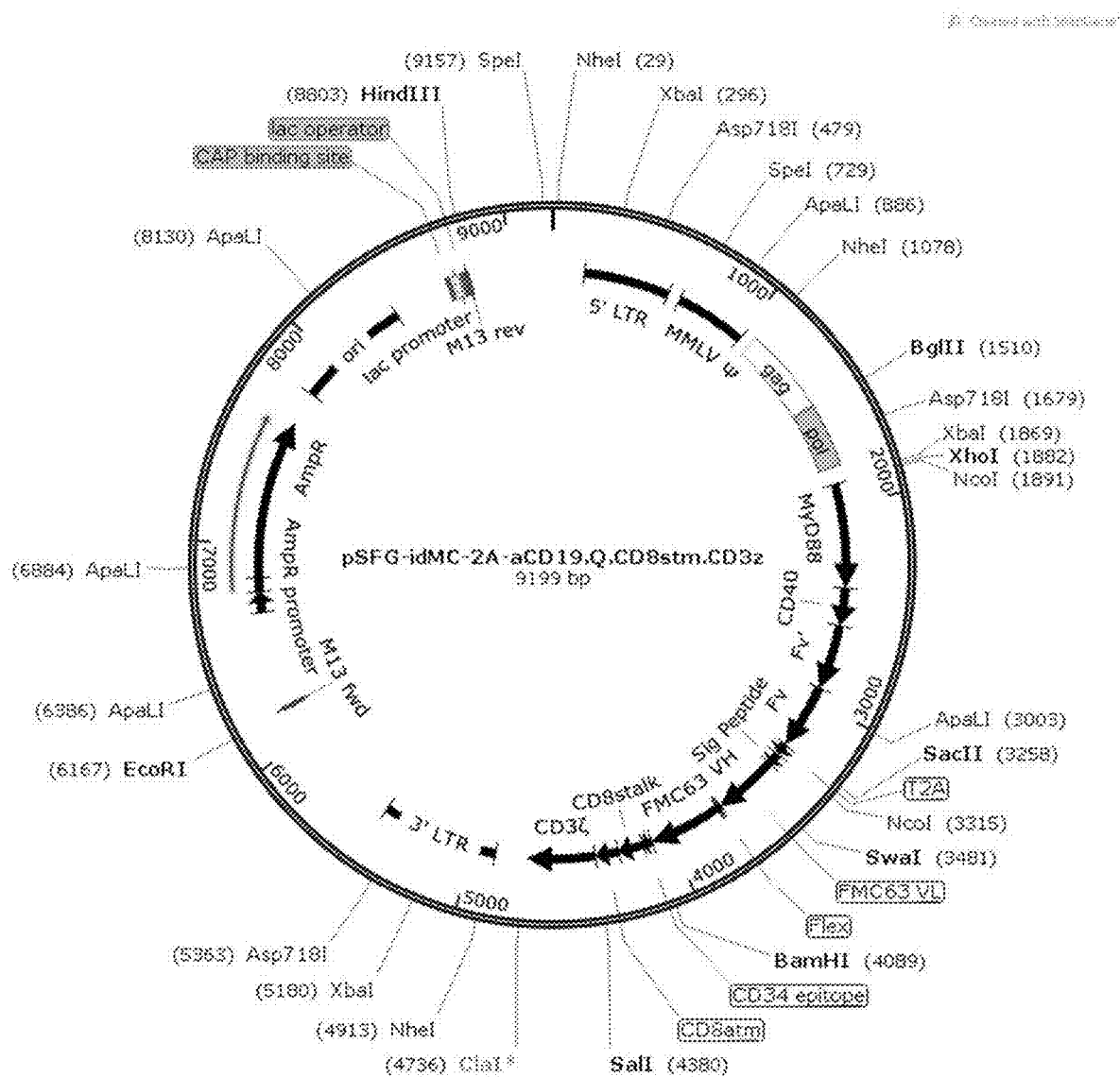
FIG. 15 is a plasmid map of vector pSFG-iΔMC-2A-aCD19-Q-8stm-CD3ζ, which does not include an amino-terminal myristoylation region.
Figure 16:
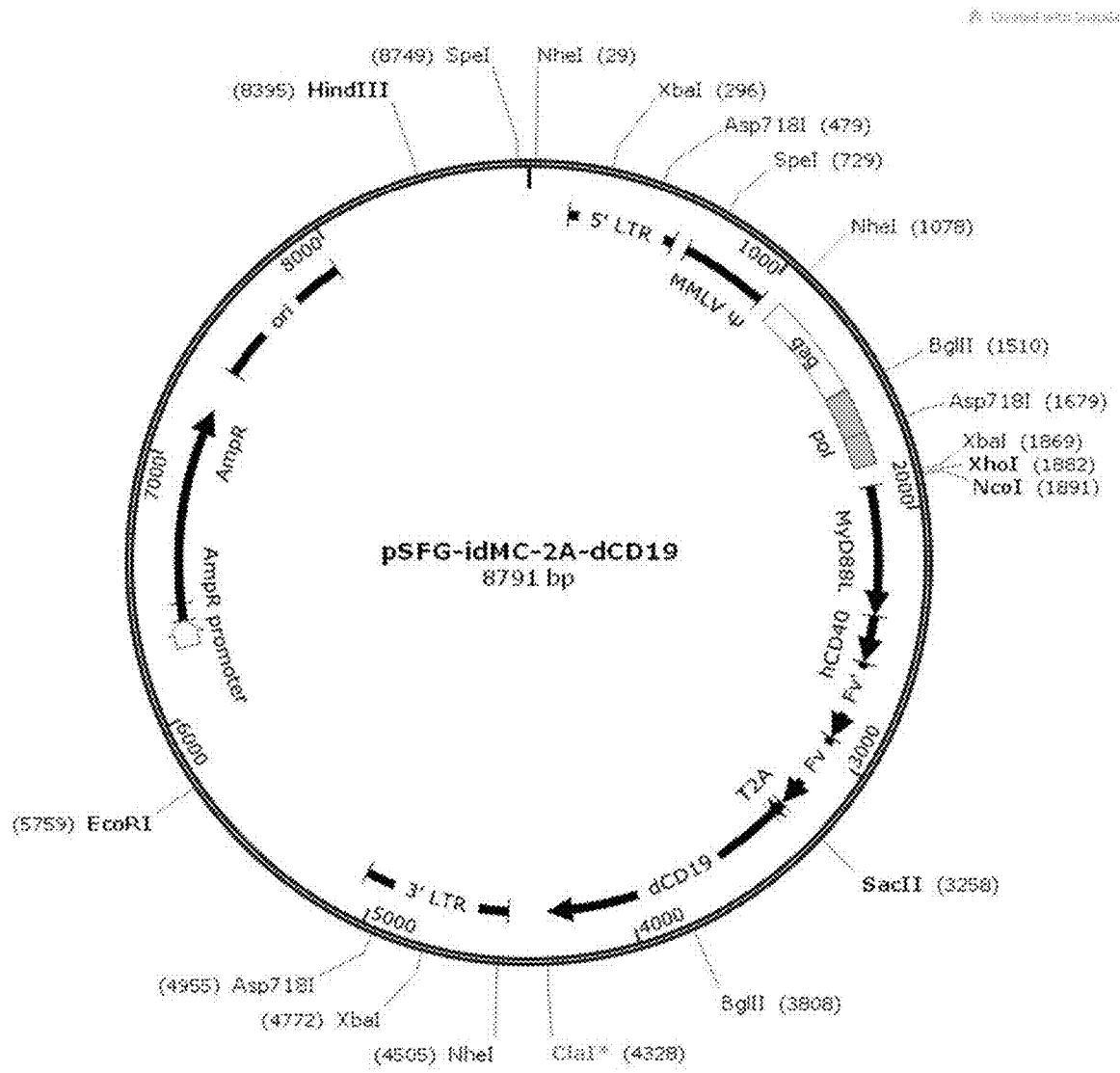
FIG. 16 is a plasmid map of vector pSFG-iΔMC-2A-ΔCD19, which does not include an amino-terminal myristoylation region.

To rigorously demonstrate the role of the myristoylation-targeting domain of "iMC", a bicistronic γ-retroviral vector was constructed using pBP180-SFG-iMC-2A-aCD19-CD34e-zeta (see FIG. 63) by replacing the ~2-kb BsrGI-SacII fragment with a similar fragment lacking the 14-amino acid myristoylation-targeted amino terminus, derived from v-Src. To further "clean-up" the parental vector, an upstream extra in-frame ATG in vector 180, which was preceded by a suboptimal ribosome-loading "Kozak" sequence was eliminated, resulting in slightly modified pBP180, called "pBP607" and the new test vector, "pBP606-pSFG-iΔMC.2A-aCD19.Q.8stm.CD3ζ", containing non-myristoylated iΔ (FIG. 15). In addition, to create a "generic" version of the non-myristoylated iMC vector, the 2nd upstream ATG, as above, was removed from ΔCD19-co-expressing iMC vector, pBP0172-SFG-iMCnoE-2A-ΔCD19, to get pBP609, and the removed the myristoylation-targeting sequence from pBP609 was removed to get "pBP608-pSFG-iΔMC-2A-ΔCD19" (FIG. 16).

Figures 17A, 17B:
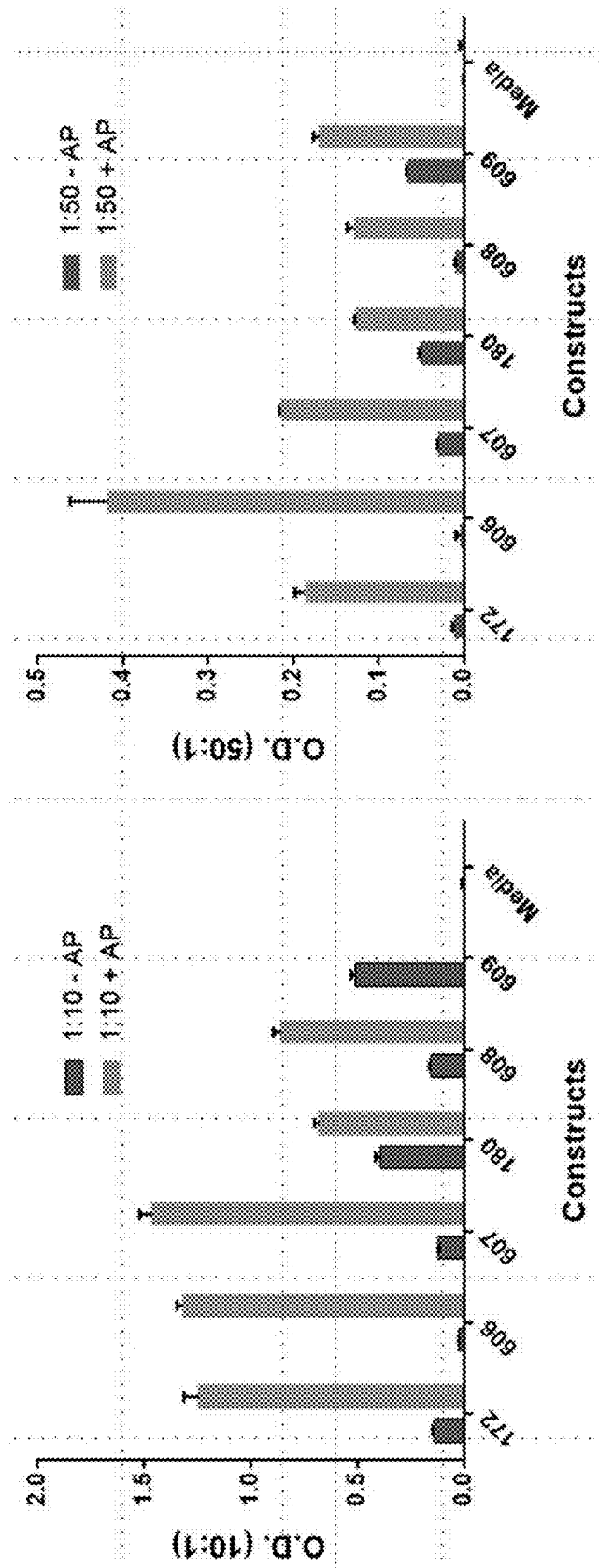
FIGS. 17A-17B.

To test the function of the non-myristoylated iMC relative to myristoylated iMC, the corresponding retroviral vectors were made from SFG-encoding plasmids and 1° human T cells were transduced with 3 sets of viral vectors, containing either myristoylated or non-myristoylated iMC with identical 5' untranslated regions or with the corresponding original vectors, pBP0172 and pBP0180, containing slightly modified 5' ends, and either ΔCD19 or anti-CD19 CAR-CD3ζ, respectively. Flow cytometry of transduced T cells two days after exposure to virus using either anti-CD19 (172, 606 and 607) or anti-CD34 (180, 608 and 609) confirmed that the infections were successful and that expression levels were comparable between vectors within each group (~80% or ~40%, respectively; not shown). Thereafter, equal numbers of cells were replated in the presence or absence of 10 nM rimiducid and cultured media was assayed by ELISA for IL-6 after 24 hrs (FIG. 17).

Equal numbers ($5^5$) of T cell blasts were added to virus-coated 24-well plates. After 48 hours, cells were harvested and assayed for CD19 expression (vectors 172, 606, and 607) or CD34 Q epitope expression (180, 608, and 609). Cells were harvested and replated with or without 10 nM rimiducid. After 24 hours, supernatants were harvested and assayed for IL-6 levels by ELISA. Supernatants were diluted either 10-fold (17a) or 50 fold (17b). 1 O.D.~300 ng/ml (from standard curve).

The results for both 172 and 180 family of vectors indicate that the non-myristoylated iΔMC constructs produced less IL-6 in the absence of rimiducid, as predicted; yet, the induced levels of IL-6 were not decreased. Therefore, non-myristoylated iΔMC may provide a more controllable rimiducid-dependent activation signal in the absence of CD3ζ signaling (comparable to TCR signaling).

To further compare non-myristoylated inducible MyD88/CD40 (iΔMC) vs myristoylated inducible MyD88/CD40 (iMC), cells containing the anti-CD19 1st generation CAR plus either iMC (180) or iΔMC (608) were cultured with or without CD19+ Raji tumor cells and with or without rimiducid, and both IL-2 and IL-6 were assayed.

Non-transduced (NT) and T cells transduced with iMC and non-myristoylated iΔMC-enabled CAR constructs were co-cultured with CD19+ Raji tumor cells at a ratio of 1:1 T cell to tumor cell in 24-well plates. T cells were subsequently stimulated with 10 nM rimiducid. After 24 hours, supernatants were collected and measured for IL-6 (18a) and IL-2 (18b) production using an ELISA.

Figures 18A, 18B:
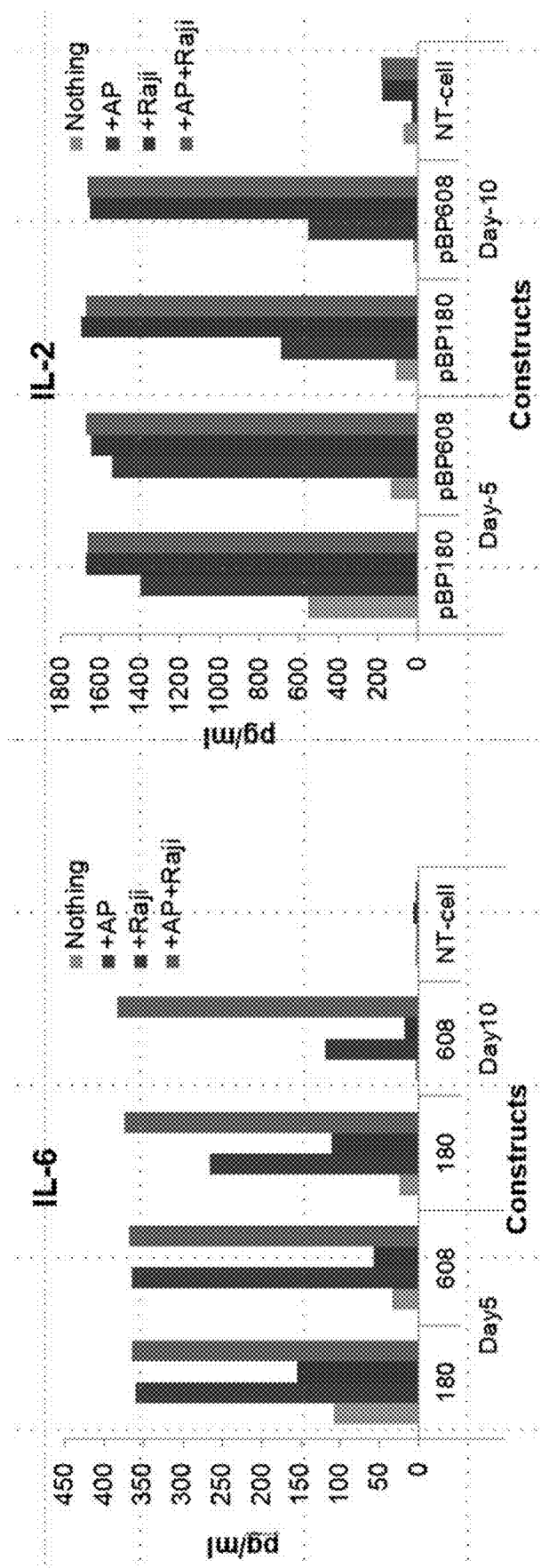
FIGS. 18A-18B.
Figure 19:
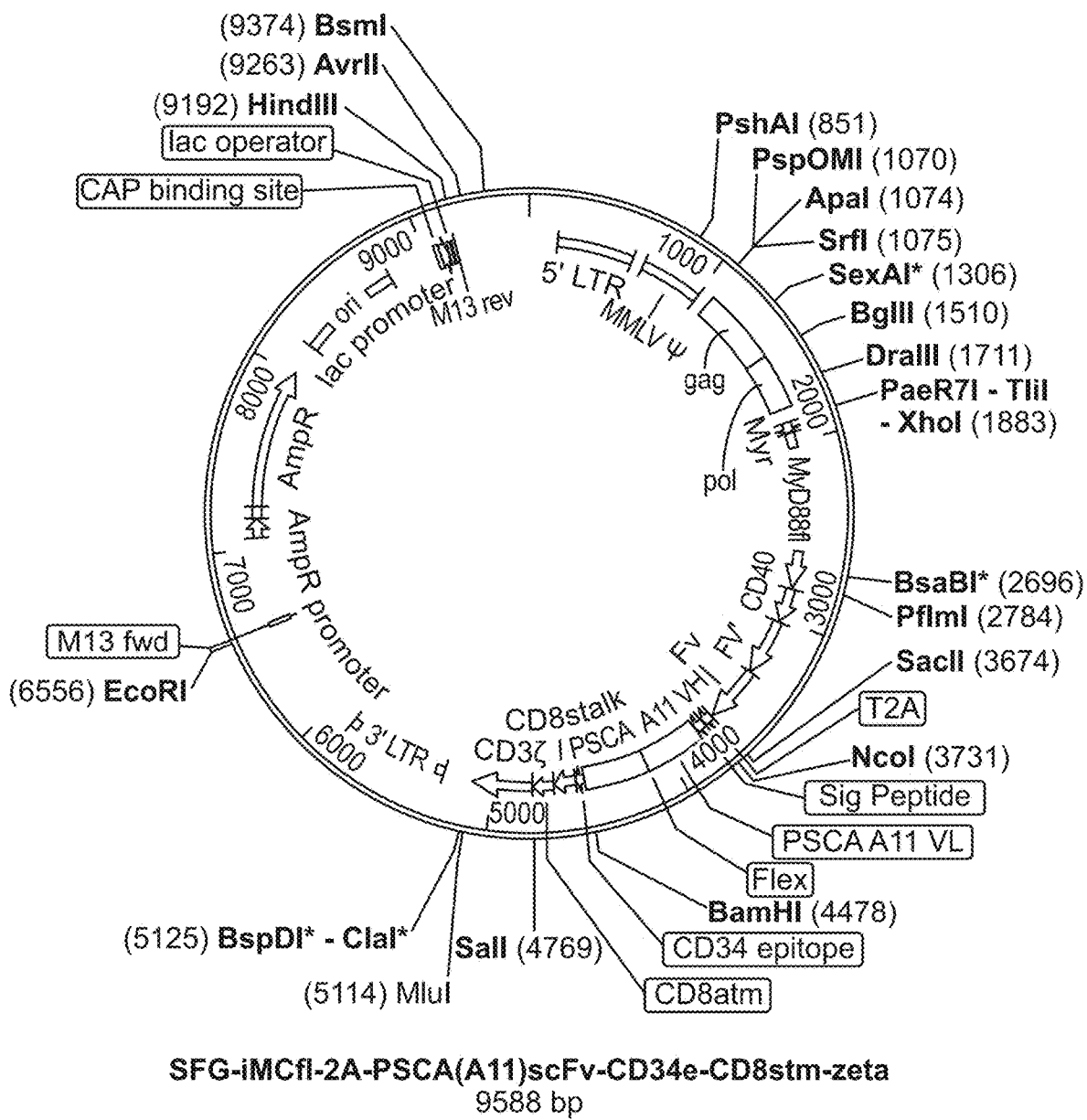
FIG. 19 is a plasmid map of vector SFG-iMCfl-2A-PSCA (A11)scFv-CD34e-CD8stm-zeta, which comprises sequences encoding a myristoylation region, an inducible CD40/full length MyD88 polypeptide and a CAR that binds to PSCA.
Figure 20:
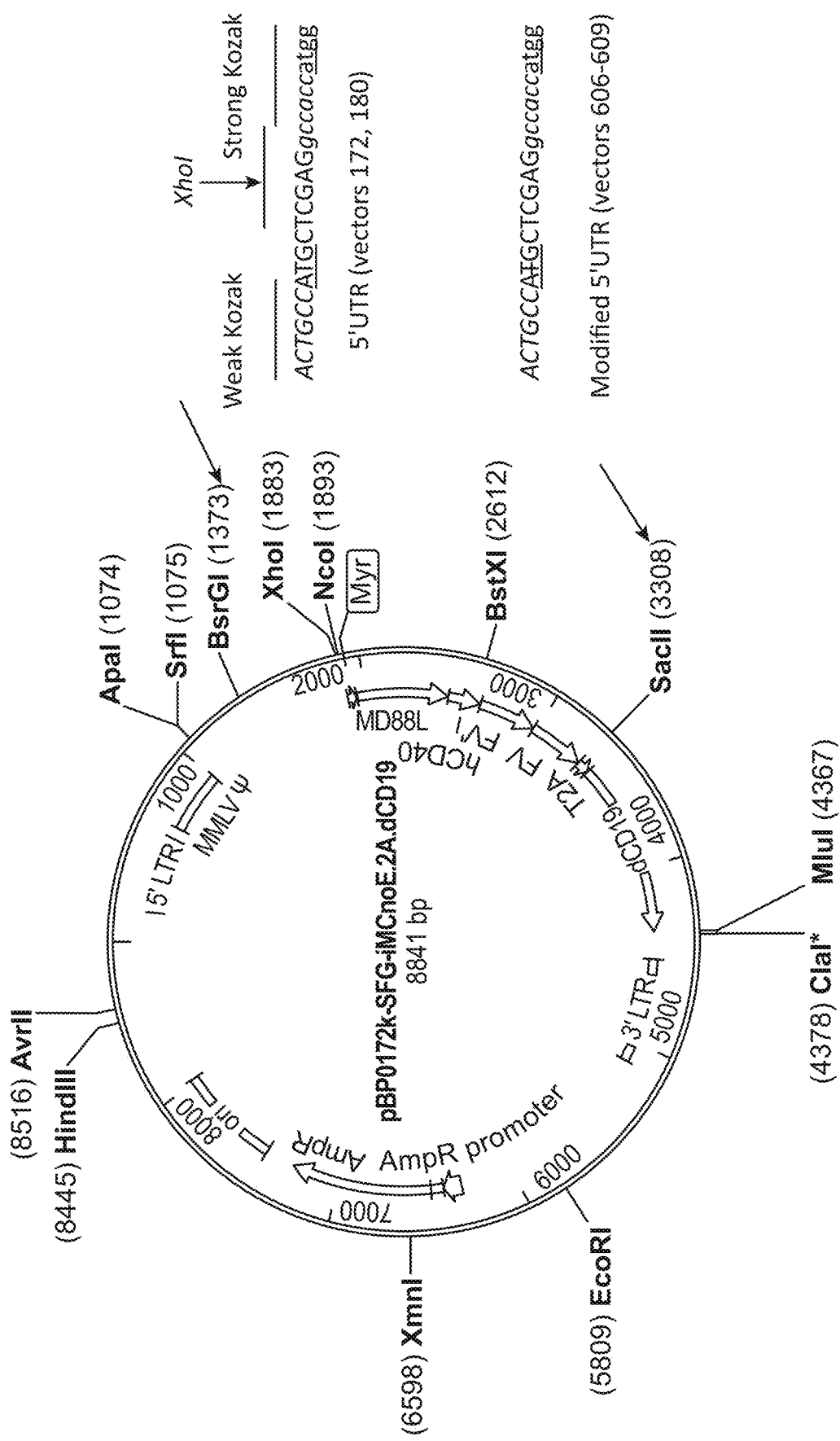
FIG. 20 is a plasmid map of vector pBPO172-SFg-iMCfl.2A.CD19, which comprises sequences encoding a myristoylation region, an inducible CD40/full length MyD88 polypeptide and CD19 polypeptide marker.
Figure 21:
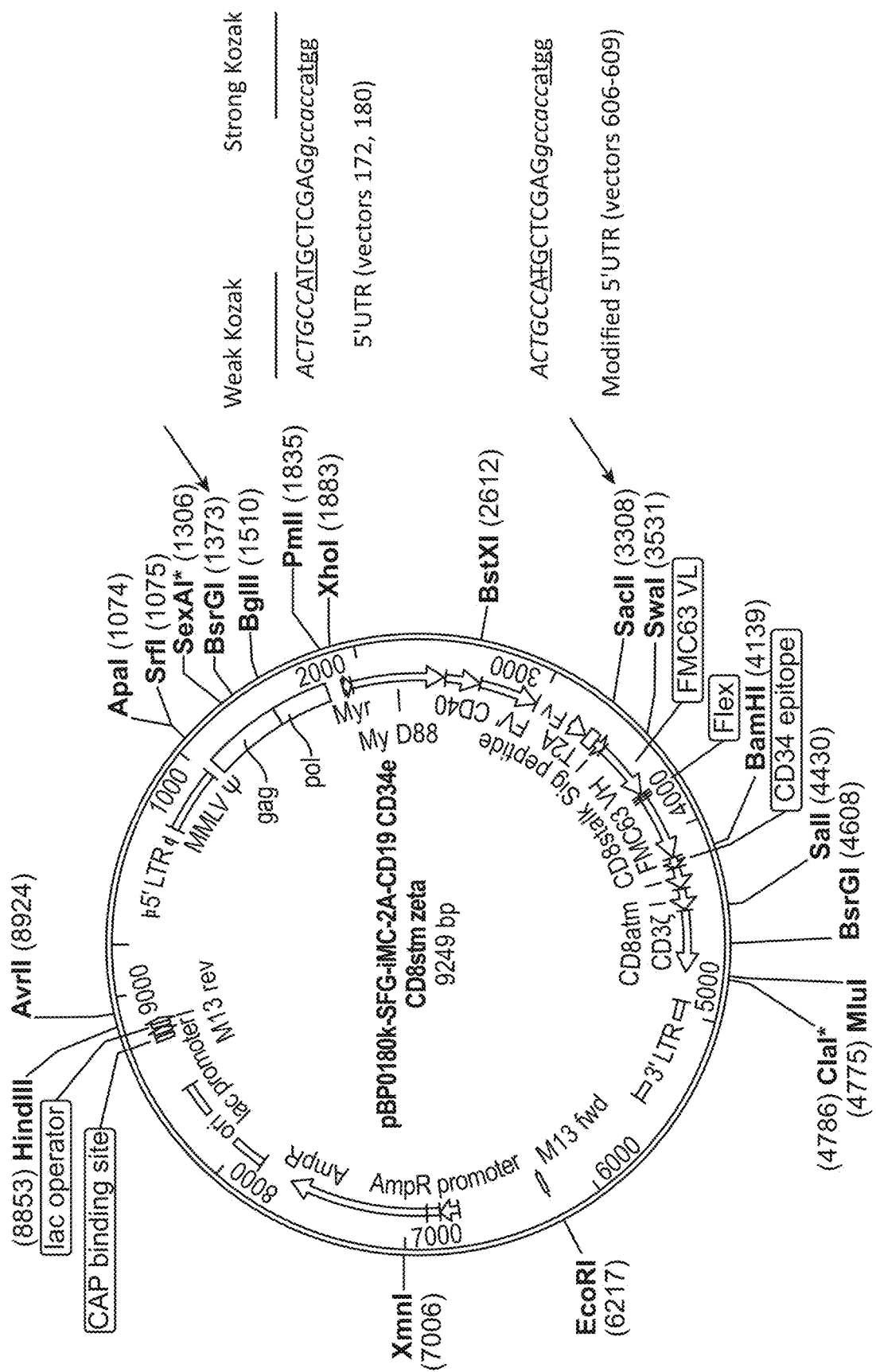
FIG. 21 is a plasmid map of vector pBPO180k-SFG-iMCfl-2A-CD19 CD34e CD8stm zeta, which comprises sequences encoding myristoylation region, an inducible CD40/full length MyD88 polypeptide and a CAR that binds to CD19.

As with the IL-6 assays above, in the absence of exogenous stimulation, iΔMC (608)-modified cells secreted less IL6 than cells expressing the initial iMC-19 construct (180) (FIG. 18, left panel). Similar results were observed for IL-2 (FIG. 18, right panel). Moreover, the presence of Raji cells did not significantly alter the basal signaling of 180 and 608-modified cells with regard to IL-6. Interestingly, the presence of Raji cells, even in the absence of rimiducid, led to high-level production of IL-2 by either iMC or iΔMC, showing that the basal signaling of iΔMC, although reduced vs iMC, is still sufficient for full CD19-dependent IL-2 production. Nevertheless, CD19hi lymphoma cells are likely to be the exception, and the rimiducid-dependence of IL-2 production is likely to be more tightly controlled in epithelial-derived tumor cells without the residual APC-like properties, conferred by B cell-derived tumors. This is because B cells express costimulatory molecules, like CD80 and CD86, plus higher levels of MHC class II, similar to other APCs, like DCs.

The removal of the myristoylation-targeting domain from iMC, as in iΔMC, confers lower rimiducid-independent basal activity of the MyD88/CD40 chimeric costimulating molecule, leading to less NF-κB signaling, and less spontaneous IL-6 production. T cell survival and expansion may be more tightly controlled in vivo using the MyD88/CD40 chimeric stimulating molecules that do not include a myristoylation region at the 5-amino terminus. T cells transduced with these constructs may have less dimer-independent toxicity and less persistence in the absence of CID. They may also allow for increased control of T cell expansion and tumor size using a titration-determined optimal level of rimiducid.

Thus also provided are embodiments wherein the methods for activating T cells are tunable in that varying dosages of AP1903 are provided, in order to control the level of costimulation by the inducible MyD88/CD40 chimeric costimulating molecules provided herein.

Example 9: Polynucleotide Sequences Used for Constructing Plasmids

| pSFG-iΔMC-2A-aCD19-Q-8stm-CD3ζ, (w optional myristoylation-targeting domain). | | |
|---|---|---|
| Fragment | Nucleotide | Peptide |
| Kozak seq | SEQ ID NO: 1<br>Gccacc | N/A |
| Myristoylation-targeting seq w linker [Optional] | SEQ ID NO: 2<br>Atggggagtagcaagagcaagcctaaggaccccagccagcgc-ctcgac | SEQ ID NO: 3<br>MGSSKSKPKDPSQR-LD |
| MyD88L (TIR-deleted) | SEQ ID NO: 4<br>atggctgcaggaggtcccggcgcggggtctgcggcccggtctc<br>ctccacatcctcccttcccctggctgctctcaacatgcgagtgcggc<br>gccgcctgtctctgttcttgaacgtgcggacacaggtggcggccga<br>ctggaccgcgctggcggaggagatggactttgagtacttggagat<br>ccggcaactggagacacaagcggaccccactggcaggctgctg<br>gacgcctggcagggacgccctggcgcctctgtaggccgactgct<br>cgatctgcttaccaagctgggccgcgacgacgtgctgctggagct<br>gggacccagcattgaggaggattgccaaaagtatatcttgaagc<br>agcagcaggaggaggctgagaagcctttacaggtggccgctgta<br>gacagcagtgtcccacggacagcagagctggcgggcatcacca<br>cacttgatgaccccctggggcatatgcctgagcgtttcgatgccttc<br>atctgctattgccccagcgacatc | SEQ ID NO: 5<br>MAAGGPGAGSAAPV<br>SSTSSLPLAALNMRV<br>RRRLSLFLNVRTQVA<br>ADWTALAEEMDFEY<br>LEIRQLETQADPTGR<br>LLDAWQGRPGASVG<br>RLLDLLTKLGRDDVL<br>LELGPSIEEDCQKYIL<br>KQQQEEAEKPLQVA<br>AVDSSVPRTAELAGI<br>TTLDDPLGHMPERF<br>DAFICYCPSDIQ |
| Linker | SEQ ID NO: 6<br>gtcgag | SEQ ID NO: 7<br>VE |
| CD40 (cytoplasmic domain) | SEQ ID NO: 8<br>aaaaaggtggccaagaagccaaccaataaggcccccaccccc<br>aagcaggagccccaggagatcaattttcccgacgatcttcctggct<br>ccaacactgctgctccagtgcaggagactttacatggatgccaac<br>cggtcacccaggaggatggcaaagagagtcgcatctcagtgca<br>ggagagacag | SEQ ID NO: 9<br>KKVAKKPTNKAPHPK<br>QEPQEINFPDDLPGS<br>NTAAPVQETLHGCQ<br>PVTQEDGKESRISVQ<br>ERQ |
| Linker | SEQ ID NO: 6<br>gtcgag | SEQ ID NO: 7<br>VE |
| Fv' (wobbled) | SEQ ID NO: 10<br>GGcGTcCAaGTcGAaACcATtagtCCcGGcGAtGG<br>caGaACaTTtCCtAAaaGgGGaCAaACaTGtGTcG<br>TcCAtTAtACaGGcATGtTgGAgGAcGGcAAaAAg<br>GTgGAcagtagtaGaGAtcGcAAtAAaCCtTTcAAaT<br>TcATGtTgGGaAAaCAaGAaGTcATtaGgGGaTG<br>GGAgGAgGGcGTgGCtCAaATGtccGTcGGcCAa<br>cGcGCtAAgCTcACcATcagcCCcGAcTAcGCaTA<br>cGGcGCtACcGGaCAtCCcGGaATtATgCCcCCtC<br>AcGCtACctTgGTgTTtGAcGTcGAaCTgtTgAAgC<br>TcGAa | SEQ ID NO: 11<br>GVQVETISPGDGRTF<br>PKRGQTCVVHYTGM<br>LEDGKKVDSSRDRN<br>KPFKFMLGKQEVIRG<br>WEEGVAQMSVGQR<br>AKLTISPDYAYGATG<br>HPGIIPPHATLVFDVE<br>LLKLE |
| Linker | SEQ ID NO: 6<br>gtcgag | SEQ ID NO: 7<br>VE |
| Fv | SEQ ID NO: 12<br>ggagtgcaggtggagactatctccccaggagacgggcgcacctt<br>ccccaagcgcggccagacctgcgtggtgcactacaccgggatg<br>cttgaagatggaaagaaagttgattcctcccgggacagaaacaa<br>gcccttttaagtttatgctaggcaagcaggaggtgatccgaggctgg<br>gaagaaggggttgcccagatgagtgtgggtcagagagccaaac<br>tgactatatctccagattatgcctatggtgccactgggcacccaggc | SEQ ID NO: 13<br>GVQVETISPGDGRTF<br>PKRGQTCVVHYTGM<br>LEDGKKVDSSRDRN<br>KPFKFMLGKQEVIRG<br>WEEGVAQMSVGQR<br>AKLTISPDYAYGATG |

-continued pSFG-iΔMC-2A-aCD19-Q-8stm-CD3ζ, (w optional myristoylation-targeting domain).

| Fragment | Nucleotide | Peptide |
|---|---|---|
| | atcatcccaccacatgccactctcgtcttcgatgtggagcttctaaa actggaa | HPGIIPPHATLVFDVE LLKLE |
| SacII (linker) | SEQ ID NO: 14<br>CCGCGG | SEQ ID NO: 15<br>PR |
| T2A | SEQ ID NO: 16<br>GAAGGCCGAGGGAGCCTGCTGACATGTGGC GATGTGGAGGAAAACCCAGGACCA | SEQ ID NO: 17<br>EGRGSLLTCGDVEE NPGP |
| NcoI (linker) | SEQ ID NO: 18<br>CCATGG | SEQ ID NO: 19<br>PW |
| Signal Peptide | SEQ ID NO: 20<br>ATGGAGTTTGGACTTTCTTGGTTGTTTTTGGT GGCAATTCTGAAGGGTGTCCAGTGTAGCAGG | SEQ ID NO: 21<br>MEFGLSWLFLVAILK GVQCSR |
| FMC63 VL | SEQ ID NO: 22<br>GACATCCAGATGACACAGACTACATCCTCCC TGTCTGCCTCTCTGGGAGACAGAGTCACCAT CAGTTGCAGGGCAAGTCAGGACATTAGTAAA TATTTAAATTGGTATCAGCAGAAACCAGATGG AACTGTTAAACTCCTGATCTACCATACATCAA GATTACACTCAGGAGTCCCATCAAGGTTCAG TGGCAGTGGGTCTGGAACAGATTATTCTCTC ACCATTAGCAACCTGGAGCAAGAAGATATTG CCACTTACTTTTGCCAACAGGGTAATACGCTT CCGTACACGTTCGGAGGGGGGACTAAGTTG GAAATAACA | SEQ ID NO: 23<br>DIQMTQTTSSLSASL GDRVTISCRASQDIS KYLNWYQQKPDGTV KLLIYHTSRLHSGVP SRFSGSGSGTDYSL TISNLEQEDIATYFCQ QGNTLPYTFGGGTK LEIT |
| Flex | SEQ ID NO: 24<br>GGCGGAGGAAGCGGAGGTGGGGGC | SEQ ID NO: 25<br>GGGSGGGG |
| FMC63 VH | SEQ ID NO: 26<br>GAGGTGAAACTGCAGGAGTCAGGACCTGGC CTGGTGGCGCCCTCACAGAGCCTGTCCGTCA CATGCACTGTCTCAGGGGTCTCATTACCCGA CTATGGTGTAAGCTGGATTCGCCAGCCTCCA CGAAAGGGTCTGGAGTGGCTGGGAGTAATAT GGGGTAGTGAAACCACATACTATAATTCAGCT CTCAAATCCAGACTGACCATCATCAAGGACA ACTCCAAGAGCCAAGTTTTCTTAAAAATGAAC AGTCTGCAAACTGATGACACAGCCATTTACTA CTGTGCCAAACATTATTACTACGGTGGTAGCT ATGCTATGGACTACTGGGGTCAAGGAACCTC AGTCACCGTCTCCTCA | SEQ ID NO: 27<br>EVKLQESGPGLVAP SQSLSVTCTVSGVSL PDYGVSWIRQPPRK GLEWLGVIWGSETT YYNSALKSRLTIIKDN SKSQVFLKMNSLQT DDTAIYYCAKHYYYG GSYAMDYWGQGTS VTVSS |
| BamHI (linker) | SEQ ID NO: 28<br>ggatcc | SEQ ID NO: 29<br>GS |
| CD34 epitope | SEQ ID NO: 30<br>GAACTTCCTACTCAGGGGACTTTCTCAAACGT TAGCACAAACGTAAGT | SEQ ID NO: 31<br>ELPTQGTFSNVSTNV S |
| CD8stalk | SEQ ID NO: 32<br>CCCGCCCCAAGACCCCCCACACCTGCGCCG ACCATTGCTTCTCAACCCCTGAGTTTGAGACC CGAGGCCTGCCGGCCAGCTGCCGGCGGGG CCGTGCATACAAGAGGACTCGATTTCGCTTG CGAC | SEQ ID NO: 33<br>PAPRPPTPAPTIASQ PLSLRPEACRPAAG GAVHTRGLDFACD |
| CD8tm + stop tf | SEQ ID NO: 34<br>ATCTATATCTGGGCACCTCTCGCTGGCACCT GTGGAGTCCTTCTGCTCAGCCTGGTTATTACT CTGTACTGTAATCACCGGAATCGCCGCCGCG TTTGTAAGTGTCCCAGG | SEQ ID NO: 35<br>IYIWAPLAGTCGVLLL SLVITLYCNHRNRRR VCKCPR |
| SalI (linker) | SEQ ID NO: 36<br>gtcgac | SEQ ID NO: 37<br>VD |
| CD3ζ | SEQ ID NO: 38<br>AGAGTGAAGTTCAGCAGGAGCGCAGACGCC CCCGCGTACCAGCAGGGCCAGAACCAGCTC TATAACGAGCTCAATCTAGGACGAAGAGAGG AGTACGATGTTTTGGACAAGAGACGTGGCCG | SEQ ID NO: 39<br>RVKFSRSADAPAYQ QGQNQLYNELNLGR REEYDVLDKRRGRD PEMGGKPRRKNPQE | pSFG-iΔMC-2A-aCD19-Q-8stm-CD3ζ, (w optional myristoylation-targeting domain).

| Fragment | Nucleotide | Peptide |
|---|---|---|
| | GGACCCTGAGATGGGGGGAAAGCCGAGAAG | GLYNELQKDKMAEA |
| | GAAGAACCCTCAGGAAGGCCTGTACAATGAA | YSEIGMKGERRRGK |
| | CTGCAGAAAGATAAGATGGCGGAGGCCTACA | GHDGLYQGLSTATK |
| | GTGAGATTGGGATGAAAGGCGAGCGCCGGA | DTYDALHMQALPPR |
| | GGGGCAAGGGGCACGATGGCCTTTACCAGG | |
| | GTCTCAGTACAGCCACCAAGGACACCTACGA | |
| | CGCCCTTCACATGCAAGCTCTTCCACCTCGTT | |
| | GA | | pSFG-idMC-2A-dCD19 (w optional Myristoylation-targeting domain).

| Fragment | Nucleotide | Peptide |
|---|---|---|
| Kozak seq. | SEQ ID NO: 1<br>Gccacc | N/A |
| Myristoylation-targeting seq w linker [Optional] | SEQ ID NO: 2<br>Atggggagtagcaagagcaagcctaaggaccccagccagcgc-ctgac | SEQ ID NO: 3<br>MGSSKSKPKDPSQR-LD |
| MyD88L (TIR-deleted) | SEQ ID NO: 4<br>atggctgcaggaggtcccggcgcggggtctgcggccccggt<br>ctcctccacatcctcccttccctggctgctctcaacatgcgag<br>tgcggcgccgcctgtctctgttcttgaacgtgcggacacaggt<br>ggcggccgactggaccgcgctggcggaggagatggactt<br>gagtacttggagatccggcaactggagacacaagcggacc<br>ccactggcaggctgctggacgcctggcagggacgccctgg<br>cgcctctgtaggccgactgctcgatctgcttaccaagctgggc<br>cgcgacgacgtgctgctggagctgggacccagcattgagg<br>aggattgccaaaagtatatcttgaagcagcagcaggagga<br>ggctgagaagcctttacaggtggccgctgtagacagcagtgt<br>cccacggacagcagagctggcgggcatcaccacacttgat<br>gacccctggggcatatgcctgagcgtttcgatgcctcatctg<br>ctattgccccagcgacatc | SEQ ID NO: 5<br>MAAGGPGAGSAAPVSSTSS<br>LPLAALNMRVRRRLSLFLNV<br>RTQVAADWTALAEEMDFEYL<br>EIRQLETQADPTGRLLDAWQ<br>GRPGASVGRLLDLLTKGRD<br>DVLLELGPSIEEDCQKYILKQ<br>QQEEAEKPLQVAAVDSSVPR<br>TAELAGITTLDDPLGHMPERF<br>DAFICYCPSDIQ |
| Linker | SEQ ID NO: 6<br>gtcgag | SEQ ID NO: 7<br>VE |
| CD40 (cytoplasmic domain) | SEQ ID NO: 8<br>aaaaaggtggccaagaagccaaccaataaggcccccac<br>cccaagcaggagccccaggagatcaattttcccgacgatctt<br>cctggctccaacactgctgctccagtgcaggagactttacatg<br>gatgccaaccggtcacccaggaggatggcaaagagagtc<br>gcatctcagtgcaggagagacag | SEQ ID NO: 9<br>KKVAKKPTNKAPHPKQEPQE<br>INFPDDLPGSNTAAPVQETLH<br>GCQPVTQEDGKESRISVQER<br>Q |
| Linker | SEQ ID NO: 6<br>gtcgag | SEQ ID NO: 7<br>VE |
| Fv' (wobbled) | SEQ ID NO: 10<br>GGcGTcCAaGTcGAaACcATtagtCCcGGcGAt<br>GGcaGaACaTTtCCtAAaaGgGGaCAaACaTG<br>tGTcGTcCAtTAtACaGGcATGtTgGAgGAcGG<br>cAAaAAgGTgGAcagtagtaGaGAtcGcAAtAAa<br>CCtTTcAAaTTcATgTtGGaAAaCAaGAaGTc<br>ATtaGgGGaTGGGAgGAgGGcGTgGCtCAaA<br>TGtccGTcGGcCAacGcGCtAAgCTcACcATca<br>gcCCcGAcTAcGCaTAcGGcGCtACcGGaCAt<br>CCcGGaATtATtCCcCCtCAcGCtACCttGgTgT<br>TtGAcGTcGAaCTgtTgAAgCTcGAa | SEQ ID NO: 11<br>GVQVETISPGDGRTFPKRGQ<br>TCVVHYTGMLEDKKVDSS<br>RDRNKPFKFMLGKQEVIRG<br>WEEGVAQMSVGQRAKLTISP<br>DYAYGATGHPGIIPPHATLVF<br>DVELLKLE |

-continued

| | pSFG-idMC-2A-dCD19 (w optional Myristoylation-targeting domain). | |
|---|---|---|
| Fragment | Nucleotide | Peptide |
| Linker | SEQ ID NO: 6<br>Gtcgag | SEQ ID NO: 7<br>VE |
| Fv | SEQ ID NO: 12<br>ggagtgcaggtggagactatctccccaggagacgggcgca<br>ccttcccaagcgcggccagacctgcgtggtgcactacacc<br>gggatgcttgaagatggaaagaaagttgattcctcccgggac<br>agaaacaagccctttaagtttatgctaggcaagcaggaggtg<br>atccgaggctgggaagaaggggttgcccagatgagtgtgg<br>gtcagagagccaaactgactatatctccagattatgcctatgg<br>tgccactgggcacccaggcatcatccaccacatgccactct<br>cgtcttcgatgtggagcttctaaaactggaa | SEQ ID NO: 13<br>GVQVETISPGDGRTFPKRGQ<br>TCVVHYTGMLEDGKKVDSS<br>RDRNKPFKFMLGKQEVIRG<br>WEEGVAQMSVGQRAKLTISP<br>DYAYGATGHPGIIPPHATLVF<br>DVELLKLE |
| SacII<br>(linker) | SEQ ID NO: 14<br>CCGCGG | SEQ ID NO: 15<br>PR |
| T2A | SEQ ID NO: 16<br>GAAGGCCGAGGGAGCCTGCTGACATGTG<br>GCGATGTGGAGGAAAACCCAGGACCA | SEQ ID NO: 17<br>EGRGSLLTCGDVEENPGP |
| ΔCD19 | SEQ ID NO: 40<br>ATGCCACCACCTCGCCTGCTGTTCTTTCT<br>GCTGTTCCTGACACCTATGGAGGTGCGAC<br>CTGAGGAACCACTGGTCGTGAAGGTCGA<br>GGAAGGCGACAATGCCGTGCTGCAGTGC<br>CTGAAAGGCACTTCTGATGGGCCAACTCA<br>GCAGCTGACCTGGTCCAGGGAGTCTCCC<br>CTGAAGCCTTTTCTGAAACTGAGCCTGGG<br>ACTGCCAGGACTGGGAATCCACATGCGC<br>CCTCTGGCTATCTGGCTGTTCATCTTCAA<br>CGTGAGCCAGCAGATGGGAGGATTCTAC<br>CTGTGCCAGCCAGGACCACCATCCGAGA<br>AGGCCTGGCAGCCTGGATGGACCGTCAA<br>CGTGGAGGGGTCTGGAGAACTGTTTAGG<br>TGGAATGTGAGTGACCTGGGAGGACTGG<br>GATGTGGGCTGAAGAACCGCTCCTCTGAA<br>GGCCCAAGTTCACCCTCAGGGAAGCTGAT<br>GAGCCCAAAACTGTACGTGTGGGCCAAA<br>GATCGGCCCGAGATCTGGGAGGGAGAAC<br>CTCCATGCCTGCCACCTAGAGACAGCCTG<br>AATCAGAGTCTGTCACAGGATCTGACAAT<br>GGCCCCCGGGTCCACTCTGTGGCTGTCT<br>TGTGGAGTCCCACCCGACAGCGTGTCCA<br>GAGGCCCTCTGTCCTGGACCCACGTGCA<br>TCCTAAGGGGCCAAAAAGTCTGCTGTCAC<br>TGGAACTGAAGGACGATCGGCCTGCCAG<br>AGACATGTGGGTCATGGAGACTGGACTG<br>CTGCTGCCACGAGCAACCGCACAGGATG<br>CTGGAAAATACTATTGCCACCGGGGCAAT<br>CTGACAATGTCCTTCCATCTGGAGATCAC<br>TGCAAGGCCCGTGCTGTGGCACTGGCTG<br>CTGCGAACCGGAGGATGGAAGGTCAGTG<br>CTGTGACACTGGCATATCTGATCTTTTGC<br>CTGTGCTCCCTGGTGGGCATTCTGCATCT<br>GCAGAGAGCCCTGGTGCTGCGGAGAAAG<br>AGAAAGAGAATGACTGACCCAACAAGAAG<br>GTTTTGA | SEQ ID NO: 41<br>MPPPRLLFFLLFLTPMEVRPE<br>EPLVVKVEEGDNAVLQCLKG<br>TSDGPTQQLTWSRESPLKPF<br>LKLSLGLPGLGIHMRPLAIWL<br>FIFNVSQQMGGFYLCQPGPP<br>SEKAWQPGWTVNVEGSGEL<br>FRWNVSDLGGLGCGLKNRS<br>SEGPSSPSGKLMSPKLYVW<br>AKDRPEIWEGEPPCLPPRDS<br>LNQSLSQDLTMAPGSTLWLS<br>CGVPPDSVSRGPLSWTHVH<br>PKGPKSLLSLELKDDRPARD<br>MWVMETGLLLPRATAQDAG<br>KYYCHRGNLTMSFHLEITAR<br>PVLWHWLLRTGGWKVSAVT<br>LAYLIFCLCSLVGILHLQRALV<br>LRRKRKRMTDPTRR |

Example 10: Examples of Particular Nucleic Acid and Amino Acid Sequences (nucleic acid sequence encoding human CD40; Genbank accession no.
NM_001250; cytoplasmic region indicated in bold).

SEQ ID NO: 42

```
  1 gccaaggctg ggcagggga gtcagcagag gcctcgctcg gcgcccagt ggtcctgccg 61 cctggtctca cctcgctatg gttcgtctgc ctctgcagtg cgtcctctgg ggctgcttgc 121 tgaccgctgt ccatccagaa ccaccactg catgcagaga aaaacagtac ctaataaaca
```

```
 181   gtcagtgctg ttctttgtgc cagccaggac agaaactggt gagtgactgc acagagttca
 241   ctgaaacgga atgccttcct tgcggtgaaa gcgaattcct agacacctgg aacagagaga
 301   cacactgcca ccagcacaaa tactgcgacc ccaacctagg cttcgggtc cagcagaagg
 361   gcacctcaga aacagacacc atctgcacct gtgaagaagg ctggcactgt acgagtgagg
 421   cctgtgagag ctgtgtcctg caccgctcat gctcgcccgg ctttggggtc aagcagattg
 481   ctacagggt ttctgatacc atctgcgagc cctgcccagt cggcttcttc tccaatgtgt
 541   catctgcttt cgaaaaatgt cacccttgga caagctgtga gaccaaagac ctggttgtgc
 601   aacaggcagg cacaaacaag actgatgttg tctgtggtcc ccaggatcgg ctgagagccc
 661   tggtggtgat ccccatcatc ttcgggatcc tgtttgccat cctcttggtg ctggtctttA
 721   tcaaaaaggt ggccaagaag ccaaccaata aggcccccca ccccaagcag gaaccccagg
 781   agatcaattt tcccgacgat cttcctggct ccaacactgc tgctccagtg caggagactt
 841   tacatggatg ccaaccggtc acccaggagg atggcaaaga gagtcgcatc tcagtgcagg
 901   agagacagtg aggctgcacc cacccaggag tgtggccacg tgggcaaaca ggcagttggc
 961   cagagagcct ggtgctgctg ctgctgtggc gtgagggtga gggctggca ctgactgggc
1021   atagctcccc gcttctgcct gcacccctgc agtttgagac aggagacctg gcactggatg
1081   cagaaacagt tcaccttgaa gaacctctca cttcaccctg gagcccatcc agtctcccaa
1141   cttgtattaa agacagaggc agaagtttgg tggtggtggt gttggggtat ggtttagtaa
1201   tatccaccag accttccgat ccagcagttt ggtgcccaga gaggcatcat ggtggcttcc
1261   ctgcgcccag gaagccatat acacagatgc ccattgcagc attgtttgtg atagtgaaca
1321   actggaagct gcttaactgt ccatcagcag gagactggct aaataaaatt agaatatatt
1381   tatacaacag aatctcaaaa acactgttga gtaaggaaaa aaggcatgc tgctgaatga
1441   tgggtatgga acttttttaaa aaagtacatg cttttatgta tgtatattgc ctatggatat
1501   atgtataaat acaatatgca tcatatattg atataacaag ggttctggaa gggtacacag
1561   aaaacccaca gctcgaagag tggtgacgtc tggggtgggg aagaagggtc tggggg
```

(amino acid sequence encoding human CD40; cytoplasmic region indicated in bold).

SEQ ID NO: 43

MVRLPLQCVLWGCLLTAVHPEPPTACREKQYLINSQCCSLCQPGQKLVSDCTEFTETECLPCGES

EFLDTWNRETHCHQHKYCDPNLGLRVQQKGTSETDTICTCEEGWHCTSEACESCVLHRSCSPGF

GVKQIATGVSDTICEPCPVGFFSNVSSAFEKCHPWTSCETKDLVVQQAGTNKTDVVCGPQDRLR

ALVVIPIIFGILFAILLVLVFIKKVAKKPTNKAPHPKQEPQEINFPDDLPGSNTAAPVQETLHGCQPV

TQEDGKESRISVQERQ

(nucleotide sequence of MyD88L with SalI linkers)

SEQ ID NO: 44 gtcgacatggctgcaggaggtcccggcgcgggtctgcggccccggtctcctccacatcctcccttcccctggctgctctcaacatgcgag tgcggcgccgcctgtctctgttcttgaacgtgcggacacaggtggcggccgactggaccgcgctggcggaggagatggactttgagtactt ggagatccggcaactggagacacaagcggaccccactggcaggctgctggacgcctggcagggacgccctggcgcctctgtaggcc gactgctcgagctgcttaccaagctgggccgcgacgacgtgctgctggagctgggacccagcattgaggaggattgccaaaagtatatct tgaagcagcagcaggaggaggctgagaagcctttacaggtggccgctgtagacagcagtgtcccacggacagcagagctggcgggc atcaccacacttgatgacccctgggcatatgcctgagcgtttcgatgccttcatctgctattgccccagcgacatcgtcgac (amino acid sequence of MYD88L)

SEQ ID NO: 45

MAAGGPGAGSAAPVSSTSSLPLAALNMRVRRRLSLFLNVRTQVAADWTALAEEMDFEYLEIRQLE

TQADPTGRLLDAWQGRPGASVGRLLELLTKLGRDDVLLELGPSIEEDCQKYILK

QQQEEAEKPLQVAAVDSSVPRTAELAGITTLDDPLGHMPERFDAFICYCPSDI (nucleotide sequence of Fv'Fvls with XhoI/SalI linkers, (wobbled codons lowercase in Fv'))

SEQ ID NO: 46 ctcgagGGcGTcCAaGTcGAaACcATtagtCCcGGcGAtGGcaGaGaACaTTtCCtAAaaGgGGaCAaACaTGt

GTcGTcCAtTAtACaGGcATGtTgGAgGAcGGcAAaAAgGTgGAcagtagtaGaGAtcGcAAtAAaCCtTTc

AAaTTcATGtTgGGaAAaCAaGAaGTcATtaGgGGaTGGGAgGAgGGcGTgGCtCAaATGtccGTcGGc

CAacGcGCtAAgCTcACcATcagcCCcGAcTAcGCaTAcGGcGCtACcGGaCAtCCcGGaATtATtCCcC

CtCAcGCtACctTgGTgTTtGAcGTcGAaCTgtTgAAgCTcGAagtcgagggagtgcaggtggaaaccatctccccag gagacgggcgcaccttccccaagcgcggccagacctgcgtggtgcactacaccgggatgcttgaagatggaaagaaagttgattcctc ccgggacagaaacaagcccttt aagtttatgctaggcaagcaggaggtgatccgaggctgggaagaaggggttgcccagatgagtgtg ggtcagagagccaaactgactatatctccagattatgcctatggtgccactgggcacccaggcatcatcccaccacatgccactctcgtctt cgatgtggagcttctaaaactggaatctggcggtggatccggagtcgag (FV'FVLS amino acid sequence)

SEQ ID NO: 47

GlyValGlnValGluThrIleSerProGlyAspGlyArgThrPheProLysArgGlyGlnThrCysValValHisTyrThrGlyMe tLeuGluAspGlyLysLysValAspSerSerArgAspArgAsnLysProPheLysPheMetLeuGlyLysGlnGluValIleA rgGlyTrpGluGluGlyValAlaGlnMetSerValGlyGlnArgAlaLysLeuThrlIeSerProAspTyrAlaTyrGlyAlaThrG lyHisProGlyIleIleProProHisAlaThrLeuValPheAspValGluLeuLeuLysLeuGlu(ValGlu)

GlyValGlnValGluThrIleSerProGlyAspGlyArgThrPheProLysArgGlyGlnThrCysValValHisTyrThrGlyMe tLeuGluAspGlyLysLysValAspSerSerArgAspArgAsnLysProPheLysPheMetLeuGlyLysGlnGluValIleA rgGlyTrpGluGluGlyValAlaGlnMetSerValGlyGlnArgAlaLysLeuThrlIeSerProAspTyrAlaTyrGlyAlaThrG lyHisProGlyIleIleProProHisAlaThrLeuValPheAspValGluLeuLeuLysLeuGluSerGlyGlyGlySerGly (MyD88 nucleotide sequence)

SEQ ID NO: 48 atggctgcaggaggtcccggcgcggggtctgcggccccggtctcctccacatcctcccttcccctggctgctctcaacatgcgagtgcggc gccgcctgtctctgttcttgaacgtgcggacacaggtggcggccgactggaccgcgctggcggaggagatggactttgagtacttggagat ccggcaactggagacacaagcggaccccactggcaggctgctggacgcctggcagggacgccctggcgcctctgtaggccgactgct cgagctgcttaccaagctgggccgcgacgacgtgctgctggagctgggacccagcattgaggaggattgccaaaagtatatcttgaagc agcagcaggaggaggctgagaagcctttacaggtggccgctgtagacagcagtgtcccacggacagcagagctggcgggcatcacc acacttgatgaccccctggggcatatgcctgagcgtttcgatgccttcatctgctattgccccagcgacatccagtttgtgcaggagatgatcc ggcaactggaacagacaaactatcgactgaagttgtgtgtgtctgaccgcgatgtcctgcctggcacctgtgtctggtctattgctagtgagct catcgaaaagaggtgccgccggatggtggtggttgtctctgatgattacctgcagagcaaggaatgtgacttccagaccaaatttgcactc agcctctctccaggtgcccatcagaagcgactgatccccatcaagtacaaggcaatgaagaaagagttccccagcatcctgaggttcatc actgtctgcgactacaccaacccctgcaccaaatcttggttctggactcgccttgccaaggccttgtccctgccc -continued (MyD88 amino acid sequence)

SEQ ID NO: 49

MAAGGPGAGSAAPVSSTSSLPLAALNMRVRRRLSLFLNVRTQVAAD

WTALAEEMDFEYLEIRQLETQADPTGRLLDAWQGRPGASVGRLLEL

LTKLGRDDVLLELGPSIEEDCQKYILKQQQEEAEKPLQVAAVDSSVP

RTAELAGITTLDDPLGHMPERFDAFICYCPSDIQFVQEMIRQLEQTN

YRLKLCVSDRDVLPGTCVWSIASELIEKRCRRMVVVSDDYLQSKE

CDFQTKFALSLSPGAHQKRLIPIKYKAMKKEFPSILRFITVCDYTNPC

TKSWFWTRLAKALSLP

Figure 22:
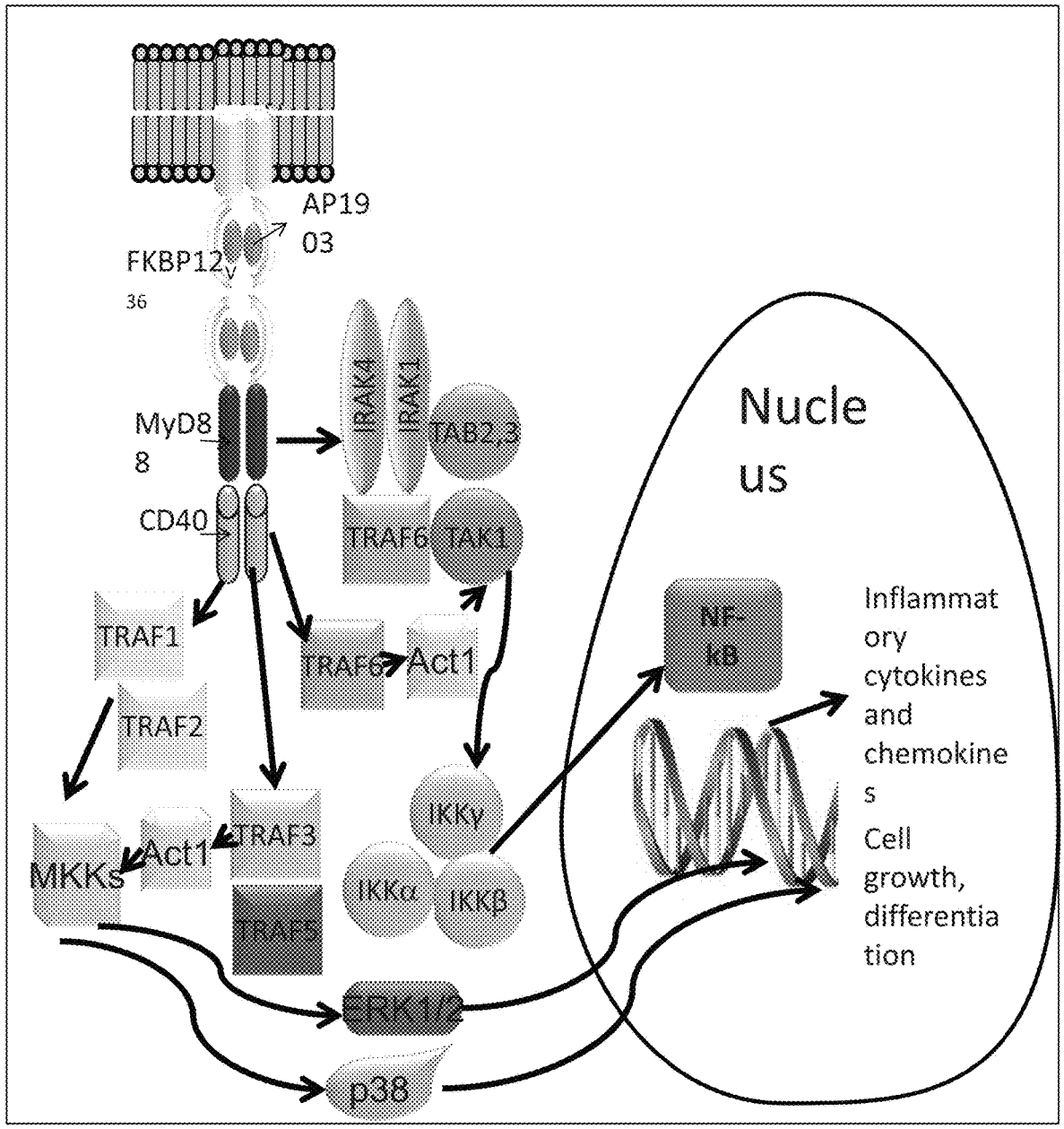
FIG. 22 is a schematic showing activation of non-dendritic cells expressing an inducible MyD88/CD40 chimeric polypeptide.
Figure 23:
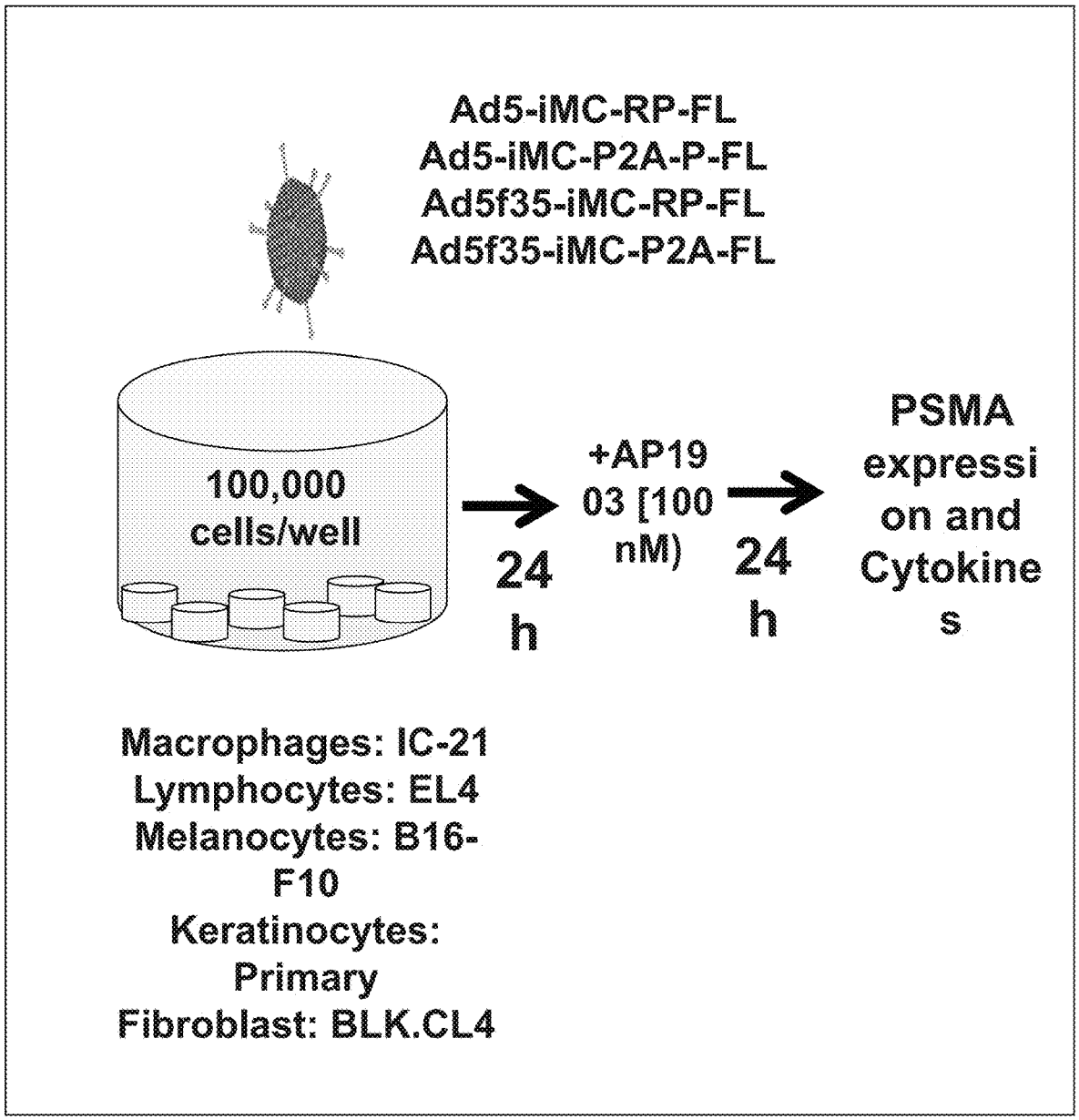
FIG. 23 is a schematic of an experimental design.
Figures 24A, 24B:
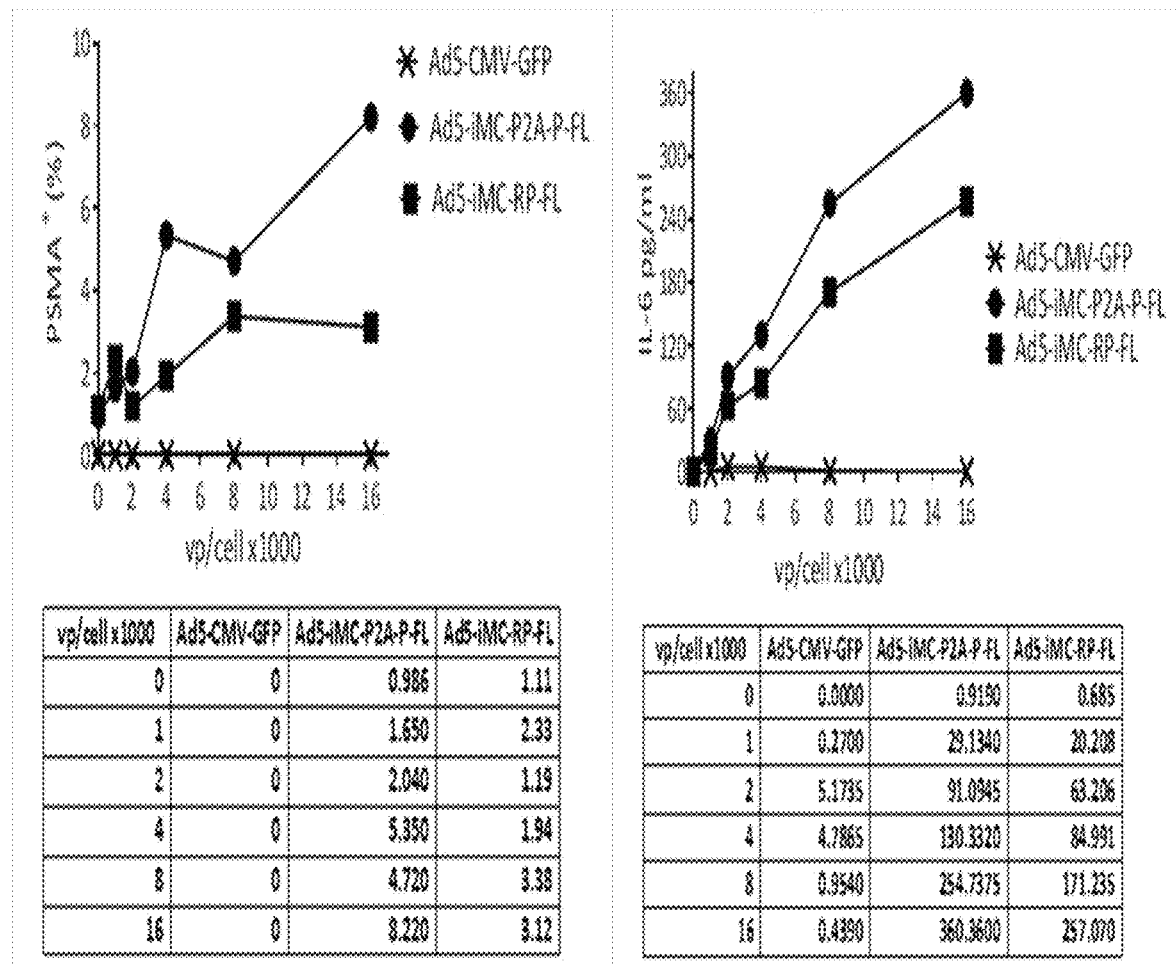
FIGS. 24A and 24B.
Figures 25A, 25B:
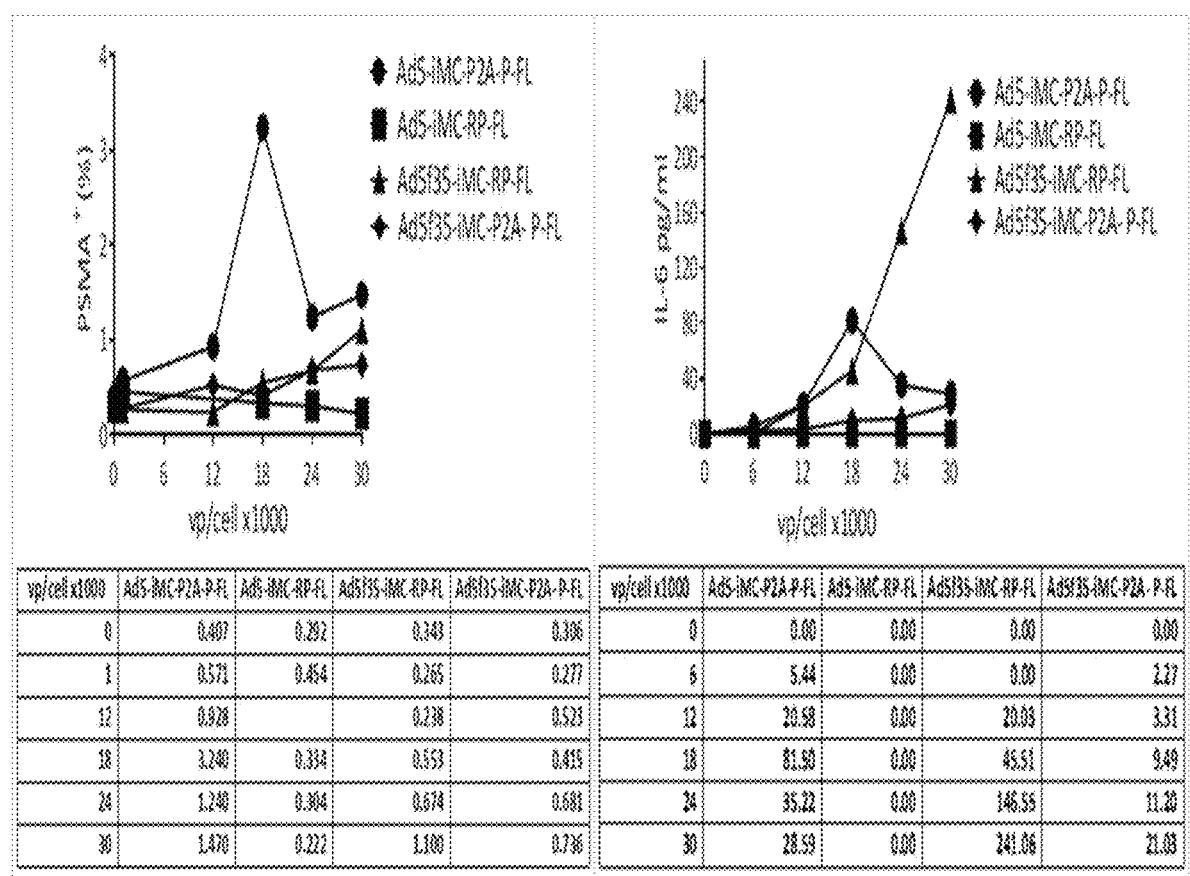
FIGS. 25A and 25B.
Figure 26A:
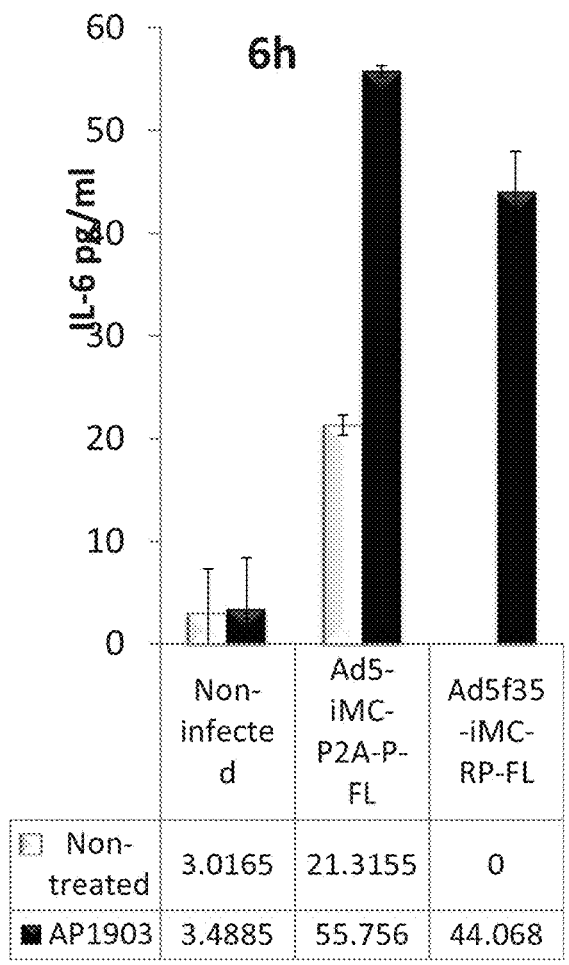
FIGS. 26A-26D.
Figure 26B:
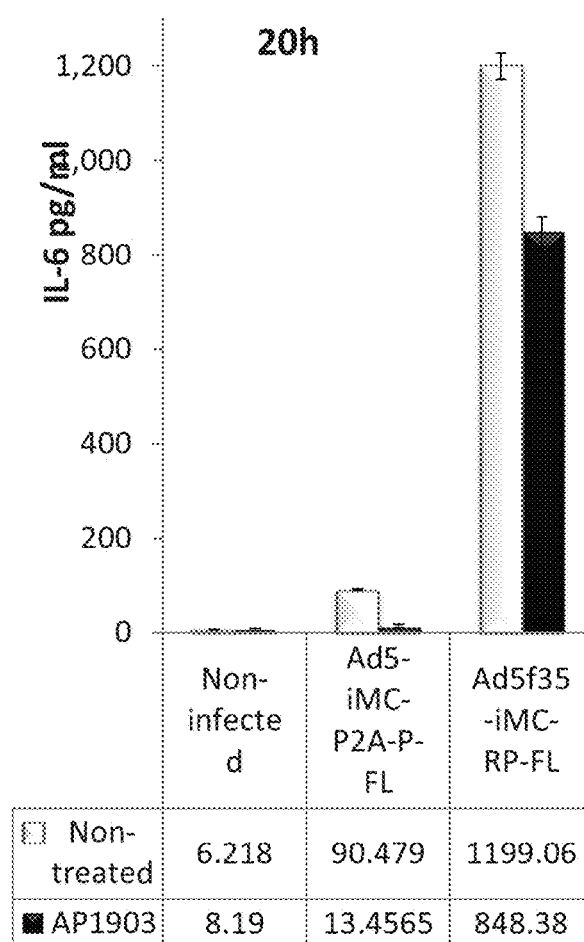
Figures 26C, 26D:
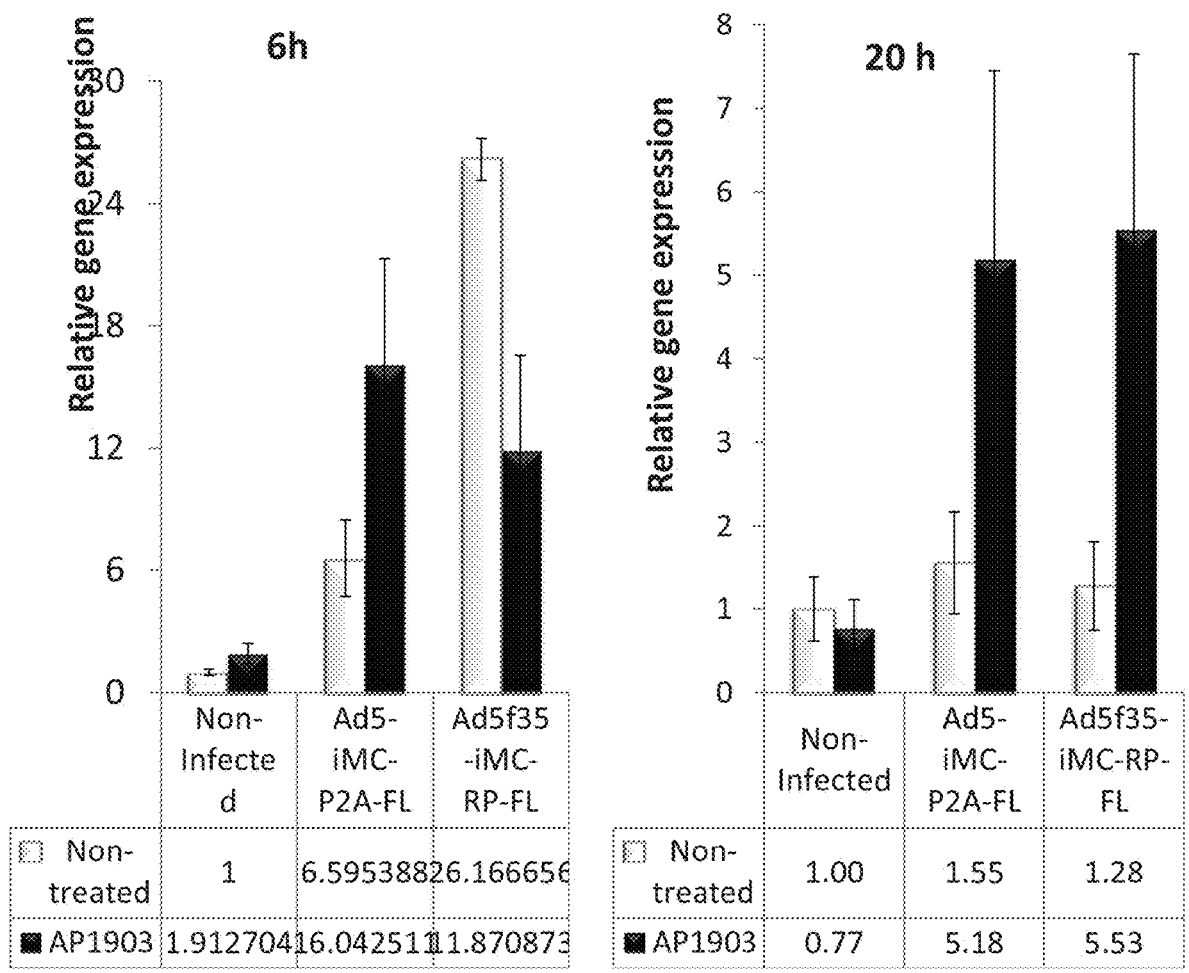

Example 11: Expression of Inducible Chimeric Polypeptides in Different Cell Types Inducible chimeric polypeptides of the present application were expressed in various cell types along with a tumor antigen. The transduced cells expressed the chimeric polypeptides and induced an immune response, demonstrated by the secretion of chemokines and cytokines. The immune response as demonstrated by, for example, IL-6 expression, was activated both in the presence and the absence of the AP1903 ligand. Cell lines included keratinocytes, melanocytes (for example, B16-F10 melanoma), macrophages (for example, IC-21), and fibroblasts (for example, BLK-CL4). FIG. 22 provides a schematic overview of the process by which expression of the chimeric polypeptide, after contacting AP1903, can induce the expression of inflammatory cytokines and chemokines in the transduced cell. FIG. 23 provides a schematic of an assay used to measure PSMA expression and cytokine secretion in transduced cells. The cells were transduced with one of four adenovirus Ad5 vectors: Ad5-iMC-RP-FL; Ad5-iMC-P2A-P-FL; Ad5f35iMC-RP-FL; or Ad5f35iMC-P2A-FL. FIG. 24 provides a graph of the results following transduction of IC-21 macrophages, showing a response to AP1903 by producing IL-6. IC-21 macrophages were cultured at 100,000 cells/ml/well in 24-well plates. Adenoviruses were added at 1000, 2000, 4000, 8000 and 16000 v.p./cell ratio and cells were incubated for 24 hours. Thereafter, 100 nM of AP1903 was added to all the wells, and the following day the cells and culture supernatants were harvested. A. Cells were labeled with anti-human PSMA antibody, LNI-17, (Biolegend, San Diego, Calif.) and PSMA expression was analyzed by flow cytometry. Represented is the percentage of PSMA$^+$ cells when compared to non-transduced cells. B. IL-6 was evaluated from the culture supernatants by ELISA (e-Bioscience, San Diego, Calif.). FIG. 25 also assesses the expression of IL-6 following AP1903 addition to macrophages transduced with the chimeric polypeptide, at different levels of cell plating and multiplicities of infection. IC-21 macrophages were cultured at 50,000 cells/ml/well in 24 well plates. Adenovirus was added at 6000, 12000, 18000, 24000 and 30000 v.p./cell ratio and cells were incubated for 24 hours. Then, 100 nM of AP1903 was added to all the wells, and the following day the cells and culture supernatants were harvested. A. Cells were labeled with anti-human PSMA antibody, LNI-17, (Biolegend, San Diego, Calif.) and PSMA expression was analyzed by flow cytometry. Represented is the percentage of PSMA$^+$ cells when compared to non-transduced cells. B. IL-6 was evaluated from the culture supernatants by ELISA (e-Bioscience, San Diego, Calif.). FIG. 26 presents the results of an assay demonstrating that the activation of the transduced cells occurred with, and without, the addition of AP1903. IC-21 macrophages were cultured at 300,000 cells/well in 6-well plates. Adenoviruses were added at 24,000 v.p./cell ratio for Ad5f35-iMC-RP-FL and at 18000 v.p./cell for Ad5-iMC-P2A-P-FL and cells were incubated for 24 hours. Then, 100 nM of AP1903 was added and culture supernatants were harvested at 6 hours and 20 hours. IL-6 was evaluated from the culture supernatants by ELISA (e-Bioscience, San Diego, Calif.).

Figure 27A:
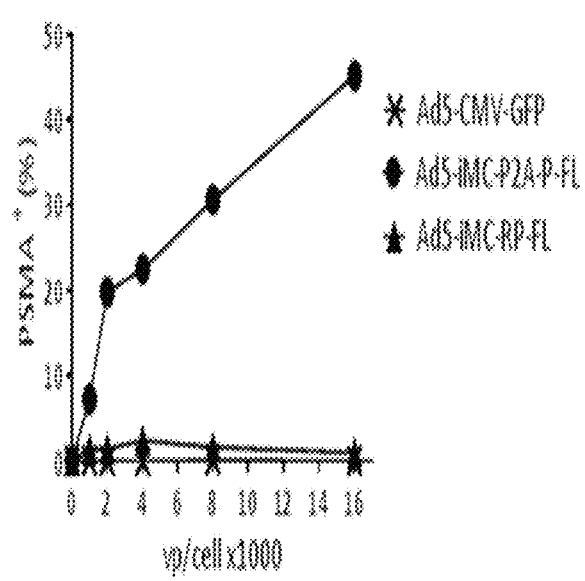
FIGS. 27A and 27B.
Figure 27B:
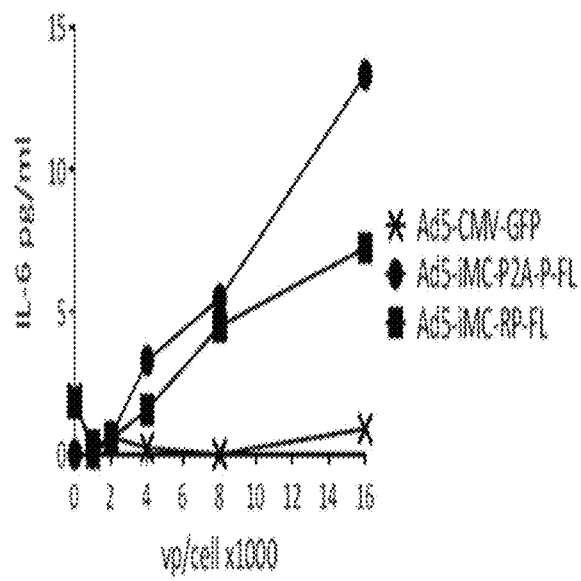
Figures 28A, 28B:
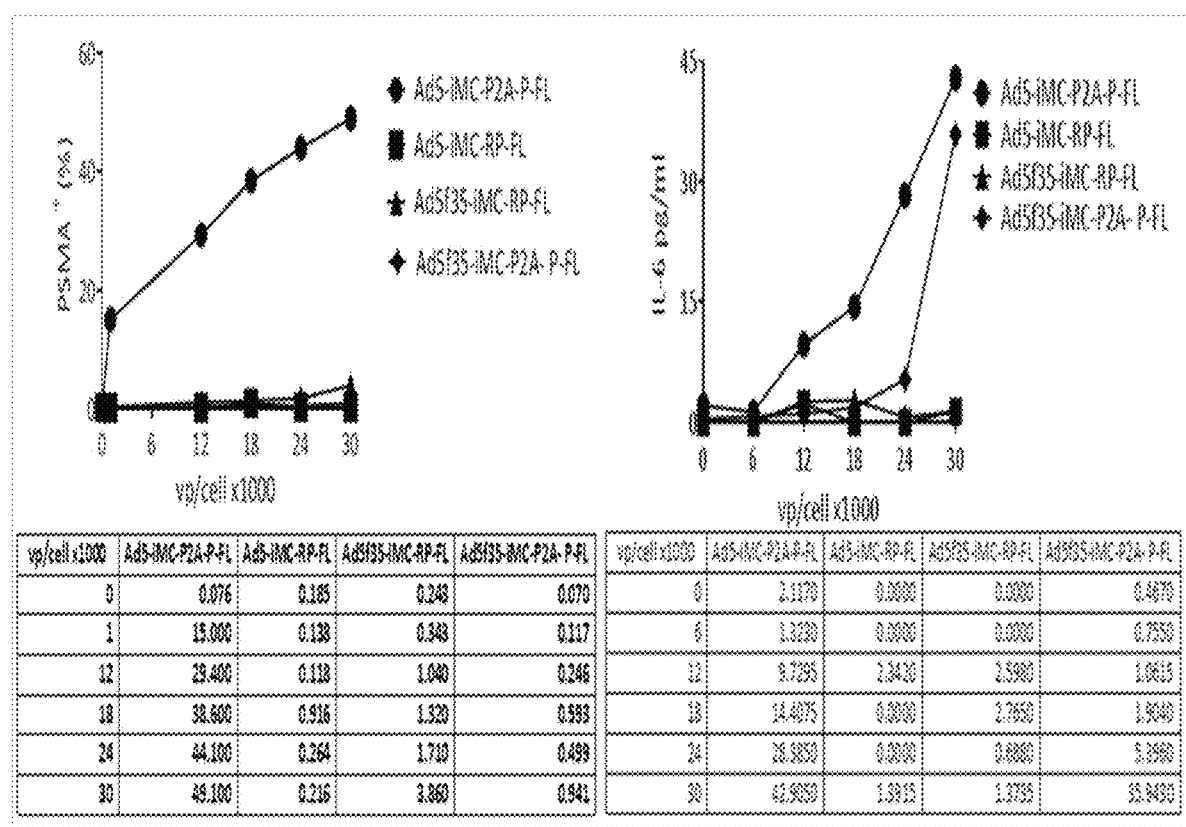
FIGS. 28A and 28B.
Figures 29A, 29B:
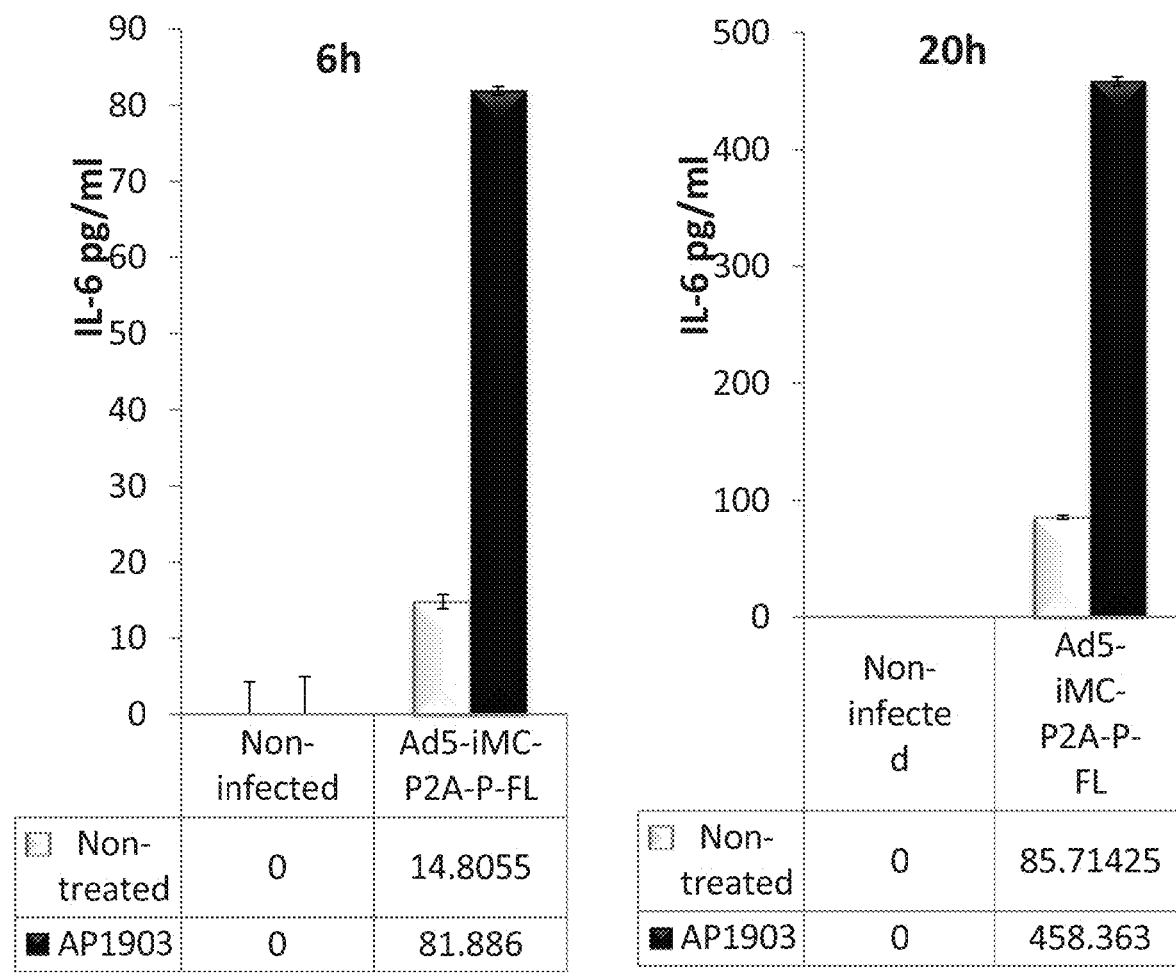
FIGS. 29A and 29B.

FIG. 27 provides a graph of the results following transduction of B16-F10 melanoma cells, showing a response to AP1903 by producing IL-6. B16.F10 melanomas were cultured at 100,000 cells/ml/well in 24 well plates. Adenoviruses were added at 1000, 2000, 4000, 8000 and 16000 virus/cell ratio and cells were incubated for 24 hours. Then, 100 nM of AP1903 was added to all the wells, and the following day the cells and culture supernatants were harvested. A. Cells were labeled with anti-human PSMA antibody, LNI-17, (Biolegend, San Diego, Calif.) and PSMA expression was analyzed by flow cytometry. Represented is the percentage of PSMA$^+$ cells when compared to non-transduced cells. B. IL-6 was evaluated from the culture supernatants by ELISA (e-Bioscience, San Diego, Calif.). FIG. 28 provides the results of the assay at a different multiplicity of infection and plating concentration. B16 melanomas were cultured at 50,000 cells/ml/well in 24-well plates. Adenoviruses were added at 6000, 12000, 18000, 24000 and 30000 virus/cell ratio and cells were incubated for 24 hours. Then, 100 nM of AP1903 was added to all the wells, and the following day the cells and culture supernatants were harvested. A. Cells were labeled with anti-human PSMA antibody, LNI-17, (Biolegend, San Diego, Calif.) and PSMA expression was analyzed by flow cytometry. Represented is the percentage of PSMA$^+$ cells when compared to non-transduced cells. B. IL-6 was evaluated from the culture supernatants by ELISA (e-Bioscience, San Diego, Calif.). FIG. 29 provides a bar graph of an IL-6 assay in the presence and absence of AP1903, showing that transduced cells produce IL-6 without the addition of AP1903. B16 melanoma cells were cultured at 300,000 cells/ml/well in 6-well plates. Adenoviruses were added at 24,000 v.p./cell ratio for Ad5f35-iMC-RP-FL and at 18000 v.p./cell for Ad5-iMC-P2A-P-FL and cells were incubated for 24 hours. Then 100 nM of AP1903 was added, and culture supernatants were harvested at 6 hours and 20 hours. IL-6 was evaluated from the culture supernatants by ELISA (e-Bioscience, San Diego, Calif.)

Figures 30A, 30B:
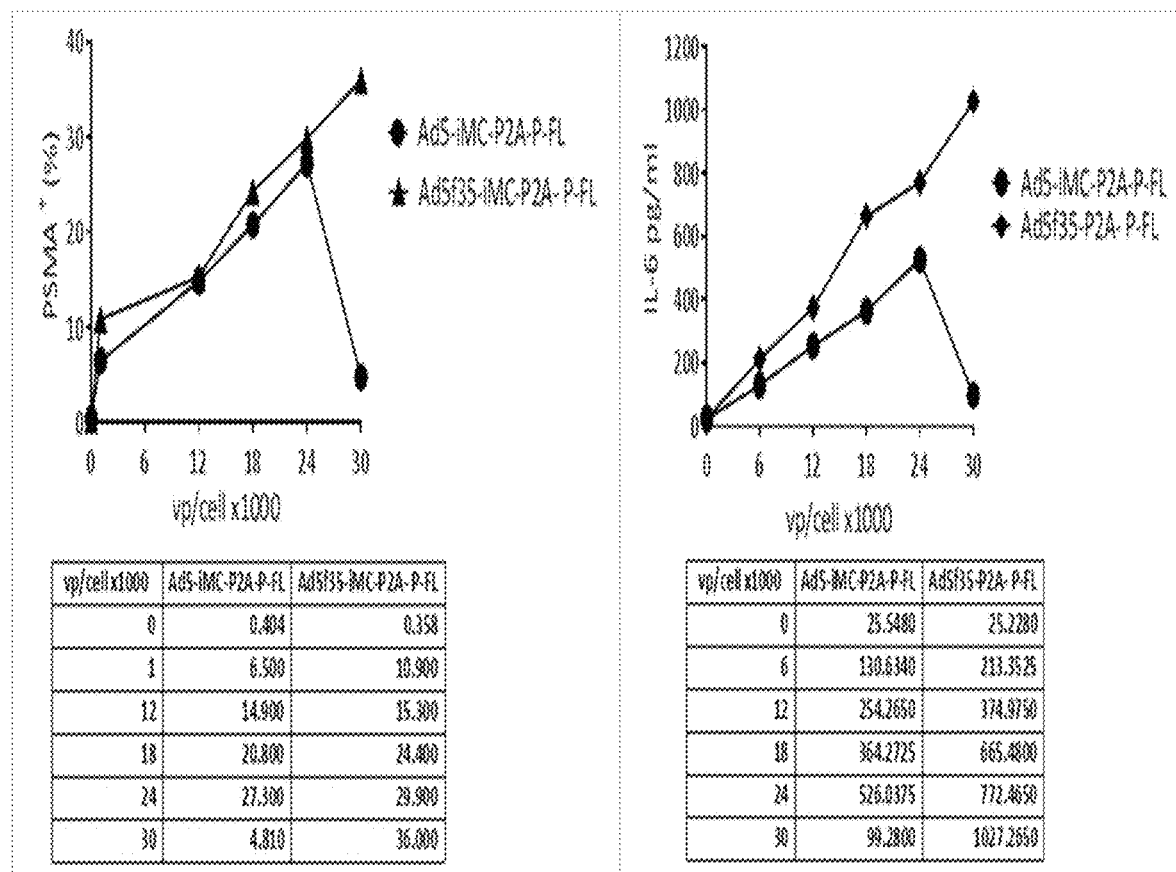
FIGS. 30A and 30B.
Figure 31A:
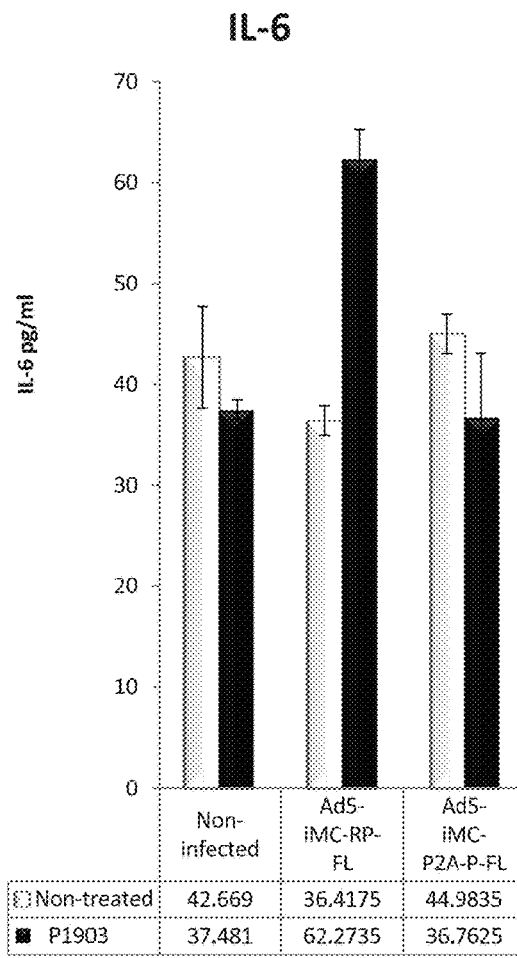
FIGS. 31A and 31B.
Figure 31B:
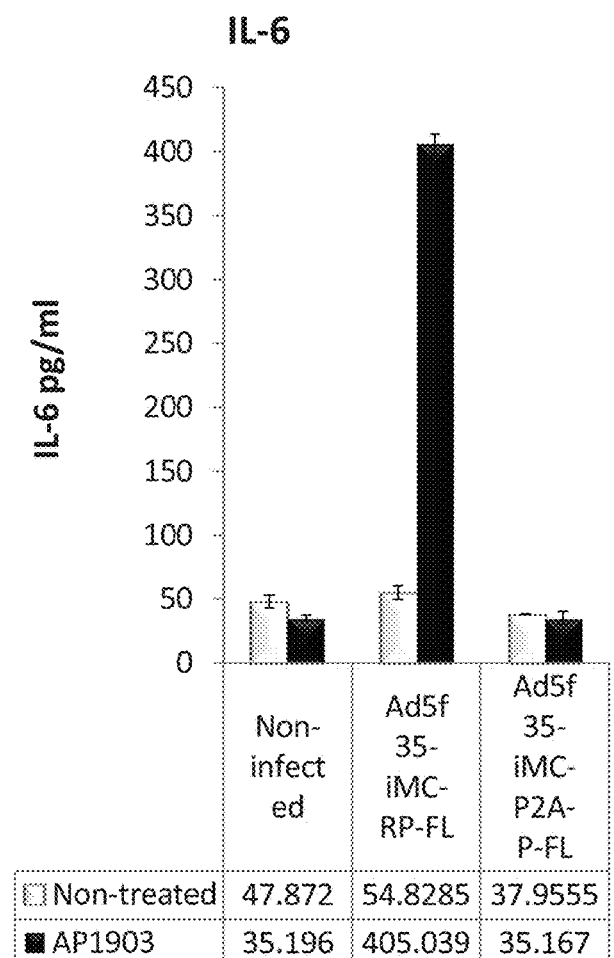

FIG. 30 provides a graph of the results following transduction of BLK CL4 fibroblasts, showing a response to AP1903 by producing IL-6. BLK.CL4 fibroblasts were cultured at 175,000 cells/ml/well in 24-well plates. Adenoviruses were added at 6000, 12000, 18000, 24000 and 30000 virus/cell ratio and cells were incubated for 24 hours. Then, 100 nM of AP1903 was added to all the wells, and the following day cells and culture supernatants were harvested. A. Cells were labeled with anti-human PSMA antibody, LNI-17, (Biolegend, San Diego, Calif.) and PSMA expression was analyzed by flow cytometry. Represented is the percentage of PSMA+ cells when compared to non-transduced cells. B. IL-6 was evaluated from the culture supernatants by ELISA (e-Bioscience, San Diego, Calif.). For FIG. 31, BLK.CL4 fibroblasts were cultured at 350,000 cells/well in 6-well plates. Adenoviruses were added at 20,000 v.p./cell ratio and cells were incubated for 24 hours. Then, 100 nM of AP1903 was added, and the following day culture supernatants were harvested. IL-6 was evaluated from the culture supernatants by ELISA (e-Bioscience, San Diego, Calif.).

Figure 32:
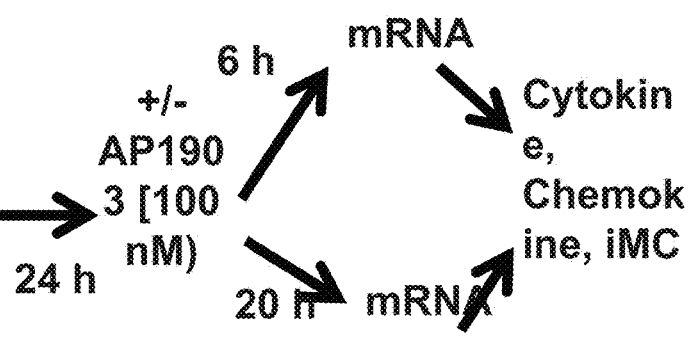
FIG. 32 is a schematic of assay designs.
Figure 33:
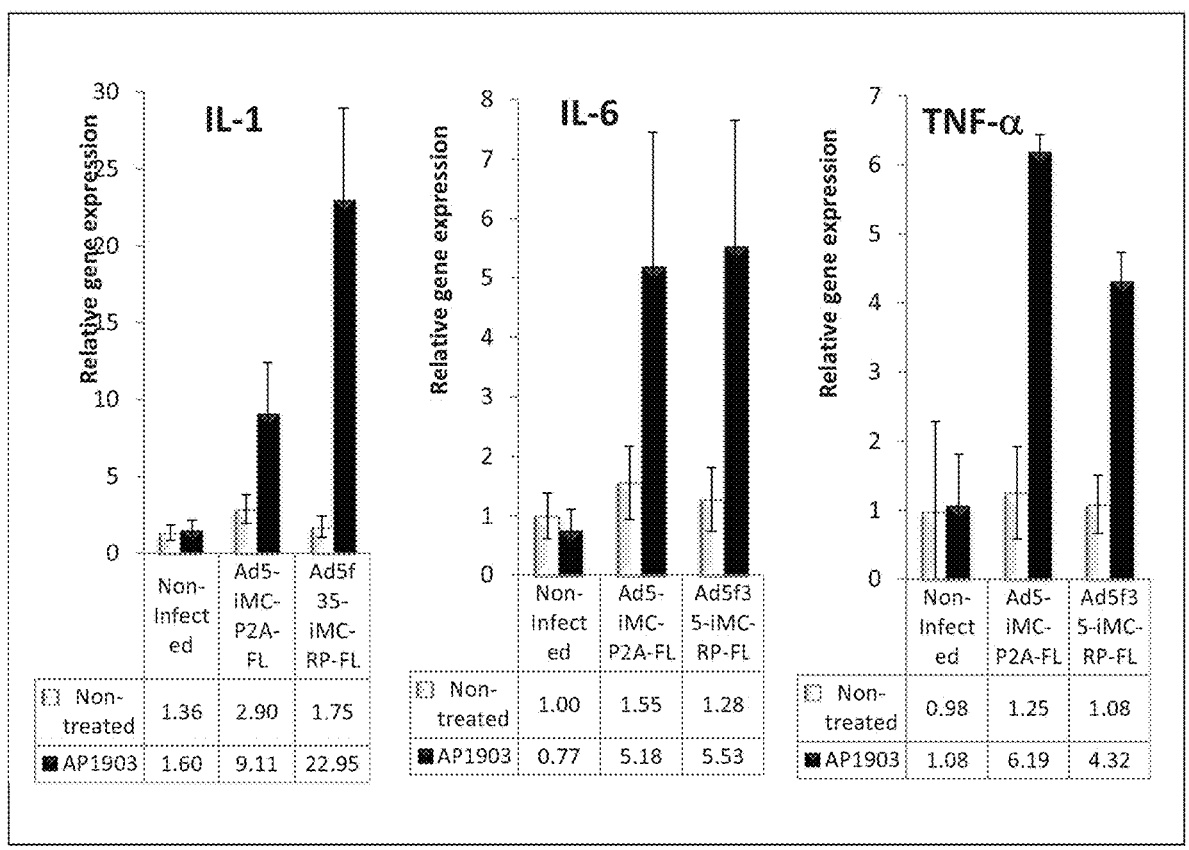
FIG. 33 provides bar graphs of iMC activation in macrophages.
Figure 34:
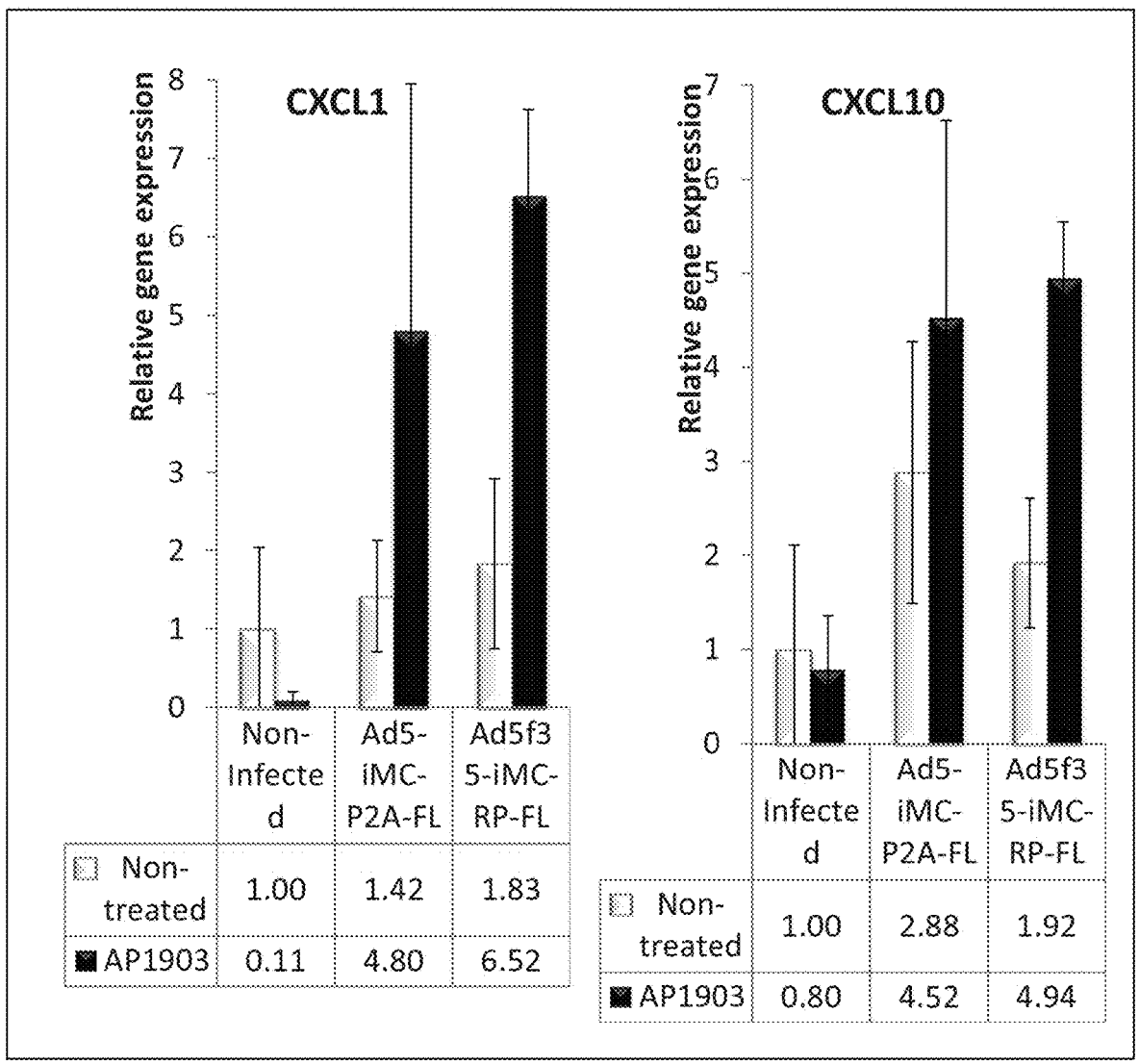
FIG. 34 provides bar graphs of iMC activation in macrophages.
Figure 35:
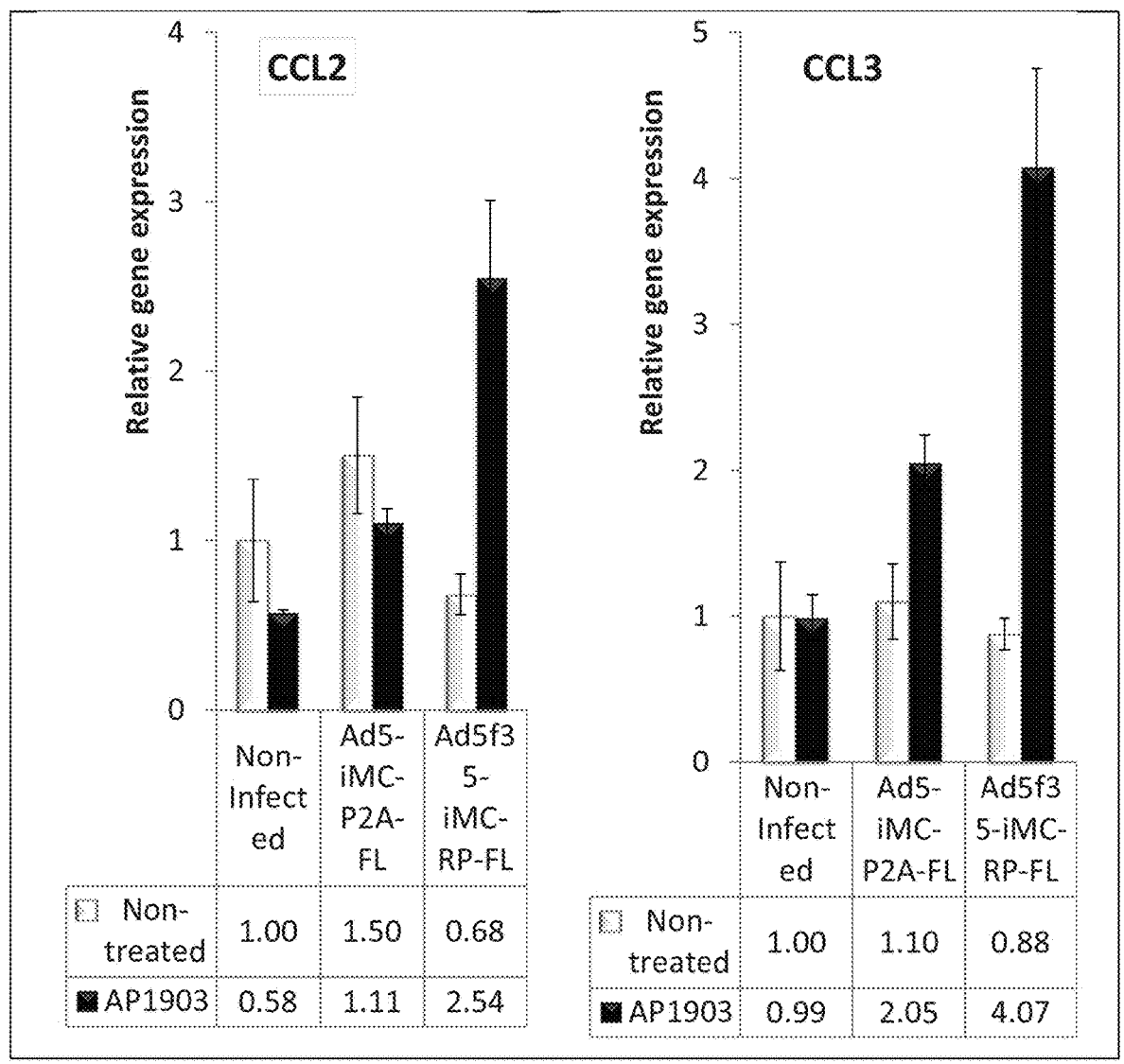
FIG. 35 provides bar graphs of iMC activation in macrophages.

FIG. 32 provides a schematic of a gene expression assay used to determine the activation of transduced cells. In this assay using macrophages, FIG. 33 represents a macrophage-based assay to study AP1903-responsiveness. IC-21 macrophages were cultured at 300,000 cells/well in 6-well plates. Adenoviruses were added at 24,000 v.p./cell ratio for Ad5f35-iMC-RP-FL and at 18,000 v.p./cell for Ad5-iMC-P2A-P-FL and cells were incubated for 24 hours. Then, 100 nM of AP1903 was added and cells were harvested after 20 hours. IL-1, IL-6 and TNF-alpha mRNA gene expression was evaluated from the cells by RT-PCR using SYBR green (Biorad, Hercules, Calif.). FIG. 34 shows the results of an assay of CXCL1 and CXCL10 gene expression. IC-21 macrophages were cultured at 300,000 cells/well in 6-well plates. Adenoviruses were added at 24,000 v.p./cell ratio for Ad5f35-iMC-RP-FL and at 18,000 v.p./cell for Ad5-iMC-P2A-P-FL and cells were incubated for 24 hours. Then, 100 nM of AP1903 was added and cells were harvested after 20 hours. CXCL1 and CXCL10 mRNA gene expression was evaluated from the cells by RT-PCR using SYBR green (Biorad, Hercules, Calif.). FIG. 35 shows the results of an assay of CCL2 and CCL3 gene expression. IC-21 macrophages were cultured at 300,000 cells/well in 6-well plates. Adenoviruses were added at 24,000 v.p./cell ratio for Ad5f35-iMC-RP-FL and at 18000 v.p./cell for Ad5-iMC-P2A-P-FL and cells were incubated for 24 hours. Then, 100 nM of AP1903 was added and cells were harvested after 20 hours. CCL2 and CCL3 mRNA gene expression was evaluated from the cells by RT-PCR using SYBR green (Biorad, Hercules, Calif.).

Included in the present Example are examples of the transduction of various cells, including melanoma, fibroblast, macrophage, and keratinocyte cell lines. Activation of IL-6 in macrophages occurred in the presence or absence of AP1903. IL-6 gene expression and gene expression of other cytokines and chemokines in the transduced cell lines was induced by AP1903.

Example 12: Plasmid Construction Sequences

The following nucleotide sequences were used to construct the Ad5-iMC-P2A-P-FL and Ad5f35-iMC-P2A-P-FL. vectors. The amino acid sequences of the polypeptides code by the nucleotide sequences are also provided.

```
Ad-iMC-2A-P-FL
Myr nt
                                                           SEQ ID NO: 50
atggggagtagcaagagcaagcctaaggaccccagccagcgc aa
                                                           SEQ ID NO: 51
MGSSKSKPKDPSQR MyD88 nt
                                                           SEQ ID NO: 52
atggctgcaggaggtcccggcgcggggtctgcggccccggtctcctccacatcctcccttcccctggctgctctcaacatgcgagtgcggc gccgcctgtctctgttcttgaacgtgcggacacaggtggcggccgactggaccgcgctggcggaggagatggactttgagtacttggagat ccggcaactggagacacaagcggaccccactggcaggctgctggacgcctggcagggacgccctggcgcctctgtaggccgactgct cgatctgcttaccaagctgggccgcgacgacgtgctgctggagctgggacccagcattgaggaggattgccaaaagtatatcttgaagca gcagcaggaggaggctgagaagcctttacaggtggccgctgtagacagcagtgtcccacggacagcagagctggcgggcatcacca cacttgatgaccccctggggcatatgcctgagcgtttcgatgccttcatctgctattgcccagcgacatc MyD88 aa
                                                           SEQ ID NO: 53
MAAGGPGAGSAAPVSSTSSLPLAALNMRVRRRLSLFLNVRTQVAADWTALAEEMDFEYLEIRQLE

TQADPTGRLLDAWQGRPGASVGRLLDLLTKLGRDDVLLELGPSIEEDCQKYILKQQQEEAEKPLQ

VAAVDSSVPRTAELAGITTLDDPLGHMPERFDAFICYCPSDI

CD40 nt
                                                           SEQ ID NO: 54
aaaaaggtggccaagaagccaaccaataaggccccccaccccaagcaggagcccaggagatcaattttcccgacgatcttcctggc tccaacactgctgctccagtgcaggagactttacatggatgccaaccggtcacccaggaggatggcaaagagagtcgcatctcagtgca ggagagacag
```

```
CD40 aa
                                                                                    SEQ ID NO: 55
KKVAKKPTNKAPHPKQEPQEINFPDDLPGSNTAAPVQETLHGCQPVTQEDGKESRISVQERQ

Fv' nt
                                                                                    SEQ ID NO: 56
GGcGTcCAaGTcGAaACcCATtagtCCcGGcGAtGGcaGaAACaTTtCCtAAaaGgGGaCAaACaTGtGTcG TcCAtTAtACaGGcATGtTgGAgGAcGGcAAaAAgGTgGAcagtagtaGaGAtcGcAAtAAaCCtTTcAAaTT cATGtTgGGaAAaCAaGAaGTcATtaGgGGaTGGGAgGAgGGcGTgGCtCAaATGtccGTcGGcCAacG cGCtAAgCTcACcATcagcCCcGAcTAcGCaTAcGGcGCtACcGGaCAtCCcGGaATtATtCCcCCtCAcG CtACctTgGTgTTtGAcGTcGAaCTgtTgAAgCTc Fv' aa
                                                                                    SEQ ID NO: 57
GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKL

Fv nt
                                                                                    SEQ ID NO: 58
ggagtgcaggtggagactatctccccaggagacgggcgcaccttccccaagcgcggccagacctgcgtggtgcactacaccgggatg cttgaagatggaaagaaagttgattcctcccgggacagaaacaagcccctttaagtttatgctaggcaagcaggaggtgatccgaggctgg gaagaagggggttgcccagatgagtgtgggtcagagagccaaactgactatatctccagattatgcctatggtgccactgggcacccagg catcatcccaccacatgccactctcgtcttcgatgtggagcttctaaaactggaa Fv aa
                                                                                    SEQ ID NO: 59
GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKLE

P3A nt
                                                                                    SEQ ID NO: 60
GCTACTAACTTCAGCCTGCTGAAGCAGGCTGGAGACGTGGAGGAGAACCCTGGACCT

P2A aa
                                                                                    SEQ ID NO: 61
ATNFSLLKQAGDVEENPGP

PSMA nt
                                                                                    SEQ ID NO: 62
ATGTGGAATCTCCTTCACGAAACCGACTCGGCTGTGGCCACCGCGCGCCGCCCGCGCTGGC

TGTGCGCTGGGGCGCTGGTGCTGGCGGGTGGCTTCTTTCTCCTCGGCTTCCTCTTCGGGTG

GTTTATAAAATCCTCCAATGAAGCTACTAACATTACTCCAAAGCATAATATGAAAGCATTTTTGG

ATGAATTGAAAGCTGAGAACATCAAGAAGTTCTTACATAATTTTACACAGATACCACATTTAGC

AGGAACAGAACAAAACTTTCAGCTTGCAAAGCAAATTCAATCCCAGTGGAAAGAATTTGGCCT

GGATTCTGTTGAGCTAGCACATTATGATGTCCTGTTGTCCTACCCAAATAAGACTCATCCCAAC

TACATCTCAATAATTAATGAAGATGGAAATGAGATTTTCAACACATCATTATTTGAACCACCTCC

TCCAGGATATGAAAATGTTTGGGATATTGTACCACCTTTCAGTGCTTTCTCTCCTCAAGGAATG

CCAgAGGGCGATCTAGTGTATGTTaactatgcacgaactgaagacttcttttaaattggaacgggacatgaaaatcaattgc tctgggaaaattgtaattgccagatatgggaaagttttcagaggaaataaggttaaaaatgcccagctggcaggggccaaaggagtcatt ctctactccgaccctgctgactactttgctcctggggtgaagtcctatccagatggttggaatcttcctggaggtggtgtccagcgtggaaatat cctaaatctgaatggtgcaggagaccctctcacaccaggttaccagcaaatgaatatgcttataggcgtggaattgcagaggctgttggt cttccaagtattcctgttcatccaattggatactatgatgcacagaagctcctagaaaaaatgggtggctcagcaccaccagatagcagctg gagaggaagtctcaaagtgccctacaatgttggacctggctttactggaaactttttctacacaaaaagtcaagatgcacatccactctacca atgaagtgacaagaatttacaatgtgataggtactctcagaggagcagtggaaccagacagatatgtcattctgggaggtcaccgggact catgggtgtttggtggtattgaccctcagagtggagcagctgttgttcatgaaattgtgaggagctttggaacactgaaaaaggaagggtgg
```

-continued

```
agacctagaagaacaattttgtttgcaagctgggatgcagaagaatttggtcttcttggttctactgagtgggcagaggagaattcaagactc cttcaagagcgtggcgtggcttatattaatgctgactcatctatagaaggaaactacactctgagagttgattgtacaccgctgatgtacagct tggtacacaacctaacaaaagagctgaaaagccctgatgaaggcttgaaggcaaatctctttatgaaagttggactaaaaaagtccttc cccagagttcagtggcatgcccaggataagcaaattgggatctggaaatgattttgaggtgttcttccaacgacttggaattgcttcaggcag agcacggtatactaaaaattgggaaacaaacaaattcagcggctatccactgtatcacagtgtctatgaaacatatgagttggtggaaaa gttttatgatccaatgtttaaatatcacctcactgtggcccaggttcgaggagggatggtgtttgagctagccaattccatagtgctcccttttgat tgtcgagattatgctgtagttttaagaaagtatgctgacaaaatctacagtattctatgaaacatccacaggaaatgaagacatacagtgtat ctttgattcacttttttctgcagtaaagaattttacagaaattgcttccaagttcagtgagagactccaggactttgacaaaagcaacccaata gtattaagaatgatgaatgatcaactcatgtttctggaaagagcatttattgatccattagggttaccagacaggccttttttataggcatgtcatc tatgctccaagcagccacaacaagtatgcagggggagtcattcccaggaatttatgatgctctgtttgatattgaaagcaaagtggacccttc caaggcctggggagaagtgaagagacagatttatgttgcagccttcacagtgcaggcagctgctgagactttgagtgaagtagcctaa
```

PSMA aa

SEQ ID NO: 63

```
MWNLLHETDSAVATARRPRWLCAGALVLAGGFFLLGFLFGWFIKSSNEATNITPKHNMKAFLDEL

KAENIKKFLHNFTQIPHLAGTEQNFQLAKQIQSQWKEFGLDSVELAHYDVLLSYPNKTHPNYISIINE

DGNEIFNTSLFEPPPPGYENVWDIVPPFSAFSPQGMPEGDLVYVNYARTEDFFKLERDMKINCSG

KIVIARYGKVFRGNKVKNAQLAGAKGVILYSDPADYFAPGVKSYPDGWNLPGGGVQRGNILNLNG

AGDPLTPGYPANEYAYRRGIAEAVGLPSIPVHPIGYYDAQKLLEKMGGSAPPDSSWRGSLKVPYN

VGPGFTGNFSTQKVKMHIHSTNEVTRIYNVIGTLRGAVEPDRYVILGGHRDSWVFGGIDPQSGAA

VVHEIVRSFGTLKKEGWRPRRTILFASWDAEEFGLLGSTEWAEENSRLLQERGVAYINADSSIEGN

YTLRVDCTPLMYSLVHNLTKELKSPDEGFEGKSLYESWTKKSPSPEFSGMPRISKLGSGNDFEVF

FQRLGIASGRARYTKNWETNKFSGYPLYHSVYETYELVEKFYDPMFKYHLTVAQVRGGMVFELAN

SIVLPFDCRDYAVVLRKYADKIYSISMKHPQEMKTYSVSFDSLFSAVKNFTEIASKFSERLQDFDKS

NPIVLRMMNDQLMFLERAFIDPLGLPDRPFYRHVIYAPSSHNKYAGESFPGIYDALFDIESKVDPSK

AWGEVKRQIYVAAFTVQAAAETLSEVA
```

Figure 37:
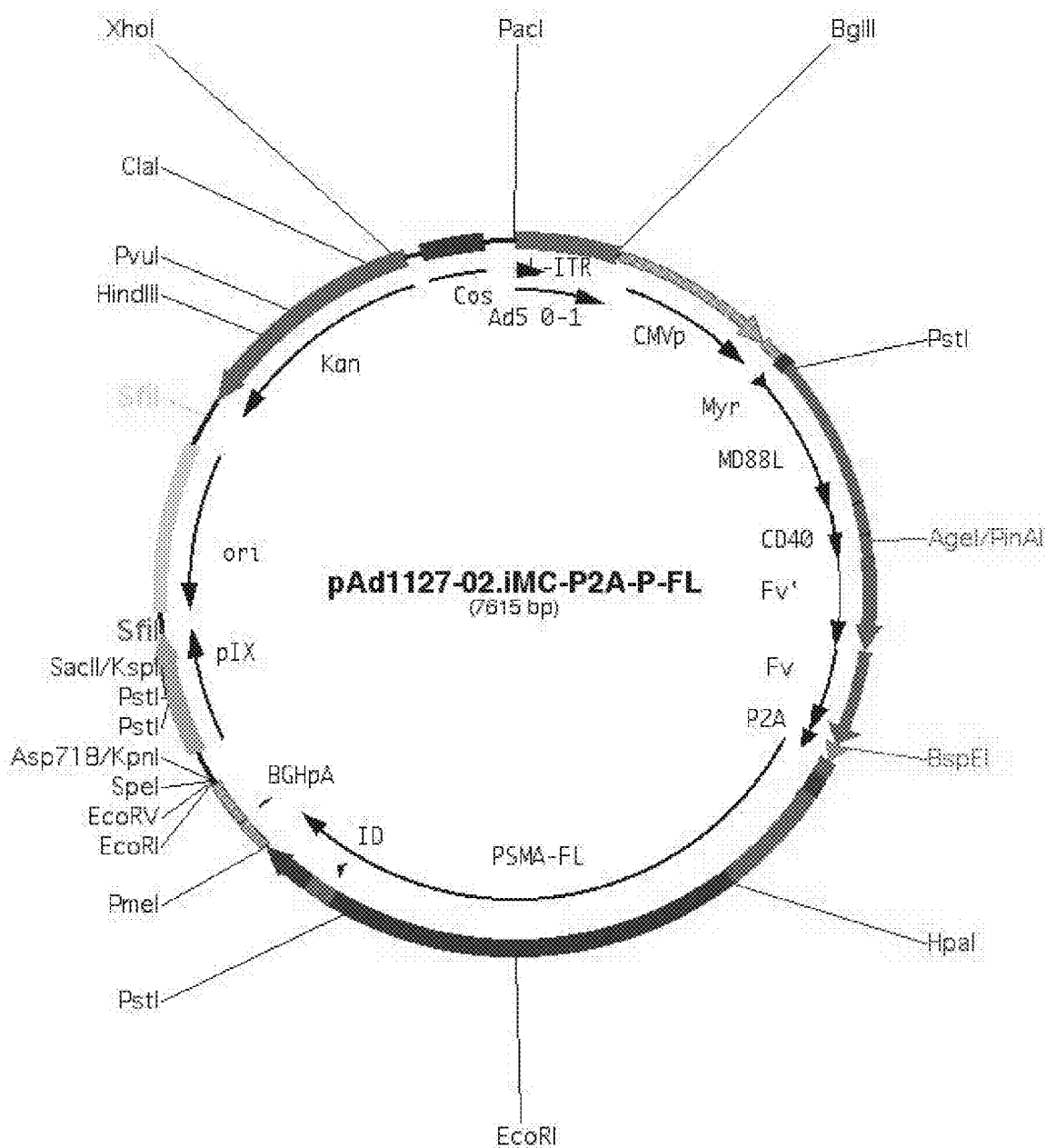
FIG. 37 is a plasmid vector map for a plasmid that may be used to produce adenovirus vectors of the examples.

A diagram of the plasmid vector is provided in FIG. 37. pAd1127-02.iMC-P2A-P-FL is the shuttle vector used to make both Ad5-iMC-P2A-P-FL and the serotype 35 pseudotyped Ad5f35-iMC-P2A-P-FL. It contains the inducible MyD88/CD40 and full length PSMA on the same transcript driven by a CMVp and bovine growth hormone poly A site.

The sequence for CMV-iMC-P2A-P-FL is below with various regions highlighted: Green: CMV promoter, Blue: Myristoylation domain, Red: MyD88L, Orange: CD40, Teal: FKBPv36 (codon-wobbled), Ambre: FKBPv36 (VVT sequence), pea-green: P2A peptide, red-underlined: PSMA-FL, brown: BGHpA Example 13: Expression of Inducible Chimeric Polypeptides in T Lymphocytes Experiments to Test Activation of iMC in Primary T Cells:
1. Generate retrovirus through transient transfection of 293T cells:
2. Transduce CD3/CD28-activated T cells with SFG-MC.Fv1.Fv2.2A.ΔCD19 plasmid vector (sequence provided in this example, and FIG. 36) and measure transduction efficiency by flow cytometry by examining CD3⁺CD19⁺ expression.
3. Activate T cells with or without 10 nM AP1903 and perform the following analyses at 24, 48 and 72 hours:
    a. Measure cytokine and chemokine production using multiplex analysis
    b. Measure activation phenotype of CD4⁺ and CD8⁺ T cells using CD25, CD69, CD80, CD86 and MHC class I and II antibodies.
    c. Measure proliferation using CFSE dilution and cell enumeration.
    d. Measure cell survival in the absence of exogenous IL-2 using ALAMARBLUE and cell enumeration assays.
4. Examine the memory phenotype of CD4 and CD8 T cells using additional markers, such as CD62L and CD45RA and CD45RO.
5. Test the resistance of resting and iMC-activated T cells in the presence of Treg cells, making TGFβ and/or IL-10.

Expected Results:
1. iMC crosslinking drives T cell activation, as assayed using the T cell activation markers listed in this example, and increases elaboration of Th1 cytokines, such as IL-2 and IFNγ, increasing T cell proliferation, and IFNγ, increasing cytotoxicity.
2. T cells are activated by iMC crosslinking with little to no change in apoptosis.
3. An increase in memory phonotype and increased resistance of CD4⁺ and CD8⁺ T cells to the inhibitory effects of Treg cells is observed.

The present example provides examples of methods used to express inducible chimeric polypeptides in T lymphocytes. Specific examples are provided using an inducible chimeric MyD88/CD40 polypeptide. Similar methods may be applied to inducible chimeric MyD88 or CD40 polypeptides.

In order to test an inducible MyD88/CD40 polypeptide iMyD88/CD40 (iMC) in T cells, a retroviral plasmid vector, pSFG.Myr-MC-Fv1-Fv2-2A-ΔCD19 ("pSFG.iMC-2A-ΔCD19"), encoding iMC and truncated CD19 marker on the same transcript, is transiently co-transfected into 293 cells along with a gag-pol expression vector and an RD114 envelope vector to make high-titer retrovirus.

The inducible polypeptide includes 2 FK506 binding proteins (FKBPs—for example, FKBP12v36 variants, or FKBP12; GenBank AH002 818) that contains an F36V mutation) linked with a Gly-Ser-Gly-Gly-Gly-Ser linker (SEQ ID NO: 192) to the MyD88 or CD40 sequence. The amino acid sequence of one of the FKBPs ($F_v2$) is codon-wobbled (e.g., the $3^{rd}$ nucleotide of each amino acid codon is altered by a silent mutation that maintained the originally encoded amino acid) to prevent homologous recombination when expressed in a retrovirus. The constructs are cloned into SFG; they may also be cloned into pLenti7.3.

293T cells are transfected with each of these constructs and 48 hours after transduction expression of the marker gene GFP or ΔCD19 is analyzed by flow cytometry. In addition to the level of GFP or ΔCD19 expression, the expressed gene products are also analyzed by western blot to confirm the expression of the chimeric polypeptides.

Transfected 293T cells are resuspended in lysis buffer (50% Tris/Gly, 10% sodium dodecyl sulfate [SDS], 4% beta-mercaptoethanol, 10% glycerol, 12% water, 4% bromophenol blue at 0.5%) containing aprotinin, leupeptin, and phenylmethylsulfonyl fluoride (Boehringer, Ingelheim, Germany) and incubated for 30 minutes on ice. After a 30-minute centrifugation, supernatant is harvested, mixed 1:2 with Laemmli buffer (Bio-Rad, Hercules, Calif.), boiled and loaded on a 10% SDS—polyacrylamide gel. The membrane is probed with rabbit anti-costimulatory polypeptide immunoglobulin G (IgG; Affinity BioReagents, Golden, Colo.; 1:500 dilutions) and with mouse anti-GFP IgG (Covance, Berkeley, Calif.; 1:25,000 dilution). Blots are then exposed to appropriate peroxidase-coupled secondary antibodies and protein expression is detected with enhanced chemiluminescence (ECL; Amersham, Arlington Heights, Ill.). The membrane is then stripped and reprobed with goat polyclonal antiactin (Santa Cruz Biotechnology; 1:500 dilutions) to check equality of loading.

Evaluation of Inducible Expression Constructs.
Cell Lines

The cancer cell lines LNCaP, PC3, DU145 and A549, and the human embryonic kidney cell line HEK-293T, are obtained from American Type Culture Collection (Rockville, Md.). Cells are maintained in complete IMDM (Sigma, St Louis, Mo.) containing 10% fetal bovine serum (Hyclone, Waltham, Mass.), and 2 mM L-glutamine in a humidified atmosphere containing 5% carbon dioxide ($CO_2$) at 37° C. Transduced T cells and PHA blasts are maintained in Cellgenix DC (Cellgenix) media supplemented with 100 U/ml IL-2 (Cellgenix)

Activation of T Cells

Activation of T cells for expansion and transduction is performed using soluble αCD3 and αCD28 (Miltenyi Biotec, Auburn, Calif.). PBMCs are resuspended in Cellgenix DC media supplemented with 100 U/ml IL-2 (Cellgenix) at $1×10^6$ cells/ml and stimulated with 0.2 μg/ml aCD3 and 0.5 μg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

Retroviral and Lentiviral Constructs

Figure 36:
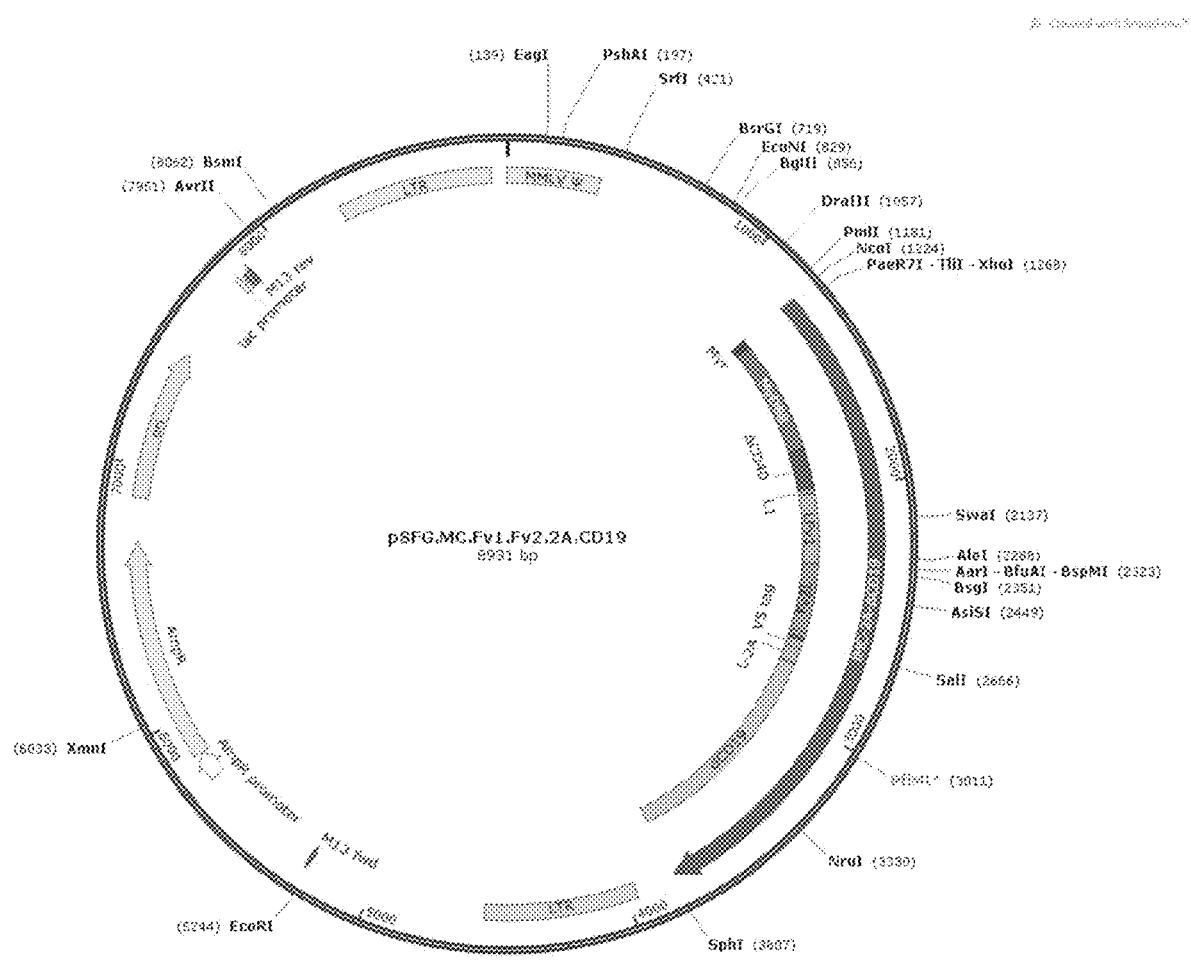
FIG. 36 is a plasmid vector map for a plasmid that may be used to produce retrovirus vectors of the examples.

Inducible chimeric polypeptide constructs are synthesized by Blue Heron Bio (Bothell, Wash.), a schematic is shown in FIG. 36. Evaluation of the expression of the chimeric polypeptide, and the expression and secretion of inflammatory cytokines and chemokines is performed by single or co-transduction of T cells with retro- or lentivirus encoding these transgenes.

Retrovirus Transduction

For the transient production of retrovirus, 293T cells are transfected with the chimeric polypeptide constructs, along with plasmids encoding gag-pol and RD 114 envelope using GENEJUICE transfection reagent (Novagen, Madison, Wis.). Virus is harvested 48 to 72 hours after transfection, snap frozen, and stored at ~80° C. until use. For the transient production of lentivirus, 293T cells are transfected with the constructs along with the plasmids pLP1 (gag/pol), pLP2 (rev) and pLP/VSVG (VSVG env) using GENEJUICE. Virus is harvested 48 to 72 hours after transfection, snap frozen, and stored at ~80° C. until use. For large-scale retrovirus production, a stable FLYRD 18-derived retroviral producer line is generated by multiple transductions with VSV-G pseudotyped transient retroviral supernatant. FLYRD18 cells with highest transgene expression are single-cell sorted, and the clone that produce the highest virus titer is expanded and used to produce virus for lymphocyte transduction. The transgene expression, function, and retroviral titer of this clone is maintained during continuous culture for more than 8 weeks. Non-tissue culture-treated 24-well plates are coated with 7 μg/ml RETRONECTIN (Takara Bio, Otsu, Shiga, Japan) for 1 hour at 37° C. or overnight at 4° C. The wells are washed with phosphate-buffered saline (PBS) then coated with retroviral supernatant by incubating the plate with 1.5 ml of supernatant for 30 minutes at 37° C. Subsequently, T cell blasts are plated at $5×10^5$ cells per well in viral supernatant supplemented with 100 U/ml IL-2. Transduction is performed over a 60-hour period. Following transduction, cells are harvested and phenotyped for CD19 or GFP expression by flow cytometry.

Cytotoxicity of Transduced T Cells

The cytotoxic activity of each transduced T cell line may be evaluated, for example, in a standard 4-hour $^{51}Cr$ release assay, as previously presented. T cells transduced with the retrovirus or lentivirus and compared against $Cr^{51}$-labeled target cells, including autologous phytohaemagglutinin (PHA) stimulated lymphocytes (PHA blasts), LNCaP, PC3 or DU145 and A549 cancer cell lines, and transgenic A549 expressing human PSMA (A549-PSMA). Target cells incubated in complete medium or 1% Triton X-100 (Sigma, St Louis, Mo.) are used to determine spontaneous and maximum $^{51}Cr$ release, respectively. The mean percentage of specific lysis of triplicate wells was calculated as 100× (experimental release–spontaneous release)/(maximal release–spontaneous release). In addition to chromium-release assays, co-culture experiments with are performed. Here, the cell lines LNCaP, PC3, DU145, A549 and A549-PSMA are transduced to express fluorescent mOrange and used as target cells. mOrange-expressing tumor cells are co-cultured with non-transduced or modified T cells at a ratio of 1:10 tumor cells to T cells in the presence of IL-2 (50 U/ml) in complete media. After 24 hours, T cells are stimulated with 100 nM AP1903. After 72 hours, cells are collected, counted and labeled with CD3 to detect T cells and percentage of mOrange tumor cells is analyzed by flow cytometry (LSRII; BD).

Phenotyping and Activation Status of Transduced T Cells

Cell surface phenotype of transduced T cells is investigated using the following monoclonal antibodies: CD3, CD4, CD8, CD19, CD25, CD27, CD28, CD44, CD45RA, CD45RO, CD62L, CD80, CD83, CD86, CD127, CD134, CD137, HLA-ABC and HLA-DR. Phenotyping is performed with and without 100 nM AP1903. Appropriate matched isotype controls are used in each experiment and cells are analyzed with a LSRII flow cytometer (BD). The chimeric polypeptide expression is assessed using anti-F (ab')2 (Jackson ImmunoResearch Laboratories, West Grove, Pa.).

Analysis of Cytokine Production of Transduced T Cells

The concentration of interferon-γ (IFN-γ), IL-2, IL-4, IL-5, IL-10, and tumor necrosis factor-α (TNFα) in T cell culture supernatants before and after (24 hours) 100 nM AP1903 stimulation is measured using the Human Th1/Th2 cytokine cytometric Bead Array (BD Pharmingen). Induced cytokine production in the culture supernatants is validated by enzyme-linked immunosorbent assay (ELISA; R&D Systems, Minneapolis, Minn.) according to the instructions of the manufacturer.

Proliferation of Transduced T Cells

The proliferative effect of AP1903-induced activation is evaluated by measuring cell growth of transduced and non-transduced T cells following exposure to AP1903. T cells are labeled with 10 μM carboxyfluorescein diacetate, succinimidyl ester (CFSE) for 10 minutes at 37° C. After incubation, cells are washed in PBS and then resuspended in Cellgenix DC media. $1 \times 10^6$ CFSE-labeled modified or non-transduced T cells are subsequently cultured in Cellgenix DC media alone, or stimulated with 100 nM AP1903. After 5 days, cells are harvested and labeled with CD3-PerCP.Cy5.5 and CD19-PE and analyzed by flow cytometry for CFSE dilution.

To evaluate whether soluble immunoglobulins affect the proliferation and expansion of the transduced T lymphocytes, cells are cultured at $1 \times 10^5$ cells/well either with serial dilution of human plasma obtained from healthy donors or serial dilution of purified human immunoglobulins (Jackson ImmunoResearch) without any addition of exogenous cytokines. After 72 hours, the cells are pulsed with 1 μCi (0.037 MBq) methyl-3[H]thymidine (Amersham Pharmacia Biotech, Piscataway, N.J.) and cultured for additional 15 hours. The cells were then harvested onto filters and dried, and counts per minute are measured in a β-scintillation counter (TriCarb 2500 TR; Packard BioScience, Meridien, Conn.). The experiments are performed in triplicate. In other experiments, control and modified T lymphocytes are cultured either with media alone or with media in which serial dilution of plasma or purified immunoglobulins are added every second day. Cells are then counted every third day using trypan blue exclusion.

In Vivo Experiments

The effect of activated T cells on tumor size in vivo may be assayed, for example, as follows. Non-obese diabetic severe combined immunodeficient (NOD/SCID) mice, 6 to 8 weeks of age, are irradiated (250 rad) and injected subcutaneously in the right flank with $10 \times 10^6$ to $15 \times 10^6$ LNCaP tumor cells resuspended in Matrigel (BD Bioscience). Two weeks later mice bearing tumors that are approximately 0.5 cm in diameter are injected into the tail vein with either non-transduced or transduced T cells (total $15 \times 10^6$). The mice are randomly segregated in 2 groups: 1 group receives CID (50 μg AP1903, intraperitoneally, twice weekly) and 1 group receives carrier only (16.7% propanediol, 22.5% PEG400, and 1.25% Tween 80, intraperitoneally, twice weekly) to expand T cells. Mice are evaluated for tumor growth by caliper measurement for 21 days. Peripheral blood samples are taken by retro-orbital eye bleeding on days 7, 14 and 21 to measure the persistence and expansion of transduced or control T cells using flow cytometric analysis for human CD3/human CD19 expressing T cells.

```
Annotated Vector sequence:
8931 bp ds-DNA
   /note="MMLV Psi"
   /note="packaging signal of Moloney murine leukemia virus
   (MMLV)"
 CDS   1226..3802
   /codon_start=1
   /note="iMC-2A-Delta-CD19"
   /translation="
aa
                                                              SEQ ID NO: 64
MGSSKSKPKDPSQRLEMAAGGPGAGSAAPVSSTSSLPLAALNMRV

RRRLSLFLNVRTQVAADWTALAEEMDFEYLEIRQLETQADPTGRLLDAWQGRPGASVGR

LLDLLTKLGRDDVLLELGPSIEEDCQKYILKQQQEEAEKPLQVAAVDSSVPRTAELAGI

TTLDDPLGHMPERFDAFICYCPSDIKKVAKKPTNKAPHPKQEPQEINFPDDLPGSNTAA

PVQETLHGCQPVTQEDGKESRISVQERQVESGGGSGGVQVETISPGDGRTFPKRGQTCV

VHYTGMLEDGKKVDSSRDRNKPFKFMLGKQEVIRGWEEGVAQMSVGQRAKLTISPDYAY

GATGHPGIIPPHATLVFDVELLKLEVEGVQVETISPGDGRTFPKRGQTCVVHYTGMLED

GKKVDSSRDRNKPFKFMLGKQEVIRGWEEGVAQMSVGQRAKLTISPDYAYGATGHPGII

PPHATLVFDVELLKLESGGGSGVDRAKRGKPIPNPLLGLDSTGSGSATNFSLLKQAGDV

EENPGPTRMPPPRLLFFLLFLTPMEVRPEEPLVVKVEEGDNAVLQCLKGTSDGPTQQLT

WSRESPLKPFLKLSLGLPGLGIHMRPLAIWLFIFNVSQQMGGFYLCQPGPPSEKAWQPG

WTVNVEGSGELFRWNVSDLGGLGCGLKNRSSEGPSSPSGKLMSPKLYVWAKDRPEIWEG
```

-continued

EPPCLPPRDSLNQSLSQDLTMAPGSTLWLSCGVPPDSVSRGPLSWTHVHPKGPKSLLSL

ELKDDRPARDMWVMETGLLLPRATAQDAGKYYCHRGNLTMSFHLEITARPVLWHWLLRT

GGWKVSAVTLAYLIFCLCSLVGILHLQRALVLRRKRKRMTDPTRRF"

```
misc_feature   1226..1267
 /note="Myr"
misc_feature   1268..1273
 /note="XhoI"
misc_feature   1274..1789
 /note="MyD88"
misc_feature   1790..1975
 /note="Delta-CD40"
misc_feature   1976
 /note="SalI"
misc_feature   1977..1981
 /note="XhoI"
misc_feature   1982..1999
 /note="L1"
misc_feature   2000..2320
 /note="LFv1"
misc_feature   2327..2647
 /note="Fv2L"
misc_feature   2648..2665
 /note="L1"
misc_feature   2666
 /note="SalI"
misc_feature   2667..2671
 /note="SalI"
misc_feature   2672..2683
 /note="Furin"
misc_feature   2684..2725
 /product="epitope tag from simian virus 5"
 /note="V5 tag"
misc_feature   2726..2794
 /note="L-2A"
misc_feature   2795..2800
 /note="MluI"
misc_feature   2801..3802
 /note="dCD19"
misc_feature   3962..4551
 /note="LTR"
primer_bind    complement(5250..5266)
 /note="M13 fwd"
 /note="common sequencing primer, one of multiple similar
 variants"
promoter   5741..5845
 /gene="bla"
 /note="AmpR promoter"
CDS   5846..6706
 /codon_start=1
 /gene="bla"
 /product="beta-lactamase"
 /note="AmpR"
 /note="confers resistance to ampicillin, carbenicillin, and
 related antibiotics"
 /translation="
aa                                                                SEQ ID NO: 65
MSIQHFRVALIPFFAAFCLPVFAHPETLVKVKDAEDQLGARVGYI
```

ELDLNSGKILESFRPEERFPMMSTFKVLLCGAVLSRIDAGQEQLGRRIHYSQNDLVEYS

PVTEKHLTDGMTVRELCSAAITMSDNTAANLLLTTIGGPKELTAFLHNMGDHVTRLDRW

EPELNEAIPNDERDTTMPVAMATTLRKLLTGELLTLASRQQLIDWMEADKVAGPLLRSA

LPAGWFIADKSGAGERGSRGIIAALGPDGKPSRIVVIYTTGSQATMDERNRQIAEIGAS

LIKHW"

```
rep_origin   6877..7465
 /direction=RIGHT
 /note="ori"
 /note="high-copy-number colE1/pMB1/pBR322/pUC origin of
 replication"
promoter   7789..7819
 /note="lac promoter"
 /note="promoter for the E. coli lac operon"
```

```
                           -continued
protein_bind    7827..7843
/bound_moiety="lac repressor encoded by lacI"
/note="lac operator"
/note="The lac repressor binds to the lac operator to
inhibit transcription in E. coli. This inhibition can be
relieved by adding lactose or
isopropyl-beta-D-thiogalactopyranoside (IPTG)."
primer_bind     7851..7867
/note="M13 rev"
/note="common sequencing primer, one of multiple similar
variants"
LTR     8276..8869
/note="long terminal repeat from Moloney murine leukemia
virus"
ORIGIN
nt
                                                             SEQ ID NO: 66
   1 aagctggcca gcaacttatc tgtgtctgtc cgattgtcta gtgtctatga ctgattttat 61 gcgcctgcgt cggtactagt tagctaacta gctctgtatc tggcggaccc gtggtggaac 121 tgacgagttc ggaacacccg gccgcaaccc tgggagacgt cccagggact tcggggccg 181 tttttgtggc ccgacctgag tcctaaaatc ccgatcgttt aggactcttt ggtgcacccc 241 ccttagagga gggatatgtg gttctggtag gagacgagaa cctaaaacag ttcccgcctc 301 cgtctgaatt tttgctttcg gtttgggacc gaagccgcgc cgcgcgtctt gtctgctgca 361 gcatcgttct gtgttgtctc tgtctgactg tgtttctgta tttgtctgaa aatatgggcc 421 cgggctagcc tgttaccact cccttaagtt tgaccttagg tcactggaaa gatgtcgagc 481 ggatcgctca caaccagtcg gtagatgtca agaagagacg ttgggttacc ttctgctctg 541 cagaatggcc aacctttaac gtcggatggc cgcgagacgg cacctttaac cgagacctca 601 tcacccaggt taagatcaag gtctttttcac ctggcccgca tggacaccca gaccaggtgg 661 ggtacatcgt gacctgggaa gccttggctt ttgaccccccc tccctgggtc aagcccttg 721 tacaccctaa gcctccgcct cctcttcctc catccgcccc gtctctcccc cttgaacctc 781 ctcgttcgac cccgcctcga tcctcccttt atccagccct cactccttct ctaggcgccc 841 ccatatggcc atatgagatc ttatatgggg cacccccgcc ccttgtaaac ttccctgacc 901 ctgacatgac aagagttact aacagcccct ctctccaagc tcacttacag gctctctact 961 tagtccagca cgaagtctgg agacctctgg cggcagccta ccaagaacaa ctggaccgac 1021 cggtggtacc tcacccttac cgagtcggcg acacagtgtg ggtccgccga caccagacta 1081 agaacctaga acctcgctgg aaaggacctt acacagtcct gctgaccacc cccaccgccc 1141 tcaaagtaga cggcatcgca gcttggatac acgccgccca cgtgaaggct gccgaccccg 1201 ggggtggacc atcctctaga ctgccatggg gagtagcaag agcaagccta aggaccccag 1261 ccagcgcctc gagatggccg ctgggggccc aggcgccgga tcagctgctc ccgtatcttc 1321 tacttcttct ttgccgctgg ctgctctgaa catgcgcgtg agaagacgcc tctccctgtt 1381 ccttaacgtt cgcacacaag tcgctgccga ttggaccgcc cttgccgaag aaatggactt 1441 tgaatacctg gaaattagac aacttgaaac acaggccgac cccactggca gactcctgga 1501 cgcatggcag ggaagacctg gtgcaagcgt tggacggctc ctggatctcc tgacaaaact 1561 gggacgcgac gacgtactgc ttgaactcgg acctagcatt gaagaagact gccaaaaata 1621 tatcctgaaa caacaacaag aagaagccga aaaacctctc caagtcgcag cagtggactc 1681 atcagtaccc cgaacagctg agcttgctgg gattactaca ctcgacgacc cactcggaca 1741 tatgcctgaa agattcgacg ctttcatttg ctattgcccc tctgacataa agaaagttgc 1801 aaagaaaccc acaaataaag ccccacaccc taaacaggaa ccccaagaaa tcaatttccc 1861 agatgatctc cctggatcta atactgccgc cccggtccaa gaaaccctgc atggttgcca
```

-continued

```
1921  gcctgtcacc caagaggacg gaaaagaatc acggattagc gtacaagaga gacaagtcga
1981  gtctggcggt ggatccggag gcgttcaagt agaaacaatc agcccaggag acggaaggac
2041  tttccccaaa cgaggccaaa catgcgtagt tcattatact gggatgctcg aagatggaaa
2101  aaaagtagat agtagtagag accgaaacaa accatttaaa tttatgttgg gaaaacaaga
2161  agtaataagg ggctgggaag aaggtgtagc acaaatgtct gttggccagc gcgcaaaact
2221  cacaatttct cctgattatg cttacggagc taccggccac cccggcatca tacccctca
2281  tgccacactg gtgtttgacg tcgaattgct caaactggaa gtcgagggag tgcaggtgga
2341  gacgattagt cctggggatg ggagaacctt tccaaagcgc ggtcagacct gtgttgtcca
2401  ctacaccggt atgctggagg acgggaagaa ggtggactct tcacgcgatc gcaataagcc
2461  tttcaagttc atgctcggca agcaggaggt gatccggggg tgggaggagg cgtggctca
2521  gatgtcggtc gggcaacgag cgaagcttac catctcaccc gactacgcgt atgggcaac
2581  gggcatccg ggaattatcc ctccccacgc tacgctcgta ttcgatgtgg agctcttgaa
2641  gcttgagtct ggcggtggat ccggagtcga ccgcgcaaag cgtggaaaac ctatacctaa
2701  tccattgctg ggcttagact caacaggcag cggaagcgca acgaattttt ccctgctgaa
2761  acaggcaggg gacgtagagg aaaatcctgg tcctacgcgt atgccccctc ctagactgct
2821  gtttttcctg ctctttctca ccccaatgga agttagacct gaggaaccac tggtcgttaa
2881  agtggaagaa ggtgataatg ctgtcctcca atgccttaaa gggaccagca acgaccaac
2941  gcagcaactg acttggagcc gggagtcccc tctcaagccg tttctcaagc tgtcacttgg
3001  cctgccaggt cttggtattc acatgcgccc ccttgccatt tggctcttca tattcaatgt
3061  gtctcaacaa atgggtggat tctacctttg ccagcccggc ccccttctg agaaagcttg
3121  gcagcctgga tggaccgtca atgttgaagg ctccggtgag ctgtttagat ggaatgtgag
3181  cgaccttggc ggactcggtt gcggactgaa aaataggagc tctgaaggac cctcttctcc
3241  ctccggtaag ttgatgtcac ctaagctgta cgtgtgggcc aaggaccgcc ccgaaatctg
3301  ggagggcgag cctccatgcc tgccgcctcg cgattcactg aaccagtctc tgtcccagga
3361  tctcactatg gcgcccggat ctactcttg gctgtcttgc ggcgttcccc cagatagcgt
3421  gtcaagagga cctctgagct ggacccacgt acaccctaag ggccctaaga gcttgttgag
3481  cctggaactg aaggacgaca gacccgcacg cgatatgtgg gtaatggaga ccggccttct
3541  gctccctcgc gctaccgcac aggatgcagg gaaatactac tgtcatagag ggaatctgac
3601  tatgagcttt catctcgaaa ttacagcacg gcccgttctt tggcattggc tcctccggac
3661  tggaggctgg aaggtgtctg ccgtaacact cgcttacttg attttttgcc tgtgtagcct
3721  ggttgggatc ctgcatcttc agcgagccct tgtattgcgc cgaaaaagaa acgaatgac
3781  tgaccctaca cgacgattct gagcatgcaa cctcgatccg gattagtcca atttgttaaa
3841  gacaggatat cagtggtcca ggctctagtt ttgactcaac aatatcacca gctgaagcct
3901  atagagtacg agccatagat aaaataaaag attttattta gtctccagaa aaaggggga
3961  atgaaagacc ccacctgtag gtttggcaag ctagcttaag taacgccatt ttgcaaggca
4021  tggaaaaata cataactgag aatagagaag ttcagatcaa ggtcaggaac agatggaaca
4081  gctgaatatg gccaaacag gatatctgtg gtaagcagtt cctgccccgg ctcagggcca
4141  agaacagatg gaacagctga atatgggcca acaggatat ctgtggtaag cagttcctgc
4201  cccggctcag ggccaagaac agatggtccc cagatgcggt ccagccctca gcagtttcta
4261  gagaaccatc agatgtttcc agggtgcccc aaggacctga atgaccctg tgccttattt
4321  gaactaacca atcagttcgc ttctcgcttc tgttcgcgcg cttctgctcc ccgagctcaa
```

```
4381 taaaagagcc cacaacccct cactcggggc gccagtcctc cgattgactg agtcgcccgg
4441 gtaccgtgt atccaataaa ccctcttgca gttgcatccg acttgtggtc tcgctgttcc
4501 ttgggagggt ctcctctgag tgattgacta cccgtcagcg ggggtctttc acacatgcag
4561 catgtatcaa aattaatttg gttttttttc ttaagtattt acattaaatg gccatagtac
4621 ttaaagttac attggcttcc ttgaaataaa catggagtat tcagaatgtg tcataaatat
4681 ttctaatttt aagatagtat ctccattggc tttctacttt ttcttttatt ttttttgtc
4741 ctctgtcttc catttgttgt tgttgttgtt tgtttgtttg tttgttggtt ggttggttaa
4801 tttttttta aagatcctac actatagttc aagctagact attagctact ctgtaaccca
4861 gggtgacctt gaagtcatgg gtagcctgct gttttagcct tcccacatct aagattacag
4921 gtatgagcta tcatttttgg tatattgatt gattgattga ttgatgtgtg tgtgtgtgat
4981 tgtgtttgtg tgtgtgactg tgaaaatgtg tgtatgggtg tgtgtgaatg tgtgtatgta
5041 tgtgtgtgtg tgagtgtgtg tgtgtgtgtg tgcatgtgtg tgtgtgtgac tgtgtctatg
5101 tgtatgactg tgtgtgtgtg tgtgtgtgtg tgtgtgtgtg tgtgtgtgtg tgtgttgtga
5161 aaaaatattc tatggtagtg agagccaacg ctccggctca ggtgtcaggt tggttttga
5221 gacagagtct ttcacttagc ttggaattca ctggccgtcg ttttacaacg tcgtgactgg
5281 gaaaaccctg gcgttaccca acttaatcgc cttgcagcac atccccettt cgccagctgg
5341 cgtaatagcg aagaggcccg caccgatcgc ccttcccaac agttgcgcag cctgaatggc
5401 gaatggcgcc tgatgcggta ttttctcctt acgcatctgt gcggtatttc acaccgcata
5461 tggtgcactc tcagtacaat ctgctctgat gccgcatagt taagccagcc ccgacacccg
5521 ccaacacccg ctgacgcgcc ctgacgggct tgtctgctcc cggcatccgc ttacagacaa
5581 gctgtgaccg tctccgggag ctgcatgtgt cagaggtttt caccgtcatc accgaaacgc
5641 gcgatgacga aagggcctcg tgatacgcct atttttatag gttaatgtca tgataataat
5701 ggtttcttag acgtcaggtg gcacttttcg gggaaatgtg cgcggaaccc ctatttgttt
5761 attttctaa atacattcaa atatgtatcc gctcatgaga caataaccct gataaatgct
5821 tcaataatat tgaaaaagga agagtatgag tattcaacat ttccgtgtcg cccttattcc
5881 cttttttgcg gcattttgcc ttcctgtttt tgctcaccca gaaacgctgg tgaaagtaaa
5941 agatgctgaa gatcagttgg gtgcacgagt gggttacatc gaactggatc tcaacagcgg
6001 taagatcctt gagagttttc gccccgaaga acgttttcca atgatgagca cttttaaagt
6061 tctgctatgt ggcgcggtat tatcccgtat tgacgccggg caagagcaac tcggtcgccg
6121 catacactat tctcagaatg acttggttga gtactcacca gtcacagaaa agcatcttac
6181 ggatggcatg acagtaagag aattatgcag tgctgccata accatgagtg ataacactgc
6241 ggccaactta cttctgacaa cgatcggagg accgaaggag ctaaccgctt ttttgcacaa
6301 catgggggat catgtaactc gccttgatcg ttgggaaccg gagctgaatg aagccatacc
6361 aaacgacgag cgtgacacca cgatgcctgt agcaatggca acaacgttgc gcaaactatt
6421 aactggcgaa ctacttactc tagcttcccg gcaacaatta atagactgga tggaggcgga
6481 taaagttgca ggaccacttc tgcgctcggc ccttccggct ggctggttta ttgctgataa
6541 atctggagcc ggtgagcgtg gtctcgcgg tatcattgca gcactggggc cagatggtaa
6601 gccctcccgt atcgtagtta tctacacgac ggggagtcag gcaactatgg atgaacgaaa
6661 tagacagatc gctgagatag gtgcctcact gattaagcat tggtaactgt cagaccaagt
6721 ttactcatat atactttaga ttgatttaaa acttcatttt taatttaaaa ggatctaggt
```

-continued

```
6781 gaagatcctt tttgataatc tcatgaccaa aatcccttaa cgtgagtttt cgttccactg 6841 agcgtcagac cccgtagaaa agatcaaagg atcttcttga gatccttttt ttctgcgcgt 6901 aatctgctgc ttgcaaacaa aaaaaccacc gctaccagcg gtggtttgtt tgccggatca 6961 agagctacca actcttttc cgaaggtaac tggcttcagc agagcgcaga taccaaatac 7021 tgtccttcta gtgtagccgt agttaggcca ccacttcaag aactctgtag caccgcctac 7081 atacctcgct ctgctaatcc tgttaccagt ggctgctgcc agtggcgata agtcgtgtct 7141 taccgggttg gactcaagac gatagttacc ggataaggcg cagcggtcgg gctgaacggg 7201 gggttcgtgc acacagccca gcttggagcg aacgacctac accgaactga gatacctaca 7261 gcgtgagcat tgagaaagcg ccacgcttcc cgaagggaga aaggcggaca ggtatccggt 7321 aagcggcagg gtcggaacag gagagcgcac gagggagctt ccaggggaa acgcctggta 7381 tctttatagt cctgtcgggt ttcgccacct ctgacttgag cgtcgatttt tgtgatgctc 7441 gtcagggggg cggagcctat ggaaaaacgc cagcaacgcg gcctttttac ggttcctggc 7501 cttttgctgg cctttgctc acatgttctt tcctgcgtta tcccctgatt ctgtggataa 7561 ccgtattacc gcctttgagt gagctgatac cgctcgccgc agccgaacga ccgagcgcag 7621 cgagtcagtg agcgaggaag cggaagagcg cccaatacgc aaaccgcctc tccccgcgcg 7681 ttggccgatt cattaatgca gctggcacga caggtttccc gactggaaag cgggcagtga 7741 gcgcaacgca attaatgtga gttagctcac tcattaggca ccccaggctt tacactttat 7801 gcttccggct cgtatgttgt gtggaattgt gagcggataa caatttcaca caggaaacag 7861 ctatgaccat gattacgcca agctttgctc ttaggagttt cctaatacat cccaaactca 7921 aatatataaa gcatttgact tgttctatgc cctaggggc gggggggaagc taagccagct 7981 ttttttaaca tttaaaatgt taattccatt ttaaatgcac agatgttttt atttcataag 8041 ggtttcaatg tgcatgaatg ctgcaatatt cctgttacca aagctagtat aaataaaaat 8101 agataaacgt ggaaattact tagagtttct gtcattaacg tttccttcct cagttgacaa 8161 cataaatgcg ctgctgagca agccagtttg catctgtcag gatcaatttc ccattatgcc 8221 agtcatatta attactagtc aattagttga ttttttatttt tgacatatac atgtgaatga 8281 aagaccccac ctgtaggttt ggcaagctag cttaagtaac gccatttgc aaggcatgga 8341 aaaatacata actgagaata gaaaagttca gatcaaggtc aggaacagat ggaacagctg 8401 aatatgggcc aaacaggata tctgtggtaa gcagttcctg ccccggctca gggccaagaa 8461 cagatggaac agctgaatat gggccaaaca ggatatctgt ggtaagcagt tcctgccccg 8521 gctcagggcc aagaacagat ggtccccaga tgcggtccag ccctcagcag tttctagaga 8581 accatcagat gtttccaggg tgccccaagg acctgaaatg accctgtgcc ttatttgaac 8641 taaccaatca gttcgcttct cgcttctgtt cgcgcgctta tgctccccga gctcaataaa 8701 agagcccaca cccctcact cggggcgcca gtcctccgat tgactgagtc gcccgggtac 8761 ccgtgtatcc aataaaccct cttgcagttg catccgactt gtggtctcgc tgttccttgg 8821 gagggtctcc tctgagtgat tgactacccg tcagcggggg tctttcattt gggggctcgt 8881 ccgggatcgg gagacccctg cccagggacc accgacccac caccgggagg t
```

Example 14: Additional Sequences

```
Myristoylation polypeptide nucleotide sequence
                                                    SEQ ID NO: 67
ATGGGGAGTAGCAAGAGCAAGCCTAAGGACCCCAGCCAGCGC Myristoylation polypeptide amino acid sequence
                                                    SEQ ID NO: 68
MGSSKSKPKDPSQR Linker nucleotide sequence (linker 1)
                                                    SEQ ID NO: 69
CTCGAG Linker amino acid sequence (linker 1)
                                                    SEQ ID NO: 70
LE Truncated MyD88 polypeptide nucleotide sequence
                                                    SEQ ID NO: 71
ATGGCCGCTGGGGGCCCAGGCGCCGGATCAGCTGCTCCCGTATCTTCTACTTCTTCTTT

GCCGCTGGCTGCTCTGAACATGCGCGTGAGAAGACGCCTCTCCCTGTTCCTTAACGTTC

GCACACAAGTCGCTGCCGATTGGACCGCCCTTGCCGAAGAAATGGACTTTGAATACCT

GGAAATTAGACAACTTGAAACACAGGCCGACCCCACTGGCAGACTCCTGGACGCATGG

CAGGGAAGACCTGGTGCAAGCGTTGGACGGCTCCTGGATCTCCTGACAAAACTGGGAC

GCGACGACGTACTGCTTGAACTCGGACCTAGCATTGAAGAAGACTGCCAAAAATATAT

CCTGAAACAACAACAAGAAGAAGCCGAAAAACCTCTCCAAGTCGCAGCAGTGGACTC

ATCAGTACCCCGAACAGCTGAGCTTGCTGGGATTACTACACTCGACGACCCCACTCGGA

CATATGCCTGAAAGATTCGACGCTTTCATTTGCTATTGCCCCTCTGACATA

Truncated MyD88 polypeptide amino acid sequence
                                                    SEQ ID NO: 72
MAAGGPGAGSAAPVSSTSSLPLAALNMRVRRRLSLFLNVRTQVAADWTALAEEMDFEYL

EIRQLETQADPTGRLLDAWQGRPGASVGRLLDLLTKLGRDDVLLELGPSIEEDCQKYILKQ

QQEEAEKPLQVAAVDSSVPRTAELAGITTLDDPLGHMPERFDAFICYCPSDI

ΔCD40 polypeptide nucleotide sequence
                                                    SEQ ID NO: 73
AAGAAAGTTGCAAAGAAACCCACAAATAAAGCCCCACACCCTAAACAGGAACCCCAA

GAAATCAATTTCCCAGATGATCTCCCTGGATCTAATACTGCCGCCCCGGTCCAAGAAAC

CCTGCATGGTTGCCAGCCTGTCACCCAAGAGGACGGAAAAGAATCACGGATTAGCGTA

CAAGAGAGACAA

ΔCD40 polypeptide amino acid sequence
                                                    SEQ ID NO: 74
KKVAKKPTNKAPHPKQEPQEINFPDDLPGSNTAAPVQETLHGCQPVTQEDGKESRISVQER

Q

Linker nucleotide sequence (linker 2)
                                                    SEQ ID NO: 75
GTCGAGTCTGGCGGTGGATCCGGA Linker amino acid sequence (linker 2)
                                                    SEQ ID NO: 76
VESGGGSG FKBPv36 (Fv1) nucleotide sequence
                                                    SEQ ID NO: 77
GGCGTTCAAGTAGAAACAATCAGCCCAGGAGACGGAAGGACTTTCCCCAAACGAGGC

CAAACATGCGTAGTTCATTATACTGGGATGCTCGAAGATGGAAAAAAAGTAGATAGTA

GTAGAGACCGAAACAAACCATTTAAATTTATGTTGGGAAAACAAGAAGTAATAAGGG

GCTGGGAAGAAGGTGTAGCACAAATGTCTGTTGGCCAGCGCGCAAAACTCACAATTTC
```

```
                                           -continued
TCCTGATTATGCTTACGGAGCTACCGGCCACCCCGGCATCATACCCCCTCATGCCACAC

TGGTGTTTGACGTCGAATTGCTCAAACTGGAA

FKBPv36 (Fv1) amino acid sequence
                                                            SEQ ID NO: 78
GVQVETISPGDGRTFPKRGQTCVVHYTGMLEDGKKVDSSRDRNKPFKFMLGKQEVIRGWE

EGVAQMSVGQRAKLTISPDYAYGATGHPGIIPPHATLVFDVELLKLE

Linker nucleotide sequence (linker 3)
                                                            SEQ ID NO: 79
GTCGAG Linker amino acid sequence (linker 3)
                                                            SEQ ID NO: 80
VE FKBPv36 (Fv2) nucleotide sequence
                                                            SEQ ID NO: 81
GGaGTgCAgGTgGAgACgATtAGtCCtGGgGAtGGgAGaACcTTtCCaAAgCGcGGtCAgACcTGt GTtGTcCAcTAcACcGGtATGCTgGAgGAcGGgAAgAAgGTgGActcTtcacGcGAtCGcAAtAAgC CtTTcAAgTTcATGcTcGGcAAgCAgGAgGTgATccGGGGgTGGGAgGAgGGcGTgGCtCAgATG TCgGTcGGgCAaCGaGCgAAgCTtACcATcTCaCCcGAcTAcGCgTATGGgGCaACgGGgCATCCg GGaATtATcCCtCCcCAcGCtACgCTcGTaTTcGAtGTgGAgcTcttgAAgCTtGag FKBPv36 (Fv2) amino acid sequence
                                                            SEQ ID NO: 82
GVQVETISPGDGRTFPKRGQTCVVHYTGMLEDGKKVDSSRDRNKPFKFMLGKQEVIRGWE

EGVAQMSVGQRAKLTISPDYAYGATGHPGIIPPHATLVFDVELLKLE

Linker nucleotide sequence (linker 4)
                                                            SEQ ID NO: 83
TCTGGCGGTGGATCCGGAGTCGAC Linker amino acid sequence (linker 4)
                                                            SEQ ID NO: 84
SGGGSGVD Furin protease consensus cleavage site nucleotide sequence
                                                            SEQ ID NO: 85
CGCGCAAAGCGT Furin protease consensus cleavage site amino acid sequence
                                                            SEQ ID NO: 86
RAKR V5 epitope nucleotide sequence
                                                            SEQ ID NO: 87
GGAAAACCTATACCTAATCCATTGCTGGGCTTAGACTCAACA V5 epitope nucleotide sequence
                                                            SEQ ID NO: 88
GKPIPNPLLGLDST Linker nucleotide sequence (linker 5)
                                                            SEQ ID NO: 89
GGCAGCGGAAGC Linker amino acid sequence (linker 5)
                                                            SEQ ID NO: 90
GSGS P2A nucleotide sequence
                                                            SEQ ID NO: 91
GCAACGAATTTTTCCCTGCTGAAACAGGCAGGGGACGTAGAGGAAAATCCTGGTCCT P2A amino acid sequence
                                                            SEQ ID NO: 92
ATNFSLLKQAGDVEENPGP Linker nucleotide sequence (linker 6)
                                                            SEQ ID NO 93
ACGCGT
```

-continued

Linker amino acid sequence (linker 6)
SEQ ID NO: 94
TR

ΔCD19 nucleotide sequence
SEQ ID NO: 95
ATGCCCCCTCCTAGACTGCTGTTTTTCCTGCTCTTTCTCACCCCAATGGAAGTTAGACCT

GAGGAACCACTGGTCGTTAAAGTGGAAGAAGGTGATAATGCTGTCCTCCAATGCCTTA

AAGGGACCAGCGACGGACCAACGCAGCAACTGACTTGGAGCCGGGAGTCCCCTCTCAA

GCCGTTTCTCAAGCTGTCACTTGGCCTGCCAGGTCTTGGTATTCACATGCGCCCCCTTGC

CATTTGGCTCTTCATATTCAATGTGTCTCAACAAATGGGTGGATTCTACCTTTGCCAGCC

CGGCCCCCCTTCTGAGAAAGCTTGGCAGCCTGGATGGACCGTCAATGTTGAAGGCTCC

GGTGAGCTGTTTAGATGGAATGTGAGCGACCTTGGCGGACTCGGTTGCGGACTGAAAA

ATAGGAGCTCTGAAGGACCCTCTTCTCCCTCCGGTAAGTTGATGTCACCTAAGCTGTAC

GTGTGGGCCAAGGACCGCCCCGAAATCTGGGAGGGCGAGCCTCCATGCCTGCCGCCTC

GCGATTCACTGAACCAGTCTCTGTCCCAGGATCTCACTATGGCGCCCGGATCTACTCTT

TGGCTGTCTTGCGGCGTTCCCCCAGATAGCGTGTCAAGAGGACCTCTGAGCTGGACCCA

CGTACACCCTAAGGGCCCTAAGAGCTTGTTGAGCCTGGAACTGAAGGACGACAGACCC

GCACGCGATATGTGGGTAATGGAGACCGGCCTTCTGCTCCCTCGCGCTACCGCACAGG

ATGCAGGGAAATACTACTGTCATAGAGGGAATCTGACTATGAGCTTTCATCTCGAAATT

ACAGCACGGCCCGTTCTTTGGCATTGGCTCCTCCGGACTGGAGGCTGGAAGGTGTCTGC

CGTAACACTCGCTTACTTGATTTTTTGCCTGTGTAGCCTGGTTGGGATCCTGCATCTTCA

GCGAGCCCTTGTATTGCGCCGAAAAAGAAAACGAATGACTGACCCTACACGACGATTC

TGA

ΔCD19 amino acid sequence
SEQ ID NO: 96
MPPPRLLFFLLFLTPMEVRPEEPLVVKVEEGDNAVLQCLKGTSDGPTQQLTWSRESPLKPFL

KLSLGLPGLGIHMRPLAIWLFIFNVSQQMGGFYLCQPGPPSEKAWQPGWTVNVEGSGELFR

WNVSDLGGLGCGLKNRSSEGPSSPSGKLMSPKLYVWAKDRPEIWEGEPPCLPPRDSLNQSL

SQDLTMAPGSTWLSCGVPPDSVSRGPLSWTHVHPKGPKSLLSLELKDDRPARDMWVME

TGLLLPRATAQDAGKYYCHRGNLTMSFHLEITARPVLWHWLLRTGGWKVSAVTLAYLIFC

LCSLVGILHLQRALVLRRKRKRMTDPTRRF

Example 15: Activation of T Cells Ex Vivo and Administration to a Human Subject Presented in this example are methods of using the modified T cells for human therapy.

These methods may be adapted for other non-T cells

Materials and Methods

Large-Scale Generation of Gene-Modified T Cells

T cells are generated from healthy volunteers, using standard methods. Briefly, peripheral blood mononuclear cells (PBMCs) from healthy donors or cancer patients are activated for expansion and transduction using soluble aCD3 and aCD28 (Miltenyi Biotec, Auburn, Calif.). PBMCs are resuspended in Cellgenix DC media supplemented with 100 U/ml IL-2 (Cellgenix) at 1×10⁶ cells/ml and stimulated with 0.2 µg/ml aCD3 and 0.5 µg/ml aCD28 soluble antibody. Cells are then cultured at 37° C., 5% CO₂ for 4 days. On day four, 1 ml of fresh media containing IL-2 is added. On day 7, cells are harvested and resuspended in Cellgenix DC media for transduction.

Plasmid and Retrovirus

The SFG-based plasmid consists of an inducible chimeric polypeptide linked, via a self-cleavable 2A-like sequence, to truncated human CD19, lacking its cytoplasmic signaling domain. In one iteration, the inducible chimeric polypeptide consists of a human FK506-binding protein (FKBP12; GenBank AH002 818) with an F36V mutation, connected via a short Val-Glu linker to a human chimeric polypeptide. The F36V mutation increases the binding affinity of FKBP12 to the synthetic homodimerizer, AP20187 or AP1903. The 2A-like sequence encodes an 20 amino acid peptide from Thosea asigna insect virus, which mediates >99% cleavage between a glycine and terminal proline residue, resulting in 19 extra amino acids in the C terminus of the inducible chimeric polypeptide, and one extra proline residue in the N terminus of CD19. CD19 consists of full-length CD19 (GenBank NM 001770) truncated at amino acid 333 (TDP-TRRF) (SEQ ID NO: 193), which shortens the intracytoplasmic domain from 242 to 19 amino acids, and removes all conserved tyrosine residues that are potential sites for phosphorylation.

A stable PG13 clone producing Gibbon ape leukemia virus (Gal-V) pseudotyped retrovirus is made by transiently transfecting Phoenix Eco cell line (ATCC product #SD3444; ATCC, Manassas, Va.) with the SFG plasmid. This produces Eco-pseudotyped retrovirus. The PG13 packaging cell line (ATCC) is transduced three times with Eco-pseudotyped retrovirus to generate a producer line that contained multiple SFG plasmid proviral integrants per cell. Single cell cloning is performed, and the PG13 clone that produced the highest titer is expanded and used for vector production.

Retroviral Transduction

Culture medium for T cell activation and expansion is serum-free Cellgenix DC medium (Cellgenix) supplemented by 100 U/ml IL-2 (Cellgenix). T cells are activated by soluble anti-CD3 and anti-CD28 (Miltenyi Biotec) for 7 days before transduction with retroviral vector. Immunomagnetic selection of ΔCD19, if necessary, is performed on day 4 after transduction; the positive fraction was expanded for a further 2 days and cryopreserved.

Scaling-Up Production of Gene-Modified Allodepleted Cells

Scale-up of the transduction process for clinical application use non-tissue culture-treated T75 flasks (Nunc, Rochester, N.Y.), which are coated with 10 ml of anti-CD3 0.5 µg/ml and anti-CD28 0.2 µg/ml or 10 ml of fibronectin 7 µg/ml at 4° C. overnight. Fluorinated ethylene propylene bags corona-treated for increased cell adherence (2PF-0072AC, American Fluoroseal Corporation, Gaithersburg, Md.) are also used. PBMCs are seeded in anti-CD3, anti-CD28-coated flasks at $1\times10^6$ cells/ml in media supplemented with 100 U/ml IL-2. For retroviral transduction, RETRONECTIN-coated flasks or bags are loaded once with 10 ml of retrovirus-containing supernatant for 2 to 3 hours. Activated T cells are seeded at $1\times10^6$ cells/ml in fresh retroviral vector-containing medium and T cell culture medium at a ratio of 3:1, supplemented with 100 U/ml IL-2. Cells are harvested the following morning and expanded in tissue-culture treated T75 or T175 flasks in culture medium supplemented with 1000/ml IL-2 at a seeding density of between about $5\times10^5$ cells/ml to $8\times10^5$ cells/ml.

CD19 Immunomagnetic Selection

Immunomagnetic selection for CD19 may be performed, in one example, 4 days after transduction. Cells are labeled with paramagnetic microbeads conjugated to monoclonal mouse anti-human CD19 antibodies (Miltenyi Biotech, Auburn, Calif.) and selected on MS or LS columns in small scale experiments and on a CLINIMACS Plus automated selection device in large scale experiments. CD19-selected cells are expanded for a further 4 days and cryopreserved on day 8 post transduction. These cells are referred to as "gene-modified cells".

Immunophenotyping and Pentamer Analysis

Flow cytometric analysis (FACSCalibur and CellQuest software; Becton Dickinson) is performed using the following antibodies: CD3, CD4, CD8, CD19, CD25, CD27, CD28, CD45RA, CD45RO, CD56 and CD62L. CD19-PE (Clone 4G7; Becton Dickinson) is found to give optimum staining and was used in all subsequent analysis. A non-transduced control is used to set the negative gate for CD19.

Statistical Analysis

Paired, 2-tailed Student's t test is used to determine the statistical significance of differences between samples. All data are represented as mean±1 standard deviation.

Example 16: Construction and Evaluation of Inducible Chimeric Signaling Molecule Expression Vectors Vector Construction and Confirmation of Expression Expression vectors suitable for use as a therapeutic agent are constructed that code for a signaling molecule fused to a human FK506-binding protein (FKBP), such as, for example, FKBP12v36(Fv). These methods may also be used to express one or more inducible signaling molecules. The inducible CSMs can be dimerized (or multimerized) using a small molecule pharmaceutical. Nucleic acids coding for the inducible CSMs are fused to nucleic acids coding for the ligand-binding domain, and inserted into the SFG retroviral or pLenti7.3 lentiviral vector, which also allows expression of the fluorescent marker, GFP.

The inducible CSM polypeptide includes 2, 3, or more, in certain embodiments, 2 or 3, FK506-binding proteins (FKBPs—for example, FKBP12v36 variants, or FKBP12; GenBank AH002 818) that contains an F36V mutation) linked with a Gly-Ser-Gly-Gly-Gly-Ser linker (SEQ ID NO: 192) to the CSM sequence. The amino acid sequence of one or more of the FKBPs ($F_v2$) is codon-wobbled (e.g., the $3^{rd}$ nucleotide of each amino acid codon is altered by a silent mutation that maintained the originally encoded amino acid) to prevent homologous recombination when expressed in a retrovirus. All constructs are cloned into SFG or pLenti7.3.

293T cells are transfected with each of these constructs and 48 hours after transduction expression of the marker gene GFP or ΔCD19 is analyzed by flow cytometry. In addition to the level of GFP or ΔCD19 expression, the expressed gene products are also analyzed by western blot to confirm the expression of the chimeric signaling molecule polypeptides. For example, antibodies that bind to the costimulatory polypeptides may be used for the western blot.

Transfected 293T cells are resuspended in lysis buffer (50% Tris/Gly, 10% sodium dodecyl sulfate [SDS], 4% beta-mercaptoethanol, 10% glycerol, 12% water, 4% bromophenol blue at 0.5%) containing aprotinin, leupeptin, and phenylmethylsulfonyl fluoride (Boehringer, Ingelheim, Germany) and incubated for 30 minutes on ice. After a 30-minute centrifugation, supernatant is harvested, mixed 1:2 with Laemmli buffer (Bio-Rad, Hercules, Calif.), boiled and loaded on a 10% SDS-polyacrylamide gel. The membrane is probed with rabbit anti-costimulatory polypeptide immunoglobulin G (IgG; Affinity BioReagents, Golden, Colo.; 1:500 dilutions) and with mouse anti-GFP IgG (Covance, Berkeley, Calif.; 1:25,000 dilution). Blots are then exposed to appropriate peroxidase-coupled secondary antibodies and protein expression is detected with enhanced chemiluminescence (ECL; Amersham, Arlington Heights, Ill.). The membrane is then stripped and reprobed with goat polyclonal antiactin (Santa Cruz Biotechnology; 1:500 dilutions) to check equality of loading.

Evaluation of Inducible CSM Expression Constructs.

Cell Lines

The cancer cell lines LNCaP, PC3, DU145 and A549, and the human embryonic kidney cell line HEK-293T, are obtained from American Type Culture Collection (Rockville, Md.). Cells are maintained in complete IMDM (Sigma, St Louis, Mo.) containing 10% fetal bovine serum (Hyclone, Waltham, Mass.), and 2 mM L-glutamine in a humidified atmosphere containing 5% carbon dioxide ($CO_2$) at 37° C. Transduced T cells and PHA blasts are maintained in Cellgenix DC (Cellgenix) media supplemented with 100 U/ml IL-2 (Cellgenix)

Activation of T Cells

Activation of T cells for expansion and transduction is performed using soluble αCD3 and αCD28 (Miltenyi Biotec, Auburn, Calif.). PBMCs are resuspended in Cellgenix DC media supplemented with 100 U/ml IL-2 (Cellgenix) at $1 \times 10^6$ cells/ml and stimulated with 0.2 µg/ml αCD3 and 0.5 µg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

Retroviral and Lentiviral Constructs

Inducible CSM (iCSM) and CAR-CD3.zeta constructs comprised of the codon-optimized single-chain variable fragments targeting PSMA, PSCA, MUC1 and Her2/Neu are synthesized by Blue Heron Bio (Bothell, Wash.). iCSM constructs consist of FKBP12v36 domains linked in-frame to costimulatory endodomains, including CD28, 4-1BB, and the CD3 zeta chain of the T cell receptor. CARs constructs are generated by cloning the scFv fragment in-frame with the human IgG1-CH2CH3 domain and with the CD3-zeta chain. Both iCSM and CAR-CD3.zeta constructs are sub-cloned into the SFG retroviral backbone or the pLenti7.3 lentiviral backbone (Invitrogen), which co-expresses emerald GFP. Evaluation of the stimulatory and co-stimulatory effect of the iCSM, and the cytotoxicity of the CAR-CD3.zeta is performed by single or co-transduction of T cells with retro- or lentivirus encoding these transgenes.

Retrovirus Transduction

For the transient production of retrovirus, 293T cells are transfected with iCSM constructs, along with plasmids encoding gag-pol and RD 114 envelope using GENEJUICE transfection reagent (Novagen, Madison, Wis.). Virus is harvested 48 to 72 hours after transfection, snap frozen, and stored at ~80° C. until use. For the transient production of lentivirus, 293T cells are transfected with iCAR constructs along with the plasmids pLP1 (gag/pol), pLP2 (rev) and pLP/VSVG (VSVG env) using GENEJUICE. Virus is harvested 48 to 72 hours after transfection, snap frozen, and stored at ~80° C. until use. For large-scale retrovirus production, a stable FLYRD 18-derived retroviral producer line is generated by multiple transductions with VSV-G pseudotyped transient retroviral supernatant. FLYRD18 cells with highest transgene expression are single-cell sorted, and the clone that produce the highest virus titer is expanded and used to produce virus for lymphocyte transduction. The transgene expression, function, and retroviral titer of this clone is maintained during continuous culture for more than 8 weeks. Non-tissue culture-treated 24-well plates are coated with 7 µg/ml RETRONECTIN (Takara Bio, Otsu, Shiga, Japan) for 1 hour at 37° C. or overnight at 4° C. The wells are washed with phosphate-buffered saline (PBS) then coated with retroviral supernatant by incubating the plate with 1.5 ml of supernatant for 30 minutes at 37° C. Subsequently, T cell blasts are plated at $5 \times 10^5$ cells per well in viral supernatant supplemented with 100 U/ml IL-2. Transduction is performed over a 60-hour period. Following transduction, cells are harvested and phenotyped for CD19 or GFP expression by flow cytometry.

Cytotoxicity of iCSM/CAR-Transduced T Cells

The cytotoxic activity of each transduced T cell line is evaluated in a standard 4-hour $^{51}Cr$ release assay, as previously presented. T cells transduced with either iCSM, PSMA CAR-CD3.zeta or both iCSM and CAR viruses are compared against $Cr^{51}$-labeled target cells, including autologous phytohaemagglutinin (PHA) stimulated lymphocytes (PHA blasts), LNCaP, PC3 or DU145 and A549 cancer cell lines, and transgenic A549 expressing human PSMA (A549-PSMA). Target cells incubated in complete medium or 1% Triton X-100 (Sigma, St Louis, Mo.) are used to determine spontaneous and maximum $^{51}Cr$ release, respectively. The mean percentage of specific lysis of triplicate wells was calculated as 100× (experimental release−spontaneous release)/(maximal release−spontaneous release). In addition to chromium-release assays, co-culture experiments with are performed. Here, the cell lines LNCaP, PC3, DU145, A549 and A549-PSMA are transduced to express fluorescent mOrange and used as target cells. mOrange-expressing tumor cells are co-cultured with non-transduced or CAR-modified T cells at a ratio of 1:10 tumor cells to T cells in the presence of IL-2 (50 U/ml) in complete media. After 24 hours, T cells bearing the iCAR are stimulated with 100 nM AP1903. After 72 hours, cells are collected, counted and labeled with CD3 to detect T cells and percentage of mOrange tumor cells is analyzed by flow cytometry (LSRII; BD).

Phenotyping and Activation Status of iCSM-Transduced T Cells

Cell surface phenotype of iCAR transduced T cells is investigated using the following monoclonal antibodies: CD3, CD4, CD8, CD19, CD25, CD27, CD28, CD44, CD45RA, CD45RO, CD62L, CD80, CD83, CD86, CD127, CD134, CD137, HLA-ABC and HLA-DR. Phenotyping is performed with and without 10-100 nM AP1903 as a iCSM stimulant. Appropriate matched isotype controls are used in each experiment and cells are analyzed with a LSRII flow cytometer (BD). CAR expression was assessed using anti-F(ab')2 (Jackson ImmunoResearch Laboratories, West Grove, Pa.).

Analysis of Cytokine Production of iCSM-Transduced T Cells

The concentration of interferon-γ (IFN-γ), IL-2, IL-4, IL-5, IL-10, and tumor necrosis factor-α (TNF) in T cell culture supernatants before and after (24 hours) 100 nM AP1903 stimulation is measured using the Human Th1/Th2 cytokine cytometric Bead Array (BD Pharmingen). Induced cytokine production in the culture supernatants is validated by enzyme-linked immunosorbent assay (ELISA; R&D Systems, Minneapolis, Minn.) according to the instructions of the manufacturer.

Proliferation of iCSM-Transduced T Cells

The proliferative effect of AP1903-induced signaling through iCSM is evaluated by measuring cell growth of transduced and non-transduced T cells following exposure to AP1903. T cells are labeled with 10 µM carboxyfluorescein diacetate, succinimidyl ester (CFSE) for 10 minutes at 37° C. After incubation, cells are washed in PBS and then resuspended in Cellgenix DC media. $1 \times 10^6$ CFSE-labeled iCSM-modified or non-transduced T cells are subsequently cultured in Cellgenix DC media alone, or stimulated with 100 nM AP1903. After 5 days, cells are harvested and labeled with CD3-PerCP.Cy5.5 and CD19-PE and analyzed by flow cytometry for CFSE dilution.

To evaluate whether soluble immunoglobulins affect the proliferation and expansion of CAR+ T lymphocytes, cells are cultured at $1 \times 10^5$ cells/well either with serial dilution of human plasma obtained from healthy donors or serial dilution of purified human immunoglobulins (Jackson ImmunoResearch) without any addition of exogenous cytokines. After 72 hours, the cells are pulsed with 1 µCi (0.037 MBq) methyl-$^3$[H]thymidine (Amersham Pharmacia Biotech, Piscataway, N.J.) and cultured for additional 15 hours. The cells were then harvested onto filters and dried, and counts per minute are measured in a β-scintillation counter (TriCarb 2500 TR; Packard BioScience, Meridien, Conn.). The experiments are performed in triplicate. In other experiments, control and CAR+ T lymphocytes are cultured either with media alone or with media in which serial dilution of plasma or purified immunoglobulins are added every second day. Cells are then counted every third day using trypan blue exclusion.

In Vivo Experiments

Non-obese diabetic severe combined immunodeficient (NOD/SCID) mice, 6 to 8 weeks of age, are irradiated (250 rad) and injected subcutaneously in the right flank with $10 \times 10^6$ to $15 \times 10^6$ LNCaP tumor cells resuspended in Matrigel (BD Bioscience). Two weeks later mice bearing tumors that are approximately 0.5 cm in diameter were injected into the tail vein with either non-transduced or iCSM/CAR-transduced T cells (total $15 \times 10^6$). The mice are randomly segregated in 2 groups: 1 group receives CID (50-125 µg AP1903, intraperitoneally, twice weekly) and 1 group receives carrier only (16.7% propanediol, 22.5% PEG400, and 1.25% Tween 80, intraperitoneally, twice weekly) to expand T cells. Mice are evaluated for tumor growth by caliper measurement for 21 days. Peripheral blood samples are taken by retro-orbital eye bleeding on days 7, 14 and 21 to measure the persistence and expansion of iCSM or control T cells using flow cytometric analysis for human CD3/human CD19 expressing T cells.

Evaluation of iCSM-Transduced T Cell Characteristics In Vivo

To ensure that expression of inducible CSMs do not alter T-cell characteristics, the phenotype, antigen-specificity, proliferative potential, and function of nontransduced or nonfunctional inducible CARs (PSMA CAR-CD3.zeta only) are compared with that of iCSM/CAR-transduced T cells. The numbers of CD4+, CD8+, CD56+, and TCR α/β+ cells in transduced and non-transduced cells are compared, as is the production of cytokines including IFN-γ, TNFα, IL-10, IL-4, IL-5, and IL-2. The growth characteristics of exponentially growing CTLs, and dependence on antigen and IL-2 for proliferation are evaluated, as is phenotypic and secretion data of type $T_H1$ and $T_H2$ cytokines upon antigen stimulation.

Example 17: Using the Inducible CSM in Human Cells for Therapy

Presented in this example are expression constructs and methods of using the expression constructs in human cells.

Materials and Methods

Large-Scale Generation of Gene-Modified T Cells

T cells are generated from healthy volunteers, using standard methods. Briefly, peripheral blood mononuclear cells (PBMCs) from healthy donors or cancer patients are activated for expansion and transduction using soluble αCD3 and αCD28 (Miltenyi Biotec, Auburn, Calif.). PBMCs are resuspended in Cellgenix DC media supplemented with 100 U/ml IL-2 (Cellgenix) at 1×106 cells/ml and stimulated with 0.2 µg/ml αCD3 and 0.5 µg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

Plasmid and Retrovirus

The SFG plasmid consists of inducible CSM linked, via a cleavable 2A-like sequence, to truncated human CD19. The inducible CSM consists of a human FK506-binding protein (FKBP12; GenBank AH002 818) with an F36V mutation, connected via a Ser-Gly-Gly-Gly-Ser linker (SEQ ID NO: 194) to a human CSM. The F36V mutation increases the binding affinity of FKBP12 to the synthetic homodimerizer, AP20187 or AP1903. The 2A-like sequence encodes a 20 amino acid peptide from Thosea asigna insect virus, which mediates >95% cleavage between a glycine and terminal proline residue, resulting in 19 extra amino acids in the C terminus of iCSM, and one extra proline residue in the N terminus of CD19. CD19 consists of full-length CD19 (GenBank NM 001770) truncated at amino acid 333 (TDP-TRRF) (SEQ ID NO: 193), which shortens the intracytoplasmic domain from 242 to 19 amino acids, and removes all conserved tyrosine residues that are potential sites for phosphorylation.

A stable PG13-based clone producing Gibbon ape leukemia virus (Gal-V) pseudotyped retrovirus is made by transiently transfecting Phoenix Eco cell line (ATCC product #SD3444; ATCC, Manassas, Va.) with the SFG plasmid. This produces Eco-pseudotyped retrovirus. The PG13 packaging cell line (ATCC) is transduced three times with Eco-pseudotyped retrovirus to generate a producer line that contained multiple SFG plasmid proviral integrants per cell. Single cell cloning is performed, and the PG13 clone that produced the highest titer is expanded and used for vector production.

RetroViral Transduction

Culture medium for T cell activation and expansion is serum-free Cellgenix DC medium (Cellgenix) supplemented by 100 U/ml IL-2 (Cellgenix). T cells are activated by soluble anti-CD3 and anti-CD28 (Miltenyi Biotec) for 7 days before transduction with retroviral vector. Immunomagnetic selection of ΔCD19, if necessary, is performed on day 4 after transduction; the positive fraction was expanded for a further 2 days and cryopreserved.

Scaling-Up Production of Gene-Modified Allodepleted Cells

Scale-up of the transduction process for clinical application use non-tissue culture-treated T75 flasks (Nunc, Rochester, N.Y.), which are coated with 10 ml of anti-CD3 0.5 µg/ml and anti-CD28 0.2 µg/ml or 10 ml of fibronectin 7 µg/ml at 4° C. overnight. Fluorinated ethylene propylene bags corona-treated for increased cell adherence (2PF-0072AC, American Fluoroseal Corporation, Gaithersburg, Md.) are also used. PBMCs are seeded in anti-CD3, anti-CD28-coated flasks at $1 \times 10^6$ cells/ml in media supplemented with 100 U/ml IL-2. For retroviral transduction, RETRONECTIN-coated flasks or bags are loaded once with 10 ml of retrovirus-containing supernatant for 2 to 3 hours. Activated T cells are seeded at $1 \times 10^6$ cells/ml in fresh retroviral vector-containing medium and T cell culture medium at a ratio of 3:1, supplemented with 100 U/ml IL-2. Cells are harvested the following morning and expanded in tissue-culture treated T75 or T175 flasks in culture medium supplemented with 100 U/ml IL-2 at a seeding density of between about $5 \times 10^5$ cells/ml to $8 \times 10^5$ cells/ml.

CD19 Immunomagnetic Selection

Immunomagnetic selection for CD19 may, for example, be performed 4 days after transduction. Cells are labeled with paramagnetic microbeads conjugated to monoclonal mouse anti-human CD19 antibodies (Miltenyi Biotech, Auburn, Calif.) and selected on MS or LS columns in small scale experiments and on a CLINIMACS Plus automated selection device in large scale experiments. CD19-selected cells are expanded for a further 4 days and cryopreserved on day 8 post transduction. These cells are referred to as "gene-modified cells".

Immunophenotyping and Pentamer Analysis

Flow cytometric analysis (FACSCalibur and CellQuest software; Becton Dickinson) is performed using the following antibodies: CD3, CD4, CD8, CD19, CD25, CD27, CD28, CD45RA, CD45RO, CD56 and CD62L. CD19-PE (Clone 4G7; Becton Dickinson) is found to give optimum staining and was used in all subsequent analysis. A non-transduced control is used to set the negative gate for CD19. CAR expression is assessed using anti-F(ab')2 (Jackson ImmunoResearch Laboratories, West Grove, Pa.).

Statistical Analysis

Paired, 2-tailed Student's t test is used to determine the statistical significance of differences between samples. All data are represented as mean±1 standard deviation.

Example 18: Measurement of AP1903-Dependent T Cell Activation

Aim: To transduce primary T cells with a retroviral vector encoding signaling molecules linked to two FKBPv36 molecules to enable AP1903 activation of the T cells. In this experiment, production of cytokines in response to dimerization was measured using a multiplex cytokine bead array.

Methods:

Design and Cloning of Inducible T Cell Molecules:
1. Two SFG-based retroviral vectors were constructed by Gibson cloning, where PCR products were amplified from pAd1127-02-iMC and inserted into the pBP0320-SFG-Myr.LFv1.Fv2L2A.ΔCD19 construct in place of the LFv1.Fv2L DNA fragment.
   a. In the first vector, the PCR product amplified was Fv'Fv, or where only the FKBPv36 fragments were inserted into the retroviral backbone, replacing LFv1.Fv2L at the XhoI and SalI sites. This vector is called pBP0171-SFG-Myr.Fv'.Fv.2A.ΔCD19, and is the control vector which lacks any T cell signaling molecules.
   b. In the second vector, the PCR product amplified was MyD88/CD40.Fv'.Fv (or iMCnoE). This was inserted into the pBP0320 plasmid at the XhoI and SalI restriction sites in place of the LFv1.Fv2L DNA sequence. This vector is called pBP0172-SFG-Myr.iMCnoE.2A.ΔCD19. The "noE" suffix indicates that this iMC DNA does not encode an epitope tag.

Production of Retrovirus:
2. Retrovirus was produced by a transient transfection method, where HEK293T cells were transfected with the following plasmids:
   a. SFG retroviral plasmids (pBP0171 or pBP0172; RV-171 or RV-172, respectively)
   b. Retroviral envelope plasmid (RD114)
   c. Gag/pol plasmid (pEQ-PAM-E)
3. At 48 and 72 hours, supernatant from the transfected cells containing replication defective retrovirus was collected and snap frozen in dry ice/ethanol and stored at −80° C. until T cell transduction.
4. To transduce primary T cells, PBMCs from healthy donors were activated with anti-CD3 and anti-CD28 antibodies in T cell growth media supplemented with 100 U/ml IL-2. After 3 days, T cells were activated and harvested and ready for retroviral transduction. To transduce the T cells, non-tissue culture-treated plates were first coated with RETRONECTIN overnight at 4° C. The RETRONECTIN was then removed, and the plates washed with PBS. Retroviral supernatants were then used to coat the RETRONECTIN plate. Activated T cells were then added to the wells and the plate was centrifuged to facilitate viral particle binding and transduction. After 48 hours, the T cells are harvested and analyzed by flow cytometry for CD3 and CD19 co-expression to determine viral transduction efficiency.

Analysis of AP1903-Induced T Cell Activation by Cytokine Production:
5. To assess AP1903-dependent T cell activation of T cells, $1 \times 10^5$ non-transduced (NT) or T cells transduced with the control retrovirus (RV-171) or the retrovirus containing iMC (RV-172) were plated in triplicate in 96-well plates and cultured at 37° C. 5% $CO_2$ with media alone, or media containing 10 nM AP1903.
6. After 24 hours, the cells were gently mixed and the plate was centrifuged. Supernatant was then collected and plated into a BIOPLEX Human Cytokine/Chemokine 27-plex plate, which measures the following cytokines and chemokines:
   a. Basic-FGF, G-CSF, GM-CSF, IFN-gamma, IL-1Ra, IL-1beta, IL-2, IL-4, IL-5, IL-6, IL-8, IL-7, IL-8, IL-9, IL-10, IL-12p70, IL-13, IL-15, IL-17RA, eotaxin, IP10, MCP-1, MIP-1alpha, MIP-1beta, PDGF-bb, RANTES, TNF-alpha and VEGF.
   b. The cytokines and chemokines in the supernatants were subsequently measured and compared to standards in the plate using a BIOPLEX MAGPIX Multiplex Reader.

Results:

Transduction Efficiency:
1. T cells from two healthy donors were transduced with retrovirus and after 48 hours, the efficiency as determined by flow cytometry for $CD3^+CD19^+$ co-expression was as follows:
   a. Donor 063
      i. NT=6.54%
      ii. RV-171=73.9%
      iii. RV-172=54.6%
   b. Donor 707
      i. NT=2.16%
      ii. RV-171=85.2%
      iii. RV-172=73.6%
2. Transduction was quite high for both vectors and donors indicating that they were not toxic to HEK293T cells and that the viral titers were good.

Cytokine/Chemokine Production
3. Analysis of cytokine and chemokine secretion showed remarkable dependency on AP1903 dimerization. The following T cell-produced cytokines and chemokines showed induction over a 24-hour period, but were absent from T cells transduced with the control vector or non-transduced T cells:
   a. GM-CSF, IFN-gamma, IL-13, IL-4, IL-5, IL-6, IL-8, IL-1beta, IL-12p70, IP10, MIP-1alpha, MIP-1beta, RANTES, and TNF-alpha
4. Additionally, other cytokines and chemokines did not appear to be induced by AP1903 activation of iMC. These include the following:
   a. Basic-FGF, G-CSF, IL-1Ra, IL-2, IL-7, IL-9, IL-10, IL-15, IL-17RA, eotaxin, MCP-1, PDGF-bb and VEGF.

Certain results are also depicted in FIGS. 66-74. NT=non-transduced activated T cells RV0171=SFG-Myr.Fv'.Fv.2A.ΔCD19; RV0172=SFG=Myr.MyD88/CD40.Fv'.Fv.2A. ΔCD19.

T cells were stimulated with 10 nM AP1903 for 24 hours then supernatants were assayed for cytokine levels.

Example 19: Measurement of AP1903-Dependent T Cell Cytotoxicity

Aim: To transduce primary T cells with a retroviral vector encoding signaling molecules linked to two FKBPv36 molecules to enable AP1903 activation of the T cells. In this experiment, two aspects of AP1903 activation were examined. First, if T cells were in close proximity to tumor cells, would their activation induce tumor cell killing? Second, if T cells were activated via AP1903, would they proliferate?

Methods:

Design and Cloning of Inducible T Cell Molecules and Production of Retrovirus

1. The methods are essentially the same as those discussed in the above Example 4. The same cells were used for this assay.

Generation of GFP-Marked CAPAN-1 (Pancreatic Adenocarcinoma) Cell Line:

2. CAPAN-1 was purchased from ATCC. Subsequently, the cell line was gene-modified by transfection with the pBP0168-pcDNA3.1-EGFPluc plasmid, which contains the gene for the EGFP/firefly luciferase fusion protein, as well as the neomycin-resistance gene, allowing stably transfected cells to be selected over time by culturing with G418 antibiotic. Following culture, clones with high GFP expression were selected and subcultured until a cell line with >95% GFP was obtained.

Co-Culture of iMC-Enabled T Cells with CAPAN-1 Tumor Cells:

3. Non-transduced T cells or cells transduced with RV-171 (control vector) or RV-172 (iMC vector) were cultured at a 5:1 ratio of T cells to tumor cells in media supplemented with 50 U/ml IL-2, and either with or without 10 nM AP1903. Co-cultures were then incubated at 37° C. and 5% $CO_2$ for 72 hours. Cultures were subsequently analyzed for the presence of $GFP^+$ tumor cells by fluorescent microscopy and by harvesting the cultures with 0.25% trypsin/EDTA and measuring the frequency of $GFP^+CD3^-$ tumor cells in the culture by flow cytometry.

Results:

4. Upon inspection of the co-culture wells, it was evident that in both donors, T cells transduced with RV-172 (iMC-containing vector) that were stimulated with AP1903 were proliferating, as evident by large T cell blast colonies. In addition, by fluorescent microscopy, co-cultures containing RV-172-transduced T cells receiving AP1903 showed very few viable $GFP^+$ tumor cells. Following these initial observations, T cells and tumor cells were harvested and analyzed by flow cytometry to determine the frequency of remaining CAPAN-1 $GFP^+$ tumor cells.

5. As observed by microscopy, flow cytometry showed a clear effect of AP1903 in co-cultures containing AP1903-treated, iMC-transduced (RV-172) T cells. The reduction of $GFP^+$ tumor cells only occurred in this condition, but not with T cells transduced with the control vector, and to a lesser extent with T cells transduced with RV-172 that did not receive dimerizer.

6. Together, these data suggests that activation of iMC in T cells is capable of inducing T cell killing and induce proliferation of AP1903-treated T cells. Collectively, with our observations regarding cytokine/chemokine production, these data indicate that iMC can be activated in T cells and that T cells retain and increase their effector functions upon iMC dimerization.

Certain results are also depicted in FIGS. 75-78.

Example 20: Activation of T Cells Ex Vivo and Administration to a Human Subject

Presented in this example are methods of using the modified T cells for human therapy. In this example, the costimulatory polypeptide cytoplasmic regions are derived from CD40 and MyD88. These methods may be adapted for other cells, such as, for example NK and NKT cells, as well as tumor-infiltrating lymphocytes, and may also be adapted for chimeric costimulating polypeptides that comprise other costimulatory polypeptide cytoplasmic regions as discussed herein.

Materials and Methods

Large-Scale Generation of Gene-Modified T Cells

T cells are generated from healthy volunteers, using standard methods. Briefly, peripheral blood mononuclear cells (PBMCs) from healthy donors or cancer patients are activated for expansion and transduction using soluble αCD3 and αCD28 (Miltenyi Biotec, Auburn, Calif.). PBMCs are resuspended in Cellgenix DC media supplemented with 100 U/ml IL-2 (Cellgenix) at $1\times10^6$ cells/ml and stimulated with 0.2 µg/ml αCD3 and 0.5 µg/ml αCD28 soluble antibody. Cells are then cultured at 37° C., 5% CO2 for 4 days. On day four, 1 ml of fresh media containing IL-2 is added. On day 7, cells are harvested and resuspended in Cellgenix DC media for transduction.

Plasmid and Retrovirus

The SFG plasmid consists of inducible chimeric polypeptide linked, via a cleavable 2A-like sequence, to truncated human CD19. The inducible chimeric polypeptide consists of a human FK506-binding protein (FKBP12; GenBank AH002 818) with an F36V mutation, connected via a Ser-Gly-Gly-Gly-Ser linker (SEQ ID NO: 194) to human chimeric polypeptide. The F36V mutation increases the binding affinity of FKBP12 to the synthetic homodimerizer, AP20187 or AP1903. The 2A-like sequence encodes an 20 amino acid peptide from Thosea asigna insect virus, which mediates >99% cleavage between a glycine and terminal proline residue, resulting in 19 extra amino acids in the C terminus of the inducible chimeric polypeptide, and one extra proline residue in the N terminus of CD19. CD19 consists of full-length CD19 (GenBank NM 001770) truncated at amino acid 333 (TDPTRRF) (SEQ ID NO: 193), which shortens the intracytoplasmic domain from 242 to 19 amino acids, and removes all conserved tyrosine residues that are potential sites for phosphorylation.

A stable PG13 clone producing Gibbon ape leukemia virus (Gal-V) pseudotyped retrovirus is made by transiently transfecting Phoenix Eco cell line (ATCC product #5D3444; ATCC, Manassas, Va.) with the SFG plasmid. This produces Eco-pseudotyped retrovirus. The PG13 packaging cell line (ATCC) is transduced three times with Eco-pseudotyped retrovirus to generate a producer line that contained multiple SFG plasmid proviral integrants per cell. Single cell cloning is performed, and the PG13 clone that produced the highest titer is expanded and used for vector production.

Retroviral Transduction

Culture medium for T cell activation and expansion is serum-free Cellgenix DC medium (Cellgenix) supplemented by 100 U/ml IL-2 (Cellgenix). T cells are activated by soluble anti-CD3 and anti-CD28 (Miltenyi Biotec) for 7 days before transduction with retroviral vector. Immunomagnetic selection of ΔCD19, if necessary, is performed on day 4 after transduction; the positive fraction was expanded for a further 2 days and cryopreserved.

Scaling-Up Production of Gene-Modified Allodepleted Cells

Scale-up of the transduction process for clinical application use non-tissue culture-treated T75 flasks (Nunc, Rochester, N.Y.), which are coated with 10 ml of anti-CD3 0.5 µg/ml and anti-CD28 0.2 µg/ml or 10 ml of fibronectin 7 µg/ml at 4° C. overnight. Fluorinated ethylene propylene bags corona-treated for increased cell adherence (2PF- 0072AC, American Fluoroseal Corporation, Gaithersburg, Md.) is also used. PBMCs are seeded in anti-CD3, anti-CD28-coated flasks at 1×10$^6$ cells/ml in media supplemented with 100 U/ml IL-2. For retroviral transduction, RETRONECTIN-coated flasks or bags are loaded once with 10 ml of retrovirus-containing supernatant for 2 to 3 hours. Activated T cells are seeded at 1×106 cells/ml in fresh retroviral vector-containing medium and T cell culture medium at a ratio of 3:1, supplemented with 100 U/ml IL-2. Cells are harvested the following morning and expanded in tissue-culture treated T75 or T175 flasks in culture medium supplemented with 100 U/ml IL-2 at a seeding density of between about 5×10$^5$ cells/ml to 8×10$^5$ cells/ml.

CD19 Immunomagnetic Selection

Immunomagnetic selection for CD19 may be performed, for example, 4 days after transduction. Cells are labeled with paramagnetic microbeads conjugated to monoclonal mouse anti-human CD19 antibodies (Miltenyi Biotech, Auburn, Calif.) and selected on MS or LS columns in small scale experiments and on a CLINIMACS Plus automated selection device in large scale experiments. CD19-selected cells are expanded for a further 4 days and cryopreserved on day 8 post transduction. These cells are referred to as "gene-modified cells."

Example 21: Treatment of a Leukemia Patient

The present example of the treatment of a leukemia patient having advanced treatment refractory leukemia, using the methods of the present application, may also be applied to other conditions or diseases, such as, for example, other hyperproliferative diseases or solid tumors.

The methods may be used essentially as discussed, with the understanding that the single chain variable fragment may vary according to the target antigen.

T cells are transduced with a nucleic acid comprising a polynucleotide coding for a chimeric signaling molecule. The T cells are also transduced with a nucleic acid comprising a polynucleotide coding for a chimeric antigen receptor. Examples of the inducible chimeric signaling molecules include, but are not limited to, those depicted in FIG. 41, comprising a CD28 polypeptide cytoplasmic stimulating region and a 4-1BB polypeptide cytoplasmic signaling regions. The inducible chimeric signaling molecules may also include a CD3 zeta polypeptide. The chimeric antigen receptor comprises a single chain variable fragment that recognizes CD19.

The patient undergoes lymphodepletive conditioning, followed by administration of the transduced CD19-targeted T cells. The T cells may be autologous, allogeneic, or non-allogeneic. Following administration of the T cells, the ligand inducer is administered to the patient, in order to expand the CD19-targeted T cells by inducing the chimeric signaling molecule. The dose may be provided, for example, daily, twice a week, or weekly. The level of tumor cells is monitored, and the ligand inducer, for example, AP1903, dosing schedule is adjusted based on the tumor cell load. Because of the concern that an unregulated, too rapid rate of T cell expansion, activation, and tumor cell killing may lead to a more severe cytokine storm that unnecessarily harms the patient, the dosing schedule is designed to achieve a complete recovery at a rate that limits toxicity and does not cause extensive harm to the patient, for example, keeping the patient out of the intensive care unit at a hospital. Once the patient achieves a complete recovery and remains disease free for a certain length of time to be determined, for example, one month, three months, six months, the dosing of AP1903 is stopped. Following treatment, in the absence of the ligand inducer, the number of CD19-targeted T cells is reduced. There may be a low level of basal signaling, allowing a small number of the quiescent CD19-targeted T cells to survive. Without the ligand inducer, these cells remain inactive and allow normal B cells to recover. If at any time in the future, the patient develops a recurrence of leukemia, dosing of the ligand inducer, AP1903, will resume, reactivating the CD19-targeted T cells and leading to re-induction of a complete response in the patient. This additional dosing may be repeated more than once, in the event of multiple recurrences.

Example 22: Measurement of iMC Activity in CAR Transduced T Cells

Aim: To transduce primary T cells with a retroviral vector encoding signaling molecules linked to two FKBPv36 molecules to allow AP1903 activation of the T cells. The experiment is designed to examine whether the inducible costimulatory molecule comprising the truncated MyD88 and CD40 polypeptides, improve killing of the GFP-modified CAPAN-1 (pancreatic adenocarcinoma) cells by T cells also transduced with a CAR recognizing prostate stem cell antigen (PSCA), which is highly expressed on CAPAN-1 tumor cells.

Methods:

Design and Cloning of Inducible T Cell Molecules:

1. Transduction of T cells is performed with RV-172 (SFG-Myr.MyD88/CD40.Fv.Fv'0.2A.ΔCD19) and RV-89 (SFG.PSCAscFv.CH2CH3.CD28.zeta). The scFv targets PSCA using the scFv from the humanized monoclonal antibody, 1G8 (derived from humanized anti-PSCA in US2012077962 A1). This is linked to the CH2CH3 region of human IgG1, which in turn is linked to CD28 which contains both the transmembrane and cytoplasmic portion of the molecule. CD28 is linked to the cytoplasmic portion of CD3 zeta.

Production of Retrovirus:

2. Essentially the Same as in the Previous Example.

Generation of GFP-Marked CAPAN-1 (Pancreatic Adenocarcinoma) Cell Line:

3. CAPAN-1 is purchased from ATCC. Subsequently, the cell line is gene-modified by transfection with the pBP0168-pcDNA3.1-EGFPluc which contains the gene for the EGFP/firefly luciferin fusion protein, as well as the neomycin resistance gene allowing stably transfected cells to be selected over time by culturing with G418 antibiotic. Following culture, clones with high GFP expression are selected and subcultured until a cell line with >95% GFP is obtained.

Co-Culture of iMC-Enabled T Cells with CAPAN-1 Tumor Cells:

4. Non-transduced or T cells co-transduced with RV-89 (PSCA CAR) and RV-172 (iMC vector) are cultured at a 5:1 ratio of T cells to tumor cells in media supplemented with 50 U/ml IL-2, and either with or without 10 nM AP1903. Co-cultures are then incubated at 37° C. and 5% CO$_2$ for 72 hours. Cultures are subsequently analyzed for the presence of GFP$^+$ tumor cells by fluorescent microscopy and by harvesting the cultures with 0.25% trypsin/EDTA and measuring the frequency of GFP$^+$CD3$^-$ tumor cells in the culture by flow cytometry.

Results:

1. The cultures are examined by fluorescent microscopy to assess an improvement in tumor cell killing in the wells that contain the inducible costimulatory molecule- and chimeric antigen receptor-transduced T cells and that received AP1903.

2. Flow cytometry is used to analyze GFP+ cells in the cultures following trypsinization to determine whether AP1903 contributes to a reduction in tumor cell number in this short culture period (72 hours). The time period for the culture may be extended to approximately 5 days. The flow cytometry plots may show the reduction in GFP+ cells in wells, at a 5:1 ratio, that were transduced with both virus and receive AP1903.

3. The remaining viable CAPAN-1-GFP cells are normalized to the conditions of NT T cells without AP1903 to show the effect of iMC activation on tumor cell killing.

Example 23: Examples of Particular Nucleic Acid and Amino Acid Sequences

CD28 nt,
SEQ ID NO: 97
TTCTGGGTACTGGTTGTAGTCGGTGGCGTACTTGCTTGTTATTCTCTTCT

TGTTACCGTAGCCTTCATTATATTCTGGGTCCGATCAAAGCGCTCAAGAC

TCCTCCATTCCGATTATATGAACATGACACCTCGCCGACCTGGTCCTACA

CGCAAACATTATCAACCCTACGCACCCCCCGAGACTTCGCTGCTTATCG

ATCC

CD28 aa,
SEQ ID NO: 98
FWVLVVVGGVLACYSLLVTVAFIIFWVRSKRSRLLHSDYMNMTPRRPGPT

RKHYQPYAPPRDFAAYRS 4-1BB nt,
SEQ ID NO: 99
AGTGTAGTTAAAAGAGGAAGAAAAAAGTTGCTGTATATATTTAAACAACC

ATTTATGAGACCAGTGCAAACCACCCAAGAAGAAGACGGATGTTCATGCA

GATTCCCAGAAGAAGAAGAAGGAGGATGTGAATTG 4-1BB aa,
SEQ ID NO: 100
SVVKRGRKKLLYIFKQPFMRPVQTTQEEDGCSCRFPEEEEGGCEL

Linker sequence (between 4-1BB and CD3 zeta) nt,
SEQ ID NO: 101
ACGCGT

Linker sequence (between 4-1BB and CD3 zeta) aa,
SEQ ID NO: 102
TR

CD3 zeta nt,
SEQ ID NO: 103
CGGGTCAAATTCAGCCGGAGTGCTGACGCCCCAGCATACCAACAGGGACA

AAACCAACTCTACAACGAGCTCAACCTGGGTAGACGCGAGGAGTACGACG

TTCTGGATAAGAGGCGGGGCCGGGACCCAGAGATGGGGGGCAAACCTCAG

CGGCGGAAGAACCCGCAGGAGGGTCTTTATAACGAGCTCCAGAAGGACAA

GATGGCGGAAGCCTATTCAGAAATTGGGATGAAAGGCGAGAGACGCAGGG

GAAAAGGTCACGATGGTCTGTATCAAGGACTGTCAACCGCCACCAAAGAC

ACTTACGATGCGCTCCACATGCAGGCCCTCCCTCCCCGC

CD3 zeta aa,
SEQ ID NO: 104
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

The following is an example of the nucleotide and amino acid sequences for a chimeric antigen receptor (CAR) sequences (in order, without scFv fragments)

Signal peptide nt,
SEQ ID NO: 105
ATGGAGTTTGGGCTGTCATGGCTGTTCCTCGTGGCCATTCTCAAAGGGGTCCAGTGTTCTCG

C

Signal peptide aa,
SEQ ID NO: 106
MGFGLSWLFLVAILKGVQCSR

Flexible linker sequence nt,
SEQ ID NO: 107
GGGGGAGGAGGTTCTGGAGGCGGCGGGAGCGGAGGAGGAGGCAGC Flexible linker sequence aa,
SEQ ID NO: 108
GGGGSGGGGSGGGGS Linker sequence (between scFv and CH2CH3) nt,
SEQ ID NO: 109
GGATCC Linker sequence (between scFv and CH2CH3) aa,
SEQ ID NO: 110
GS -continued IgG1 CH2CH3 nt,
SEQ ID NO: 111
GATCCAGCCGAACCCAAATCCCCCGATAAAACACATACTTGCCCCCCTTGTCCCGCACCAGA

ATTGCTTGGCGGACCTTCCGTTTTTCTTTTTCCCCCCAAACCTAAAGATACCCTGATGATTTCC

CGAACCCCTGAAGTTACGTGCGTAGTCGTAGATGTGTCTCACGAAGATCCAGAAGTAAAATTT

AACTGGTACGTAGATGGAGTCGAAGTTCACAACGCAAAGACGAAGCCCCGAGAAGAACAATA

TAATTCCACATACCGAGTAGTTAGCGTTCTCACCGTACTGCATCAGGACTGGCTTAACGGCAA

AGAATATAAATGTAAGGTCTCAAACAAAGCACTCCCAGCCCCTATCGAAAAGACTATCTCCAAA

GCTAAAGGACAACCCCGCGAACCCCAGGTCTATACACTTCCCCCCTCACGCGATGAACTCAC

TAAAAATCAGGTTTCCCTTACTTGTCTTGTCAAAGGCTTCTACCCTAGCGATATCGCAGTCGAA

TGGGAATCCAATGGCCAGCCCGAAAACAACTATAAAACAACCCCACCTGTCCTCGATTCAGAT

GGCTCATTCTTTCTCTATTCCAAACTGACTGTAGACAAATCCCGATGGCAACAAGGTAACGTG

TTCTCTTGCTCAGTCATGCATGAAGCGCTTCATAACCATTACACACAAAAATCTCTCTCACTGT

CTCCCGGAAAGAAGGACCCC

IgG1 CH2CH3 aa,
SEQ ID NO: 112
DPAEPKSPDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKKDP

Linker sequence (between scFv and CH2CH3) nt,
SEQ ID NO: 113
CTCGAG

Linker sequence (between scFv and CH2CH3) aa,
SEQ ID NO: 114
LE

CD3 zeta transmembrane nt,
SEQ ID NO: 115
AAACTGTGTTACCTCCTCGATGGCATCCTCTTTATTTATGGCGTGATTCTGACCGCATTGTTTC

TCCGAGTAAAATTCTCTAGATCCGCAGACGCTCCCGCATATCAGCAAGGACAAAATCAGCTTT

ATAACGAACTTAACCTCGGCAGACGCGAAGAATACGATGTACTGGACAAGAGAAGAGGAAGA

GATCCCGAAATGGGCGGAAAACCCCAGAGAAGAAAGAATCCCCAAGAAGGTCTTTATAACGA

ACTGCAGAAAGATAAAATGGCCGAAGCGTACAGTGAAATTGGTATGAAAGGAGAAAGAAGAC

GCGGAAAAGGACATGACGGACTCTACCAAGGACTCTCAACTGCTACTAAAGATACATACGAC

GCCCTTCATATGCAAGCCCTCCCCCCGAGATAA

CD3 zeta transmembrane aa,
SEQ ID NO: 116
KLCYLLDGILFIYGVILTALFLRVKFSRSADAPAYQQGQNQLYNELNLGRREEYDVLDKRRGRDPE

MGGKPQRRKNPQEGLYNELQKDKMAEAYSEIGMKGERRRGKGHDGLYQGLSTATKDTYDALHM

QALPPR

Additional chimeric signaling molecule sequences
OX40 nt,
SEQ ID NO: 117
GTTGCCGCCATCCTGGGCCTGGGCCTGGTGCTGGGGCTGCTGGGCCCCCTGGCCATCCTGC

TGGCCCTGTACCTGCTCCGGGACCAGAGGCTGCCCCCCGATGCCCACAAGCCCCCTGGGGG

AGGCAGTTTCCGGACCCCCATCCAAGAGGAGCAGGCCGACGCCCACTCCACCCTGGCCAAG

ATC

OX40 aa,
SEQ ID NO: 118
VAAILGLGLVLGLLGPLAILLALYLLRRDQRLPPDAHKPPGGGSFRTPIQEEQADAHSTLAKI

SEQ ID NO: 22 nucleotide sequence of 5'LTR sequence,
SEQ ID NO: 119
TGAAAGACCCCACCTGTAGGTTTGGCAAGCTAGCTTAAGTAACGCCATTTTGCAAGGCATGGA

AAAATACATAACTGAGAATAGAAAAGTTCAGATCAAGGTCAGGAACAGATGGAACAGCTGAAT

ATGGGCCAAACAGGATATCTGTGGTAAGCAGTTCCTGCCCCGGCTCAGGGCCAAGAACAGAT

GGAACAGCTGAATATGGGCCAAACAGGATATCTGTGGTAAGCAGTTCCTGCCCCGGCTCAGG

GCCAAGAACAGATGGTCCCCAGATGCGGTCCAGCCCTCAGCAGTTTCTAGAGAACCATCAGA

TGTTTCCAGGGTGCCCCAAGGACCTGAAATGACCCTGTGCCTTATTTGAACTAACCAATCAGT

TCGCTTCTCGCTTCTGTTCGCGCGCTTATGCTCCCCGAGCTCAATAAAAGAGCCCACAACCCC

TCACTCGGGGCGCCAGTCCTCCGATTGACTGAGTCGCCCGGGTACCCGTGTATCCAATAAAC

CCTCTTGCAGTTGCATCCGACTTGTGGTCTCGCTGTTCCTTGGGAGGGTCTCCTCTGAGTGAT

TGACTACCCGTCAGCGGGGGTCTTTCA

Additional Sequences
Thosea asigna virus-2A from capsid protein precursor nucleotide sequence
SEQ ID NO, 120
GCCGAGGGCAGGGGAAGTCTTCTAACATGCGGGGACGTGGAGGAAAATCCCGGGCCC Thosea asigna virus-2A from capsid protein precursor amino acid sequence,
SEQ ID NO: 121
AEGRGSLLTCGDVEENPGP 3'LTR nucleotide sequence,
SEQ ID NO: 122
TGAAAGACCCCACCTGTAGGTTTGGCAAGCTAGCTTAAGTAACGCCATTTTGCAAGGCATGGA

AAAATACATAACTGAGAATAGAGAAGTTCAGATCAAGGTCAGGAACAGATGGAACAGCTGAAT

ATGGGCCAAACAGGATATCTGTGGTAAGCAGTTCCTGCCCCGGCTCAGGGCCAAGAACAGAT

GGAACAGCTGAATATGGGCCAAACAGGATATCTGTGGTAAGCAGTTCCTGCCCCGGCTCAGG

GCCAAGAACAGATGGTCCCCAGATGCGGTCCAGCCCTCAGCAGTTTCTAGAGAACCATCAGA

TGTTTCCAGGGTGCCCCAAGGACCTGAAATGACCCTGTGCCTTATTTGAACTAACCAATCAGT

TCGCTTCTCGCTTCTGTTCGCGCGCTTCTGCTCCCCGAGCTCAATAAAAGAGCCCACAACCCC

TCACTCGGGGCGCCAGTCCTCCGATTGACTGAGTCGCCCGGGTACCCGTGTATCCAATAAAC

CCTCTTGCAGTTGCATCCGACTTGTGGTCTCGCTGTTCCTTGGGAGGGTCTCCTCTGAGTGAT

TGACTACCCGTCAGCGGGGGTCTTTCA (nucleotide sequence of linker-$F_v$1-$F_v$2-linker with XhoI/SalI sites,
(wobbled codons lowercase in $F_v$2')),
SEQ ID NO: 123
CTCGAGTCTGGCGGTGGATCCGGAGGCGTTCAAGTAGAAACAATCAGCCCAGGAGACGGAA

GGACTTTCCCCAAACGAGGCCAAACATGCGTAGTTCATTATACTGGGATGCTCGAAGATGGAA

AAAAAGTAGATAGTAGTAGAGACCGAAACAAACCATTTAAATTTATGTTGGGAAAACAAGAAGT

AATAAGGGGCTGGGAAGAAGGTGTAGCACAAATGTCTGTTGGCCAGCGCGCAAAACTCACAA

TTTCTCCTGATTATGCTTACGGAGCTACCGGCCACCCCGGCATCATACCCCCTCATGCCACAC

TGGTGTTTGACGTCGAATTGCTCAAACTGGAAGTCGAGGGaGTgCAgGTgGAgACgATtAGtCCt

GGgGAtGGgAGaACcTTtCCaAaGCGcGGtCAgACcTGtGTtGTcCAcTAcACcGGtATGCTgGAgGAc

GGgAAgAAgGTgGActcTtcacGcGAtCGcAAtAAgCCtTTcAAgTTcATGCTcGGcAAgCAgGAgGTgATc

-continued cGGGGgTGGGAgGAgGGcGTgGCtCAgATGTCgGTcGGgCAacGaGcGaAgCTtACcATcTCaCCcG

AcTAcGCgTAtGGgGCaAcGGGgCAtCCgGGaATtATcCCtCCcCAcGCtACgCTcGTaTTcGAtGTgGA gcTcttgAAgCTtGagTCTGGCGGTGGATCCGGAGTCGAC ($F_V.F_{VLS}$ amino acid sequence),
SEQ ID NO: 124

LESGGGSGGVQVETISPGDGRTFPKRGQTCVVHYTGMLEDGKKVDSSRDRNKPFKFMLGKQEVI

RGWEEGVAQMSVGQRAKLTISPDYAYGATGHPGIIPPHATLVFDVELLKLEVEGVQVETISPGDGR

TFPKRGQTCVVHYTGMLEDGKKVDSSRDRNKPFKFMLGKQEVIRGWEEGVAQMSVGQRAKLTIS

PDYAYGATGHPGIIPPHATLVFDVELLKLESGGGSGVD

FKBPv36 (Fv1) nucleotide sequence,
SEQ ID NO: 125

GGCGTTCAAGTAGAAACAATCAGCCCAGGAGACGGAAGGACTTTCCCCAAACGAGGCCAAAC

ATGCGTAGTTCATTATACTGGGATGCTCGAAGATGGAAAAAAAGTAGATAGTAGTAGAGACCG

AAACAAACCATTTAAATTTATGTTGGGAAAACAAGAAGTAATAAGGGGCTGGGAAGAAGGTGT

AGCACAAATGTCTGTTGGCCAGCGCGCAAAACTCACAATTTCTCCTGATTATGCTTACGGAGC

TACCGGCCACCCCGGCATCATACCCCCTCATGCCACACTGGTGTTTGACGTCGAATTGCTCA

AACTGGAA

FKBPv36 (Fv1) amino acid sequence,
SEQ ID NO: 126

GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKLE

FKBPv36 (Fv2) nucleotide sequence,
SEQ ID NO: 127

GGaGTgCAgGTgGAgACgATtAGtCCtGGgGAtGGgAGaACcTTtCCaAAgCGcGGtCAgACcTgTGTt

GTcCAcTAcACcGGtATGCTgGAgGAcGGgAAgAAgGTgGActcTtcacGcGAtCGcAAtAAgCCtTTcAA gTTcATGcTcGGcAAgCAgGAgGTgATccGGGGgTGGGAgGAgGGcGTgGCtCAgATGTCgGTcGGg CAacGaGcGaAgCTtACcATcTCaCCcGAcTAcGCgTAtGGgGCaAcGGGgCAtCCgGGaATtATcCCt CCcCAcGCtACgCTcGTaTTcGAtGTgGAgcTcttgAAgCTtGag FKBPv36 (Fv2) amino acid sequence,
SEQ ID NO: 128

GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKLE

Example 24: Additional Sequences for Inducible MyD88/CD40 Chimeric Polypeptide

Myristoylation polypeptide nucleotide sequence,
SEQ ID NO: 129

ATGGGGAGTAGCAAGAGCAAGCCTAAGGACCCCAGCCAGCGC

Myristoylation polypeptide amino acid sequence,
SEQ ID NO: 130

MGSSKSKPKDPSQR

Linker nucleotide sequence (linker 1),
SEQ ID NO: 131

CTCGAG

Linker amino acid sequence (linker 1),
SEQ ID NO: 132

LE

Truncated MyD88 polypeptide nucleotide sequence,
SEQ ID NO: 133
ATGGCCGCTGGGGGCCCAGGCGCCGGATCAGCTGCTCCCGTATCTTCTACTTCTTCTTTGCC

GCTGGCTGCTCTGAACATGCGCGTGAGAAGACGCCTCTCCCTGTTCCTTAACGTTCGCACAC

AAGTCGCTGCCGATTGGACCGCCCTTGCCGAAGAAATGGACTTTGAATACCTGGAAATTAGAC

AACTTGAAACACAGGCCGACCCCACTGGCAGACTCCTGGACGCATGGCAGGGAAGACCTGG

TGCAAGCGTTGGACGGCTCCTGGATCTCCTGACAAAACTGGGACGCGACGACGTACTGCTTG

AACTCGGACCTAGCATTGAAGAAGACTGCCAAAAATATATCCTGAAACAACAACAAGAAGAAG

CCGAAAAACCTCTCCAAGTCGCAGCAGTGGACTCATCAGTACCCCGAACAGCTGAGCTTGCT

GGGATTACTACACTCGACGACCCACTCGGACATATGCCTGAAAGATTCGACGCTTTCATTTGC

TATTGCCCCTCTGACATA

Truncated MyD88 polypeptide amino acid sequence,
SEQ ID NO: 134
MAAGGPGAGSAAPVSSTSSLPLAALNMRVRRRLSLFLNVRTQVAADWTALAEEMDFEYLEIRQLE

TQADPTGRLLDAWQGRPGASVGRLLDLLTKLGRDDVLLELGPSIEEDCQKYILKQQQEEAEKPLQ

VAAVDSSVPRTAELAGITTLDDPLGHMPERFDAFICYCPSDI

ΔCD40 polypeptide nucleotide sequence,
SEQ ID NO: 135
AAGAAAGTTGCAAAGAAACCCACAAATAAAGCCCCACACCCTAAACAGGAACCCCAAGAAATC

AATTTCCCAGATGATCTCCCTGGATCTAATACTGCCGCCCCGGTCCAAGAAACCCTGCATGGT

TGCCAGCCTGTCACCCAAGAGGACGGAAAAGAATCACGGATTAGCGTACAAGAGAGACAA

ΔCD40 polypeptide amino acid sequence,
SEQ ID NO: 136
KKVAKKPTNKAPHPKQEPQEINFPDDLPGSNTAAPVQETLHGCQPVTQEDGKESRISVQERQ Linker nucleotide sequence (linker 2),
SEQ ID NO: 137
GTCGAGTCTGGCGGTGGATCCGGA Linker amino acid sequence (linker 2),
SEQ ID NO: 138
VESGGGSG FKBPv36 (Fv1) nucleotide sequence,
SEQ ID NO: 139
GGCGTTCAAGTAGAAACAATCAGCCCAGGAGACGGAAGGACTTTCCCCAAACGAGGCCAAAC

ATGCGTAGTTCATTATACTGGGATGCTCGAAGATGGAAAAAAAGTAGATAGTAGTAGAGACCG

AAACAAACCATTTAAATTTATGTTGGGAAAACAAGAAGTAATAAGGGGCTGGGAAGAAGGTGT

AGCACAAATGTCTGTTGGCCAGCGCGCAAAACTCACAATTTCTCCTGATTATGCTTACGGAGC

TACCGGCCACCCCGGCATCATACCCCCTCATGCCACACTGGTGTTTGACGTCGAATTGCTCA

AACTGGAA

FKBPv36 (Fv1) amino acid sequence,
SEQ ID NO: 140
GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKLE

Linker nucleotide sequence (linker 3),
SEQ ID NO: 141
GTCGAG

Linker amino acid sequence (linker 3),
SEQ ID NO: 142
VE

-continued

```
FKBPv36 (Fv2) nucleotide sequence,
                                                       SEQ ID NO: 143
GGaGTgCAgGTgGAgACgATtAGtCCtGGgGAtGGgAGaACcTTtCCaAAgCGcGGtCAgACcTGtGTt GTcCAcTAcACcGGtATGCTgGAgGAcGGgAAgAAgGTgGActcTtcacGcGAtCGcAAtAAgCCtTTcAA gTTcATGcTcGGcAAgCAgGAgGTgATccGGGGgTGGGAgGAgGGcGTgGCtCAgATGTCgGTcGGg CAaCGaGCgAAgCTtACcATcTCaCCcGAcTAcGCgTAtGGgGCaACgGGgCATCCgGGaATtATcCCt CCcCAcGCtACgCTcGTaTTcGAtGTgGAgcTcttgAAgCTtGag FKBPv36 (Fv2) amino acid sequence,
                                                       SEQ ID NO: 144
GVQVETISPGDGRTFPKRGQTCVVHYTGMLEDGKKVDSSRDRNKPFKFMLGKQEVIRGWEEGV

AQMSVGQRAKLTISPDYAYGATGHPGIIPPHATLVFDVELLKLE

Linker nucleotide sequence (linker 4),
                                                       SEQ ID NO: 145
TCTGGCGGTGGATCCGGAGTCGAC Linker amino acid sequence (linker 4),
                                                       SEQ ID NO: 146
SGGGSGVD Furin protease consensus cleavage site nucleotide sequence,
                                                       SEQ ID NO: 147
CGCGCAAAGCGT Furin protease consensus cleavage site amino acid sequence,
                                                       SEQ ID NO: 148
RAKR V5 epitope nucleotide sequence,
                                                       SEQ ID NO: 149
GGAAAACCTATACCTAATCCATTGCTGGGCTTAGACTCAACA V5 epitope nucleotide sequence,
                                                       SEQ ID NO: 150
GKPIPNPLLGLDST Linker nucleotide sequence (linker 5),
                                                       SEQ ID NO: 151
GGCAGCGGAAGC Linker amino acid sequence (linker 5),
                                                       SEQ ID NO: 152
GSGS P2A nucleotide sequence,
                                                       SEQ ID NO: 153
GCAACGAATTTTTCCCTGCTGAAACAGGCAGGGGACGTAGAGGAAAATCCTGGTCCT P2A amino acid sequence,
                                                       SEQ ID NO: 154
ATNFSLLKQAGDVEENPGP Linker nucleotide sequence (linker 6)
                                                        SEQ ID NO 155
ACGCGT Linker amino acid sequence (linker 6),
                                                       SEQ ID NO: 156
TR ΔCD19 nucleotide sequence,
                                                       SEQ ID NO: 157
ATGCCCCCTCCTAGACTGCTGTTTTTCCTGCTCTTTCTCACCCCAATGGAAGTTAGACCTGAG

GAACCACTGGTCGTTAAAGTGGAAGAAGGTGATAATGCTGTCCTCCAATGCCTTAAAGGGACC

AGCGACGGACCAACGCAGCAACTGACTTGGAGCCGGGAGTCCCCTCTCAAGCCGTTTCTCAA

GCTGTCACTTGGCCTGCCAGGTCTTGGTATTCACATGCGCCCCCTTGCCATTTGGCTCTTCAT

ATTCAATGTGTCTCAACAAATGGGTGGATTCTACCTTTGCCAGCCCGGCCCCCCTTCTGAGAA

AGCTTGGCAGCCTGGATGGACCGTCAATGTTGAAGGCTCCGGTGAGCTGTTTAGATGGAATG
```

-continued

```
TGAGCGACCTTGGCGGACTCGGTTGCGGACTGAAAAATAGGAGCTCTGAAGGACCCTCTTCT

CCCTCCGGTAAGTTGATGTCACCTAAGCTGTACGTGTGGGCCAAGGACCGCCCCGAAATCTG

GGAGGGCGAGCCTCCATGCCTGCCGCCTCGCGATTCACTGAACCAGTCTCTGTCCCAGGATC

TCACTATGGCGCCCGGATCTACTCTTTGGCTGTCTTGCGGCGTTCCCCCAGATAGCGTGTCA

AGAGGACCTCTGAGCTGGACCCACGTACACCCTAAGGGCCCTAAGAGCTTGTTGAGCCTGGA

ACTGAAGGACGACAGACCCGCACGCGATATGTGGGTAATGGAGACCGGCCTTCTGCTCCCTC

GCGCTACCGCACAGGATGCAGGGAAATACTACTGTCATAGAGGGAATCTGACTATGAGCTTT

CATCTCGAAATTACAGCACGGCCCGTTCTTTGGCATTGGCTCCTCCGGACTGGAGGCTGGAA

GGTGTCTGCCGTAACACTCGCTTACTTGATTTTTTGCCTGTGTAGCCTGGTTGGGATCCTGCA

TCTTCAGCGAGCCCTTGTATTGCGCCGAAAAAGAAAACGAATGACTGACCCTACACGACGATT

CTGA
```

ΔCD19 amino acid sequence,
SEQ ID NO: 158
```
MPPPRLLFFLLFLTPMEVRPEEPLVVKVEEGDNAVLQCLKGTSDGPTQQLTWSRESPLKPFLKLSL

GLPGLGIHMRPLAIWLFIFNVSQQMGGFYLCQPGPPSEKAWQPGWTVNVEGSGELFRWNVSDL

GGLGCGLKNRSSEGPSSPSGKLMSPKLYVWAKDRPEIWEGEPPCLPPRDSLNQSLSQDLTMAP

GSTLWLSCGVPPDSVSRGPLSWTHVHPKGPKSLLSLELKDDRPARDMWVMETGLLLPRATAQDA

GKYYCHRGNLTMSFHLEITARPVLHWLLRTGGWKVSAVTLAYLIFCLCSLVGILHLQRALVLRRK

RKRMTDPTRRF
```

Truncated MyD88 lacking the TIR domain
SEQ ID NO: 159
```
MAAGGPGAGSAAPVSSTSSLPLAALNMRVRRRLSLFLNVRTQVAADWTALAEEEMDFEYLEIRQLE

TQADPTGRLLDAWQGRPGASVGRLLDLLTKLGRDDVLLELGPSIEEDCQKYILKQQQEEAEKPLQ

VAAVDSSVPRTAELAGITTLDDPLGHMPERFDAFICYCPSDI
```

CD40 without the extracellular domain
SEQ ID NO: 160
```
AAGAAAGTTGCAAAGAAACCCACAAATAAAGCCCCACACCCTAAACAGGAACCCCAAGAAATC

AATTTCCCAGATGATCTCCCTGGATCTAATACTGCCGCCCCGGTCCAAGAAACCCTGCATGGT

TGCCAGCCTGTCACCCAAGAGGACGGAAAAGAATCACGGATTAGCGTACAAGAGAGACAA
```

CD40 without the extracellular domain
SEQ ID NO: 161
```
KKVAKKPTNKAPHPKQEPQEINFPDDLPGSNTAAPVQETLHGCQPVTQEDGKESRISVQERQ
```

CD3 zeta
SEQ ID NO: 162
```
AGAGTGAAGTTCAGCAGGAGCGCAGACGCCCCCGCGTACCAGCAGGGCCAGAACCAGCTCT

ATAACGAGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACAATGAAC

TGCAGAAAGATAAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGGACACCTACGAC

GCCCTTCACATGCAGGCCCTGCCCCCTCGC
```

CD3 zeta
SEQ ID NO: 163
```
RVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR
```

Provided below is an example of a plasmid insert coding for a chimeric antigen receptor that binds to Her2/Neu. The chimeric antigen receptor may be further modified by including costimulatory polypeptides such as, for example, but not limited to, CD28, OX40, and 4-1BB.

```
Signal peptide
                                             SEQ ID NO: 164
ATGGAGTTTGGACTTTCTTGGTTGTTTTTGGTGGCAATTCTGAAGGGTGTCCAGTGTAGCAGG Signal peptide
                                             SEQ ID NO: 165
MEFGLSWLFLVAILKGVQCSR FRP5 variable light chain (anti-Her2)
                                             SEQ ID NO: 166
GACATCCAATTGACACAATCACACAAATTTCTCTCAACTTCTGTAGGAGACAGAGTGAGCATAA

CCTGCAAAGCATCCCAGGACGTGTACAATGCTGTGGCTTGGTACCAACAGAAGCCTGGACAA

TCCCCAAAATTGCTGATTTATTCTGCCTCTAGTAGGTACACTGGGGTACCTTCTCGGTTTACG

GGCTCTGGGTCCGGACCAGATTTCACGTTCACAATCAGTTCCGTTCAAGCTGAAGACCTCGCT

GTTTATTTTTGCCAGCAGCACTTCCGAACCCCTTTTACTTTTGGCTCAGGCACTAAGTTGGAAA

TCAAGGCTTTG

FRP5 variable light chain (anti-Her2)
                                             SEQ ID NO: 167
DIQLTQSHKFLSTSVGDRVSITCKASQDVYNAVAWYQQKPGQSPKLLIYSASSRYTGVPSRFTGS

GSGPDFTFTISSVQAEDLAVYFCQQHFRTPFTFGSGTKLEIKAL

Flexible linker
                                             SEQ ID NO: 168
GGCGGAGGAAGCGGAGGTGGGGGC Flexible linker
                                             SEQ ID NO: 169
GGGSGGGG FRP5 variable heavy chain (anti-Her2/Neu)
                                             SEQ ID NO: 170
GAAGTCCAATTGCAACAGTCAGGCCCCGAATTGAAAAAGCCCGGCGAAACAGTGAAGATATC

TTGTAAAGCCTCCGGTTACCCTTTTACGAACTATGGAATGAACTGGGTCAAACAAGCCCCTGG

ACAGGGATTGAAGTGGATGGGATGGATCAATACATCAACAGGCGAGTCTACCTTCGCAGATG

ATTTCAAAGGTCGCTTTGACTTCTCACTGGAGACCAGTGCAAATACCGCCTACCTTCAGATTAA

CAATCTTAAAAGCGAGGATATGGCAACCTACTTTTGCGCAAGATGGGAAGTTTATCACGGGTA

CGTGCCATACTGGGGACAAGGAACGACAGTGACAGTTAGTAGC

FRP5 variable heavy chain (anti-Her2/Neu)
                                             SEQ ID NO: 171
EVQLQQSGPELKKPGETVKISCKASGYPFTNYGMNWVKQAPGQGLKWMGWINTSTGESTFADD

FKGRFDFSLETSANTAYLQINNLKSEDMATYFCARWEVYHGYVPYVVGQGTTVTVSS

Linker
                                             SEQ ID NO: 172
GGATCC

Linker
                                             SEQ ID NO: 173
GS

CD34 minimal epitope
                                             SEQ ID NO: 174
GAACTTCCTACTCAGGGGACTTTCTCAAACGTTAGCACAAACGTAAGT CD34 minimal epitope
                                             SEQ ID NO: 175
ELPTQGTFSNVSTNVS
```

```
CD8 alpha stalk
                                                   SEQ ID NO: 176
CCCGCCCCAAGACCCCCCACACCTGCGCCGACCATTGCTTCTCAACCCCTGAGTTTGAGACC

CGAGGCCTGCCGGCCAGCTGCCGGCGGGGCCGTGCATACAAGAGGACTCGATTTCGCTTGC

GAC

CD8 alpha stalk
                                                   SEQ ID NO: 177
PAPRPPTPAPTIASQPLSLRPEACRPAAGGAVHTRGLDFACD CD8 alpha transmembrane region
                                                   SEQ ID NO: 178
ATCTATATCTGGGCACCTCTCGCTGGCACCTGTGGAGTCCTTCTGCTCAGCCTGGTTATTACT

CTGTACTGTAATCACCGGAATCGCCGCCGCGTTTGTAAGTGTCCCAGG

CD8 alpha transmembrane region
                                                   SEQ ID NO: 179
IYIWAPLAGTCGVLLLSLVITLYCNHRNRRRVCKCPR Linker
                                                   SEQ ID NO: 180
Ctcgag Linker
                                                   SEQ ID NO: 181
LE CD3 zeta cytoplasmic domain
                                                   SEQ ID NO: 182
AGAGTGAAGTTCAGCAGGAGCGCAGACGCCCCCGCGTACCAGCAGGGCCAGAACCAGCTCT

ATAACGAGCTCAATCTAGGACGAAGAGAGGAGTACGATGTTTTGGACAAGAGACGTGGCCGG

GACCCTGAGATGGGGGGAAAGCCGAGAAGGAAGAACCCTCAGGAAGGCCTGTACAATGAAC

TGCAGAAAGATAAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGGACACCTACGAC

GCCCTTCACATGCAGGCCCTGCCCCCTCGC

CD3 zeta cytoplasmic domain
                                                   SEQ ID NO: 183
RVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

Additional sequences
CD28 nt,
                                                   SEQ ID NO: 184
TTCTGGGTACTGGTTGTAGTCGGTGGCGTACTTGCTTGTTATTCTCTTCTTGTTACCGTAGCCT

TCATTATATTCTGGGTCCGATCAAAGCGCTCAAGACTCCTCCATTCCGATTATATGAACATGAC

ACCTCGCCGACCTGGTCCTACACGCAAACATTATCAACCCTACGCACCCCCCCGAGACTTCG

CTGCTTATCGATCC

CD28 aa,
                                                   SEQ ID NO: 185
FWVLVVVGGVLACYSLLVTVAFIIFWVRSKRSRLLHSDYMNMTPRRPGPTRKHYQPYAPPRDFAA

YRS

OX40 nt,
                                                   SEQ ID NO: 186
GTTGCCGCCATCCTGGGCCTGGGCCTGGTGCTGGGGCTGCTGGGCCCCCTGGCCATCCTGC

TGGCCCTGTACCTGCTCCGGGACCAGAGGCTGCCCCCCGATGCCCACAAGCCCCCTGGGGG

AGGCAGTTTCCGGACCCCCATCCAAGAGGAGCAGGCCGACGCCCACTCCACCCTGGCCAAG

ATC
```

-continued

OX40 aa,

SEQ ID NO: 187

VAAILGLGLVLGLLGPLAILLALYLLRRDQRLPPDAHKPPGGGSFRTPIQEEQADAHSTLAKI 4-1BB nt,

SEQ ID NO: 188

AGTGTAGTTAAAAGAGGAAGAAAAAAGTTGCTGTATATATTTAAACAACCATTTATGAGACCAG

TGCAAACCACCCAAGAAGAAGACGGATGTTCATGCAGATTCCCAGAAGAAGAAGAAGGAGGA

TGTGAATTG 4-1BB aa,

SEQ ID NO: 189

SVVKRGRKKLLYIFKQPFMRPVQTTQEEDGCSCRFPEEEEGGCEL

Example 25: Activation of Primary T Cells with Inducible MyD88, CD40, or MyD88/CD40

FIG. 41 provides a schematic of inducible MyD88, CD40, and MyD88/CD40 chimeric polypeptides. To examine whether MyD88, CD40 or both molecules should be included as endodomains in potential chimeric antigen receptor constructs, four distinct vectors were designed containing the AP1903-binding domains only (Fv'Fv), or genetically fused with MyD88 (iMyD88), CD40 (iCD40) or with both MyD88 and CD40 (iMC) (FIG. 41a). CD3/CD28-activated T cells were transduced, and the transduction efficiency of each of the vectors was measured by flow cytometric detection of CD19 on the surface of CD3 T cells (CD3+CD19+), showing that each of the retroviruses were sufficiently expressed in primary T cells (57%-95%) compared to non-transduced T cells (FIG. 41b). The ability of iMyD88, iCD40 or iMC to activate T cells following exposure to AP1903 by measuring IFN-γ and IL-6 production by ELISA was then assayed. It was observed that only iMC-transduced T cells produced significant quantities of both IFN-γ and IL-6 following AP1903 activation, whereas neither NT, iMyD88, nor iCD40 showed cytokine production (FIGS. 41c and d). These data suggest that MyD88 and CD40 synergize as activation signaling molecules in human T cells, and that a CAR molecule should benefit from inclusion of the composite MC signaling domain.

A set of experiments was performed to examine whether MyD88, CD40 or both components were required for optimum T cell stimulation using the iMC molecule. It was observed that neither MyD88 nor CD40 could sufficiently induce T cell activation, as measured by cytokine production (IL-2 and IL-6), but when combined as a single fusion protein, could induce potent T cell activation (FIG. 41).

Apart from survival and growth advantages, MC-induced costimulation may also provide additional functions to CAR-modified T cells. Medzhitov and colleagues recently demonstrated that MyD88 signaling was critical for both Th1 and Th17 responses and that it acted via IL-1 to render CD4+ T cells refractory to regulatory T cell (Treg)-driven inhibition. Experiments with iMC show that IL-1a and β are secreted following AP1903 activation. In addition, Martin et al demonstrated that CD40 signaling in CD8+ T cells via Ras, PI3K and protein kinase C, result in NF-κB-dependent induction of cytotoxic mediators granzyme and perforin that lyse CD4+CD25+ Treg cells. Thus, MyD88 and CD40 co-activation may render CAR-T cells resistant to the immunosuppressive effects of Treg cells, a function that could be critically important in the treatment of solid tumors and other types of cancers.

An inducible MyD88/CD40 chimeric stimulating molecule may also be expressed in a cell along with a CAR, which may, for example, comprise the scFv polypeptide, and the CD3-ζ chain. In this method, the iCSM molecule is used in combination with a CAR, thereby segregating CAR signaling into two separate functions. This second function, provided by the CAR, provides antigen-specific cytotoxicity to the engineered T cells. For example, a CAR with specificity against PSMA may be expressed in T cells along with a MyD88/CD40 inducible chimeric stimulating molecule. Also, the MyD88/CD40 inducible CSM and the CAR portions may be transfected or transduced into the cells either on the same vector, in cis, or on separate vectors, in trans. Thus, the two polypeptides may be expressed using two nucleic acids, such as, for example, two plasmids or two viruses, and the T cells may be, for example, transfected twice, or in particular embodiments, the two nucleic acids may be co-transfected. In other embodiments, the two polypeptides may be expressed in one nucleic acid, such as, for example, in the same plasmid or virus. The nucleic acid may express the two polypeptides using two separate promoters, one for the CAR and one for the iCSM. Or, in other embodiments, the two polypeptides may be expressed using the same promoter. In this embodiment, the two polypeptides may be separated by a cleavable polypeptide, such as, for example, a 2A sequence. The engineered T may, for example, be administered to a subject to generate a specific immune response, for example one directed against a prostate cancer tumor.

In some embodiments, the inducible chimeric stimulating molecule does not comprise CD40. It is understood that the methods, constructs, polypeptide, and cells provided for the MyD88/CD40 chimeric stimulating molecules may be modified as necessary for expression and use of the MyD88 chimeric stimulating molecules.

REFERENCES

The following references are cited in, or provide additional information that may be relevant, including, for example, in the examples herein.

1. Till B G, Jensen M C, Wang J, et al: CD20-specific adoptive immunotherapy for lymphoma using a chimeric antigen receptor with both CD28 and 4-1BB domains: pilot clinical trial results. Blood 119:3940-50, 2012.
2. Pule M A, Savoldo B, Myers G D, et al: Virus-specific T cells engineered to coexpress tumor-specific receptors: persistence and antitumor activity in individuals with neuroblastoma. Nat Med 14:1264-70, 2008.
3. Kershaw M H, Westwood J A, Parker L L, et al: A phase I study on adoptive immunotherapy using gene-modified T cells for ovarian cancer. Clin Cancer Res 12:6106-15, 2006.

4. Carpenito C, Milone M C, Hassan R, et al: Control of large, established tumor xenografts with genetically retargeted human T cells containing CD28 and CD137 domains. Proc Natl Acad Sci USA 106:3360-5, 2009.
5. Song D G, Ye Q, Poussin M, et al: CD27 costimulation augments the survival and antitumor activity of redirected human T cells in vivo. Blood 119:696-706, 2012.
6. Kalos M, Levine B L, Porter D L, et al: T cells with chimeric antigen receptors have potent antitumor effects and can establish memory in patients with advanced leukemia. Sci Transl Med 3:95ra73, 2011.
7. Porter D L, Levine B L, Kalos M, et al: Chimeric antigen receptor-modified T cells in chronic lymphoid leukemia. N Engl J Med 365:725-33, 2011.
8. Brentjens R J, Davila M L, Riviere I, et al: CD19-targeted T cells rapidly induce molecular remissions in adults with chemotherapy-refractory acute lymphoblastic leukemia. Sci Transl Med 5:177ra38, 2013.
9. Pule M A, Straathof K C, Dotti G, et al: A chimeric T cell antigen receptor that augments cytokine release and supports clonal expansion of primary human T cells. Mol Ther 12:933-41, 2005.
10. Finney H M, Akbar A N, Lawson A D: Activation of resting human primary T cells with chimeric receptors: costimulation from CD28, inducible costimulator, CD134, and CD137 in series with signals from the TCR zeta chain. J Immunol 172:104-13, 2004.
11. Guedan S, Chen X, Madar A, et al: ICOS-based chimeric antigen receptors program bipolar TH17/TH1 cells. Blood, 2014.
12. Narayanan P, Lapteva N, Seethammagari M, et al: A composite MyD88/CD40 switch synergistically activates mouse and human dendritic cells for enhanced antitumor efficacy. J Clin Invest 121:1524-34, 2011.
13. Anurathapan U, Chan R C, Hindi H F, et al: Kinetics of tumor destruction by chimeric antigen receptor-modified T cells. Mol Ther 22:623-33, 2014.
14. Craddock J A, Lu A, Bear A, et al: Enhanced tumor trafficking of GD2 chimeric antigen receptor T cells by expression of the chemokine receptor CCR2b. J Immunother 33:780-8, 2010.
15. Lee D W, Gardner R, Porter D L, et al: Current concepts in the diagnosis and management of cytokine release syndrome. Blood 124:188-95, 2014.
16. Becker M L, Near R, Mudgett-Hunter M, et al: Expression of a hybrid immunoglobulin-T cell receptor protein in transgenic mice. Cell 58:911-21, 1989.
17. Goverman J, Gomez S M, Segesman K D, et al: Chimeric immunoglobulin-T cell receptor proteins form functional receptors: implications for T cell receptor complex formation and activation. Cell 60:929-39, 1990.
18. Gross G, Waks T, Eshhar Z: Expression of immunoglobulin-T-cell receptor chimeric molecules as functional receptors with antibody-type specificity. Proc Natl Acad Sci USA 86:10024-8, 1989.
19. Kuwana Y, Asakura Y, Utsunomiya N, et al: Expression of chimeric receptor composed of immunoglobulin-derived V regions and T-cell receptor-derived C regions. Biochem Biophys Res Commun 149:960-8, 1987.
20. Jensen M C, Popplewell L, Cooper L J, et al: Antitransgene rejection responses contribute to attenuated persistence of adoptively transferred CD20/CD19-specific chimeric antigen receptor redirected T cells in humans. Biol Blood Marrow Transplant 16:1245-56, 2010.
21. Park J R, Digiusto D L, Slovak M, et al: Adoptive transfer of chimeric antigen receptor re-directed cytolytic T lymphocyte clones in patients with neuroblastoma. Mol Ther 15:825-33, 2007.
22. Ramos C A, Dotti G: Chimeric antigen receptor (CAR)-engineered lymphocytes for cancer therapy. Expert Opin Biol Ther 11:855-73, 2011.
23. Finney H M, Lawson A D, Bebbington C R, et al: Chimeric receptors providing both primary and costimulatory signaling in T cells from a single gene product. J Immunol 161:2791-7, 1998.
24. Hombach A, Wieczarkowiecz A, Marquardt T, et al: Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol 167:6123-31, 2001.
25. Maher J, Brentjens R J, Gunset G, et al: Human T-lymphocyte cytotoxicity and proliferation directed by a single chimeric TCRzeta/CD28 receptor. Nat Biotechnol 20:70-5, 2002.
26. Imai C, Mihara K, Andreansky M, et al: Chimeric receptors with 4-1BB signaling capacity provoke potent cytotoxicity against acute lymphoblastic leukemia. Leukemia 18:676-84, 2004.
27. Wang J, Jensen M, Lin Y, et al: Optimizing adoptive polyclonal T cell immunotherapy of lymphomas, using a chimeric T cell receptor possessing CD28 and CD137 costimulatory domains. Hum Gene Ther 18:712-25, 2007.
28. Zhao Y, Wang Q J, Yang S, et al: A herceptin-based chimeric antigen receptor with modified signaling domains leads to enhanced survival of transduced T lymphocytes and antitumor activity. J Immunol 183:5563-74, 2009.
29. Milone M C, Fish J D, Carpenito C, et al: Chimeric receptors containing CD137 signal transduction domains mediate enhanced survival of T cells and increased anti-leukemic efficacy in vivo. Mol Ther 17:1453-64, 2009.
30. Yvon E, Del Vecchio M, Savoldo B, et al: Immunotherapy of metastatic melanoma using genetically engineered GD2-specific T cells. Clin Cancer Res 15:5852-60, 2009.
31. Savoldo B, Ramos C A, Liu E, et al: CD28 costimulation improves expansion and persistence of chimeric antigen receptor-modified T cells in lymphoma patients. J Clin Invest 121:1822-6, 2011.
32. Kalinski P, Hilkens C M, Wierenga E A, et al: T-cell priming by type-1 and type-2 polarized dendritic cells: the concept of a third signal. Immunol Today 20:561-7, 1999.
33. Kemnade J O, Seethammagari M, Narayanan P, et al: Off-the-shelf Adenoviral-mediated Immunotherapy via Bicistronic Expression of Tumor Antigen and iMyD88/CD40 Adjuvant. Mol Ther, 2012.
34. Schenten D, Nish S A, Yu S, et al: Signaling through the adaptor molecule MyD88 in CD4$^+$ T cells is required to overcome suppression by regulatory T cells. Immunity 40:78-90, 2014.
35. Martin S, Pahari S, Sudan R, et al: CD40 signaling in CD8$^+$CD40$^+$ T cells turns on contra-T regulatory cell functions. J Immunol 184:5510-8, 2010.

Example 26: Expression of MyD88/CD40 Costimulating Molecules in T Cell-Receptor-Expressing Cells and Tumor Infiltrating Lymphocytes The modified cells that express the MyD88/CD40 inducible costimulating molecules provided herein may also express a T cell receptor. In these examples, the T cell receptor may be endogenous to the cell, or may be provided to the cell through transfection or transformation with a nucleic acid comprising a polynucleotide encoding a T cell receptor. In certain examples, the T cell receptor may be expressed on the same nucleic acid vector as the MyD88/CD40 inducible costimulating molecule. In some examples, the modified cells are tumor infiltrating lymphocytes.

Example 27: Inducing Controlled Levels of Costimulation of CAR-T Cell Activity by Administration of Varying Dosages of Multimeric Ligand Although rapid and complete elimination of target cells (for example, tumor cells) may be desired in some clinical scenarios, there are many other scenarios in which partial elimination and reduction of these cells may be more desirable. The likelihood of such scenarios is governed by various properties inherent to the chimeric antigen receptor (CAR)-T cell target and the types of associated adverse events (AEs). These properties include the molecule and organ targeted the severity of toxicity, and the rapidity of onset. There are at least 5 different types of CAR-T cell targets that have different profiles with respect to these properties that govern efficacy and safety that may be associated with clinical scenarios that might benefit from delivery of more controlled amounts of the multimeric ligand in order to achieve the appropriate level of CAR-T cell activity for each patient—obtaining a sufficient therapeutic effect, yet balancing with the need to avoid adverse events, such as, for example, cytokine storms or off-target toxicity. In these examples, more controlled levels of costimulation may be desired, using sufficient dosages of the multimeric ligand for therapy, and avoiding an excess of activity which may lead to adverse side effects.

Category 1: Differentiation antigens (e.g., MART, gp100, CEA, Her-2/neu) are expressed at low levels in adults. CAR T cells that target these antigens have been associated with high rates of serious and life threatening AEs that have limited their clinical viability, and most have not progressed passed early stage trials. Unexpected patient complications and death has occurred due to low level expression of these antigens in normal organs (e.g., lung).

Category 2: Targets non-essential tissue (e.g., CD19 on B-cells, thyroglobulin on thyroid, PSMA on prostate cells). These CAR T cells have shown dramatic anti-cancer activity in patients, but have also been associated with SAEs including patient deaths, often related to tumor lysis syndrome and cytokine storm in patients otherwise responding to treatment.

Category 3: Cancer-testis antigens (CTAs) (e.g., NY-ESO-1, MAGE-A1, -A3; 50% of cancers express either of these two families.) CTAs are expressed in germ cells and some tumors. Similar concerns as Category 1 due to cross-reactivity with family members.

Category 4: Unique antigens (e.g., EGFRvIII) are probably best when available, but still only minority of tumors.

Category 5: Tumor stroma (e.g., VEGF-R2, FAP) High in tumor, low level in normal tissue. There have been a few complete responses (CRs) but the potential risk for SAEs is high.

A costimulatory molecule rheostat that could "dial in" increasing levels of CAR-T cell therapy with higher doses of chemical inducer, such as, for example, AP1903 or AP20187, and decreasing levels when needed to avoid adverse events might better fill the unmet clinical need by allowing a measured response to different clinical scenarios of cell therapy toxicity. Using the inducible MyD88/CD40 costimulatory molecule technology as a rheostat would maintain the ability to achieve >90% rapid killing at a full dose of 0.5-1 mg/kg, while allowing clinically titratable therapy, such as anti-tumor therapy.

In one embodiment, a dose escalation from 0.01 to 1 mg/kg is given in as little as 15-30 minute increments, or increments over greater periods of time, such as hour, half day, 24 hour, or even daily, weekly, or monthly increments, while the patient's adverse event(s) is monitored for response.

In another embodiment, a continuous infusion pump is used to initiate an AP1903 infusion at a very low dose and is slowly titrated higher in as little as 15-30 minute increments and the patient's adverse event is monitored.

In another embodiment, a slow release formulation (oral, IM, SQ, SL) of AP1903 is given over several days or weeks to slowly achieve control of a subacute, non-life-threatening cell therapy.

Example 28: Representative Embodiments

Provided hereafter are examples of certain embodiments of the technology.

A1. A Nucleic Acid Comprising
   a) a first polynucleotide encoding an inducible chimeric stimulating molecule, wherein the inducible chimeric stimulating molecule comprises (i) a MyD88 polypeptide region or a truncated MyD88 polypeptide region lacking the TIR domain; (ii) a CD40 cytoplasmic polypeptide region lacking the CD40 extracellular domain, and (iii) a multimerization region; and
   b) a second polynucleotide encoding a chimeric antigen receptor.

A2. The nucleic acid of embodiment A1, wherein the inducible chimeric stimulating molecule further comprises (iv) a membrane targeting region.

A3. The nucleic acid of embodiment A1, wherein the chimeric stimulating molecule is a polypeptide which comprises regions (i)-(iii) in order from the amino to the carboxyl terminal of the polypeptide of (i), (ii), (iii).

A4. The nucleic acid of embodiment A2, wherein the chimeric stimulating molecule is a polypeptide which comprises regions (i)-(iv) in order from the amino to the carboxyl terminal of the polypeptide of (iv), (i), (ii), (iii).

A5. The nucleic acid of any one of embodiments A1-A4, wherein the multimerization region is a ligand binding region.

A6. The nucleic acid of embodiment A5, wherein the ligand binding region is an FKBP12 region.

A7. The nucleic acid of embodiment A6, wherein the FKBP12 region is an FKBP12v36 region.

A8. The nucleic acid of embodiment A6, wherein the FKBP12 region is Fv'Fvls.

A9. The nucleic acid of embodiment A9, wherein the multimerization region comprises a polypeptide having an amino acid sequence of SEQ ID NO: 11, or a functional fragment thereof, and a polypeptide having an amino acid sequence of SEQ ID NO: 13, or a functional fragment thereof, or further comprises a polypeptide that is encoded by a nucleotide sequence in SEQ ID NO: 12, or a functional fragment thereof.

A10. The nucleic acid of embodiment A10, wherein the multimerization region further comprises a polypeptide having an amino acid sequence of SEQ ID NO: 13, or a functional fragment thereof or further comprises a polypeptide that is encoded by a nucleotide sequence in SEQ ID NO: 12, or a functional fragment thereof.

A11. The nucleic acid of embodiment A9, further comprising an Fv polypeptide variant wherein residue 36 is valine.

A12. The nucleic acid of any one of embodiments A5-A11, wherein the ligand is an FK506 dimer or a dimeric FK506 analog ligand.

A13. The nucleic acid of embodiment A12, wherein the ligand is AP1903.

A14. The nucleic acid of any one of embodiments A1-A13, wherein at least one of regions (i)-(iv) is encoded by a codon-optimized nucleotide sequence.

A15. The nucleic acid of any one of embodiments A1-A14, further comprising a promoter that is operably linked to both the first polynucleotide and the second polynucleotide.

A16. The nucleic acid of any one of embodiments A1-A14, further comprising a first promoter operably linked to the first polynucleotide and a second promoter operably linked to the second polynucleotide.

A17. The nucleic acid of any one of embodiments A1-A15, further comprising a third polynucleotide encoding a linker polypeptide between the first and second polynucleotides, wherein the linker polypeptide separates the translation products of the first and second polynucleotides during or after translation.

A18. The nucleic acid of embodiment A17, wherein the linker polypeptide is a 2A polypeptide.

A19. The nucleic acid of any one of embodiments A1-A18, wherein the chimeric antigen receptor comprises
(i) a transmembrane region; (ii) a T cell activation molecule; and (iii) an antigen recognition moiety.

A20. The nucleic acid of embodiment A19, wherein the chimeric antigen receptor further comprises a co-stimulatory molecule.

A21. The nucleic acid of embodiment A20, wherein the co-stimulatory molecule is selected from the group consisting of CD28, OX40, and 4-1BB.

A22. The nucleic acid of any one of embodiments A19-A21, wherein the T cell activation molecule is an ITAM-containing, Signal 1 conferring molecule.

A23. The nucleic acid of any one of embodiments A19-A22, wherein the T cell activation molecule is a CD3ζ polypeptide.

A24. The nucleic acid of any one of embodiments A19-A22, wherein the T cell activation molecule is an Fc epsilon receptor gamma (FcεR1γ) subunit polypeptide.

A25. The nucleic acid of any one of embodiments A19-A24, wherein the antigen recognition moiety binds to an antigen on a tumor cell.

A26. The nucleic acid of any one of embodiments A19-A24, wherein the antigen recognition moiety binds to an antigen on a cell involved in a hyperproliferative disease.

A27. The nucleic acid of any one of embodiments A19-A24, wherein the antigen recognition moiety binds to an antigen selected from the group consisting of PSMA, PSCA, MUC1, CD19, ROR1, Mesothelin, GD2, CD123, MUC16, and Her2/Neu.

A28. The nucleic acid of any one of embodiments A19-A24, wherein the antigen recognition moiety binds to PSCA.

A29. The nucleic acid of any one of embodiments A19-A24, wherein the antigen recognition moiety binds to CD19.

A30. The nucleic acid of any one of embodiments A19-A24, wherein the antigen recognition moiety binds to Her2/Neu.

A31. The nucleic acid of any one of embodiments A19-A24, wherein the antigen recognition moiety binds to a viral or bacterial antigen.

A32. The nucleic acid of any one of embodiments A19-A31, wherein the antigen recognition moiety is a single chain variable fragment.

A33. The nucleic acid of any one of embodiments A19-A32, wherein the transmembrane region is a CD28 transmembrane region.

A34. The nucleic acid of any one of embodiments A19-A32, wherein the transmembrane region is a CD8 transmembrane region.

A35. The nucleic acid of embodiment A34, further comprising a CD8 stalk region.

A36. The nucleic acid of any one of embodiments A1-A35, wherein the chimeric stimulating molecule comprises a MyD88 polypeptide having the amino acid sequence of SEQ ID NO: 49 or a truncated MyD88 polypeptide having the amino acid sequence of SEQ ID NO: 137, or a functional fragment thereof.

A37. The nucleic acid of any one of embodiments A1-A36, wherein the MyD88 polypeptide has the amino acid sequence of SEQ ID NO: 49.

A38. The nucleic acid of any one of embodiments A1-A37, wherein the cytoplasmic CD40 polypeptide has the amino acid sequence of SEQ ID NO: 9, or a functional fragment thereof.

A40. The nucleic acid of any one of embodiments A23-A38, wherein the CD3 polypeptide comprises an amino acid sequence of SEQ ID NO: 39, or a functional fragment thereof.

A41. The nucleic acid of any one of embodiments A2-A40, wherein the membrane targeting region is selected from the group consisting of a myristoylation region, palmitoylation region, prenylation region, and transmembrane sequences of receptors.

A42. The nucleic acid of any one of embodiments A2-A40, wherein the membrane targeting region is a myristoylation region.

A43. The nucleic acid of embodiment A42, wherein the myristoylation region has an amino acid sequence of SEQ ID NO: 3 or a functional fragment thereof.

A44. The nucleic acid of any one of embodiments A1-A43, wherein the nucleic acid is contained within a viral vector.

A45. The nucleic acid of embodiment A44, wherein the viral vector is a retroviral vector.

A46. The nucleic acid of embodiment A44, wherein the retroviral vector is a murine leukemia virus vector.

A47. The nucleic acid of embodiment A44, wherein the retroviral vector is an SFG vector.

A48. The nucleic acid of embodiment A44, wherein the viral vector is an adenoviral vector.

A49. The nucleic acid of embodiment A44, wherein the viral vector is a lentiviral vector.

A50. The nucleic acid of embodiment A44, wherein the viral vector is selected from the group consisting of adeno-associated virus (AAV), Herpes virus, and Vaccinia virus.

A51. The nucleic acid of any one of embodiments A1-A43, wherein the nucleic acid is contained within a plasmid.

A52. A chimeric stimulating molecule polypeptide encoded by the nucleic acid of any one of embodiments A2-A19

A53. A modified cell transfected or transduced with a nucleic acid of any one of embodiments A1-A51.

A54. The modified cell of embodiment A53, wherein the modified cell is a T cell, tumor infiltrating lymphocyte, NK-T cell, TCR-expressing cell, or NK cell.

A55. The modified cell of embodiment A53, wherein the cell is a T cell.

A56. The modified cell of any one of embodiments A53-A55, wherein the cell is obtained or prepared from bone marrow.

A57. The modified cell of any one of embodiments A53-A55, wherein the cell is obtained or prepared from umbilical cord blood.

A58. The modified cell of any one of embodiments A53-A55, wherein the cell is obtained or prepared from peripheral blood.

A59. The modified cell of any one of embodiments A53-A55, wherein the cell is obtained or prepared from peripheral blood mononuclear cells.

A60. The modified cell of any one of embodiments A53-A55, wherein the cell is a human cell.

A61. The modified cell of any one of embodiments A53-A60, wherein the cell is transfected or transduced by the nucleic acid vector using a method selected from the group consisting of electroporation, sonoporation, biolistics (e.g., Gene Gun with Au-particles), lipid transfection, polymer transfection, nanoparticles, or polyplexes.

A62. A method for stimulating a T cell-mediated immune response in a subject, comprising administering
 a) a modified cell of any one of embodiments A53-A61 to the subject; and
 b) an effective amount of a multimeric ligand that binds to the multimerization region to stimulate a T cell-mediated immune response in the subject.

A63. The method of embodiment A62, wherein the chimeric antigen receptor binds to a target cell.

A64. The method of embodiment A63, wherein the target cell is a tumor cell.

A65. The method of any one of embodiments A63-A64, wherein the number or concentration of target cells in the subject is reduced following administration of the modified cell.

A66. The method of any one of embodiments A62-A65, further comprising measuring the number or concentration of target cells in a first sample obtained from the subject before administering the modified cell or ligand, measuring the number or concentration of target cells in a second sample obtained from the subject after administration of the modified cell and ligand, and determining an increase or decrease of the number or concentration of target cells in the second sample compared to the number or concentration of target cells in the first sample.

A67. The method of embodiment A66, wherein the concentration of target cells in the second sample is decreased compared to the concentration of target cells in the first sample.

A68. The method of embodiment A66, wherein the concentration of target cells in the second sample is increased compared to the concentration of target cells in the first sample.

A69. The method of any one of embodiments A66-A68, wherein an additional dose of ligand is administered to the subject.

A69.1. The method of any one of embodiments A62-A69, wherein an effective amount of multimeric ligand is an amount effective to reduce the number or concentration of target cells and to reduce the symptoms of cytoxicity.

A69.2. The method of embodiment A62-A69.1, wherein following administration of the multimeric ligand, the level of cytoxicity symptoms is determined in the subject, and (i) the administration of the multimeric ligand is discontinued or (ii) an additional dose of multimeric ligand is administered that is lower than the previous dose of multimeric ligand administered.

A69.3. The method of embodiment A62-A69.1, wherein following administration of the multimeric ligand, the level of cytoxicity symptoms is determined in the subject, and an additional dose of multimeric ligand is administered that is higher than the previous dose of multimeric ligand administered.

A69.4. The method of embodiment A62-A69.1, wherein following administration of the multimeric ligand, the number or concentration of target cells in the subject is determined, and (i) the administration of the multimeric ligand is discontinued or (ii) an additional dose of multimeric ligand is administered that is lower than the previous dose of multimeric ligand administered.

A69.5. The method of embodiment A62-A69.1, wherein following administration of the multimeric ligand, the number or concentration of target cells in the subject is determined, and an additional dose of multimeric ligand is administered that is higher than the previous dose of multimeric ligand administered.

A69.6. The method of embodiment 69.5 wherein the additional dose of multimeric ligand is from 120% to 200% greater than the previous dose.

A69.7. The method of embodiment A69.5, wherein the additional dose of multimeric ligand is about 150% greater than the previous dose.

A70. A method for providing anti-tumor immunity to a subject, comprising administering to the subject an effective amount of a modified cell of any one of embodiments A53-A61 and administering a ligand that binds to the multimerization region to provide anti-tumor immunity to the subject.

A71. A method for treating a subject having a disease or condition associated with an elevated expression of a target antigen, comprising administering to the subject an effective amount of a modified cell of any one of embodiments A53-A61, and an effective amount of a ligand that binds to the multimerization region.

A72. The method of embodiment A71, wherein the target antigen is a tumor antigen.

A73. The method of any one of embodiments A53-A72, wherein the modified cells are autologous T cells.

A74. The method of any one of embodiments A53-A72, wherein the modified cells are allogeneic T cells.

A75. A method for reducing the size of a tumor in a subject, comprising administering a modified cell of any one of embodiments A53-A61 to the subject, wherein the antigen recognition moiety binds to an antigen on the tumor.

A76. The method of any one of embodiments A62-A75, wherein the subject has been diagnosed as having a tumor.

A76. The method of any one of embodiments A62-A76, wherein the subject has cancer.

A77. The method of any one of embodiments A62-A76, wherein the subject has a solid tumor.

A78. The method of any one of embodiments A62-A76, wherein the modified cell is a tumor infiltrating lymphocyte or a T cell.

A79. The method of any one of embodiments A62-A78, wherein the modified cell is delivered to a tumor bed.

A80. The method of embodiment A76, wherein the cancer is present in the blood or bone marrow of the subject.

A81. The method of any one of embodiments A62-A76, wherein the subject has a blood or bone marrow disease.

A82. The method of any one of embodiments A62-A76, wherein the subject has been diagnosed with any condition or condition that can be alleviated by stem cell transplantation.

A83. The method of any one of embodiments A62-A76, wherein the subject has been diagnosed with sickle cell anemia or metachromatic leukodystrophy.

A84. The method of any one of embodiments A62-A76, wherein the subject has been diagnosed with a condition selected from the group consisting of a primary immune deficiency condition, hemophagocytosis lymphohistiocytosis (HAH) or other hemophagocytic condition, an inherited marrow failure condition, a hemoglobinopathy, a metabolic condition, and an osteoclast condition.

A84. The method of any one of embodiments A62-A76, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Aeukocyte Adhesion Deficiency, DOCA 8 Deficiency, IL-10 Deficiency/IL-10 Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

A85. The method of any one of embodiments A62-A84, further comprising determining whether an additional dose of the ligand should be administered to the subject.

A86. The method of any one of embodiments A62-A85, further comprising administering an additional dose of the ligand to the subject, wherein the disease or condition symptoms remain or are detected following a reduction in symptoms.

A86.1. The method of any one of embodiments A71-A86, wherein an effective amount of multimeric ligand is an amount effective to reduce the number or concentration of target antigen-expressing cells or the degree of tissue infiltration of the target antigen-expressing cells and to reduce the symptoms of cytotoxicity.

A86.2. The method of embodiment A71-A86.1, wherein following administration of the multimeric ligand, the level of cytoxicity symptoms is determined in the subject, and (i) the administration of the multimeric ligand is discontinued or (ii) an additional dose of multimeric ligand is administered that is lower than the previous dose of multimeric ligand administered.

A86.3. The method of embodiment A71-A86, wherein following administration of the multimeric ligand, the level of cytoxicity symptoms is determined in the subject, and an additional dose of multimeric ligand is administered that is higher than the previous dose of multimeric ligand administered.

A86.4. The method of embodiment A71-A86.3, wherein following administration of the multimeric ligand, the number or concentration of target antigen-expressing cells or the degree of tissue infiltration of the target antigen-expressing cells in the subject is determined, and (i) the administration of the multimeric ligand is discontinued or (ii) an additional dose of multimeric ligand is administered that is lower than the previous dose of multimeric ligand administered.

A86.5. The method of embodiment A71-A86.3, wherein following administration of the multimeric ligand, the number or concentration of target antigen-expressing cells or the degree of tissue infiltration of the target antigen-expressing cells in the subject is determined, and an additional dose of multimeric ligand is administered that is higher than the previous dose of multimeric ligand administered.

A87. The method of any one of embodiments A62-A86.5, further comprising
  identifying the presence, absence or stage of a condition or disease in a subject; and
  transmitting an indication to administer the ligand of any one of embodiments A53-A61, maintain a subsequent dosage of the ligand, or adjust a subsequent dosage of the ligand administered to the subject based on the presence, absence or stage of the condition or disease identified in the subject.

A88. The method of any one of embodiments A62-A87, wherein the condition is leukemia.

A89. The method of any one of embodiments A62-A87, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

A90. The method of any one of embodiments A62-A89, wherein the modified cell is transfected or transduced ex vivo.

A91. The modified cell of any one of embodiments A62-A89, wherein the modified cell is transfected or transduced in vivo.

A92. The method of any one of embodiments A62-A90 wherein the ligand is AP1903.

A93. A method for expressing a chimeric stimulating molecule in a cell, comprising contacting a nucleic acid of any one of embodiments A1 to A51 with a cell under conditions in which the nucleic acid is incorporated into the cell, whereby the cell expresses the chimeric antigen receptor from the incorporated nucleic acid.

A94. The method of embodiment A93, wherein the nucleic acid is contacted with the cell ex vivo.

A95. The method of embodiment A93, wherein the nucleic acid is contacted with the cell in vivo.

B1. A method for treating a subject having a disease or condition associated with an elevated expression of a target antigen, comprising administering a multimeric ligand that binds to a multimeric ligand binding region, wherein
  a) the multimeric ligand binds to an inducible chimeric stimulating molecule comprising the multimeric ligand region, a MyD88 polypeptide region or a truncated MyD88 polypeptide region lacking the TIR domain, and a CD40 cytoplasmic polypeptide region lacking the CD40 extracellular domain;
  b) T cells circulating in the subject express (i) the inducible chimeric stimulating molecule; and (ii) a chimeric antigen receptor that binds to the target antigen;
  c) the target antigen is present on target cells circulating in the subject; and
  d) the number or concentration of target cells in the subject is reduced following administration of the multimeric ligand.

B2. The method of embodiment B1, wherein the inducible chimeric stimulating molecule further comprises a membrane targeting region.

B3. The method of any one of embodiments B1 or B2, wherein the chimeric stimulating molecule-expressing T cells comprise a nucleic acid of any one of embodiments A1-A51.

B4. The method of any one of embodiments B1-B3, wherein the target antigen is expressed by a tumor cell, and the chimeric antigen receptor binds to the tumor cell.

B5. The method of any one of embodiments B1-B4, further comprising measuring the number or concentration of target cells in a first sample obtained from the subject before administering the modified cell or ligand, measuring the number or concentration of target cells in a second sample obtained from the subject after administration of the modified cell and ligand, and determining an increase or decrease of the number or concentration of target cells in the second sample compared to the number or concentration of target cells in the first sample.

B6. The method of embodiment B5, wherein the concentration of target cells in the second sample is decreased compared to the concentration of target cells in the first sample.

B7. The method of embodiment B5, wherein the concentration of target cells in the second sample is increased compared to the concentration of target cells in the first sample.

B8. The method of any one of embodiments B1-B7, wherein an additional dose of the ligand is administered to the subject.

B9. The method of any one of embodiments B1-B8, wherein the target antigen is a tumor antigen.

B10. The method of any one of embodiments B1-B9, wherein the subject has been diagnosed as having a tumor.

B11. The method of any one of embodiments B1-B9, wherein the subject has cancer.

B12. The method of any one of embodiments B1-B11, wherein the subject has a solid tumor.

B13. The method of embodiment B11, wherein the cancer is present in the blood or bone marrow of the subject.

B14. The method of any one of embodiments B1-B13, wherein the subject has a blood or bone marrow disease.

B15. The method of any one of embodiments B1-B9, wherein the subject has been diagnosed with any condition or condition that can be alleviated by stem cell transplantation.

B16. The method of any one of embodiments B1-B9, wherein the subject has been diagnosed with sickle cell anemia or metachromatic leukodystrophy.

B17. The method of any one of embodiments B1-B9, wherein the subject has been diagnosed with a condition selected from the group consisting of a primary immune deficiency condition, hemophagocytosis lymphohistiocytosis (HAH) or other hemophagocytic condition, an inherited marrow failure condition, a hemoglobinopathy, a metabolic condition, and an osteoclast condition.

B18. The method of any one of embodiments B1-B9, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

B19. The method of any one of embodiments B1-B18, further comprising determining whether an additional dose of the multimeric ligand should be administered to the subject.

B20. The method of any one of embodiments B1-B18, further comprising administering an additional dose of the multimeric ligand to the subject, wherein the disease or condition symptoms remain or are detected following a reduction in symptoms.

B21. The method of any one of embodiments B1-B18, further comprising identifying the presence, absence or stage of a condition or disease in a subject; and transmitting an indication to administer the multimeric ligand to the subject, maintain a subsequent dosage of the multimeric ligand, or adjust a subsequent dosage of the multimeric ligand administered to the subject based on the presence, absence or stage of the condition or disease identified in the subject.

B22. The method of any one of embodiments B1-B21, wherein the condition is leukemia.

B23. The method of any one of embodiments B1-B9, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

B24. The method of any one of embodiments B1-B23 wherein the ligand is AP1903.

C1. A modified T cell transfected or transduced with a nucleic acid comprising a polynucleotide encoding an inducible chimeric stimulating molecule, wherein the inducible chimeric stimulating molecule comprises (i) a MyD88 polypeptide region or a truncated MyD88 polypeptide region lacking the TIR domain; (ii) a CD40 cytoplasmic polypeptide region lacking the CD40 extracellular domain, and (iii) a multimerization region.

C2. The modified T cell of embodiment C1, wherein the inducible chimeric stimulating molecule further comprises (iv) a membrane targeting region.

C3. The modified T cell of embodiment C1, wherein the chimeric stimulating molecule is a polypeptide which comprises regions (i)-(iii) in order from the amino to the carboxyl terminal of the polypeptide of (i), (ii), (iii).

C4. The modified T cell of embodiment C2, wherein the chimeric stimulating molecule is a polypeptide which comprises regions (i)-(iv) in order from the amino to the carboxyl terminal of the polypeptide of (iv), (i), (ii), (iii).

C5. The modified T cell of any one of embodiments C1-C4, wherein the multimerization region is a ligand binding region.

C6. The modified T cell of embodiment C5, wherein the ligand binding region is an FKBP12 region.

C7. The modified T cell of embodiment C6, wherein the FKBP12 region is an FKBP12v36 region.

C8. The modified T cell of embodiment C6, wherein the FKBP12 region is Fv'Fvls.

C9. The modified T cell of embodiment C5, the multimerization region comprises a polypeptide having an amino acid sequence of SEQ ID NO: 11, or a functional fragment thereof, and a polypeptide having an amino acid sequence of SEQ ID NO: 13, or a functional fragment thereof, or further comprises a polypeptide that is encoded by a nucleotide sequence in SEQ ID NO: 12, or a functional fragment thereof.

C10. The modified T cell of embodiment C9, wherein the multimerization region further comprises a polypeptide having an amino acid sequence of SEQ ID NO: 13, or a functional fragment thereof or further comprises a polypeptide that is encoded by a nucleotide sequence in SEQ ID NO: 12, or a functional fragment thereof.

C11. The modified T cell of embodiment C9, further comprising an Fv polypeptide variant wherein residue 36 is valine.

C12. The modified T cell of any one of embodiments C5-C11, wherein the ligand is an FK506 dimer or a dimeric FK506 analog ligand.

C13. The modified T cell of embodiment C12, wherein the ligand is AP1903.

C14. The modified T cell of any one of embodiments C1-C13, wherein at least one of regions (i)-(iv) is encoded by a codon-optimized nucleotide sequence.

C15. The modified T cell of any one of embodiments C1-C14, further comprising a promoter that is operably linked to the polynucleotide encoding the inducible chimeric stimulating molecule.

C16. The modified T cell of any one of embodiments C1-C15, wherein the modified cell further comprises a polynucleotide encoding a chimeric antigen receptor.

C17. The modified T cell of embodiment C16 wherein the chimeric antigen receptor comprises (i) a transmembrane region; (ii) a T cell activation molecule; and (iii) an antigen recognition moiety.

C18. The modified T cell of any one of embodiments C1-C15, wherein the modified cell further comprises a polynucleotide encoding a T cell receptor.

C19. The modified T cell of any one of embodiments C1-C15, wherein the modified cell is transfected or transduced with a nucleic acid comprising a polynucleotide encoding a T cell receptor or a T cell receptor-based chimeric antigen receptor.

C20. The modified T cell of embodiment C16, wherein the chimeric antigen receptor further comprises a co-stimulatory molecule.

C21. The modified T cell of embodiment C20, wherein the co-stimulatory molecule is selected from the group consisting of CD28, OX40, and 4-1BB.

C22. The modified T cell of embodiment C17, wherein the T cell activation molecule is an ITAM-containing, Signal 1 conferring molecule.

C23. The modified T cell of embodiment C17, wherein the T cell activation molecule is a CD3 polypeptide.

C24. The modified T cell of embodiment C17, wherein the T cell activation molecule is an Fc epsilon receptor gamma (FcεR1γ) subunit polypeptide.

C25. The modified T cell of any one of embodiments C17 or C22-C24, wherein the antigen recognition moiety binds to an antigen on a tumor cell.

C26. The modified T cell of any one of embodiments C17 or C22-C24, wherein the antigen recognition moiety binds to an antigen on a cell involved in a hyperproliferative disease.

C27. The modified T cell of any one of embodiments C17 or C22-C26, wherein the antigen recognition moiety binds to an antigen selected from the group consisting of PSMA, PSCA, MUC1, CD19, ROR1, Mesothelin, GD2, CD123, MUC16, and Her2/Neu.

C28. The modified T cell of any one of embodiments C17 or C22-C24, wherein the antigen recognition moiety binds to PSCA.

C29. The modified T cell of any one of embodiments C17 or C22-C24, wherein the antigen recognition moiety binds to CD19.

C30. The modified T cell of any one of embodiments C17 or C22-C24, wherein the antigen recognition moiety binds to Her2/Neu.

C31. The modified T cell of any one of embodiments C17 or C22-C24, wherein the antigen recognition moiety binds to a viral or bacterial antigen.

C32. The modified T cell of any one of embodiments C17 or C22-C31, wherein the antigen recognition moiety is a single chain variable fragment.

C33. The modified T cell of any one of embodiments C17 or C22-C32, wherein the transmembrane region is a CD28 transmembrane region.

C34. The modified T cell of any one of embodiments C17 or C22-C32, wherein the transmembrane region is a CD8 transmembrane region.

C35. The modified T cell of embodiment C34, wherein the chimeric antigen receptor further comprises a CD8 stalk region.

C36. The modified T cell of any one of embodiments C1-C35, wherein the chimeric stimulating molecule comprises a truncated MyD88 polypeptide having the amino acid sequence of SEQ ID NO: 5, or a functional fragment thereof.

C37. The modified T cell of any one of embodiments C1-C36, wherein the MyD88 polypeptide has the amino acid sequence of SEQ ID NO: 49.

C38. The modified T cell of any one of embodiments C1-C37, wherein the cytoplasmic CD40 polypeptide has the amino acid sequence of SEQ ID NO: 9, or a functional fragment thereof.

C40. The modified T cell of any one of embodiments C23-C38, wherein the CD3 polypeptide comprises an amino acid sequence of SEQ ID NO: 39, or a functional fragment thereof.

C41. The modified T cell of any one of embodiments C2-C40, wherein the membrane targeting region is selected from the group consisting of a myristoylation region, palmitoylation region, prenylation region, and transmembrane sequences of receptors.

C42. The modified T cell of any one of embodiments C2-C40, wherein the membrane targeting region is a myristoylation region.

C43. The modified T cell of embodiment C42, wherein the myristoylation region has an amino acid sequence of SEQ ID NO: 3 or a functional fragment thereof.

C44-C61 Reserved.

C62. A method for stimulating a T cell-mediated immune response in a subject, comprising administering
  a) a modified T cell of any one of embodiments C1-C43 to the subject; and
  b) an effective amount of a multimeric ligand that binds to the multimerization region to stimulate a T cell-mediated immune response in the subject.

C63. The method of embodiment C62, wherein the chimeric antigen receptor binds to a target cell.

C64. The method of embodiment C63, wherein the target cell is a tumor cell.

C65. The method of any one of embodiments C62-C64, wherein the number or concentration of target cells in the subject is reduced following administration of the ligand.

C66. The method of any one of embodiments C62-C65, further comprising measuring the number or concentration of target cells in a first sample obtained from the subject before administering the modified cell or ligand, measuring the number or concentration of target cells in a second sample obtained from the subject after administration of the modified cell and ligand, and determining an increase or decrease of the number or concentration of target cells in the second sample compared to the number or concentration of target cells in the first sample.
C67. The method of embodiment C66, wherein the concentration of target cells in the second sample is decreased compared to the concentration of target cells in the first sample.
C68. The method of embodiment C66, wherein the concentration of target cells in the second sample is increased compared to the concentration of target cells in the first sample.
C69. The method of any one of embodiments C62-C68, wherein an additional dose of the ligand is administered to the subject.
C70. A method for providing anti-tumor immunity to a subject, comprising administering to the subject an effective amount of a modified T cell of any one of embodiments C1-C43 and administering a ligand that binds to the multimerization region to provide anti-tumor immunity to the subject.
C71. A method for treating a subject having a disease or condition associated with an elevated expression of a target antigen, comprising administering to the subject an effective amount of a modified T cell of any one of embodiments C1-C43, and an effective amount of a ligand that binds to the multimerization region.
C72. The method of embodiment C71, wherein the target antigen is a tumor antigen.
C73. The method of any one of embodiments C62-C72, wherein the modified T cells are autologous T cells.
C74. The method of any one of embodiments C62-C72, wherein the modified T cells are allogeneic T cells.
C75. A method for reducing the size of a tumor in a subject, comprising administering a modified T cell of any one of embodiments C1-C43 to the subject, wherein the antigen recognition moiety binds to an antigen on the tumor.
C76. The method of any one of embodiments C62-C75, wherein the subject has been diagnosed as having a tumor.
C76. The method of any one of embodiments C62-C75, wherein the subject has cancer.
C77. The method of any one of embodiments C62-C75, wherein the subject has a solid tumor.
C78. The method of any one of embodiments C62-C75, wherein the modified T cell is a tumor infiltrating lymphocyte, a NK cell, or a NK-T cell.
C79. The method of any one of embodiments C62-C75, wherein the modified T cell is delivered to a tumor bed.
C80. The method of embodiment C76, wherein the cancer is present in the blood or bone marrow of the subject.
C81. The method of any one of embodiments C62-C75, wherein the subject has a blood or bone marrow disease.
C82. The method of any one of embodiments C62-C75, wherein the subject has been diagnosed with any condition or condition that can be alleviated by stem cell transplantation.
C83. The method of any one of embodiments C62-C75, wherein the subject has been diagnosed with sickle cell anemia or metachromatic leukodystrophy.
C84. The method of any one of embodiments C62-C75, wherein the subject has been diagnosed with a condition selected from the group consisting of a primary immune deficiency condition, hemophagocytosis lymphohistiocytosis (HAH) or other hemophagocytic condition, an inherited marrow failure condition, a hemoglobinopathy, a metabolic condition, and an osteoclast condition.
C84. The method of any one of embodiments C62-C76, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.
C85. The method of any one of embodiments C62-C84, further comprising determining whether an additional dose of the ligand should be administered to the subject.
C86. The method of any one of embodiments C62-C85, further comprising administering an additional dose of the ligand to the subject, wherein the disease or condition symptoms remain or are detected following a reduction in symptoms.
C87. The method of any one of embodiments C62-C86, further comprising
  identifying the presence, absence or stage of a condition or disease in a subject; and
  transmitting an indication to administer the ligand of any one of embodiments C53-C61, maintain a subsequent dosage of the ligand, or adjust a subsequent dosage of the ligand administered to the subject based on the presence, absence or stage of the condition or disease identified in the subject.
C88. The method of any one of embodiments C62-C87, wherein the condition is leukemia.
C89. The method of any one of embodiments C62-C87, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.
C90. The method of any one of embodiments C62-C89, wherein the modified T cell is transfected or transduced ex vivo.
C91. The modified T cell of any one of embodiments C62-C89, wherein the modified T cell is transfected or transduced in vivo.
C92. The method of any one of embodiments C62-C90 wherein the ligand is AP1903.
D1. A nucleic acid comprising a polynucleotide encoding an inducible chimeric stimulating molecule, wherein the inducible chimeric stimulating molecule comprises (i) a MyD88 polypeptide region or a truncated MyD88 polypeptide region lacking the TIR domain; (ii) a CD40 cytoplasmic polypeptide region lacking the CD40 extracellular domain, and (iii) a multimerization region.

D2. The nucleic acid of embodiment D1, wherein the chimeric stimulating molecule is a polypeptide which comprises regions (i)-(iii) in order from the amino to the carboxyl terminal of the polypeptide of (i), (ii), (iii).

D3. The nucleic acid of any one of embodiments D1-D2, wherein the multimerization region is a ligand binding region.

D3. The nucleic acid of embodiment D3, wherein the ligand binding region is an FKBP12 region.

D4. The nucleic acid of embodiment D3, wherein the FKBP12 region is an FKBP12v36 region.

D5. The nucleic acid of embodiment D3, wherein the FKBP12 region is Fv'Fvls.

D6. The nucleic acid of embodiment D3, wherein the multimerization region comprises a polypeptide having an amino acid sequence of SEQ ID NO: 11, or a functional fragment thereof, and a polypeptide having an amino acid sequence of SEQ ID NO: 13.

D7. The nucleic acid of embodiment D6, wherein the multimerization region further comprises a polypeptide having an amino acid sequence of SEQ ID NO: 13, or a functional fragment thereof.

D8. The nucleic acid of embodiment D6, further comprising an Fv polypeptide variant wherein residue 36 is valine.

D9. The nucleic acid of any one of embodiments D1-D8, wherein the ligand is an FK506 dimer or a dimeric FK506 analog ligand.

D10. The nucleic acid of embodiment D9, wherein the ligand is AP1903.

D11. The nucleic acid of any one of embodiments D1-D10, wherein at least one of regions (i)-(iii) is encoded by a codon-optimized nucleotide sequence.

D12. The nucleic acid of any one of embodiments D1-D11, further comprising a promoter that is operably linked to the polynucleotide.

D13. The nucleic acid of any one of embodiments D1-D12, wherein the nucleic acid is contained within a viral vector.

D14. The nucleic acid of embodiment D13, wherein the viral vector is a retroviral vector.

D15. The nucleic acid of embodiment D14, wherein the retroviral vector is a murine leukemia virus vector.

D16. The nucleic acid of embodiment D14, wherein the retroviral vector is an SFG vector.

D17. The nucleic acid of embodiment D13, wherein the viral vector is an adenoviral vector.

18. The nucleic acid of embodiment D13, wherein the viral vector is a lentiviral vector.

D19. The nucleic acid of embodiment D13, wherein the viral vector is selected from the group consisting of adeno-associated virus (AAV), Herpes virus, and Vaccinia virus.

D20. The nucleic acid of any one of embodiments D1-D12, wherein the nucleic acid is contained within a plasmid.

D21. A modified cell transfected or transduced with a nucleic acid of any one of embodiments D1-D20.

D22. The modified cell of embodiment D21, wherein the modified cell is a T cell, tumor infiltrating lymphocyte, NK-T cell, TCR-expressing cell, or NK cell.

D23. The modified cell of embodiment D21, wherein the cell is a T cell.

D24. The modified cell of any one of embodiments D21-D23, wherein the cell is obtained or prepared from bone marrow.

D25. The modified cell of any one of embodiments D21-D23, wherein the cell is obtained or prepared from umbilical cord blood.

D26. The modified cell of any one of embodiments D21-D23, wherein the cell is obtained or prepared from peripheral blood.

D27. The modified cell of any one of embodiments D21-D23, wherein the cell is obtained or prepared from peripheral blood mononuclear cells.

D28. The modified cell of any one of embodiments D21-D27, wherein the cell is a human cell.

D29. The modified cell of any one of embodiments D21-D28, wherein the cell is transfected or transduced by the nucleic acid vector using a method selected from the group consisting of electroporation, sonoporation, biolistics (e.g., Gene Gun with Au-particles), lipid transfection, polymer transfection, nanoparticles, or polyplexes.

D30. The modified cell of any one of embodiments D1-D29, wherein the modified cell further comprises a polynucleotide encoding a T cell receptor.

D31. The modified cell of any one of embodiments D1-D29, wherein the modified cell is transfected or transduced with a nucleic acid comprising a polynucleotide encoding a T cell receptor or a T cell receptor-based chimeric antigen receptor.

D32. The modified cell of any one of embodiments D21-D29, wherein the modified cell further comprises a polynucleotide encoding a chimeric antigen receptor.

D33. The modified cell of embodiment D32 wherein the chimeric antigen receptor comprises (i) a transmembrane region; (ii) a T cell activation molecule; and (iii) an antigen recognition moiety.

D34. The modified cell of embodiment D33, wherein the chimeric antigen receptor further comprises a co-stimulatory molecule.

D35. The modified cell of embodiment D34, wherein the co-stimulatory molecule is selected from the group consisting of CD28, OX40, and 4-1BB.

D36. The modified cell of embodiment D33, wherein the T cell activation molecule is an ITAM-containing, Signal 1 conferring molecule.

D37. The modified cell of embodiment D33, wherein the T cell activation molecule is a CD3 polypeptide.

D38. The modified cell of embodiment D33, wherein the T cell activation molecule is an Fc epsilon receptor gamma (FcεR1γ) subunit polypeptide.

D39. The modified cell of any one of embodiments D32-D38, wherein the antigen recognition moiety binds to an antigen on a tumor cell.

D40. The modified cell of any one of embodiments D32-D38, wherein the antigen recognition moiety binds to an antigen on a cell involved in a hyperproliferative disease.

D41. The modified cell of any one of embodiments D32-D40, wherein the antigen recognition moiety binds to an antigen selected from the group consisting of PSMA, PSCA, MUC1, CD19, ROR1, Mesothelin, GD2, CD123, MUC16, and Her2/Neu.

D42. The modified cell of any one of embodiments D32-D40, wherein the antigen recognition moiety binds to PSCA.

D43. The modified cell of any one of embodiments D32-D40, wherein the antigen recognition moiety binds to CD19.

D44. The modified cell of any one of embodiments D32-D40, wherein the antigen recognition moiety binds to Her2/Neu.

D45. The modified cell of any one of embodiments D32-D38, wherein the antigen recognition moiety binds to a viral or bacterial antigen.

D46. The modified cell of any one of embodiments D32-D45, wherein the antigen recognition moiety is a single chain variable fragment.

D47. The modified cell of any one of embodiments D32-D46, wherein the transmembrane region is a CD28 transmembrane region.

D48. The modified cell of any one of embodiments D32-D46, wherein the transmembrane region is a CD8 transmembrane region.

D49. The modified cell of embodiment D48, wherein the chimeric antigen receptor further comprises a CD8 stalk region.

D50. The modified cell of any one of embodiments D21-D49, wherein the chimeric stimulating molecule comprises a truncated MyD88 polypeptide having the amino acid sequence of SEQ ID NO: 5, or a functional fragment thereof.

D51. The modified cell of any one of embodiments D21-D50, wherein the MyD88 polypeptide has the amino acid sequence of SEQ ID NO: 49

D52. The modified cell of any one of embodiments D21-D51, wherein the cytoplasmic CD40 polypeptide has the amino acid sequence of SEQ ID NO: 9, or a functional fragment thereof.

D53. The modified cell of any one of embodiments D32-D52, wherein the CD3 polypeptide comprises an amino acid sequence of SEQ ID NO: 39, or a functional fragment thereof.

D54. A method for stimulating a T cell-mediated immune response in a subject, comprising administering
  a) a modified cell of any one of embodiments D21-D53 to the subject; and
  b) an effective amount of a multimeric ligand that binds to the multimerization region to stimulate a T cell-mediated immune response in the subject.

D55. Reserved.

D56. The method of embodiment D54, wherein the chimeric antigen receptor binds to a target cell.

D57. The method of embodiment D56, wherein the target cell is a tumor cell.

D58. The method of any one of embodiments D56 or D57, wherein the number or concentration of target cells in the subject is reduced following administration of the ligand.

D59. The method of any one of embodiments D56-D58, further comprising measuring the number or concentration of target cells in a first sample obtained from the subject before administering the modified cell or ligand, measuring the number or concentration of target cells in a second sample obtained from the subject after administration of the modified cell and the ligand, and determining an increase or decrease of the number or concentration of target cells in the second sample compared to the number or concentration of target cells in the first sample.

D60. The method of embodiment D59, wherein the concentration of target cells in the second sample is decreased compared to the concentration of target cells in the first sample.

D61. The method of embodiment D59, wherein the concentration of target cells in the second sample is increased compared to the concentration of target cells in the first sample.

D62. The method of any one of embodiments D54-D61, wherein an additional dose of ligand is administered to the subject.

D63. A method for providing anti-tumor immunity to a subject, comprising administering to the subject an effective amount of a modified cell of any one of embodiments D21-D53 and administering a ligand that binds to the multimerization region to provide anti-tumor immunity to the subject.

D64. A method for treating a subject having a disease or condition associated with an elevated expression of a target antigen, comprising administering to the subject an effective amount of a modified cell of any one of embodiments D32-D53, and an effective amount of a ligand that binds to the multimerization region.

D65. The method of embodiment D64, wherein the target antigen is a tumor antigen.

D66. The method of any one of embodiments D64 or D65, wherein the modified cells are T cells.

D67. The method of any one of embodiments D64 or D65, wherein the modified cells are allogeneic T cells.

D68. A method for reducing the size of a tumor in a subject, comprising administering a modified cell of any one of embodiments D32-D53 to the subject, wherein the antigen recognition moiety binds to an antigen on the tumor.

D69. The method of any one of embodiments D54-D69, wherein the subject has been diagnosed as having a tumor.

D70. The method of any one of embodiments D54-D70, wherein the subject has cancer.

D71. The method of any one of embodiments D54-D70, wherein the subject has a solid tumor.

D72. The method of any one of embodiments D54-D71, wherein the modified cell is a tumor infiltrating lymphocyte.

D73. The method of any one of embodiments D54-D72, wherein the modified cell is delivered to a tumor bed.

D74. The method of embodiment D70, wherein the cancer is present in the blood or bone marrow of the subject.

D75. The method of any one of embodiments D54-D74, wherein the subject has a blood or bone marrow disease.

D76. The method of any one of embodiments D54-D75, wherein the subject has been diagnosed with any condition or condition that can be alleviated by stem cell transplantation.

D77. The method of any one of embodiments D54-D75, wherein the subject has been diagnosed with sickle cell anemia or metachromatic leukodystrophy.

D78. The method of any one of embodiments D54-D75, wherein the subject has been diagnosed with a condition selected from the group consisting of a primary immune deficiency condition, hemophagocytosis lymphohistiocytosis (HAH) or other hemophagocytic condition, an inherited marrow failure condition, a hemoglobinopathy, a metabolic condition, and an osteoclast condition.

D79. The method of any one of embodiments D54-D75, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

D80. The method of any one of embodiments D54-D79, further comprising determining whether an additional dose of the ligand should be administered to the subject.

D81. The method of any one of embodiments D54-D80, further comprising administering an additional dose of the ligand to the subject, wherein the disease or condition symptoms remain or are detected following a reduction in symptoms.

D82. The method of any one of embodiments D54-D80, further comprising
identifying the presence, absence or stage of a condition or disease in a subject; and
transmitting an indication to administer the ligand, maintain a subsequent dosage of the ligand, or adjust a subsequent dosage of the ligand administered to the subject based on the presence, absence or stage of the condition or disease identified in the subject.

D83. The method of any one of embodiments D54-D82, wherein the condition is leukemia.

D84. The method of any one of embodiments D54-D82, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

D85. The method of any one of embodiments D54-D82, wherein the modified cell is transfected or transduced ex vivo.

D86. The modified cell of any one of embodiments D21-D53, wherein the modified cell is transfected or transduced in vivo.

D87. The method of any one of embodiments D54-D86, wherein the ligand is AP1903.

Example 29: Additional Representative Embodiments

Provided hereafter are examples of certain embodiments of the technology.

A1. A method for activating a T cell, comprising:
transfecting or transducing a T cell with a nucleic acid comprising
a polynucleotide that encodes a chimeric protein, wherein the chimeric protein comprises
a) a membrane targeting region,
b) a multimerization region, and
c) a MyD88 polypeptide;
whereby the T cell is activated.

A2. A method for activating a T cell, comprising:
transfecting or transducing a T cell with a nucleic acid comprising
a polynucleotide that encodes a chimeric protein, wherein the chimeric protein comprises
a) a membrane targeting region,
b) a multimerization region, and
c) a CD40 cytoplasmic region, wherein the CD40 polypeptide does not have a functional extracellular domain;
whereby the T cell is activated.

B1. A method for activating a T cell, comprising:
transfecting or transducing a T cell with a nucleic acid comprising
a polynucleotide that encodes a chimeric protein, wherein the chimeric protein comprises
a) a membrane targeting region,
b) a multimerization region,
c) a MyD88 polypeptide, and
d) a CD40 polypeptide cytoplasmic region, wherein the CD40 polypeptide does not have a functional extracellular domain;
whereby the T cell is activated.

C1. A method for activating a T cell, comprising:
transfecting or transducing a T cell with a nucleic acid comprising
a polynucleotide that encodes a chimeric protein, wherein the chimeric protein comprises
a) a membrane targeting region,
b) a multimerization region, and
c) a CD40 polypeptide cytoplasmic region, wherein the CD40 polypeptide does not have a functional extracellular domain;
whereby the T cell is activated.

D1. The method of any one of embodiments A1-C1, wherein the T cell is a primary T cell.

D2. The method of any one of embodiments A1-C1, wherein the T cell is a cytotoxic T cell.

D3. The method of any one of embodiments A1-C1, wherein the T cell is a natural killer cell.

D4. The method of any one of embodiments A1-C1, wherein the T cell is a helper T cell.

D4.1. The method of any one of embodiments A1 to D4, wherein the T cell is an isolated T cell.

D5. The method of any one of embodiments A1-D4.1, comprising contacting the T cell with a ligand that binds to the multimerization region resulting in multimerization, whereby the T cell is activated.

D6. The method of any one of embodiments A1-D5, wherein the nucleic acid is contained within a viral vector.

D7. The method of embodiment D6, wherein the viral vector is a lentiviral vector.

D8. The method of embodiment D6, wherein the viral vector is a retroviral vector.

D9. The method of embodiment D8, wherein the retroviral vector is produced using the plasmid vector of FIG. 36.

D10. The method of any one of embodiments A1-D5, wherein the nucleic acid is contained within a plasmid.

D11. The method of embodiment D10, wherein the nucleic acid is not contained within a plasmid or a virus.

D12. The method of any one of embodiments A1-D10, wherein the polynucleotide is operably linked to a promoter.

D13. The method of any one of embodiments A1, B1, or D1-D12, wherein the MyD88 polypeptide is a truncated MyD88 polypeptide lacking the TIR domain.

D14. The method of embodiment D13, wherein the MyD88 polypeptide has the amino acid sequence of SEQ ID NO: 5, or a functional fragment thereof.

D15. The method of embodiments D13 or D14, wherein the MyD88 polypeptide is encoded by a polynucleotide comprising the sequence of SEQ ID NO: 4, or a functional fragment thereof.

D16. The method of any one of embodiments A1-D15, further comprising transfecting or transducing the T cell with a nucleic acid comprising a polynucleotide that encodes a tumor antigen-targeting chimeric antigen receptor (CAR).

D17. The method of any one of embodiments D16, wherein the targeted tumor antigen is a prostate cancer antigen.

D18. The method of any one of embodiments D16, wherein the targeted tumor antigen is a prostate specific membrane antigen.

D19. The method of any one of embodiments A1-D18, wherein the membrane targeting region is selected from the group consisting of a myristoylation region, palmitoylation region, prenylation region, and transmembrane sequences of receptors.

D20. The method of embodiment D19, wherein the membrane targeting region is a myristoylation region.

D21. The method of any one of embodiments A1-D20, wherein the multimerization region is a ligand binding region selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

D22. The method of embodiment D21, wherein the ligand binding region is an FKBP12 region.

D23. The method of embodiment D22, wherein the FKBP12 region is an FKBP12v36 region.

D24. The method of embodiment D21, wherein the FKBP region is Fv'Fvls.

D25. The method of any one of embodiments D5-D24, wherein the ligand is an FK506 dimer or a dimeric FK506 analog ligand.

D26. The method of embodiment D25, wherein the ligand is AP1903.

D27. The method of any one of embodiments A1-D26, wherein the CD40 cytoplasmic polypeptide region has an amino acid sequence of the cytoplasmic region of SEQ ID NO: 9, or a functional fragment thereof.

D28. The method of any one of embodiments B1-D27, wherein the CD40 cytoplasmic polypeptide region is encoded by a nucleotide sequence in SEQ ID NO: 8, or a functional fragment thereof.

D29. Reserved

D30. Reserved

D31. The method of any one of embodiments A1-D29, wherein the multimerization region has an amino acid sequence of SEQ ID NO: 11 or a functional fragment thereof.

D32. The method of any one of embodiments A1-D30, wherein the multimerization region is encoded by a nucleotide sequence in SEQ ID NO: 10, or a functional fragment thereof.

D33. The method of embodiment D31, wherein the multimerization region further comprises a polypeptide having an amino acid sequence of SEQ ID NO: 13, or a functional fragment thereof.

D33.1. The method of embodiment D31, wherein the multimerization region further comprises a polypeptide encoded by a nucleotide sequence in SEQ ID NO: 12, or a functional fragment thereof.

D33.1. The method of embodiment D31, wherein the multimerization region further comprises a polypeptide having an amino acid sequence of SEQ ID NO: 13, or a functional fragment thereof.

D33.2. The method of embodiment D31, wherein the multimerization region further comprises a polypeptide encoded by a nucleotide sequence in SEQ ID NO: 12, or a functional fragment thereof.

D33.3. The method of embodiment D33.1 or D33.2, wherein the multimerization region further comprises a polypeptide having an amino acid sequence of SEQ ID NO: 27 or SEQ ID NO: 32, or a functional fragment thereof.

D33.4. The method of embodiment D33.1 or D33.2, wherein the multimerization region further comprises a polypeptide encoded by a nucleotide sequence in SEQ ID NO: 12 or SEQ ID NO: 10, or a functional fragment thereof.

D34. The method of any one of embodiments A1-D33.24, wherein the membrane targeting region is a myristoylation region.

D35. The method of embodiment D34, wherein the myristoylation region has an amino acid sequence of SEQ ID NO: 3, or a functional fragment thereof.

D36. The method of embodiments D34, wherein the myristoylation region is encoded by a nucleotide sequence in SEQ ID NO: 2, or a functional fragment thereof.

D37. The method of any one of embodiments A1-D36, wherein the T cell is a human T cell.

D38. The method of any one of embodiments D1-D37, wherein the T cell is contacted with the multimeric ligand in vivo.

E1. A method of inducing an immune response against a tumor antigen in a subject, comprising activating a T cell according to a method of any one of embodiments A1-D37 and administering the activated T cell to a subject.

E2. A method of reducing in a subject the size of a tumor having a surface tumor antigen, comprising activating a T cell according to a method of any one of embodiments A1-D37.

E3. The method of embodiment E2, wherein the tumor is a prostate cancer tumor.

E3. A method of treating prostate cancer in a subject, comprising activating a T cell according to a method of any one of embodiments A1-D37, wherein the tumor antigen is a prostate cancer antigen, and administering the activated T cell to a subject.

E4. The method of embodiment E3, wherein the tumor antigen is PSMA.

E5. The method of any one of embodiments E1-E4, wherein the subject is human.

E6. The method of any one of embodiments E1-E5, wherein the subject has prostate cancer.

E7. The method of any one of embodiments E1-E6, wherein the T cell is contacted with the multimeric ligand in vivo.

E8. The method of any one of embodiments E1-E7, comprising administering the multimeric ligand to the subject.

E9. The method of embodiment E8, wherein the multimeric ligand is AP1903.

E10. The method of any of embodiments E2-E9, comprising measuring the size of the tumor before and/or after administration of the T cell.

E11. The method of any one of embodiments E2-E9, comprising determining a serum PSA level of the subject, before and/or after administration of the T cell.

E12. The method of any one of embodiments E2-E11, wherein the subject has prostate cancer having a Gleason score of 7 or greater.

E13. The method of any one of embodiments E2-E11, wherein the subject has prostate cancer having a Gleason score of 8 or greater.

F1. A T cell, comprising a nucleic acid comprising
   a polynucleotide that encodes a chimeric protein, wherein the chimeric protein comprises
     a) a membrane targeting region,
     b) a multimerization region, and
     c) a MyD88 polypeptide.

F2. A T cell, comprising a nucleic acid comprising
   a polynucleotide that encodes a chimeric protein, wherein the chimeric protein comprises
     a) a membrane targeting region,
     b) a multimerization region,
     c) a MyD88 polypeptide, and d) a CD40 polypeptide cytoplasmic region wherein the CD40 polypeptide does not have a functional extracellular domain.

F3. A T cell, comprising a nucleic acid comprising a polynucleotide that encodes a chimeric protein, wherein the chimeric protein comprises
a) a membrane targeting region,
b) a multimerization region, and
c) a CD40 polypeptide cytoplasmic region wherein the CD40 polypeptide does not have a functional extracellular domain.

F4. The T cell of any one of embodiments F1-F3, further comprising a nucleic acid comprising a promoter operably linked to a polynucleotide encoding a tumor antigen.

F5. Reserved.

F6. Reserved.

F7. The T cell of any one of embodiments F1-F7, wherein the T cell is a primary T cell.

F8. The T cell of any one of embodiments F1-F7, wherein the T cell is a cytotoxic T cell.

F9. Reserved

F10. The T cell of any one of embodiments F1-F7, wherein the T cell is a helper T cell.

F10.1. The T cell of any one of embodiments F1-F10, wherein the T cell is an isolated T cell.

F11. The T cell of any one of embodiments F1-F3, or F7-F10.1, wherein the nucleic acid is contained within a viral vector.

F12. The T cell of embodiment F11, wherein the viral vector is a lentiviral vector.

F13. The T cell of embodiments F11, wherein the viral vector is a retroviral vector.

F14. The T cell of embodiment F13, wherein the retroviral vector is produced using the plasmid vector of FIG. 36.

F15. The T cell of any one of embodiments F1-F3, or F7-F10.1, wherein the nucleic acid is contained within a plasmid.

F16. Reserved.

F17. The T cell of any one of embodiments F1-F16, wherein the polynucleotide is operably linked to a promoter.

F18. The T cell of any one of embodiments F1-F2, or F4-F18, wherein the MyD88 polypeptide is a truncated MyD88 polypeptide lacking the TIR domain.

F19. The T cell of embodiment 18, wherein the MyD88 polypeptide has the amino acid sequence of SEQ ID NO: 5, or a functional fragment thereof.

F20. The T cell of embodiments F18 or F19, wherein the MyD88 polypeptide is encoded by a polynucleotide comprising the sequence of SEQ ID NO: 4, or a functional fragment thereof.

F21. Reserved.

F22. The T cell of embodiment F4, wherein the tumor antigen is a prostate cancer antigen.

F23. The T cell of embodiment F22, wherein the tumor antigen is a prostate specific membrane antigen.

F24. The T cell of any one of embodiments F1-F23, wherein the membrane targeting region is selected from the group consisting of a myristoylation region, palmitoylation region, prenylation region, and transmembrane sequences of receptors.

F25. The T cell of embodiment F24, wherein the membrane targeting region is a myristoylation region.

F26. The T cell of any one of embodiments F1-F25, wherein the multimerization region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

F27. The T cell of embodiment F26, wherein the multimerization region is an FKBP12 region.

F28. The T cell of embodiment F27, wherein the FKBP12 region is an FKBP12v36 region.

F29. The T cell of embodiment F26, wherein the FKBP region is Fv'Fvls.

F30. The T cell of any one of embodiments F1-F29, in a composition comprising a multimeric ligand capable of binding to the multimerization region.

F30.1. The T cell of embodiment F30, wherein the multimeric ligand is an FK506 dimer or a dimeric FK506 analog ligand.

F31. The T cell of embodiment F30.1, wherein the multimeric ligand is AP1903.

F32. The T cell of any one of embodiments F2-F3, or F5-F31, wherein the CD40 cytoplasmic polypeptide region has an amino acid sequence of the cytoplasmic region of SEQ ID NO: 9, or a functional fragment thereof.

F33. The T cell of any one of embodiments F2-F3, or F5-F31, wherein the CD40 cytoplasmic polypeptide region is encoded by a nucleotide sequence in SEQ ID NO: 8, or a functional fragment thereof.

F34.-F35. Reserved.

F36. The T cell of any one of embodiments F1-F35, wherein the multimerization region has an amino acid sequence of SEQ ID NO: 11, or a functional fragment thereof.

F37. The T cell of any one of embodiments F1-F36, wherein the multimerization region is encoded by a nucleotide sequence in SEQ ID NO:10, or a functional fragment thereof.

F37.1. The method of embodiment F36, wherein the multimerization region further comprises a polypeptide having an amino acid sequence of SEQ ID NO: 13, or a functional fragment thereof.

F37.2. The method of embodiment F37, wherein the multimerization region further comprises a polypeptide encoded by a nucleotide sequence in SEQ ID NO: 12, or a functional fragment thereof.

F37.3. The method of embodiment F37.1, wherein the multimerization region further comprises a polypeptide having an amino acid sequence of SEQ ID NO: 13, or a functional fragment thereof.

F37.4. The method of embodiment F37.2, wherein the multimerization region further comprises a polypeptide encoded by a nucleotide sequence in SEQ ID NO: 12, or a functional fragment thereof.

F38. The T cell of any one of embodiments F1-F37, wherein the membrane targeting region is a myristoylation region.

F39. The T cell of embodiment F38, wherein the myristoylation region has an amino acid sequence of SEQ ID NO: 13, or a functional fragment thereof.

F40. The T cell of embodiments F38, wherein the myristoylation region is encoded by a nucleotide sequence in SEQ ID NO: 2, or a functional fragment thereof.

F41. The T cell of any one of embodiments F1-F39, wherein the T cell is a human T cell.

G1. A method of inducing an immune response against a tumor antigen in a subject, comprising administering a T cell of any one of embodiments F1-F14 to a subject.

G2. A method of reducing tumor size in a subject, comprising administering a T cell of any one of embodiments F1-F41 to a subject.

G3. The method of embodiment G2, wherein the tumor is a prostate cancer tumor.

G4. A method of treating prostate cancer in a subject, comprising administering a T cell of any one of embodiments F1-F41 to a subject, wherein the tumor antigen is a prostate cancer antigen.
G5. The method of embodiment G4, wherein the tumor antigen is PSMA.
G6. The method of any one of embodiments G1-G5, wherein the subject is human.
G7. The method of any one of embodiments G1-G6, wherein the subject has prostate cancer.
G8. The method of any one of embodiments G1-G7, wherein the T cell is contacted with a multimeric ligand that binds to the multimerization region ex vivo before administration of the T cell to the subject.
G9. The method of any one of embodiments G1-G8, further comprising administering the multimeric ligand to the subject.
G10. The method of embodiment G9, wherein the multimeric ligand is AP1903.
G11. The method of embodiments G2-G10, comprising measuring the size of the tumor before and/or after administration of the T cell.
G12. The method of embodiments G2-G10, comprising determining a serum PSA level of the subject, before and/or after administration of the T cell.
G13. The method of embodiments G2-G12, wherein the subject has prostate cancer having a Gleason score of 7 or greater.
G14. The method of embodiments G2-G12, wherein the subject has prostate cancer having a Gleason score of 8 or greater.
G15. The method of embodiments G2-G10, comprising measuring the level of tumor vasculature before and after administration of the T cell.
H1. A method for activating a T cell in a subject, comprising: administering to the subject a nucleic acid comprising a polynucleotide that encodes a chimeric protein, wherein the chimeric protein comprises
    a) a membrane targeting region,
    b) a multimerization region, and
    c) a MyD88 polypeptide region;
    whereby the T cell is activated.
H2. A method for activating a T cell in a subject, comprising administering to the subject a nucleic acid comprising a polynucleotide that encodes a chimeric protein, wherein the chimeric protein comprises
    a) a membrane targeting region,
    b) a multimerization region,
    c) a MyD88 polypeptide, and
    d) a CD40 polypeptide cytoplasmic region, wherein the CD40 polypeptide does not have a functional extracellular domain;
    whereby the T cell is activated.
H3. A method for activating a T cell in a subject, comprising administering to the subject a nucleic acid comprising a polynucleotide that encodes a chimeric protein, wherein the chimeric protein comprises
    a) a membrane targeting region,
    b) a multimerization region, and
    c) a CD40 polypeptide cytoplasmic region, wherein the CD40 polypeptide does not have a functional extracellular domain;
    whereby the T cell is activated.
H4. A method of inducing an immune response against a tumor antigen in a subject, comprising administering a nucleic acid according to the method of any one of embodiments H1-H3 to a subject.

H5. A method of reducing tumor size in a subject, comprising administering a nucleic acid according to the method of any one of embodiments H1-H3 to a subject.
H6. The method of embodiment H5, wherein the tumor is a prostate cancer tumor.
H7. A method of treating prostate cancer in a subject, comprising administering a nucleic acid according to the method of any one of embodiments H1-H3 to a subject, further comprising administering a nucleic acid coding for a prostate cancer antigen.
H8. The method of embodiment H4, wherein the tumor antigen is PSMA.
H6. The method of any one of embodiments H1-H5, wherein the subject is human.
H7. The method of any one of embodiments H1-H6, wherein the subject has prostate cancer.
H8. The method of any one of embodiments H1-H7, further comprising administering a multimeric ligand that binds to the multimerization region.
H9. The method of embodiment H8, wherein the multimeric ligand is AP1903.
H10. The method of embodiments H4-H9, comprising measuring the size of the tumor before and/or after administration of the T cell.
H11. The method of embodiments H4-H10, comprising determining a serum PSA level of the subject, before and/or after administration of the nucleic acid.
H12. The method of embodiments H4-H11, wherein the subject has prostate cancer having a Gleason score of 7 or greater.
H13. The method of embodiments H4-H11, wherein the subject has prostate cancer having a Gleason score of 8 or greater.
H14. The method of embodiments H4-H13, comprising measuring the level of tumor vasculature before and after administration of the nucleic acid.

Example 30: Additional Representative Embodiments

Provided hereafter are examples of certain embodiments of the technology.
A1. A method for activating a cell, wherein the cell is not a dendritic cell or a B cell, comprising:
transfecting or transducing the cell with a nucleic acid comprising
a polynucleotide that encodes a chimeric protein, wherein the chimeric protein comprises
    a) a membrane targeting region,
    b) a multimerization region, and
    c) a MyD88 polypeptide;
whereby the cell is activated.
B1. A method for activating a cell, wherein the cell is not a dendritic cell or a B cell, comprising:
transfecting or transducing a the cell with a nucleic acid comprising a polynucleotide that encodes a chimeric protein, wherein the chimeric protein comprises
    a) a membrane targeting region,
    b) a multimerization region,
    c) a MyD88 polypeptide, and
    d) a CD40 polypeptide cytoplasmic region, wherein the CD40 polypeptide does not have a functional extracellular domain;
    whereby the cell is activated.

C1. A method for activating a cell, wherein the cell is not a dendritic cell or a B cell, comprising:
transfecting or transducing the cell with a nucleic acid comprising
a polynucleotide that encodes a chimeric protein, wherein the chimeric protein comprises
   a) a membrane targeting region,
   b) a multimerization region, and
   c) a CD40 polypeptide cytoplasmic region, wherein the CD40 polypeptide does not have a functional extracellular domain;
whereby the cell is activated.

D1. The method of any one of embodiments A1-C1, wherein the cell is a natural killer cell.

D2. The method of any one of embodiments A1-C1, wherein the cell is a non-lymphocytic hematopoietic cell.

D2.1. The method of any one of embodiments A1-C1, wherein the cell is a non-hematopoietic cell.

D3. The method of any one of embodiments A1-C1, wherein the cell is a macrophage.

D4. The method of any one of embodiments A1-C1, wherein the cell is a myeloma cell.

D4.1. The method of any one of embodiments A1 to C1, wherein the cell is a keratinocyte or a fibroblast.

D5. The method of any one of embodiments A1-D4.1, comprising contacting the cell with a ligand that binds to the multimerization region resulting in multimerization, whereby the cell is activated.

D6. The method of any one of embodiments A1-D5, wherein the nucleic acid is contained within a viral vector.

D7. The method of embodiment D6, wherein the viral vector is a lentiviral vector.

D8. The method of embodiment D6, wherein the viral vector is a retroviral vector.

D8.1. The method of embodiment D6, wherein the viral vector is an adenoviral vector.

D9. The method of embodiment D8, wherein the retroviral vector is produced using the plasmid vector of FIG. 36.

D10. The method of any one of embodiments A1-D5, wherein the nucleic acid is contained within a plasmid.

D11. The method of embodiment D10, wherein the nucleic acid is not contained within a plasmid or a virus.

D12. The method of any one of embodiments A1-D10, wherein the polynucleotide is operably linked to a promoter.

D13. The method of any one of embodiments A1, B1, or D1-D12, wherein the MyD88 polypeptide is a truncated MyD88 polypeptide lacking the TIR domain.

D14. The method of embodiment D13, wherein the MyD88 polypeptide has the amino acid sequence of SEQ ID NO: 5, or a functional fragment thereof.

D15. The method of embodiments D13 or D14, wherein the MyD88 polypeptide is encoded by a polynucleotide comprising the sequence of SEQ ID NO: 4, or a functional fragment thereof.

D16. The method of any one of embodiments A1-D15, further comprising transfecting or transducing the cell with a nucleic acid comprising a polynucleotide that encodes a tumor antigen-targeting chimeric antigen receptor (CAR).

D17. The method of any one of embodiments D16, wherein the targeted tumor antigen is a prostate cancer antigen.

D18. The method of any one of embodiments D16, wherein the targeted tumor antigen is a prostate specific membrane antigen.

D19. The method of any one of embodiments A1-D18, wherein the membrane targeting region is selected from the group consisting of a myristoylation region, palmitoylation region, prenylation region, and transmembrane sequences of receptors.

D20. The method of embodiment D19, wherein the membrane targeting region is a myristoylation region.

D21. The method of any one of embodiments A1-D20, wherein the multimerization region is a ligand binding region selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

D22. The method of embodiment D21, wherein the ligand binding region is an FKBP12 region.

D23. The method of embodiment D22, wherein the FKBP12 region is an FKBP12v36 region.

D24. The method of embodiment D21, wherein the FKBP region is Fv'Fvls.

D25. The method of any one of embodiments D5-D24, wherein the ligand is an FK506 dimer or a dimeric FK506 analog ligand.

D26. The method of embodiment D25, wherein the ligand is AP1903.

D27. The method of any one of embodiments A1-D26, wherein the CD40 cytoplasmic polypeptide region has an amino acid sequence of the cytoplasmic region of SEQ ID NO: 9, or a functional fragment thereof.

D28. The method of any one of embodiments B1-D27, wherein the CD40 cytoplasmic polypeptide region is encoded by a nucleotide sequence in SEQ ID NO: 8, or a functional fragment thereof.

D29-D30. Reserved.

D31. The method of any one of embodiments A1-D29, wherein the multimerization region has an amino acid sequence of SEQ ID NO: 11 or a functional fragment thereof.

D32. The method of any one of embodiments A1-D30, wherein the multimerization region is encoded by a nucleotide sequence in SEQ ID NO: 10, or a functional fragment thereof.

D33. The method of embodiment D31, wherein the multimerization region further comprises a polypeptide having an amino acid sequence of SEQ ID NO: 13, or a functional fragment thereof.

D33.1. The method of embodiment D31, wherein the multimerization region further comprises a polypeptide encoded by a nucleotide sequence in SEQ ID NO: 12, or a functional fragment thereof.

D33.1. The method of embodiment D31, wherein the multimerization region further comprises a polypeptide having an amino acid sequence of SEQ ID NO: 13, or a functional fragment thereof.

D33.2. The method of embodiment D31, wherein the multimerization region further comprises a polypeptide encoded by a nucleotide sequence in SEQ ID NO: 12, or a functional fragment thereof.

D33.3. The method of embodiment D33.1 or D33.2, wherein the multimerization region further comprises a polypeptide having an amino acid sequence of SEQ ID NO: 11 or SEQ ID NO: 13, or a functional fragment thereof.

D33.4. The method of embodiment D33.1 or D33.2, wherein the multimerization region further comprises a polypeptide encoded by a nucleotide sequence in SEQ ID NO: 10 or SEQ ID NO: 12, or a functional fragment thereof.

D34. The method of any one of embodiments A1-D33.24, wherein the membrane targeting region is a myristoylation region.

D35. The method of embodiment D34, wherein the myristoylation region has an amino acid sequence of SEQ ID NO: 3, or a functional fragment thereof.

D36. The method of embodiments D34, wherein the myristoylation region is encoded by a nucleotide sequence in SEQ ID NO: 2, or a functional fragment thereof.

D37. The method of any one of embodiments A1-D36, wherein the cell is a human cell.

D38. The method of any one of embodiments D1-D37, wherein the cell is contacted with the multimeric ligand in vivo.

E1. A method of inducing an immune response against a tumor antigen in a subject, comprising activating a cell according to a method of any one of embodiments A1-D37 and administering the activated cell to a subject.

E2. A method of reducing in a subject the size of a tumor having a surface tumor antigen, comprising activating a cell according to a method of any one of embodiments A1-D37.

E3. The method of embodiment E2, wherein the tumor is a prostate cancer tumor.

E3. A method of treating prostate cancer in a subject, comprising activating a cell according to a method of any one of embodiments A1-D37, wherein the tumor antigen is a prostate cancer antigen, and administering the activated cell to a subject.

E4. The method of embodiment E3, wherein the tumor antigen is PSMA.

E5. The method of any one of embodiments E1-E4, wherein the subject is human.

E6. The method of any one of embodiments E1-E5, wherein the subject has prostate cancer.

E7. The method of any one of embodiments E1-E6, wherein the cell is contacted with the multimeric ligand in vivo.

E8. The method of any one of embodiments E1-E7, comprising administering the multimeric ligand to the subject.

E9. The method of embodiment E8, wherein the multimeric ligand is AP1903.

E10. The method of any of embodiments E2-E9, comprising measuring the size of the tumor before and/or after administration of the cell.

E11. The method of any one of embodiments E2-E9, comprising determining a serum PSA level of the subject, before and/or after administration of the cell.

E12. The method of any one of embodiments E2-E11, wherein the subject has prostate cancer having a Gleason score of 7 or greater.

E13. The method of any one of embodiments E2-E11, wherein the subject has prostate cancer having a Gleason score of 8 or greater.

F1. A cell, comprising a nucleic acid comprising a polynucleotide that encodes a chimeric protein, wherein the chimeric protein comprises
  a) a membrane targeting region,
  b) a multimerization region, and
  c) a MyD88 polypeptide.

F2. A cell, comprising a nucleic acid comprising a polynucleotide that encodes a chimeric protein, wherein the chimeric protein comprises
  a) a membrane targeting region,
  b) a multimerization region,
    c) a MyD88 polypeptide, and
    d) a CD40 polypeptide cytoplasmic region wherein the CD40 polypeptide does not have a functional extracellular domain,
wherein the cell is not a dendritic cell or a B cell.

F3. A cell, comprising a nucleic acid comprising a polynucleotide that encodes a chimeric protein, wherein the chimeric protein comprises
  a) a membrane targeting region,
  b) a multimerization region, and
    c) a CD40 polypeptide cytoplasmic region wherein the CD40 polypeptide does not have a functional extracellular domain.

F4. The cell of any one of embodiments F1-F3, further comprising a nucleic acid comprising a promoter operably linked to a polynucleotide encoding a tumor antigen.

F5. The cell of any one of embodiments F1-F4, wherein the cell is a natural killer cell.

F6. The cell of any one of embodiments F1-F4, wherein the cell is a non-lymphocytic hematopoietic cell.

F7. The cell of any one of embodiments F1-F4, wherein the cell is a non-hematopoietic cell.

F8. The cell of any one of embodiments F1-F4, wherein the cell is a macrophage.

F9. The cell of any one of embodiments F1-F4, wherein the cell is a keratinocyte.

F10. The cell of any one of embodiments F1-F4, wherein the cell is a fibroblast.

F10.1. The cell of any one of embodiments F1-F4, wherein the cell is a melanoma cell.

F11. The cell of any one of embodiments F1-F3, or F7-F10.1, wherein the nucleic acid is contained within a viral vector.

F12. The cell of embodiment F11, wherein the viral vector is a lentiviral vector.

F13. The cell of embodiments F11, wherein the viral vector is a retroviral vector.

F14. The cell of embodiment F13, wherein the retroviral vector is produced using the plasmid vector of FIG. 36.

F15. The cell of any one of embodiments F1-F3, or F7-F10.1, wherein the nucleic acid is contained within a plasmid.

F16. Reserved.

F17. The cell of any one of embodiments F1-F16, wherein the polynucleotide is operably linked to a promoter.

F18. The cell of any one of embodiments F1-F2, or F4-F18, wherein the MyD88 polypeptide is a truncated MyD88 polypeptide lacking the TIR domain.

F19. The cell of embodiment 18, wherein the MyD88 polypeptide has the amino acid sequence of SEQ ID NO: 5, or a functional fragment thereof.

F20. The cell of embodiments F18 or F19, wherein the MyD88 polypeptide is encoded by a polynucleotide comprising the sequence of SEQ ID NO: 4, or a functional fragment thereof.

F21. Reserved.

F22. The cell of embodiment F4, wherein the tumor antigen is a prostate cancer antigen.

F23. The cell of embodiment F22, wherein the tumor antigen is a prostate specific membrane antigen.

F24. The cell of any one of embodiments F1-F23, wherein the membrane targeting region is selected from the group consisting of a myristoylation region, palmitoylation region, prenylation region, and transmembrane sequences of receptors.

F25. The cell of embodiment F24, wherein the membrane targeting region is a myristoylation region.

F26. The cell of any one of embodiments F1-F25, wherein the multimerization region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

F27. The cell of embodiment F26, wherein the multimerization region is an FKBP12 region.

F28. The cell of embodiment F27, wherein the FKBP12 region is an FKBP12v36 region.

F29. The cell of embodiment F26, wherein the FKBP region is Fv'Fvls.

F30. The cell of any one of embodiments F1-F29, in a composition comprising a multimeric ligand capable of binding to the multimerization region.

F30.1. The cell of embodiment F30, wherein the multimeric ligand is an FK506 dimer or a dimeric FK506 analog ligand.

F31. The cell of embodiment F30.1, wherein the multimeric ligand is AP1903.

F32. The cell of any one of embodiments F2-F3, or F5-F31, wherein the CD40 cytoplasmic polypeptide region has an amino acid sequence of the cytoplasmic region of SEQ ID NO: 9, or a functional fragment thereof.

F33. The cell of any one of embodiments F2-F3, or F5-F31, wherein the CD40 cytoplasmic polypeptide region is encoded by a nucleotide sequence in SEQ ID NO: 8, or a functional fragment thereof.

F34-F35. Reserved.

F36. The cell of any one of embodiments F1-F35, wherein the multimerization region has an amino acid sequence of SEQ ID NO: 11, or a functional fragment thereof.

F37. The cell of any one of embodiments F1-F36, wherein the multimerization region is encoded by a nucleotide sequence in SEQ ID NO:10, or a functional fragment thereof.

F37.1. The method of embodiment F36, wherein the multimerization region further comprises a polypeptide having an amino acid sequence of SEQ ID NO: 13, or a functional fragment thereof.

F37.2. The method of embodiment F37, wherein the multimerization region further comprises a polypeptide encoded by a nucleotide sequence in SEQ ID NO: 12, or a functional fragment thereof.

F37.3. The method of embodiment F37.1, wherein the multimerization region further comprises a polypeptide having an amino acid sequence of SEQ ID NO: 13, or a functional fragment thereof.

F37.4. The method of embodiment F37.2, wherein the multimerization region further comprises a polypeptide encoded by a nucleotide sequence in SEQ ID NO: 12, or a functional fragment thereof.

F38. The cell of any one of embodiments F1-F37, wherein the membrane targeting region is a myristoylation region.

F39. The cell of embodiment F38, wherein the myristoylation region has an amino acid sequence of SEQ ID NO: 3, or a functional fragment thereof.

F40. The cell of embodiments F38, wherein the myristoylation region is encoded by a nucleotide sequence in SEQ ID NO: 2, or a functional fragment thereof.

F41. The cell of any one of embodiments F1-F39, wherein the cell is a human cell.

G1. A method of inducing an immune response against a tumor antigen in a subject, comprising administering a cell of any one of embodiments F1-F14 to a subject.

G2. A method of reducing tumor size in a subject, comprising administering a cell of any one of embodiments F1-F41 to a subject.

G3. The method of embodiment G2, wherein the tumor is a prostate cancer tumor.

G4. A method of treating prostate cancer in a subject, comprising administering a cell of any one of embodiments F1-F41 to a subject, wherein the tumor antigen is a prostate cancer antigen.

G5. The method of embodiment G4, wherein the tumor antigen is PSMA.

G6. The method of any one of embodiments G1-G5, wherein the subject is human.

G7. The method of any one of embodiments G1-G6, wherein the subject has prostate cancer.

G8. The method of any one of embodiments G1-G7, wherein the cell is contacted with a multimeric ligand that binds to the multimerization region ex vivo before administration of the cell to the subject.

G9. The method of any one of embodiments G1-G8, further comprising administering the multimeric ligand to the subject.

G10. The method of embodiment G9, wherein the multimeric ligand is AP1903.

G11. The method of embodiments G2-G10, comprising measuring the size of the tumor before and/or after administration of the cell.

G12. The method of embodiments G2-G10, comprising determining a serum PSA level of the subject, before and/or after administration of the cell.

G13. The method of embodiments G2-G12, wherein the subject has prostate cancer having a Gleason score of 7 or greater.

G14. The method of embodiments G2-G12, wherein the subject has prostate cancer having a Gleason score of 8 or greater.

G15. The method of embodiments G2-G10, comprising measuring the level of tumor vasculature before and after administration of the cell.

H1. A method for activating a cell in a subject, comprising: administering to the subject a nucleic acid comprising a polynucleotide that encodes a chimeric protein, wherein the chimeric protein comprises
  a) a membrane targeting region,
  b) a multimerization region, and
  c) a MyD88 polypeptide;
whereby the cell is activated, and wherein the cell is not a dendritic cell or a B cell.

H2. A method for activating a cell in a subject, comprising administering to the subject a nucleic acid comprising a polynucleotide that encodes a chimeric protein, wherein the chimeric protein comprises
  a) a membrane targeting region,
  b) a multimerization region,
  c) a MyD88 polypeptide, and
  d) a CD40 polypeptide cytoplasmic region, wherein the CD40 polypeptide does not have a functional extracellular domain;
whereby the cell is activated.

H3. A method for activating a cell in a subject, comprising administering to the subject a nucleic acid comprising a polynucleotide that encodes a chimeric protein, wherein the chimeric protein comprises
  a) a membrane targeting region,
  b) a multimerization region, and
  c) a CD40 polypeptide cytoplasmic region, wherein the CD40 polypeptide does not have a functional extracellular domain;
whereby the cell is activated.

H4. A method of inducing an immune response against a tumor antigen in a subject, comprising administering a nucleic acid according to the method of any one of embodiments H1-H3 to a subject.
H5. A method of reducing tumor size in a subject, comprising administering a nucleic acid according to the method of any one of embodiments H1-H3 to a subject.
H6. The method of embodiment H5, wherein the tumor is a prostate cancer tumor.
H7. A method of treating prostate cancer in a subject, comprising administering a nucleic acid according to the method of any one of embodiments H1-H3 to a subject, further comprising administering a nucleic acid coding for a prostate cancer antigen.
H8. The method of embodiment H4, wherein the tumor antigen is PSMA.
H6. The method of any one of embodiments H1-H5, wherein the subject is human.
H7. The method of any one of embodiments H1-H6, wherein the subject has prostate cancer.
H8. The method of any one of embodiments H1-H7, further comprising administering a multimeric ligand that binds to the multimerization region.
H9. The method of embodiment H8, wherein the multimeric ligand is AP1903.
H10. The method of embodiments H4-H9, comprising measuring the size of the tumor before and/or after administration of the cell.
H11. The method of embodiments H4-H10, comprising determining a serum PSA level of the subject, before and/or after administration of the nucleic acid.
H12. The method of embodiments H4-H11, wherein the subject has prostate cancer having a Gleason score of 7 or greater.
H13. The method of embodiments H4-H11, wherein the subject has prostate cancer having a Gleason score of 8 or greater.
H14. The method of embodiments H4-H13, comprising measuring the level of tumor vasculature before and after administration of the nucleic acid.
H15. The, method of any one of embodiments H1-H14, wherein the cell is a natural killer cell.
H16. The method of any one of embodiments H1-H14, wherein the cell is a non-lymphocytic hematopoietic cell.
H17. The method of any one of embodiments H1-H14, wherein the cell is a non-hematopoietic cell.
H18. The method of any one of embodiments H1-H14, wherein the cell is a macrophage.
H19. The method of any one of embodiments H1-H14, wherein the cell is a keratinocyte.
H20. The method of any one of embodiments H1-H14, wherein the cell is a fibroblast.
H21. The method of any one of embodiments H1-H14, wherein the cell is a melanoma cell
J1. A cell transduced or transfected with a composition comprising a nucleic acid that comprises a polynucleotide encoding an inducible chimeric signaling molecule, wherein the inducible chimeric signaling molecule comprises a membrane targeting region, a multimerizing region, and a truncated MyD88 polypeptide lacking the TIR domain.
J1.1. The cell of embodiment J1, wherein the inducible chimeric signaling molecule further comprises a cytoplasmic CD40 polypeptide lacking the extracellular domain.
J1.2. A cell transduced or transfected with a composition comprising a nucleic acid that comprises a polynucleotide encoding an inducible chimeric signaling molecule, wherein the inducible chimeric signaling molecule comprises a membrane targeting region, a multimerizing region, and a cytoplasmic CD40 polypeptide lacking the extracellular domain.
J2. The cell of any of embodiments J1 or J1.2, wherein the truncated MyD88 polypeptide has the amino acid sequence of SEQ ID NO: 5, or a functional fragment thereof.
J2.1. The cell of any of embodiments J1.1 or J1.2, wherein the cytoplasmic CD40 polypeptide has the amino acid sequence of SEQ ID NO: 9, or a functional fragment thereof.
J3. The cell of any of embodiments J1-J2.1, wherein the membrane-targeting region is a myristoylation targeting sequence.
J4-J6. Reserved
J7. The cell of any one of embodiments J1-J3, wherein the inducible chimeric signaling molecule further comprises a CD3 polypeptide.
J8. The cell of any one of embodiments J1-J7, wherein the multimerizing region is selected from the group consisting of FKBP, cyclophilin receptor, steroid receptor, tetracycline receptor, heavy chain antibody subunit, light chain antibody subunit, and mutated sequences thereof.
J9. The cell of any one of embodiments J1-J8, wherein the multimerizing region is an FKBP12 region.
J10. The cell of any one of embodiments J1-J9, wherein the FKBP12 region is an FKBP12v36 region.
J11. The cell of any one of embodiments J1-J8, wherein the multimerizing region is Fv'Fvls.
J12. The cell of any one of embodiments J1-J8, wherein the multimerizing region binds a ligand selected from the group consisting of an FK506 dimer and a dimeric FK506 analog ligand.
J13. The cell of any one of embodiments J1-J12, wherein the ligand is AP1903 or AP20187.
J14. The cell of any one of embodiments J1-J13, wherein the multimerizing region has an amino acid sequence of SEQ ID NO: 11 or a functional fragment thereof.
J15. The cell of any one of embodiments J1-J14, wherein the multimerizing region is encoded by a nucleotide sequence in SEQ ID NO: 10, or a functional fragment thereof.
J16. The cell of embodiment J14, wherein the multimerizing region further comprises a polypeptide having an amino acid sequence of SEQ ID NO: 13, or a functional fragment thereof.
J17. The cell of embodiment J15, wherein the multimerizing region further comprises a polypeptide encoded by a nucleotide sequence in SEQ ID NO: 12, or a functional fragment thereof.
J18. The cell of embodiments J14 or J16, wherein the multimerizing region further comprises a polypeptide having an amino acid sequence of SEQ ID NO: 13, or a functional fragment thereof.
J19. The cell of embodiments J15 or J17, wherein the multimerizing region further comprises a polypeptide encoded by a nucleotide sequence in SEQ ID NO: 12, or a functional fragment thereof.
J20. The cell of any one of embodiments J14, J16, or J18, wherein the multimerizing region further comprises a polypeptide having an amino acid sequence of SEQ ID NO: 11 or SEQ ID NO: 13, or a functional fragment thereof.
J21. The cell of any one of embodiments J15, J17, or J19, wherein the multimerizing region further comprises a polypeptide encoded by a nucleotide sequence in SEQ ID NO: 10 or SEQ ID NO: 12, or a functional fragment thereof.
J22. The cell of any of embodiments J1-J21, wherein the nucleic acid comprises a promoter sequence operably linked to the polynucleotide.
J23. The cell of any one of embodiments J1-J22, wherein the nucleic acid is contained within a viral vector.

J24. The cell of embodiment J23, wherein the viral vector is a retroviral vector.
J25. The cell of embodiment J24, wherein the retroviral vector is a murine leukemia virus vector.
J26. The cell of embodiment J24, wherein the retroviral vector is an SFG vector.
J27. The cell of embodiment J23, wherein the viral vector is an adenoviral vector.
J28. The cell of embodiment J23, wherein the viral vector is a lentiviral vector.
J29. The cell of any one of embodiments J1-J22, wherein the nucleic acid is contained within a plasmid.
J30. Reserved.
J31. The cell of any one of embodiments J1-J30, wherein the cell is a T cell, tumor infiltrating lymphocyte, NK-T cell, or NK cell.
J32. The cell of embodiment J31, wherein the cell is a T cell.
J33. The cell of any one of embodiments J1-J32, wherein the cell is obtained or prepared from bone marrow.
J34. The cell of any one of embodiments J1-J32, wherein the cell is obtained or prepared from umbilical cord blood.
J35. The cell of any one of embodiments J1-J32, wherein the cell is obtained or prepared from peripheral blood.
J36. The cell of any one of embodiments J1-J32, wherein the cell is obtained or prepared from peripheral blood mononuclear cells.
J37. The cell of any one of embodiments J31-J36, wherein the cell is a human cell.
J38. The cell of any one of embodiments J1-J37, wherein the cell is further transformed or transduced with a nucleic acid comprising a polynucleotide that encodes an inducible chimeric signaling molecule comprising a signal peptide, a single chain variable fragment, a CH2-CH3 hinge region and a CD3ζ polypeptide.
J38.1. The cell of embodiment J38, wherein the inducible chimeric signaling molecule does not comprise a CD3 polypeptide.
J38.2. The cell of embodiments J38 or J38.1, wherein the inducible chimeric signaling molecule comprises a CD3 polypeptide.
J39. The cell of any one of embodiments J38-J38.2, wherein the single chain variable fragment binds to an antigen on a tumor cell.
J40. The cell of any one of embodiments J38-J38.2, wherein the single chain variable fragment binds to an antigen on a cell involved in a hyperproliferative disease.
J41. The cell of any one of embodiments J38-J40, wherein the single chain variable fragment is selected from the group consisting of αPSMA, αPSCA, αMUC1, αCD19, αROR1, αMesothelin, αGD2, αCD123, αMUC16, and αHer2/Neu single chain variable fragments.
J42. The cell of any of embodiments J38-J40, wherein the single chain variable fragment is an αCD19 single chain variable fragment.
J42.1. The cell of any of embodiments J38-J40, wherein the single chain variable fragment is an αPSCA single chain variable fragment.
J43. A method for inducing an immune response, comprising contacting a cell of embodiments J1-J42.1 with a ligand that binds to the multimerizing region resulting in multimerization of the inducible chimeric signaling molecule.
J44. The method of embodiment J43, wherein the cell is contacted with the ligand in vivo.
J45. The method of embodiment J43 or J44, wherein the ligand is dimeric.
J46. The method of embodiment J45, wherein the ligand is dimeric FK506, or a dimeric FK506-like analog.
J47. The method of embodiment J45, wherein the ligand is AP1903 or AP20187.
J48. The method of any one of embodiments J43-J47, further comprising administering the transfected or transduced cell to a subject.
J49. The method of embodiment J48, wherein the cell is administered to the subject by intravenous administration.
J50-J56. Reserved.
J56. The method of any one of embodiments J43-J49, wherein the subject has been diagnosed with a tumor.
J57. The method of any one of embodiments J43-J49, wherein the subject has cancer.
J58 The method of any one of embodiments J43-J49, wherein the subject has a solid tumor.
J59. The method of embodiment J58, wherein the cell is a tumor infiltrating lymphocyte or a T cell.
J60. The method of embodiments J58 or J59, wherein the cell is delivered to the tumor bed.
J61. The method of embodiment J57, wherein the cancer is present in the blood or bone marrow of the subject.
J62. The method of any one of embodiments J43-J49, wherein the subject has a blood or bone marrow disease.
J63. The method of any one of embodiments J43-J49, wherein the subject has been diagnosed with any condition or disorder that can be alleviated by stem cell transplantation.
J64. The method of any one of embodiments J43-J49, wherein the subject has been diagnosed with sickle cell anemia or metachromatic leukodystrophy.
J65. The method of any one of embodiments J43-J49, wherein the patient has been diagnosed with a condition selected from the group consisting of a primary immune deficiency disorder, hemophagocytosis lymphohistiocytosis (HLH) or other hemophagocytic disorder, an inherited marrow failure disorder, a hemoglobinopathy, a metabolic disorder, and an osteoclast disorder.
J66. The method of any one of embodiments J43-J49, wherein the condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCK 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.
J67. A method for treating leukemia in a subject, comprising administering a cell of any one of embodiments J1 to J42.1, and administering a multimeric ligand to the subject.
J68. The method of embodiment J67, wherein the single chain variable fragment binds to CD19.
J69. The method of embodiments J67 or J68, wherein the multimeric ligand is AP1903 or AP20187.
J70. The method of any of embodiments J67-J69, wherein the cell is a T cell.
J71. The method of any one of embodiments J43-J70, wherein the subject is human.
J72. The method of any one of embodiments J43-J71, further comprising determining whether an additional dose of the multimeric ligand should be administered to the subject.

J73. The method of any one of embodiments J43-J72, further comprising administering an additional dose of the multimeric ligand to the subject, wherein the disease or condition symptoms remain or are detected following a reduction in symptoms.

J74. The method of embodiment J73, wherein the subject has been diagnosed with a disease or condition before administration of the cell of any one of embodiments 1-42.1, and after administration of the multimeric ligand the disease or condition is detected, an additional dose of the multimeric ligand is administered to the subject.

J75. The method of any one of embodiments J43-J74, further comprising
identifying the presence, absence or stage of a condition or disease in a subject, and
transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the condition or disease identified in the subject.

J76. The method of any one of embodiments J72-J75, wherein the condition is cancer.

J77. The method of any one of embodiments J72-J75, wherein the condition is leukemia.

J78. The method of any one of embodiments J72-J75, wherein the condition is a solid tumor.

J79. The method of embodiment J78, comprising
determining the presence or absence of a tumor size increase and/or increase in the number of tumor cells in a subject relative to the tumor size and/or the number of tumor cells following administration of the multimeric ligand, and
administering an additional dose of the multimeric ligand to the subject in the event the presence of a tumor size increase and/or increase in the number of tumor cells is determined.

J80. The method of embodiment J77, comprising
determining the presence or absence of an increase in CD19-expressing B cells in the subject relative to the level of CD19-expressing B cells following administration of the multimeric ligand, and
administering an additional dose of the multimeric ligand to the subject in the event the presence of an increase in CD19-expressing B cells in the subject is determined.

J81. The method of embodiment J79, wherein the tumor size and/or the number of tumor cells is decreased following administration of the multimeric ligand relative to the tumor size and/or number of tumor cells before administration of the multimeric ligand.

J82. The method of embodiment J80, wherein the level of CD19-expressing B cells is decreased following administration of the multimeric ligand relative to the level of CD19-expressing B cells before administration of the multimeric ligand.

J83. The method of any one of embodiments J43-J74, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

K1. A composition comprising a nucleic acid that comprises a polynucleotide encoding an inducible chimeric antigen receptor, wherein the inducible chimeric antigen receptor comprises a multimerizing region, a truncated MyD88 polypeptide lacking the TIR domain, and a single chain variable fragment.

K1.1. The composition of embodiment K1, wherein the inducible chimeric antigen receptor further comprises a cytoplasmic CD40 polypeptide lacking the extracellular domain.

K1.2. A composition comprising a nucleic acid that comprises a polynucleotide encoding an inducible chimeric antigen receptor, wherein the inducible chimeric antigen receptor comprises a multimerizing region, a cytoplasmic CD40 polypeptide lacking the extracellular domain, and a single chain variable fragment.

K2. The composition of any embodiments K1 or K1.2, wherein the truncated MyD88 polypeptide has the amino acid sequence of SEQ ID NO: 5, or a functional fragment thereof.

K2.1. The composition of any of embodiments K1.1 or K1.2, wherein the cytoplasmic CD40 polypeptide has the amino acid sequence of SEQ ID NO: 4, or a functional fragment thereof.

K3-K6. Reserved

K7. The composition of any one of embodiments K1-K2.1, wherein the inducible chimeric antigen receptor further comprises a CD3 polypeptide.

K8. The composition of any one of embodiments K1-K7, wherein the multimerizing region is selected from the group consisting of FKBP, cyclophilin receptor, steroid receptor, tetracycline receptor, heavy chain antibody subunit, light chain antibody subunit, and mutated sequences thereof.

K9. The composition of any one of embodiments K1-K8, wherein the multimerizing region is an FKBP12 region.

K10. The composition of any one of embodiments K1-K9, wherein the multimerizing region is an FKBP12v36 region.

K11. The composition of any one of embodiments K1-K8, wherein the multimerizing region is Fv'Fvls.

K12. The composition of any one of embodiments K1-K8, wherein the multimerizing region binds a ligand selected from the group consisting of an FK506 dimer and a dimeric FK506 analog ligand.

K13. The composition of any one of embodiments K1-K12, wherein the ligand is AP1903 or AP20187.

K14. The composition of any one of embodiments K1-K13, wherein the multimerizing region has an amino acid sequence of SEQ ID NO: 11 or a functional fragment thereof.

K15. The composition of any one of embodiments K1-K14, wherein the multimerizing region is encoded by a nucleotide sequence in SEQ ID NO: 10, or a functional fragment thereof.

K16. The composition of embodiment K14, wherein the multimerizing region further comprises a polypeptide having an amino acid sequence of SEQ ID NO: 13, or a functional fragment thereof.

K17. The composition of embodiment K15, wherein the multimerizing region further comprises a polypeptide encoded by a nucleotide sequence in SEQ ID NO: 12, or a functional fragment thereof.

K18. The composition of embodiments K14 or K16, wherein the multimerizing region further comprises a polypeptide having an amino acid sequence of SEQ ID NO: 13, or a functional fragment thereof.

K19. The composition of embodiments K15 or K17, wherein the multimerizing region further comprises a polypeptide encoded by a nucleotide sequence in SEQ ID NO: 12, or a functional fragment thereof.

K20. The composition of any one of embodiments K14, K16, or K18, wherein the multimerizing region further comprises a polypeptide having an amino acid sequence of SEQ ID NO: 11 or SEQ ID NO: 13, or a functional fragment thereof.

K21. The composition of any one of embodiments K15, K17, or K19, wherein the multimerizing region further comprises a polypeptide encoded by a nucleotide sequence in SEQ ID NO: 10 or SEQ ID NO: 12, or a functional fragment thereof.

K22. The composition of any one of embodiments K1-K21, wherein the nucleic acid comprises a promoter sequence operably linked to the polynucleotide.

K23. The composition of any one of embodiments K1-K22, wherein the nucleic acid is contained within a viral vector.

K24. The composition of embodiment K23, wherein the viral vector is a retroviral vector.

K25. The composition of embodiment K24, wherein the retroviral vector is a murine leukemia virus vector.

K26. The composition of embodiment K24, wherein the retroviral vector is an SFG vector.

K27. The composition of embodiment K23, wherein the viral vector is an adenoviral vector.

K28. The composition of embodiment K23, wherein the viral vector is a lentiviral vector.

K29. The composition of any one of embodiments K1-K22, wherein the nucleic acid is contained within a plasmid.

K30. A cell transduced or transformed with a composition of any one of embodiments K1-K29.

K31. The cell of embodiments K30, wherein the cell is a T cell, tumor infiltrating lymphocyte, NK-T cell, or NK cell.

K32. The cell of embodiment K31, wherein the cell is a T cell.

K33. The cell of any one of embodiments K1-K3, wherein the cell is obtained or prepared from bone marrow.

K34. The cell of any one of embodiments K1-K3, wherein the cell is obtained or prepared from umbilical cord blood.

K35. The cell of any one of embodiments K1-K3, wherein the cell is obtained or prepared from peripheral blood.

K36. The cell of any one of embodiments K1-K3, wherein the cell is obtained or prepared from peripheral blood mononuclear cells.

K37. The cell of any one of embodiments K31-K3, wherein the cell is a human cell.

K38. Reserved.

K39. The cell of any one of embodiments K1-K37, wherein the single chain variable fragment binds to an antigen on a tumor cell.

K40. The cell of any one of embodiments K1-K37, wherein the single chain variable fragment binds to an antigen on a cell involved in a hyperproliferative disease.

K41. The cell of any one of embodiments K1-K40, wherein the single chain variable fragment is selected from the group consisting of αPSMA, αPSCA, αMUC1, αCD19, αROR1, αMesothelin, αGD2, αCD123, αMUC16, and αHer2/Neu single chain variable fragments.

K42. The cell of any of embodiments K1-K40, wherein the single chain variable fragment is an αCD19 single chain variable fragment.

K42.1. The cell of any of embodiments K1-K40, wherein the single chain variable fragment is an αPSCA single chain variable fragment.

K43. A method for inducing an immune response, comprising contacting a cell of embodiments K1-K42.1 with a ligand that binds to the multimerizing region resulting in multimerization of the inducible chimeric antigen receptor.

K44. The method of embodiment K43, wherein the cell is contacted with the ligand in vivo.

K45. The method of embodiments K43 or K44, wherein the ligand is dimeric.

K46. The method of embodiment K45, wherein the ligand is dimeric FK506, or a dimeric FK506-like analog.

K47. The method of embodiment K45, wherein the ligand is AP1903 or AP20187.

K48. The method of any one of embodiments K43-K47, further comprising administering the transfected or transduced cell to a subject.

K49. The method of embodiment K48, wherein the cell is administered to the subject by intravenous administration.

K50-K56. Reserved.

K56. The method of any one of embodiments K43-K49, wherein the subject has been diagnosed with a tumor.

K57. The method of any one of embodiments K43-K49, wherein the subject has cancer.

K58 The method of any one of embodiments K43-K49, wherein the subject has a solid tumor.

K59. The method of embodiment K58, wherein the cell is a tumor infiltrating lymphocyte or a T cell.

K60. The method of embodiments K58 or K59, wherein the cell is delivered to the tumor bed.

K61. The method of embodiment K57, wherein the cancer is present in the blood or bone marrow of the subject.

K62. The method of any one of embodiments K43-K49, wherein the subject has a blood or bone marrow disease.

K63. The method of any one of embodiments K43-K49, wherein the subject has been diagnosed with any condition or disorder that can be alleviated by stem cell transplantation.

K64. The method of any one of embodiments K43-K49, wherein the subject has been diagnosed with sickle cell anemia or metachromatic leukodystrophy.

K65. The method of any one of embodiments K43-K49, wherein the patient has been diagnosed with a condition selected from the group consisting of a primary immune deficiency disorder, hemophagocytosis lymphohistiocytosis (HLH) or other hemophagocytic disorder, an inherited marrow failure disorder, a hemoglobinopathy, a metabolic disorder, and an osteoclast disorder.

K66. The method of any one of embodiments K43-K49, wherein the condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCK 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

K67. A method for treating leukemia in a subject, comprising administering a cell of any one of embodiments K1 to K42.1, and administering a multimeric ligand to the subject.

K68. The method of embodiment K67, wherein the single chain variable fragment binds to CD19.

K69. The method of embodiments K67 or K68, wherein the multimeric ligand is AP1903 or AP20187.

K70. The method of any of embodiments K67-K69, wherein the cell is a T cell.

K71. The method of any one of embodiments K43-K70, wherein the subject is human.

K72. The method of any one of embodiments K43-K71, further comprising determining whether an additional dose of the multimeric ligand should be administered to the subject.

K73. The method of any one of embodiments K43-K72, further comprising administering an additional dose of the multimeric ligand to the subject, wherein the disease or condition symptoms remain or are detected following a reduction in symptoms.

K74. The method of embodiment K73, wherein the subject has been diagnosed with a disease or condition before administration of the cell of any one of embodiments 1-42.1, and after administration of the multimeric ligand the disease or condition is detected, an additional dose of the multimeric ligand is administered to the subject.

K75. The method of any one of embodiments K43-K74, further comprising
identifying the presence, absence or stage of a condition or disease in a subject, and
transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the condition or disease identified in the subject.

K76. The method of any one of embodiments K72-K75, wherein the condition is cancer.

K77. The method of any one of embodiments K72-K75, wherein the condition is leukemia.

K78. The method of any one of embodiments K72-K75, wherein the condition is a solid tumor.

K79. The method of embodiment K78, comprising
determining the presence or absence of a tumor size increase and/or increase in the number of tumor cells in a subject relative to the tumor size and/or the number of tumor cells following administration of the multimeric ligand, and
administering an additional dose of the multimeric ligand to the subject in the event the presence of a tumor size increase and/or increase in the number of tumor cells is determined.

K80. The method of embodiment K77, comprising
determining the presence or absence of an increase in CD19-expressing B cells in the subject relative to the level of CD19-expressing B cells following administration of the multimeric ligand, and
administering an additional dose of the multimeric ligand to the subject in the event the presence of an increase in CD19-expressing B cells in the subject is determined.

K81. The method of embodiment C79, wherein the tumor size and/or the number of tumor cells is decreased following administration of the multimeric ligand relative to the tumor size and/or number of tumor cells before administration of the multimeric ligand.

K82. The method of embodiment K80, wherein the level of CD19-expressing B cells is decreased following administration of the multimeric ligand relative to the level of CD19-expressing B cells before administration of the multimeric ligand.

K83. The method of any one of embodiments K43-K74, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

L1. A nucleic acid comprising a polynucleotide encoding an inducible chimeric stimulating molecule, wherein the chimeric stimulating molecule comprises (i) a membrane targeting region; (ii) a MyD88 polypeptide or a truncated MyD88 polypeptide lacking the TIR domain; (iii) a CD40 cytoplasmic polypeptide region lacking the CD40 extracellular domain, and (iv) a multimerization region.

L2. A nucleic acid comprising a polynucleotide encoding a chimeric stimulating molecule, wherein the chimeric stimulating molecule comprises (i) a membrane targeting region; (ii) a MyD88 polypeptide or a truncated MyD88 polypeptide lacking the TIR domain, and a multimerization region.

L3. A nucleic acid comprising a polynucleotide encoding an inducible chimeric stimulating molecule, wherein the chimeric stimulating molecule comprises (i) a membrane targeting region; (ii) a CD40 cytoplasmic polypeptide region lacking the CD40 extracellular domain, and (iii) a multimerization region.

L4. The nucleic acid of any one of embodiments L1-L3, wherein the chimeric stimulating molecule further comprises a T cell activation molecule.

L4.1. The nucleic acid of any one of embodiments L1-L4, wherein the multimerization region is a ligand binding region selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

L4.2. The nucleic acid of embodiment L4.1, wherein the ligand binding region is an FKBP12 region.

L4.3. The nucleic acid of embodiment L4.2, wherein the FKBP12 region is an FKBP12v36 region.

L4.4. The nucleic acid of embodiment 4.2, wherein the FKBP region is Fv'Fvls.

L4.5. The nucleic acid of any one of embodiments L4.1-L4.4, wherein the ligand is an FK506 dimer or a dimeric FK506 analog ligand.

L4.6. The nucleic acid of embodiment L4.5, wherein the ligand is AP1903.

L4.7. The nucleic acid of any one of embodiments L1-L4.6, wherein the CD40 cytoplasmic polypeptide region has an amino acid sequence of the cytoplasmic region of SEQ ID NO: 9, or a functional fragment thereof.

L4.8. The nucleic acid of any one of embodiments L1-L4.7, wherein the CD40 cytoplasmic polypeptide region is encoded by a nucleotide sequence in SEQ ID NO: 8, or a functional fragment thereof.

L4.9. The nucleic acid of any one of embodiments L1-L4.8, wherein the multimerization region has an amino acid sequence of SEQ ID NO: 11 or a functional fragment thereof.

L4.10. The nucleic acid of any one of embodiments L1-L4.9, wherein the multimerization region is encoded by a nucleotide sequence in SEQ ID NO: 10, or a functional fragment thereof.

L4.11. The nucleic acid of embodiment L4.9, wherein the multimerization region further comprises a polypeptide having an amino acid sequence of SEQ ID NO: 13, or a functional fragment thereof.

L4.12. The nucleic acid of embodiment L4.10, wherein the multimerization region further comprises a polypeptide encoded by a nucleotide sequence in SEQ ID NO: 12, or a functional fragment thereof.

L4.13. The nucleic acid of embodiment L4.11, wherein the multimerization region further comprises a polypeptide having an amino acid sequence of SEQ ID NO: 13, or a functional fragment thereof.

L4.14. The nucleic acid of embodiment L4.12, wherein the multimerization region further comprises a polypeptide encoded by a nucleotide sequence in SEQ ID NO: 12, or a functional fragment thereof.

L4.15. The nucleic acid of any one of embodiments L4.11 or L4.13, wherein the multimerization region further comprises a polypeptide having an amino acid sequence of SEQ ID NO: 11 or SEQ ID NO: 13, or a functional fragment thereof.

L4.16. The nucleic acid of any one of embodiments L4.12 or L4.14, wherein the multimerization region further comprises a polypeptide encoded by a nucleotide sequence in SEQ ID NO: 10 or SEQ ID NO: 12, or a functional fragment thereof.

L4.17. The nucleic acid of any one of embodiments L1-L4.16, wherein the membrane targeting region is a myristoylation region.

L4.18. The nucleic acid of embodiment L4.17, wherein the myristoylation region has an amino acid sequence of SEQ ID NO: 3, or a functional fragment thereof.

L4.19. The nucleic acid of embodiment L4.17, wherein the myristoylation region is encoded by a nucleotide sequence in SEQ ID NO: 2, or a functional fragment thereof.

L4.20. The nucleic acid of any one of embodiments L1-L4.19, further comprising a polynucleotide encoding a chimeric antigen receptor.

L4.21. A nucleic acid comprising
a first polynucleotide encoding an inducible chimeric stimulating molecule, wherein the inducible chimeric stimulating molecule comprises (i) a membrane targeting region; (ii) a MyD88 polypeptide or a truncated MyD88 polypeptide lacking the TIR domain; (iii) a CD40 cytoplasmic polypeptide region lacking the CD40 extracellular domain, and a multimerization region; and a second polynucleotide encoding a chimeric antigen receptor.

L4.22. The nucleic acid of embodiment L4.21, wherein the multimerization is a ligand binding region.

L4.23. The nucleic acid of embodiment 4.22, wherein the ligand binding region is an FKBP12 region.

L4.24. The nucleic acid of embodiment L4.23, wherein the FKBP12 region is an FKBP12v36 region.

L4.25. The nucleic acid of embodiment L4.23, wherein the FKBP12 region is Fv'Fvls.

L4.26. The nucleic acid of any one of embodiments L4.21-L4.25, wherein the ligand is an FK506 dimer or a dimeric FK506 analog ligand.

L4.27. The nucleic acid of embodiment L4.26, wherein the ligand is AP1903.

L4.28. The nucleic acid of any one of embodiments 4.21-4.27, further comprising at least one promoter.

L4.29. The nucleic acid of any one of embodiments 4.21-4.27, further comprising at least two promoters.

L4.30. The nucleic acid of embodiment L4.28, wherein one promoter is operably linked to both the first and second polynucleotide.

L4.31. The nucleic acid of any one of embodiments L4.21-L4.30, further comprising a third polynucleotide encoding a linker polypeptide between the first and second polynucleotides, wherein the linker polypeptide separates the translation products of the first and second polynucleotides during or after translation.

L4.32. The nucleic acid of embodiment L4.31, wherein the linker polypeptide is a 2A polypeptide.

L4.33. The nucleic acid of any one of embodiments L4.21-L4.32, wherein the nucleic acid encodes a polypeptide comprising a chimeric stimulating molecule, a 2A polypeptide, and a caspase-9 polypeptide.

L4.34. The nucleic acid of any one of embodiments L4.21-L4.33, therein the first polynucleotide is operably linked to a first promoter, and the second polynucleotide is operably linked to a second promoter.

L4.35. The nucleic acid of any one of embodiments L4.21-L4.34, wherein two RNA transcripts are produced complementary to the two polynucleotides.

L5. The nucleic acid of any one of embodiments L4-L4.35, wherein the T cell activation molecule is an ITAM-containing signal 1 conferring molecule.

L6. The nucleic acid of any one of embodiments L4-L4.19, wherein the T cell activation molecule is a CD3 polypeptide.

L6.1. The nucleic acid of any one of embodiments L4-L4.19, wherein the T cell activation molecule is an Fc epsilon receptor gamma (FcεR1γ) subunit polypeptide.

L7. The nucleic acid of any one of embodiments L1-L6.1, wherein the truncated MyD88 polypeptide has the amino acid sequence of SEQ ID NO: 5, or a functional fragment thereof.

L8. The nucleic acid of any one of embodiments L1, or L2-L7, wherein the cytoplasmic CD40 polypeptide has the amino acid sequence of SEQ ID NO: 4, or a functional fragment thereof.

L9. The nucleic acid of any one of embodiments L6-L8, wherein the CD3 polypeptide comprises an amino acid sequence of SEQ ID NO: 39, or a functional fragment thereof.

L10. The nucleic acid of any one of embodiments L1-L9, wherein the membrane targeting region is selected from the group consisting of a myristoylation region, palmitoylation region, prenylation region, and transmembrane sequences of receptors.

L11. The nucleic acid of any one of embodiments L1-L10, wherein the membrane targeting region is a myristoylation region.

L11.1. The nucleic acid of any one of embodiments L1-L10, wherein the polynucleotide encoding the chimeric stimulating molecule does not include a dimerization or multimerization molecule binding region.

L12. The nucleic acid of any one of embodiments L1-L11.1, wherein the nucleic acid comprises a promoter sequence operably linked to the polynucleotide.

L13. The nucleic acid of any one of embodiments L1-L12, wherein the nucleic acid is contained within a viral vector.

L14. The nucleic acid of embodiment L13, wherein the viral vector is a retroviral vector.

L15. The nucleic acid of embodiment L14, wherein the retroviral vector is a murine leukemia virus vector.

L16. The nucleic acid of embodiment L14, wherein the retroviral vector is an SFG vector.

L17. The nucleic acid of embodiment L13, wherein the viral vector is an adenoviral vector.

L18. The nucleic acid of embodiment L13, wherein the viral vector is a lentiviral vector.

L18.1. The nucleic acid of embodiment L13, wherein the viral vector is selected from the group consisting of adeno-associated virus (AAV), Herpes virus, and Vaccinia virus.

L19. The nucleic acid of any one of embodiments L1-L12, wherein the nucleic acid is contained within a plasmid.

L20. A chimeric stimulating molecule polypeptide encoded by the nucleic acid of any one of embodiments L1-L19

L21. A modified cell transfected or transduced with a nucleic acid of any one of embodiments L1-L19.

L22. The modified cell of embodiment L21, wherein the modified cell is a T cell, tumor infiltrating lymphocyte, NK-T cell, TCR-expressing cell, or NK cell.

L23. The modified cell of embodiment L21, wherein the cell is a T cell.

L24. The modified cell of any one of embodiments L21-L23, wherein the cell is obtained or prepared from bone marrow.

L25. The modified cell of any one of embodiments L21-L23, wherein the cell is obtained or prepared from umbilical cord blood.

L26. The modified cell of any one of embodiments L21-L25, wherein the cell is obtained or prepared from peripheral blood.

L27. The modified cell of any one of embodiments L21-L25, wherein the cell is obtained or prepared from peripheral blood mononuclear cells.

L28. The modified cell of any one of embodiments L21-L27, wherein the cell is a human cell.

L29. The modified cell of any one of embodiments L21-L28, wherein the modified cell further comprises a polynucleotide encoding a chimeric antigen receptor.

L30. The modified cell of embodiment L29, wherein the chimeric antigen receptor comprises an antigen-recognition moiety.

L30.1. The modified cell of any one of embodiments L21-L30, wherein the cell is a T cell.

L30.2. The modified cell of any one of embodiments L21-L28, wherein the modified cell further comprises a polynucleotide encoding a T cell receptor.

L30.3. The modified cell of any one of embodiments L21-28, wherein the modified cell further comprises a polynucleotide encoding a T cell receptor-based CAR.

L30.4. The modified cell of any one of embodiments L30.2 or L30.3, wherein modified cell is transfected or transduced with a nucleic acid comprising a polynucleotide encoding the T cell receptor or T cell receptor-based CAR.

L31. The modified cell of any one of embodiments L27.1 or L30, wherein the antigen-recognition moiety is a single chain variable fragment.

L31.1. The modified cell of any one of embodiments L29-L31, wherein the chimeric antigen receptor or T cell receptor binds to an antigen on a tumor cell.

L32. The modified cell of any one of embodiments L29-L31.1, wherein the chimeric antigen receptor or T cell receptor binds to an antigen on a cell involved in a hyper-proliferative disease.

L33. The modified cell of any one of embodiments L29-L31.1, wherein the chimeric antigen receptor or T cell receptor binds to an antigen selected from the group consisting of PSMA, PSCA, MUC1, CD19, ROR1, Mesothelin, GD2, CD123, MUC16, and Her2/Neu.

L34 The modified cell of any one of embodiments L29-L33, wherein the chimeric antigen receptor or T cell receptor binds to CD19.

L35. The modified cell of any one of embodiments L29-L33, wherein the chimeric antigen receptor or T cell receptor binds to Her2$^+$.

L36. The modified cell of any one of embodiments L29-L33, wherein the antigen recognition moiety binds to a viral or bacterial antigen.

L36.1. The modified cell of any one of embodiments L29-L36, wherein the cell is transfected or transduced by the nucleic acid vector using a method selected from the group consisting of electroporation, sonoporation, biolistics (e.g., Gene Gun with Au-particles), lipid transfection, polymer transfection, nanoparticles, or polyplexes.

L37. A method for stimulating a T cell-mediated immune response in a subject, comprising administering a modified cell of any one of embodiments L21-L36.1 to the subject.

L37.1. The method of embodiment L37, wherein the modified cell comprises a chimeric antigen receptor or T cell receptor that binds to an antigen on a target cell.

L38. The method of embodiment L37.1, wherein the target cell is a tumor cell.

L39. The method of any one of embodiments L37-L38, wherein the number or concentration of target cells in the subject is reduced following administration of the modified cell.

L40. The method of any one of embodiments L37-L39, comprising measuring the number or concentration of target cells in a first sample obtained from the subject before administering the modified cell, measuring the number concentration of target cells in a second sample obtained from the subject after administration of the modified cell, and determining an increase or decrease of the number or concentration of target cells in the second sample compared to the number or concentration of target cells in the first sample.

L41. The method of embodiment L40, wherein the concentration of target cells in the second sample is decreased compared to the concentration of target cells in the first sample.

L42. The method of embodiment L40, wherein the concentration of target cells in the second sample is increased compared to the concentration target cells in the first sample.

L43. The method of any one of embodiments L40-L42, wherein an additional dose of modified cells is administered to the subject.

L44. A method for providing anti-tumor immunity to a subject, comprising administering to the subject an effective amount of a modified cell of any one of embodiments L21-L36.1.

L45. A method for treating a subject having a disease or condition associated with an elevated expression of a target antigen, comprising administering to the subject an effective amount of a modified cell of any one of embodiments L21-L36.1.

L46. The method of embodiment L45, wherein the target antigen is a tumor antigen.

L47. The method of any one of embodiments L37-L46, wherein the modified cells are autologous T cells.

L48. The method of any one of embodiments L37-L46, wherein the modified cells are allogeneic T cells.

L50. A method for reducing the size of a tumor in a subject, comprising administering a modified cell of any one of embodiments L29-L36.1 to the subject, wherein the antigen recognition moiety binds to an antigen on the tumor.

L51. The method of any one of embodiments L37-L50, wherein the subject has been diagnosed as having a tumor.

L52. The method of any one of embodiments L37-L51, wherein the subject has cancer.

L53. The method of any one of embodiments L37-L51, wherein the subject has a solid tumor.

L54. The method of any one of embodiments L37-L53, wherein the modified cell is a tumor infiltrating lymphocyte or a T cell.

L55. The method of any one of embodiments L37-L54, wherein the modified cell is delivered to a tumor bed.

L56. The method of embodiment L52, wherein the cancer is present in the blood or bone marrow of the subject.

L57. The method of any one of embodiments L37-L51, wherein the subject has a blood or bone marrow disease.

L58. The method of any one of embodiments L37-L51, wherein the subject has been diagnosed with any condition or condition that can be alleviated by stem cell transplantation.

L59. The method of any one of embodiments L37-L51, wherein the subject has been diagnosed with sickle cell anemia or metachromatic leukodystrophy.

L60. The method of any one of embodiments L37-L51, wherein the patient has been diagnosed with a condition selected from the group consisting of a primary immune deficiency condition, hemophagocytosis lymphohistiocytosis (HLH) or other hemophagocytic condition, an inherited marrow failure condition, a hemoglobinopathy, a metabolic condition, and an osteoclast condition.

L61. The method of any one of embodiments L37-L51, wherein the disease or condition is selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XLP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

L62. The method of any one of embodiments L37-L61, further comprising determining whether an additional dose of the modified cell should be administered to the subject.

L63. The method of any one of embodiments L37-L62, further comprising administering an additional dose of the modified cell to the subject, wherein the disease or condition symptoms remain or are detected following a reduction in symptoms.

L64. The method of any one of embodiments L37-L63, further comprising identifying the presence, absence or stage of a condition or disease in a subject; and
  transmitting an indication to administer modified cell of any one of embodiments L31-L36, maintain a subsequent dosage of the modified cell, or adjust a subsequent dosage of the modified cell administered to the patient based on the presence, absence or stage of the condition or disease identified in the subject.

L65. The method of any one of embodiments L37-L64, wherein the condition is leukemia.

L66. Reserved.

L67. The method of any one of embodiments L37-L64, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

L68. The method of any one of embodiments L37-L67, wherein the modified cell is transfected or transduced in vivo.

L69. The modified cell of any one of embodiments L21-L67, wherein the modified cell is transfected or transduced in vivo.

L70. A method for expressing a chimeric stimulating molecule in a cell, comprising contacting a nucleic acid of any one of embodiments L1 to L20 with a cell under conditions in which the nucleic acid is incorporated into the cell, whereby the cell expresses the chimeric antigen receptor from the incorporated nucleic acid.

L71. The method of embodiment L70, wherein the nucleic acid is contacted with the cell ex vivo.

L72. The method of embodiment L70, wherein the nucleic acid is contacted with the cell in vivo.

M1. The nucleic acid, modified cell, or method of any one of embodiments L4.20-L72, wherein the nucleic acid codes for a chimeric antigen receptor, or the modified cell comprises a chimeric antigen receptor.

M2. The nucleic acid, modified cell, or method of embodiment M1, wherein the chimeric antigen receptor comprises (i) a transmembrane region; (ii) a T cell activation molecule; and (iii) an antigen recognition moiety.

M3. The nucleic acid, modified cell, or method of any one of embodiments M1-M2, wherein the chimeric antigen receptor comprises (i) a transmembrane region; (ii) a T cell activation molecule; and (iii) an antigen recognition moiety.

M4. The nucleic acid, modified cell, or method of embodiment M3, wherein the chimeric antigen receptor further comprises a co-stimulatory molecule.

M5. The nucleic acid, modified cell, or method of embodiment M4, wherein the co-stimulatory molecule is selected from the group consisting of CD28, OX40, and 4-1BB.

M6. The nucleic acid, modified cell, or method of any one of embodiments M2-M5, wherein the T cell activation molecule is an ITAM-containing, Signal 1 conferring molecule.

M7. The nucleic acid, modified cell, or method of any one of embodiments M2-M5, wherein the T cell activation molecule is a CD3 zeta polypeptide.

M8. The nucleic acid, modified cell, or method of any one of embodiments M2-M5, wherein the T cell activation molecule is an Fc receptor gamma polypeptide.

M9. The nucleic acid, modified cell, or method of any one of embodiments M2-M8, wherein the antigen recognition moiety binds to an antigen on a tumor cell.

M9. The nucleic acid, modified cell, or method of any one of embodiments M2-M8, wherein the antigen recognition moiety binds to an antigen on a cell involved in a hyperproliferative disease.

M10. The nucleic acid, modified cell, or method of any one of embodiments M2-M8, wherein the antigen recognition moiety binds to an antigen selected from the group consisting of PSMA, PSCA, MUC1, CD19, ROR1, Mesothelin, GD2, CD123, MUC16, and Her2/Neu.

M11. The nucleic acid, modified cell, or method of any one of embodiments M2-M8, wherein the antigen recognition moiety binds to PSCA.

M12. The nucleic acid, modified cell, or method of any one of embodiments M2-M8, wherein the antigen recognition moiety binds to CD19.

M13. The nucleic acid, modified cell, or method of any one of embodiments M2-M8, wherein the antigen recognition moiety binds to a viral or bacterial antigen.

M14. The nucleic acid, modified cell, or method of any one of embodiments M2-M13, wherein the antigen recognition moiety is a single chain variable fragment.

M15. The nucleic acid, modified cell, or method of any one of embodiments M2-M14, wherein the transmembrane region is a CD28 transmembrane region.

M16. The nucleic acid, modified cell, or method of any one of embodiments M2-M14, wherein the transmembrane region is a CD8 transmembrane region.

M17. The nucleic acid, modified cell, or method of embodiment M16, further comprising a CD8 stalk region.

M18. The nucleic acid, modified cell, or method of any one of embodiments M2-M17, wherein the antigen recognition moiety binds to Her2/Neu.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A modified T cell comprising a nucleic acid that comprises a polynucleotide sequence encoding an inducible chimeric stimulating molecule, wherein the inducible chimeric stimulating molecule comprises:
   (a) a MyD88 polypeptide region or a truncated MyD88 polypeptide region lacking the TIR domain;
   (b) a CD40 cytoplasmic polypeptide region lacking the CD40 extracellular domain; and
   (c) an intracellular multimerizing region that comprises two or more FKBP12 regions, wherein each FKBP12 region comprises the amino acid sequence of SEQ ID NO:11,
   wherein the inducible chimeric stimulating molecule does not comprise a membrane targeting region.

2. The modified T cell of claim 1, wherein the intracellular multimerizing region comprises two FKBP12 regions.

3. The modified T cell of claim 1, wherein the inducible chimeric stimulating molecule comprises a truncated MyD88 polypeptide region lacking the TIR domain.

4. The modified T cell of claim 3, wherein the truncated MyD88 polypeptide region comprises the amino acid sequence of SEQ ID NO: 5.

5. The modified T cell of claim 3, wherein the CD40 cytoplasmic polypeptide region comprises the amino acid sequence of SEQ ID NO: 9.

6. The modified T cell of claim 3, wherein the truncated MyD88 polypeptide region consists of the amino acid sequence of SEQ ID NO: 5.

7. The modified T cell of claim 1, wherein the CD40 cytoplasmic polypeptide region consists of the amino acid sequence of SEQ ID NO: 9.

8. The modified T cell of claim 2, wherein each FKBP12 region consists of the amino acid sequence of SEQ ID NO: 11.

9. The modified T cell of claim 1, wherein the nucleic acid is a plasmid vector or viral vector.

10. The modified T cell of claim 1, wherein the modified T cell is a CAR-T cell.

11. The modified T cell of claim 1, wherein the inducible chimeric stimulating molecule comprises
   (a) a truncated MyD88 polypeptide region lacking the TIR domain;
   (b) a CD40 cytoplasmic polypeptide region lacking the CD40 extracellular domain; and
   (c) an intracellular multimerizing region that comprises two FKBP12 regions, wherein each FKBP12 region comprises the amino acid sequence of SEQ ID NO:11.

12. The modified T cell of claim 11, wherein the modified T cell is a CAR-T cell.

13. The modified T cell of claim 1, wherein the modified T cell is a primary T cell.

14. The modified T cell of claim 1, wherein the nucleic acid is integrated into the genome of the modified T cell.

15. The modified T cell of claim 1, wherein the inducible chimeric stimulating molecule consists essentially of:
   (a) a truncated MyD88 polypeptide region lacking the TIR domain;
   (b) a CD40 cytoplasmic polypeptide region lacking the CD40 extracellular domain; and
   (c) an intracellular multimerizing region that comprises two FKBP12 regions, wherein each FKBP12 region comprises the amino acid sequence of SEQ ID NO:11.

\* \* \* \* \*

SEQUENCE LISTING

```
<160> NUMBER OF SEQ ID NOS: 196

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 gccacc                                                                     6

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atggggagta gcaagagcaa gcctaaggac cccagccagc gcctcgac                       48

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 3

Met Gly Ser Ser Lys Ser Lys Pro Lys Asp Pro Ser Gln Arg Leu Asp
1               5                   10                  15

<210> SEQ ID NO 4
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atggctgcag gaggtcccgg cgcggggtct gcggccccgg tctcctccac atcctccctt    60
cccctggctg ctctcaacat gcgagtgcgg cgccgcctgt ctctgttctt gaacgtgcgg   120
acacaggtgg cggccgactg gaccgcgctg gcggaggaga tggactttga gtacttggag   180
atccggcaac tggagacaca agcggacccc actggcaggc tgctggacgc ctggcaggga   240
cgccctggcg cctctgtagg ccgactgctc gatctgctta ccaagctggg ccgcgacgac   300
gtgctgctgg agctgggacc cagcattgag gaggattgcc aaaagtatat cttgaagcag   360
cagcaggagg aggctgagaa gcctttacag gtggccgctg tagacagcag tgtcccacgg   420
acagcagagc tggcgggcat caccacactt gatgaccccc tggggcatat gcctgagcgt   480
ttcgatgcct tcatctgcta ttgccccagc gacatc                             516
```

<210> SEQ ID NO 5
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
                20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
        50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
        130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln
                165                 170

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 gtcgag                                                                    6

<210> SEQ ID NO 7
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Glu
1

<210> SEQ ID NO 8
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
aaaaaggtgg ccaagaagcc aaccaataag gcccccacc ccaagcagga gccccaggag         60
atcaattttc ccgacgatct tcctggctcc aacactgctg ctccagtgca ggagacttta        120
catggatgcc aaccggtcac ccaggaggat ggcaaagaga gtcgcatctc agtgcaggag        180
agacag                                                                  186

<210> SEQ ID NO 9
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 10
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
ggcgtccaag tcgaaaccat tagtcccggc gatggcagaa catttcctaa aagggggacaa      60 acatgtgtcg tccattatac aggcatgttg gaggacggga aaaaggtgga cagtagtaga     120
gatcgcaata aacctttcaa attcatgttg ggaaaacaag aagtcattag gggatgggag     180
gagggcgtgg ctcaaatgtc cgtcggccaa cgcgctaagc tcaccatcag ccccgactac     240
gcatacggcg ctaccggaca tcccggaatt attccccctc acgctacctt ggtgtttgac     300
gtcgaactgt tgaagctcga a                                                321
```

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 12
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
ggagtgcagg tggagactat ctcccccagga gacgggcgca ccttccccaa gcgcggccag      60
acctgcgtgg tgcactacac cgggatgctt gaagatggaa agaaagttga ttcctcccgg     120
gacagaaaca agccctttaa gtttatgcta ggcaagcagg aggtgatccg aggctgggaa     180
gaaggggttg cccagatgag tgtgggtcag agagccaaac tgactatatc tccagattat     240
gcctatggtg ccactgggca cccaggcatc atcccaccac atgccactct cgtcttcgat     300
gtggagcttc taaaactgga a                                                321
```

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

```
<210> SEQ ID NO 14
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 ccgcgg                                                                     6

<210> SEQ ID NO 15
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Arg
1

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaaggccgag ggagcctgct gacatgtggc gatgtggagg aaaacccagg acca             54

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
```

```
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 ccatgg                                                                    6

<210> SEQ ID NO 19
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Trp
1

<210> SEQ ID NO 20
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atggagtttg actttcttg gttgttttg gtggcaattc tgaagggtgt ccagtgtagc          60
agg                                                                      63

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Glu Phe Gly Leu Ser Trp Leu Phe Leu Val Ala Ile Leu Lys Gly
1               5                   10                  15

Val Gln Cys Ser Arg
            20

<210> SEQ ID NO 22
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gacatccaga tgacacagac tacatcctcc ctgtctgcct ctctgggaga cagagtcacc         60
atcagttgca ggcaagtca ggacattagt aaatatttaa attggtatca gcagaaacca        120
gatggaactg ttaaactcct gatctaccat acatcaagat tacactcagg agtcccatca       180
aggttcagtg gcagtgggtc tggaacagat tattctctca ccattagcaa cctggagcaa       240
gaagatattg ccacttactt ttgccaacag ggtaatacgc ttccgtacac gttcggaggg       300
gggactaagt tggaaataac a                                                 321
```

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 24
ggcggaggaa gcggaggtgg gggc                                          24

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 25

Gly Gly Gly Ser Gly Gly Gly Gly
1               5

<210> SEQ ID NO 26
<211> LENGTH: 360
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 26
gaggtgaaac tgcaggagtc aggacctggc ctggtggcgc cctcacagag cctgtccgtc      60
acatgcactg tctcaggggt ctcattaccc gactatggtg taagctggat tcgccagcct     120
ccacgaaagg gtctggagtg gctgggagta atatggggta gtgaaaccac atactataat     180
tcagctctca aatccagact gaccatcatc aaggacaact ccaagagcca agttttctta     240

```
aaaatgaaca gtctgcaaac tgatgacaca gccatttact actgtgccaa acattattac    300
tacggtggta gctatgctat ggactactgg ggtcaaggaa cctcagtcac cgtctcctca    360
```

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 28
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
ggatcc                                                                 6
```

<210> SEQ ID NO 29
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ser
1

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
gaacttccta ctcaggggac tttctcaaac gttagcacaa acgtaagt                  48
```

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

```
Glu Leu Pro Thr Gln Gly Thr Phe Ser Asn Val Ser Thr Asn Val Ser
1               5                   10                  15
```

<210> SEQ ID NO 32
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
cccgccccaa gaccccccac acctgcgccg accattgctt ctcaacccct gagtttgaga      60
cccgaggcct gccggccagc tgccggcggg gccgtgcata caagaggact cgatttcgct     120
tgcgac                                                                126
```

<210> SEQ ID NO 33
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40
```

<210> SEQ ID NO 34
<211> LENGTH: 111
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
atctatatct gggcacctct cgctggcacc tgtggagtcc ttctgctcag cctggttatt      60
actctgtact gtaatcaccg gaatcgccgc cgcgtttgta agtgtcccag g              111
```

<210> SEQ ID NO 35
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Ile Tyr Ile Trp Ala Pro Leu Ala Gly Thr Cys Gly Val Leu Leu Leu
1               5                   10                  15
```

```
Ser Leu Val Ile Thr Leu Tyr Cys Asn His Arg Asn Arg Arg Arg Val
            20                  25                  30

Cys Lys Cys Pro Arg
        35

<210> SEQ ID NO 36
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 gtcgac                                                                      6

<210> SEQ ID NO 37
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Asp
1

<210> SEQ ID NO 38
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
agagtgaagt tcagcaggag cgcagacgcc cccgcgtacc agcagggcca gaaccagctc         60
tataacgagc tcaatctagg acgaagagag gagtacgatg ttttggacaa gagacgtggc        120
cgggaccctg agatgggggg aaagccgaga aggaagaacc ctcaggaagg cctgtacaat        180
gaactgcaga agataagat ggcggaggcc tacagtgaga ttgggatgaa aggcgagcgc         240
cggaggggca aggggcacga tggcctttac cagggtctca gtacagccac caaggacacc        300
tacgacgccc ttcacatgca agctcttcca cctcgttga                               339

<210> SEQ ID NO 39
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60
```

```
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
             85                  90                  95

Thr Lys Asp Thr Tyr Asp Ala Leu His Met Gln Ala Leu Pro Pro Arg
        100                 105                 110
```

<210> SEQ ID NO 40
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atgccaccac ctcgcctgct gttctttctg ctgttcctga cacctatgga ggtgcgacct      60
gaggaaccac tggtcgtgaa ggtcgaggaa ggcgacaatg ccgtgctgca gtgcctgaaa     120
ggcacttctg atgggccaac tcagcagctg acctggtcca gggagtctcc cctgaagcct     180
tttctgaaac tgagcctggg actgccagga ctgggaatcc acatgcgccc tctggctatc     240
tggctgttca tcttcaacgt gagccagcag atgggaggat tctacctgtg ccagccagga     300
ccaccatccg agaaggcctg gcagcctgga tggaccgtca acgtggaggg gtctggagaa     360
ctgtttaggt ggaatgtgag tgacctggga ggactgggat gtgggctgaa gaaccgctcc     420
tctgaaggcc aagttcacc ctcagggaag ctgatgagcc aaaaactgta cgtgtgggcc      480
aaagatcggc ccgagatctg ggagggagaa cctccatgcc tgccacctag agacagcctg     540
aatcagagtc tgtcacagga tctgacaatg gcccccgggt ccactctgtg gctgtcttgt     600
ggagtcccac ccgacagcgt gtccagaggc cctctgtcct ggacccacgt gcatcctaag     660
gggccaaaaa gtctgctgtc actggaactg aaggacgatc ggcctgccag agacatgtgg     720
gtcatggaga ctggactgct gctgccacga gcaaccgcac aggatgctgg aaaatactat     780
tgccaccggg gcaatctgac aatgtccttc atctggaga  tcactgcaag gcccgtgctg     840
tggcactggc tgctgcgaac cggaggatgg aaggtcagtg ctgtgacact ggcatatctg     900
atcttttgcc tgtgctccct ggtgggcatt ctgcatctgc agagagccct ggtgctgcgg     960
agaaagagaa agagaatgac tgacccaaca agaaggtttt ga                      1002
```

<210> SEQ ID NO 41
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Pro Pro Pro Arg Leu Leu Phe Phe Leu Leu Phe Leu Thr Pro Met
  1               5                  10                  15

Glu Val Arg Pro Glu Glu Pro Leu Val Val Lys Val Glu Glu Gly Asp
             20                  25                  30

Asn Ala Val Leu Gln Cys Leu Lys Gly Thr Ser Asp Gly Pro Thr Gln
         35                  40                  45

Gln Leu Thr Trp Ser Arg Glu Ser Pro Leu Lys Pro Phe Leu Lys Leu
     50                  55                  60

Ser Leu Gly Leu Pro Gly Leu Gly Ile His Met Arg Pro Leu Ala Ile
```

```
                65                  70                  75                  80
        Trp Leu Phe Ile Phe Asn Val Ser Gln Gln Met Gly Gly Phe Tyr Leu
                            85                  90                  95

Cys Gln Pro Gly Pro Ser Glu Lys Ala Trp Gln Pro Gly Trp Thr
                        100                 105                 110

Val Asn Val Glu Gly Ser Gly Glu Leu Phe Arg Trp Asn Val Ser Asp
                        115                 120                 125

Leu Gly Gly Leu Gly Cys Gly Leu Lys Asn Arg Ser Ser Glu Gly Pro
                    130                 135                 140

Ser Ser Pro Ser Gly Lys Leu Met Ser Pro Lys Leu Tyr Val Trp Ala
        145                 150                 155                 160

Lys Asp Arg Pro Glu Ile Trp Glu Gly Glu Pro Cys Leu Pro Pro
                        165                 170                 175

Arg Asp Ser Leu Asn Gln Ser Leu Ser Gln Asp Leu Thr Met Ala Pro
                        180                 185                 190

Gly Ser Thr Leu Trp Leu Ser Cys Gly Val Pro Pro Asp Ser Val Ser
                    195                 200                 205

Arg Gly Pro Leu Ser Trp Thr His Val His Pro Lys Gly Pro Lys Ser
                    210                 215                 220

Leu Leu Ser Leu Glu Leu Lys Asp Asp Arg Pro Ala Arg Asp Met Trp
        225                 230                 235                 240

Val Met Glu Thr Gly Leu Leu Leu Pro Arg Ala Thr Ala Gln Asp Ala
                        245                 250                 255

Gly Lys Tyr Tyr Cys His Arg Gly Asn Leu Thr Met Ser Phe His Leu
                        260                 265                 270

Glu Ile Thr Ala Arg Pro Val Leu Trp His Trp Leu Leu Arg Thr Gly
                    275                 280                 285

Gly Trp Lys Val Ser Ala Val Thr Leu Ala Tyr Leu Ile Phe Cys Leu
                    290                 295                 300

Cys Ser Leu Val Gly Ile Leu His Leu Gln Arg Ala Leu Val Leu Arg
        305                 310                 315                 320

Arg Lys Arg Lys Arg Met Thr Asp Pro Thr Arg Arg Phe
                        325                 330

<210> SEQ ID NO 42
<211> LENGTH: 1616
<212> TYPE: DNA
<213> ORGANISM: Homo sapiens

<400> SEQUENCE: 42
gccaaggctg gggcagggga gtcagcagag gcctcgctcg ggcgcccagt ggtcctgccg      60
cctggtctca cctcgctatg gttcgtctgc ctctgcagtg cgtcctctgg ggctgcttgc     120
tgaccgctgt ccatccagaa ccacccactg catgcagaga aaacagtac ctaataaaca      180 gtcagtgctg ttctttgtgc cagccaggac agaaactggt gagtgactgc acagagttca     240
ctgaaacgga atgccttcct tgcggtgaaa gcgaattcct agacacctgg aacagagaga     300
cacactgcca ccagcacaaa tactgcgacc ccaacctagg gcttcgggtc agcagaagg      360 gcacctcaga aacagacacc atctgcacct gtgaagaagg ctggcactgt acgagtgagg     420
cctgtgagag ctgtgtcctg caccgctcat gctcgcccgg ctttgggtc aagcagattg      480 ctacaggggt ttctgatacc atctgcgagc cctgcccagt cggcttcttc tccaatgtgt     540
catctgcttt cgaaaaatgt cacccttgga caagctgtga gaccaaagac ctggttgtgc     600
aacaggcagg cacaaacaag actgatgttg tctgtggtcc ccaggatcgg ctgagagccc     660
```

```
tggtggtgat cccatcatc ttcgggatcc tgtttgccat cctcttggtg ctggtctttta    720 tcaaaaaggt ggccaagaag ccaaccaata aggccccca ccccaagcag gaaccccagg    780
agatcaattt tcccgacgat cttcctggct ccaacactgc tgctccagtg caggagactt    840
tacatggatg ccaaccggtc acccaggagg atggcaaaga gagtcgcatc tcagtgcagg    900
agagacagtg aggctgcacc cacccaggag tgtggccacg tgggcaaaca ggcagttggc    960
cagagagcct ggtgctgctg ctgctgtggc gtgagggtga ggggctggca ctgactgggc   1020
atagctcccc gcttctgcct gcaccccctgc agtttgagac aggagacctg gcactggatg   1080
cagaaacagt tcaccttgaa gaacctctca cttcaccctg gagcccatcc agtctcccaa   1140
cttgtattaa agacagaggc agaagtttgg tggtggtggt gttggggtat ggtttagtaa   1200
tatccaccag accttccgat ccagcagttt ggtgcccaga gaggcatcat ggtggcttcc   1260
ctgcgcccag gaagccatat acacagatgc ccattgcagc attgtttgtg atagtgaaca   1320
actggaagct gcttaactgt ccatcagcag gagactggct aaataaaatt agaatatatt   1380
tatacaacag aatctcaaaa acactgttga gtaaggaaaa aaaggcatgc tgctgaatga   1440
tgggtatgga acttttaaa aaagtacatg cttttatgta tgtatattgc ctatggatat   1500
atgtataaat acaatatgca tcatatattg atataacaag ggttctggaa gggtacacag   1560
aaaacccaca gctcgaagag tggtgacgtc tggggtgggg aagaagggtc tgggggg     1616
```

<210> SEQ ID NO 43
<211> LENGTH: 277
<212> TYPE: PRT
<213> ORGANISM: Homo sapiens

<400> SEQUENCE: 43

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205
```

```
Leu Leu Val Leu Val Phe Ile Lys Lys Val Ala Lys Lys Pro Thr Asn
    210                 215                 220
Lys Ala Pro His Pro Lys Gln Glu Pro Gln Glu Ile Asn Phe Pro Asp
225                 230                 235                 240
Asp Leu Pro Gly Ser Asn Thr Ala Ala Pro Val Gln Glu Thr Leu His
                245                 250                 255
Gly Cys Gln Pro Val Thr Gln Glu Asp Gly Lys Glu Ser Arg Ile Ser
            260                 265                 270
Val Gln Glu Arg Gln
        275

<210> SEQ ID NO 44
<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gtcgacatgg ctgcaggagg tcccggcgcg gggtctgcgg ccccggtctc ctccacatcc      60
tcccttcccc tggctgctct caacatgcga gtgcggcgcc gcctgtctct gttcttgaac     120
gtgcggacac aggtggcggc cgactggacc gcgctggcgg aggagatgga ctttgagtac     180
ttggagatcc ggcaactgga gacacaagcg acccccactg gcaggctgct ggacgcctgg     240
cagggacgcc ctggcgcctc tgtaggccga ctgctcgagc tgcttaccaa gctgggccgc     300
gacgacgtgc tgctggagct gggacccagc attgaggagg attgccaaaa gtatatcttg     360
aagcagcagc aggaggaggc tgagaagcct ttacaggtgg ccgctgtaga cagcagtgtc     420
ccacggacag cagagctggc gggcatcacc acacttgatg accccctggg gcatatgcct     480
gagcgtttcg atgccttcat ctgctattgc cccagcgaca tcgtcgac                  528

<210> SEQ ID NO 45
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Ala Ala Gly Gly Pro Gly Ala Gly Ser Ala Ala Pro Val Ser Ser
1               5                   10                  15
Thr Ser Ser Leu Pro Leu Ala Ala Leu Asn Met Arg Val Arg Arg Arg
            20                  25                  30
Leu Ser Leu Phe Leu Asn Val Arg Thr Gln Val Ala Ala Asp Trp Thr
        35                  40                  45
Ala Leu Ala Glu Glu Met Asp Phe Glu Tyr Leu Glu Ile Arg Gln Leu
    50                  55                  60
Glu Thr Gln Ala Asp Pro Thr Gly Arg Leu Leu Asp Ala Trp Gln Gly
65                  70                  75                  80
Arg Pro Gly Ala Ser Val Gly Arg Leu Leu Glu Leu Leu Thr Lys Leu
                85                  90                  95
Gly Arg Asp Asp Val Leu Leu Glu Leu Gly Pro Ser Ile Glu Glu Asp
            100                 105                 110
Cys Gln Lys Tyr Ile Leu Lys Gln Gln Gln Glu Glu Ala Glu Lys Pro
        115                 120                 125
```

```
Leu Gln Val Ala Ala Val Asp Ser Ser Val Pro Arg Thr Ala Glu Leu
        130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 46
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
ctcgagggcg tccaagtcga aaccattagt cccggcgatg gcagaacatt tcctaaaagg      60
ggacaaacat gtgtcgtcca ttatacaggc atgttggagg acggcaaaaa ggtggacagt    120
agtagagatc gcaataaacc tttcaaattc atgttgggaa acaagaagt cattagggga     180 tgggaggagg gcgtggctca aatgtccgtc ggccaacgcg ctaagctcac catcagcccc    240
gactacgcat acggcgctac cggacatccc ggaattattc cccctcacgc taccttggtg    300
tttgacgtcg aactgttgaa gctcgaagtc gagggagtgc aggtggaaac catctcccca    360
ggagacgggc gcaccttccc caagcgcggc cagacctgcg tggtgcacta caccgggatg    420
cttgaagatg gaaagaaagt tgattcctcc cgggacagaa acaagccctt taagtttatg    480
ctaggcaagc aggaggtgat ccgaggctgg gaagaagggg ttgcccagat gagtgtgggt    540
cagagagcca aactgactat atctccagat tatgcctatg gtgccactgg gcacccaggc    600
atcatcccac acatgccac tctcgtcttc gatgtggagc ttctaaaact ggaatctggc    660
ggtggatccg gagtcgag                                                  678

<210> SEQ ID NO 47
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Val Glu Gly Val Gln
            100                 105                 110

Val Glu Thr Ile Ser Pro Gly Asp Gly Arg Thr Phe Pro Lys Arg Gly
        115                 120                 125
```

```
Gln Thr Cys Val Val His Tyr Thr Gly Met Leu Glu Asp Gly Lys Lys
    130                 135                 140

Val Asp Ser Ser Arg Asp Arg Asn Lys Pro Phe Lys Phe Met Leu Gly
145                 150                 155                 160

Lys Gln Glu Val Ile Arg Gly Trp Glu Glu Gly Val Ala Gln Met Ser
                165                 170                 175

Val Gly Gln Arg Ala Lys Leu Thr Ile Ser Pro Asp Tyr Ala Tyr Gly
            180                 185                 190

Ala Thr Gly His Pro Gly Ile Ile Pro Pro His Ala Thr Leu Val Phe
        195                 200                 205

Asp Val Glu Leu Leu Lys Leu Glu Ser Gly Gly Ser Gly
    210                 215                 220

<210> SEQ ID NO 48
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca gcggaccccc actggcaggc tgctggacgc ctggcaggga     240
cgccctggcg cctctgtagg ccgactgctc gagctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatccagt tgtgcagga tgatccgg      540 caactggaac agacaaacta tcgactgaag ttgtgtgtgt ctgaccgcga tgtcctgcct     600
ggcacctgtg tctggtctat tgctagtgag ctcatcgaaa agaggtgccg ccggatggtg     660
gtggttgtct ctgatgatta cctgcagagc aaggaatgtg acttccagac caaatttgca     720
ctcagcctct ctccaggtgc ccatcagaag cgactgatcc ccatcaagta caggcaatg      780 aagaaagagt tccccagcat cctgaggttc atcactgtct gcgactacac caaccctgc      840 accaaatctt ggttctggac tcgccttgcc aaggccttgt ccctgccc                  888

<210> SEQ ID NO 49
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45
```

```
Ala Leu Ala Glu Glu Met Asp Phe Glu Tyr Leu Glu Ile Arg Gln Leu
        50                  55                  60

Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Glu Leu Leu Thr Lys Leu
                     85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
    195                 200                 205

Ser Glu Leu Ile Glu Lys Arg Cys Arg Arg Met Val Val Val Val Ser
210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
    275                 280                 285

Leu Ala Lys Ala Leu Ser Leu Pro
290                 295

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atggggagta gcaagagcaa gcctaaggac cccagccagc gc                          42

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Met Gly Ser Ser Lys Ser Lys Pro Lys Asp Pro Ser Gln Arg
 1               5                  10

<210> SEQ ID NO 52
<211> LENGTH: 516
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca agcggacccc actggcaggc tgctggacgc ctggcaggga     240
cgccctggcg cctctgtagg ccgactgctc gatctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatc                               516
```

<210> SEQ ID NO 53
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Met Ala Ala Gly Gly Pro Gly Ala Gly Ser Ala Ala Pro Val Ser Ser
1               5                   10                  15
Thr Ser Ser Leu Pro Leu Ala Ala Leu Asn Met Arg Val Arg Arg Arg
            20                  25                  30
Leu Ser Leu Phe Leu Asn Val Arg Thr Gln Val Ala Ala Asp Trp Thr
        35                  40                  45
Ala Leu Ala Glu Glu Met Asp Phe Glu Tyr Leu Glu Ile Arg Gln Leu
    50                  55                  60
Glu Thr Gln Ala Asp Pro Thr Gly Arg Leu Leu Asp Ala Trp Gln Gly
65                  70                  75                  80
Arg Pro Gly Ala Ser Val Gly Arg Leu Leu Asp Leu Leu Thr Lys Leu
                85                  90                  95
Gly Arg Asp Asp Val Leu Leu Glu Leu Gly Pro Ser Ile Glu Glu Asp
            100                 105                 110
Cys Gln Lys Tyr Ile Leu Lys Gln Gln Gln Glu Glu Ala Glu Lys Pro
        115                 120                 125
Leu Gln Val Ala Ala Val Asp Ser Ser Val Pro Arg Thr Ala Glu Leu
    130                 135                 140
Ala Gly Ile Thr Thr Leu Asp Asp Pro Leu Gly His Met Pro Glu Arg
145                 150                 155                 160
Phe Asp Ala Phe Ile Cys Tyr Cys Pro Ser Asp Ile
                165                 170
```

<210> SEQ ID NO 54
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 54
aaaaaggtgg ccaagaagcc aaccaataag gccccccacc ccaagcagga gccccaggag    60 atcaatttc  ccgacgatct tcctggctcc aacactgctg ctccagtgca ggagacttta   120
catggatgcc aaccggtcac ccaggaggat ggcaaagaga gtcgcatctc agtgcaggag   180
agacag                                                              186

<210> SEQ ID NO 55
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 56
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
ggcgtccaag tcgaaaccat tagtcccggc gatggcagaa catttcctaa aaggggacaa    60
acatgtgtcg tccattatac aggcatgttg gaggacggca aaaggtgga cagtagtaga   120 gatcgcaata aacctttcaa attcatgttg gaaaacaag aagtcattag ggatgggag    180 gagggcgtgg ctcaaatgtc cgtcggccaa cgcgctaagc tcaccatcag ccccgactac   240
gcatacggcg ctaccggaca tcccggaatt attccccctc acgctacctt ggtgtttgac   300
gtcgaactgt tgaagctc                                                318

<210> SEQ ID NO 57
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60
```

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu
            100                 105

<210> SEQ ID NO 58
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ggagtgcagg tggagactat ctccccagga gacgggcgca ccttcccaa gcgcggccag      60 acctgcgtgg tgcactacac cgggatgctt gaagatggaa agaaagttga ttcctcccgg    120
gacagaaaca agccctttaa gtttatgcta ggcaagcagg aggtgatccg aggctgggaa    180
gaaggggttg cccagatgag tgtgggtcag agagccaaac tgactatatc tccagattat    240
gcctatggtg ccactgggca cccaggcatc atcccaccac atgccactct cgtcttcgat    300
gtggagcttc taaaactgga a                                              321

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 60
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gctactaact tcagcctgct gaagcaggct ggagacgtgg aggagaaccc tggacct       57

<210> SEQ ID NO 61

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Thr Asn Phe Ser Leu Leu Lys Gln Ala Gly Asp Val Glu Glu Asn
1               5                   10                  15

Pro Gly Pro

<210> SEQ ID NO 62
<211> LENGTH: 2253
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atgtggaatc tccttcacga aaccgactcg gctgtggcca ccgcgcgccg cccgcgctgg     60
ctgtgcgctg gggcgctggt gctggcgggt ggcttctttc cctcggctt cctcttcggg    120 tggtttataa atcctccaa tgaagctact aacattactc caaagcataa tatgaaagca    180
tttttggatg aattgaaagc tgagaacatc aagaagttct acataatttt acacagata    240 ccacatttag caggaacaga acaaaacttt cagcttgcaa agcaaattca atcccagtgg    300
aaagaatttg gcctggattc tgttgagcta gcacattatg atgtcctgtt gtcctaccca    360
aataagactc atcccaacta catctcaata attaatgaag atggaaatga gattttcaac    420
acatcattat ttgaaccacc tcctccagga tatgaaaatg tttgggatat tgtaccacct    480
ttcagtgctt tctctcctca aggaatgcca gagggcgatc tagtgtatgt taactatgca    540
cgaactgaag acttctttaa attggaacgg gacatgaaaa tcaattgctc tgggaaaatt    600
gtaattgcca gatatgggaa agttttcaga ggaaataagg ttaaaaatgc ccagctggca    660
ggggccaaag gagtcattct ctactccgac cctgctgact actttgctcc tggggtgaag    720
tcctatccag atggttggaa tcttcctgga ggtggtgtcc agcgtggaaa tatcctaaat    780
ctgaatggtg caggagaccc tctcacacca ggttacccag caaatgaata tgcttatagg    840
cgtggaattg cagaggctgt tggtcttcca gtattcctg ttcatccaat tggatactat    900
gatgcacaga agctcctaga aaaatgggt ggctcagcac accagatag cagctggaga    960 ggaagtctca agtgcccta caatgttgga cctggcttta ctggaaactt ttctacacaa   1020
aaagtcaaga tgcacatcca ctctaccaat gaagtgacaa gaatttacaa tgtgataggt   1080
actctcagag gagcagtgga accagacaga tatgtcattc tgggaggtca ccgggactca   1140
tgggtgtttg gtggtattga ccctcagagt ggagcagctg ttgttcatga aattgtgagg   1200
agctttggaa cactgaaaaa ggaagggtgg agacctagaa gaacaatttt gtttgcaagc   1260
tgggatgcag aagaatttgg tcttcttggt tctactgagt gggcagagga gaattcaaga   1320
ctccttcaag agcgtggcgt ggcttatatt aatgctgact catctataga aggaaactac   1380
actctgagag ttgattgtac accgctgatg tacagcttgg tacacaacct aacaaaagag   1440
ctgaaaagcc ctgatgaagg ctttgaaggc aaatctcttt atgaaagttg gactaaaaaa   1500
agtccttccc cagagttcag tggcatgccc aggataagca attgggatc tggaaatgat   1560 tttgaggtgt tcttccaacg acttggaatt gcttcaggca gagcacggta tactaaaaat   1620
```

```
tgggaaacaa acaaattcag cggctatcca ctgtatcaca gtgtctatga acatatgag    1680 ttggtggaaa agttttatga tccaatgttt aaatatcacc tcactgtggc ccaggttcga   1740
ggagggatgg tgtttgagct agccaattcc atagtgctcc cttttgattg tcgagattat   1800
gctgtagttt taagaaagta tgctgacaaa atctacagta tttctatgaa acatccacag   1860
gaaatgaaga catacagtgt atcatttgat tcactttttt ctgcagtaaa gaattttaca   1920
gaaattgctt ccaagttcag tgagagactc caggactttg acaaaagcaa cccaatagta   1980
ttaagaatga tgaatgatca actcatgttt ctggaaagag catttattga tccattaggg   2040
ttaccagaca ggccttttta taggcatgtc atctatgctc caagcagcca caacaagtat   2100 gcagggagt cattcccagg aatttatgat gctctgtttg atattgaaag caaagtggac    2160
ccttccaagg cctggggaga agtgaagaga cagatttatg ttgcagcctt cacagtgcag   2220
gcagctgctg agactttgag tgaagtagcc taa                                2253
```

<210> SEQ ID NO 63
<211> LENGTH: 750
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Trp Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
```

```
                    245                 250                 255
Asn Ile Leu Asn Leu Asn Gly Ala Gly Asp Pro Leu Thr Pro Gly Tyr
                260                 265                 270
Pro Ala Asn Glu Tyr Ala Tyr Arg Arg Gly Ile Ala Glu Ala Val Gly
                275                 280                 285
Leu Pro Ser Ile Pro Val His Pro Ile Gly Tyr Tyr Asp Ala Gln Lys
    290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
                340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
        370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
        435                 440                 445
Tyr Ile Asn Ala Asp Ser Ser Ile Glu Gly Asn Tyr Thr Leu Arg Val
    450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
                500                 505                 510
Ser Lys Leu Gly Ser Gly Asn Asp Phe Glu Val Phe Phe Gln Arg Leu
            515                 520                 525
Gly Ile Ala Ser Gly Arg Ala Arg Tyr Thr Lys Asn Trp Glu Thr Asn
        530                 535                 540
Lys Phe Ser Gly Tyr Pro Leu Tyr His Ser Val Tyr Glu Thr Tyr Glu
545                 550                 555                 560
Leu Val Glu Lys Phe Tyr Asp Pro Met Phe Lys Tyr His Leu Thr Val
                565                 570                 575
Ala Gln Val Arg Gly Gly Met Val Phe Glu Leu Ala Asn Ser Ile Val
                580                 585                 590
Leu Pro Phe Asp Cys Arg Asp Tyr Ala Val Val Leu Arg Lys Tyr Ala
            595                 600                 605
Asp Lys Ile Tyr Ser Ile Ser Met Lys His Pro Gln Glu Met Lys Thr
        610                 615                 620
Tyr Ser Val Ser Phe Asp Ser Leu Phe Ser Ala Val Lys Asn Phe Thr
625                 630                 635                 640
Glu Ile Ala Ser Lys Phe Ser Glu Arg Leu Gln Asp Phe Asp Lys Ser
                645                 650                 655
Asn Pro Ile Val Leu Arg Met Met Asn Asp Gln Leu Met Phe Leu Glu
                660                 665                 670
```

```
Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 64
<211> LENGTH: 858
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Gly Ser Ser Lys Ser Lys Pro Lys Asp Pro Ser Gln Arg Leu Glu
1               5                   10                  15

Met Ala Ala Gly Gly Pro Gly Ala Gly Ser Ala Ala Pro Val Ser Ser
                20                  25                  30

Thr Ser Ser Leu Pro Leu Ala Ala Leu Asn Met Arg Val Arg Arg Arg
            35                  40                  45

Leu Ser Leu Phe Leu Asn Val Arg Thr Gln Val Ala Ala Asp Trp Thr
    50                  55                  60

Ala Leu Ala Glu Glu Met Asp Phe Glu Tyr Leu Glu Ile Arg Gln Leu
65                  70                  75                  80

Glu Thr Gln Ala Asp Pro Thr Gly Arg Leu Leu Asp Ala Trp Gln Gly
                85                  90                  95

Arg Pro Gly Ala Ser Val Gly Arg Leu Leu Asp Leu Leu Thr Lys Leu
            100                 105                 110

Gly Arg Asp Asp Val Leu Leu Glu Leu Gly Pro Ser Ile Glu Glu Asp
        115                 120                 125

Cys Gln Lys Tyr Ile Leu Lys Gln Gln Gln Glu Glu Ala Glu Lys Pro
    130                 135                 140

Leu Gln Val Ala Ala Val Asp Ser Ser Val Pro Arg Thr Ala Glu Leu
145                 150                 155                 160

Ala Gly Ile Thr Thr Leu Asp Asp Pro Leu Gly His Met Pro Glu Arg
                165                 170                 175

Phe Asp Ala Phe Ile Cys Tyr Cys Pro Ser Asp Ile Lys Lys Val Ala
            180                 185                 190

Lys Lys Pro Thr Asn Lys Ala Pro His Pro Lys Gln Glu Pro Gln Glu
        195                 200                 205

Ile Asn Phe Pro Asp Asp Leu Pro Gly Ser Asn Thr Ala Ala Pro Val
    210                 215                 220

Gln Glu Thr Leu His Gly Cys Gln Pro Val Thr Gln Glu Asp Gly Lys
225                 230                 235                 240

Glu Ser Arg Ile Ser Val Gln Glu Arg Gln Val Glu Ser Gly Gly Gly
                245                 250                 255

Ser Gly Gly Val Gln Val Glu Thr Ile Ser Pro Gly Asp Gly Arg Thr
            260                 265                 270

Phe Pro Lys Arg Gly Gln Thr Cys Val Val His Tyr Thr Gly Met Leu
```

-continued

```
              275                 280                 285
Glu Asp Gly Lys Lys Val Asp Ser Ser Arg Asp Arg Asn Lys Pro Phe
290                 295                 300

Lys Phe Met Leu Gly Lys Gln Glu Val Ile Arg Gly Trp Glu Glu Gly
305                 310                 315                 320

Val Ala Gln Met Ser Val Gly Gln Arg Ala Lys Leu Thr Ile Ser Pro
            325                 330                 335

Asp Tyr Ala Tyr Gly Ala Thr Gly His Pro Gly Ile Ile Pro Pro His
            340                 345                 350

Ala Thr Leu Val Phe Asp Val Glu Leu Leu Lys Leu Glu Val Glu Gly
            355                 360                 365

Val Gln Val Glu Thr Ile Ser Pro Gly Asp Gly Arg Thr Phe Pro Lys
370                 375                 380

Arg Gly Gln Thr Cys Val Val His Tyr Thr Gly Met Leu Glu Asp Gly
385                 390                 395                 400

Lys Lys Val Asp Ser Ser Arg Asp Arg Asn Lys Pro Phe Lys Phe Met
            405                 410                 415

Leu Gly Lys Gln Glu Val Ile Arg Gly Trp Glu Glu Gly Val Ala Gln
            420                 425                 430

Met Ser Val Gly Gln Arg Ala Lys Leu Thr Ile Ser Pro Asp Tyr Ala
            435                 440                 445

Tyr Gly Ala Thr Gly His Pro Gly Ile Ile Pro Pro His Ala Thr Leu
450                 455                 460

Val Phe Asp Val Glu Leu Leu Lys Leu Glu Ser Gly Gly Ser Gly
465                 470                 475                 480

Val Asp Arg Ala Lys Arg Gly Lys Pro Ile Pro Asn Pro Leu Leu Gly
            485                 490                 495

Leu Asp Ser Thr Gly Ser Gly Ser Ala Thr Asn Phe Ser Leu Leu Lys
            500                 505                 510

Gln Ala Gly Asp Val Glu Glu Asn Pro Gly Pro Thr Arg Met Pro Pro
            515                 520                 525

Pro Arg Leu Leu Phe Phe Leu Leu Phe Leu Thr Pro Met Glu Val Arg
530                 535                 540

Pro Glu Glu Pro Leu Val Val Lys Val Glu Glu Gly Asp Asn Ala Val
545                 550                 555                 560

Leu Gln Cys Leu Lys Gly Thr Ser Asp Gly Pro Thr Gln Gln Leu Thr
            565                 570                 575

Trp Ser Arg Glu Ser Pro Leu Lys Pro Phe Leu Lys Leu Ser Leu Gly
            580                 585                 590

Leu Pro Gly Leu Gly Ile His Met Arg Pro Leu Ala Ile Trp Leu Phe
            595                 600                 605

Ile Phe Asn Val Ser Gln Gln Met Gly Gly Phe Tyr Leu Cys Gln Pro
            610                 615                 620

Gly Pro Pro Ser Glu Lys Ala Trp Gln Pro Gly Trp Thr Val Asn Val
625                 630                 635                 640

Glu Gly Ser Gly Glu Leu Phe Arg Trp Asn Val Ser Asp Leu Gly Gly
            645                 650                 655

Leu Gly Cys Gly Leu Lys Asn Arg Ser Ser Glu Gly Pro Ser Ser Pro
            660                 665                 670

Ser Gly Lys Leu Met Ser Pro Lys Leu Tyr Val Trp Ala Lys Asp Arg
            675                 680                 685

Pro Glu Ile Trp Glu Gly Glu Pro Pro Cys Leu Pro Pro Arg Asp Ser
690                 695                 700
```

```
Leu Asn Gln Ser Leu Ser Gln Asp Leu Thr Met Ala Pro Gly Ser Thr
705                 710                 715                 720

Leu Trp Leu Ser Cys Gly Val Pro Asp Ser Val Ser Arg Gly Pro
            725                 730                 735

Leu Ser Trp Thr His Val His Pro Lys Gly Pro Lys Ser Leu Leu Ser
            740                 745                 750

Leu Glu Leu Lys Asp Asp Arg Pro Ala Arg Asp Met Trp Val Met Glu
        755                 760                 765

Thr Gly Leu Leu Leu Pro Arg Ala Thr Ala Gln Asp Ala Gly Lys Tyr
    770                 775                 780

Tyr Cys His Arg Gly Asn Leu Thr Met Ser Phe His Leu Glu Ile Thr
785                 790                 795                 800

Ala Arg Pro Val Leu Trp His Trp Leu Arg Thr Gly Gly Trp Lys
            805                 810                 815

Val Ser Ala Val Thr Leu Ala Tyr Leu Ile Phe Cys Leu Cys Ser Leu
            820                 825                 830

Val Gly Ile Leu His Leu Gln Arg Ala Leu Val Leu Arg Arg Lys Arg
            835                 840                 845

Lys Arg Met Thr Asp Pro Thr Arg Arg Phe
    850                 855

<210> SEQ ID NO 65
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
```

|     | 195 |     |     | 200 |     |     |     | 205 |     |
|-----|-----|-----|-----|-----|-----|-----|-----|-----|-----|

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
            275                 280                 285

<210> SEQ ID NO 66
<211> LENGTH: 8931
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
aagctggcca gcaacttatc tgtgtctgtc cgattgtcta gtgtctatga ctgattttat      60
gcgcctgcgt cggtactagt tagctaacta gctctgtatc tggcggaccc gtggtggaac     120
tgacgagttc ggaacacccg ccgcaaccc tgggagacgt cccagggact cggggggccg     180 ttttgtggc ccgacctgag tcctaaaatc ccgatcgttt aggactcttt ggtgcacccc     240
ccttagagga gggatatgtg gttctggtag gagacgagaa cctaaaacag ttcccgcctc     300
cgtctgaatt tttgctttcg gtttgggacc gaagccgcgc cgcgcgtctt gtctgctgca     360
gcatcgttct gtgttgtctc tgtctgactg tgtttctgta tttgtctgaa aatatgggcc     420
cgggctagcc tgttaccact cccttaagtt tgaccttagg tcactggaaa gatgtcgagc     480
ggatcgctca caaccagtcg gtagatgtca agaagagacg ttgggttacc ttctgctctg     540
cagaatggcc aaccttttaac gtcggatggc cgcgagacgg cacctttaac cgagacctca     600
tcacccaggt taagatcaag gtcttttcac ctggcccgca tggacaccca gaccaggtgg     660
ggtacatcgt gacctgggaa gccttggctt ttgacccccc tccctgggtc aagccctttg     720
tacaccctaa gcctccgcct cctcttcctc catccgcccc gtctctcccc cttgaacctc     780
ctcgttcgac cccgcctcga tcctcccttt atccagccct cactccttct ctaggcgccc     840
ccatatggcc atatgagatc ttatatgggg caccccgcc ccttgtaaac ttccctgacc     900
ctgacatgac aagagttact aacagcccct ctctccaagc tcacttacag gctctctact     960
tagtccagca cgaagtctgg agacctctgg cggcagccta ccaagaacaa ctggaccgac    1020
cggtggtacc tcacccttac cgagtcggcg acacagtgtg ggtccgccga caccagacta    1080
agaacctaga acctcgctgg aaaggacctt acacagtcct gctgaccacc cccaccgccc    1140
tcaaagtaga cggcatcgca gcttggatac acgccgccca cgtgaaggct gccgaccccg    1200
ggggtggacc atcctctaga ctgccatggg gagtagcaag agcaagccta aggaccccag    1260
ccagcgcctc gagatggccg ctgggggccc aggcgccgga tcagctgctc ccgtatcttc    1320
tacttcttct ttgccgctgg ctgctctgaa catgcgcgtg agaagacgcc tctccctgtt    1380
ccttaacgtt cgcacacaag tcgctgccga ttggaccgcc cttgccgaag aaatggactt    1440
tgaatacctg gaaattagac aacttgaaac acaggccgac cccactggca gactcctgga    1500
cgcatggcag ggaagacctg gtgcaagcgt tggacggctc ctggatctcc tgacaaaact    1560

-continued

```
gggacgcgac gacgtactgc ttgaactcgg acctagcatt gaagaagact gccaaaaata    1620
tatcctgaaa caacaacaag aagaagccga aaaacctctc caagtcgcag cagtggactc    1680
atcagtaccc cgaacagctg agcttgctgg gattactaca ctcgacgacc cactcggaca    1740
tatgcctgaa agattcgacg cttttcattt g ctattgcccc tctgacataa agaaagttgc    1800
aaagaaaccc acaaataaag ccccacaccc taaacaggaa ccccaagaaa tcaatttccc    1860
agatgatctc cctggatcta atactgccgc cccggtccaa gaaaccctgc atggttgcca    1920
gcctgtcacc caagaggacg gaaaagaatc acggattagc gtacaagaga gacaagtcga    1980
gtctggcggt ggatccggag gcgttcaagt agaaacaatc agcccaggag acggaaggac    2040
tttccccaaa cgaggccaaa catgcgtagt tcattatact gggatgctcg aagatggaaa    2100
aaaagtagat agtagtagag accgaaacaa accatttaaa tttatgttgg gaaaacaaga    2160
agtaataagg ggctgggaag aaggtgtagc acaaatgtct gttggccagc gcgcaaaact    2220
cacaatttct cctgattatg cttacggagc taccggccac cccggcatca taccccctca    2280
tgccacactg gtgtttgacg tcgaattgct caaactggaa gtcgagggag tgcaggtgga    2340
gacgattagt cctggggatg ggagaacctt tccaaagcgc ggtcagacct gtgttgtcca    2400
ctacaccggt atgctggagg acgggaagaa ggtggactct tcacgcgatc gcaataagcc    2460
tttcaagttc atgctcggca agcaggaggt gatccggggg tgggaggagg gcgtggctca    2520
gatgtcggtc gggcaacgag cgaagcttac catctcaccc gactacgcgt atgggcaac    2580 ggggcatccg ggaattatcc ctccccacgc tacgctcgta ttcgatgtgg agctcttgaa    2640
gcttgagtct ggcggtggat ccggagtcga ccgcgcaaag cgtggaaaac ctatacctaa    2700
tccattgctg ggcttagact caacaggcag cggaagcgca acgaatttt ccctgctgaa    2760 acaggcaggg gacgtagagg aaaatcctgg tcctacgcgt atgcccccte ctagactgct    2820 gttttcctg ctctttctca ccccaatgga agttagacct gaggaaccac tggtcgttaa    2880
agtggaagaa ggtgataatg ctgtcctcca atgccttaaa gggaccagcg acggaccaac    2940
gcagcaactg acttggagcc gggagtcccc tctcaagccg tttctcaagc tgtcacttgg    3000
cctgccaggt cttggtattc acatgcgccc ccttgccatt tggctcttca tattcaatgt    3060
gtctcaacaa atgggtggat tctacctttg ccagcccggc ccccttctg agaaagcttg    3120 gcagcctgga tggaccgtca atgttgaagg ctccggtgag ctgtttagat ggaatgtgag    3180
cgaccttggc ggactcggtt gcggactgaa aaataggagc tctgaaggac cctcttctcc    3240
ctccggtaag ttgatgtcac ctaagctgta cgtgtgggcc aaggaccgcc ccgaaatctg    3300
ggagggcgag cctccatgcc tgccgcctcg cgattcactg aaccagtctc tgtcccagga    3360
tctcactatg gcgcccggat ctactctttg gctgtcttgc ggcgttcccc cagatagcgt    3420
gtcaagagga cctctgagct ggacccacgt acaccctaag ggccctaaga gcttgttgag    3480
cctggaactg aaggacgaca gacccgcacg cgatatgtgg gtaatggaga ccggccttct    3540
gctccctcgc gctaccgcac aggatgcagg gaaatactac tgtcatagag ggaatctgac    3600
tatgagcttt catctcgaaa ttacagcacg gcccgttctt tggcattggc tcctccggac    3660
tggaggctgg aaggtgtctg ccgtaacact cgcttacttg attttttgcc tgtgtagcct    3720
ggttgggatc ctgcatcttc agcgagccct tgtattgcgc cgaaaaagaa aacgaatgac    3780
tgaccctaca cgacgattct gagcatgcaa cctcgatccg gattagtcca atttgttaaa    3840
gacaggatat cagtggtcca ggctctagtt ttgactcaac aatatcacca gctgaagcct    3900
```

```
atagagtacg agccatagat aaaataaaag attttattta gtctccagaa aaaggggga    3960
atgaaagacc ccacctgtag gtttggcaag ctagcttaag taacgccatt ttgcaaggca    4020
tggaaaaata cataactgag aatagagaag ttcagatcaa ggtcaggaac agatggaaca    4080
gctgaatatg ggccaaacag gatatctgtg gtaagcagtt cctgcccgg ctcagggcca    4140
agaacagatg gaacagctga atatgggcca aacaggatat ctgtggtaag cagttcctgc    4200
cccggctcag ggccaagaac agatggtccc cagatgcggt ccagccctca gcagtttcta    4260
gagaaccatc agatgtttcc agggtgcccc aaggacctga atgaccctg tgccttatt    4320
gaactaacca atcagttcgc ttctcgcttc tgttcgcgcg cttctgctcc ccgagctcaa    4380
taaagagcc cacaacccct cactcggggc gccagtcctc cgattgactg agtcgcccgg    4440
gtacccgtgt atccaataaa ccctcttgca gttgcatccg acttgtggtc tcgctgttcc    4500
ttgggagggt ctcctctgag tgattgacta cccgtcagcg ggggtctttc acacatgcag    4560
catgtatcaa aattaatttg gttttttttc ttaagtattt acattaaatg gccatagtac    4620
ttaaagttac attggcttcc ttgaaataaa catggagtat tcagaatgtg tcataaatat    4680
ttctaatttt aagatagtat ctccattggc tttctacttt ttcttttatt ttttttttgtc    4740
ctctgtcttc catttgttgt tgttgttgtt tgtttgttg tttgttggtt ggttggttaa    4800
ttttttttta aagatcctac actatagttc aagctagact attagctact ctgtaaccca    4860
gggtgacctt gaagtcatgg gtagcctgct gttttagcct tcccacatct aagattacag    4920
gtatgagcta tcattttggg tatattgatt gattgattga ttgatgtgtg tgtgtgtgat    4980
tgtgtttgtg tgtgtgactg tgaaaatgtg tgtatgggtg tgtgtgaatg tgtgtatgta    5040
tgtgtgtgtg tgagtgtgtg tgtgtgtgtg tgcatgtgtg tgtgtgtgac tgtgtctatg    5100
tgtatgactg tgtgtgtgtg tgtgtgtgtg tgtgtgtgtg tgtgtgtgtg tgtgttgtga    5160
aaaaatattc tatggtagtg agagccaacg ctccggctca ggtgtcaggt tggttttga    5220
gacagagtct ttcacttagc ttggaattca ctggccgtcg ttttacaacg tcgtgactgg    5280
gaaaaccctg gcgttaccca acttaatcgc cttgcagcac atccccttt cgccagctgg    5340
cgtaatagcg aagaggcccg caccgatcgc ccttcccaac agttgcgcag cctgaatggc    5400
gaatggcgcc tgatgcggta ttttctcctt acgcatctgt gcggtatttc acaccgcata    5460
tggtgcactc tcagtacaat ctgctctgat gccgcatagt taagccagcc ccgacacccg    5520
ccaacacccg ctgacgcgcc ctgacgggct tgtctgctcc cggcatccgc ttacagacaa    5580
gctgtgaccg tctccgggag ctgcatgtgt cagaggtttt caccgtcatc accgaaacgc    5640
gcgatgacga agggcctcg tgatacgcct atttttatag gttaatgtca tgataataat    5700
ggtttcttag acgtcaggtg gcacttttcg gggaaatgtg cgcggaaccc ctatttgttt    5760
attttttctaa atacattcaa atatgtatcc gctcatgaga caataaccct gataaatgct    5820
tcaataatat tgaaaaagga agagtatgag tattcaacat ttccgtgtcg cccttattcc    5880
cttttttgcg gcattttgcc ttcctgtttt tgctcaccca gaaacgctgg tgaaagtaaa    5940
agatgctgaa gatcagttgg gtgcacgagt gggttacatc gaactggatc tcaacagcgg    6000
taagatcctt gagagttttc gccccgaaga acgttttcca atgatgagca cttttaaagt    6060
tctgctatgt ggcgcggtat tatcccgtat tgacgccggg caagagcaac tcggtcgccg    6120
catacactat tctcagaatg acttggttga gtactcacca gtcacagaaa agcatcttac    6180
ggatggcatg acagtaagag aattatgcag tgctgccata accatgagtg ataacactgc    6240
ggccaactta cttctgacaa cgatcggagg accgaaggag ctaaccgctt ttttgcacaa    6300
```

```
catgggggat catgtaactc gccttgatcg ttgggaaccg gagctgaatg aagccatacc    6360
aaacgacgag cgtgacacca cgatgcctgt agcaatggca acaacgttgc gcaaactatt    6420
aactggcgaa ctacttactc tagcttcccg gcaacaatta atagactgga tggaggcgga    6480
taaagttgca ggaccacttc tgcgctcggc ccttccggct ggctggttta ttgctgataa    6540
atctggagcc ggtgagcgtg ggtctcgcgg tatcattgca gcactggggc cagatggtaa    6600
gccctcccgt atcgtagtta tctacacgac ggggagtcag gcaactatgg atgaacgaaa    6660
tagacagatc gctgagatag gtgcctcact gattaagcat tggtaactgt cagaccaagt    6720
ttactcatat atactttaga ttgatttaaa acttcatttt taatttaaaa ggatctaggt    6780
gaagatcctt tttgataatc tcatgaccaa atcccttaa cgtgagtttt cgttccactg    6840
agcgtcagac cccgtagaaa agatcaaagg atcttcttga tccttttttt ttctgcgcgt    6900
aatctgctgc ttgcaaacaa aaaaaccacc gctaccagcg gtggtttgtt tgccggatca    6960
agagctacca actctttttc cgaaggtaac tggcttcagc agagcgcaga taccaaatac    7020
tgtccttcta gtgtagccgt agttaggcca ccacttcaag aactctgtag caccgcctac    7080
atacctcgct ctgctaatcc tgttaccagt ggctgctgcc agtggcgata agtcgtgtct    7140
taccgggttg gactcaagac gatagttacc ggataaggcg cagcggtcgg gctgaacggg    7200
gggttcgtgc acacagccca gcttggagcg aacgacctac accgaactga gatacctaca    7260
gcgtgagcat tgagaaagcg ccacgcttcc cgaagggaga aaggcggaca ggtatccggt    7320
aagcggcagg gtcggaacag gagagcgcac gagggagctt ccaggggaa acgcctggta    7380 tctttatagt cctgtcgggt ttcgccacct ctgacttgag cgtcgatttt tgtgatgctc    7440
gtcagggggg cggagcctat ggaaaaacgc cagcaacgcg gcctttttac ggttcctggc    7500
cttttgctgg ccttttgctc acatgttctt tcctgcgtta tcccctgatt ctgtggataa    7560
ccgtattacc gcctttgagt gagctgatac cgctcgccgc agccgaacga ccgagcgcag    7620
cgagtcagtg agcgaggaag cggaagagcg cccaatacgc aaaccgcctc tccccgcgcg    7680
ttggccgatt cattaatgca gctggcacga caggtttccc gactggaaag cgggcagtga    7740
gcgcaacgca attaatgtga gttagctcac tcattaggca ccccaggctt tacactttat    7800
gcttccggct cgtatgttgt gtggaattgt gagcggataa caatttcaca caggaaacag    7860
ctatgaccat gattacgcca agctttgctc ttaggagttt cctaatacat cccaaactca    7920
aatatataaa gcatttgact tgttctatgc cctagggggc gggggaagc taagccagct    7980 ttttttaaca tttaaaatgt taattccatt ttaaatgcac agatgttttt atttcataag    8040
ggtttcaatg tgcatgaatg ctgcaatatt cctgttacca aagctagtat aaataaaaat    8100
agataaacgt ggaaattact tagagtttct gtcattaacg tttccttcct cagttgacaa    8160
cataaatgcg ctgctgagca agccagtttg catctgtcag gatcaatttc ccattatgcc    8220
agtcatatta attactagtc aattagttga ttttatttt tgacatatac atgtgaatga    8280
aagaccccac ctgtaggttt ggcaagctag cttaagtaac gccatttgc aaggcatgga    8340 aaaatacata actgagaata gaaaagttca gatcaaggtc aggaacagat ggaacagctg    8400
aatatgggcc aaacaggata tctgtggtaa gcagttcctg ccccggctca gggccaagaa    8460
cagatggaac agctgaatat gggccaaaca ggatatctgt ggtaagcagt tcctgccccg    8520
gctcagggcc aagaacagat ggtccccaga tgcggtccag ccctcagcag tttctagaga    8580
accatcagat gtttccaggg tgccccaagg acctgaaatg accctgtgcc ttatttgaac    8640
```

```
taaccaatca gttcgcttct cgcttctgtt cgcgcgctta tgctccccga gctcaataaa    8700
agagcccaca acccctcact cggggcgcca gtcctccgat tgactgagtc gcccgggtac    8760
ccgtgtatcc aataaaccct cttgcagttg catccgactt gtggtctcgc tgttccttgg    8820
gagggtctcc tctgagtgat tgactacccg tcagcggggg tctttcattt ggggctcgt    8880 ccgggatcgg gagacccctg cccagggacc accgacccac caccgggagg t             8931
```

```
<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atggggagta gcaagagcaa gcctaaggac cccagccagc gc                         42

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Gly Ser Ser Lys Ser Lys Pro Lys Asp Pro Ser Gln Arg
1               5                   10

<210> SEQ ID NO 69
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69 ctcgag                                                                  6

<210> SEQ ID NO 70
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Glu
1

<210> SEQ ID NO 71
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atggccgctg ggggcccagg cgccggatca gctgctcccg tatcttctac ttcttctttg    60
ccgctggctg ctctgaacat gcgcgtgaga agacgcctct ccctgttcct taacgttcgc   120
```

```
acacaagtcg ctgccgattg gaccgccctt gccgaagaaa tggactttga atacctggaa      180
attagacaac ttgaaacaca ggccgacccc actggcagac tcctggacgc atggcaggga      240
agacctggtg caagcgttgg acggctcctg gatctcctga caaaactggg acgcgacgac      300
gtactgcttg aactcggacc tagcattgaa gaagactgcc aaaaatatat cctgaaacaa      360
caacaagaag aagccgaaaa acctctccaa gtcgcagcag tggactcatc agtaccccga      420
acagctgagc ttgctgggat tactacactc gacgaccac tcggacatat gcctgaaaga       480
ttcgacgctt tcatttgcta ttgcccctct gacata                                516

<210> SEQ ID NO 72
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 73
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
aagaaagttg caaagaaacc cacaaataaa gccccacacc ctaaacagga accccaagaa       60
atcaatttcc cagatgatct ccctggatct aatactgccg ccccggtcca agaaaccctg      120
catggttgcc agcctgtcac ccaagaggac ggaaaagaat cacggattag cgtacaagag      180
agacaa                                                                 186

<210> SEQ ID NO 74
```

<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gtcgagtctg gcggtggatc cgga                                          24

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Val Glu Ser Gly Gly Gly Ser Gly
1               5

<210> SEQ ID NO 77
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
ggcgttcaag tagaaacaat cagcccagga gacggaagga ctttccccaa acgaggccaa    60
acatgcgtag ttcattatac tgggatgctc gaagatggaa aaaaagtaga tagtagtaga   120
gaccgaaaca aaccatttaa atttatgttg ggaaaacaag aagtaataag gggctgggaa   180
gaaggtgtag cacaaatgtc tgttggccag cgcgcaaaac tcacaatttc tcctgattat   240
gcttacggag ctaccggcca ccccggcatc ataccccctc atgccacact ggtgtttgac   300
gtcgaattgc tcaaactgga a                                             321

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 79
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79 gtcgag                                                              6

<210> SEQ ID NO 80
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Val Glu
1

<210> SEQ ID NO 81
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
ggagtgcagg tggagacgat tagtcctggg gatgggagaa cctttccaaa gcgcggtcag      60
acctgtgttg tccactacac cggtatgctg gaggacggga agaaggtgga ctcttcacgc     120
gatcgcaata agccttttcaa gttcatgctc ggcaagcagg aggtgatccg ggggtgggag    180
gagggcgtgg ctcagatgtc ggtcgggcaa cgagcgaagc ttaccatctc acccgactac    240
gcgtatgggg caacggggca tccgggaatt atccctcccc acgctacgct cgtattcgat    300
gtggagctct tgaagcttga g                                              321

<210> SEQ ID NO 82
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 82

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Val Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tctggcggtg gatccggagt cgac                                              24

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Gly Gly Gly Ser Gly Val Asp
1               5

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cgcgcaaagc gt                                                           12

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Lys Arg
```

-continued

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ggaaaaccta tacctaatcc attgctgggc ttagactcaa ca                           42

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Lys Pro Ile Pro Asn Pro Leu Leu Gly Leu Asp Ser Thr
1               5                   10

<210> SEQ ID NO 89
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ggcagcggaa gc                                                            12

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Ser Gly Ser
1

<210> SEQ ID NO 91
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gcaacgaatt tttccctgct gaaacaggca ggggacgtag aggaaaatcc tggtcct           57

<210> SEQ ID NO 92
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Ala Thr Asn Phe Ser Leu Leu Lys Gln Ala Gly Asp Val Glu Glu Asn
1               5                   10                  15

Pro Gly Pro

<210> SEQ ID NO 93
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93 acgcgt                                                                    6

<210> SEQ ID NO 94
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Arg
1

<210> SEQ ID NO 95
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
atgccccctc ctagactgct gttttcctg ctctttctca ccccaatgga agttagacct          60
gaggaaccac tggtcgttaa agtggaagaa ggtgataatg ctgtcctcca atgccttaaa        120
gggaccagcg acggaccaac gcagcaactg acttggagcc gggagtcccc tctcaagccg        180
tttctcaagc tgtcacttgg cctgccaggt cttggtattc acatgcgccc ccttgccatt        240
tggctcttca tattcaatgt gtctcaacaa atgggtggat ctacctttg ccagcccggc         300 cccccttctg agaaagcttg gcagcctgga tggaccgtca atgttgaagg ctccggtgag        360
ctgtttagat ggaatgtgag cgaccttggc ggactcggtt gcggactgaa aaataggagc        420
tctgaaggac cctcttctcc ctccggtaag ttgatgtcac ctaagctgta cgtgtgggcc        480
aaggaccgcc ccgaaatctg ggagggcgag cctccatgcc tgccgcctcg cgattcactg        540
aaccagtctc tgtcccagga tctcactatg gcgcccggat ctactctttg gctgtcttgc        600
ggcgttcccc cagatagcgt gtcaagagga cctctgagct ggaccacgt acaccctaag         660 ggccctaaga gcttgttgag cctggaactg aaggacgaca gacccgcacg cgatatgtgg        720
gtaatggaga ccggccttct gctccctcgc gctaccgcac aggatgcagg gaaatactac        780
tgtcatagag ggaatctgac tatgagcttt catctcgaaa ttacagcacg gcccgttctt        840
tggcattggc tcctccggac tggaggctgg aaggtgtctg ccgtaacact cgcttacttg        900
attttttgcc tgtgtagcct ggttgggatc ctgcatcttc agcgagccct tgtattgcgc        960
cgaaaaagaa aacgaatgac tgaccctaca cgacgattct ga                         1002
```

<210> SEQ ID NO 96
<211> LENGTH: 333
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                325                 330

<210> SEQ ID NO 97
<211> LENGTH: 204
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 97
ttctgggtac tggttgtagt cgtggcgta cttgcttgtt attctcttct tgttaccgta      60
gccttcatta tattctgggt ccgatcaaag cgctcaagac tcctccattc cgattatatg    120
aacatgacac ctcgccgacc tggtcctaca cgcaaacatt atcaaccta cgcaccccc     180 cgagacttcg ctgcttatcg atcc                                            204

<210> SEQ ID NO 98
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Phe Trp Val Leu Val Val Gly Gly Val Leu Ala Cys Tyr Ser Leu
1               5                  10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 99
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
agtgtagtta aaagaggaag aaaaaagttg ctgtatatat ttaaacaacc atttatgaga     60
ccagtgcaaa ccacccaaga agaagacgga tgttcatgca gattcccaga agaagaagaa    120
ggaggatgtg aattg                                                     135

<210> SEQ ID NO 100
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ser Val Val Lys Arg Gly Arg Lys Lys Leu Leu Tyr Ile Phe Lys Gln
1               5                  10                  15

Pro Phe Met Arg Pro Val Gln Thr Thr Gln Glu Glu Asp Gly Cys Ser
            20                  25                  30

Cys Arg Phe Pro Glu Glu Glu Glu Gly Gly Cys Glu Leu
        35                  40                  45

<210> SEQ ID NO 101
<211> LENGTH: 6

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 acgcgt                                                                      6

<210> SEQ ID NO 102
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Arg
1

<210> SEQ ID NO 103
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
cgggtcaaat tcagccggag tgctgacgcc ccagcatacc aacagggaca aaaccaactc          60
tacaacgagc tcaacctggg tagacgcgag gagtacgacg ttctggataa gaggcggggc         120
cgggacccag agatgggggg caaacctcag cggcggaaga acccgcagga gggtctttat         180
aacgagctcc agaaggacaa gatggcggaa gcctattcag aaattgggat gaaaggcgag         240
agacgcaggg gaaaaggtca cgatggtctg tatcaaggac tgtcaaccgc caccaaagac         300
acttacgatg cgctccacat gcaggccctc cctccccgc                                339

<210> SEQ ID NO 104
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110
```

Arg

<210> SEQ ID NO 105
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atggagtttg ggctgtcatg gctgttcctc gtggccattc tcaaaggggt ccagtgttct    60
cgc                                                                 63

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Met Gly Phe Gly Leu Ser Trp Leu Phe Leu Val Ala Ile Leu Lys Gly
1               5                   10                  15

Val Gln Cys Ser Arg
            20

<210> SEQ ID NO 107
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gggggaggag gttctggagg cggcgggagc ggaggaggag gcagc                   45

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Gly Gly Ser Gly Gly Gly Ser Gly Gly Gly Gly Ser
1               5                   10                  15

<210> SEQ ID NO 109
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109 ggatcc                                                               6

<210> SEQ ID NO 110
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Ser
1

<210> SEQ ID NO 111
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
gatccagccg aacccaaatc ccccgataaa acacatactt gcccccttg tcccgcacca      60
gaattgcttg gcggaccttc cgttttctt tttcccccca aacctaaaga taccctgatg     120
atttcccgaa cccctgaagt tacgtgcgta gtcgtagatg tgtctcacga agatccagaa   180
gtaaaattta actggtacgt agatggagtc gaagttcaca acgcaaagac gaagccccga    240
gaagaacaat ataattccac ataccgagta gttagcgttc tcaccgtact gcatcaggac    300
tggcttaacg gcaaagaata taaatgtaag gtctcaaaca aagcactccc agcccctatc    360
gaaaagacta tctccaaagc taaggacaa ccccgcgaac cccaggtcta tacacttccc    420
ccctcacgcg atgaactcac taaaaatcag gtttccctta cttgtcttgt caaaggcttc    480
tacccctagcg atatcgcagt cgaatgggaa tccaatggcc agcccgaaaa caactataaa   540
acaaccccac ctgtcctcga ttcagatggc tcattctttc tctattccaa actgactgta    600
gacaaatccc gatggcaaca aggtaacgtg ttctcttgct cagtcatgca tgaagcgctt    660
cataaccatt acacacaaaa atctctctca ctgtctcccg gaagaagga cccc          714
```

<210> SEQ ID NO 112
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Asp Pro Ala Glu Pro Lys Ser Pro Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125
```

Gly Gln Pro Arg Glu Pro Gln Val Tyr Thr Leu Pro Pro Ser Arg Asp
            130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
                195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys Lys Asp Pro
225                 230                 235

<210> SEQ ID NO 113
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113 ctcgag                                                                     6

<210> SEQ ID NO 114
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Glu
1

<210> SEQ ID NO 115
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
aaactgtgtt acctcctcga tggcatcctc tttatttatg gcgtgattct gaccgcattg       60
tttctccgag taaaattctc tagatccgca gacgctcccg catatcagca aggacaaaat      120
cagctttata acgaacttaa cctcggcaga cgcgaagaat acgatgtact ggacaagaga      180
agaggaagag atcccgaaat gggcggaaaa ccccagagaa gaaagaatcc caagaaggt      240 ctttataacg aactgcagaa agataaaatg gccgaagcgt acagtgaaat tggtatgaaa      300
ggagaaagaa gacgcggaaa aggacatgac ggactctacc aaggactctc aactgctact      360
aaagatacat acgacgccct tcatatgcaa gccctccccc cgagataa                   408

<210> SEQ ID NO 116
<211> LENGTH: 135
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 116

Lys Leu Cys Tyr Leu Leu Asp Gly Ile Leu Phe Ile Tyr Gly Val Ile
1               5                   10                  15

Leu Thr Ala Leu Phe Leu Arg Val Lys Phe Ser Arg Ser Ala Asp Ala
            20                  25                  30

Pro Ala Tyr Gln Gln Gly Gln Asn Gln Leu Tyr Asn Glu Leu Asn Leu
        35                  40                  45

Gly Arg Arg Glu Glu Tyr Asp Val Leu Asp Lys Arg Gly Arg Asp
    50                  55                  60

Pro Glu Met Gly Gly Lys Pro Gln Arg Arg Lys Asn Pro Gln Glu Gly
65                  70                  75                  80

Leu Tyr Asn Glu Leu Gln Lys Asp Lys Met Ala Glu Ala Tyr Ser Glu
                85                  90                  95

Ile Gly Met Lys Gly Glu Arg Arg Arg Gly Lys Gly His Asp Gly Leu
            100                 105                 110

Tyr Gln Gly Leu Ser Thr Ala Thr Lys Asp Thr Tyr Asp Ala Leu His
        115                 120                 125

Met Gln Ala Leu Pro Pro Arg
    130                 135

<210> SEQ ID NO 117
<211> LENGTH: 186
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 117
gttgccgcca tcctgggcct gggcctggtg ctggggctgc tgggcccct ggccatcctg      60 ctggccctgt acctgctccg ggaccagagg ctgcccccccg atgcccacaa gccccctggg     120
ggaggcagtt ccggaccccc catccaagag gagcaggccg acgcccactc caccctggcc     180
aagatc                                                                186

<210> SEQ ID NO 118
<211> LENGTH: 63
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 118

Val Ala Ala Ile Leu Gly Leu Gly Leu Val Leu Gly Leu Leu Gly Pro
1               5                   10                  15

Leu Ala Ile Leu Leu Ala Leu Tyr Leu Leu Arg Arg Asp Gln Arg Leu
            20                  25                  30

Pro Pro Asp Ala His Lys Pro Pro Gly Gly Gly Ser Phe Arg Thr Pro
        35                  40                  45

Ile Gln Glu Glu Gln Ala Asp Ala His Ser Thr Leu Ala Lys Ile
    50                  55                  60

<210> SEQ ID NO 119
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

| | | | | | |
|---|---|---|---|---|---|
| tgaaagaccc | cacctgtagg | tttggcaagc | tagcttaagt | aacgccattt | tgcaaggcat | 60 |
| ggaaaaatac | ataactgaga | atagaaaagt | tcagatcaag | gtcaggaaca | gatggaacag | 120 |
| ctgaatatgg | gccaaacagg | atatctgtgg | taagcagttc | ctgccccggc | tcagggccaa | 180 |
| gaacagatgg | aacagctgaa | tatgggccaa | acaggatatc | tgtggtaagc | agttcctgcc | 240 |
| ccggctcagg | gccaagaaca | gatggtcccc | agatgcggtc | cagccctcag | cagtttctag | 300 |
| agaaccatca | gatgtttcca | gggtgcccca | aggacctgaa | atgaccctgt | gccttatttg | 360 |
| aactaaccaa | tcagttcgct | ctctcgcttct | gttcgcgcgc | ttatgctccc | cgagctcaat | 420 |
| aaaagagccc | acaacccctc | actcggggcg | ccagtcctcc | gattgactga | gtcgcccggg | 480 |
| tacccgtgta | tccaataaac | cctcttgcag | ttgcatccga | cttgtggtct | cgctgttcct | 540 |
| tgggagggtc | tcctctgagt | gattgactac | ccgtcagcgg | gggtctttca | | 590 |

<210> SEQ ID NO 120
<211> LENGTH: 57
<212> TYPE: DNA
<213> ORGANISM: Thosea asigna virus

<400> SEQUENCE: 120
gccgagggca ggggaagtct tctaacatgc ggggacgtgg aggaaaatcc cgggccc          57

<210> SEQ ID NO 121
<211> LENGTH: 19
<212> TYPE: PRT
<213> ORGANISM: Thosea asigna virus

<400> SEQUENCE: 121

Ala Glu Gly Arg Gly Ser Leu Leu Thr Cys Gly Asp Val Glu Glu Asn
1               5                   10                  15

Pro Gly Pro

<210> SEQ ID NO 122
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

| | | | | | |
|---|---|---|---|---|---|
| tgaaagaccc | cacctgtagg | tttggcaagc | tagcttaagt | aacgccattt | tgcaaggcat | 60 |
| ggaaaaatac | ataactgaga | atagagaagt | tcagatcaag | gtcaggaaca | gatggaacag | 120 |
| ctgaatatgg | gccaaacagg | atatctgtgg | taagcagttc | ctgccccggc | tcagggccaa | 180 |
| gaacagatgg | aacagctgaa | tatgggccaa | acaggatatc | tgtggtaagc | agttcctgcc | 240 |
| ccggctcagg | gccaagaaca | gatggtcccc | agatgcggtc | cagccctcag | cagtttctag | 300 |
| agaaccatca | gatgtttcca | gggtgcccca | aggacctgaa | atgaccctgt | gccttatttg | 360 |
| aactaaccaa | tcagttcgct | ctctcgcttct | gttcgcgcgc | ttctgctccc | cgagctcaat | 420 |
| aaaagagccc | acaacccctc | actcggggcg | ccagtcctcc | gattgactga | gtcgcccggg | 480 |
| tacccgtgta | tccaataaac | cctcttgcag | ttgcatccga | cttgtggtct | cgctgttcct | 540 |
| tgggagggtc | tcctctgagt | gattgactac | ccgtcagcgg | gggtctttca | | 590 |

<210> SEQ ID NO 123
<211> LENGTH: 696
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
ctcgagtctg gcggtggatc cggaggcgtt caagtagaaa caatcagccc aggagacgga      60
aggactttcc ccaaacgagg ccaaacatgc gtagttcatt atactgggat gctcgaagat     120
ggaaaaaaag tagatagtag tagagaccga aacaaaccat ttaaatttat gttgggaaaa     180
caagaagtaa taaggggctg ggaagaaggt gtagcacaaa tgtctgttgg ccagcgcgca     240
aaactcacaa tttctcctga ttatgcttac ggagctaccg gccaccccgg catcataccc     300
cctcatgcca cactggtgtt tgacgtcgaa ttgctcaaac tggaagtcga gggagtgcag     360
gtggagacga ttagtcctgg ggatgggaga acctttccaa agcgcggtca gacctgtgtt     420
gtccactaca ccggtatgct ggaggacggg aagaaggtgg actcttcacg cgatcgcaat     480
aagcctttca gttcatgct cggcaagcag gaggtgatcc ggggtggga ggaggcgtg       540
gctcagatgt cggtcgggca acgagcgaag cttaccatct caccctgacta cgcgtatggg     600
gcaacggggc atccgggaat tatccctccc cacgctacgc tcgtattcga gtgtggagctc    660
ttgaagcttg agtctggcgg tggatccgga gtcgac                                696
```

<210> SEQ ID NO 124
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

```
Leu Glu Ser Gly Gly Gly Ser Gly Gly Val Gln Val Glu Thr Ile Ser
  1               5                  10                  15

Pro Gly Asp Gly Arg Thr Phe Pro Lys Arg Gly Gln Thr Cys Val Val
                 20                  25                  30

His Tyr Thr Gly Met Leu Glu Asp Gly Lys Lys Val Asp Ser Ser Arg
             35                  40                  45

Asp Arg Asn Lys Pro Phe Lys Phe Met Leu Gly Lys Gln Glu Val Ile
         50                  55                  60

Arg Gly Trp Glu Glu Gly Val Ala Gln Met Ser Val Gly Gln Arg Ala
 65                  70                  75                  80

Lys Leu Thr Ile Ser Pro Asp Tyr Ala Tyr Gly Ala Thr Gly His Pro
                 85                  90                  95

Gly Ile Ile Pro Pro His Ala Thr Leu Val Phe Asp Val Glu Leu Leu
            100                 105                 110

Lys Leu Glu Val Glu Gly Val Gln Val Glu Thr Ile Ser Pro Gly Asp
        115                 120                 125

Gly Arg Thr Phe Pro Lys Arg Gly Gln Thr Cys Val Val His Tyr Thr
    130                 135                 140

Gly Met Leu Glu Asp Gly Lys Lys Val Asp Ser Ser Arg Asp Arg Asn
145                 150                 155                 160

Lys Pro Phe Lys Phe Met Leu Gly Lys Gln Glu Val Ile Arg Gly Trp
                165                 170                 175
```

Glu Glu Gly Val Ala Gln Met Ser Val Gly Gln Arg Ala Lys Leu Thr
            180                 185                 190

Ile Ser Pro Asp Tyr Ala Tyr Gly Ala Thr Gly His Pro Gly Ile Ile
        195                 200                 205

Pro Pro His Ala Thr Leu Val Phe Asp Val Glu Leu Leu Lys Leu Glu
210                 215                 220

Ser Gly Gly Gly Ser Gly Val Asp
225                 230

<210> SEQ ID NO 125
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
ggcgttcaag tagaaacaat cagcccagga gacggaagga ctttccccaa acgaggccaa    60
acatgcgtag ttcattatac tgggatgctc gaagatggaa aaaagtaga tagtagtaga   120 gaccgaaaca aaccatttaa atttatgttg ggaaaacaag aagtaataag gggctgggaa   180
gaaggtgtag cacaaatgtc tgttggccag cgcgcaaaac tcacaatttc tcctgattat   240
gcttacggag ctaccggcca ccccggcatc ataccccctc atgccacact ggtgtttgac   300
gtcgaattgc tcaaactgga a                                             321

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 127
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
ggagtgcagg tggagacgat tagtcctggg gatgggagaa cctttccaaa gcgcggtcag    60
acctgtgttg tccactacac cggtatgctg gaggacggga agaaggtgga ctcttcacgc   120
gatcgcaata agcctttcaa gttcatgctc ggcaagcagg aggtgatccg ggggtgggag   180
gagggcgtgg ctcagatgtc ggtcgggcaa cgagcgaagc ttaccatctc acccgactac   240
gcgtatgggg caacggggca tccgggaatt atccctcccc acgctacgct cgtattcgat   300
gtggagctct tgaagcttga g                                             321
```

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129

```
atggggagta gcaagagcaa gcctaaggac cccagccagc gc                       42
```

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Met Gly Ser Ser Lys Ser Lys Pro Lys Asp Pro Ser Gln Arg
1               5                   10
```

<210> SEQ ID NO 131
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131 ctcgag                                                                    6

<210> SEQ ID NO 132
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Leu Glu
1

<210> SEQ ID NO 133
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
atggccgctg ggggcccagg cgccggatca gctgctcccg tatcttctac ttcttctttg     60
ccgctggctg ctctgaacat gcgcgtgaga agacgcctct ccctgttcct taacgttcgc    120
acacaagtcg ctgccgattg gaccgcccct tgccgaagaaa tggactttga atacctggaa    180
attagacaac ttgaaacaca ggccgacccc actggcagac tcctggacgc atggcaggga    240
agacctggtg caagcgttgg acggctcctg gatctcctga caaaactggg acgcgacgac    300
gtactgcttg aactcggacc tagcattgaa gaagactgcc aaaaatatat cctgaaacaa    360
caacaagaag aagccgaaaa acctctccaa gtcgcagcag tggactcatc agtaccccga    420
acagctgagc ttgctgggat tactacactc gacgacccac tcggacatat gcctgaaaga    480
ttcgacgctt tcatttgcta ttgcccctct gacata                              516

<210> SEQ ID NO 134
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
                20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
        50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
                100                 105                 110

```
Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170
```

```
<210> SEQ ID NO 135
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
aagaaagttg caaagaaacc cacaaataaa gccccacacc ctaaacagga accccaagaa     60
atcaatttcc cagatgatct ccctggatct aatactgccg ccccggtcca agaaaccctg   120
catggttgcc agcctgtcac ccaagaggac ggaaaagaat cacggattag cgtacaagag   180
agacaa                                                               186
```

```
<210> SEQ ID NO 136
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60
```

```
<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gtcgagtctg gcggtggatc cgga                                            24
```

```
<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138
```

```
<210> SEQ ID NO 139
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
ggcgttcaag tagaaacaat cagcccagga gacggaagga ctttccccaa acgaggccaa      60
acatgcgtag ttcattatac tgggatgctc gaagatggaa aaaagtagta tagtagtaga    120
gaccgaaaca aaccatttaa atttatgttg ggaaaacaag aagtaataag gggctgggaa    180
gaaggtgtag cacaaatgtc tgttggccag cgcgcaaaac tcacaatttc tcctgattat    240
gcttacggag ctaccggcca ccccggcatc ataccccctc atgccacact ggtgtttgac    300
gtcgaattgc tcaaactgga a                                               321

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140
```

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

```
<210> SEQ ID NO 141
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 gtcgag                                                                  6

<210> SEQ ID NO 142
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 142

Val Glu
1

<210> SEQ ID NO 143
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
ggagtgcagg tggagacgat tagtcctggg gatgggagaa cctttccaaa gcgcggtcag      60
acctgtgttg tccactacac cggtatgctg gaggacggga agaaggtgga ctcttcacgc     120
gatcgcaata agcctttcaa gttcatgctc ggcaagcagg aggtgatccg ggggtgggag     180
gagggcgtgg ctcagatgtc ggtcgggcaa cgagcgaagc ttaccatctc acccgactac     240
gcgtatgggg caacggggca tccgggaatt atccctcccc acgctacgct cgtattcgat     300
gtggagctct tgaagcttga g                                               321

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tctggcggtg gatccggagt cgac                                             24

<210> SEQ ID NO 146
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 146

Ser Gly Gly Gly Ser Gly Val Asp
1               5

<210> SEQ ID NO 147
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
cgcgcaaagc gt                                                         12

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ala Lys Arg
1

<210> SEQ ID NO 149
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggaaaaccta tacctaatcc attgctgggc ttagactcaa ca                        42

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Lys Pro Ile Pro Asn Pro Leu Leu Gly Leu Asp Ser Thr
1               5                   10

<210> SEQ ID NO 151
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggcagcggaa gc                                                         12

<210> SEQ ID NO 152
<211> LENGTH: 4
```

<210> SEQ ID NO 152
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Ser Gly Ser
1

<210> SEQ ID NO 153
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcaacgaatt tttccctgct gaaacaggca ggggacgtag aggaaaatcc tggtcct        57

<210> SEQ ID NO 154
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Thr Asn Phe Ser Leu Leu Lys Gln Ala Gly Asp Val Glu Glu Asn
1               5                   10                  15

Pro Gly Pro

<210> SEQ ID NO 155
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155 acgcgt                                                                 6

<210> SEQ ID NO 156
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Thr Arg
1

<210> SEQ ID NO 157
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157 atgcccccctc ctagactgct gttttttcctg ctctttctca ccccaatgga agttagacct       60

```
gaggaaccac tggtcgttaa agtggaagaa ggtgataatg ctgtcctcca atgccttaaa      120
gggaccagcg acggaccaac gcagcaactg acttggagcc gggagtcccc tctcaagccg      180
tttctcaagc tgtcacttgg cctgccaggt cttggtattc acatgcgccc ccttgccatt      240
tggctcttca tattcaatgt gtctcaacaa atgggtggat ctacctttg ccagcccggc      300 cccccttctg agaaagcttg gcagcctgga tggaccgtca atgttgaagg ctccggtgag      360
ctgtttagat ggaatgtgag cgaccttggc ggactcggtt gcggactgaa aataggagc      420 tctgaaggac cctcttctcc ctccggtaag ttgatgtcac ctaagctgta cgtgtgggcc      480
aaggaccgcc ccgaaatctg ggagggcgag cctccatgcc tgccgcctcg cgattcactg      540
aaccagtctc tgtcccagga tctcactatg gcgcccggat ctactctttg gctgtcttgc      600
ggcgttcccc cagatagcgt gtcaagagga cctctgagct ggaccacgt acaccctaag      660 ggccctaaga gcttgttgag cctggaactg aaggacgaca gacccgcacg cgatatgtgg      720
gtaatggaga ccggccttct gctccctcgc gctaccgcac aggatgcagg gaaatactac      780
tgtcatagag ggaatctgac tatgagcttt catctcgaaa ttacagcacg gcccgttctt      840
tggcattggc tcctccggac tggaggctgg aaggtgtctg ccgtaacact cgcttacttg      900
attttttgcc tgtgtagcct ggttgggatc ctgcatcttc agcgagccct tgtattgcgc      960
cgaaaaagaa aacgaatgac tgaccctaca cgacgattct ga                        1002
```

<210> SEQ ID NO 158
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190
```

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Phe
                325                 330

<210> SEQ ID NO 159
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile
                165                 170

<210> SEQ ID NO 160
<211> LENGTH: 186
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 160
aagaaagttg caaagaaacc cacaaataaa gccccacacc ctaaacagga accccaagaa    60
atcaatttcc cagatgatct ccctggatct aatactgccg ccccggtcca agaaaccctg   120
catggttgcc agcctgtcac ccaagaggac ggaaaagaat cacggattag cgtacaagag   180
agacaa                                                             186

<210> SEQ ID NO 161
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Glu Arg Gln
    50                  55                  60

<210> SEQ ID NO 162
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga agataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336

<210> SEQ ID NO 163
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys

```
            50                  55                  60
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 164
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164

```
atggagtttg actttcttg gttgttttg gtggcaattc tgaagggtgt ccagtgtagc    60
agg                                                                63
```

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

```
Met Glu Phe Gly Leu Ser Trp Leu Phe Leu Val Ala Ile Leu Lys Gly
  1               5                  10                  15

Val Gln Cys Ser Arg
             20
```

<210> SEQ ID NO 166
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166

```
gacatccaat tgacacaatc acacaaattt ctctcaactt ctgtaggaga cagagtgagc    60
ataacctgca aagcatccca ggacgtgtac aatgctgtgg cttggtacca acagaagcct   120
ggacaatccc caaaattgct gatttattct gcctctagta ggtacactgg ggtaccttct   180
cggtttacgg gctctgggtc cggaccagat ttcacgttca caatcagttc cgttcaagct   240
gaagacctcg ctgtttattt ttgccagcag cacttccgaa ccccttttac ttttggctca   300
ggcactaagt tggaaatcaa ggctttg                                       327
```

<210> SEQ ID NO 167
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

```
Asp Ile Gln Leu Thr Gln Ser His Lys Phe Leu Ser Thr Ser Val Gly
  1               5                  10                  15
```

```
Asp Arg Val Ser Ile Thr Cys Lys Ala Ser Gln Asp Val Tyr Asn Ala
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Ser Arg Phe Thr Gly
    50                  55                  60

Ser Gly Ser Gly Pro Asp Phe Thr Phe Thr Ile Ser Ser Val Gln Ala
65                  70                  75                  80

Glu Asp Leu Ala Val Tyr Phe Cys Gln Gln His Phe Arg Thr Pro Phe
                85                  90                  95

Thr Phe Gly Ser Gly Thr Lys Leu Glu Ile Lys Ala Leu
            100                 105
```

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggcggaggaa gcggaggtgg gggc                                          24

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
Gly Gly Gly Ser Gly Gly Gly Gly
1               5
```

<210> SEQ ID NO 170
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
gaagtccaat tgcaacagtc aggcccccgaa ttgaaaaagc ccggcgaaac agtgaagata    60
tcttgtaaag cctccggtta cccttttacg aactatggaa tgaactgggt caaacaagcc   120
cctggacagg gattgaagtg gatgggatgg atcaatacat caacaggcga gtctaccttc   180
gcagatgatt tcaaaggtcg ctttgacttc tcactggaga ccagtgcaaa taccgcctac   240
cttcagatta caatcttaa aagcgaggat atggcaacct acttttgcgc aagatgggaa   300
gtttatcacg ggtacgtgcc atactgggga caaggaacga cagtgacagt tagtagc      357

<210> SEQ ID NO 171
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
50                  55                  60

Lys Gly Arg Phe Asp Phe Ser Leu Glu Thr Ser Ala Asn Thr Ala Tyr
65              70                  75                  80

Leu Gln Ile Asn Asn Leu Lys Ser Glu Asp Met Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser
        115

<210> SEQ ID NO 172
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172 ggatcc                                                                    6

<210> SEQ ID NO 173
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Ser
1

<210> SEQ ID NO 174
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gaacttccta ctcaggggac tttctcaaac gttagcacaa acgtaagt                     48

<210> SEQ ID NO 175
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Leu Pro Thr Gln Gly Thr Phe Ser Asn Val Ser Thr Asn Val Ser
1               5                   10                  15

<210> SEQ ID NO 176
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
cccgccccaa gacccccac acctgcgccg accattgctt ctcaacccct gagtttgaga      60
cccgaggcct gccggccagc tgccggcggg gccgtgcata caagaggact cgatttcgct    120
tgcgac                                                               126

<210> SEQ ID NO 177
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40

<210> SEQ ID NO 178
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
atctatatct gggcacctct cgctggcacc tgtggagtcc ttctgctcag cctggttatt      60
actctgtact gtaatcaccg gaatcgccgc cgcgtttgta agtgtcccag g              111

<210> SEQ ID NO 179
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn Arg Arg Arg Val
            20                  25                  30

Cys Lys Cys Pro Arg
        35

<210> SEQ ID NO 180
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180 ctcgag                                                                    6

<210> SEQ ID NO 181
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Leu Glu
1

<210> SEQ ID NO 182
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182
agagtgaagt tcagcaggag cgcagacgcc cccgcgtacc agcagggcca gaaccagctc        60
tataacgagc tcaatctagg acgaagagag gagtacgatg ttttggacaa gagacgtggc       120
cgggaccctg agatgggggg aaagccgaga aggaagaacc ctcaggaagg cctgtacaat       180
gaactgcaga agataagat ggcggaggcc tacagtgaga ttgggatgaa aggcgagcgc        240
cggaggggca aggggcacga tggcctttac cagggtctca gtacagccac caaggacacc       300
tacgacgccc ttcacatgca ggccctgccc cctcgc                                 336

<210> SEQ ID NO 183
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 184
<211> LENGTH: 204
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 184
ttctgggtac tggttgtagt cggtggcgta cttgcttgtt attctcttct tgttaccgta       60
gccttcatta tattctgggt ccgatcaaag cgctcaagac tcctccattc cgattatatg      120
aacatgacac ctcgccgacc tggtcctaca cgcaaacatt atcaaccctc cgcacccccc      180
cgagacttcg ctgcttatcg atcc                                             204

<210> SEQ ID NO 185
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Phe Trp Val Leu Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 186
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
gttgccgcca tcctgggcct gggcctggtg ctggggctgc tgggccccct ggccatcctg       60
ctggccctgt acctgctccg ggaccagagg ctgcccccccg atgcccacaa gccccctggg      120
ggaggcagtt tccgacccc catccaagag gagcaggccg acgcccactc caccctggcc      180
aagatc                                                                 186

<210> SEQ ID NO 187
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Val Ala Ala Ile Leu Gly Leu Gly Leu Val Leu Gly Leu Leu Gly Pro
1               5                   10                  15

Leu Ala Ile Leu Leu Ala Leu Tyr Leu Leu Arg Arg Asp Gln Arg Leu
            20                  25                  30

Pro Pro Asp Ala His Lys Pro Pro Gly Gly Gly Ser Phe Arg Thr Pro
        35                  40                  45
```

```
Ile Gln Glu Glu Gln Ala Asp Ala His Ser Thr Leu Ala Lys Ile
    50                  55                  60
```

<210> SEQ ID NO 188
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
agtgtagtta aaagaggaag aaaaaagttg ctgtatatat ttaaacaacc atttatgaga    60
ccagtgcaaa ccacccaaga agaagacgga tgttcatgca gattcccaga agaagaagaa   120
ggaggatgtg aattg                                                    135

<210> SEQ ID NO 189
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Ser Val Val Lys Arg Gly Arg Lys Lys Leu Leu Tyr Ile Phe Lys Gln
1               5                   10                  15

Pro Phe Met Arg Pro Val Gln Thr Thr Gln Glu Glu Asp Gly Cys Ser
            20                  25                  30

Cys Arg Phe Pro Glu Glu Glu Glu Gly Gly Cys Glu Leu
        35                  40                  45
```

<210> SEQ ID NO 190
<211> LENGTH: 16
<212> TYPE: PRT
<213> ORGANISM: Homo sapiens

<400> SEQUENCE: 190

```
Met Gly Ser Asn Lys Ser Lys Pro Lys Asp Ala Ser Gln Arg Arg Arg
1               5                   10                  15
```

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 191

```
Met Gly Cys Xaa Cys
1               5
```

<210> SEQ ID NO 192
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 192

Gly Ser Gly Gly Gly Ser
1               5

<210> SEQ ID NO 193
<211> LENGTH: 7
<212> TYPE: PRT
<213> ORGANISM: Homo sapiens

<400> SEQUENCE: 193

Thr Asp Pro Thr Arg Arg Phe
1               5

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Gly Gly Gly Ser
1               5

<210> SEQ ID NO 195
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
actgccatgc tcgaggccac catgg                                         25

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
actgccagct cgaggccacc atgg                                          24
```